United States Patent
Villain-Guillot et al.

(10) Patent No.: US 10,626,144 B2
(45) Date of Patent: Apr. 21, 2020

(54) PEPTIDE DERIVATIVES AND USES THEREOF

(71) Applicant: Nosopharm, Nimes (FR)

(72) Inventors: Philippe Villain-Guillot, Montpellier (FR); Maxime Gualtieri, Aubais (FR); Emilie Racine, Bouillargues (FR)

(73) Assignee: Nosopharm, Nimes (FR)

(*) Notice: Subject to any disclaimer, the term of this patent is extended or adjusted under 35 U.S.C. 154(b) by 82 days.

(21) Appl. No.: 15/507,934

(22) PCT Filed: Sep. 25, 2015

(86) PCT No.: PCT/EP2015/072185
§ 371 (c)(1),
(2) Date: Mar. 1, 2017

(87) PCT Pub. No.: WO2016/046409
PCT Pub. Date: Mar. 31, 2016

(65) Prior Publication Data
US 2017/0298097 A1 Oct. 19, 2017

(30) Foreign Application Priority Data
Sep. 26, 2014 (EP) .................................... 14306504

(51) Int. Cl.
| | |
|---|---|
| *C07K 7/06* | (2006.01) |
| *A61K 38/08* | (2019.01) |
| *A61K 45/06* | (2006.01) |
| *A61K 38/00* | (2006.01) |

(52) U.S. Cl.
CPC ............. *C07K 7/06* (2013.01); *A61K 38/08* (2013.01); *A61K 45/06* (2013.01); *A61K 38/00* (2013.01)

(58) Field of Classification Search
None
See application file for complete search history.

(56) References Cited

FOREIGN PATENT DOCUMENTS

| FR | 1451623 A | 1/1966 |
| WO | 01/21189 A1 | 3/2001 |
| WO | 2007/133689 A2 | 11/2007 |
| WO | 2009/106073 A2 | 9/2009 |
| WO | 2013/045600 A1 | 4/2013 |
| WO | 2013/171753 A1 | 11/2013 |

OTHER PUBLICATIONS

Merck Manual (https://www.merckmanuals.com/professional/infectious-diseases/bacteria-and-antibacterial-drugs/overview-of-bacteria accessed Feb. 2, 2019).*
Garau: Lancet Infect. Disease, 2002.*
Berge, S.M. et al., Pharmaceutical Salts, J. Pharm. Sci., 1977, vol. 66, No. 1, pp. 1-19.
Berwe, M. et al., Scalable Synthesis of the Desoxy-biphenomycin B Core, Org. Process Res. Dev., 2011, vol. 15, 1348-1357.
Freeman, N. S. et al., Microwave-Assisted Solid-Phase Aza-peptide Synthesis: Aza Scan of a PKB/Akt Inhibitor Using Aza-arginine and Aza-proline Precursors, J. Org. Chem., 2011, vol. 76, pp. 3078-3085.
Gomase, V.S. et al., Prediction of MHC Binding Peptides and Epitopes from Alfalfa mosaic virus, Current Drug Discovery Technologies, 2007, vol. 4, No. 2, pp. 117-125.
Gould, P.L., Salt selection for basic drugs, Int. J. Pharmaceutics, 1986, vol. 33, pp. 201-217.
Merrifield R. B., Solid Phase Peptide Synthesis. I. The Synthesis of a Tetrapeptide, J. Am. Chem. Soc., 1963, vol. 85, p. 2149-2154.
Parsons, T.D. et al., Aminoglycoside Antibiotics Block Voltage-dependent Calcium Channels in Intact Vertebrate Nerve Terminals, J. Gen. Physiol., 1992, vol. 99, No. 4, pp. 491-504.
Schmidt, U. and Wild, J., Total Synthesis of Hexaacetylcelenamide A, Angew. Chem. Int. Ed. Engl., 1984, vol. 23, pp. 991-993.
Suzuki, D. et al, Characterization of murine T-cell epitopes on mycobacterial DNA-binding protein 1 (MDP1) using DNA vaccination, Vaccine, 2010, vol. 28, No. 8, pp. 2020-2025.
Wagner, J. et al., ?-Conotoxin GVIA Binding to a High-Affinity Receptor in Brain: Characterization, Calcium Sensitivity, and Solubilization, J. Neurosci., 1988, vol. 8, No. 9, pp. 3354-3359.

* cited by examiner

*Primary Examiner* — James H Alstrum-Acevedo
*Assistant Examiner* — Tara L Martinez
(74) *Attorney, Agent, or Firm* — Banner & Witcoff, Ltd.

(57) ABSTRACT

The invention provides for novel peptide derivatives and compositions comprising the same. The invention further provides methods of treatment comprising administering novel peptide derivatives and/or compositions comprising the same.

16 Claims, No Drawings

PEPTIDE DERIVATIVES AND USES THEREOF

RELATED APPLICATIONS

This application is a National Stage Application under 35 U.S.C. 371 of co-pending PCT application PCT/EP2015/072185 designating the United States and filed Sep. 25, 2015; which claims the benefit of EP application number 14306504.3 and filed Sep. 26, 2014 each of which are hereby incorporated by reference in their entireties.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

FIELD OF THE INVENTION

The present invention relates to new peptide-based compounds and compositions comprising the same, and to the use of such compounds and compositions thereof in the treatment of microbial disease.

BACKGROUND OF THE INVENTION

Microbial infections are responsible for both global pandemics and local epidemics, and may result in serious mortalities if left untreated or appropriate treatment is not provided. Importantly, many available antibiotics are increasingly ineffective due to acquisition of resistance by many microbes. Exemplary multiresistant bacterial pathogens include methicillin-resistant *Staphylococcus aureus* (MRSA), vancomycin-resistant enterococci (VRE), extended spectrum ß-lactamase formers (ESBL), carbapenem-resistant Enterobacteriaceae (CRE), multiresistant *Pseudomonas* and *Acinetobacter* species. For these bacteria, only a few of the existing antibiotics are therapeutically effective.

There is a need for novel antibiotic compounds. There is also a need for novel and effective treatments for bacterial infections and a variety of disease states for which bacterial infections are implicated.

We reported in WO2013045600 the discovery of a novel class of antibiotics that we first called the Odilomycins, and that we then renamed the Odilorhabdins. The 3 first odilorhabdin molecules are naturally produced by the bacteria *Xenorhabdus nematophila*. Odilorhabdins have interesting antibacterial activities against bacterial pathogens, including against multidrug-resistant clinical isolates. However, a drawback of the original Odilorhabdins is their affinity to calcium channels (type N) conferring them significant adverse events. These adverse events preclude the direct use of the natural Odilorhabdins as drugs. We succeeded to overcome this issue by designing much safer synthetic analogs of the Odilorhabdins that retain antibacterial activity, following a medicinal chemistry program and structure-activity relationships studies. These safer antibacterial analogs are the purpose of this patent application.

SUMMARY OF THE INVENTION

In one aspect, the invention is directed to a class of compounds of formula (I) $R_a$-$Xaa_1$-$Xaa_2$-$Xaa_3$-$Xaa_4$-$Xaa_5$-$Xaa_6$-$Xaa_7$-$Xaa_8$-$Xaa_9$-$R_b$ (I) as defined in claim 1.

The invention also discloses compounds of formula (I) wherein $R_b$ is $Xaa_{10}$-$R_e$
$Xaa_{10}$ is

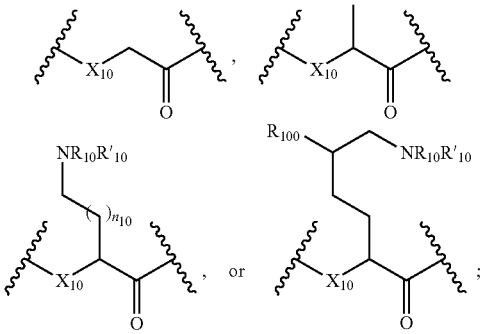

$X_{10}$ is independently NH, O, preferably $X_{10}$ is NH
$R_{10}$, $R'_{10}$ is independently H, —C(NH)NH$_2$, —(C$_1$-C$_3$)-alkyl, —C(O)—(C$_1$-C$_3$)-alkyl, or —C(O)—(C$_1$-C$_3$)-haloalkyl;
$R_{100}$ is H, OH or halogen; and $n_{10}$ is an integer from 1-4;

Compounds of formula (I) with Rb=Rc show lower affinity to N-type calcium channels (see example 11), and thus improved tolerability with significantly reduced risks of serious adverse events.

The subject matter of the present invention also concerns a combination of at least one compound according to the invention with at least one other antibiotic. Preferably said combination is a combination of two antibiotics: a compound of the present invention with another antibiotic. The combination of at least one compound according to the invention with at least one other antibiotic may be administered to a subject simultaneously, separately or sequentially in time.

In another aspect, the invention is directed to pharmaceutical compositions comprising a compound of formula (I) and a pharmaceutically acceptable carrier.

In yet another aspect, methods of treatment for bacterial infection to a subject in need thereof are provided comprising administration of a compound of formula (I), or pharmaceutical compositions comprising a compound of formula (I). The compounds and/or compositions of the invention may be useful, for example, in treatment, suppression, and/or prevention of bacterial infection and/or disease.

In some embodiments, the invention is directed to a method of treating a bacterial infection in a subject in need thereof comprising administration of a therapeutically effective amount of a compound of formula (I), or a pharmaceutical composition comprising a compound of formula (I).

In some embodiments, the invention is directed to a method of killing bacteria comprising contacting said bacteria with a compound of formula (I), or a pharmaceutical composition comprising a compound of formula (I).

Still other objects and advantages of the invention will become apparent to those of skill in the art from the disclosure herein, which is simply illustrative and not restrictive. Thus, other embodiments will be recognized by the skilled artisan without departing from the spirit and scope of the invention.

DETAILED DESCRIPTION OF THE INVENTION

The invention provides antibacterial compounds, methods and/or compositions, and methods and compositions that are useful for treating, suppressing and/or preventing bacterial infections in subjects. In some embodiments, the methods comprise administering to a subject a therapeutically effective amount of a compound of formula I, or a pharmaceutically acceptable salt thereof, or a composition comprising a compound of formula I, or a pharmaceutically acceptable salt thereof, and a pharmaceutically acceptable carrier. The composition or method may optionally comprise one or more additional anti-bacterial agents.

In particular, embodiments relate to methods of treatment, suppression, and/or prevention of diseases or conditions relating to bacterial infection comprising administration of a compound of formula I, or pharmaceutically acceptable salt thereof.

Abbreviations and Definitions

The term "halogen", as used in the present invention, refers to a fluorine, bromine, chlorine or iodine atom, preferably fluorine, chlorine or iodine, more preferably fluorine.

The term "$(C_1-C_6)$alkyl", as used in the present invention, refers to a straight or branched monovalent saturated hydrocarbon chain containing from 1 to 6 carbon atoms including, but not limited to, methyl, ethyl, n-propyl, iso-propyl, n-butyl, iso-butyl, sec-butyl, t-butyl, n-pentyl, n-hexyl, and the like.

The term "$(C_1-C_6)$haloalkyl", as used in the present invention, refers to a $(C_1-C_6)$alkyl group as defined above substituted by at least one halogen atom, and preferably by at least one fluorine atom. It can be in particular a trifluoromethyl group.

The term "$(C_2-C_6)$alkenyl", as used in the present invention, refers to a straight or branched monovalent unsaturated hydrocarbon chain containing from 2 to 6 carbon atoms and comprising at least one double bond including, but not limited to, ethenyl, propenyl, butenyl, pentenyl, hexenyl and the like.

The term "$(C_2-C_6)$alkynyl", as used in the present invention, refers to a straight or branched monovalent unsaturated hydrocarbon chain containing from 2 to 6 carbon atoms and comprising at least one triple bond including, but not limited to, ethynyl, propynyl, butynyl, pentynyl, hexynyl and the like.

The term "$(C_1-C_6)$alkoxy", as used in the present invention, refers to a $(C_1-C_6)$alkyl group as defined above bound to the molecule via an oxygen atom, including, but not limited to, methoxy, ethoxy, n-propoxy, iso-propoxy, n-butoxy, iso-butoxy, sec-butoxy, t-butoxy, n-pentoxy, n-hexoxy, and the like.

The term "$(C_3-C_{10})$cycloalkyl", as used in the present invention, refers to a hydrocarbon ring having 3 to 10 carbon atoms including, but not limited to, cyclopropyl, cyclopentyl, cyclohexyl and the like.

The term "aryl", as used in the present invention, refers to an aromatic hydrocarbon group comprising preferably 5 to 10 carbon atoms and comprising one or more fused rings, such as, for example, a phenyl or naphtyl group. Advantageously, it will be a phenyl group.

The term "$(C_1-C_6)$alkyl-aryl", as used in the present invention, refers to an aryl group as defined above bound to the molecule via an alkyl group as defined above. In particular, an aralkyl group is a benzyl group.

The term "heteroaryl" as used in the present invention refers to an aromatic group, preferably a 5- to 10-membered aromatic group, comprising one or more fused rings, in which the atoms of the ring(s) consist of one or more, advantageously 1 to 4, and more advantageously 1 or 2, heteroatoms, such as a nitrogen, oxygen or sulphur atom, the remainder being carbon atoms. A heteroaryl group can be notably thienyl, furanyl, pyrrolyl, etc.

The term "$(C_1-C_6)$alkyl-RADICAL", as used in the present invention, refers to a RADICAL, as defined by its chemical formula or name in the term, bound to the molecule via an alkyl group as defined above.

The term "compound of the invention" as used herein means a compound of formula (I) or any subgenus or species thereof. The term is also intended to encompass pharmaceutically acceptable salts thereof.

The term "composition(s) of the invention" as used herein means compositions comprising a compound of the invention. The compositions of the invention may further comprise other agents such as, for example, carriers, excipients, stabilants, lubricants, solvents, and the like.

A "pharmaceutical composition" refers to a mixture of one or more of the compounds of the invention with other chemical components, such as physiologically acceptable carriers and excipients. The purpose of a pharmaceutical composition is to facilitate administration of a compound to an organism or subject.

The term "pharmaceutically acceptable salt" is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids; and salts derived from inorganic or organic bases including, for example sodium, potassium, calcium, ammonium or tetrafluoroborate. Exemplary pharmaceutically acceptable salts are found, for example, in Berge, S. M. et al., *J. Pharm. Sci.* 1977, 66, 2, and Gould, P. L., *Int. J. Pharmaceutics* 1986, 33, 201-217; each hereby incorporated by reference in its entirety.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington's Pharmaceutical Sciences (Alfonso Gennaro ed., Krieger Publishing Company (1997); Remington's: The Science and Practice of Pharmacy, $21^{st}$ Ed. (Lippincot, Williams & Wilkins (2005); Modern Pharmaceutics, vol. 121 (Gilbert Banker and Christopher Rhodes, CRC Press (2002); each of which hereby incorporated by reference in its entirety).

The configuration at the α-carbon atoms in the amino acid residues may be "D" or "L", and may be independent of the configurations of other amino acid residues in the compounds of formula (I). The configuration at the hydroxyl groups in the amino acid side chains may be "R" or "S", and may be independent of the configurations of other hydroxyl groups in the compounds of formula (I). Thus, in some embodiments, one or more hydroxyl groups have the "R" configuration. In some embodiments, one or more hydroxyl groups have the "S" configuration. In some embodiments, each of the hydroxyl groups have the "R" configuration. In some embodiments, each of the hydroxyl groups have the "S" configuration.

Unless otherwise indicated, the compounds of formula (I) include all stereoisomers including, e.g., enantiomers and diastereomers. Exemplary isomers also include cis- and trans-double bonds. The compounds of formula (I) further include isomerically enriched compounds as well as isomeric mixtures, racemic mixtures and single enantiomers.

$R_a$ is H, —$(C_1$-$C_3)$-alkyl, —C(O)—$(C_1$-$C_3)$-alkyl, or —C(O)—$(C_1$-$C_3)$-haloalkyl, advantageously H or —$(C_1$-$C_3)$-alkyl. In some embodiments, $R_a$ is H, —$(C_1$-$C_3)$-alkyl, —C(O)—$(C_1$-$C_2)$-alkyl, or —C(O)—$(C_1$-$C_3)$-haloalkyl, advantageously H or —$(C_1$-$C_3)$-alkyl. In some embodiments, $R_a$ is H, methyl, acetyl, or trihaloacetyl, in particular H, methyl, acetyl, or trifluoroacetyl. In some embodiments, $R_a$ is H, methyl, or acetyl, in particular H or methyl. In some embodiments, $R_a$ is H. In some embodiments, $R_a$ is methyl.

$Xaa_1$ is

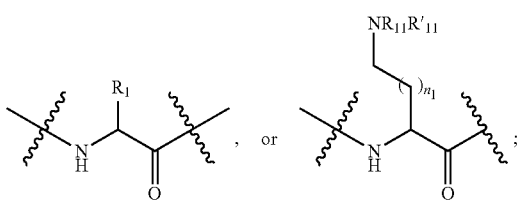

$R_1$, $R_{11}$, $R'_{11}$ is independently H, —$(C_1$-$C_3)$-alkyl, —C(O)—$(C_1$-$C_3)$-alkyl, or —C(O)—$(C_1$-$C_3)$-haloalkyl;

$n_1$ is an integer from 1-4. Advantageously, $n_1$ is an integer from 1-3, in particular $n_1$ is 1, 2 or 3. In some embodiments, $R_1$, $R_{11}$, $R'_{11}$ is independently H, methyl, ethyl, —C(O)—$(C_1$-$C_2)$-alkyl, or —C(O)—$(C_1$-$C_2)$-haloalkyl; and $n_1$ is an integer from 1-3. In some embodiments, $R_1$, $R_{11}$, $R'_{11}$ is independently H, methyl, acetyl or trifluoroacetyl. In particular, in these embodiments, $R'_{11}$ is H. Advantageously, $R_1$ is H, —$(C_1$-$C_3)$-alkyl, in particular H, methyl, ethyl, $R_{11}$ is H, methyl, ethyl, —C(O)—$(C_1$-$C_2)$-alkyl, or —C(O)—$(C_1$-$C_2)$-haloalkyl, in particular H, methyl, acetyl or trifluoroacetyl and $R'_{11}$ is H.

The configuration of asymmetric carbon atom bearing the radical $R_1$ or —$(CH_2)_{n1}$—$NR_{11}R'_{11}$ is preferably S.

In some embodiments, $Xaa_1$ is

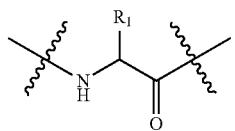

In some embodiments, $Xaa_1$ is

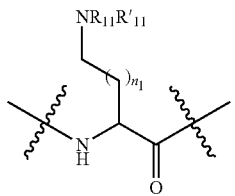

Advantageously, $Xaa_1$ is

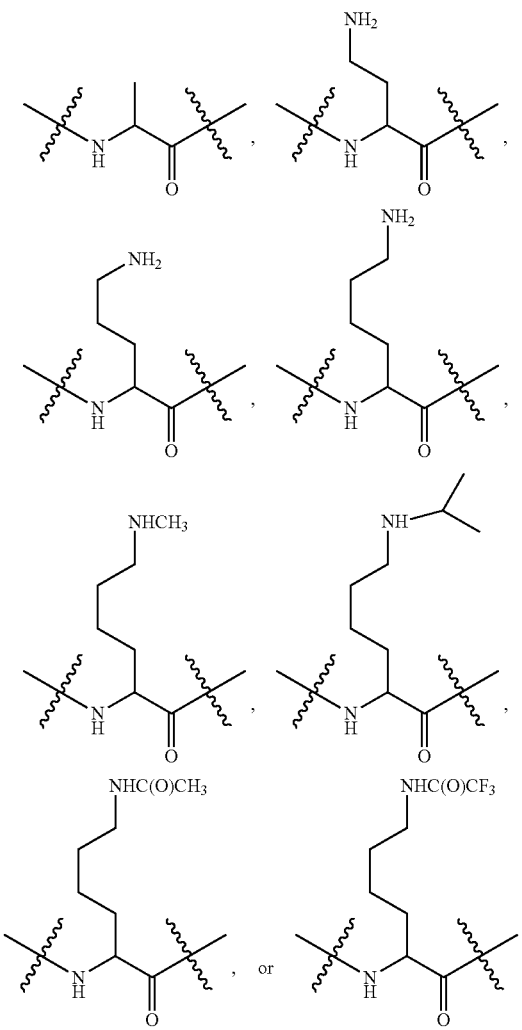

In particular, $Xaa_1$ is

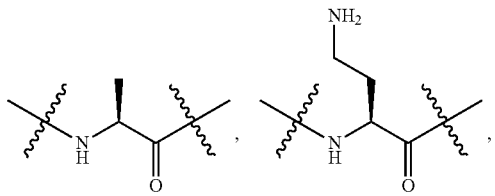

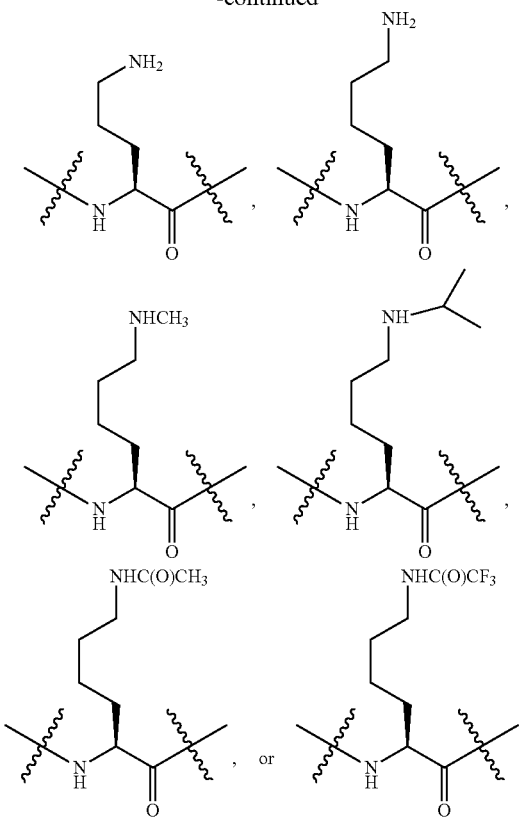
In some embodiments, Xaa₁ is
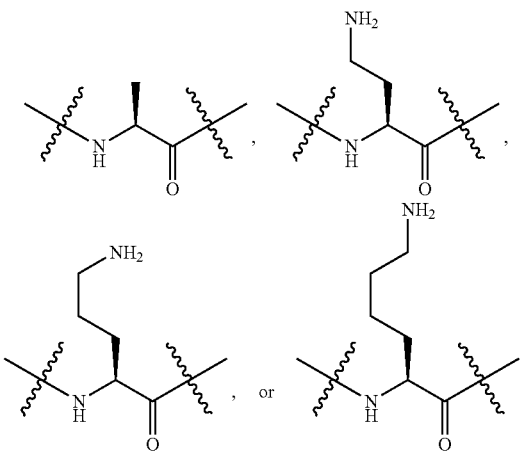
In some embodiments, Xaa₁ is
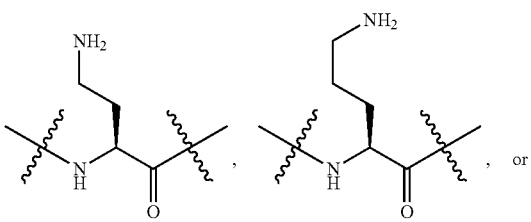
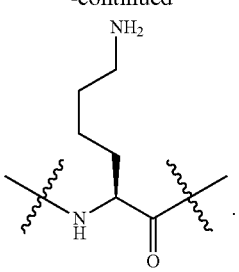
In some embodiments, Xaa₁ is
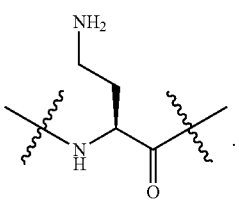 [SMILES: *N[C@@H](CCN)C(*)=O]
In some embodiments, Xaa₁ is
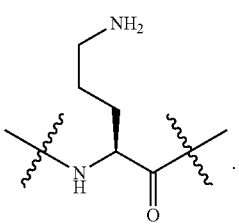 [SMILES: *N[C@@H](CCCN)C(*)=O]
In some embodiments, Xaa₁ is
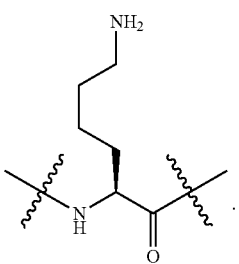 [SMILES: *N[C@@H](CCCCN)C(*)=O]
Xaa₂ is
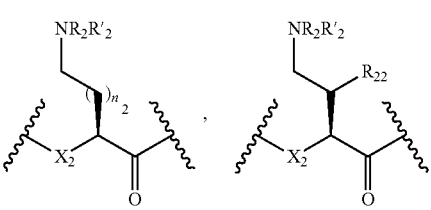

-continued

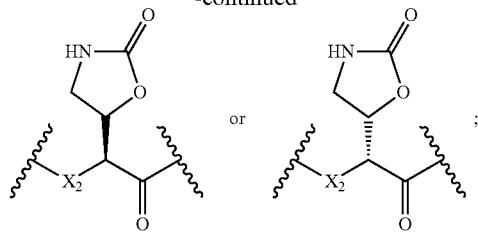

In some embodiments, Xaa$_2$ is

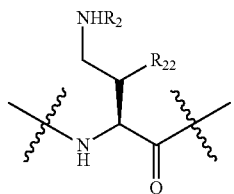

$X_2$ is independently NH, N(Me), O, $R_2$, $R'_2$ is independently H, —($C_1$-$C_3$)-alkyl, —C(O)—($C_1$-$C_3$)-alkyl, or —C(O)—($C_1$-$C_3$)-haloalkyl; $R_{22}$ is independently OH, halogen, —($C_1$-$C_3$)-alkyl, —($C_1$-$C_3$)-alkoxy, O—C(O)—($C_1$-$C_6$)-alkyl or —O—C(O)—($C_1$-$C_6$)-haloalkyl; and $n_2$ is an integer from 1-3.

$X_2$ is preferably NH, N(Me), more preferably NH. In another embodiment, $X_2$ is O.

Advantageously, $R_2$ is independently H, methyl, ethyl, —C(O)—($C_1$-$C_2$)-alkyl, or —C(O)—($C_1$-$C_2$)-haloalkyl; more advantageously H, methyl, acetyl or trifluoroacetyl. In this embodiment, $R'_2$ is advantageously H, methyl, ethyl, more advantageously H.

$n_2$ is an integer from 1-3, in particular 1, 2 or 3, advantageously $n_2$ is 1.

Advantageously, $R_{22}$ is independently OH, fluorine, methyl, or methoxy, —O—C(O)—$CH_3$, —O—C(O)—$CF_3$, in particular OH, —O—C(O)—$CH_3$, —O—C(O)—$CF_3$. In this embodiment, $R_2$, $R'_2$ are as defined above. In particular $R_2$ is independently H, methyl, acetyl or trifluoroacetyl, advantageously H, $R'_2$ is H.

In some embodiments, Xaa$_2$ is

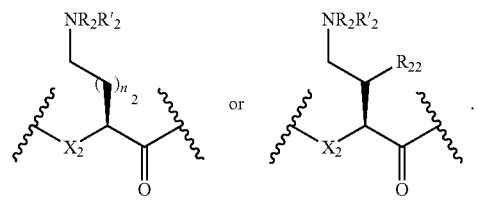

In particular, Xaa$_2$ is

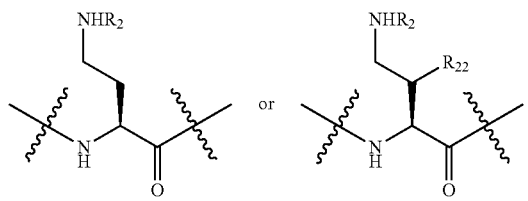

In some embodiments, Xaa$_2$ is

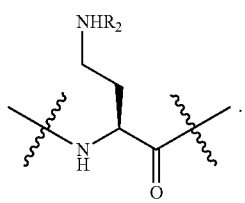

Xaa$_3$ is

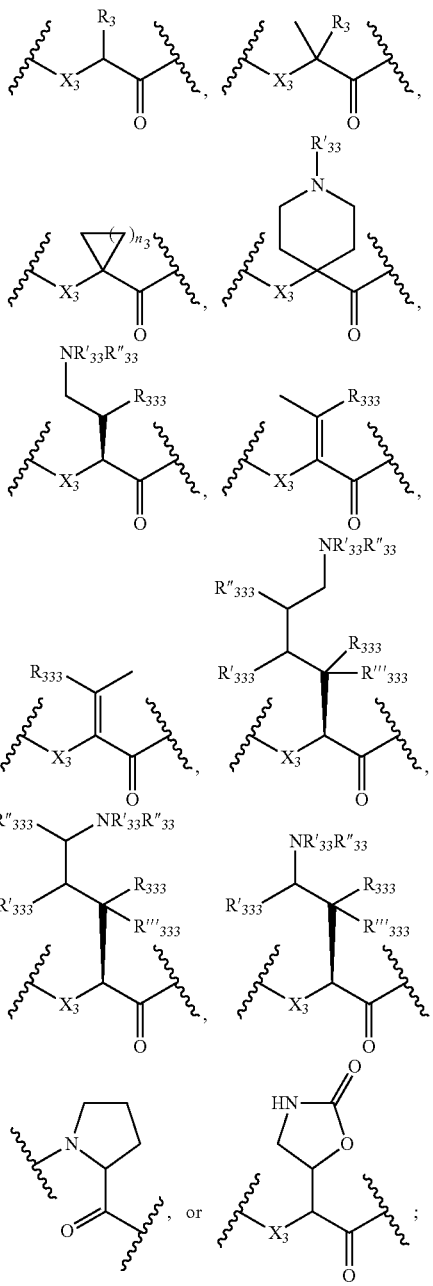

$X_3$ is independently N($R_{33}$), O; $R_3$ is independently H, halogen, $NH_2$, —($C_1$-$C_6$)-alkyl, —($C_1$-$C_6$)-haloalkyl, —($C_3$-$C_8$)-cycloalkyl, —($C_1$-$C_6$)-alkenyl, —($C_1$-$C_6$)-alkynyl, —($C_1$-$C_6$)-alkyl-OR$_{33}$, ($C_1$-$C_6$)-alkyl-SR$_{33}$, ($C_1$-$C_6$)-alkyl-NR$_{33}$R'$_{33}$, ($C_1$-$C_6$)-alkyl-C(O)NR$_{33}$R'$_{33}$, ($C_1$-$C_6$)-alkyl-C(O) OR$_{33}$, ($C_1$-$C_6$)-alkyl-heteroaryl wherein said alkyl is optionally substituted with —OH or —O—C(O)—($C_1$-$C_6$)-alkyl or —O—C(O)—($C_1$-$C_6$)-haloalkyl, wherein said heteroaryl is optionally substituted with —($C_1$-$C_3$)-alkyl, or ($C_1$-$C_6$)-alkyl-aryl wherein said aryl is optionally substituted with —OH, —($C_1$-$C_3$)-alkyl, —($C_1$-$C_3$)-alkoxy or halogen; R$_{33}$, R'$_{33}$, R"$_{33}$ is independently H, —C(NH)NH$_2$, —($C_1$-$C_3$)-alkyl, —C(O)—($C_1$-$C_3$)-alkyl, or —C(O)—($C_1$-$C_3$)-haloalkyl; R$_{333}$, R'$_{333}$, R"$_{333}$, R'''$_{333}$ is independently H, OH, halogen, —($C_1$-$C_3$)-alkyl, —($C_1$-$C_3$)-alkoxy, —O—CO—($C_1$-$C_3$)-alkyl or —O—CO—($C_1$-$C_3$)-haloalkyl; and $n_3$ is an integer from 1-3.

In an embodiment $X_3$ is N(R$_{33}$), in particular (NH) or (NCH$_3$). In another embodiment $X_3$ is O.

The configuration of asymmetric carbon atom between —$X_3$ and —C(O) is preferably S. Accordingly, Xaa$_3$ is advantageously

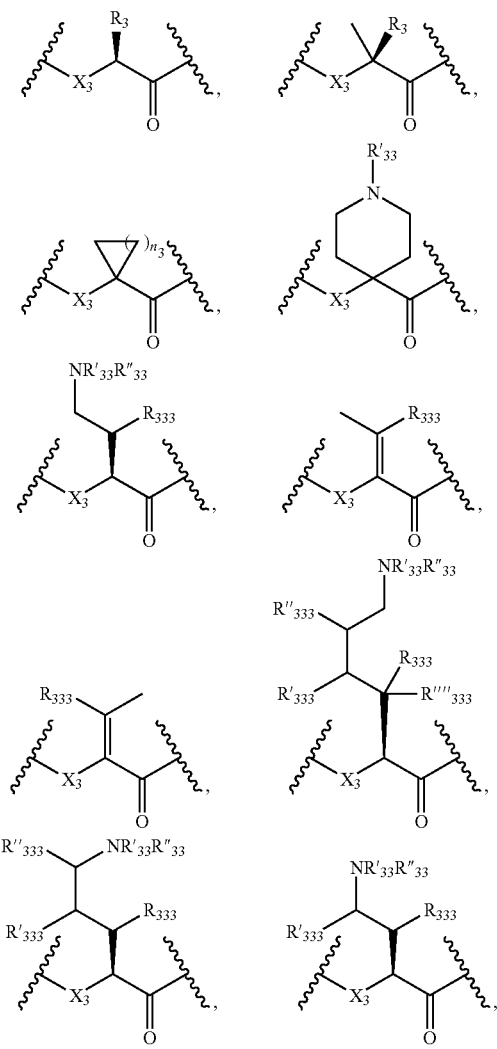

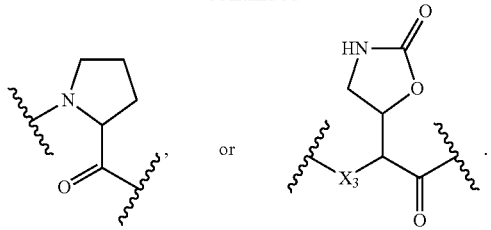

$X_3$ is advantageously N(R$_{33}$), in particular (NH) or (NCH$_3$). R$_{33}$ is advantageously independently H, —C(NH)NH$_2$, methyl, ethyl, —C(O)—CH$_3$, —C(O)—C$_2$H$_5$ or —C(O)—CF$_3$, advantageously H, methyl. When R$_{33}$ is beared by $X_3$, it is more advantageously H. R'$_{33}$, R"$_{33}$ is advantageously independently H, —C(NH)NH$_2$, —($C_1$-$C_3$)-alkyl, —C(O)—($C_1$-$C_3$)-alkyl, or —C(O)—($C_1$-$C_3$)-haloalkyl. R"$_{33}$ is advantageously independently H, —($C_1$-$C_3$)-alkyl, more advantageously H.

R$_{333}$ is advantageously independently OH, halogen, —($C_1$-$C_3$)-alkyl, —($C_1$-$C_3$)-alkoxy, —O—CO—($C_1$-$C_3$)-alkyl or —O—CO—($C_1$-$C_3$)-haloalkyl. R'$_{333}$ is advantageously independently H, OH, halogen, —($C_1$-$C_3$)-alkyl, or —($C_1$-$C_3$)-alkoxy, advantageously H, methyl, ethyl, —OCH$_3$, more advantageously H. R"$_{333}$ is advantageously independently H, OH, halogen, —($C_1$-$C_3$)-alkyl, or —($C_1$-$C_3$)-alkoxy, advantageously H, methyl, ethyl, —OCH$_3$, more advantageously. H. R'''$_{333}$ is advantageously independently H, OH, halogen, —($C_1$-$C_3$)-alkyl, or —($C_1$-$C_3$)-alkoxy, advantageously H.

R$_3$ is advantageously independently H, halogen, NH$_2$, —($C_1$-$C_6$)-alkyl, —($C_1$-$C_6$)-haloalkyl, —($C_3$-$C_8$)-cycloalkyl, —($C_1$-$C_6$)-alkenyl, —($C_1$-$C_6$)-alkynyl, —($C_1$-$C_6$)-alkyl-OR$_{33}$, ($C_1$-$C_6$)-alkyl-SR$_{33}$, ($C_1$-$C_6$)-alkyl-NR$_{33}$R'$_{33}$, ($C_1$-$C_6$)-alkyl-C(O)NR$_{33}$R'$_{33}$, ($C_1$-$C_6$)-alkyl-C(O)OR$_{33}$, ($C_1$-$C_6$)-alkyl-heteroaryl wherein said alkyl is optionally substituted with —OH or —O—C(O)—($C_1$-$C_6$)-alkyl or —O—C(O)—($C_1$-$C_6$)-haloalkyl, wherein said heteroaryl is optionally substituted with —($C_1$-$C_3$)-alkyl, or ($C_1$-$C_6$)-alkyl-aryl wherein said aryl is optionally substituted with —OH, —($C_1$-$C_3$)-alkyl, —($C_1$-$C_3$)-alkoxy or halogen. Advantageously, R$_3$ is a independently H, halogen, NH$_2$, —($C_1$-$C_6$)-alkyl, —($C_1$-$C_6$)-haloalkyl, —($C_3$-$C_8$)-cycloalkyl, —($C_1$-$C_6$)-alkenyl, —($C_1$-$C_6$)-alkynyl, —($C_1$-$C_6$)-alkyl-OR$_{33}$, ($C_1$-$C_6$)-alkyl-SR$_{33}$, ($C_1$-$C_6$)-alkyl-NR$_{33}$R'$_{33}$, ($C_1$-$C_6$)-alkyl-C(O)NR$_{33}$R'$_{33}$, ($C_1$-$C_6$)-alkyl-C(O)OR$_{33}$, ($C_1$-$C_6$)-alkyl-heteroaryl wherein said heteroaryl is optionally substituted with —($C_1$-$C_3$)-alkyl, or ($C_1$-$C_6$)-alkyl-aryl wherein said aryl is optionally substituted with —OH, —($C_1$-$C_3$)-alkyl, —($C_1$-$C_3$)-alkoxy or halogen. More advantageously, R$_3$ is a independently H, halogen, —($C_1$-$C_4$)-alkyl, —($C_1$-$C_4$)-alkenyl, —($C_1$-$C_4$)-alkynyl, —($C_1$-$C_4$)-alkyl-OH, —($C_1$-$C_4$)-alkyl-SH, ($C_1$-$C_4$)-alkyl-NHR$_{33}$, ($C_1$-$C_4$)-alkyl-C(O)NHR$_{33}$, ($C_1$-$C_4$)-alkyl-C(O)OH, ($C_1$-$C_4$)-alkyl-heteroaryl wherein said heteroaryl is selected from imidazole, pyrazole, oxazole, isoxazole, thiazole, pyrole, furane, thiophene, pyrazine, pyridazine, pyridine, or pyrimidine, more particular from imidazole, pyrole, thiazole, furane, or thiophene, more particular from imidazole, oxazole, thiazole, more particular imidazole, or ($C_1$-$C_4$)-alkyl-aryl wherein said aryl is benzène, In an embodiment, $Xaa_3$ is

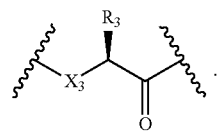

$X_3$ is advantageously $N(R_{33})$. $R_{33}$ is advantageously independently H, —C(NH)NH$_2$, methyl, ethyl, —C(O)—CH$_3$, —C(O)—C$_2$H$_5$ or —C(O)—CF$_3$, advantageously H, methyl, more advantageously H. $R_3$ is advantageously independently H, halogen, NH$_2$, —(C$_1$-C$_6$)-alkyl, —(C$_1$-C$_6$)-haloalkyl, —(C$_3$-C$_8$)-cycloalkyl, —(C$_1$-C$_6$)-alkenyl, —(C$_1$-C$_6$)-alkynyl, —(C$_1$-C$_6$)-alkyl-OR$_{33}$, (C$_1$-C$_6$)-alkyl-SR$_{33}$, (C$_1$-C$_6$)-alkyl-NR$_{33}$R'$_{33}$, (C$_1$-C$_6$)-alkyl-C(O)NR$_{33}$R'$_{33}$, (C$_1$-C$_6$)-alkyl-C(O)OR$_{33}$, (C$_1$-C$_6$)-alkyl-heteroaryl wherein said alkyl is optionally substituted with —OH or —O—C(O)—(C$_1$-C$_6$)-alkyl or —O—C(O)—(C$_1$-C$_6$)-haloalkyl, wherein said heteroaryl is optionally substituted with —(C$_1$-C$_3$)-alkyl, or (C$_1$-C$_6$)-alkyl-aryl wherein said aryl is optionally substituted with —OH, —(C$_1$-C$_3$)-alkyl, —(C$_1$-C$_3$)-alkoxy or halogen. Advantageously, $R_3$ is a independently H, halogen, NH$_2$, —(C$_1$-C$_6$)-alkyl, —(C$_1$-C$_6$)-haloalkyl, —(C$_3$-C$_8$)-cycloalkyl, —(C$_1$-C$_6$)-alkenyl, —(C$_1$-C$_6$)-alkynyl, —(C$_1$-C$_6$)-alkyl-OR$_{33}$, (C$_1$-C$_6$)-alkyl-SR$_{33}$, (C$_1$-C$_6$)-alkyl-NR$_{33}$R'$_{33}$, (C$_1$-C$_6$)-alkyl-C(O)NR$_{33}$R'$_{33}$, (C$_1$-C$_6$)-alkyl-C(O)OR$_{33}$, (C$_1$-C$_6$)-alkyl-heteroaryl wherein said heteroaryl is optionally substituted with —(C$_1$-C$_3$)-alkyl, or (C$_1$-C$_6$)-alkyl-aryl wherein said aryl is optionally substituted with —OH, —(C$_1$-C$_3$)-alkyl, —(C$_1$-C$_3$)-alkoxy or halogen. More advantageously, $R_3$ is a independently H, halogen, —(C$_1$-C$_4$)-alkyl, —(C$_1$-C$_4$)-haloalkyl, —(C$_1$-C$_4$)-alkenyl, —(C$_1$-C$_4$)-alkynyl, —(C$_1$-C$_4$)-alkyl-OH, (C$_1$-C$_4$)-alkyl-SH, (C$_1$-C$_4$)-alkyl-NHR$_{33}$, (C$_1$-C$_4$)-alkyl-C(O)NHR$_{33}$, (C$_1$-C$_4$)-alkyl-C(O)OH, (C$_1$-C$_4$)-alkyl-heteroaryl wherein said heteroaryl is selected from imidazole, pyrazole, oxazole, isoxazole, thiazole, pyrole, furane, thiophene, pyrazine, pyridazine, pyridine, or pyrimidine, more particular from imidazole, pyrole, thiazole, furane, or thiophène, more particular from imidazole, oxazole, thiazole, more particular imidazole, or (C$_1$-C$_4$)-alkyl-aryl wherein said aryl is benzene.

In another embodiment, $Xaa_3$ is

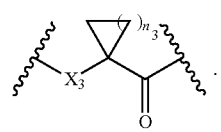

$X_3$ is advantageously $N(R_{33})$. $R_{33}$ is advantageously independently H, —C(NH)NH$_2$, methyl, ethyl, —C(O)—CH$_3$, —C(O)—C$_2$H$_5$ or —C(O)—CF$_3$, advantageously H, methyl, more advantageously H. $n_3$ is an integer from 1-3, in particular. $n_3$ is 1, 2 or 3.

In another embodiment, $Xaa_3$ is

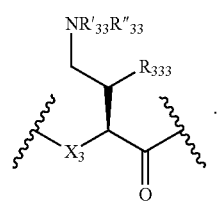

$X_3$ is advantageously $N(R_{33})$. $R_{33}$, $R'_{33}$, $R''_{33}$ is independently H, —C(NH)NH$_2$, —(C$_1$-C$_3$)-alkyl, —C(O)—(C$_1$-C$_3$)-alkyl, or —C(O)—(C$_1$-C$_3$)-haloalkyl; $R_{333}$ is independently H, OH, halogen, —(C$_1$-C$_3$)-alkyl, —(C$_1$-C$_3$)-alkoxy, —O—CO—(C$_1$-C$_3$)-alkyl or —O—CO—(C$_1$-C$_3$)-haloalkyl. $R_{33}$ is advantageously independently H, methyl, ethyl, advantageously H, methyl, more advantageously H. $R'_{33}$, $R''_{33}$ is advantageously independently H, —C(NH)NH$_2$, —(C$_1$-C$_3$)-alkyl, —C(O)—(C$_1$-C$_3$)-alkyl, or —C(O)—(C$_1$-C$_3$)-haloalkyl. $R'_{33}$ is advantageously independently H, —C(NH)NH$_2$, —(C$_1$-C$_3$)-alkyl, —C(O)—(C$_1$-C$_3$)-alkyl, or —C(O)—(C$_1$-C$_3$)-haloalkyl. $R''_{33}$ is advantageously independently H, —(C$_1$-C$_3$)-alkyl, more advantageously H. $R_{333}$ is advantageously independently OH, halogen, —(C$_1$-C$_3$)-alkyl, —(C$_1$-C$_3$)-alkoxy, —O—CO—(C$_1$-C$_3$)-alkyl or —O—CO—(C$_1$-C$_3$)-haloalkyl, more advantageously OH, halogen, OCH$_3$, —O—CO—CH$_3$, —O—CO—CF$_3$. The configuration of the asymmetric carbon atom bearing $R_{333}$ is advantageously S.

In a embodiment, $Xaa_3$ is selected from

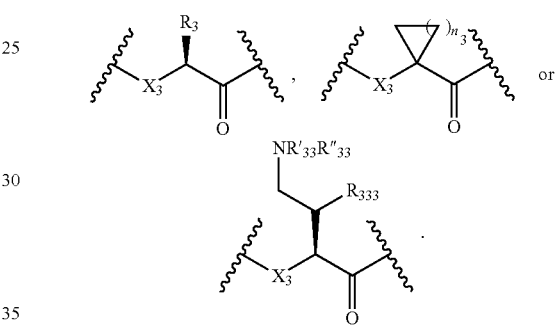

$X_3$; $R_3$; $R_{33}$, $R'_{33}$, $R''_{33}$; $R_{333}$, $R'_{333}$, $R''_{333}$, $R'''_{333}$; and $n_3$ are as defined above.

$Xaa_4$ is

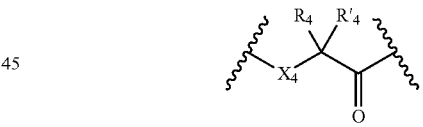

$X_4$ is independently NH, N(Me), O and $R_4$, $R'_4$ is independently H, —(C$_1$-C$_3$)-alkyl, or —(C$_1$-C$_3$)-haloalkyl. In a embodiment, $R_4$ is —(C$_1$-C$_3$)-alkyl, or —(C$_1$-C$_3$)-haloalkyl and R'4 is H or both $R_4$ and $R'_4$ are H.

In some embodiments, $Xaa_4$ is

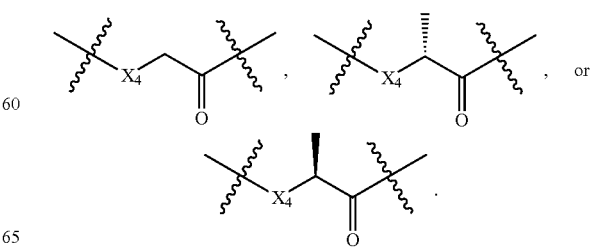

In some embodiments, Xaa$_4$ is

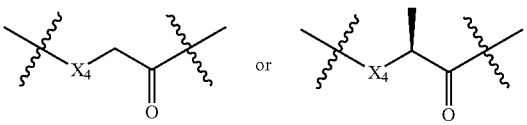

In some embodiments, Xaa$_4$ is

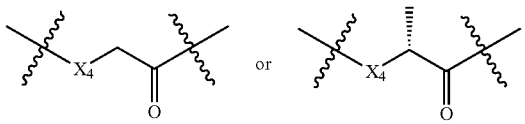

In some embodiments, Xaa$_4$ is

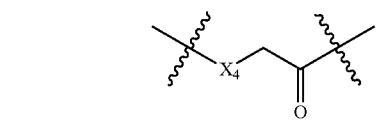

X$_4$ is independently NH, N(Me), O, advantageously NH, N(Me), more advantageously NH.

Xaa$_5$ is

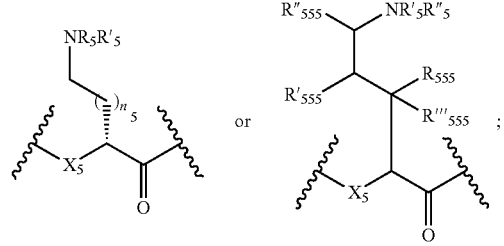

X$_5$ is independently NH, N(Me), O, R$_5$, R'$_5$ is independently H, —(C$_1$-C$_3$)-alkyl, —C(O)—(C$_1$-C$_3$)-alkyl, or —C(O)—(C$_1$-C$_3$)-haloalkyl; R$_{555}$, R'$_{555}$, R''$_{555}$, R'''$_{555}$ is independently H, OH, halogen, —(C$_1$-C$_3$)-alkyl, or —(C$_1$-C$_3$)-alkoxy; and n$_5$ is an integer from 1-3. In some embodiments, R$_5$, R'$_5$ is independently is H, methyl, acetyl or trifluoroacetyl. In some embodiments, R$_5$ R'$_5$ is independently H or methyl. In some embodiments, R$_5$, R'$_5$ is independently H. In some embodiments n$_5$ is 2. In these embodiments, X$_5$ is independently NH, N(Me), O, advantageously NH, N(Me), more advantageously NH.

In some embodiments, Xaa$_5$ is

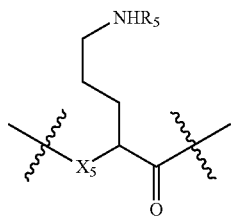

and R$_5$ is H, methyl, acetyl or trifluoroacetyl.

In some embodiments, Xaa$_5$ is

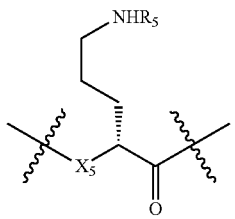

and R$_5$ is H, methyl, acetyl or trifluoroacetyl. In some embodiments, Xaa$_5$ is

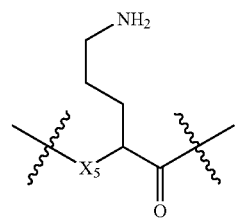

In some embodiments, Xaa$_5$ is

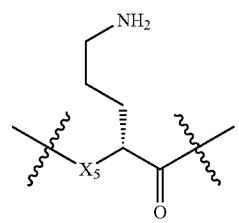

In all these embodiments, X$_5$ is independently NH, N(Me), O, advantageously NH, N(Me), more advantageously NH.

Xaa$_6$ is

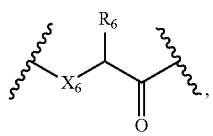 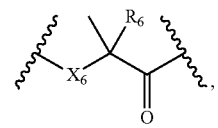

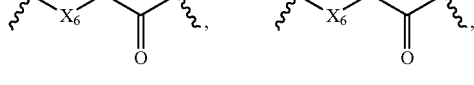

-continued

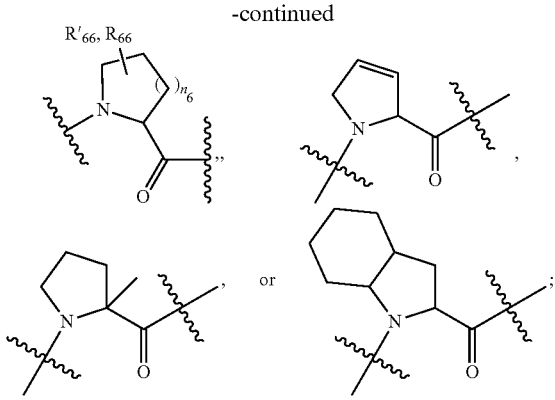

$X_6$ is independently $N(R_{66})$, O; $R_6$ is independently H, halogen, $NH_2$, —$(C_1$-$C_6)$-alkyl, —$(C_1$-$C_6)$-haloalkyl, —$(C_3$-$C_8)$-cycloalkyl, —$(C_1$-$C_6)$-alkenyl, —$(C_1$-$C_6)$-alkynyl, —$(C_1$-$C_6)$-alkyl-$OR_{66}$, $(C_1$-$C_6)$-alkyl-$SR_{66}$, $(C_1$-$C_6)$-alkyl-$NR_{66}R'_{66}$, $(C_1$-$C_6)$-alkyl-$C(O)NR_{66}R'_{66}$, $(C_1$-$C_6)$-alkyl-$C(O)OR_{66}$, $(C_1$-$C_6)$-alkyl-heteroaryl wherein said alkyl is optionally substituted with —OH or —O—C(O)—$(C_1$-$C_6)$-alkyl or —O—C(O)—$(C_1$-$C_6)$-haloalkyl, wherein said heteroaryl is optionally substituted with —$(C_1$-$C_3)$-alkyl, or $(C_1$-$C_6)$-alkyl-aryl wherein said aryl is optionally substituted with —OH, —$(C_1$-$C_3)$-alkyl, —$(C_1$-$C_3)$-alkoxy or halogen;

$R_{66}$, $R'_{66}$ is independently H, OH, halogen, —$C(NH)NH_2$, —$(C_1$-$C_3)$-alkyl, —$(C_1$-$C_3)$-haloalkyl, —$C(O)$—$(C_1$-$C_3)$-alkyl, —$C(O)$—$(C_1$-$C_3)$-haloalkyl, —$NH_2$, $NH(C_1$-$C_3)$-alkyl, or $N[(C_1$-$C_3)$-alkyl][$(C_1$-$C_3)$-alkyl]; and $n_6$ is an integer from 0-3.

$R_{66}$ is advantageously independently H or $CH_3$ or halogen. $R'_{66}$ is advantageously independently H, OH, halogen, —$C(NH)NH_2$, —$C(O)$—$(C_1$-$C_3)$-alkyl, —$C(O)$—$(C_1$-$C_3)$-haloalkyl, —$NH_2$, $NH(C_1$-$C_3)$-alkyl, or $N[(C_1$-$C_3)$-alkyl][$(C_1$-$C_3)$-alkyl]. $R_6$ is advantageously independently H or $CH_3$.

In an embodiment $X_6$ is $N(R_{66})$, advantageously (NH) or ($NCH_3$). In another embodiment $X_6$ is O.

In some embodiments, $Xaa_6$ is

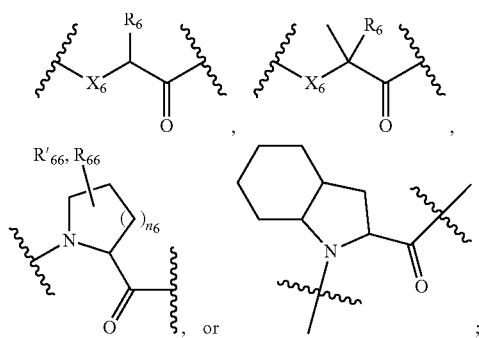

$R_6$ is independently H, —$(C_1$-$C_3)$-alkyl, or —$(C_1$-$C_3)$-haloalkyl; $R_{66}$ is advantageously H or $CH_3$ or halogen, $R'_{66}$ is independently H, halogen, methyl, OH, O—$(C_1$-$C_3)$-alkyl, —$(C_1$-$C_3)$-haloalkyl $NR_{666}$ $R'_{666}$, $R_{666}$, $R'_{666}$ is independently H, —$(C_1$-$C_3)$-alkyl, or —$(C_1$-$C_3)$-haloalkyl; and $n_6$ is an integer from 0-3. $X_6$ is independently $N(R_{66})$, O, advantageously $N(R_{66})$, more advantageously NH or $N(CH_3)$.

In some embodiments, $Xaa_6$ is

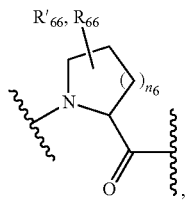

$R_{66}$ is advantageously H or $CH_3$ or halogen, $R'_{66}$ is independently H, halogen, methyl, OH, O—$(C_1$-$C_3)$-alkyl, $(C_1$-$C_3)$-haloalkyl, $NR_{666}R'_{666}$, $R_{666}$, $R'_{666}$ is independently H, —$(C_1$-$C_3)$-alkyl, or —$(C_1$-$C_3)$-haloalkyl; and $n_6$ is an integer from 0-3. Advantageously, $n_6$ is 0, 1 or 2. $R_{66}$ is advantageously H or F. $R'_{66}$ is advantageously H, halogen, methyl, $CF_3$, OH, $OCH_3$, $NHR_{666}$, $R_{666}$ is H, —$(C_1$-$C_3)$-alkyl, or —$(C_1$-$C_3)$-haloalkyl. $R'_{66}$ is more advantageously H, F, methyl, $CF_3$, $NH_2$, OH. $R_{66}$, $R'_{66}$ can be beared by the same carbon atom. The configuration of the carbon atom bearing $R_{66}$, $R'_{66}$ or $R_{66}$ and $R'_{66}$ can be S or R, advantageously S.

In all these embodiments, the configuration of the carbon atom linked to —$X_6$ and to —C(O)— is advantageously S.

In some embodiments, $Xaa_6$ is

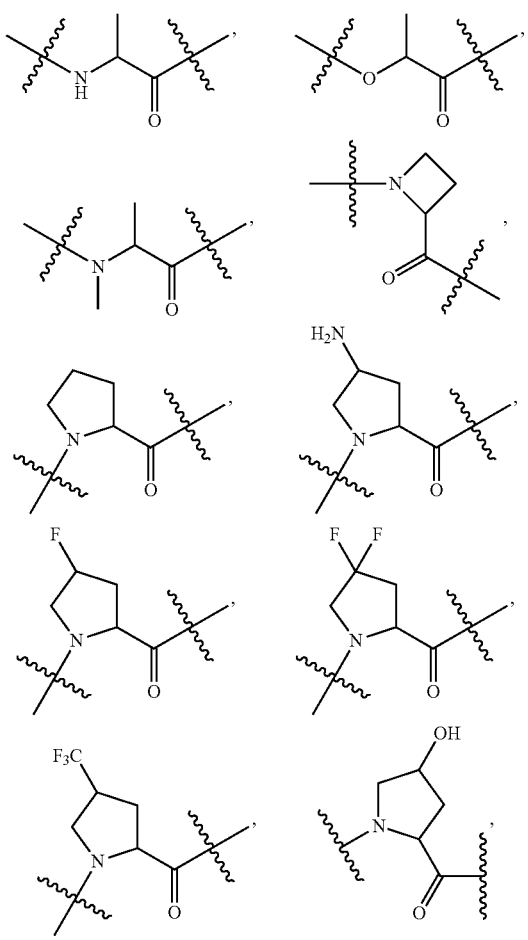

-continued

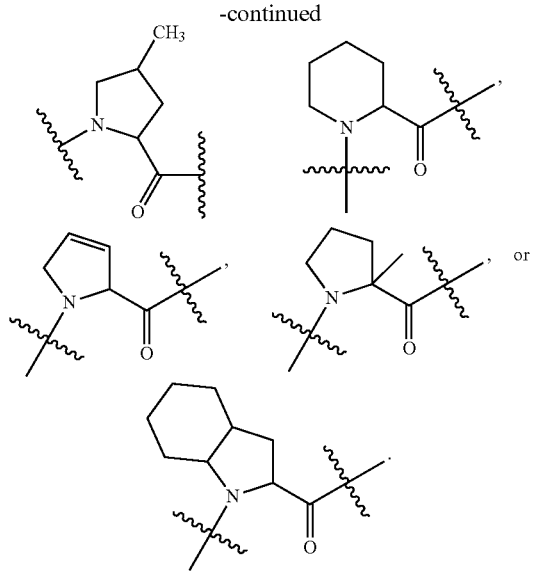

In some embodiments, Xaa₆ is

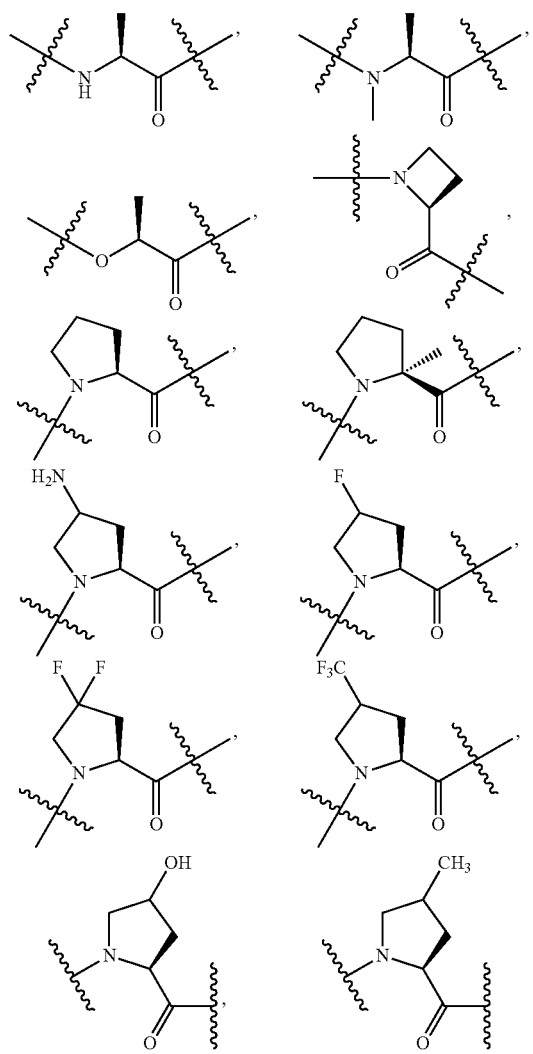

-continued

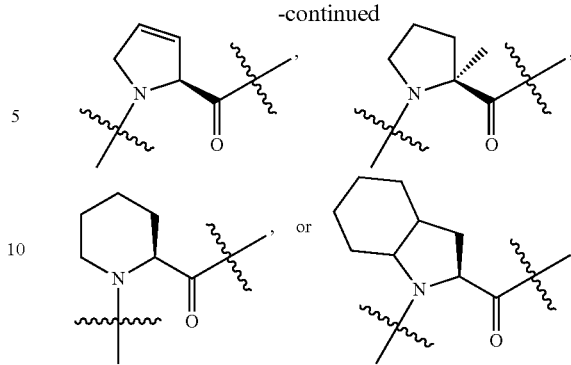

Xaa₇ is

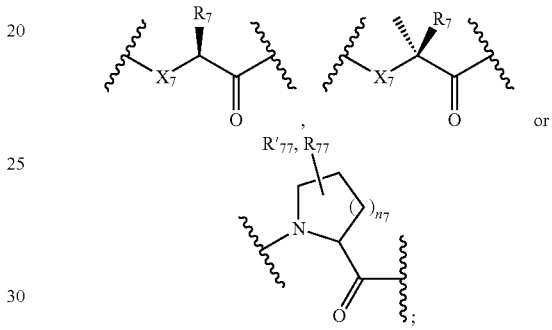

$X_7$ is independently $N(R_{77})$, O; $R_7$ is H, —$(C_1$-$C_6)$-haloalkyl, —$(C_1$-$C_6)$-alkenyl, —$(C_1$-$C_6)$-alkynyl, —$(C_1$-$C_6)$-alkyl-$OR_{77}$, $(C_1$-$C_6)$-alkyl-$SR_{77}$, $(C_1$-$C_6)$-alkyl-S(O)—$R_{77}$, $(C_1$-$C_6)$-alkyl-$S(O)_2$—$R_{77}$, —$(C_1$-$C_6)$-alkyl-$NR_{77}R'_{77}$, —$(C_1$-$C_6)$-alkyl-C(O)$OR_{77}$, —$(C_1$-$C_6)$-alkyl-C(O)$NR_{77}R'_{77}$, —$(C_1$-$C_6)$-alkyl-heteroaryl or —$(C_1$-$C_6)$-alkyl-aryl wherein aryl or heteroaryl is optionally mono- or poly-substituted with —OH, —$NH_2$, —COOH, —$CONH_2$, —CN, —$CF_3$, —$(C_1$-$C_6)$-alkyl, —$(C_1$-$C_3)$-alkoxy or halogen; $R_{77}$, $R'_{77}$ is independently H, OH, halogen, —$(C_1$-$C_3)$-alkyl, —$(C_1$-$C_3)$-haloalkyl, —C(O)—$NH_2$, —C(NH)—$NH_2$, —C(O)—$(C_1$-$C_3)$-alkyl, —C(O)—$(C_1$-$C_3)$-haloalkyl, —$NH_2$, $NH(C_1$-$C_3)$-alkyl, or $N[(C_1$-$C_3)$-alkyl][$(C_1$-$C_3)$-alkyl]; and $n_7$ is an integer from 0-3.

In an embodiment $X_7$ is $N(R_{77})$, advantageously (NH) or ($NCH_3$). In another embodiment $X_7$ is O.

In some embodiments, Xaa₇ is s

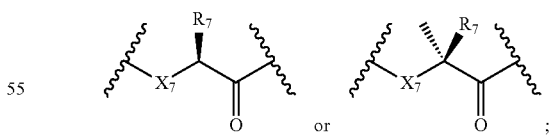

$X_7$ is independently $N(R_{77})$, O, $R_7$ is H, —$(C_1$-$C_6)$-alkyl, —$(C_1$-$C_6)$-haloalkyl, —$(C_1$-$C_6)$-alkenyl, —$(C_1$-$C_6)$-alkynyl, —$(C_1$-$C_6)$-alkyl-$OR_{77}$, $(C_1$-$C_6)$-alkyl-$SR_{77}$, $(C_1$-$C_6)$-alkyl-S(O)—$R_{77}$, $(C_1$-$C_6)$-alkyl-$S(O)_2$—$R_{77}$, —$(C_1$-$C_6)$-alkyl-$NR_{77}R'_{77}$, —$(C_1$-$C_6)$-alkyl-C(O)$OR_{77}$, —$(C_1$-$C_6)$-alkyl-C(O)$NR_{77}R'_{77}$, —$(C_1$-$C_6)$-alkyl-heteroaryl, or —$(C_1$-$C_6)$-alkyl-aryl wherein heteroaryl or aryl is optionally mono- or poly-substituted with —OH, $NH_2$, —COOH, —$CONH_2$, —CN, —$CF_3$, —$(C_1$-$C_6)$-alkyl, —$(C_1$-$C_3)$-alkoxy or halogen; and $R_{77}$, $R'_{77}$ is independently H, —($C_1$-$C_3$)-alkyl, —C(O)—($C_1$-$C_3$)-alkyl, —C(O)—($C_1$-$C_3$)-haloalkyl, —C(O)—$NH_2$, or —C(NH)—$NH_2$. $X_7$ is advantageously N($R_{77}$), more advantageously (NH) or (NCH$_3$). Alternatively $X_7$ is O.

$R_7$ is advantageously H, —($C_1$-$C_6$)-alkyl, —($C_1$-$C_6$)-haloalkyl, —($C_1$-$C_6$)-alkenyl, —($C_1$-$C_6$)-alkynyl, —($C_1$-$C_6$)-alkyl-O$R_{77}$, ($C_1$-$C_6$)-alkyl-S$R_{77}$, ($C_1$-$C_6$)-alkyl-S(O)$R_{77}$, ($C_1$-$C_6$)-alkyl-S(O)$_2R_{77}$, ($C_1$-$C_6$)-alkyl-N$R_{77}R'_{77}$, —($C_1$-$C_6$)-alkyl-C(O)O$R_{77}$, —($C_1$-$C_6$)-alkyl-C(O)N$R_{77}R'_{77}$, —($C_1$-$C_6$)-alkyl-heteroaryl or —($C_1$-$C_6$)-alkyl-aryl wherein aryl or heteroaryl is optionally mono- or poly-substituted with —OH, $NH_2$, —COOH, —CONH$_2$, —CN, —CF$_3$, —($C_1$-$C_3$)-alkyl, —($C_1$-$C_3$)-alkoxy or halogen and wherein the heteroaryl is selected from pyridine, pyrimidine, pyrazine, pyridazine, quinoleine, isoquinoleine, quinoxaline, quinoxaline, imidazole, oxazole, thiazole, furane, pyrrole, thiophene, benzimidazole, benzoxazole, benzothiazole, benzothiophene, indole, isoindole, benzofurane or triazole and the aryl is benzene or naphtalene. The heteroaryl is advantageously pyridine, indole, isoindole, benzothiophène, benzofurane, imidazole, oxazole, thiazole, furane, pyrrole, thiophene or triazole, more advantageously pyridine, isoindole, imidazole, thiophene. The aryl or heteroaryl is advantageously mono-, di- or tri-substituted with OH, NH$_2$, —COOH, —CONH$_2$, —CN, —CF$_3$, —($C_1$-$C_3$)-alkyl, —($C_1$-$C_3$)-alkoxy or halogen, in particular with OH, NH$_2$, COOH, —CONH$_2$, —CN, —CF$_3$, —CH$_3$, —OCH$_3$, F, Cl, or I.

In some embodiments, $R_7$ is —($C_1$-$C_3$)-alkyl, —($C_1$-$C_3$)-haloalkyl, —($C_1$-$C_3$)-alkenyl, —($C_1$-$C_3$)-alkynyl, —($C_1$-$C_6$)-alkyl-O$R_{77}$, —($C_1$-$C_6$)-alkyl-S$R_{77}$, —($C_1$-$C_3$)-alkyl-S(O)$R_{77}$, —($C_1$-$C_3$)-alkyl-S(O)2$R_{77}$, —($C_1$-$C_3$)-alkyl-C(O)O$R_{77}$, —($C_1$-$C_3$)-alkyl-C(O)NH$R_{77}$, —($C_1$-$C_3$)-alkyl-heteroaryl, or —($C_1$-$C_3$)-alkyl-aryl wherein aryl or heteroaryl is mono- or poly-substituted as described above; and $R_{77}$ is independently H or —($C_1$-$C_3$)-alkyl.

$X_7$ is advantageously N

In some embodiments, Xaa$_7$ is

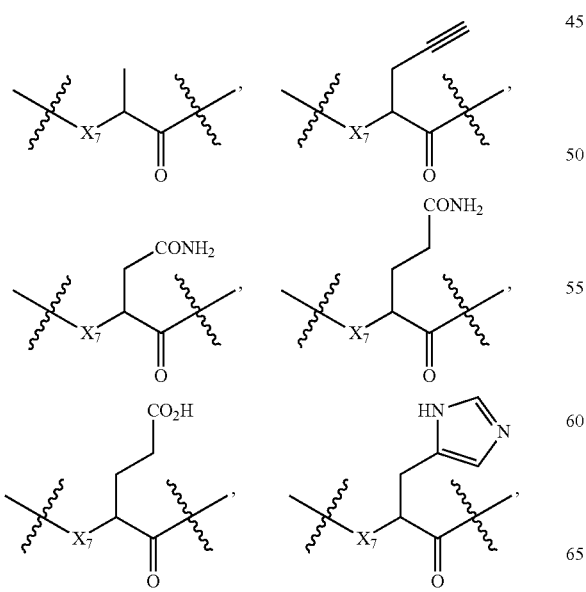

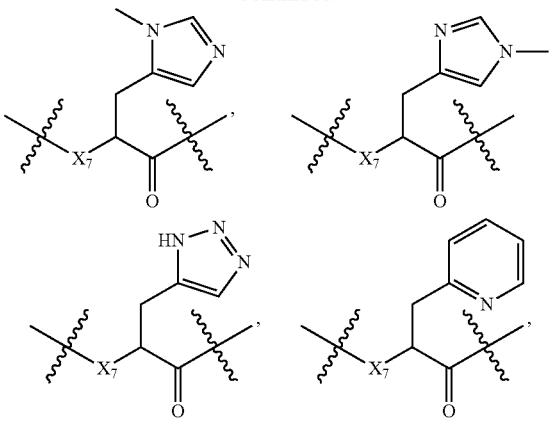

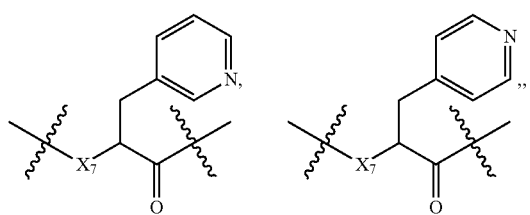

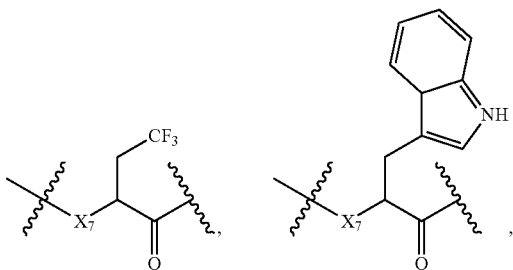

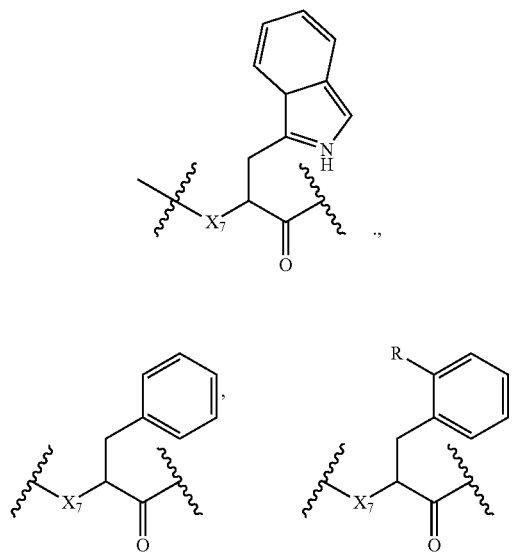

with R is —C(O)NH$_2$, F, Cl, I, CH$_3$, CF$_3$, CN, OH, OMe, tBu, NH$_2$, COOH, 23
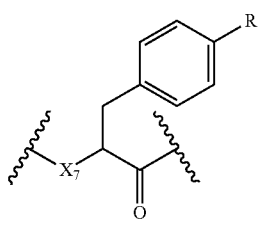
with R is —C(O)NH₂, F, Cl, I, CH₃, CF₃, CN, OH, OMe, tBu, NH₂, COOH,
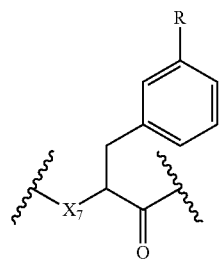
with R is —C(O)NH₂, F, Cl, I, CH₃, CF₃, CN, OH, OMe, tBu, NH₂, COOH,
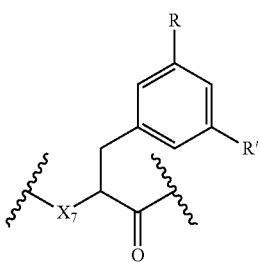
with R, R' is independently —C(O)NH₂, F, Cl, I, CH₃, CF₃, CN, OH, OMe, tBu, NH₂, COOH,
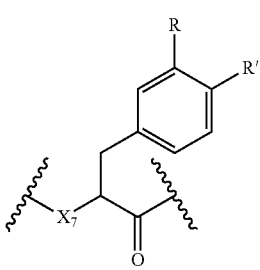
with R, R' is independently —C(O)NH₂, F, Cl, I, CH₃, CF₃, CN, OH, OMe, tBu, NH₂, COOH,
24
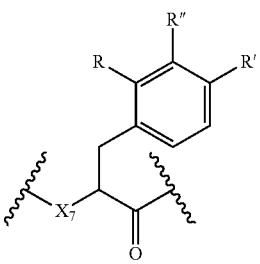
with R, R', R" is independently —C(O)NH₂, F, Cl, I, CH₃, CF₃, CN, OH, OMe, tBu, NH₂, COOH,
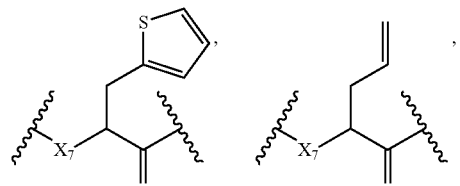
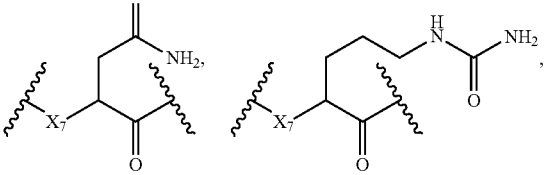
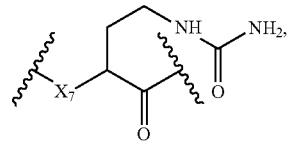
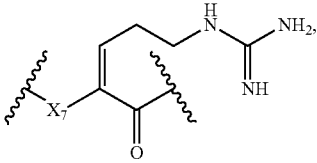
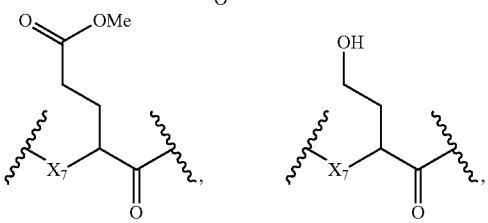
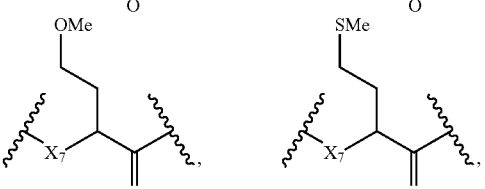
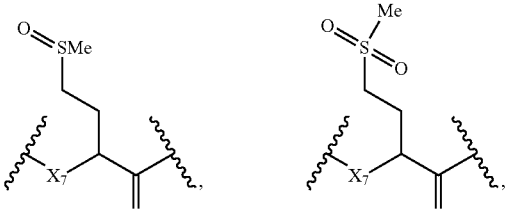

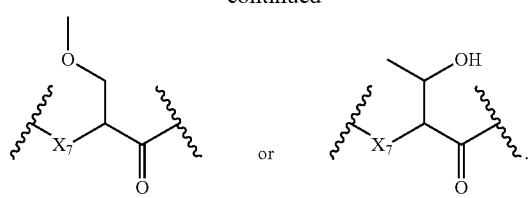

In all these embodiments, $X_7$ is independently NH, N(Me), O, advantageously NH, N(Me), more advantageously NH.

In all these embodiments, the configuration of the carbon atom linked to —$X_7$— and to —(CO)— is advantageously S.

In some embodiments, Xaa$_7$ is

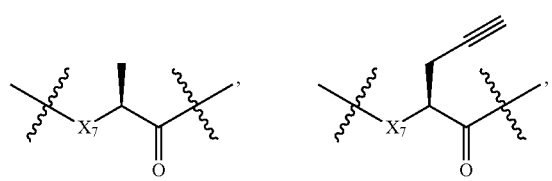

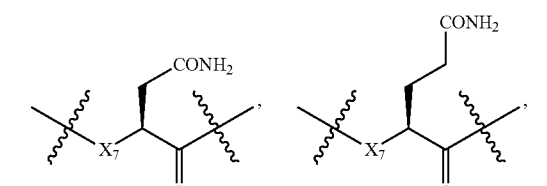

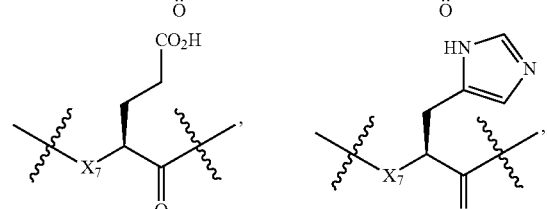

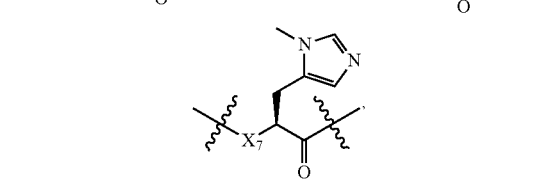

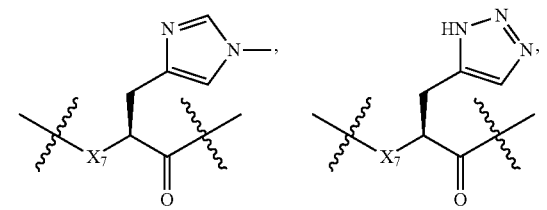

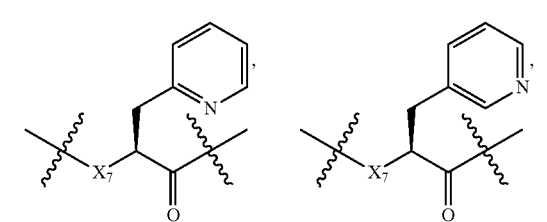

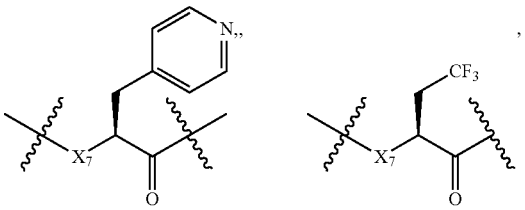

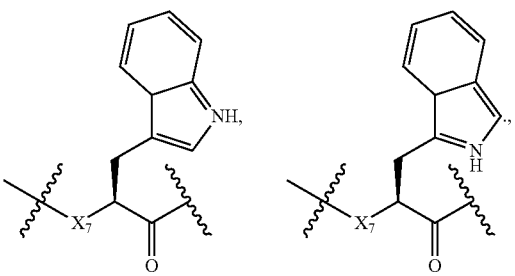

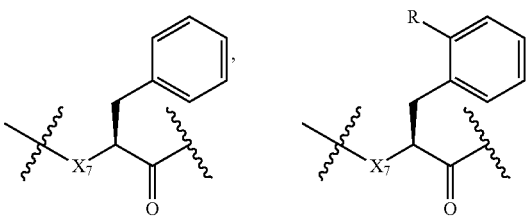

with R is —C(O)NH$_2$, F, Cl, I, CH$_3$, CF$_3$, CN, OH, OMe, tBu, NH$_2$, COOH,

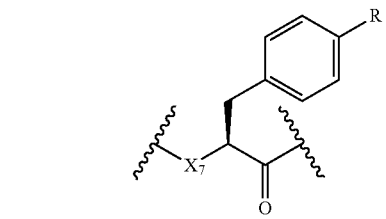

with R is —C(O)NH$_2$, F, Cl, I, CH$_3$, CF$_3$, CN, OH, OMe, tBu, NH$_2$, COOH,

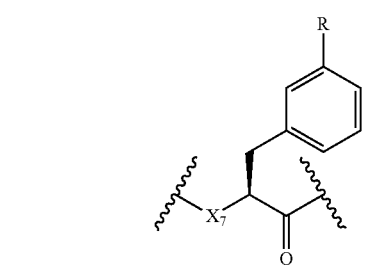

with R is —C(O)NH$_2$, F, Cl, I, CH$_3$, CF$_3$, CN, OH, OMe, tBu, NH$_2$, COOH,

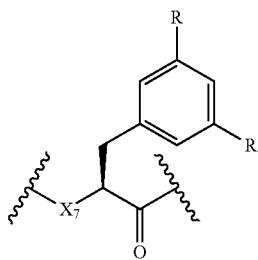
with R is —C(O)NH$_2$, F, Cl, I, CH$_3$, CF$_3$, CN, OH, OMe, tBu, NH$_2$, COOH,
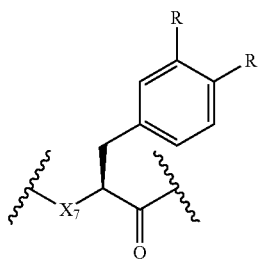
with R is —C(O)NH$_2$, F, Cl, I, CH$_3$, CF$_3$, CN, OH, OMe, tBu, NH$_2$, COOH,
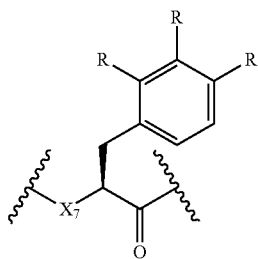
with R is —C(O)NH$_2$, F, Cl, I, CH$_3$, CF$_3$, CN, OH, OMe, tBu, NH$_2$, COOH,
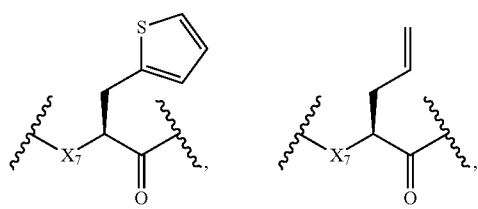
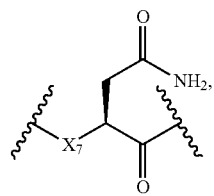
-continued
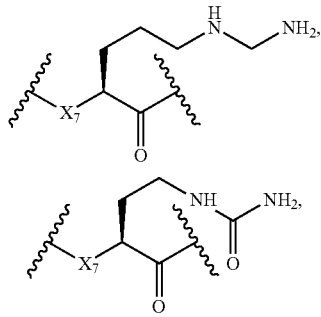
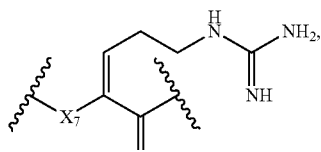
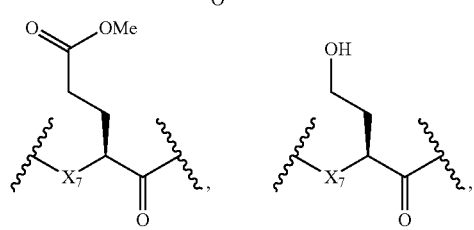
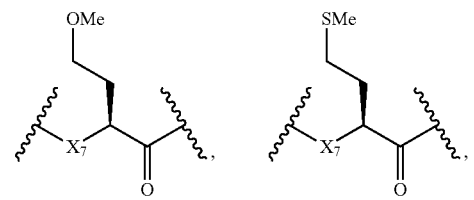
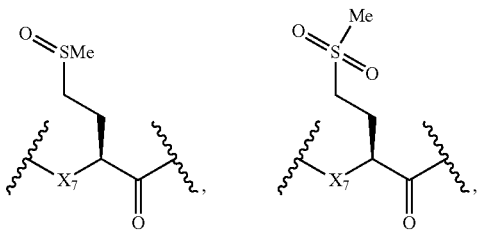
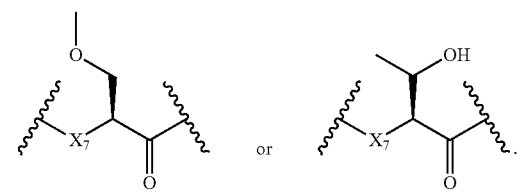
In all these embodiments, X$_7$ is independently NH, N(Me), O, advantageously NH, N(Me), more advantageously NH.
Xaa$_8$ is
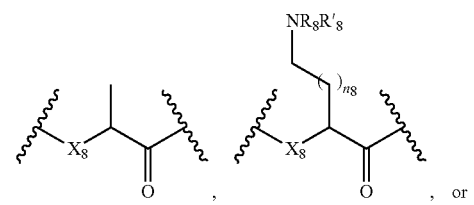

-continued

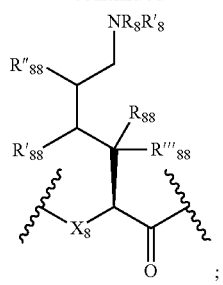

$X_8$ is independently NH, N(Me), O, preferably NH, N(Me), more preferably NH; $R_8$, $R'_8$ is independently H, —($C_1$-$C_3$)-alkyl, —C(O)—($C_1$-$C_3$)-alkyl, or —C(O)—($C_1$-$C_3$)-haloalkyl; $R_{88}$, $R'_{88}$, $R''_{88}$, $R'''_{88}$ is independently H, OH—($C_1$-$C_3$)-alkyl, —($C_1$-$C_3$)-alkoxy, or halogen, in particular H, OH or halogen; and $n_8$ is an integer from 1-4.

In some embodiments, $Xaa_8$ is

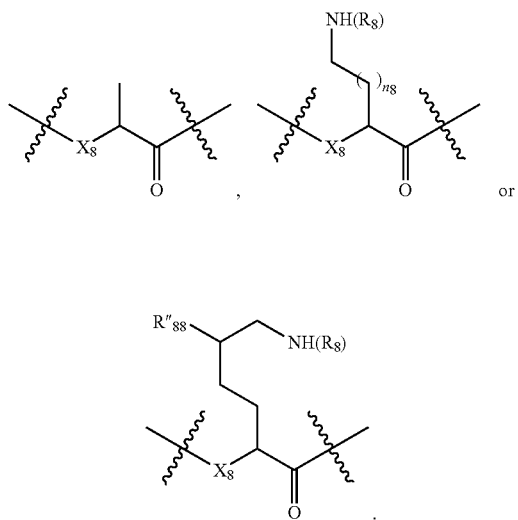

In some embodiments, $Xaa_8$ is

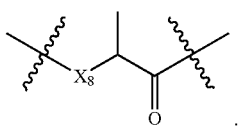

In some embodiments, $Xaa_8$ is

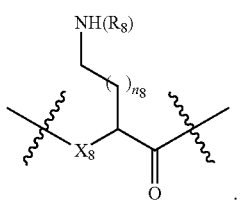

In some embodiments, $Xaa_8$ is

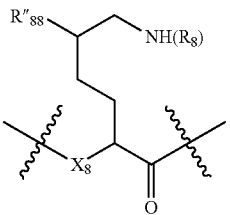

In all these embodiments, $X_8$ is independently NH, N(Me), O, advantageously NH, N(Me), more advantageously NH.

In some embodiments, $R_8$ is independently H, methyl, ethyl, —C(O)—($C_1$-$C_2$)-alkyl, or —C(O)—($C_1$-$C_2$)-haloalkyl; and $n_8$ is an integer from 1-3. In some embodiments, $R_8$ is independently H, methyl, acetyl or trifluoroacetyl, in particular H. $n_8$ is 1, 2 or 3, in particular 3.

In some embodiments, $Xaa_8$ is

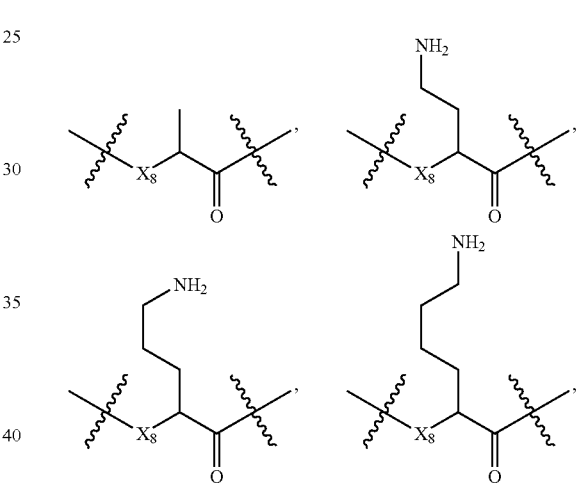

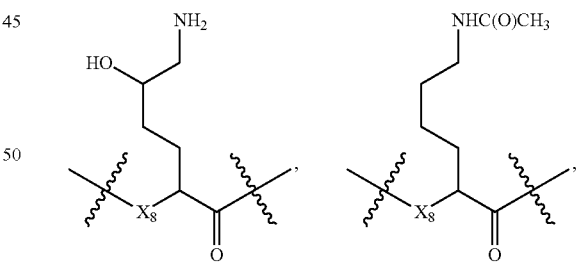

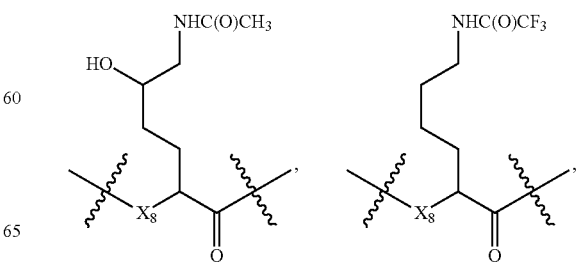

-continued

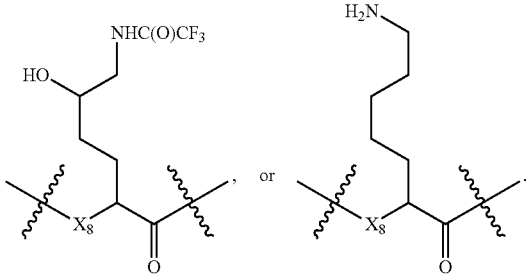

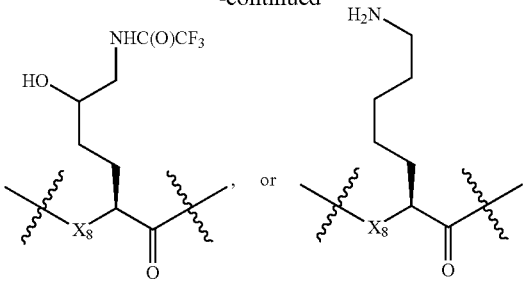

In all these embodiments, $X_8$ is independently NH, N(Me), O, advantageously NH, N(Me), more advantageously NH.

In all these embodiments, the configuration of the carbon atom linked to —$X_8$ and to —C(O)— is advantageously S.

In some embodiments, $Xaa_8$ is

In some embodiments, $Xaa_8$ is

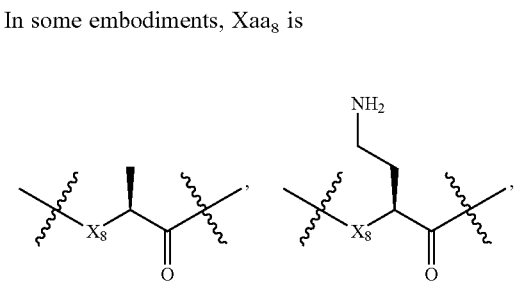

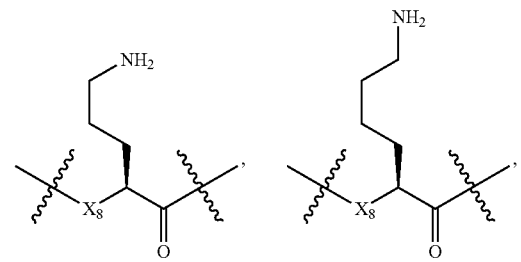

In some embodiments, $Xaa_8$ is

In some embodiments, $Xaa_8$ is

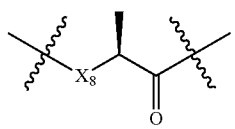

In some embodiments, $Xaa_8$ is

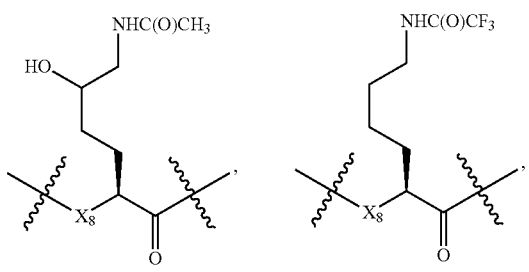

In all these embodiments, $X_8$ is independently NH, N(Me), O, advantageously NH, N(Me), more advantageously NH.

$Xaa_9$ is

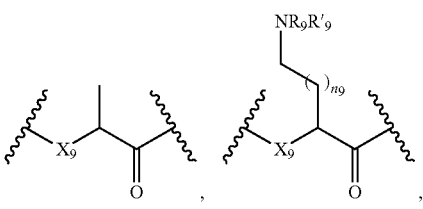

33

-continued

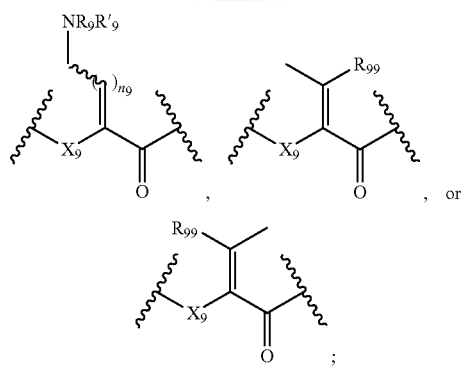

$X_9$ is independently NH, N(Me), O, in particular NH or N(Me), more particularly NH; $R_9$, $R'_9$ is independently H, —C(NH)NH$_2$, —C(O)NH$_2$, —(C$_1$-C$_6$)-alkyl, —(C$_1$-C$_6$)-haloalkyl, —C(O)—(C$_1$-C$_3$)-alkyl, or —C(O)—(C$_1$-C$_3$)-haloalkyl; $R_{99}$ is H, or —(C$_1$-C$_3$)-alkyl; and $n_9$ is independently an integer from 1-3.

In some embodiments, Xaa$_9$ is

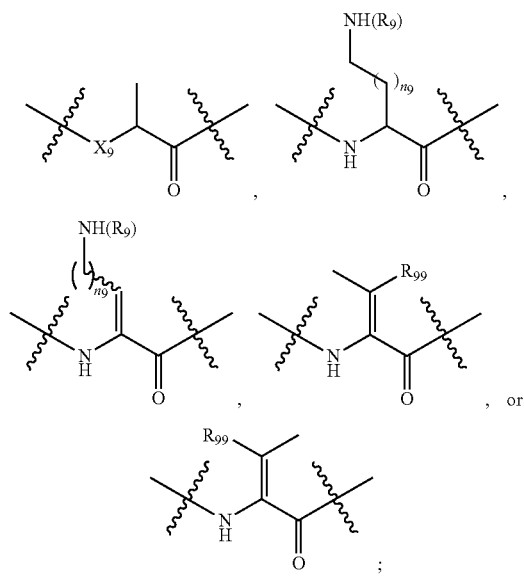

$R_9$ is independently H, —C(NH)NH$_2$, —C(O)NH$_2$, —(C$_1$-C$_3$)-alkyl, —(C$_1$-C$_3$)-haloalkyl, —C(O)—(C$_1$-C$_3$)-alkyl, or —C(O)—(C$_1$-C$_3$)-haloalkyl; $R_{99}$ is H, or —(C$_1$-C$_3$)-alkyl; and $n_9$ is independently an integer from 1-3.

In some embodiments, Xaa$_9$ is

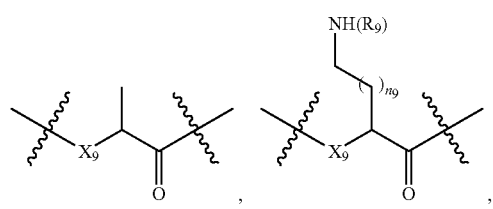

34

-continued

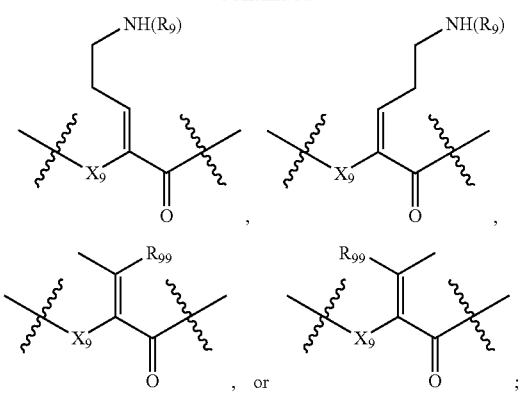

$X_9$ is independently NH, N(Me), O, in particular NH or N(Me), more particularly NH; $R_9$ is independently H, —C(NH)NH$_2$, —C(O)NH$_2$, or —(C$_1$-C$_3$)-alkyl; $R_{99}$ is H, or —(C$_1$-C$_3$)-alkyl; and $n_9$ is independently an integer from 1-2.

In some embodiments, Xaa$_9$ is

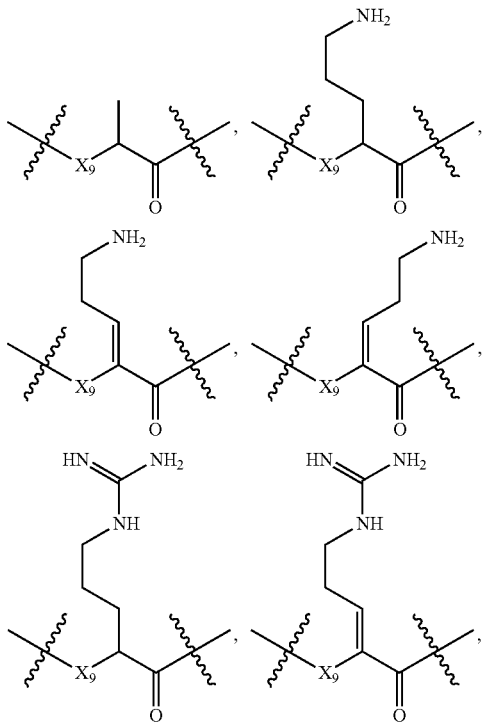

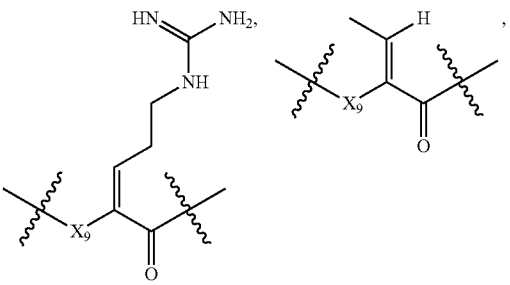

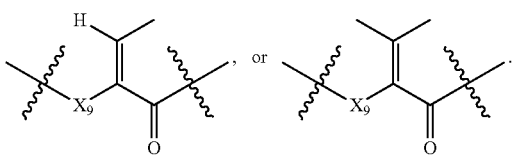

In all these embodiments, $X_9$ is independently NH, N(Me), O, in particular NH or N(Me), more particularly NH.

In some embodiments, $Xaa_9$ is

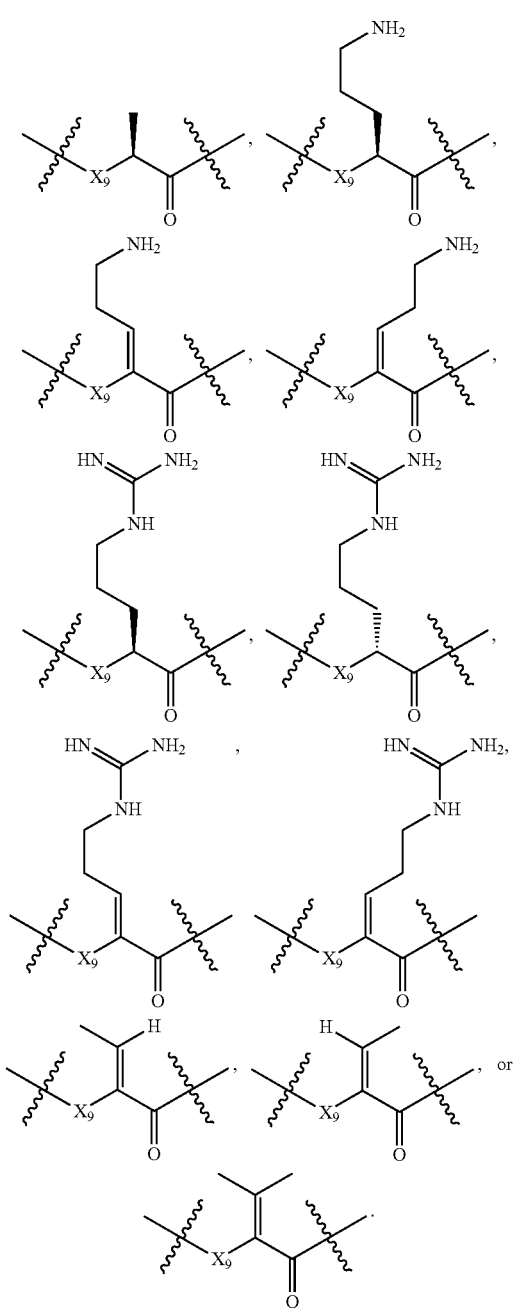

In all these embodiments, $X_9$ is independently NH, N(Me), O, in particular NH or N(Me), more particularly NH.

In some embodiments, $Xaa_9$ is

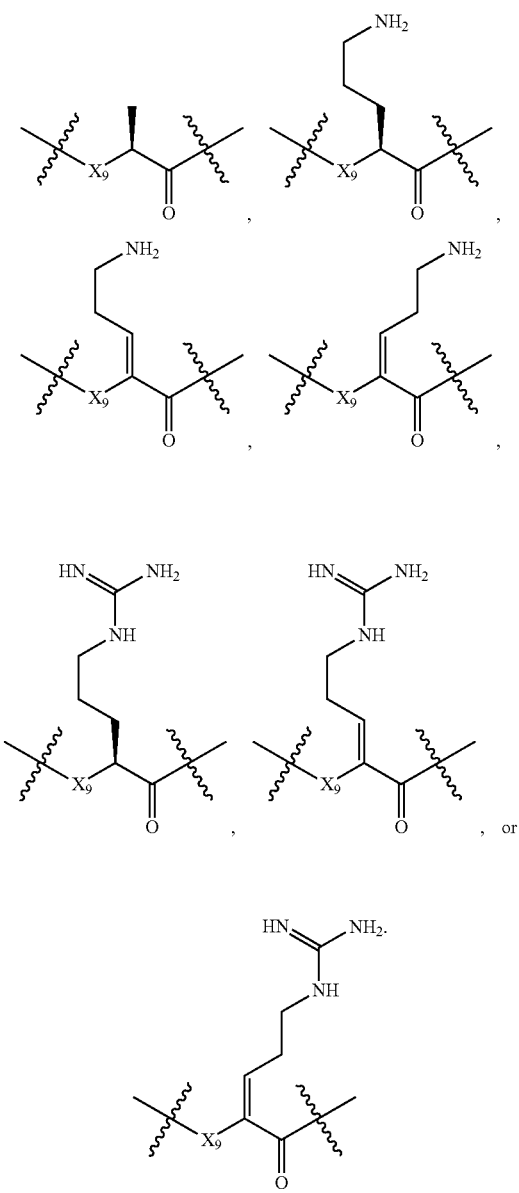

In all these embodiments, $X_9$ is independently NH, N(Me), O, in particular NH or N(Me), more particularly NH.

In some embodiments, $Xaa_9$ is

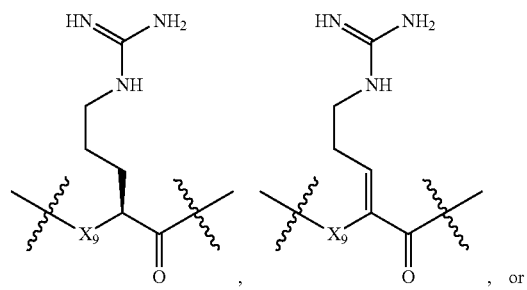

-continued

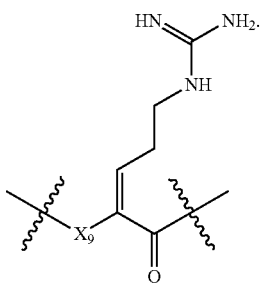

In some embodiments, Xaa$_9$ is

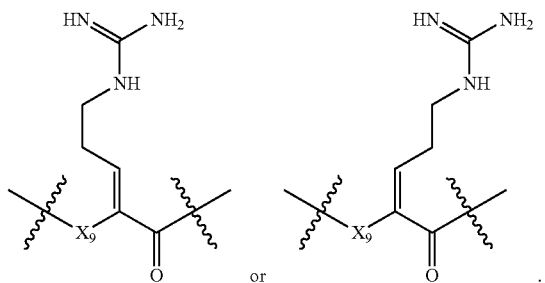

In some embodiments, Xaa$_9$ is

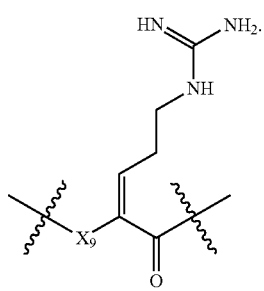

In some embodiments, Xaa$_9$ is

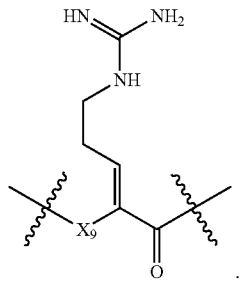

In all these embodiments, X$_9$ is independently NH, N(Me), O, in particular NH or N(Me), more particularly NH.

Xaa$_{10}$ is

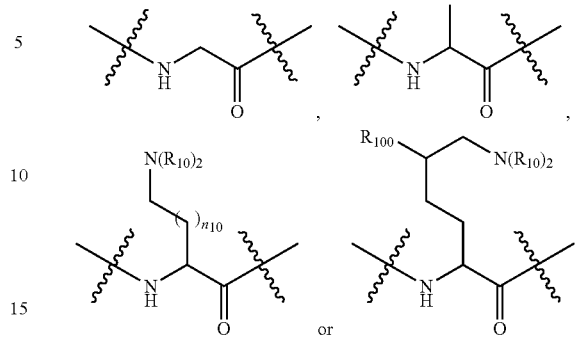

R$_{10}$ is independently H, —C(NH)NH$_2$, —(C$_1$-C$_3$)-alkyl, —C(O)—(C$_1$-C$_3$)-alkyl, or —C(O)—(C$_1$-C$_3$)-haloalkyl; R$_{100}$ is H, OH or halogen; and n$_{10}$ is an integer from 1-4.

In some embodiments, Xaa$_{10}$ is

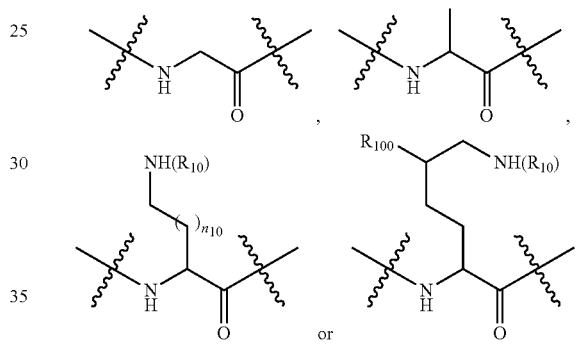

R$_{10}$ is independently H, —C(NH)NH$_2$, —(C$_1$-C$_3$)-alkyl, —C(O)—(C$_1$-C$_3$)-alkyl, or —C(O)—(C$_1$-C$_3$)-haloalkyl; R$_{100}$ is H, OH or halogen; and n$_{10}$ is an integer from 1-3.

In some embodiments, Xaa$_{10}$ is

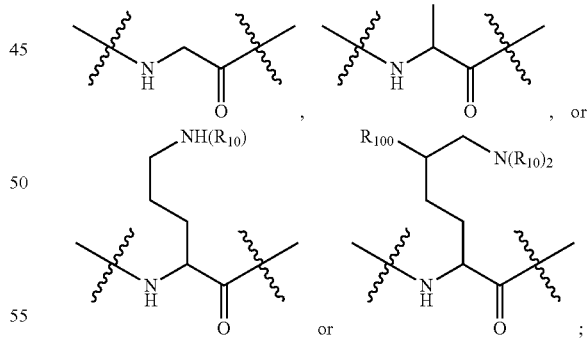

R$_{10}$ is independently H, —C(NH)NH$_2$, —(C$_1$-C$_2$)-alkyl, acetyl, trifluoromethyl; and R$_{100}$ is H, OH or halogen.

In some embodiments, Xaa$_{10}$ is

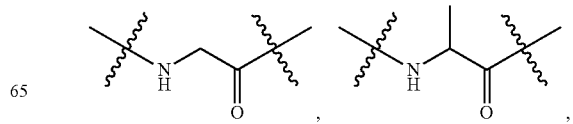

-continued

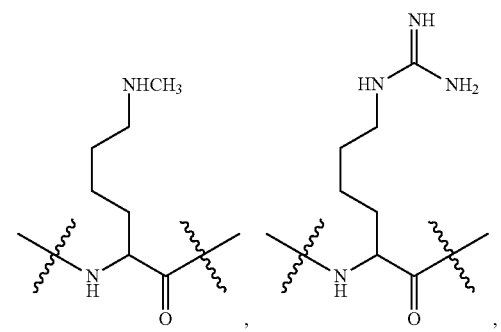

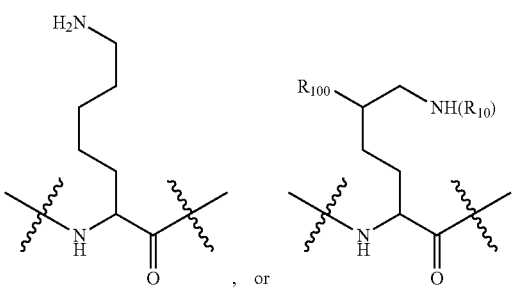

, or

In some embodiments, $Xaa_{10}$ is

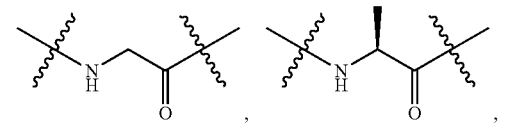

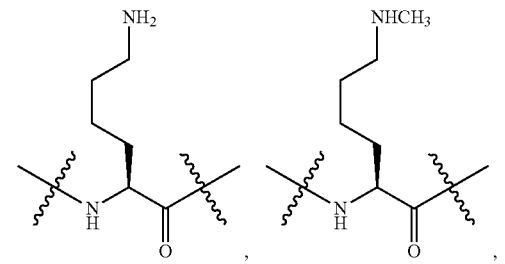

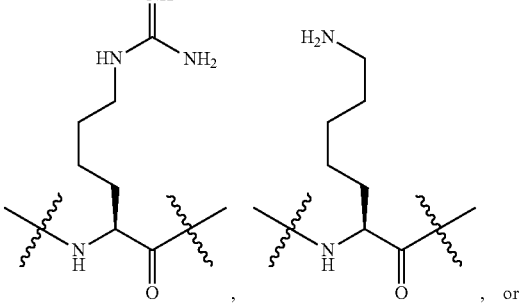

, or

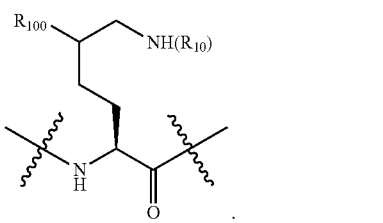

In some embodiments, $Xaa_{10}$ is

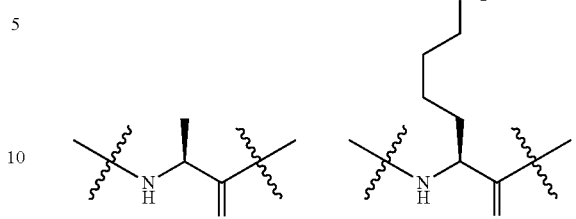

or .

In some embodiments, $Xaa_{10}$ is

.

In some embodiments, $Xaa_{10}$ is

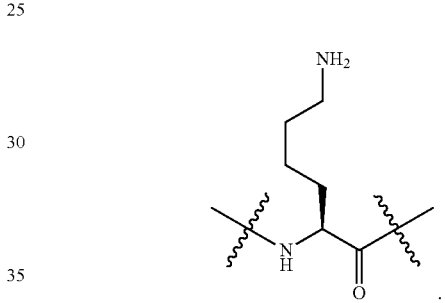

.

$Xaa_{10}$ is absent and thus $R_b$ is $R_c$.

$R_c$ is OH, —N($R_d$)(R'$_d$), —($C_3$-$C_8$)-aminocycloalkyl, or —($C_1$-$C_6$)-alkoxy. In some embodiments, $R_c$ is OH, —NH($R_d$), —($C_3$-$C_8$)-aminocycloalkyl, or —($C_1$-$C_6$)-alkoxy. In some embodiments, $R_c$ is OH, —NH($R_d$), —($C_5$-$C_6$)-aminocycloalkyl, or —($C_1$-$C_4$)-alkoxy. In some embodiments, $R_c$ is OH, —NH($R_d$), —($C_5$-$C_6$)-aminocycloalkyl, or —($C_1$-$C_4$)-alkoxy. In some embodiments, $R_c$ is OH or —NH($R_d$). In some embodiments, $R_c$ is OH. In some embodiments, $R_e$ is —NH($R_d$).

$R_d$, R'$_d$ is independently H, OH, —($C_1$-$C_6$)-alkyl, —($C_1$-$C_3$)-hydroxyalkyl, —($C_1$-$C_6$)-alkyl-N($R_e$)(R'$_e$), —C(O)—($C_1$-$C_3$)-haloalkyl, aryl or heteroaryl. In some embodiments, $R_d$ is independently H, OH, —($C_1$-$C_6$)-alkyl, —($C_1$-$C_3$)-hydroxyalkyl, —($C_1$-$C_6$)-alkyl-N($R_e$)$_2$, —C(O)—($C_1$-$C_3$)-haloalkyl, aryl or heteroaryl and R'$_d$ is H. In some embodiments, $R_d$ is independently H, OH, —($C_1$-$C_4$)-alkyl, —($C_1$-$C_3$)-hydroxyalkyl, —($C_1$-$C_4$)-alkyl-NH($R_e$), or —C(O)—($C_1$-$C_3$)-haloalkyl. In some embodiments, $R_d$ is independently H, OH, —($C_1$-$C_2$)-alkyl, —($C_2$-$C_4$)-hydroxyalkyl, or —($C_1$-$C_4$)-alkyl-NH($R_e$). In some embodiments, $R_d$ is independently H, OH, or —($C_1$-$C_4$)-alkyl-NH($R_e$). In some embodiments, $R_d$ is independently H or OH. In some embodiments, $R_d$ is —($C_1$-$C_4$)-alkyl-NH($R_e$).

In some embodiments, $R_e$, R'$_e$, is independently H, —($C_1$-$C_6$)-alkyl, or —C(O)—($C_1$-$C_3$)-haloalkyl. In some embodiments, $R_e$ is independently H, —($C_1$-$C_3$)-alkyl, or —C(O)—($C_1$-$C_2$)-haloalkyl. In some embodiments, $R_e$ is independently H, methyl, ethyl, or trifluromethyl. In some embodiments, $R_e$ is independently H or methyl. In some embodiments, $R_e$ is H. In some embodiments, $R_e$ is methyl. In these embodiments $R'_e$, is advantageously H.

In a embodiment, $X_2$ is independently NH, N(Me), $X_3$ is N, $X_4$ is independently NH, N(Me), $X_5$ is independently NH, N(Me), $X_6$ is N, $X_7$ is N, $X_8$ is independently NH, N(Me), and $X_9$ is independently NH, N(Me).

Advantageously:

$R_c$ is OH, —$N(R_d)_2$, —$(C_3$-$C_8)$-aminocycloalkyl, or —$(C_1$-$C_3)$-alkoxy; particularly OH, —$N(R_d)_2$, or —$(C_1$-$C_3)$-alkoxy $R_d$ is independently H, OH, —$(C_1$-$C_3)$-alkyl, —$(C_1$-$C_3)$-hydroxyalkyl, —$(C_1$-$C_6)$-alkyl-$N(R_e)(R'_e)$, —C(O)—$(C_1$-$C_3)$-haloalkyl or phenyl; particularly $R_d$ is H, —$(C_1$-$C_6)$-alkyl-$N(R_e)(R'_e)$, more particularly $R_d$ is H Xaa$_1$ is

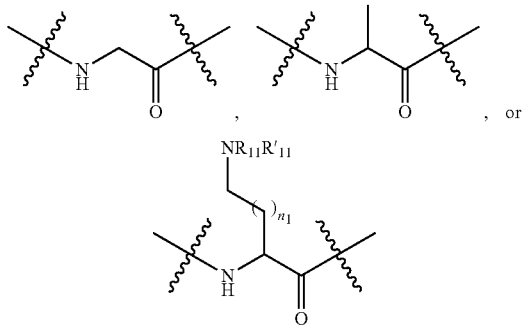

Xaa2 is

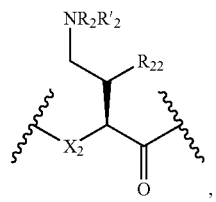

in particular $R_{22}$ is OH, $R_2$, $R'_2$ are both H
Xaa3 is as defined above, in particular Xaa3 is

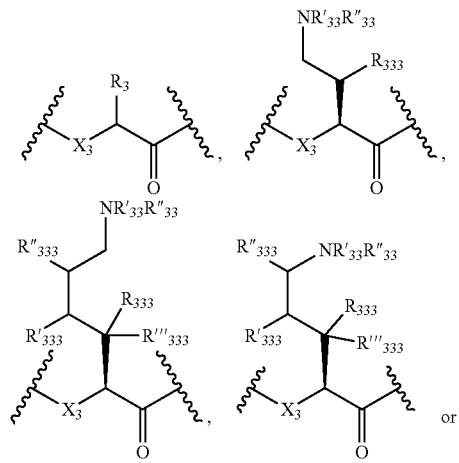

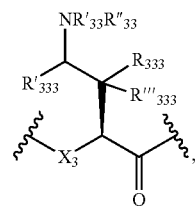

Xaa4 is

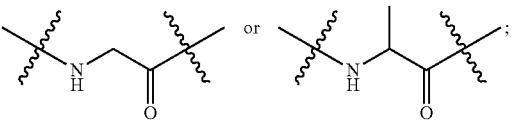

Xaa5 is as defined above with $R_5$, $R'_5$ is independently H, —C(O)—$(C_1$-$C_3)$-alkyl, or —C(O)—$(C_1$-$C_3)$-haloalkyl, particularly $R_5$, $R'_5$ are H;

Xaa6 is as defined above, in particular Xaa6 is

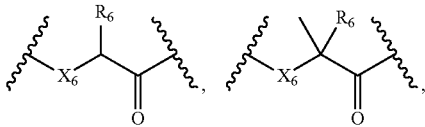

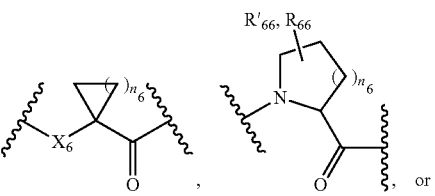

Xaa7 is

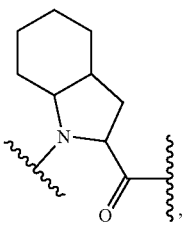

Xaa8 is as defined above with $R_{88}$, $R'_{88}$, $R''_{88}$ is independently H or OH, in particular Xaa8 is

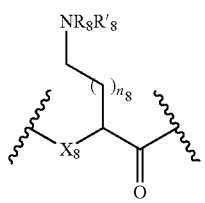

Xaa9 is as defined above with $R_9$, $R'_9$ is independently H, —C(NH)NH$_2$, —C(O)NH$_2$, —(C$_1$-C$_6$)-alkyl, —C(O)—(C$_1$-C$_3$)-alkyl, or —C(O)—(C$_1$-C$_3$)-haloalkyl, in particular Xaa9 is

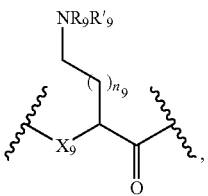

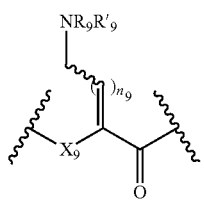

$R'_9$ is H and R9 is, —C(NH)NH$_2$, —C(O)NH$_2$, —(C$_1$-C$_6$)-alkyl, —C(O)—(C$_1$-C$_3$)-alkyl, or —C(O)—(C$_1$-C$_3$)-haloalkyl The Other Radicals are as Defined Above In particular, $R_{333}$, $R'_{333}$, $R''_{333}$ is OH, halogen or —(C$_1$-C$_3$)-alkoxy.

In particular:

Xaa$_5$ is

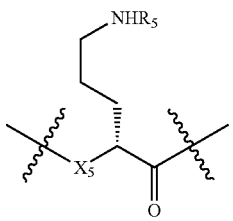

and $R_5$ is H, —(C$_1$-C$_3$)-alkyl, —C(O)—(C$_1$-C$_3$)-alkyl, or —C(O)—(C$_1$-C$_3$)-haloalkyl, advantageously $R_5$ is H. In particular $X_5$ is NH.

In an embodiment,

Xaa$_4$ is

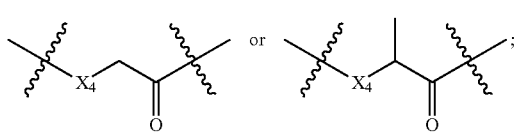

in particular $X_4$ is NH

Xaa$_5$ is

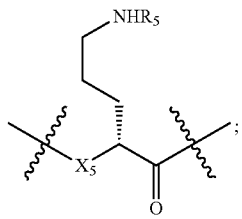

and $R_5$ is H, —(C$_1$-C$_3$)-alkyl, —C(O)—(C$_1$-C$_3$)-alkyl, or —C(O)—(C$_1$-C$_3$)-haloalkyl, in particular H; in particular $X_5$ is NH The other radicals are as defined above, in particular:

Xaa$_1$ is advantageously

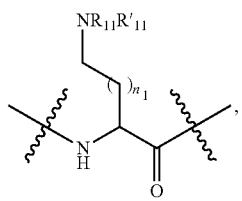

Xaa2 is advantageously

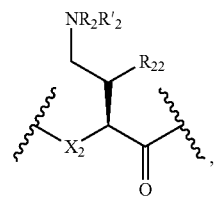

with $R_{22}$=OH, $R_2$=$R'_2$=H and $X_2$=NH

Xaa8 is advantageously

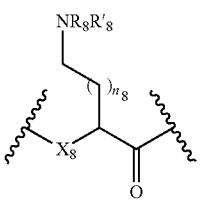

with $X_8$=NH, $R_8$=$R'_8$=H

Xaa9 is advantageously

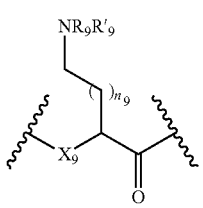

with $X_9$=NH,

In an embodiment, $R_a$ is H, methyl, —C(O)—($C_1$-$C_2$)-alkyl, or trifluoroacetyl, advantageously H, methyl;

$R_b$ is $R_c$;

$R_c$ is OH, $NH_2$, NHOH, —($C_2$-$C_6$)-alkyl-NH($R_e$), —NH($C_1$-$C_3$)-alkyl, —NH($C_2$-$C_4$)-alkyl-OH, —NH-phenyl, N-piperidinyl, or —($C_1$-$C_3$)-alkoxy, advantageously OH, $NH_2$, or —($C_1$-$C_3$)-alkoxy;

$R_e$ is H or trifluoroacetyl;

$Xaa_1$ is

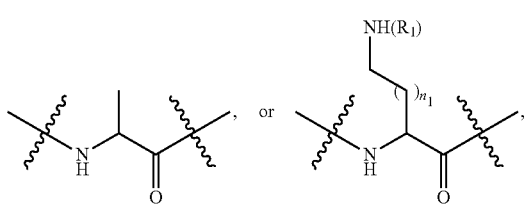

$R_1$ is H, —($C_1$-$C_2$)-alkyl, acetyl, or trifluoroacetyl, advantageously H, —($C_1$-$C_2$)-alkyl;

$n_1$ is an integer from 1-3;

$Xaa_2$ is

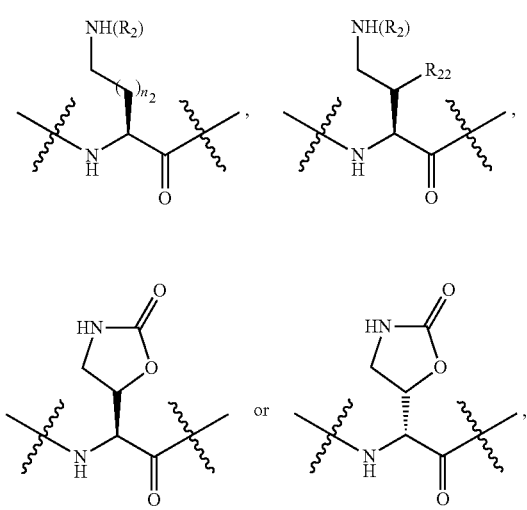

advantageously

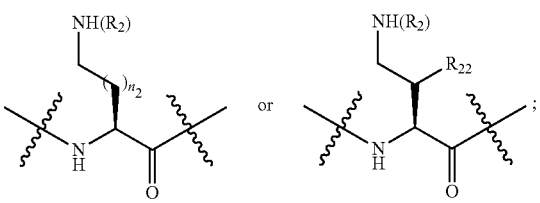

$R_2$ is H, —($C_1$-$C_2$)-alkyl, acetyl or trifluoroacetyl, advantageously H;

$R_{22}$ is OH, fluorine, methyl, or methoxy, advantageously OH;

$Xaa_3$ is

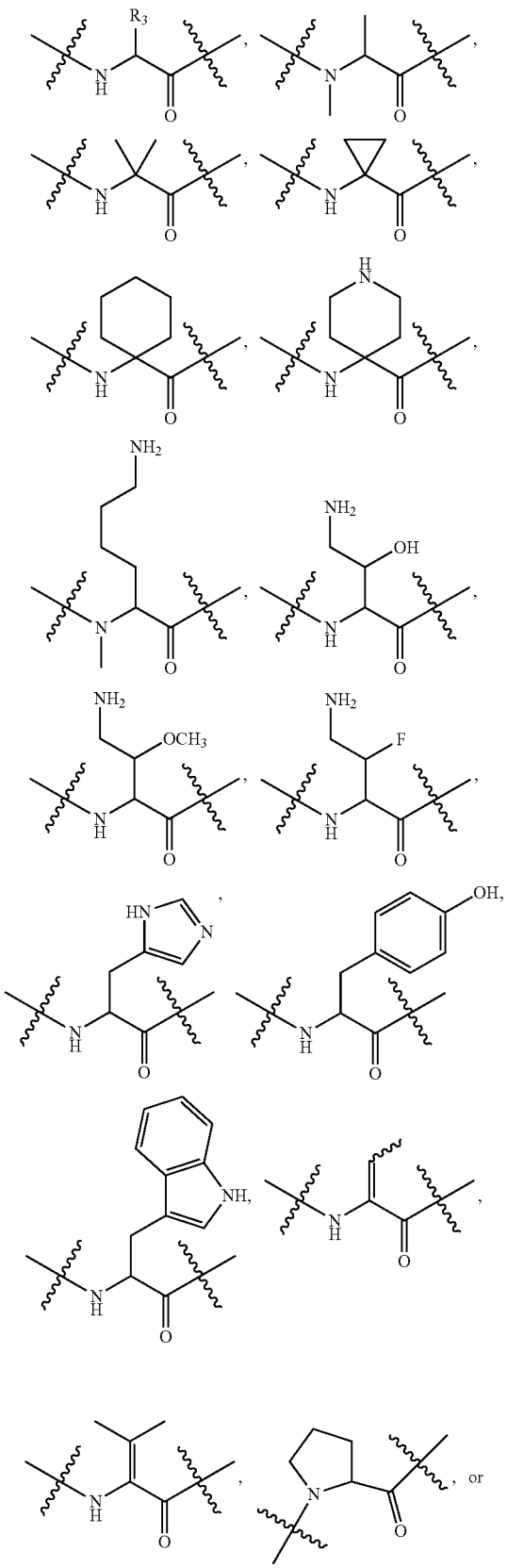

-continued

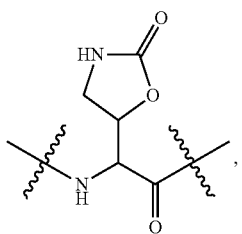 [SMILES: *NC(C(*)=O)C1CNC(=O)O1]

advantageously

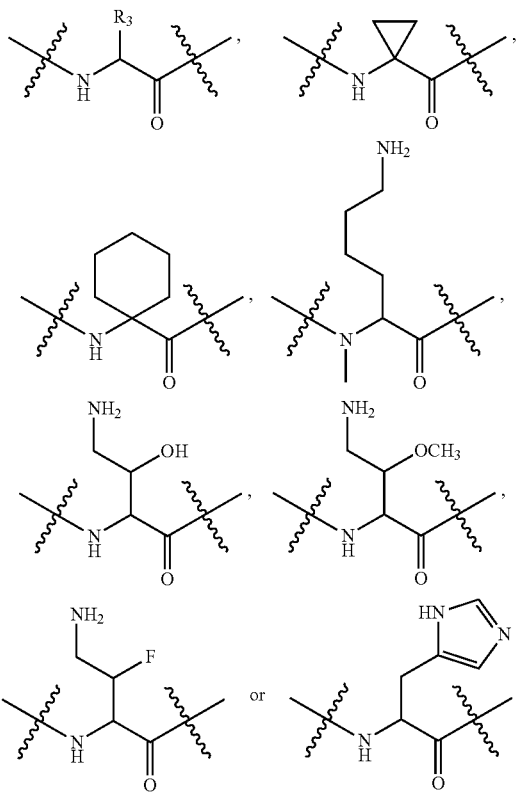

R₃ is H, fluoro, NH₂, —(C₁-C₆)-alkyl, —(C₁-C₆)-alkenyl, —(C₁-C₆)-alkynyl, —(C₁-C₂)-haloalkyl, —(C₃-C₅)-cycloalkyl, —(C₁-C₂)-hydroxyalkyl, —CH₂SH, —CH₂CH₂SCH₃, (C₁-C₄)-alkyl-NH(R₃₃), (C₁-C₆)-alkyl-C(O)NH₂, or (C₁-C₆)-alkyl-C(O)OH, advantageously H, —(C₁-C₆)-alkynyl, —(C₁-C₂)-hydroxyalkyl, (C₁-C₄)-alkyl-NH(R₃₃), (C₁-C₆)-alkyl-C(O)NH₂;

R₃₃ is H, —(C₁-C₃)-alkyl, acetyl, trifluoroacetyl, or —C(NH)NH₂, advantageously H, —(C₁-C₃)-alkyl, acetyl, or —C(NH)NH₂;

Xaa₄ is

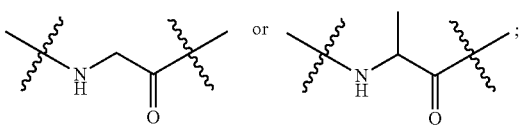

Xaa₅ is

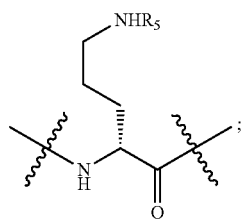

R₅ is H, acetyl or trifluoroacetyl, advantageously H;

Xaa₆ is

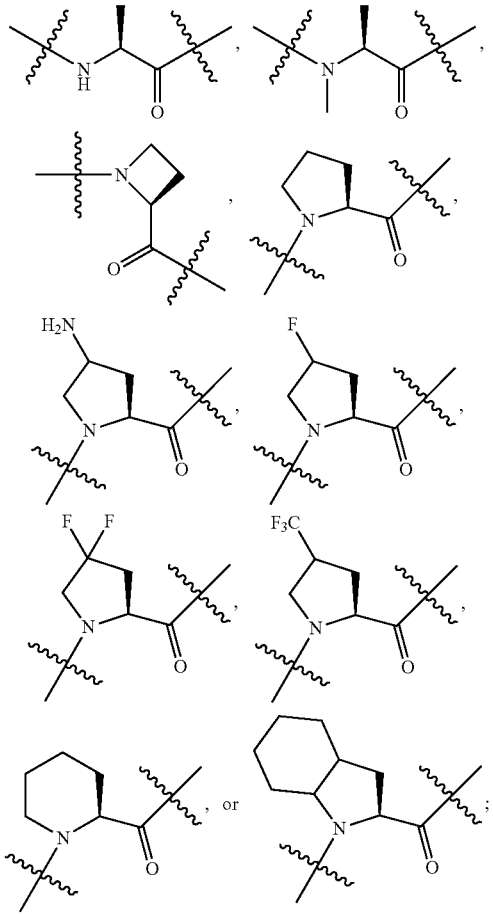

Xaa₇ is

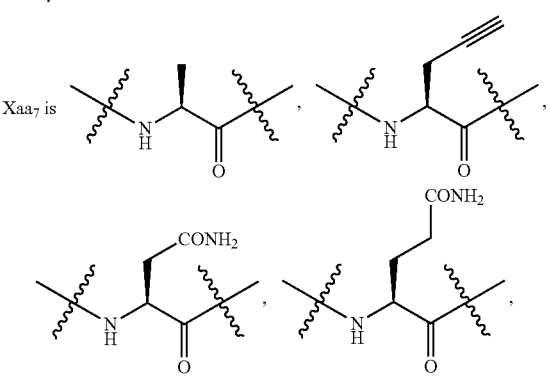

-continued
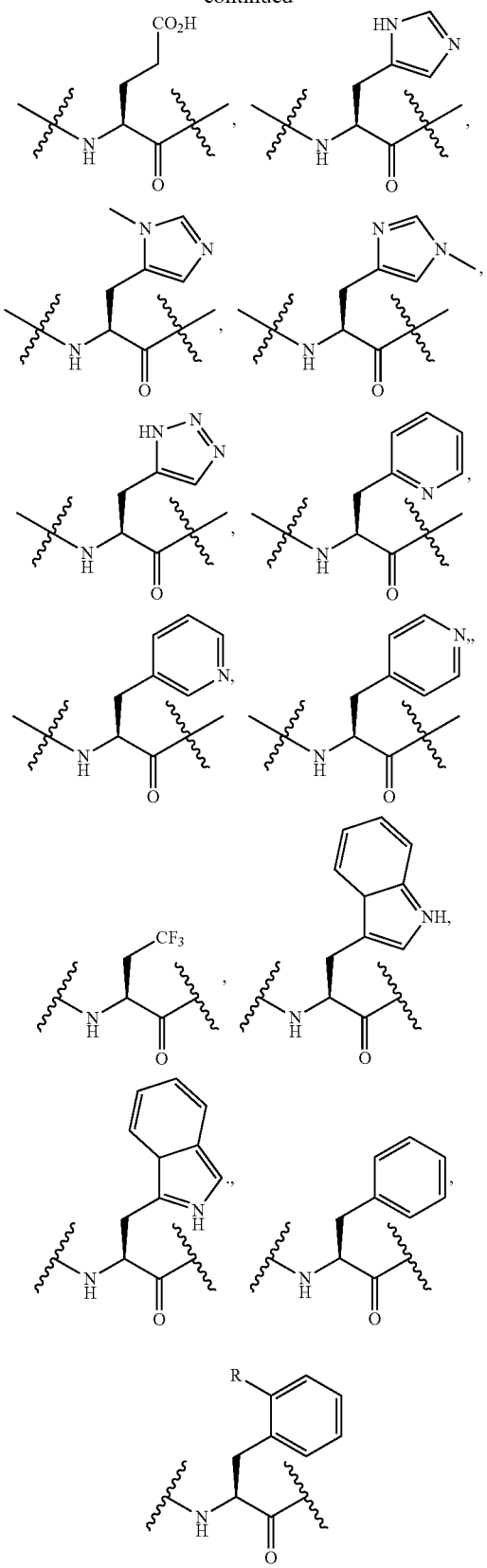
with R is —C(O)NH$_2$, F, Cl, I, CH$_3$, CF$_3$, CN, OH, OMe, tBu, NH$_2$, COOH,
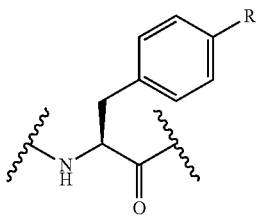
with R is —C(O)NH$_2$, F, Cl, I, CH$_3$, CF$_3$, CN, OH, OMe, tBu, NH$_2$, COOH,
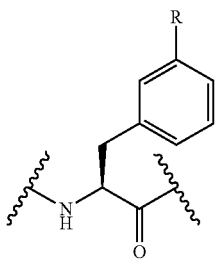
with R is —C(O)NH$_2$, F, Cl, I, CH$_3$, CF$_3$, CN, OH, OMe, tBu, NH$_2$, COOH,
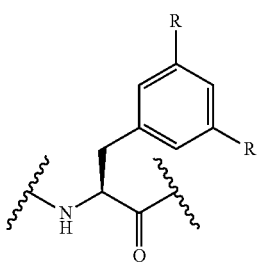
with R is —C(O)NH$_2$, F, Cl, I, CH$_3$, CF$_3$, CN, OH, OMe, tBu, NH$_2$, COOH,
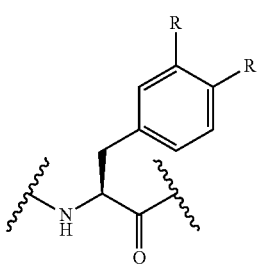
with R is —C(O)NH$_2$, F, Cl, I, CH$_3$, CF$_3$, CN, OH, OMe, tBu, NH$_2$, COOH,

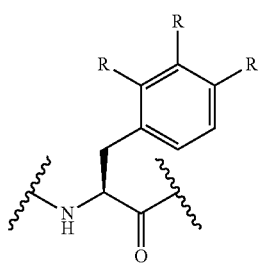
with R is —C(O)NH$_2$, F, Cl, I, CH$_3$, CF$_3$, CN, OH, OMe, tBu, NH$_2$, COOH,
Xaa$_8$ is
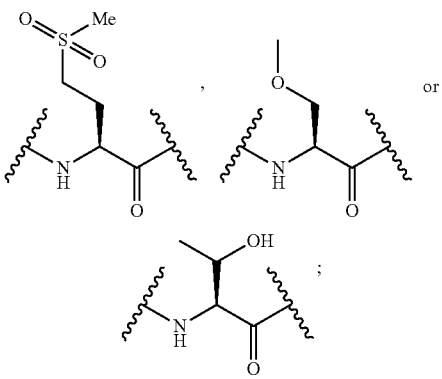
advantageously
R$_8$ is H, acetyl or trifluoroacetyl, advantageously H;
n$_8$ is independently an integer from 2-4, advantageously n=3;
Xaa$_9$ is
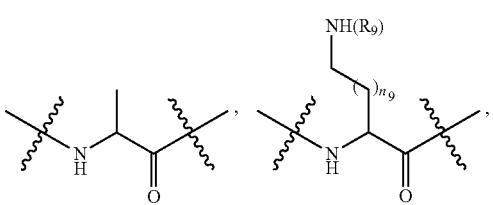

-continued
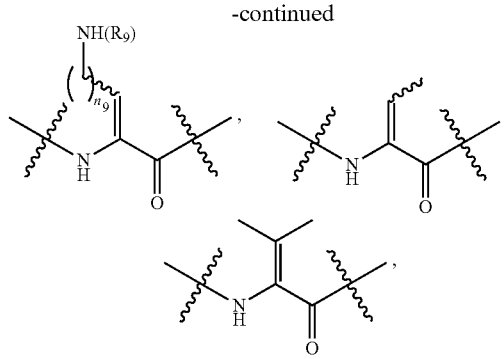
advantageously
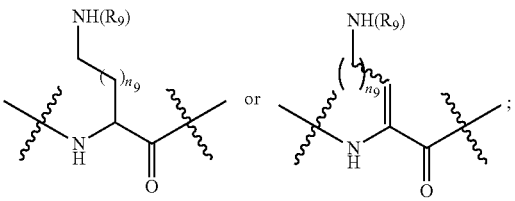
$R_9$ is H or —C(NH)NH$_2$;
$n_9$ is an integer from 2-4, advantageously n=2.
In some embodiments, the compound is selected from the group consisting of
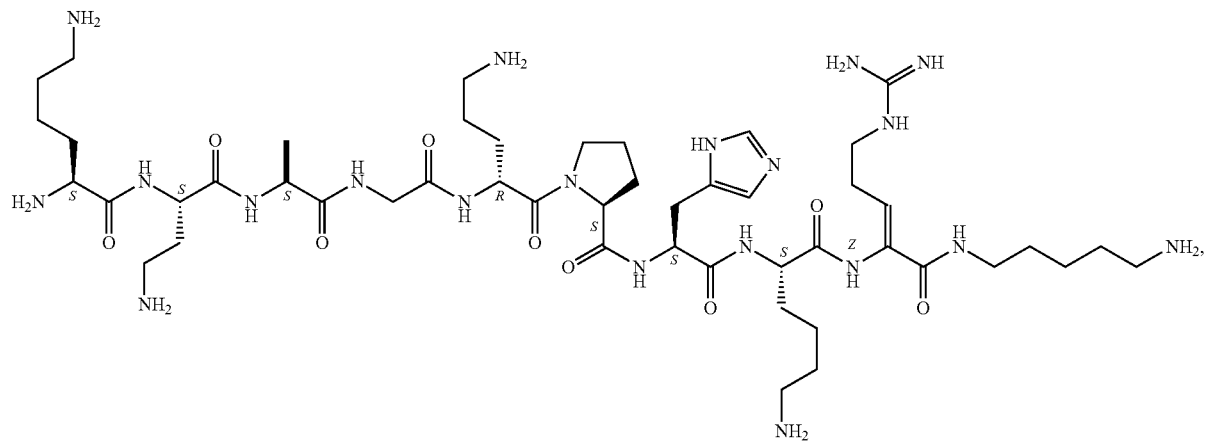
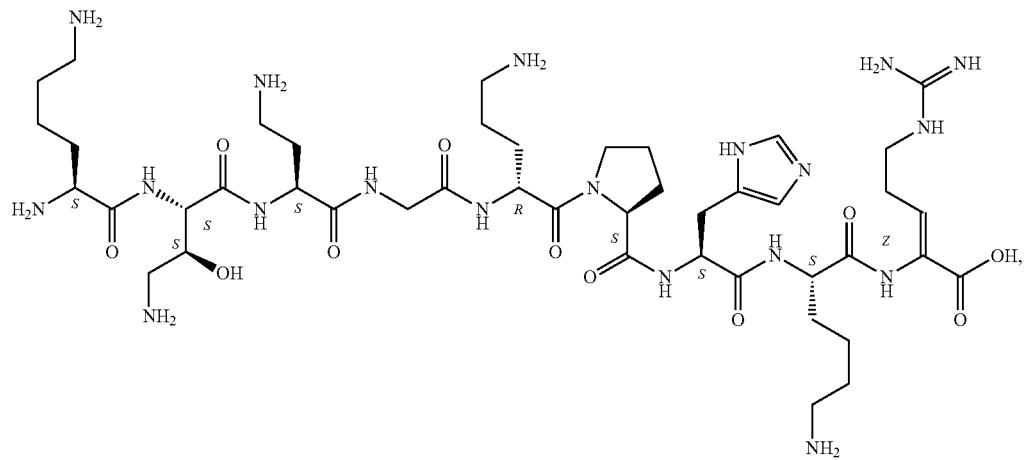

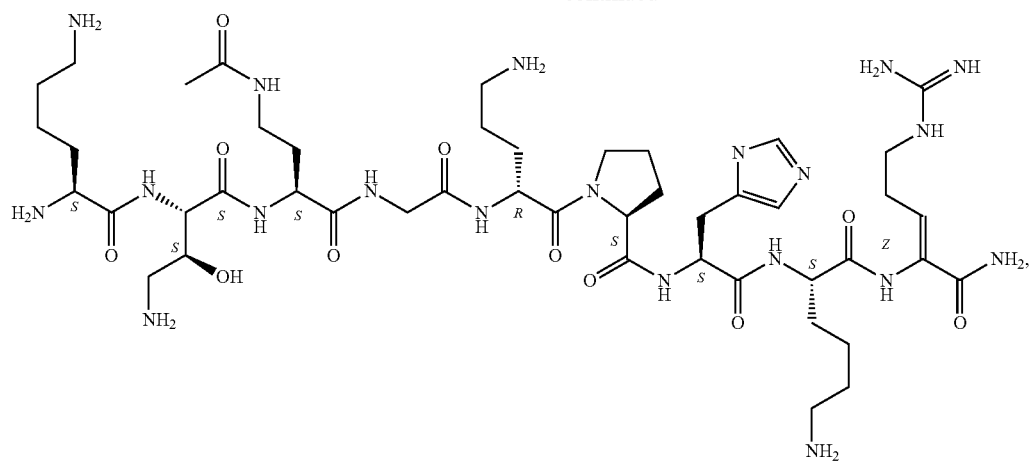
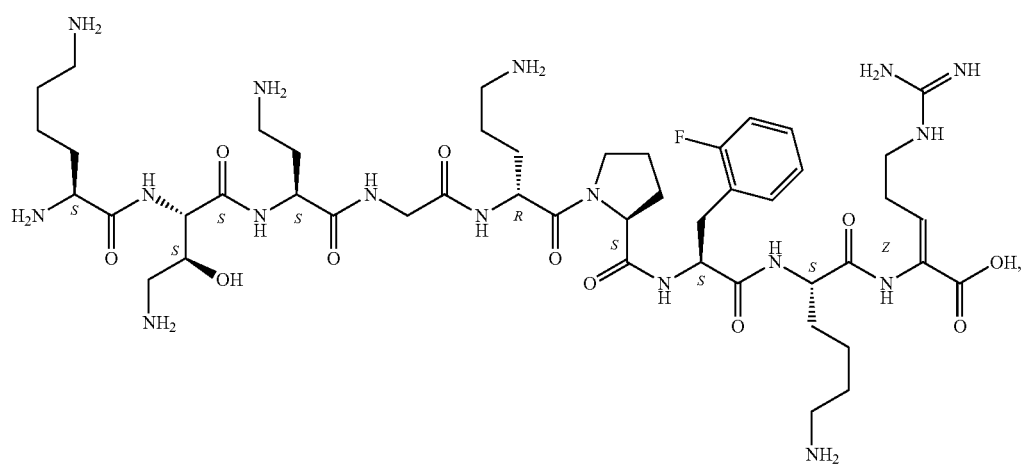
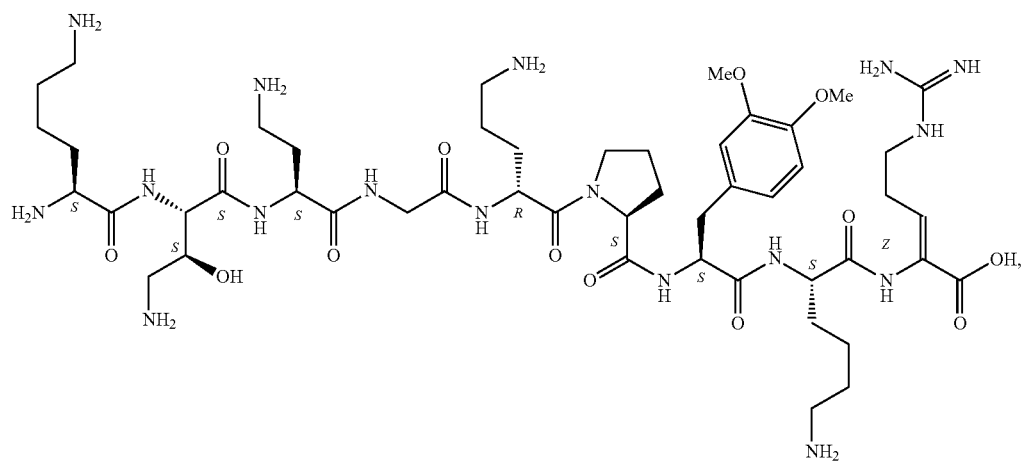

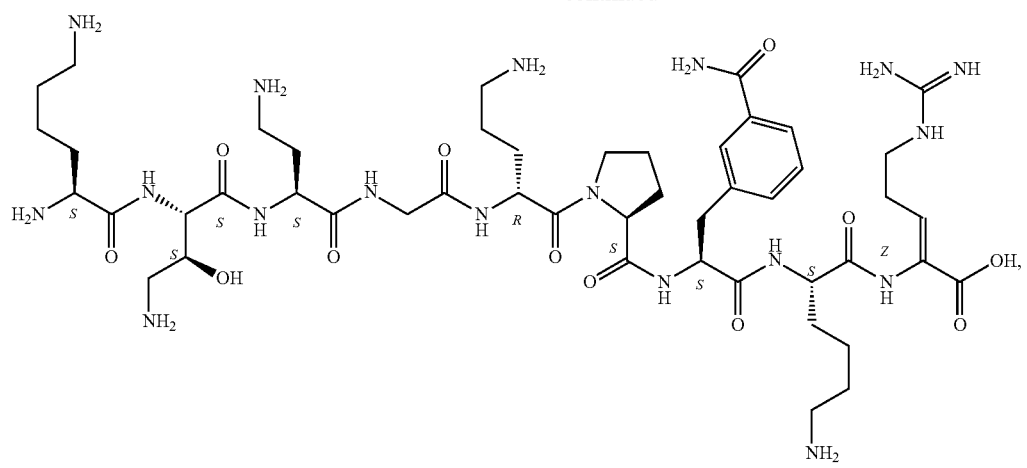

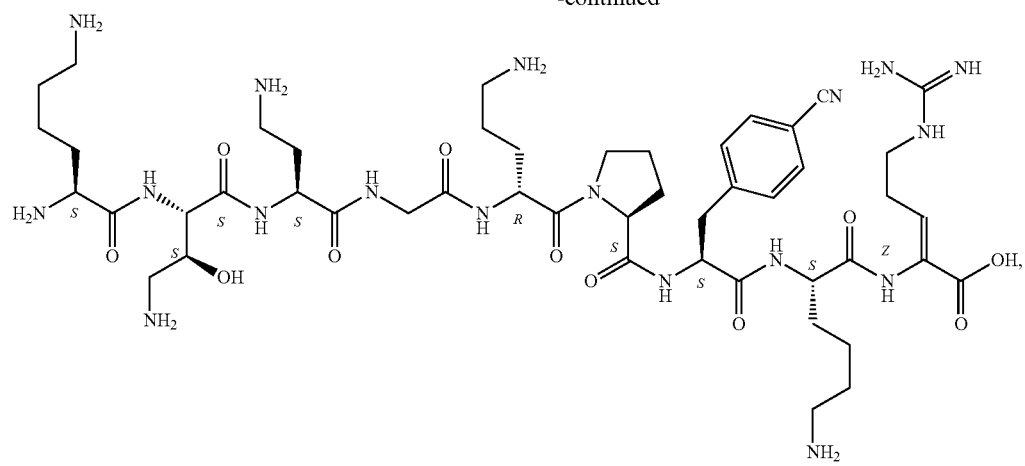
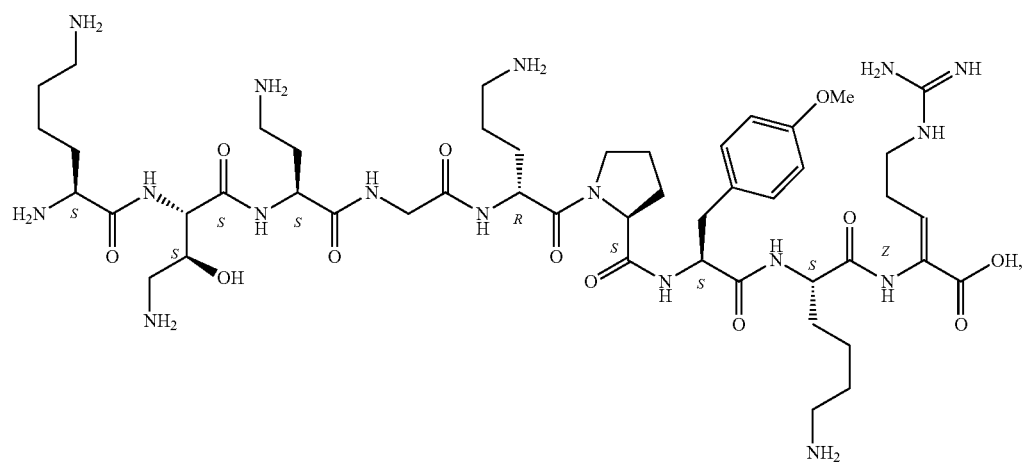
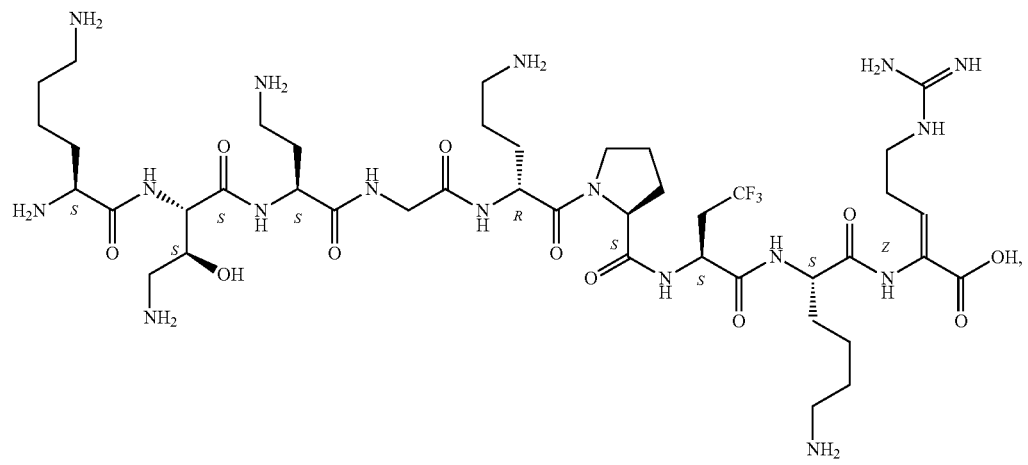

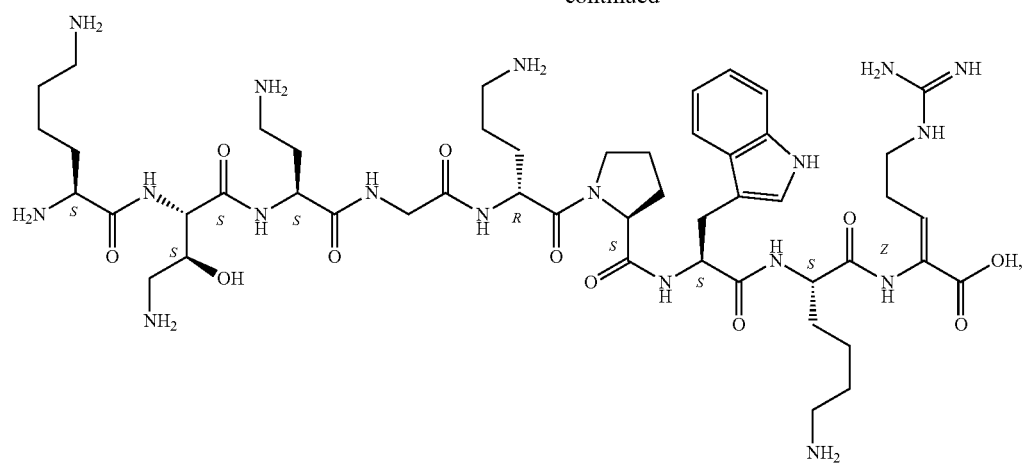
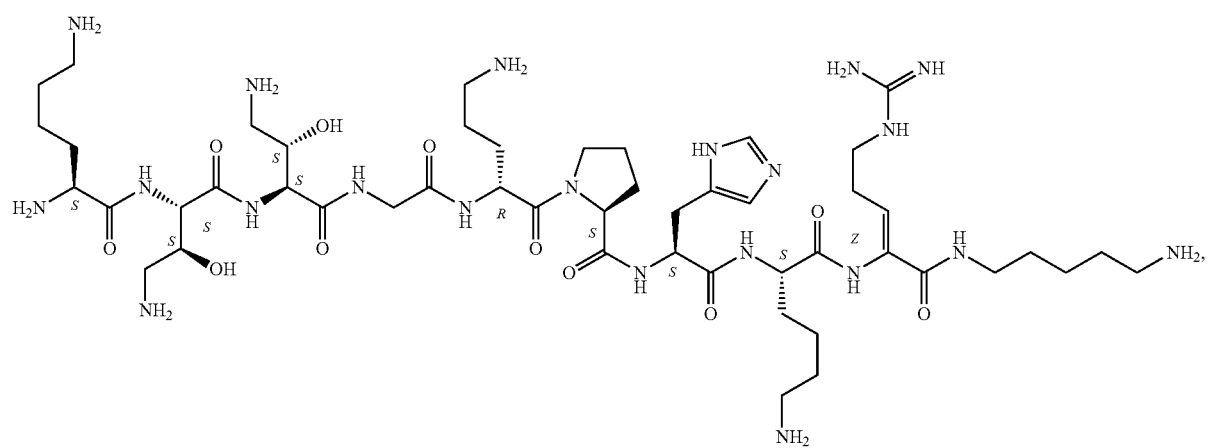
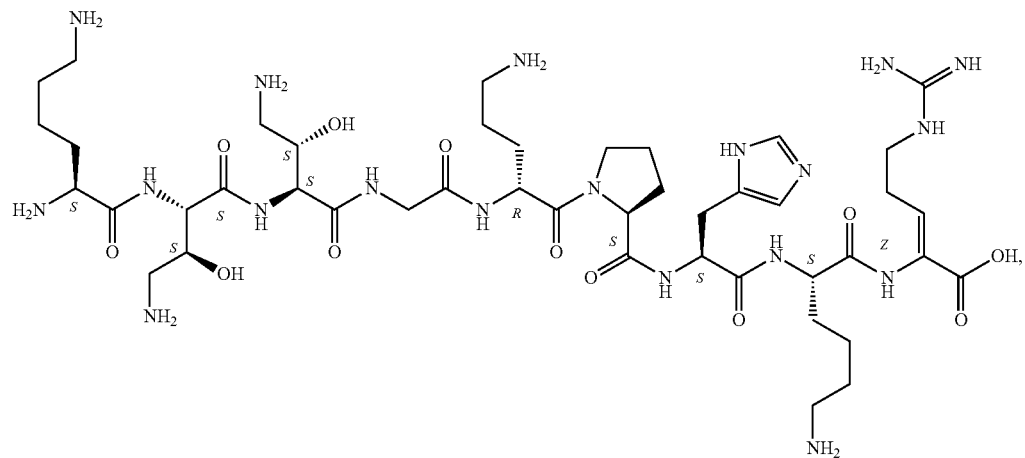

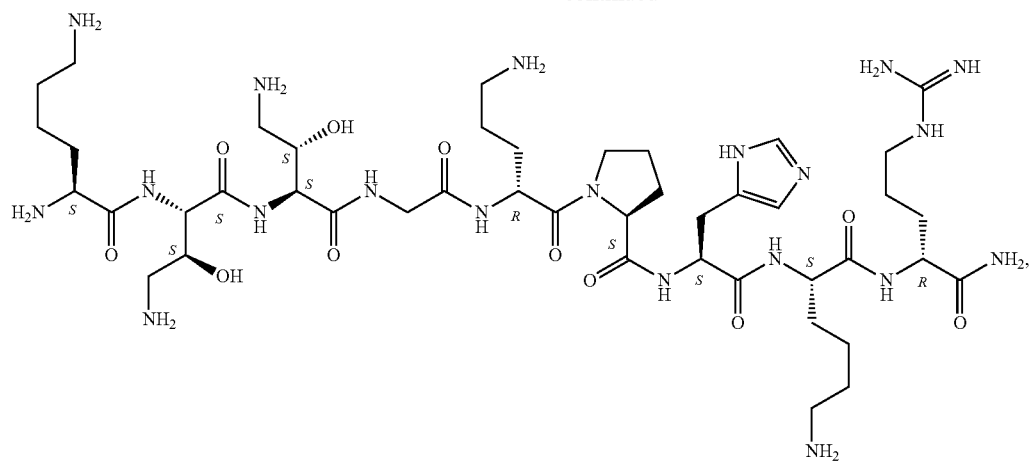
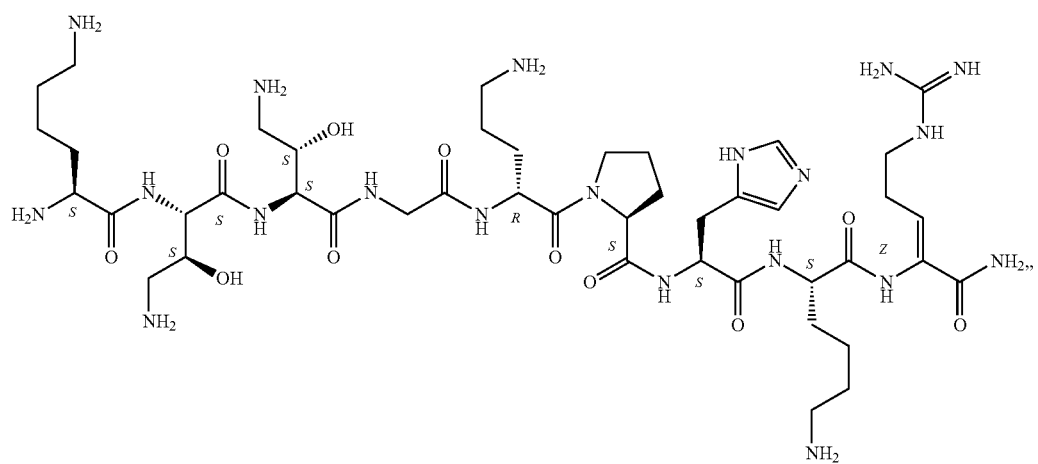
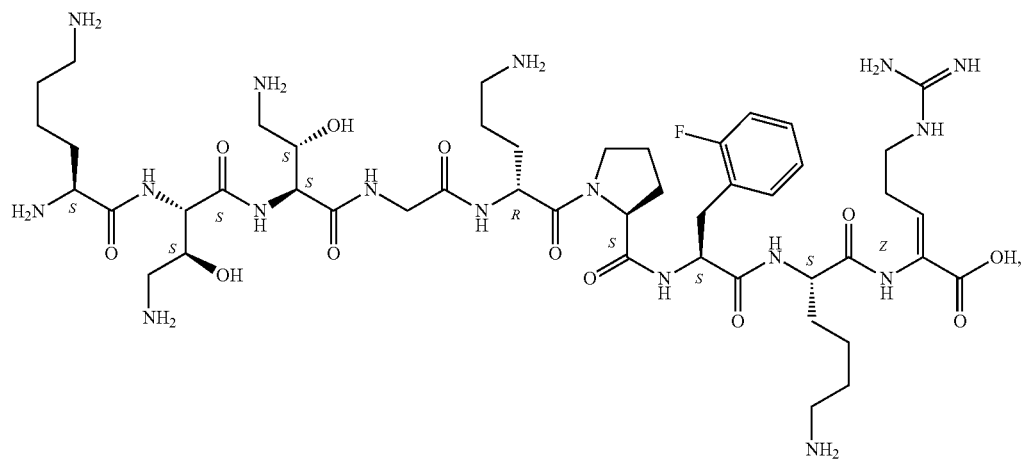

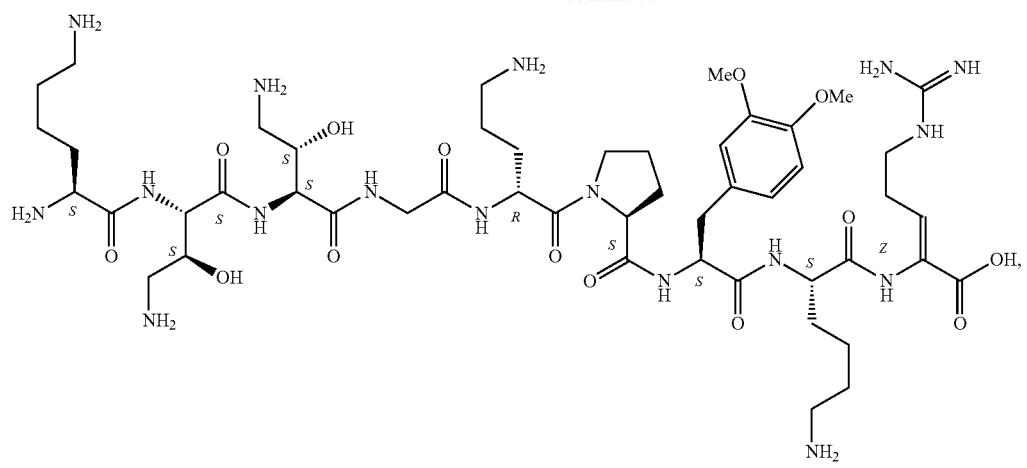
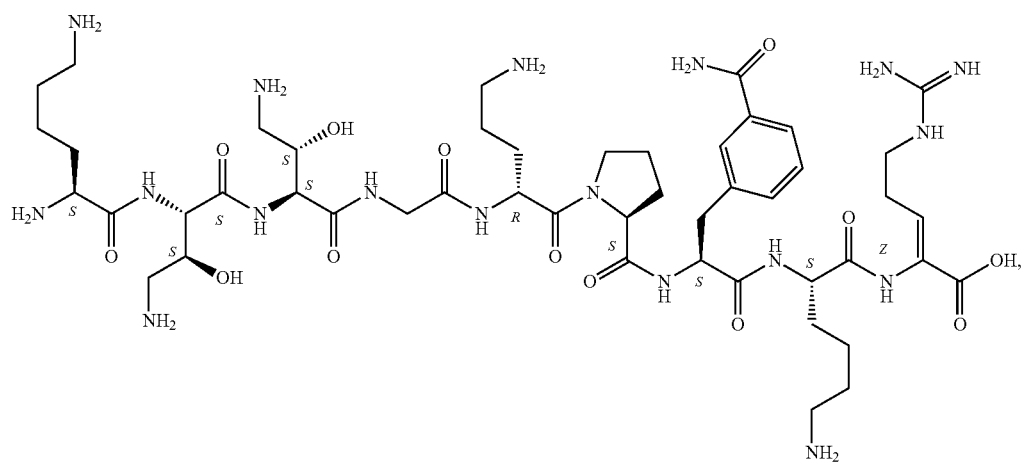
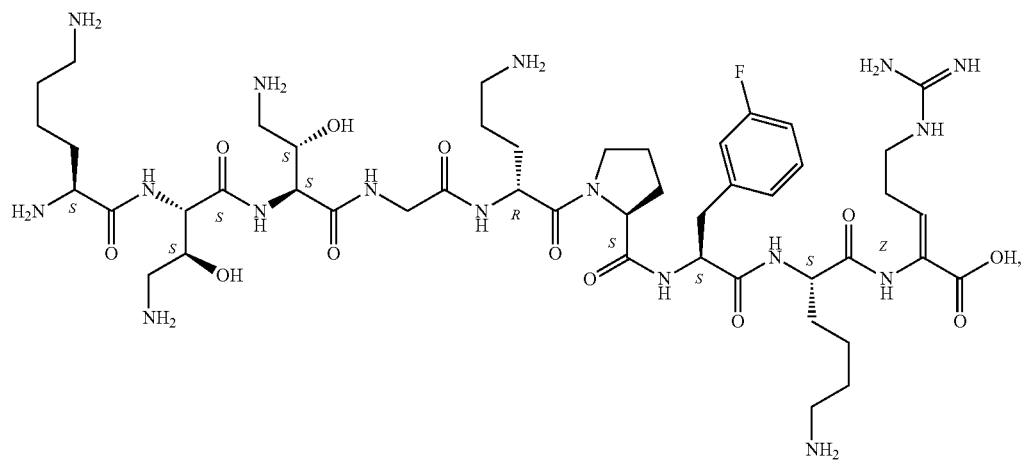

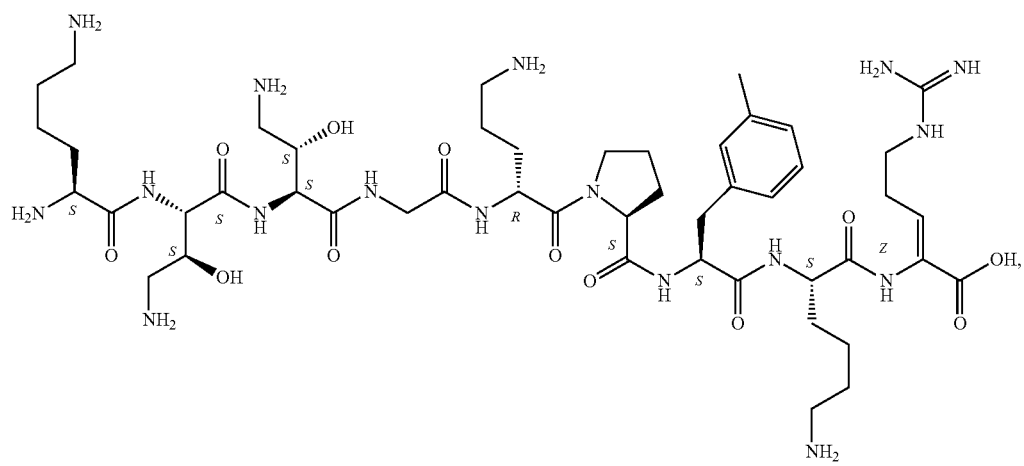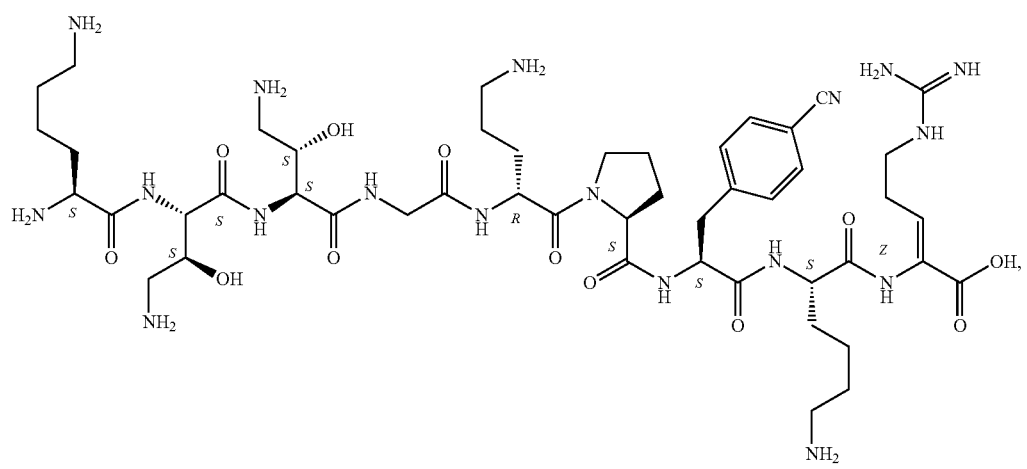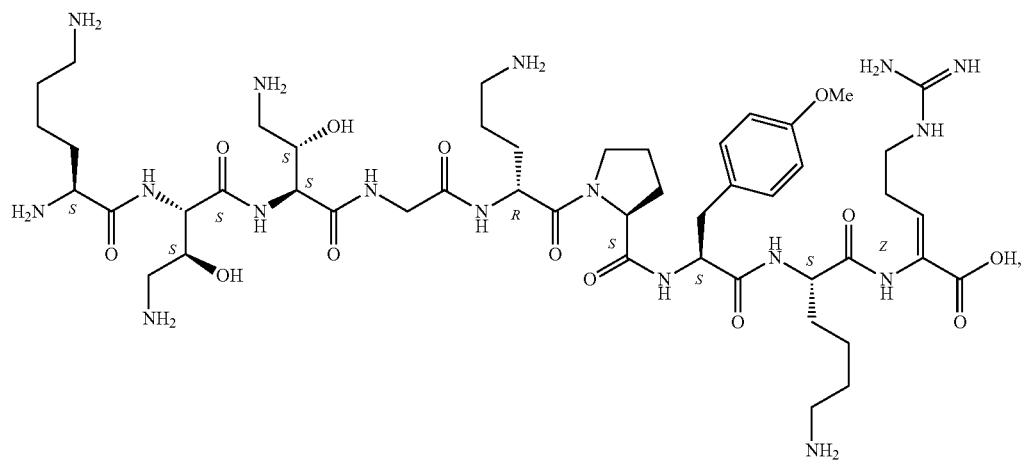

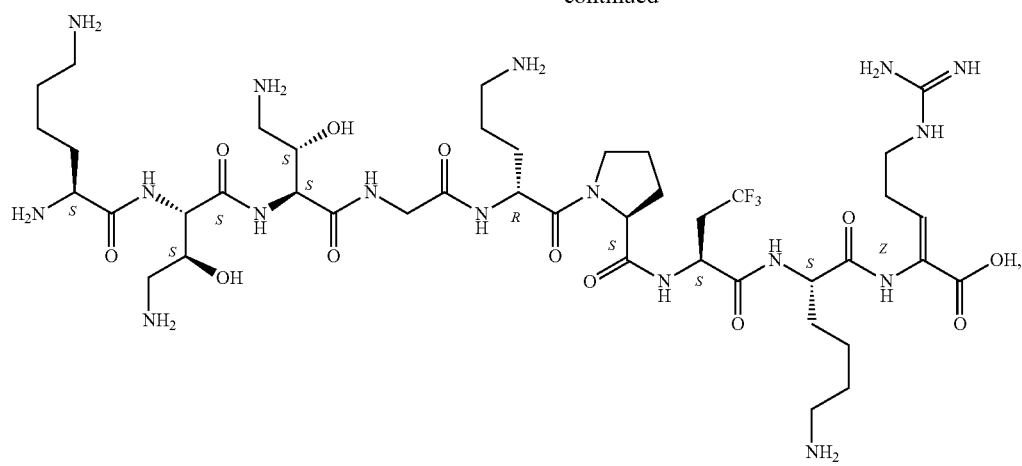
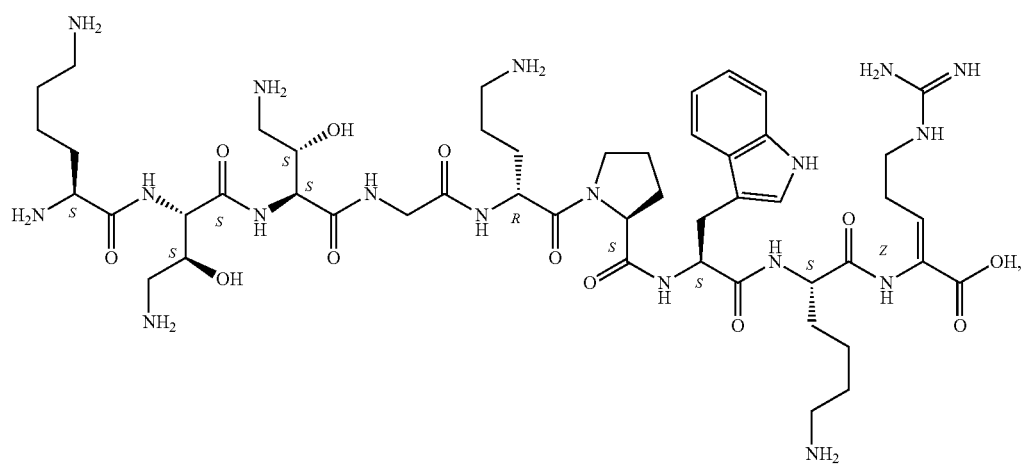
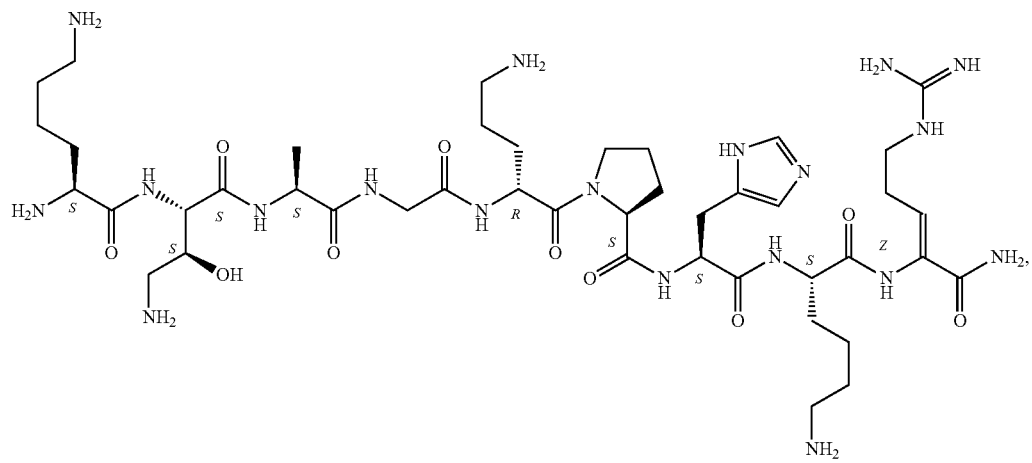

-continued
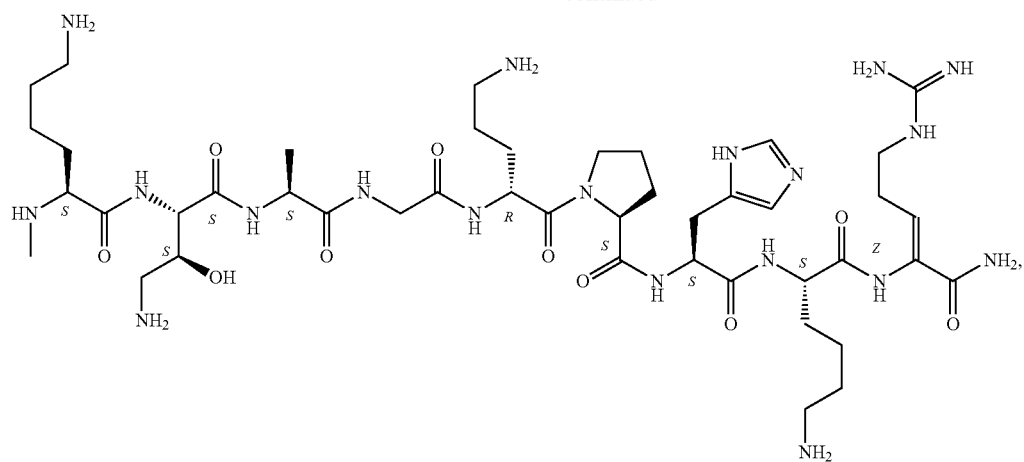
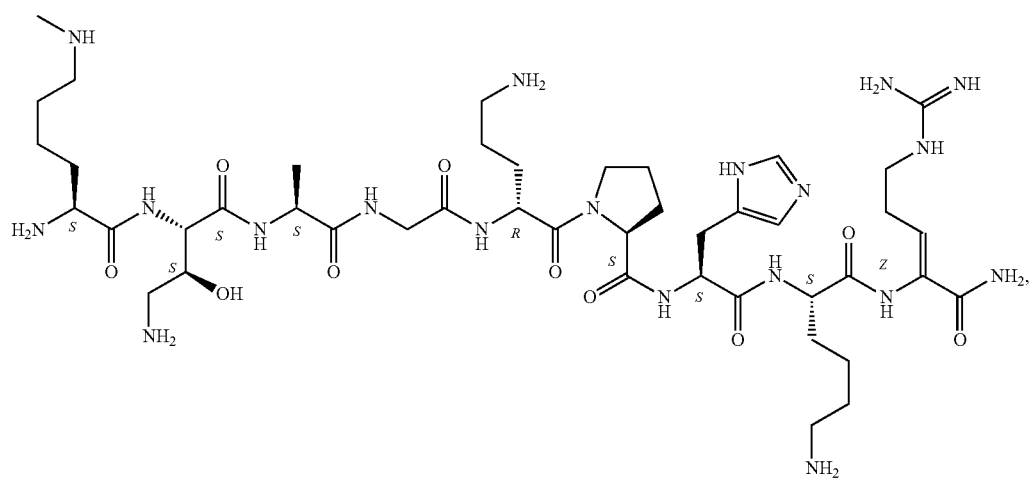
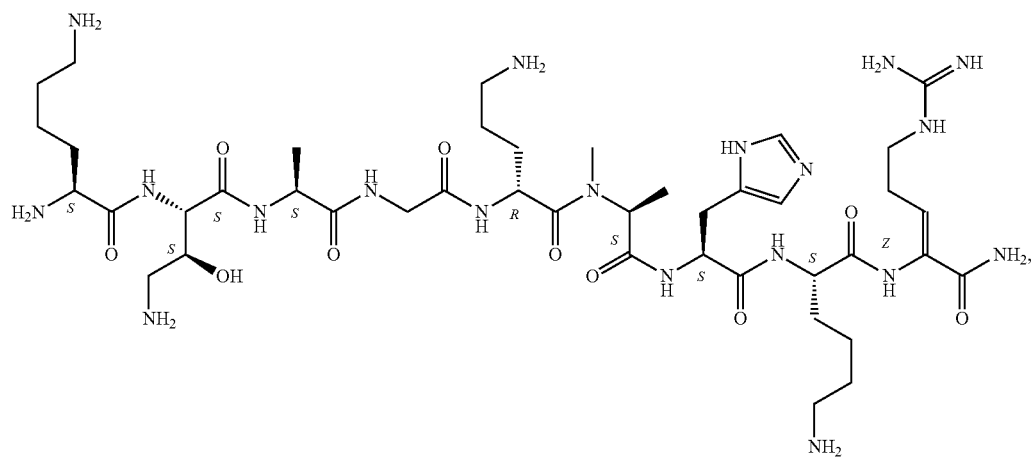

-continued
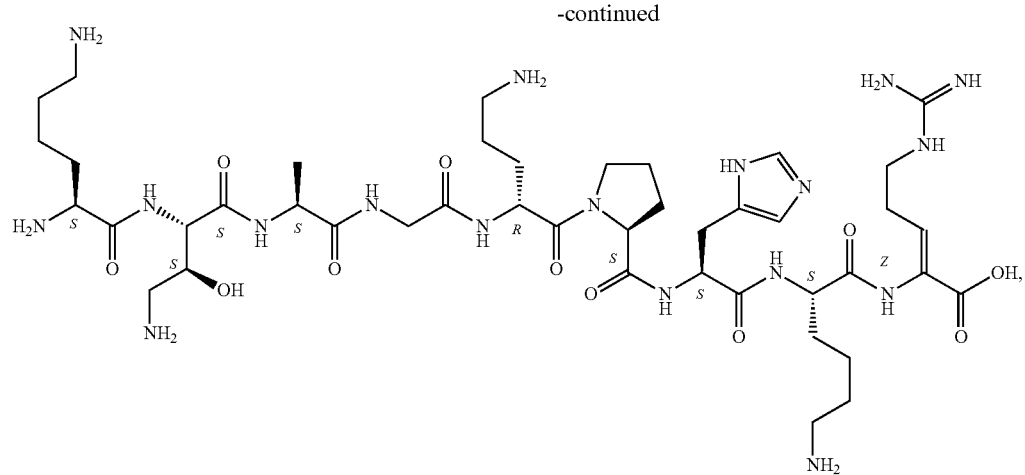
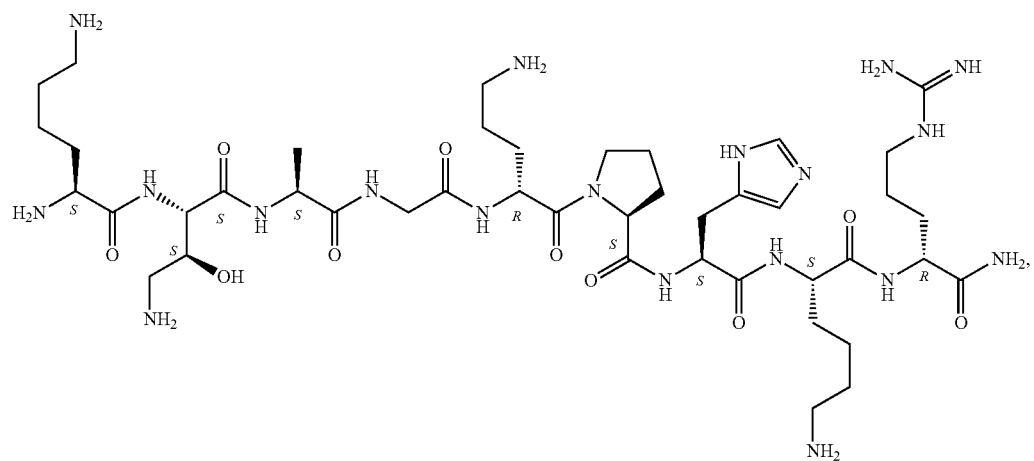
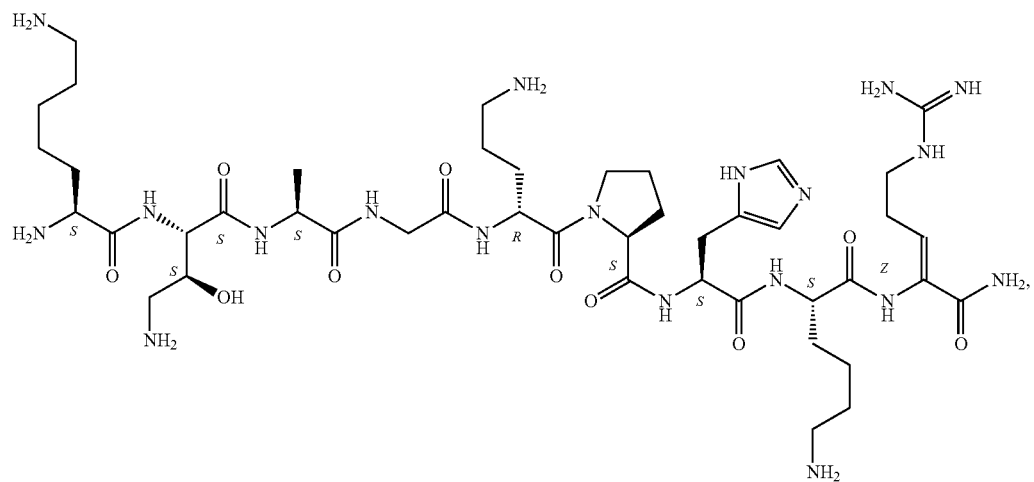

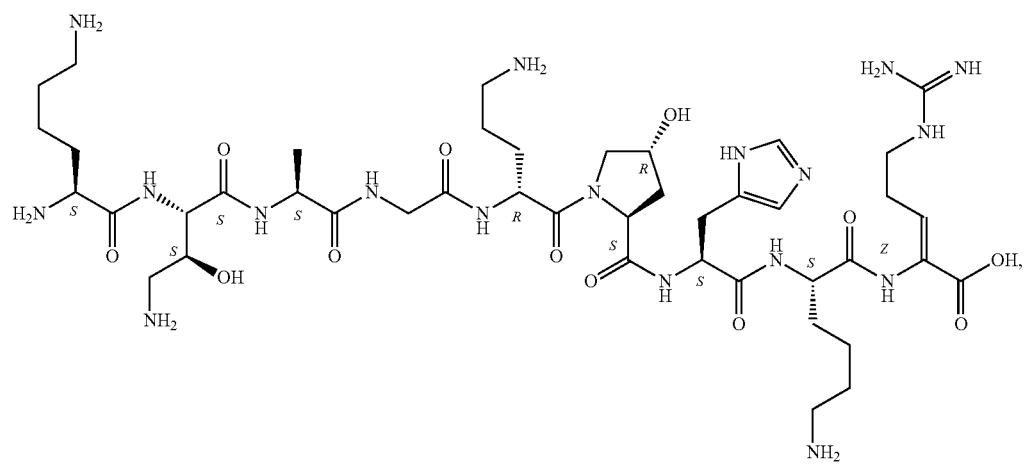
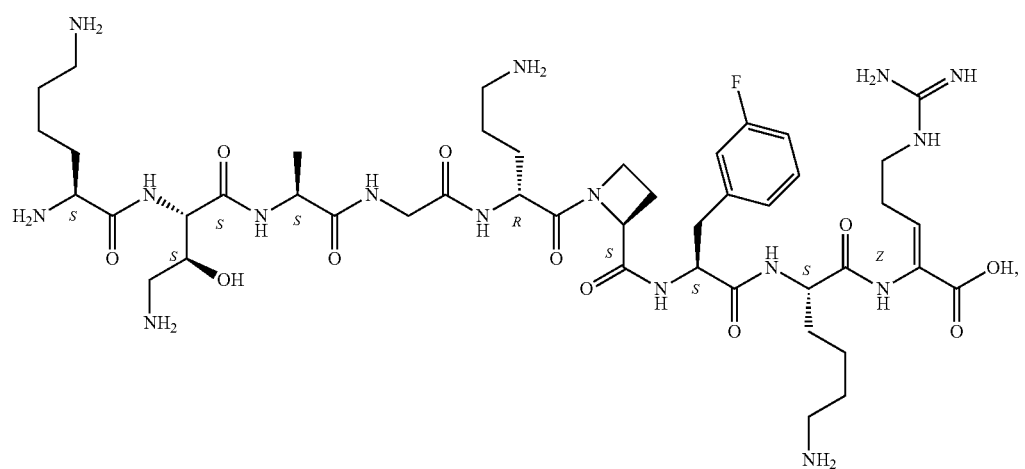
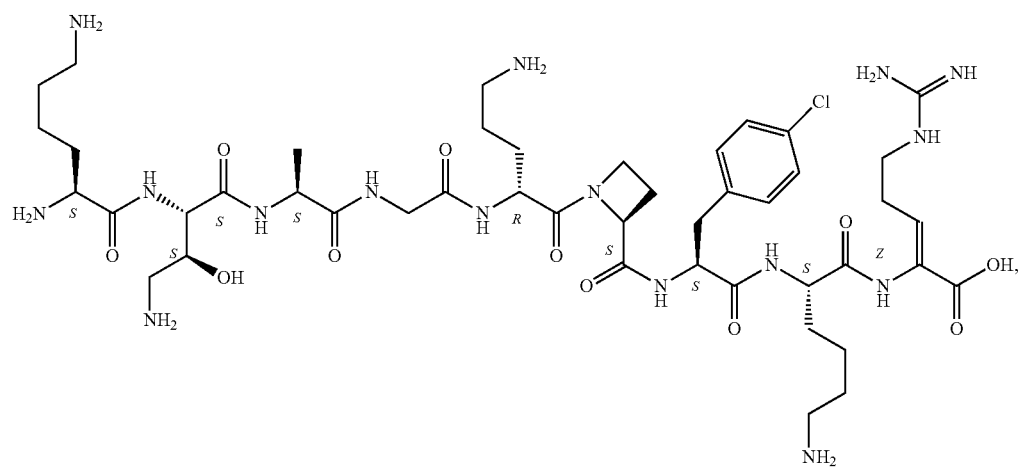

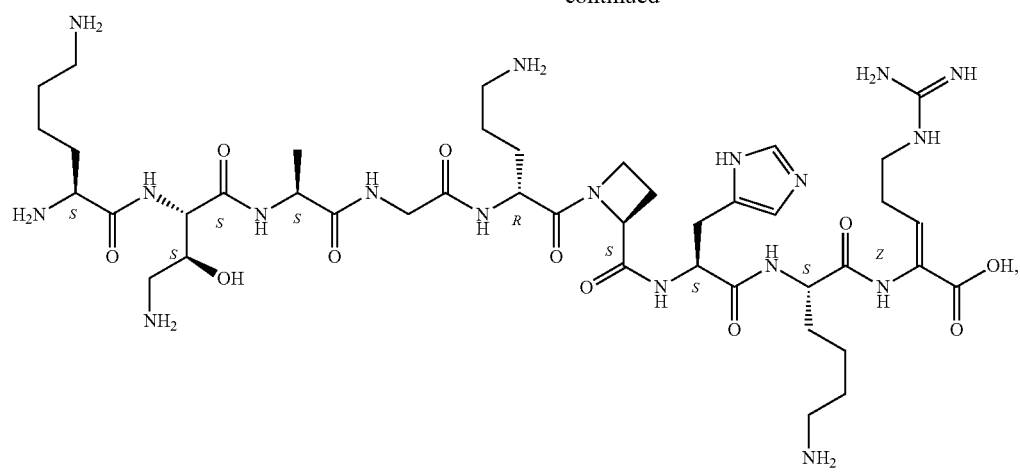
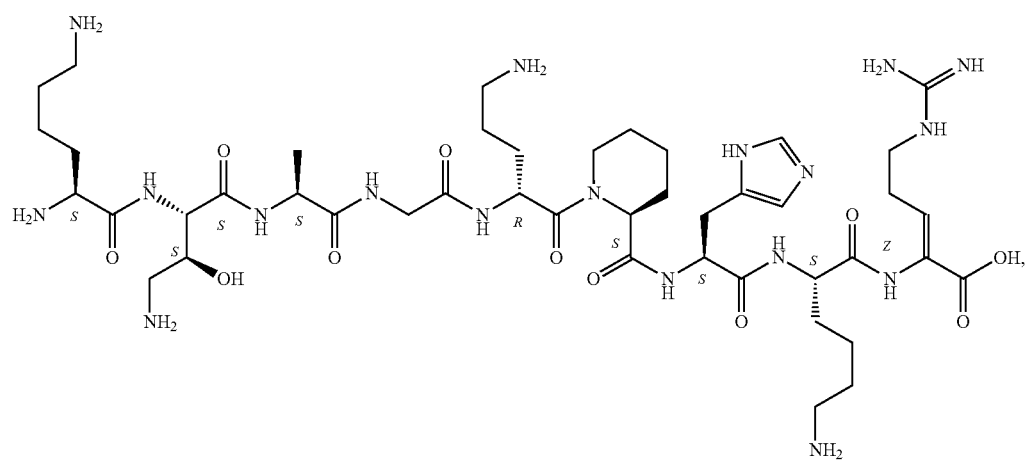
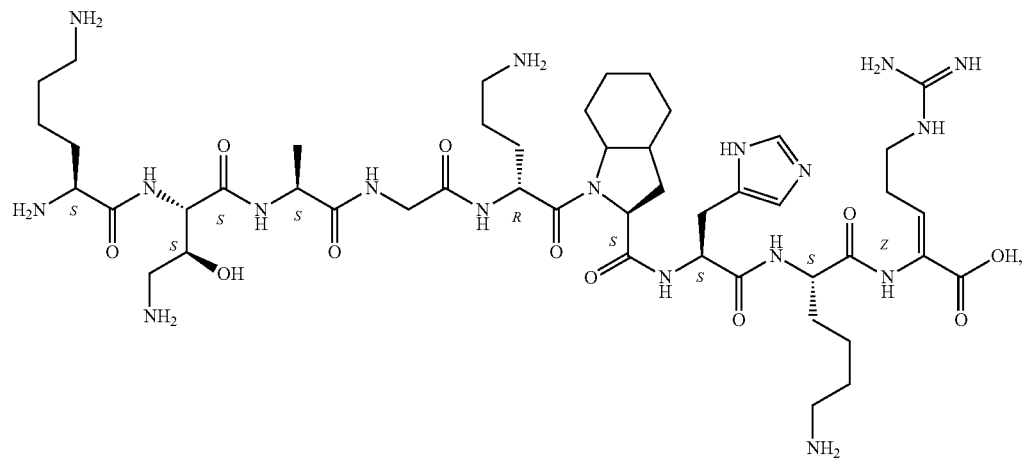

-continued
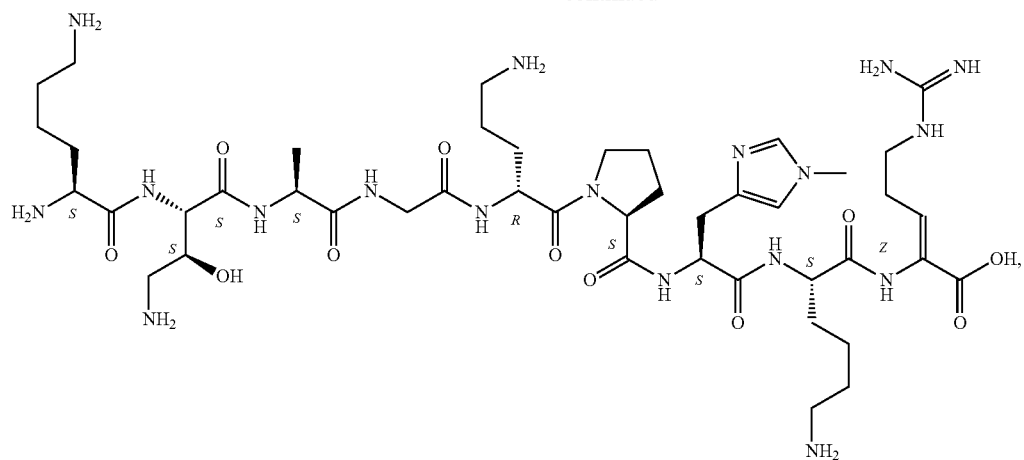
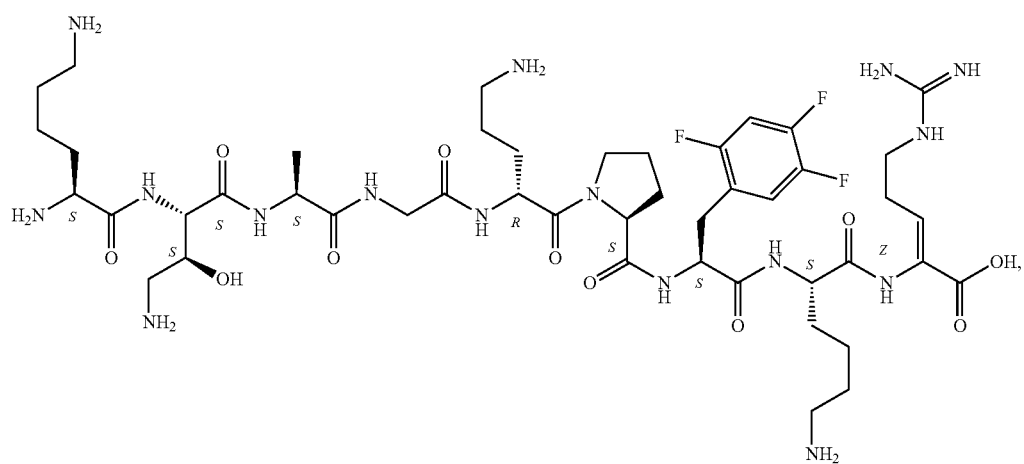
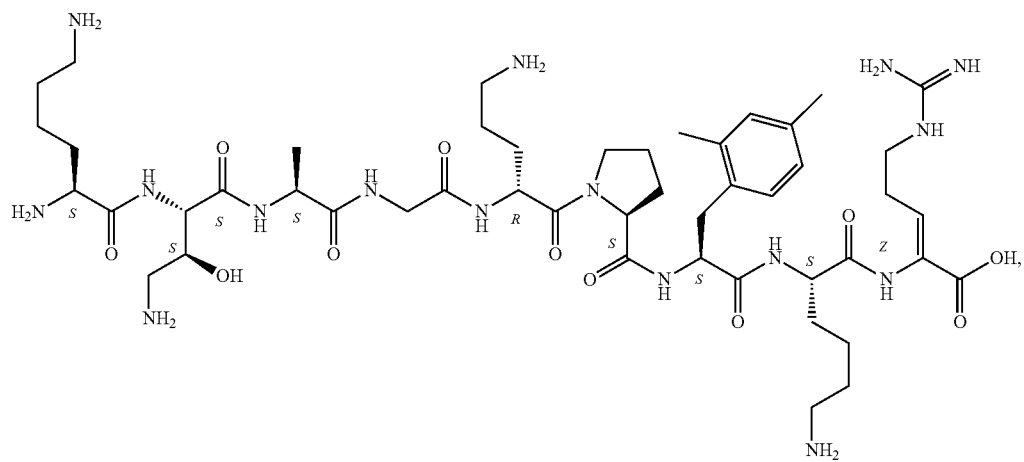

-continued
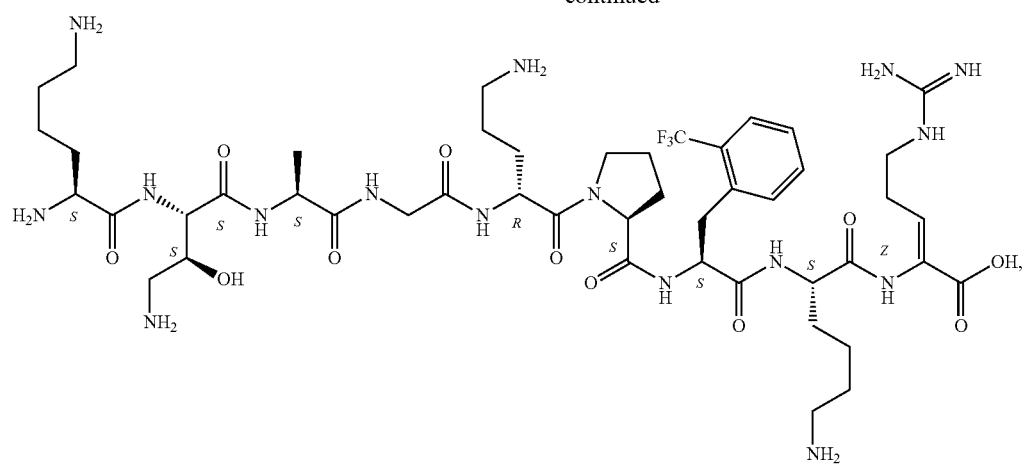
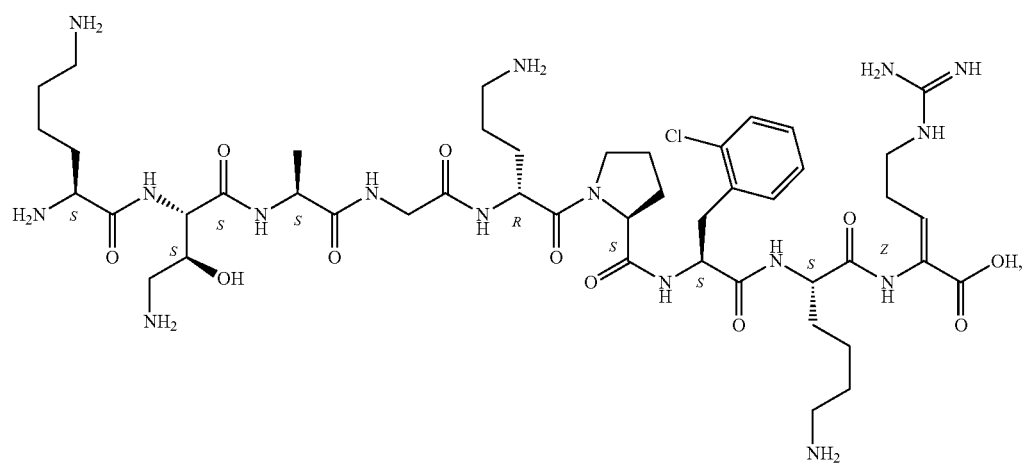
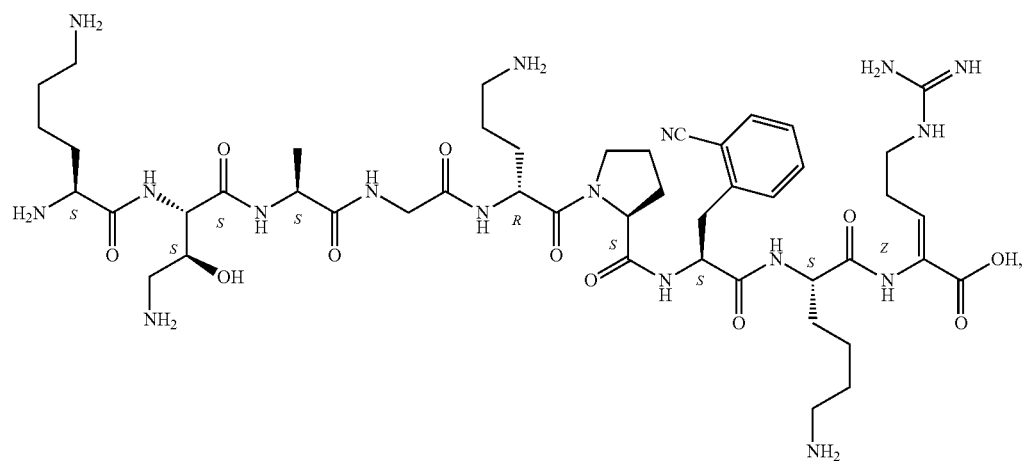

-continued
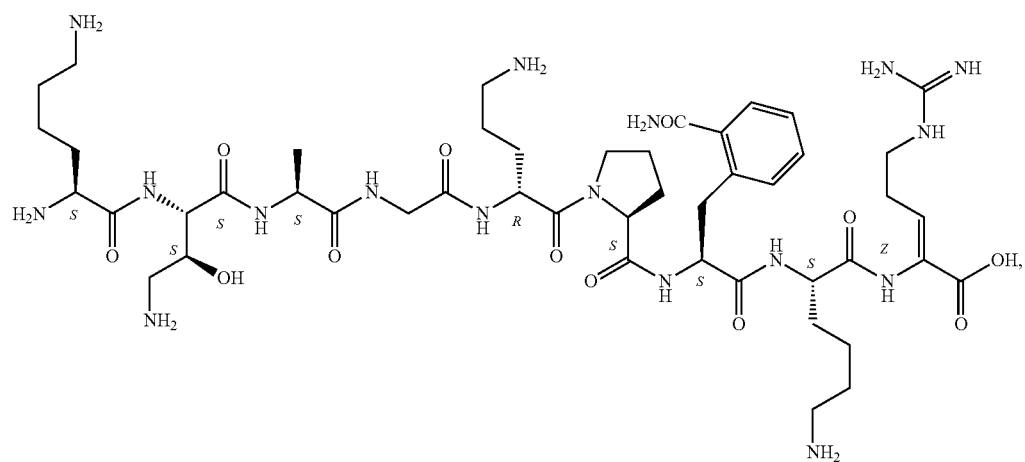
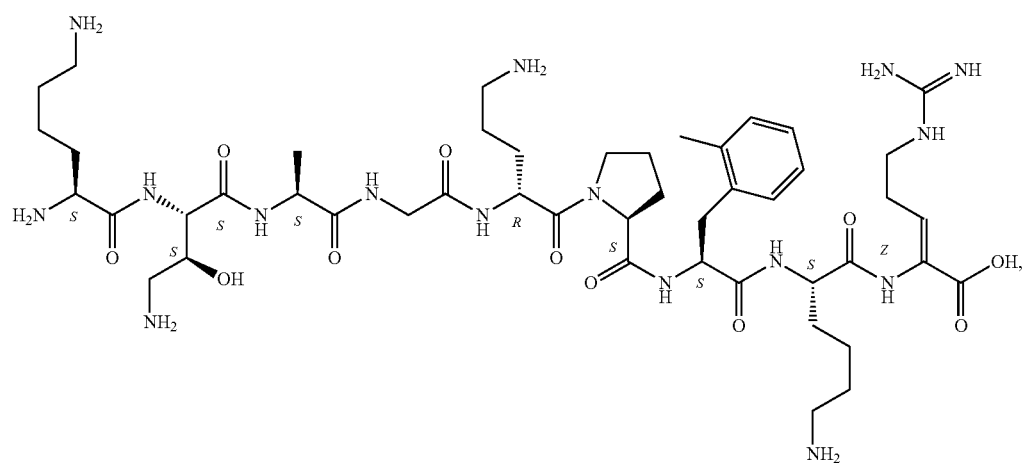
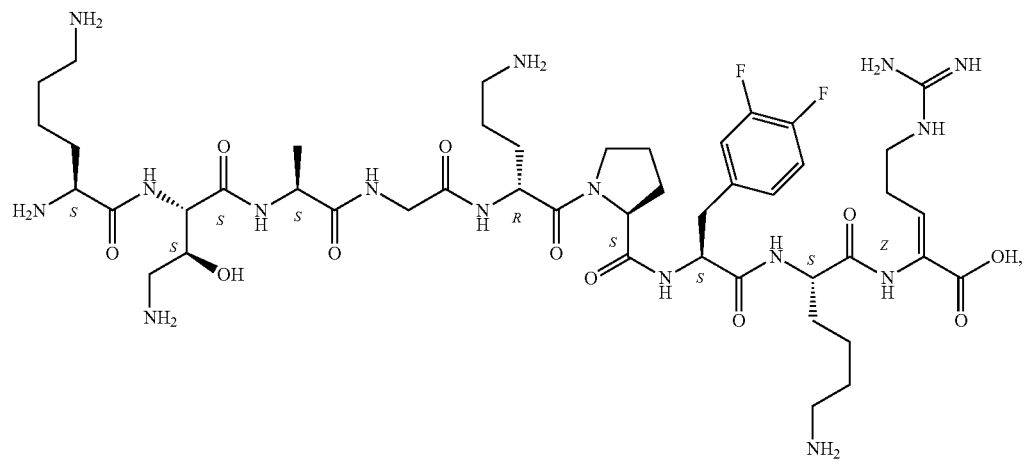

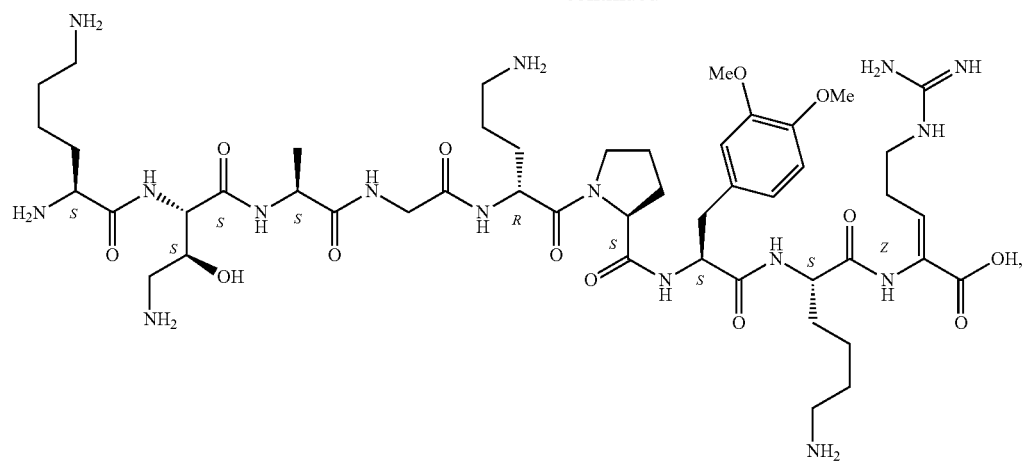
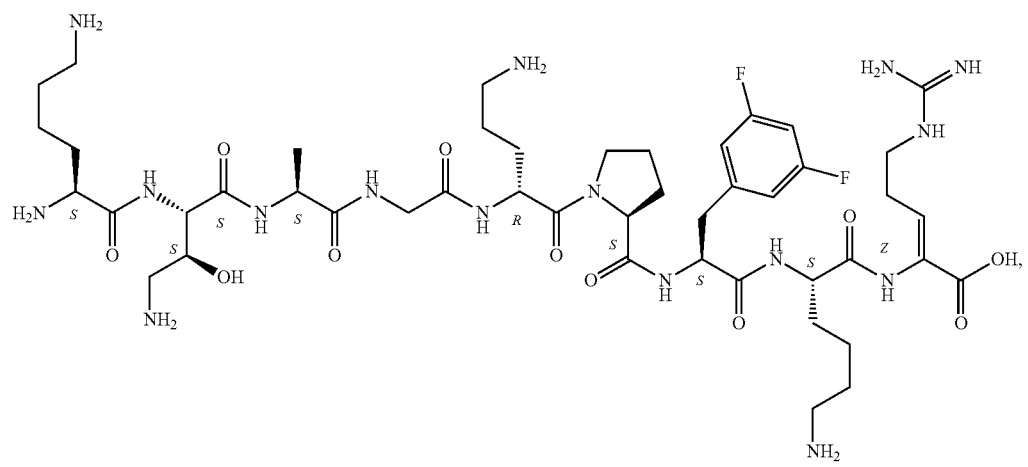
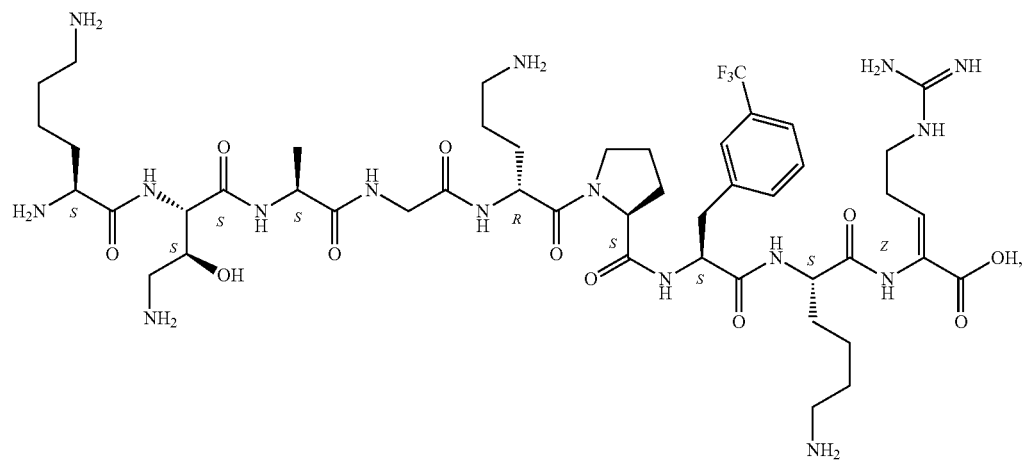

-continued
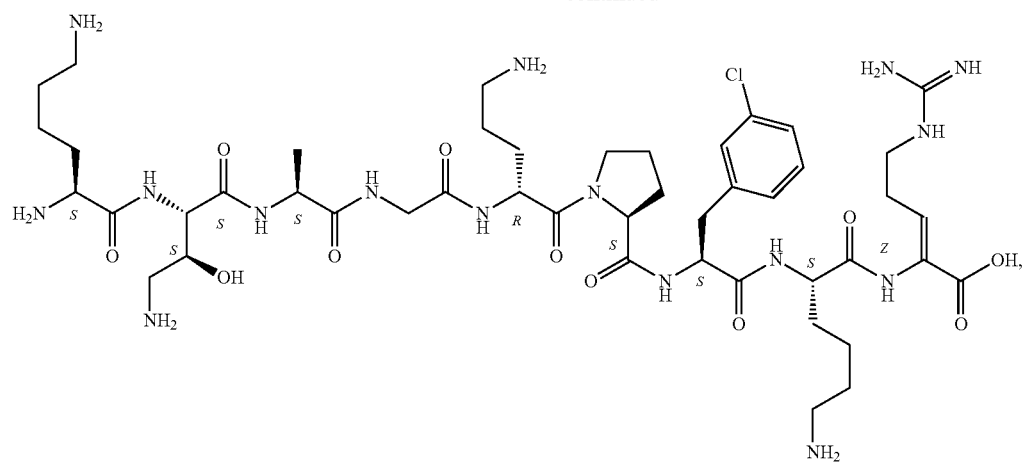
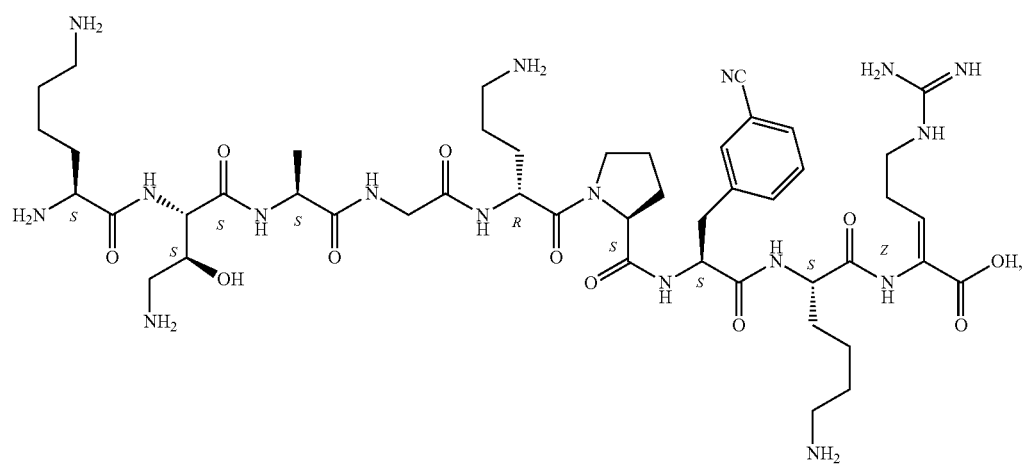
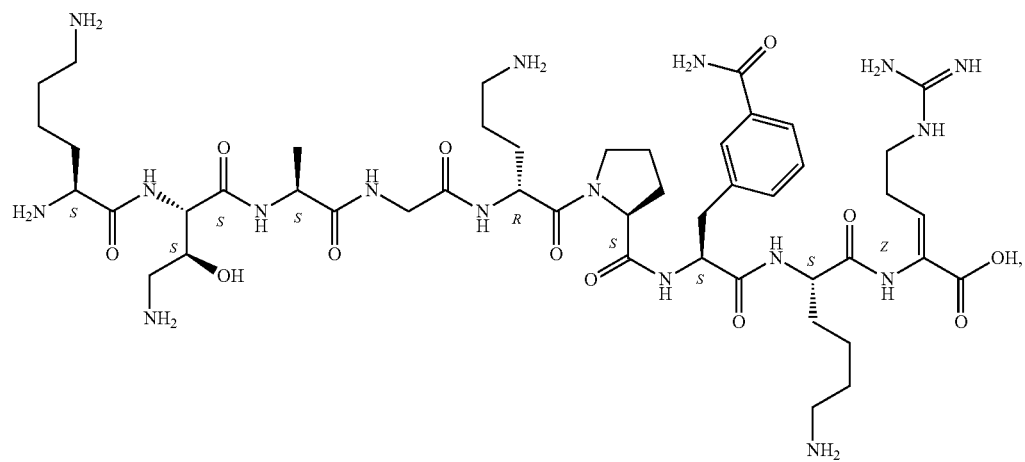

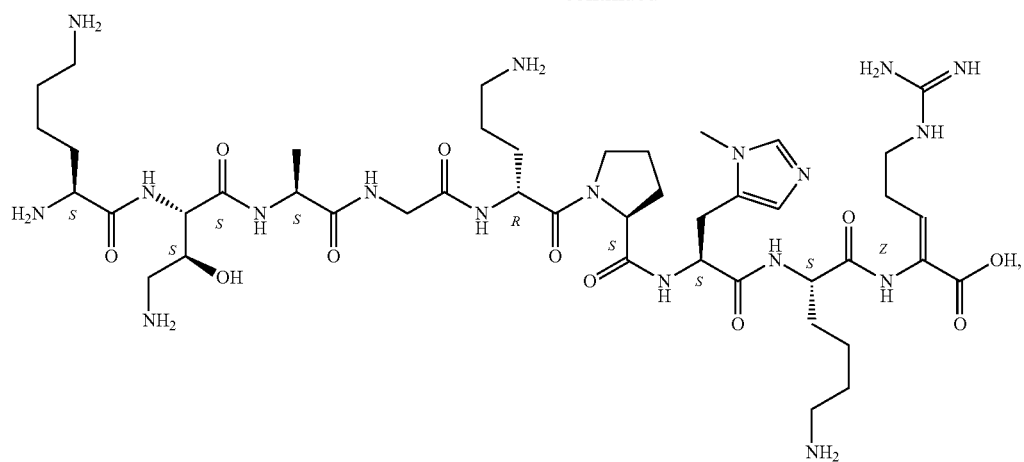
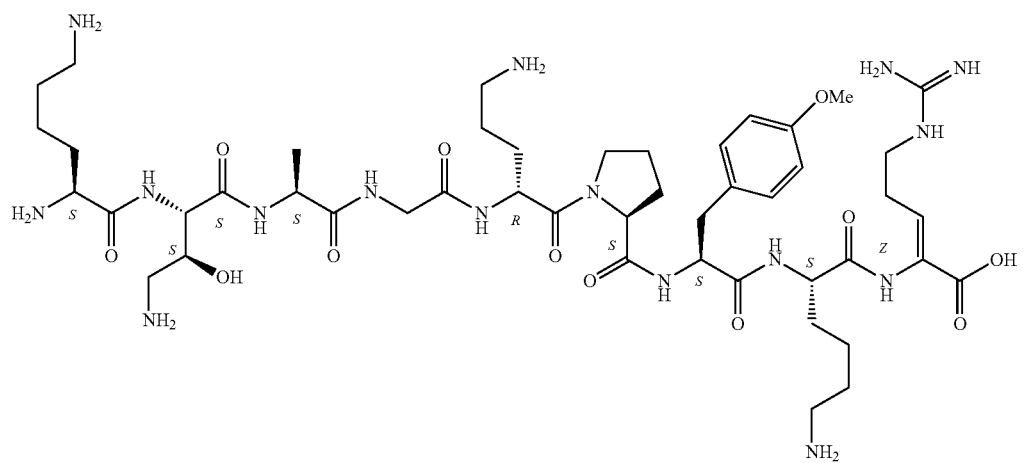
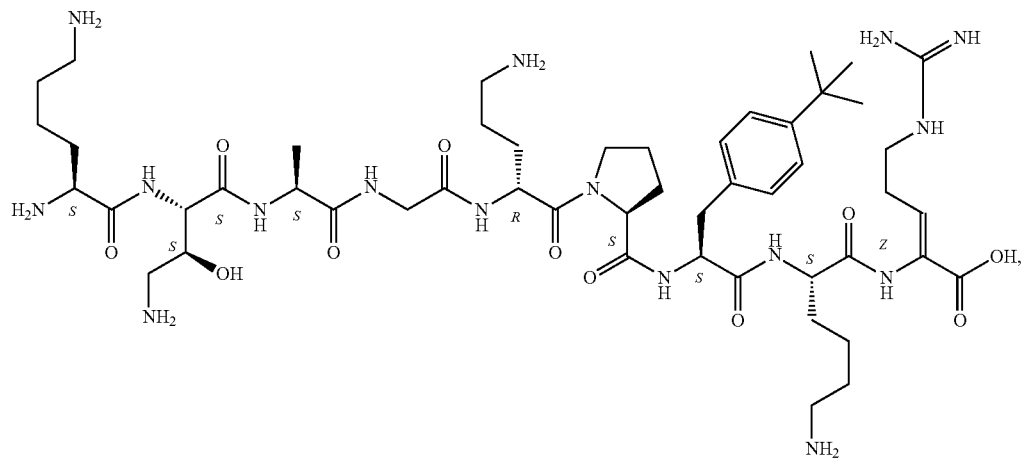

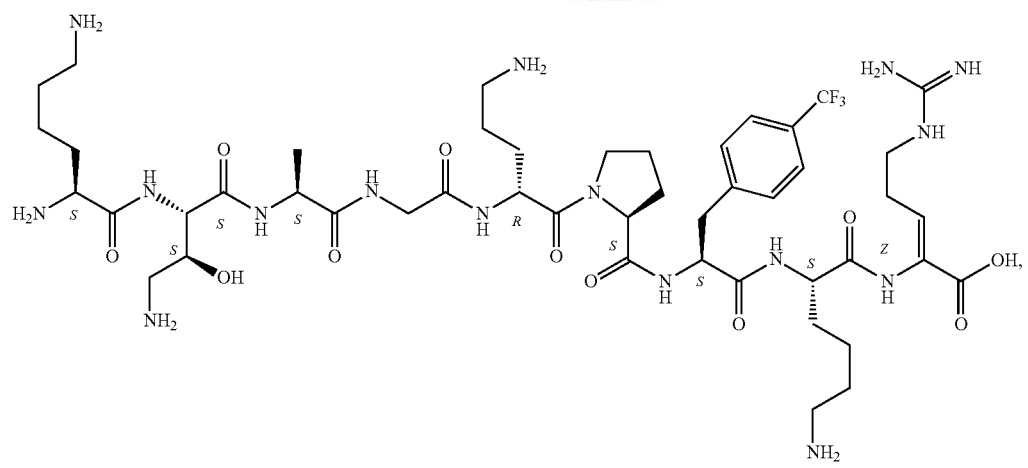
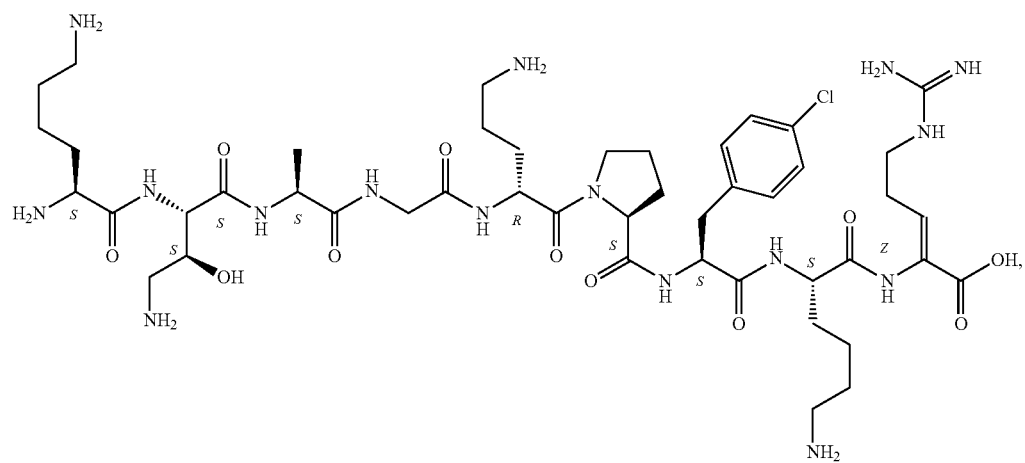
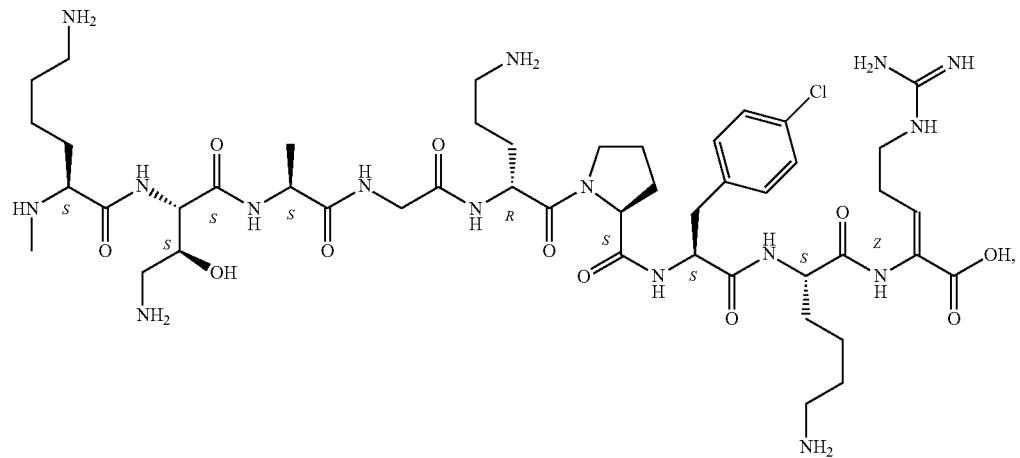

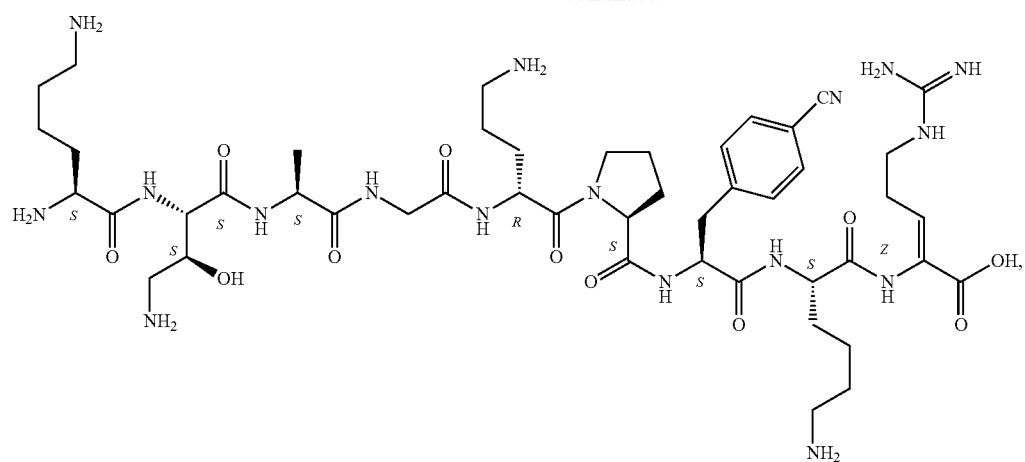
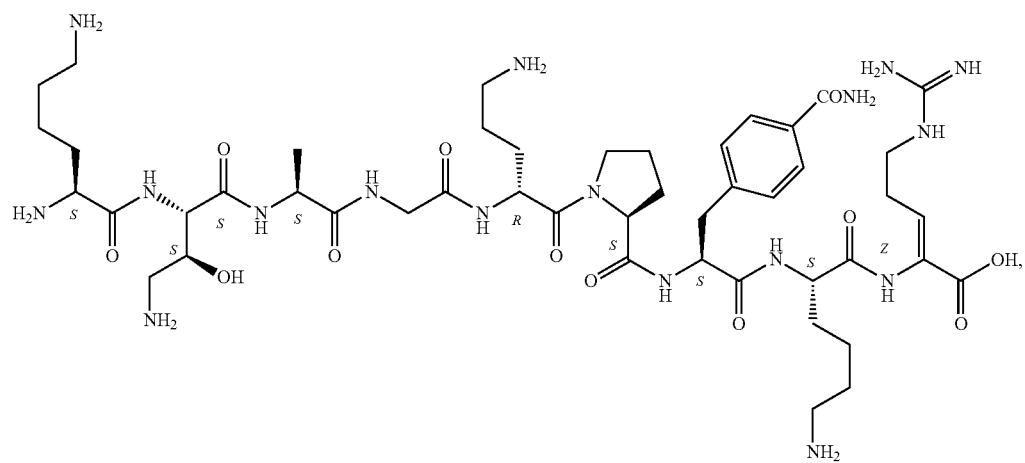
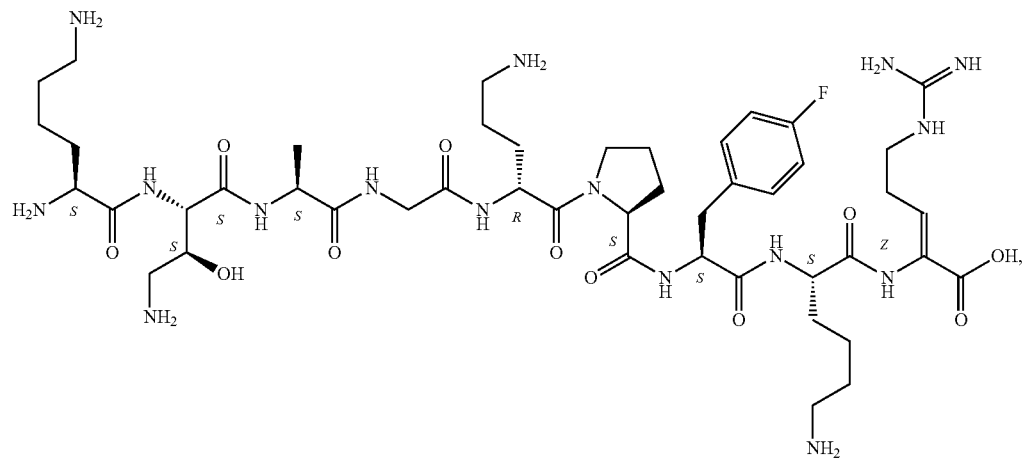

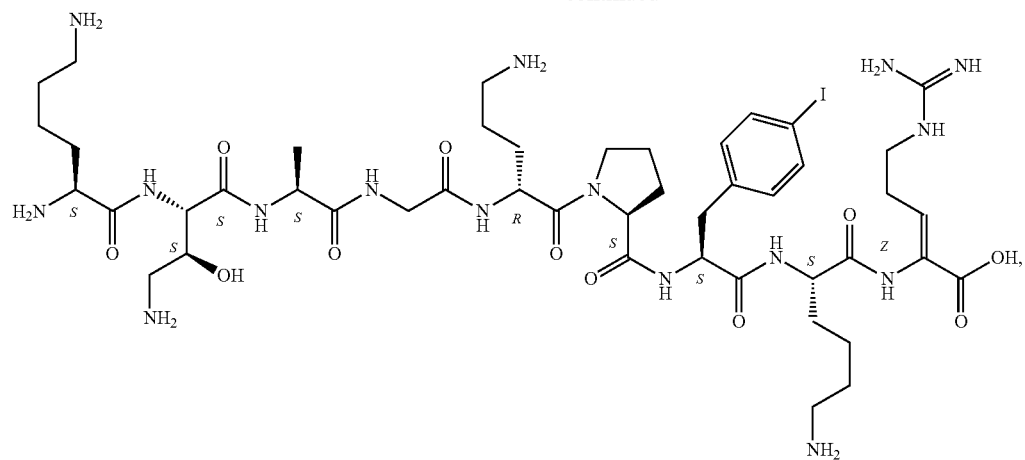
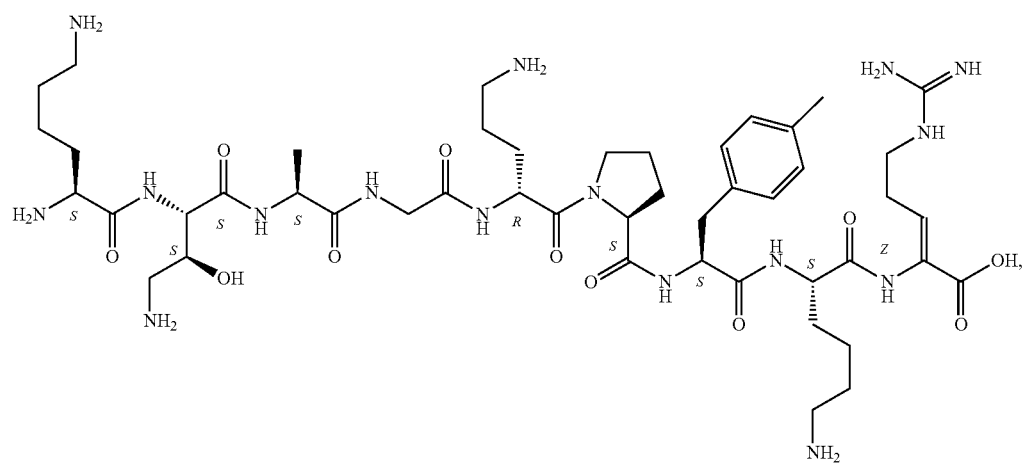
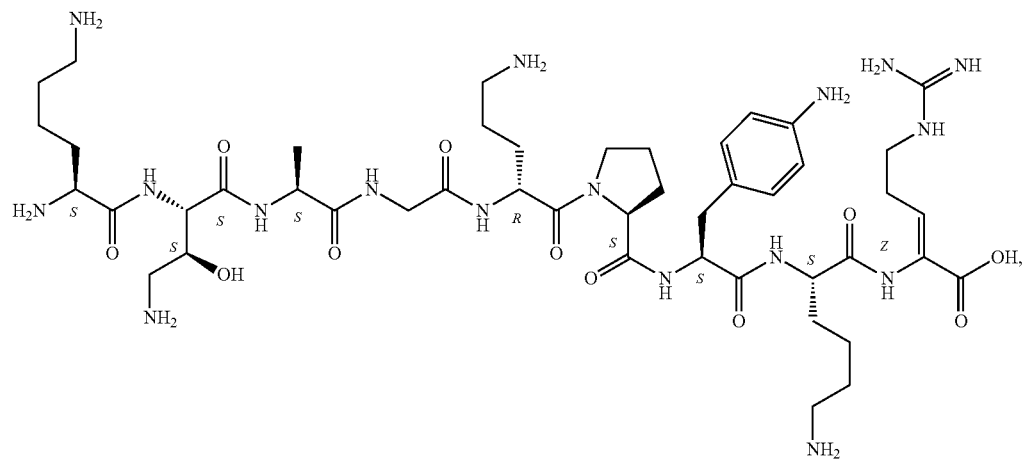

-continued
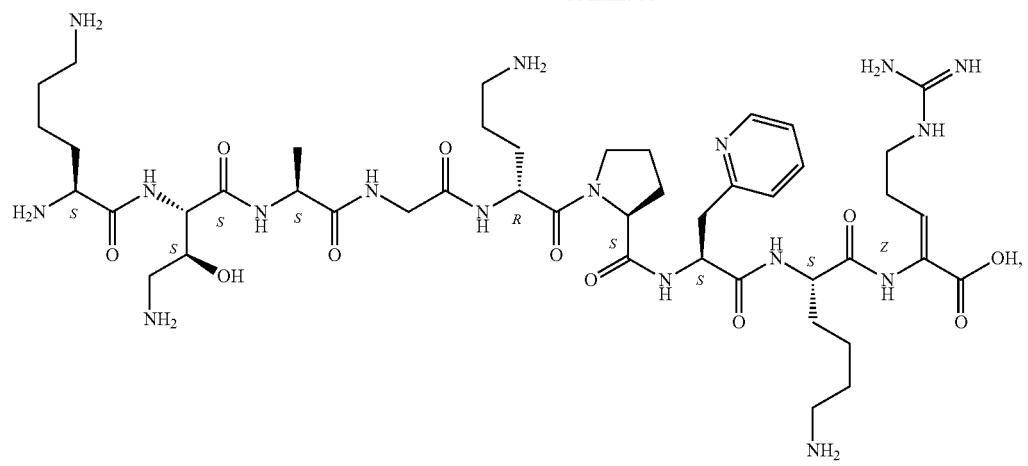
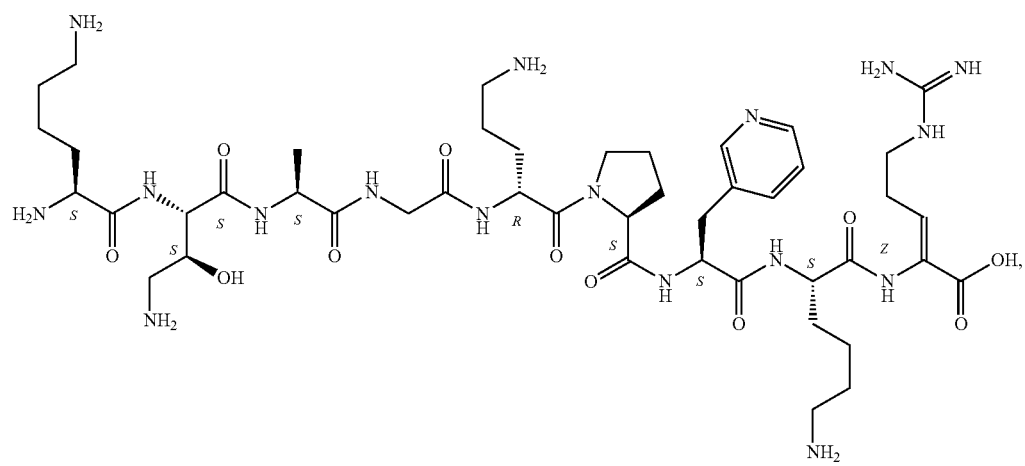
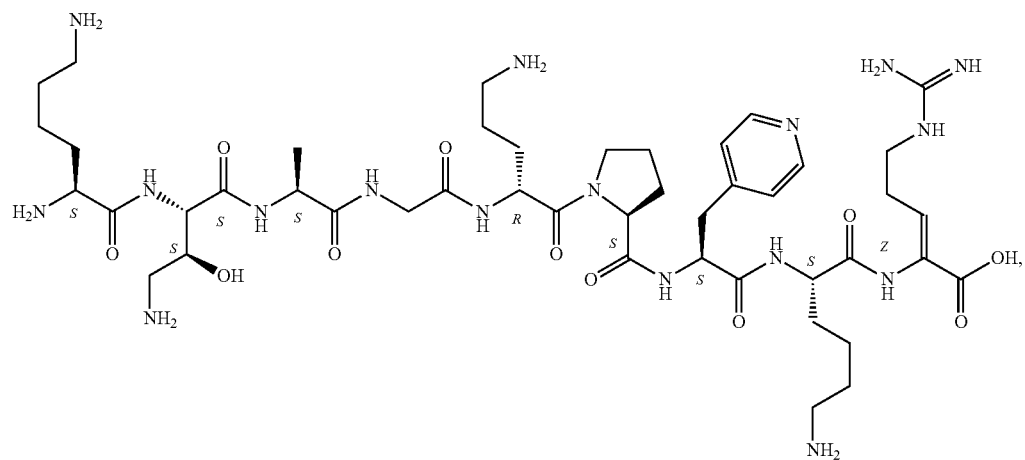

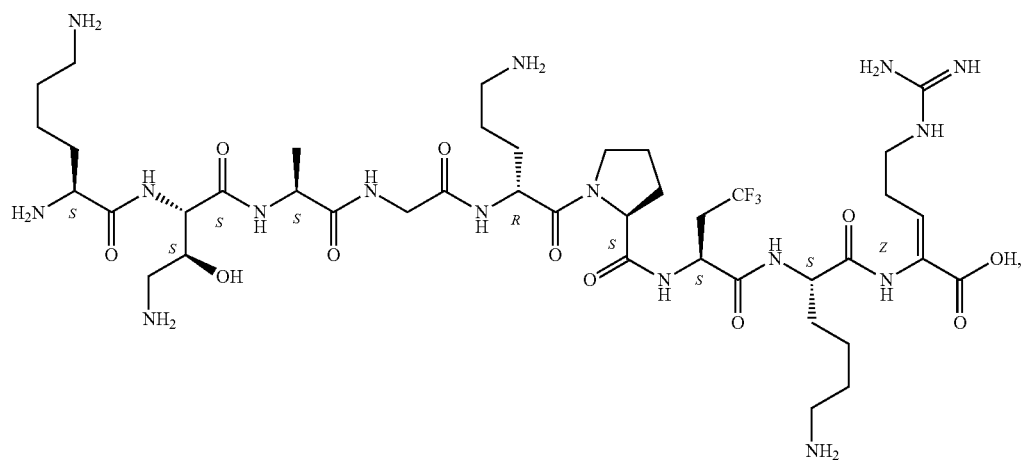
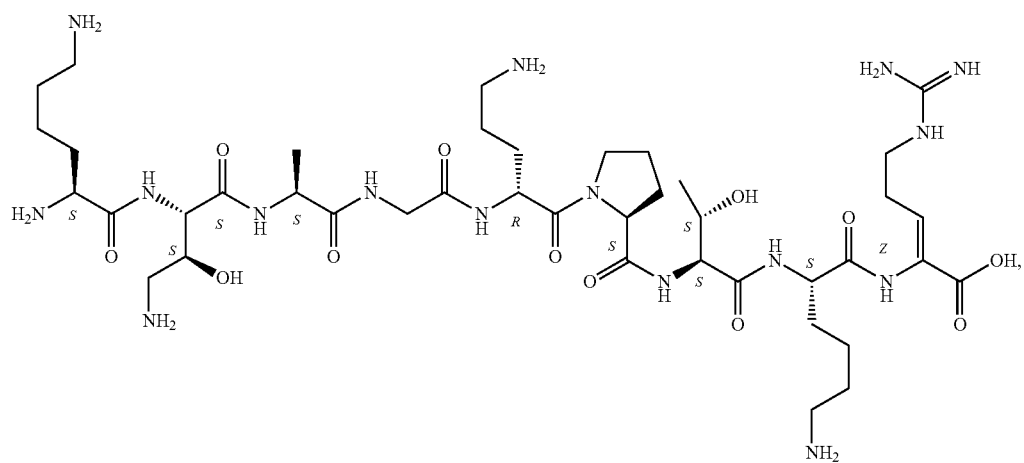
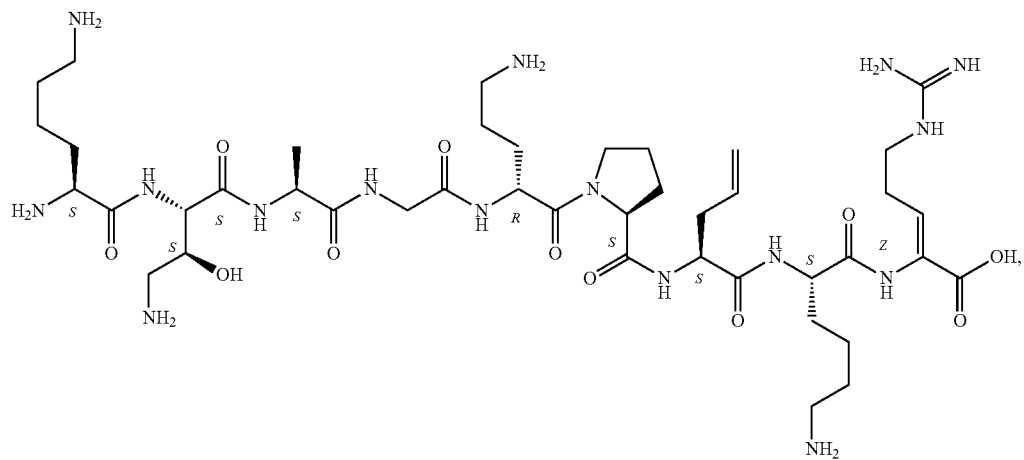

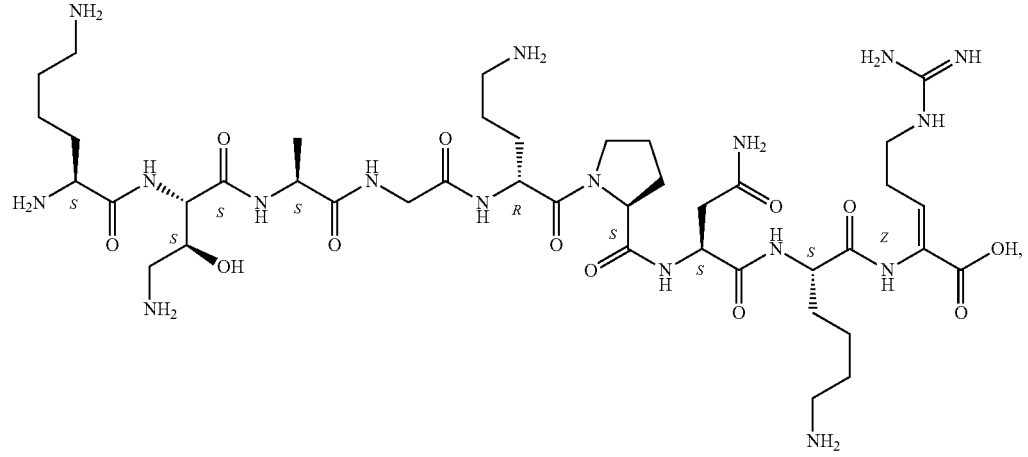
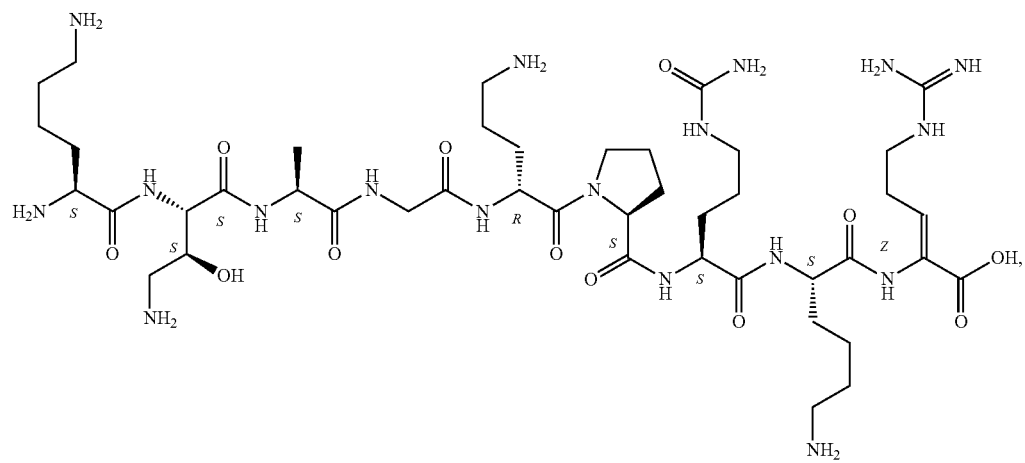
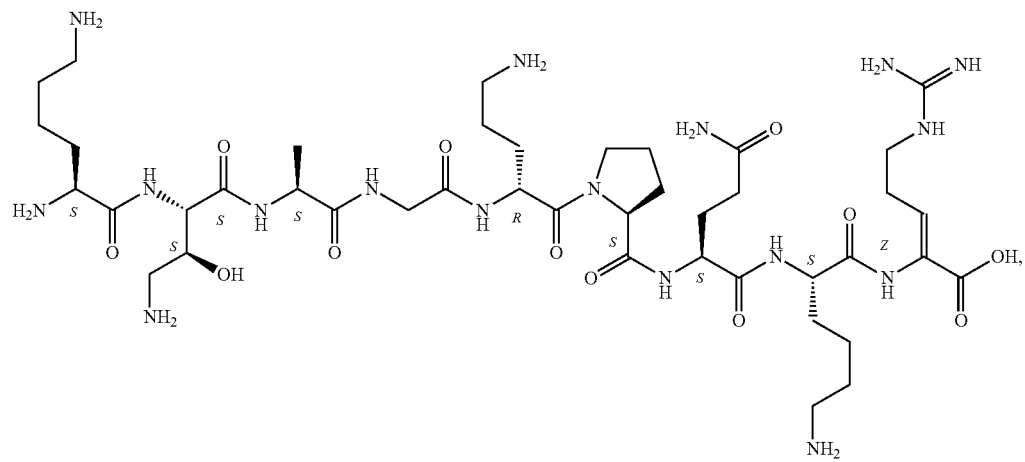

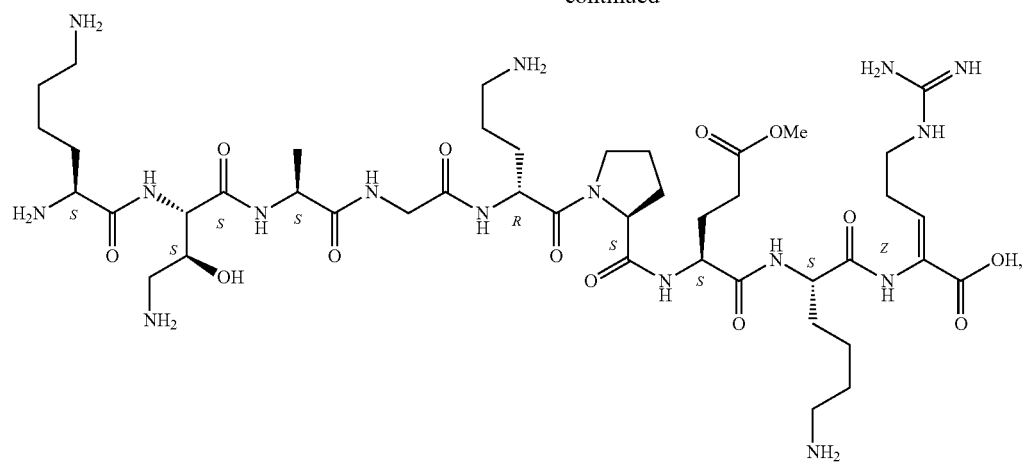
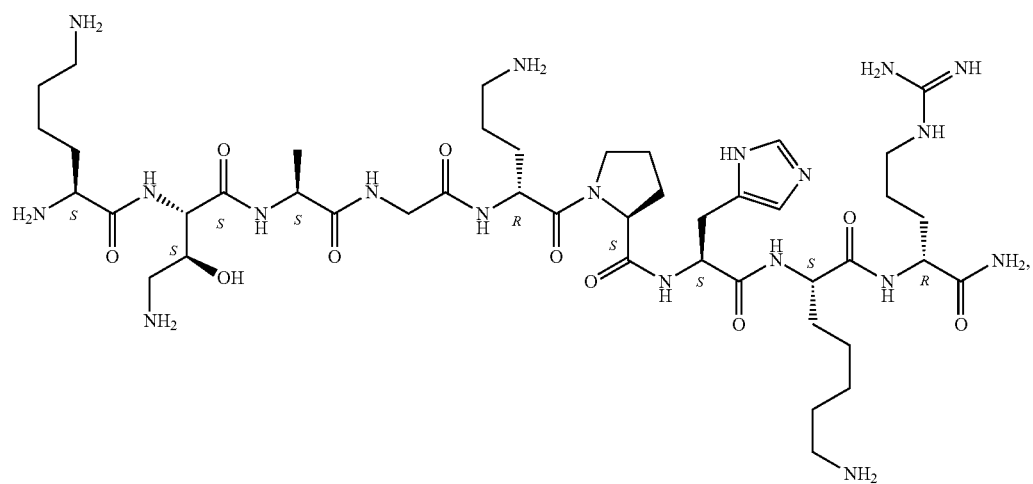
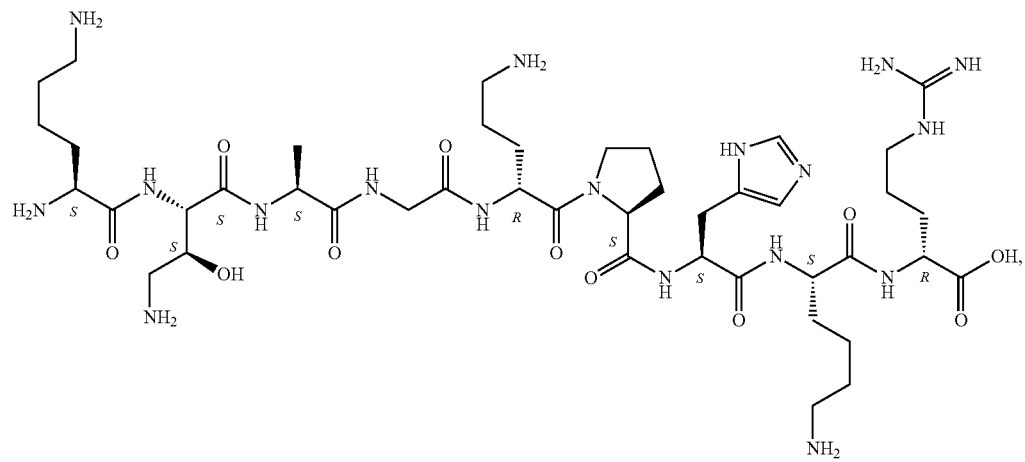

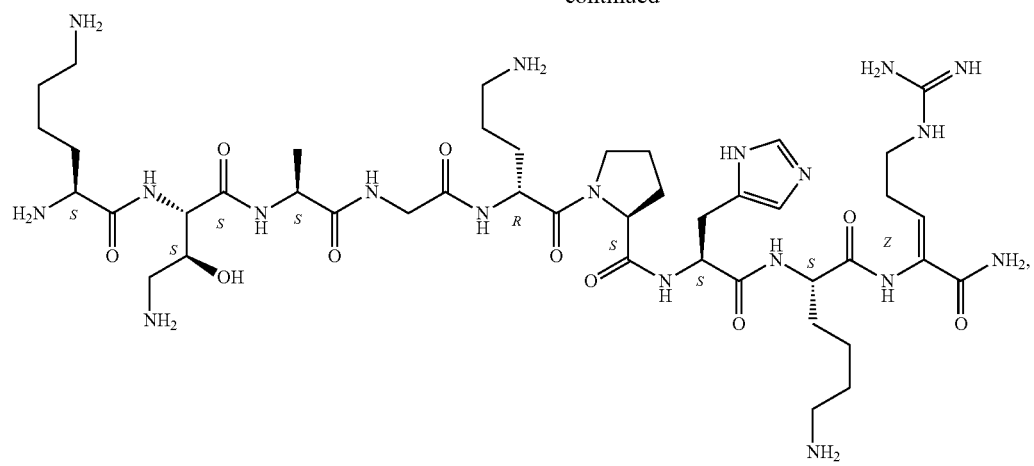
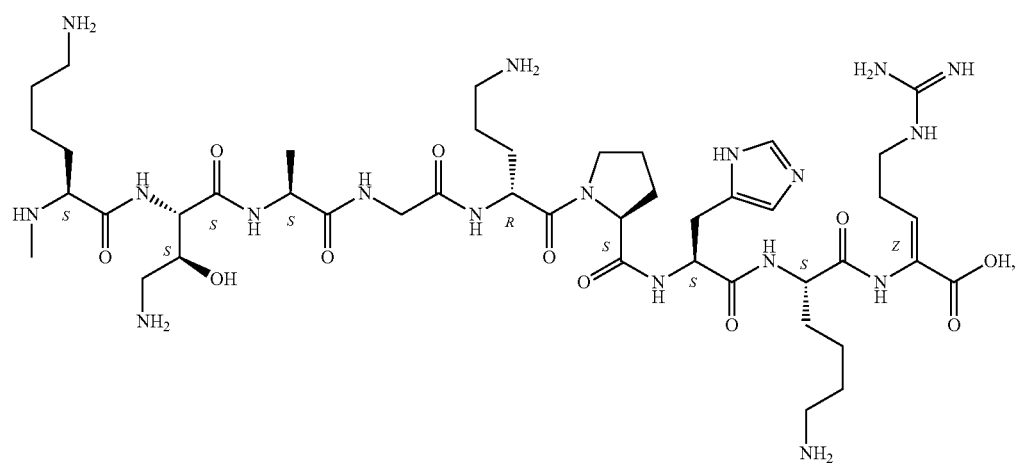
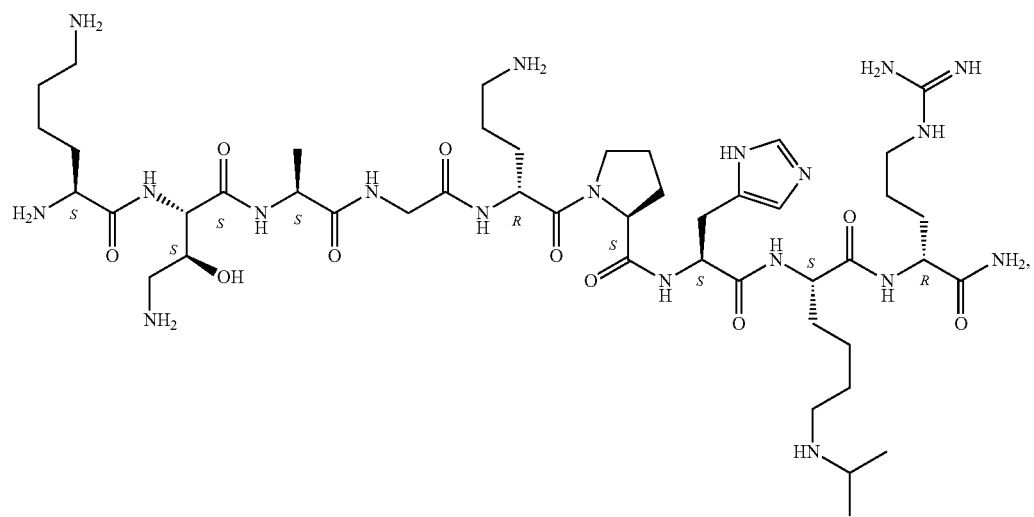

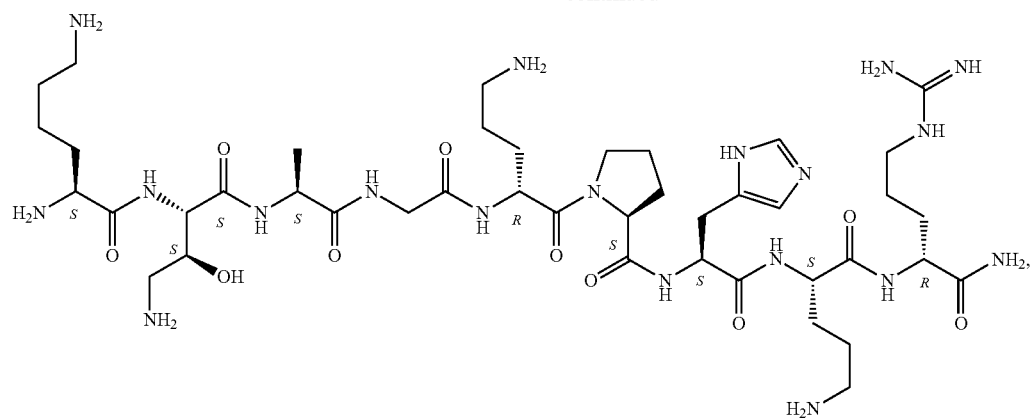
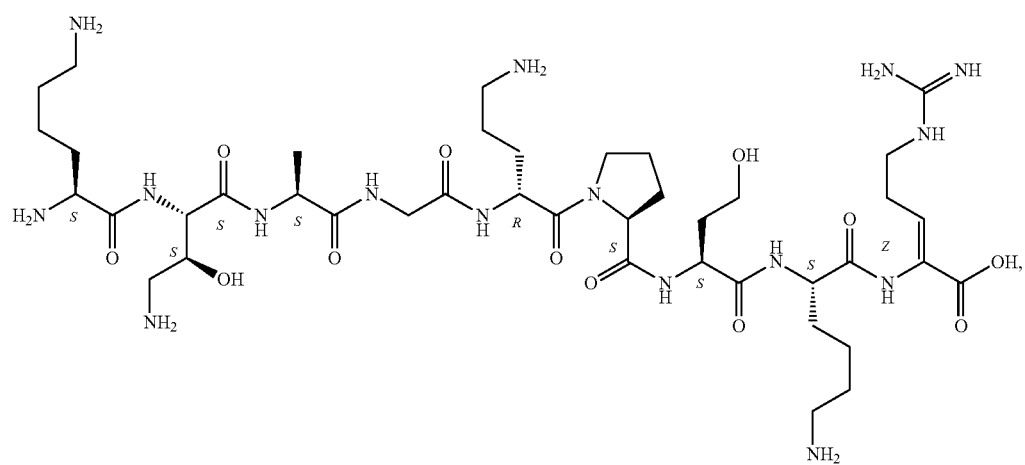
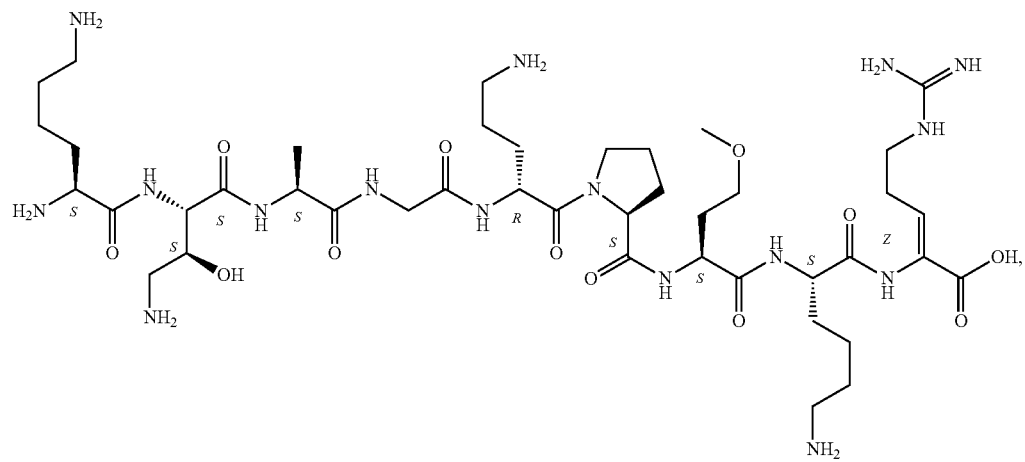

-continued
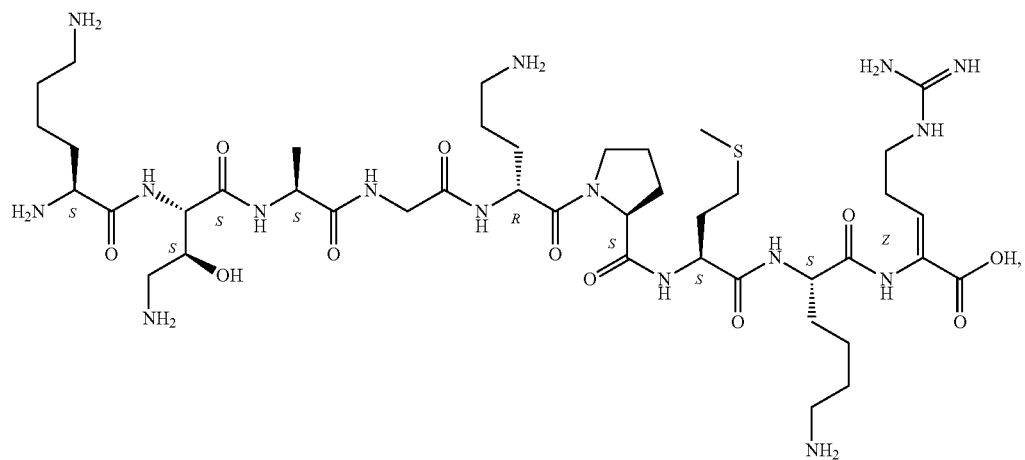
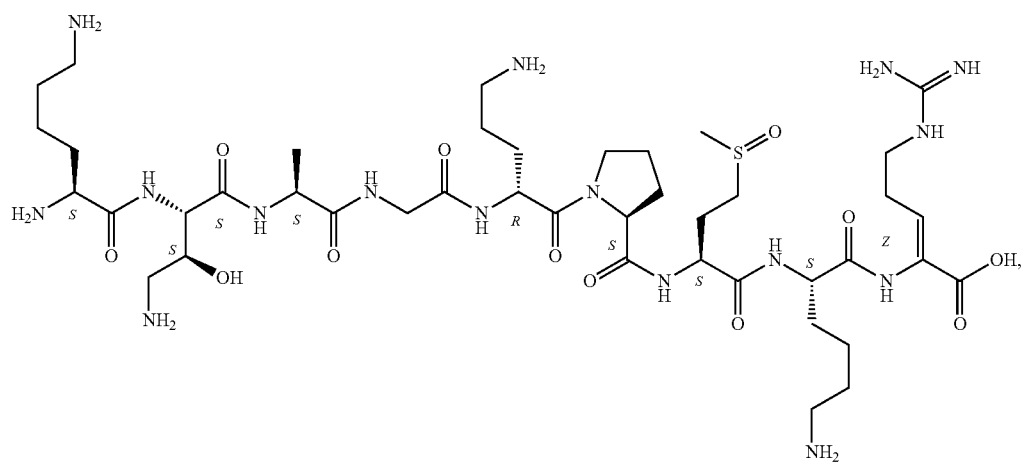
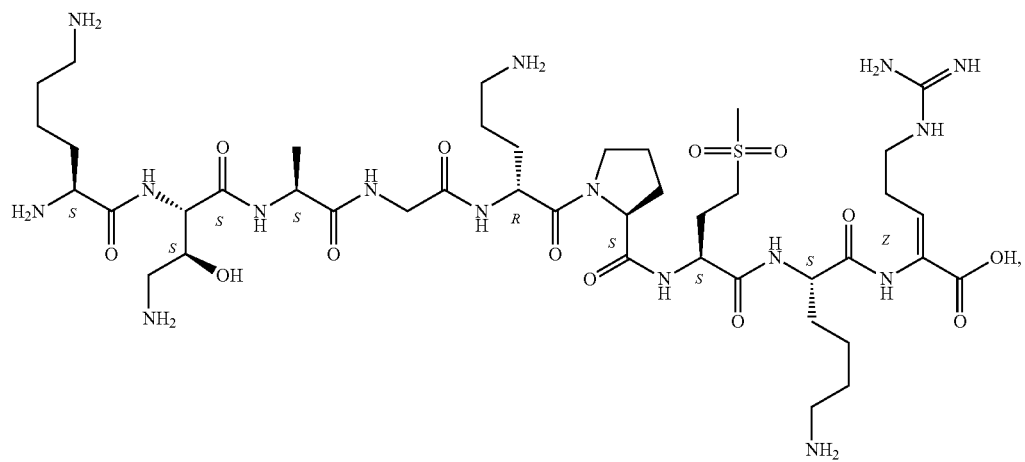

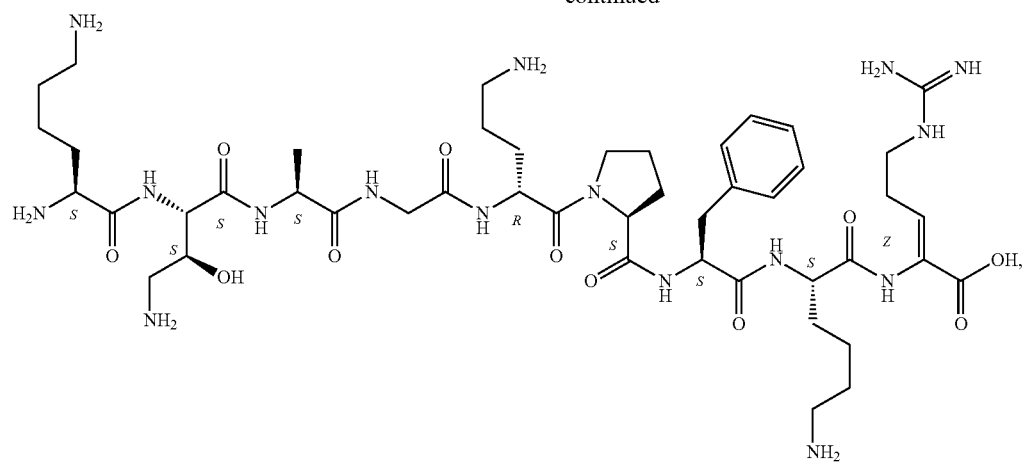
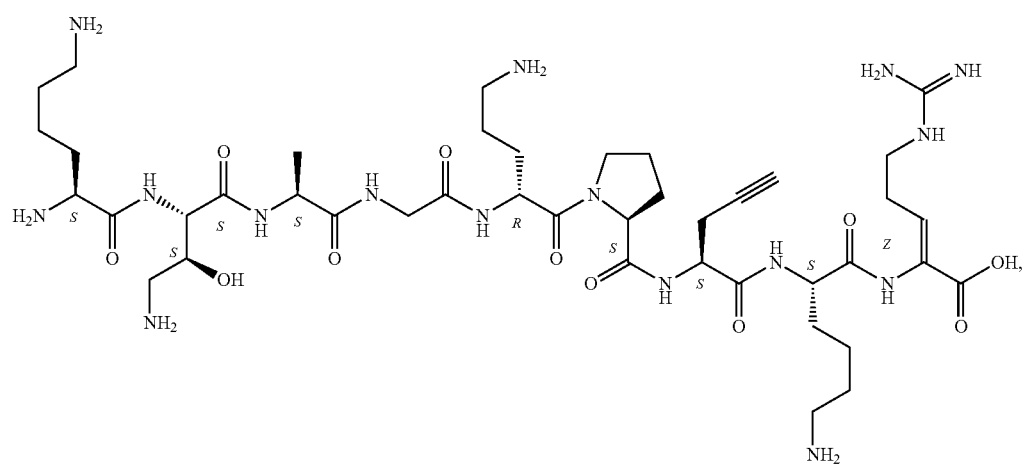
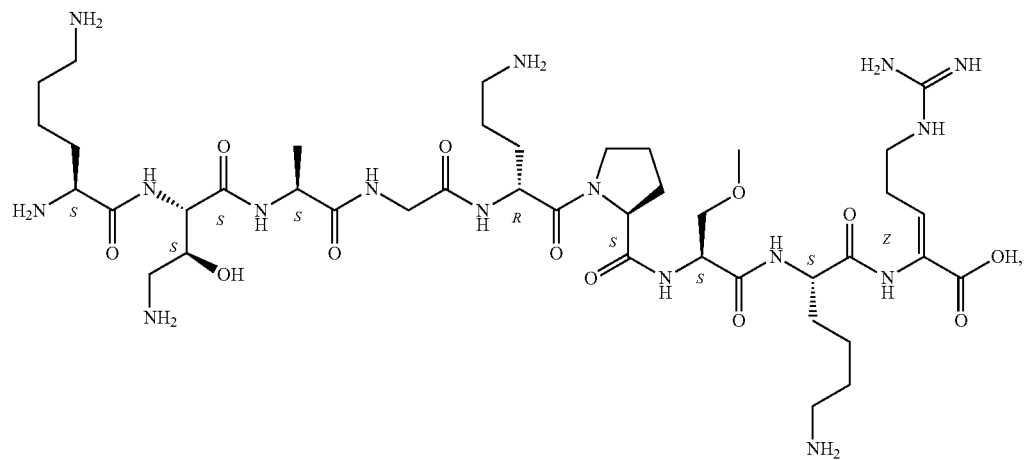

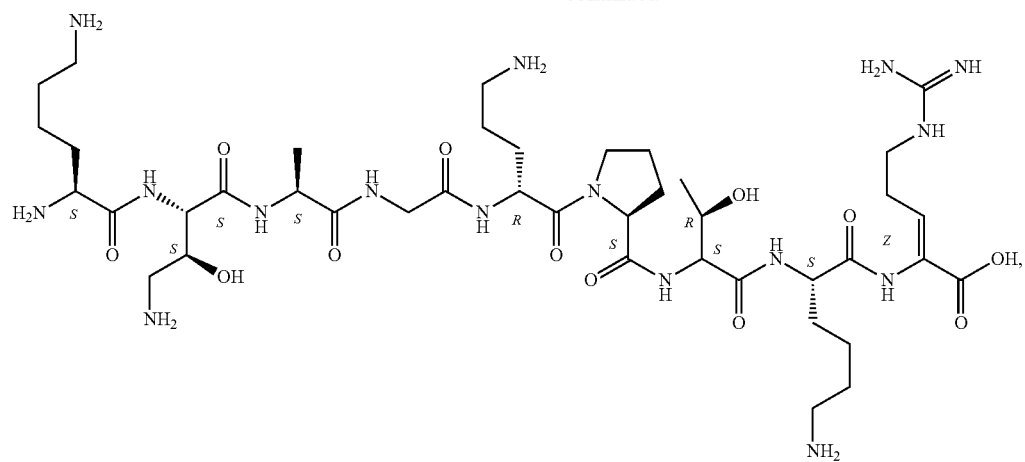
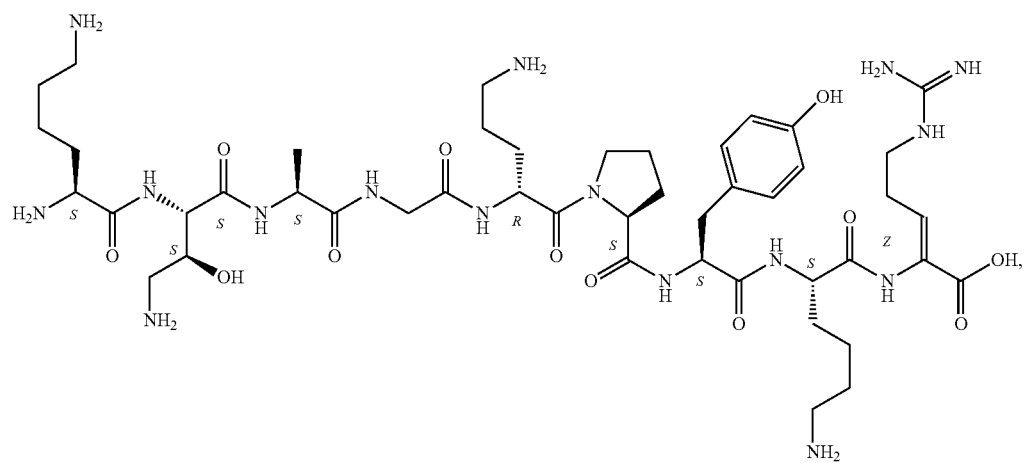
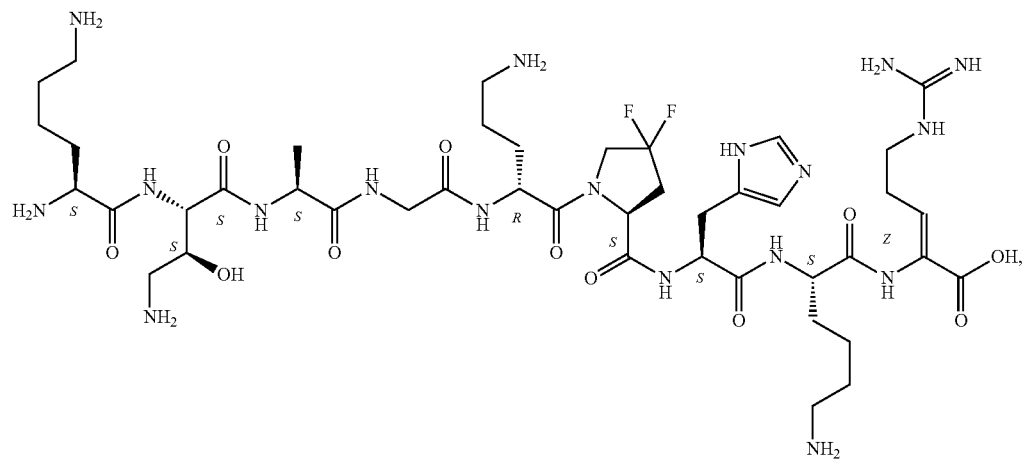

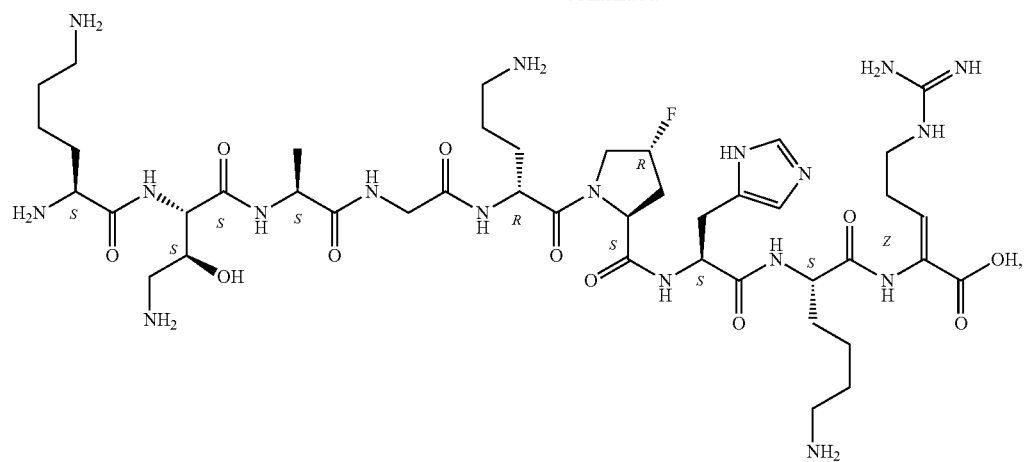
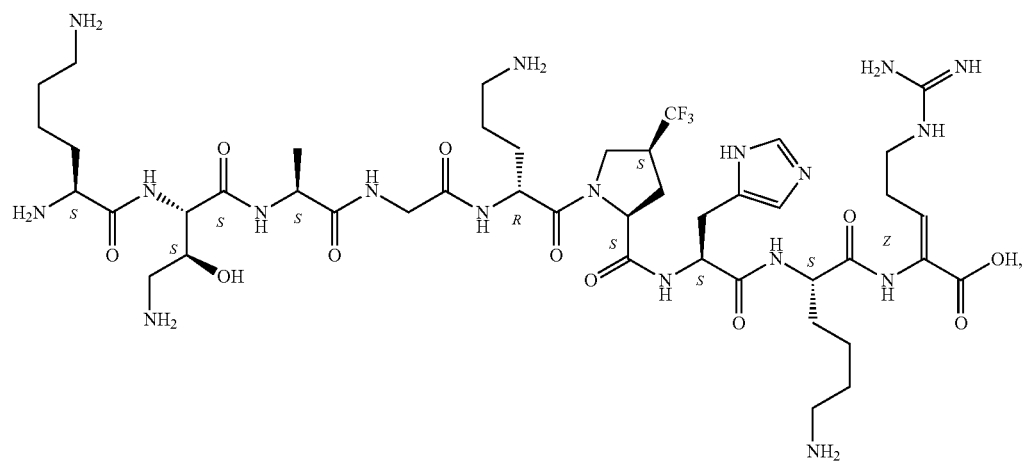
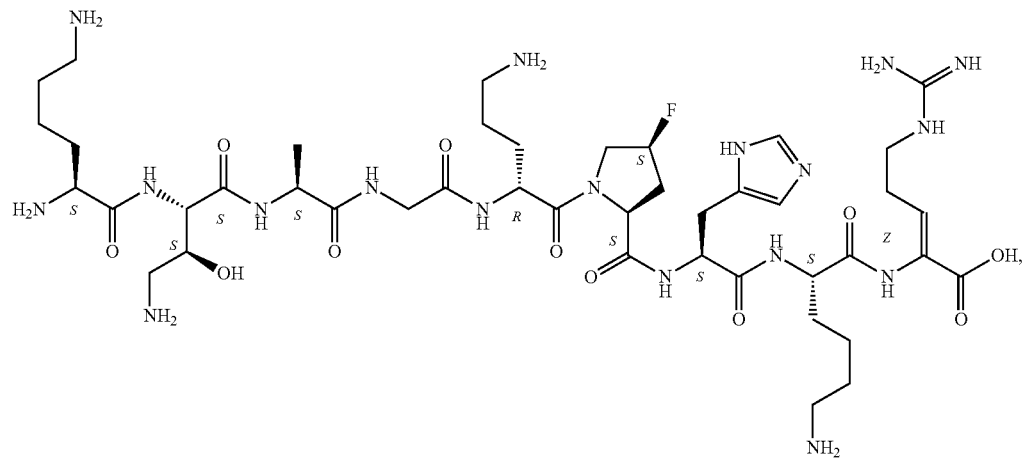

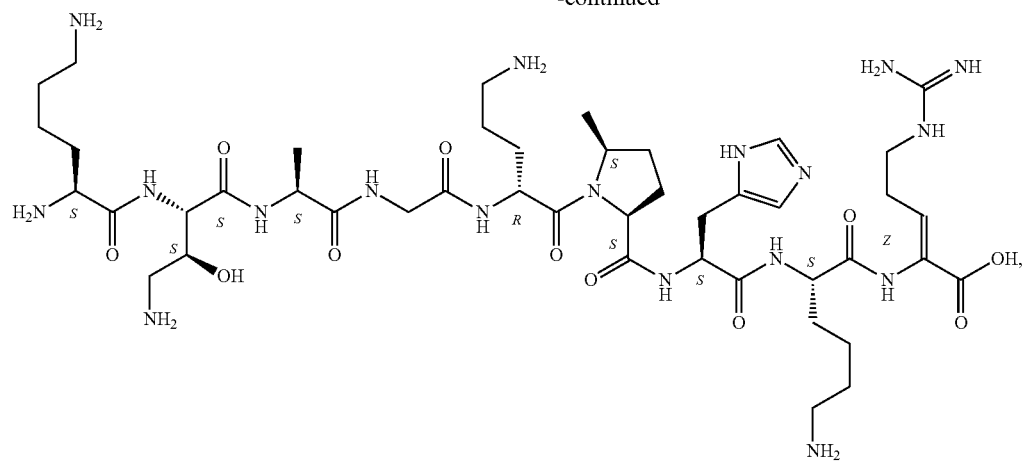
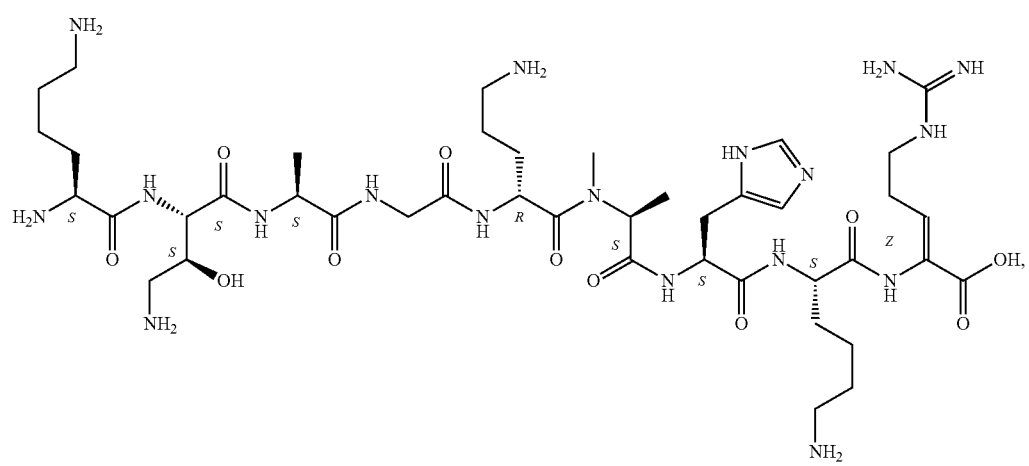
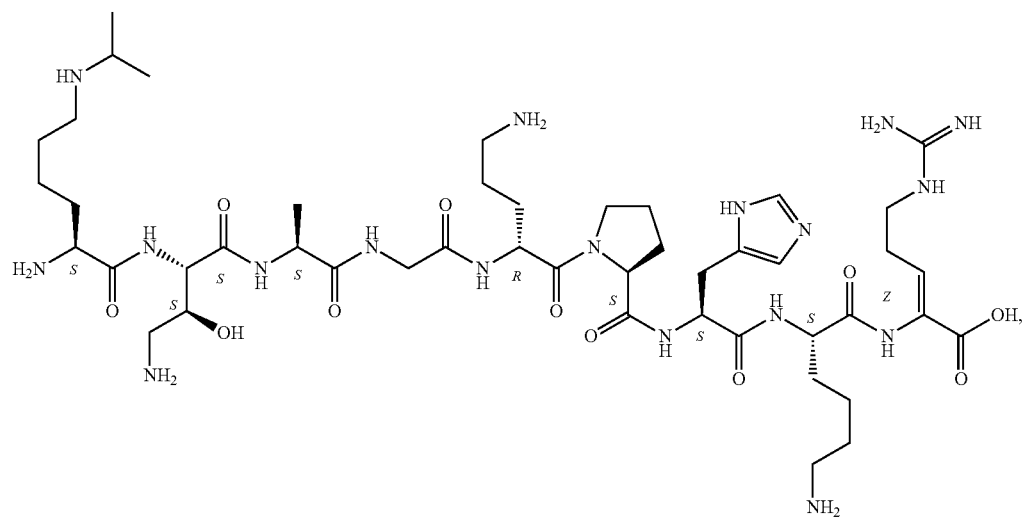

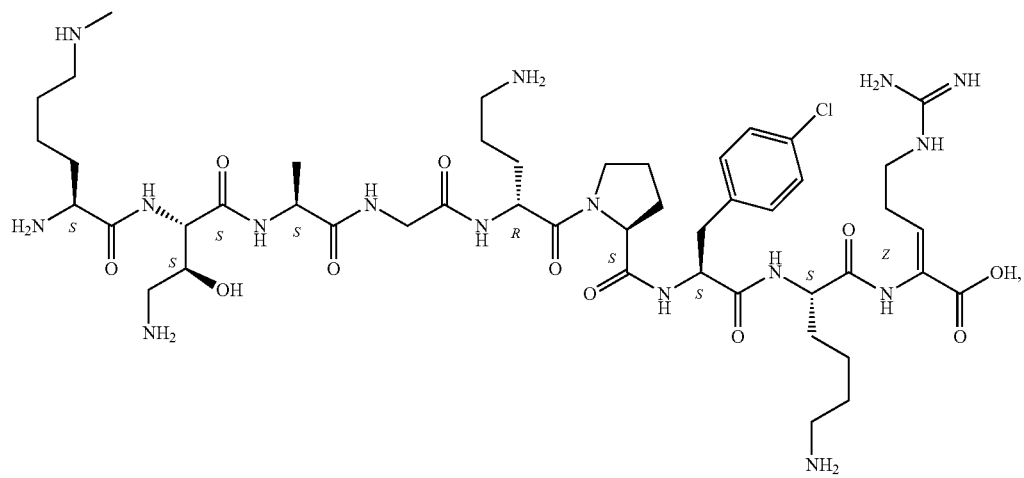
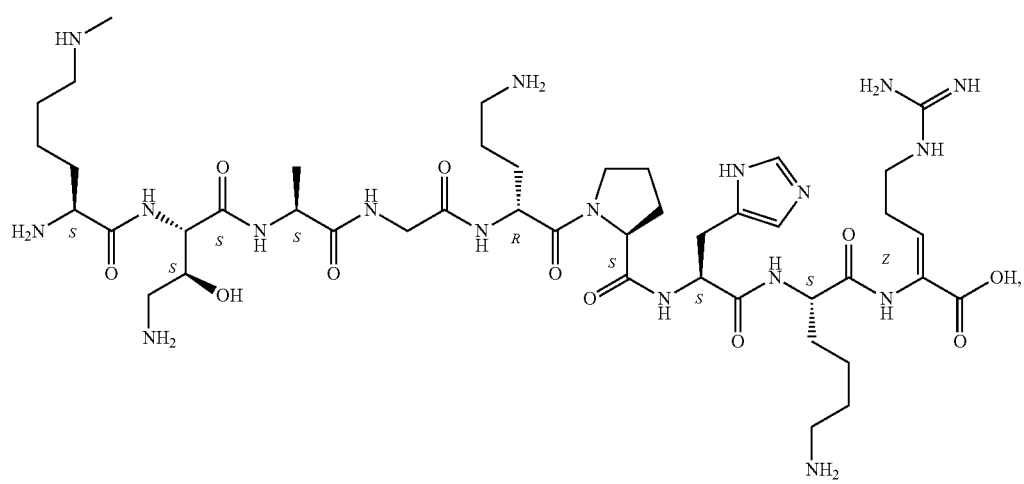
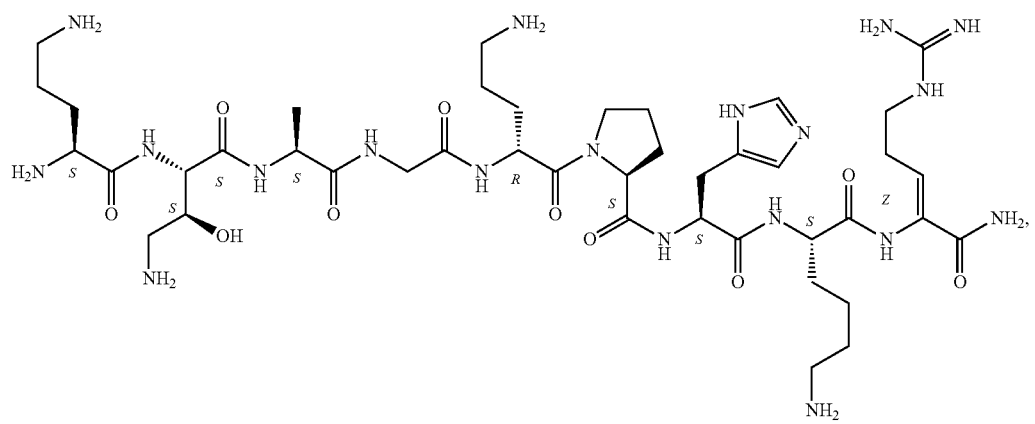

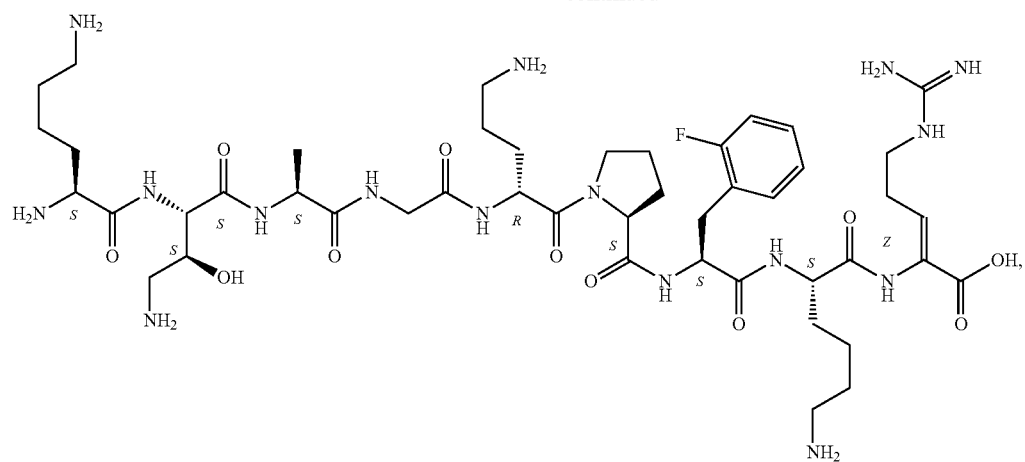
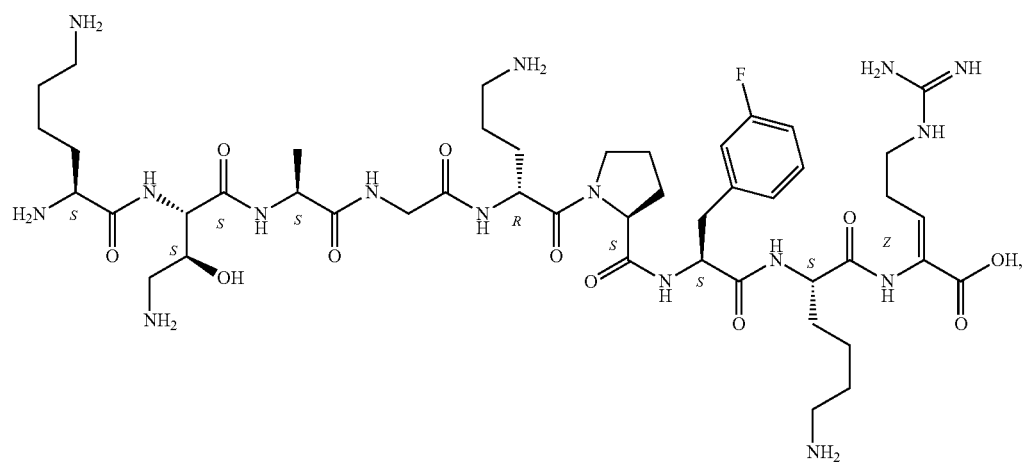
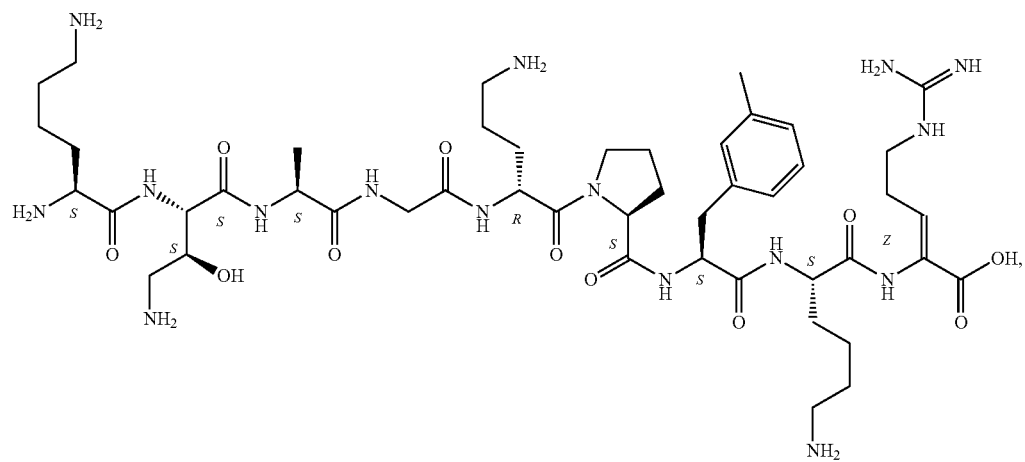

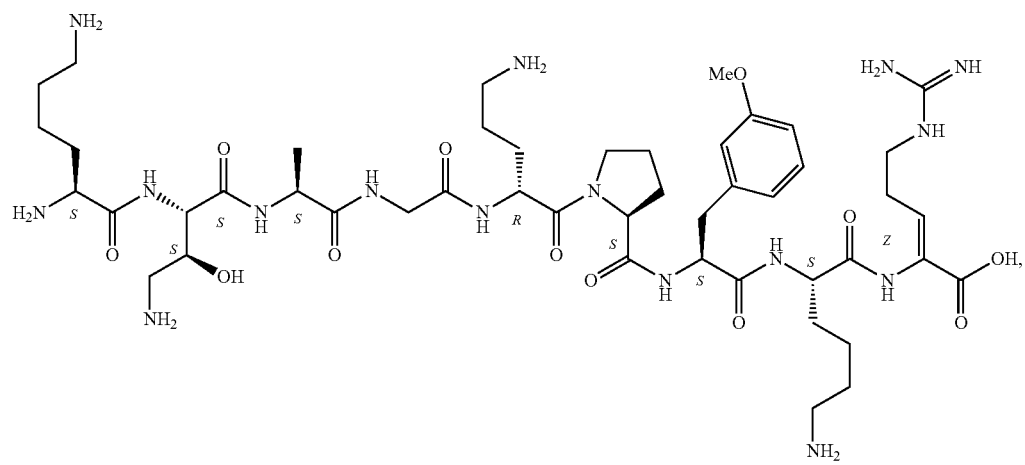
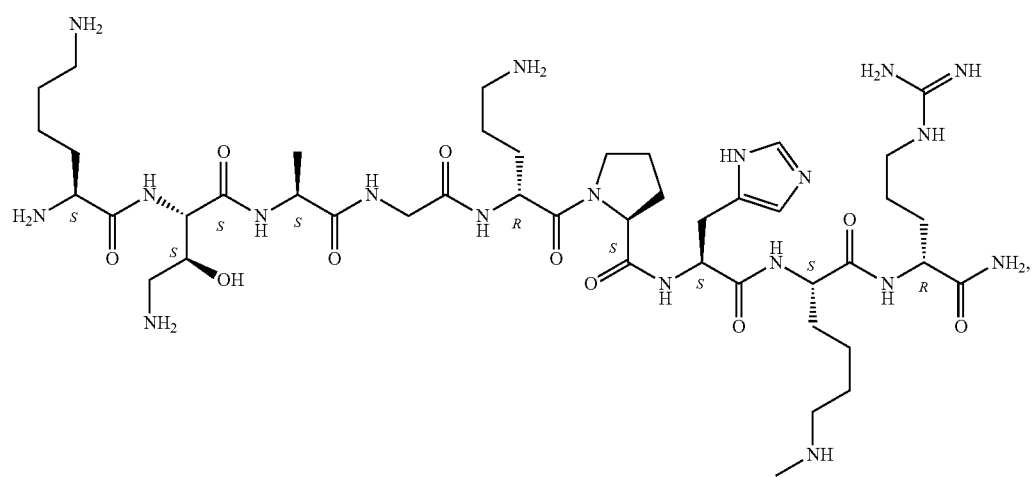
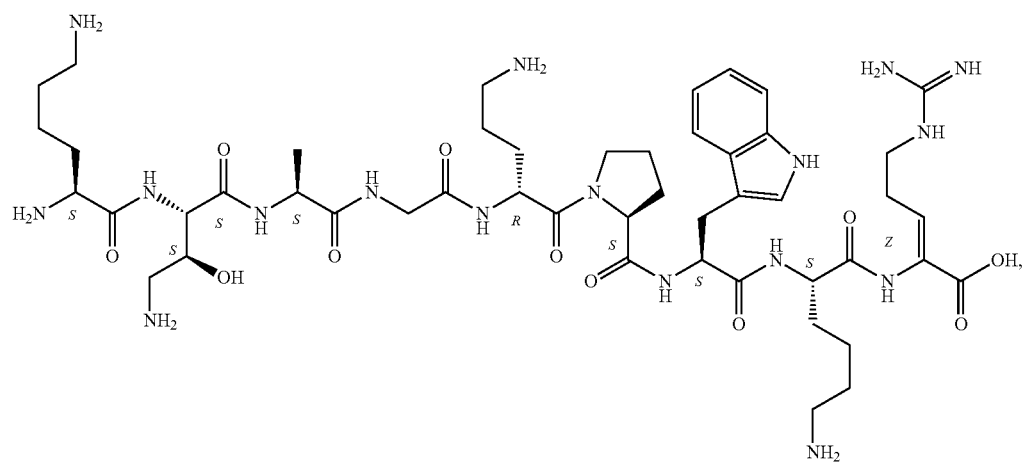

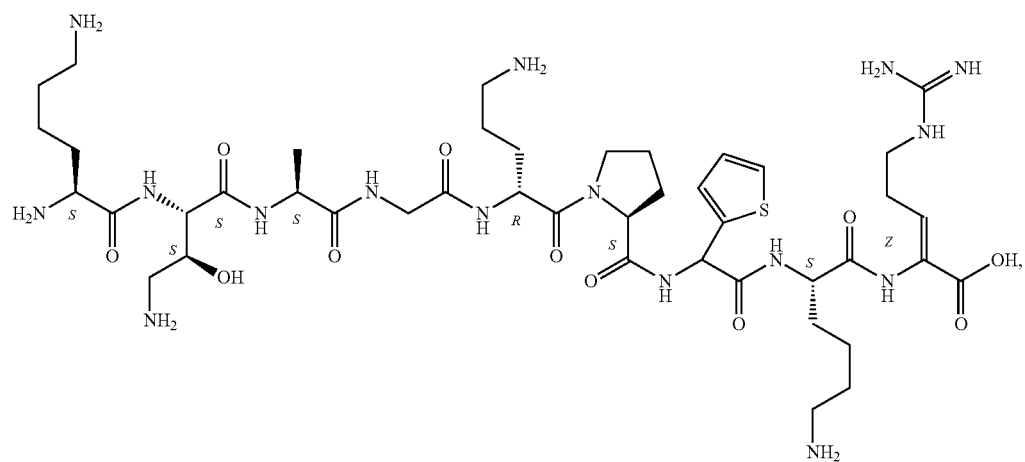
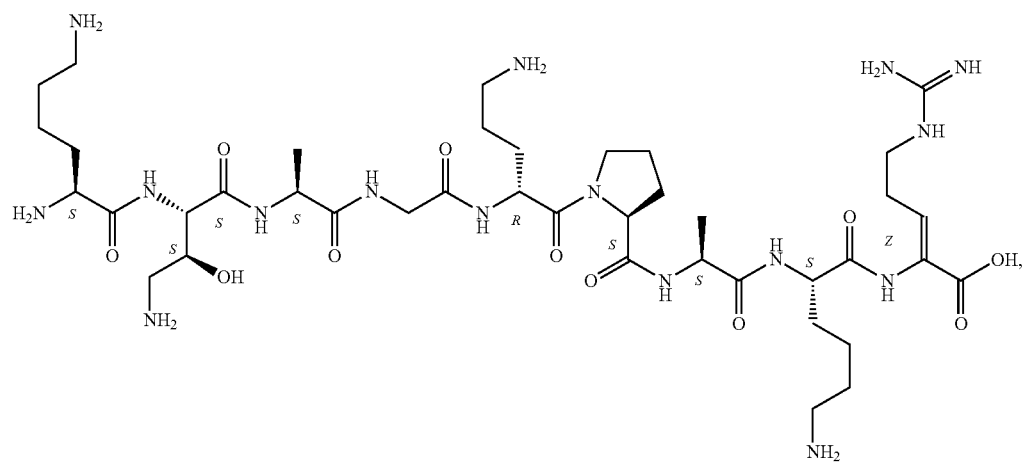
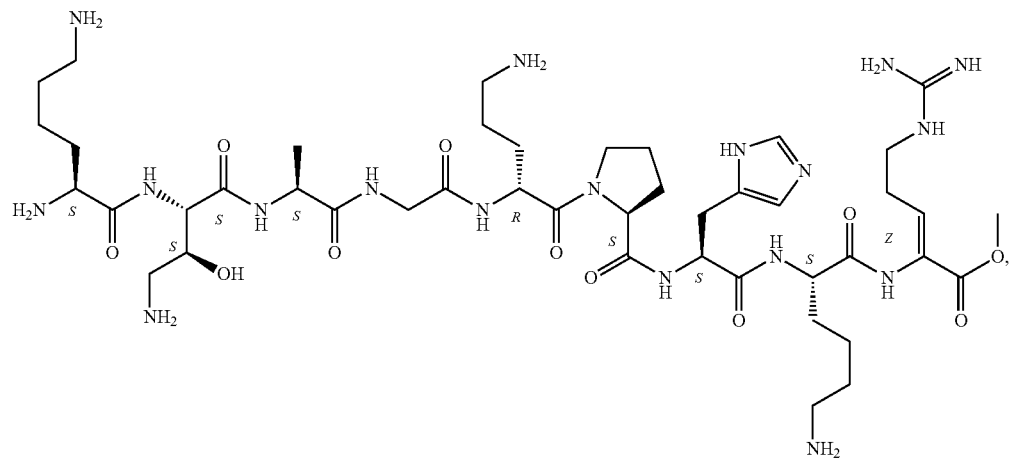

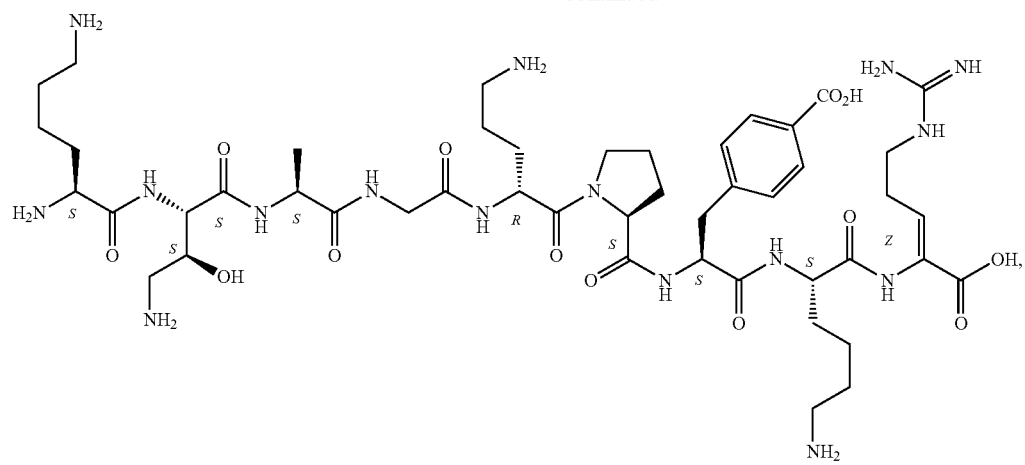
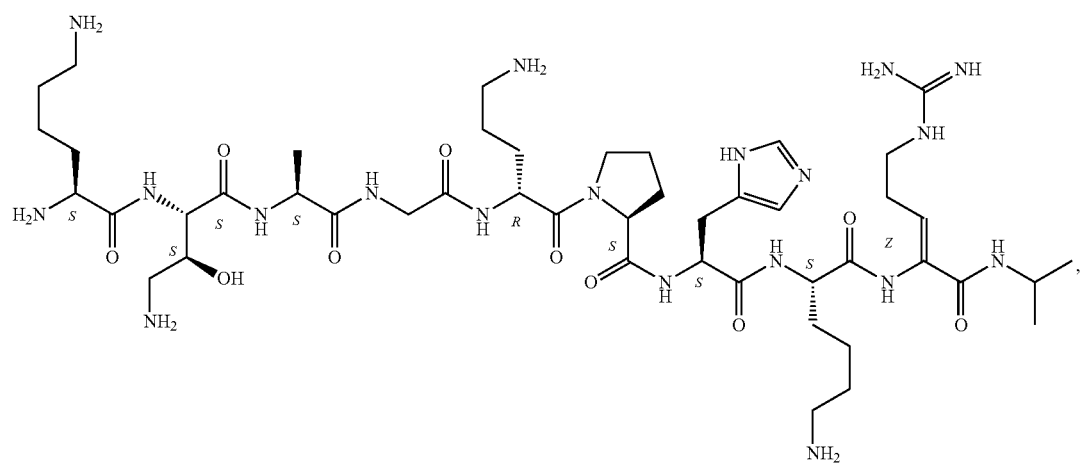
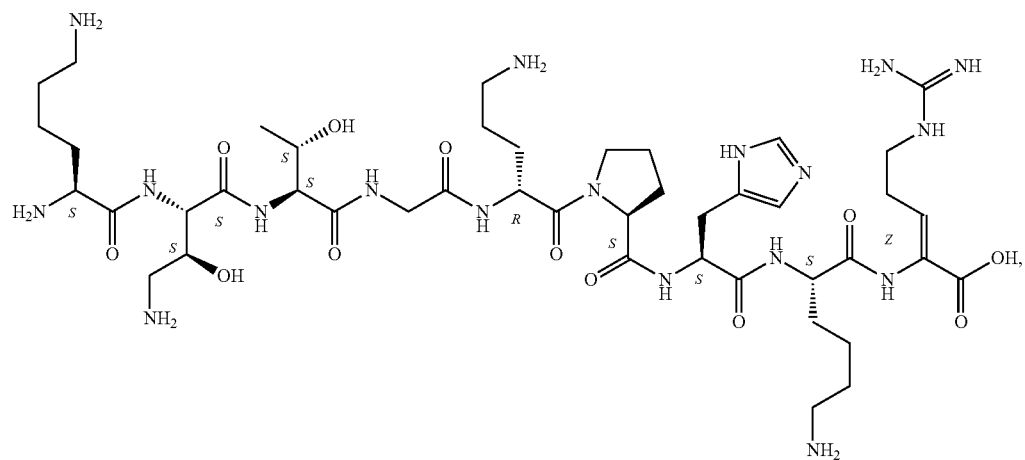

-continued
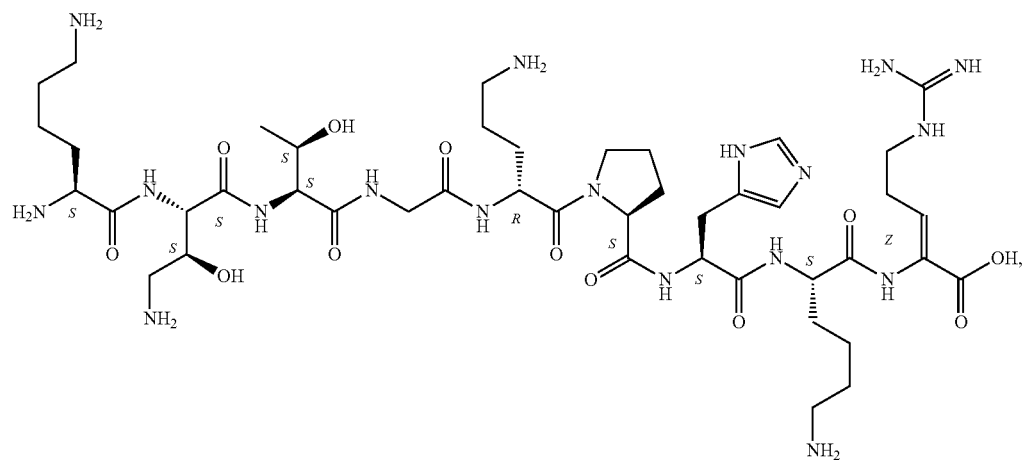
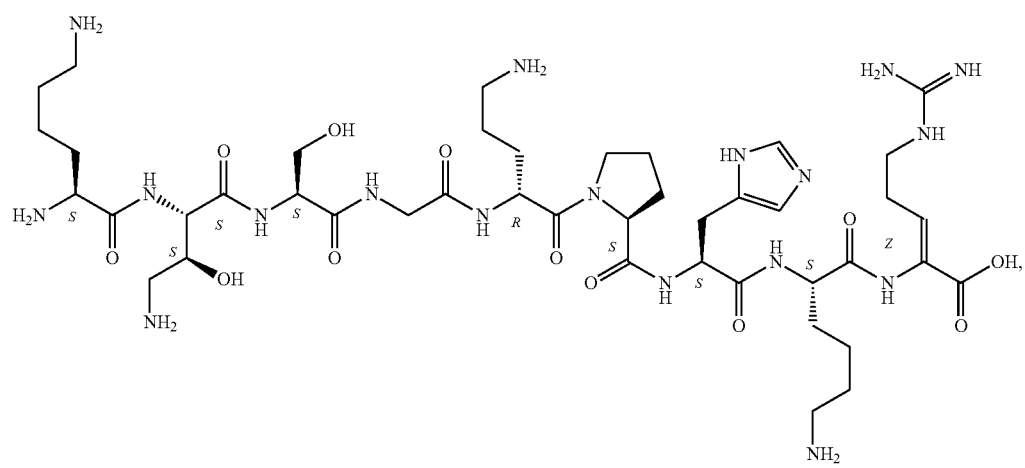
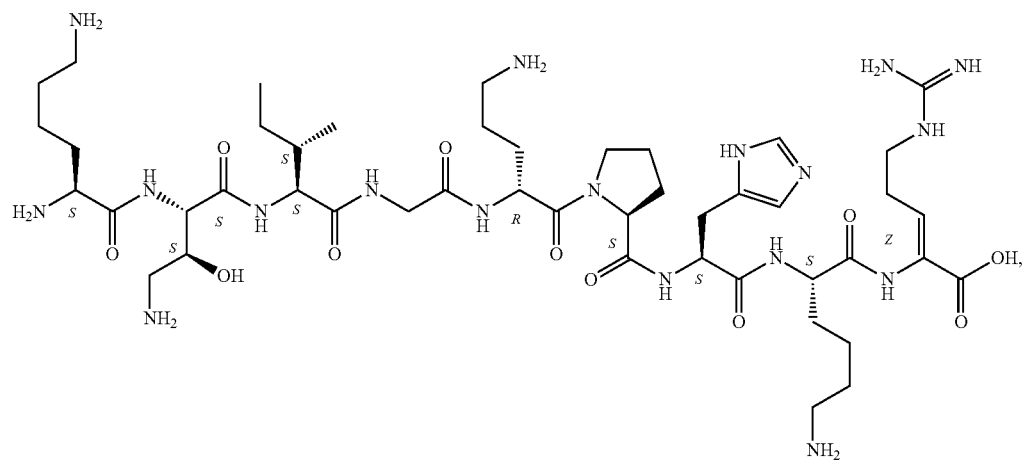

-continued
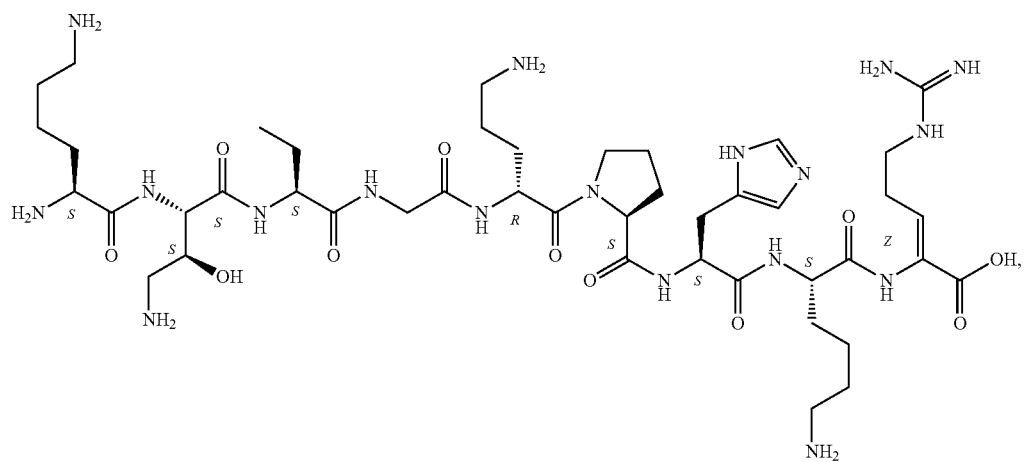
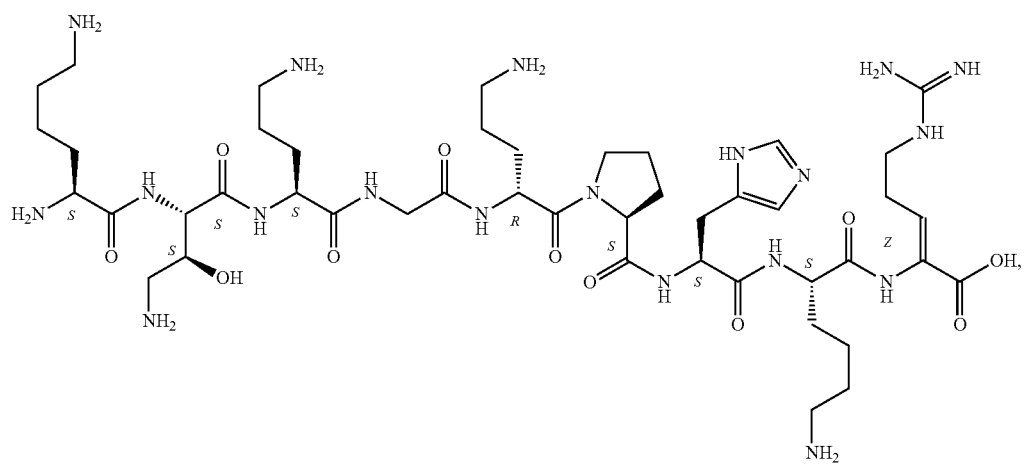
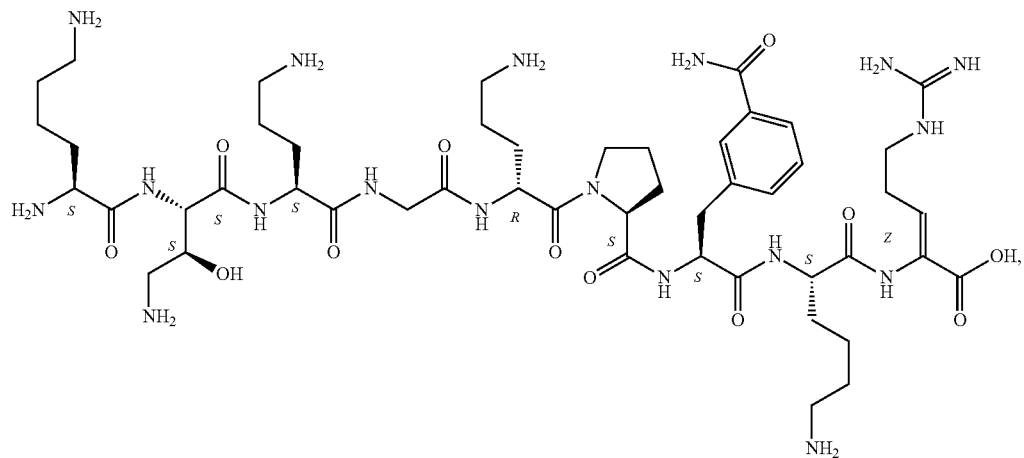

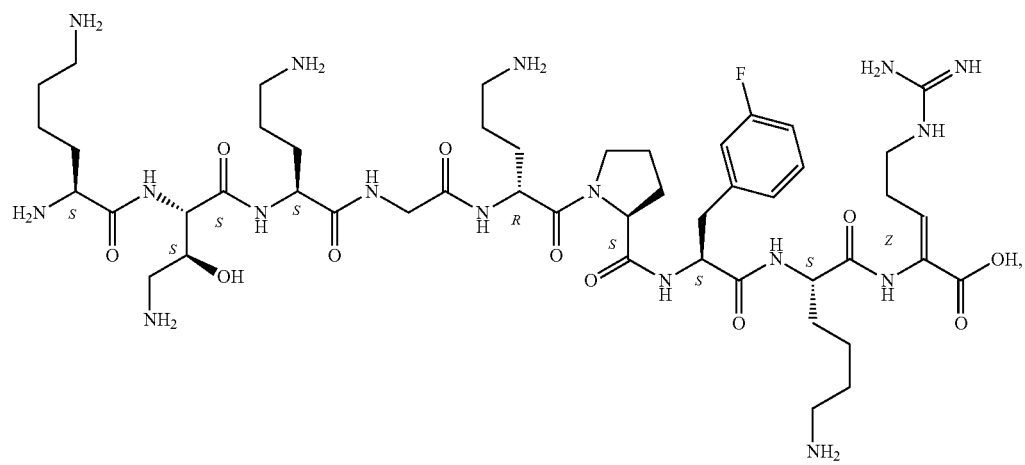
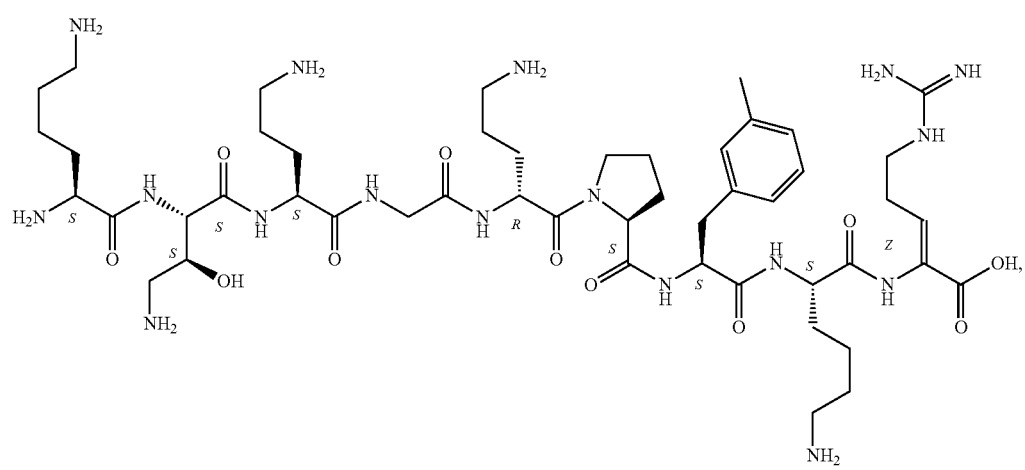
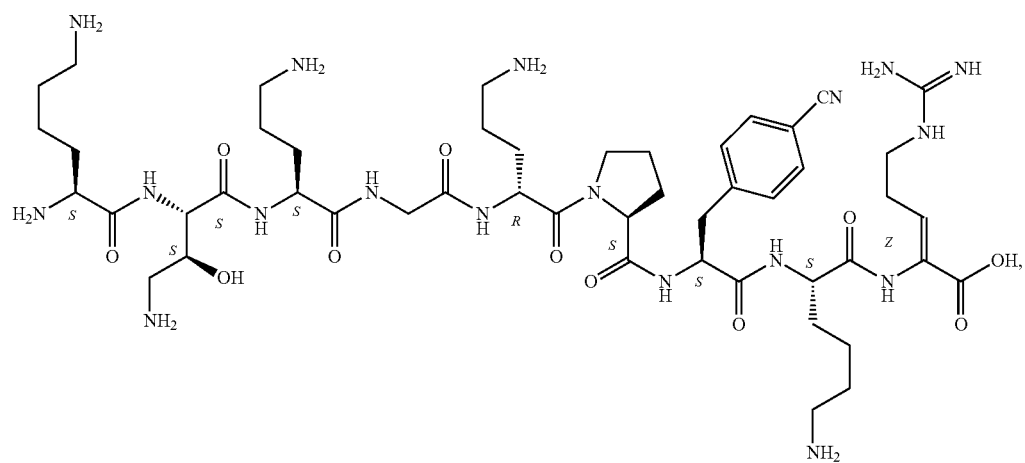

-continued
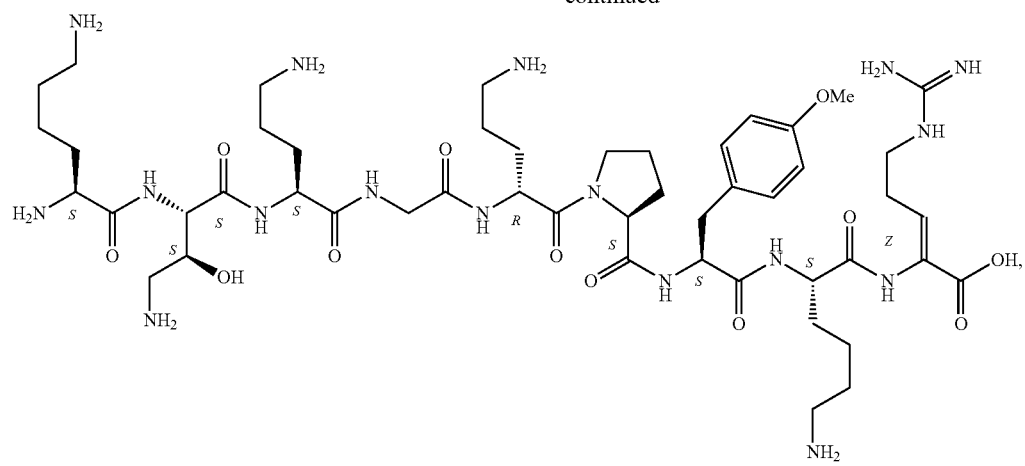
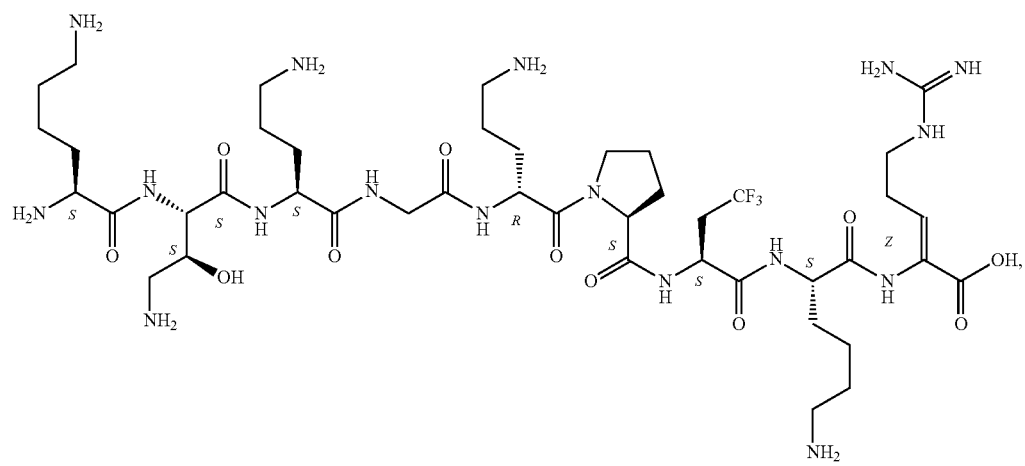
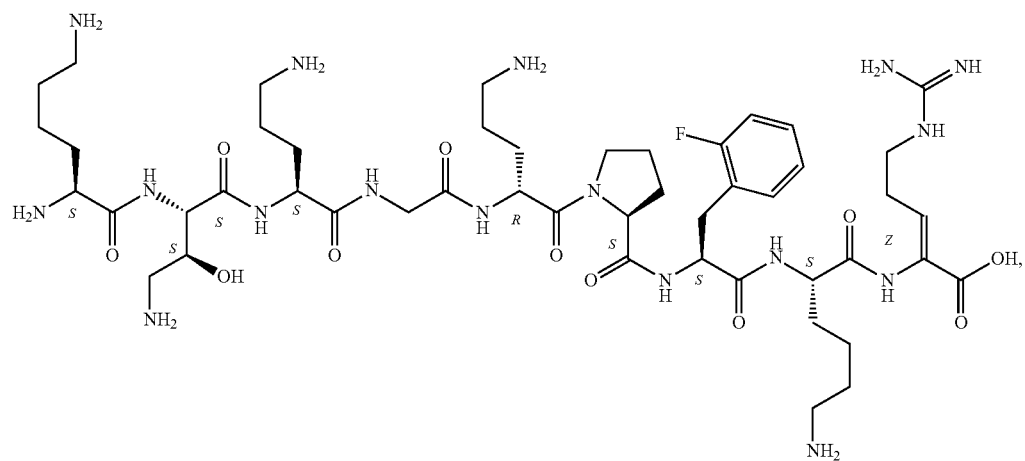

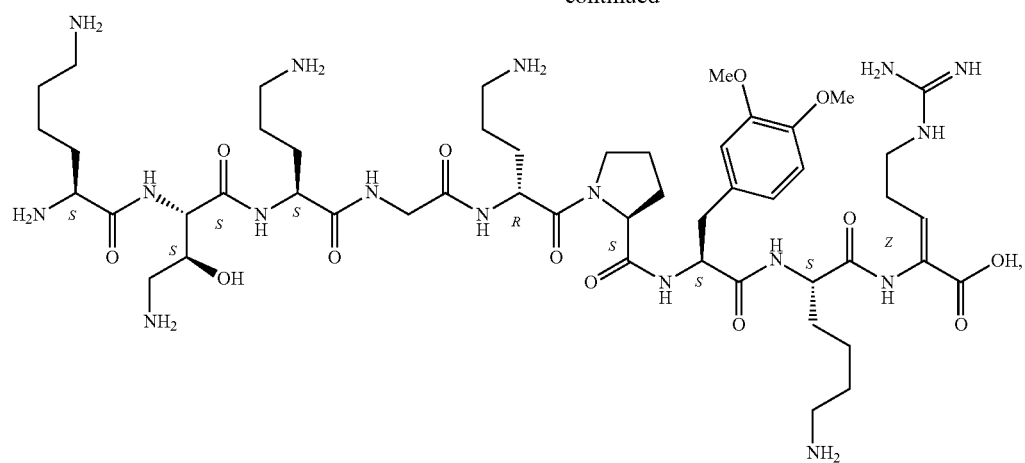
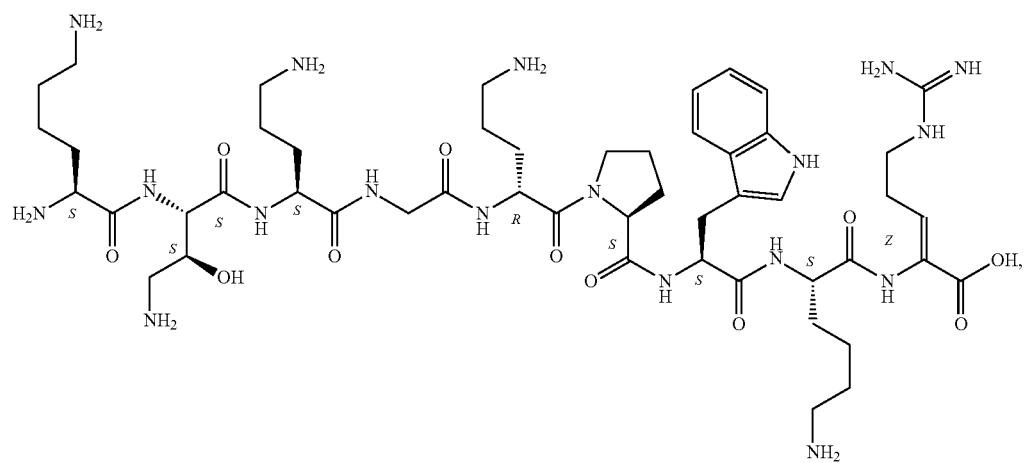
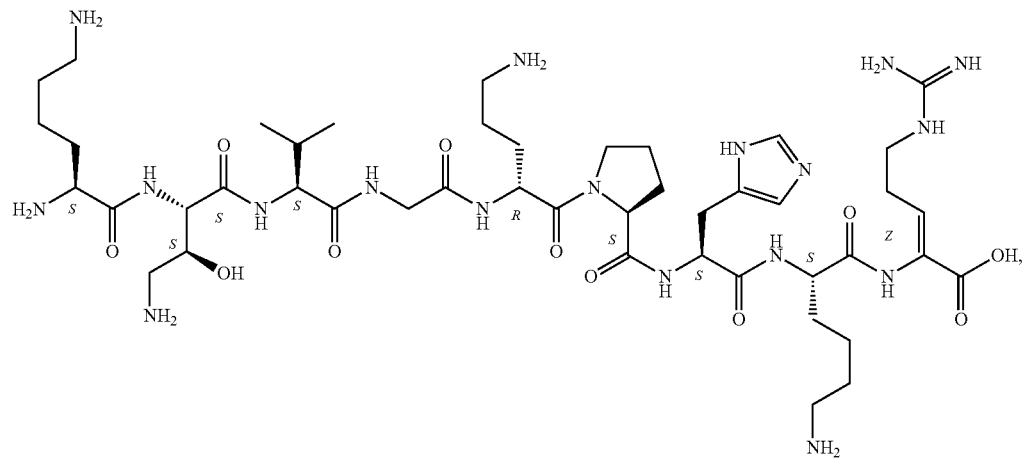

-continued
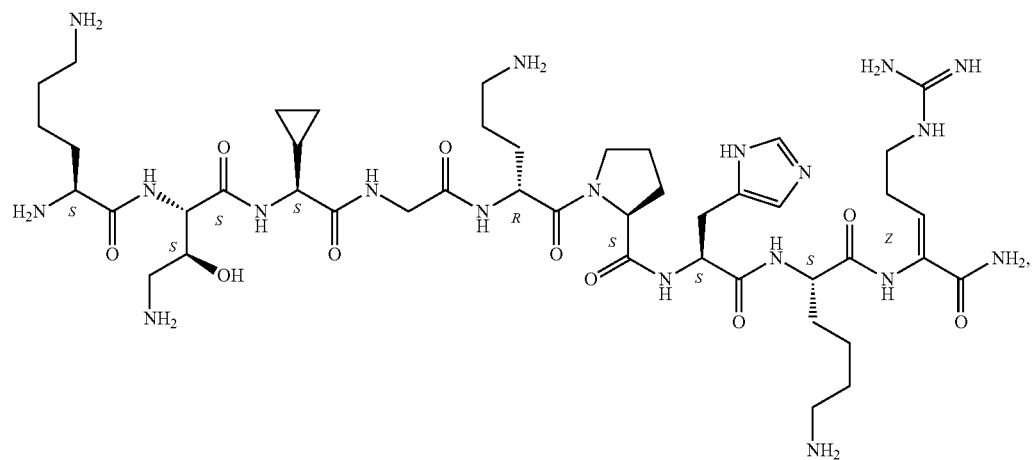
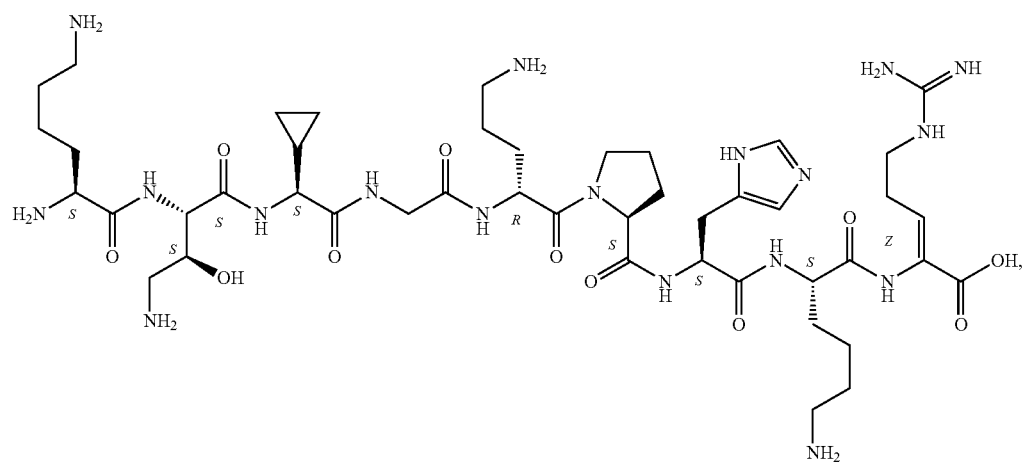
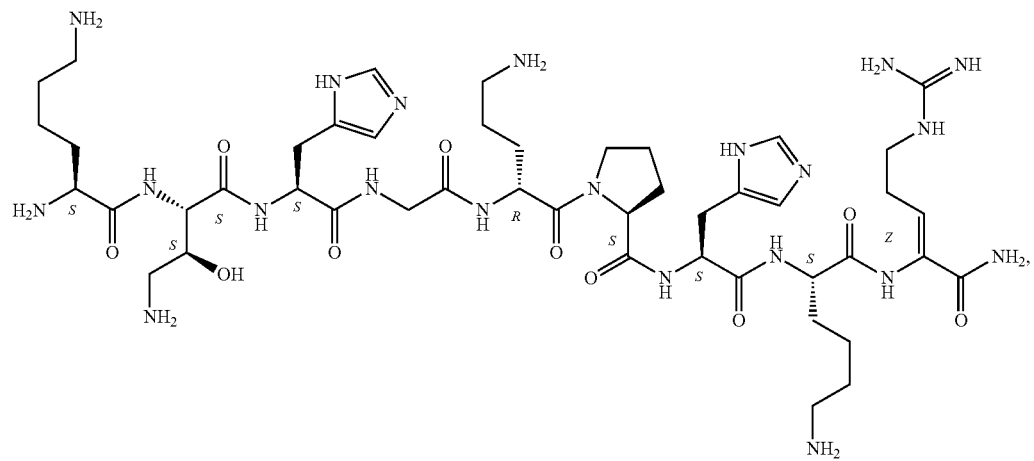

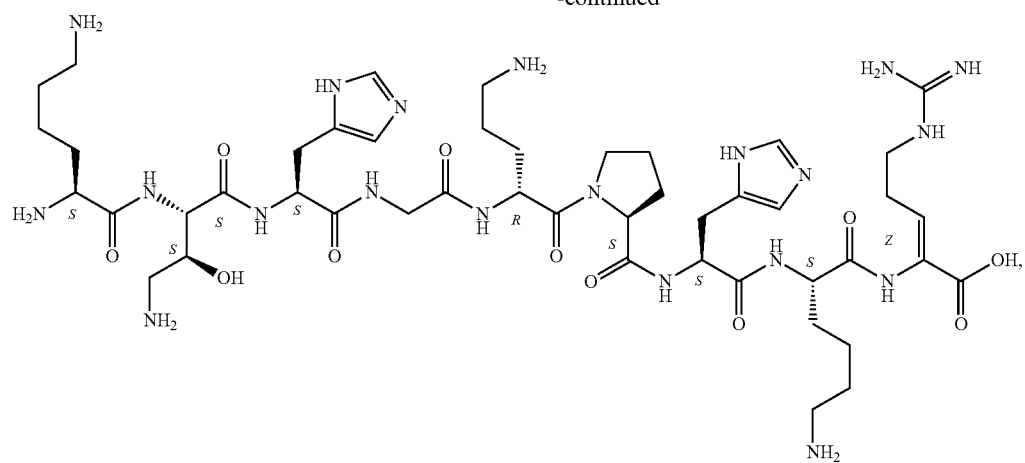
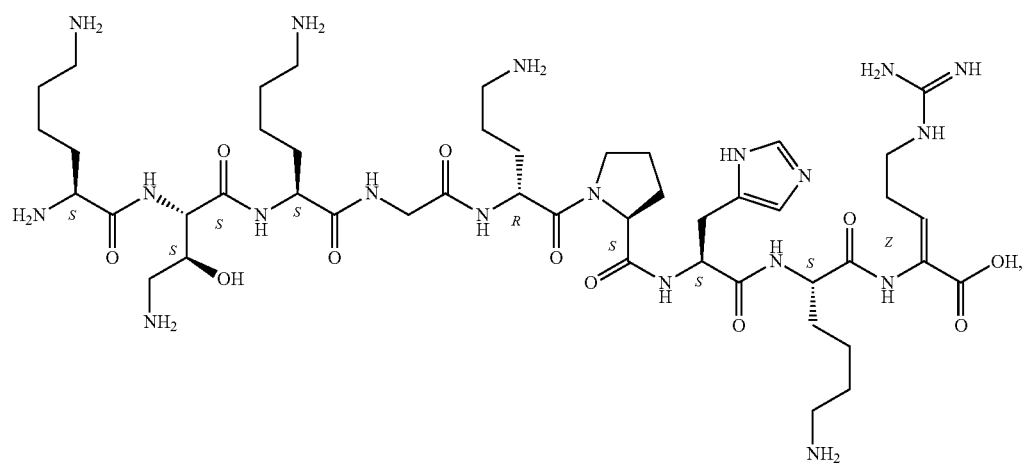
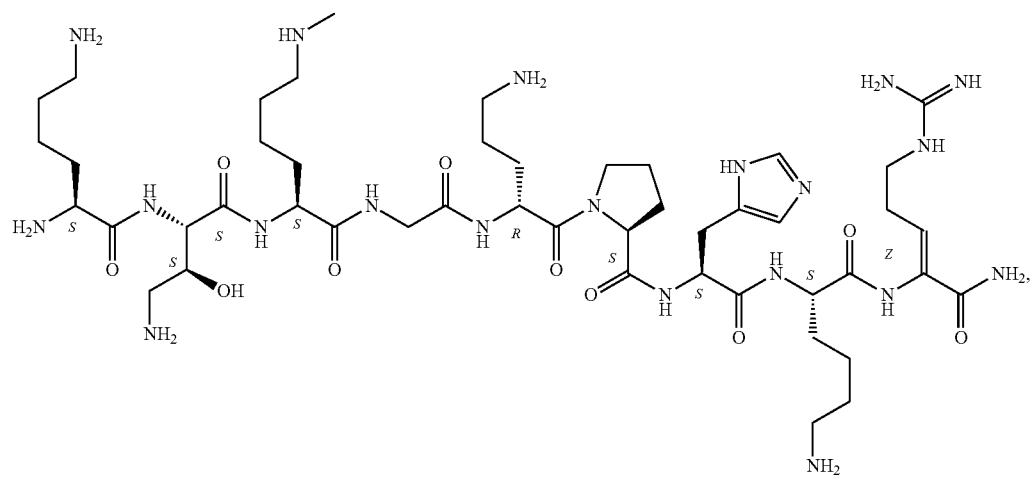

-continued
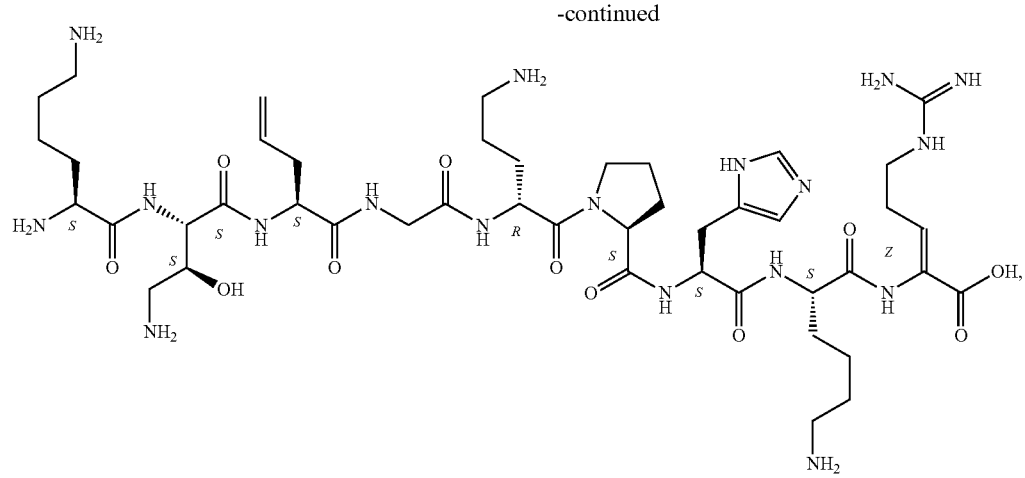
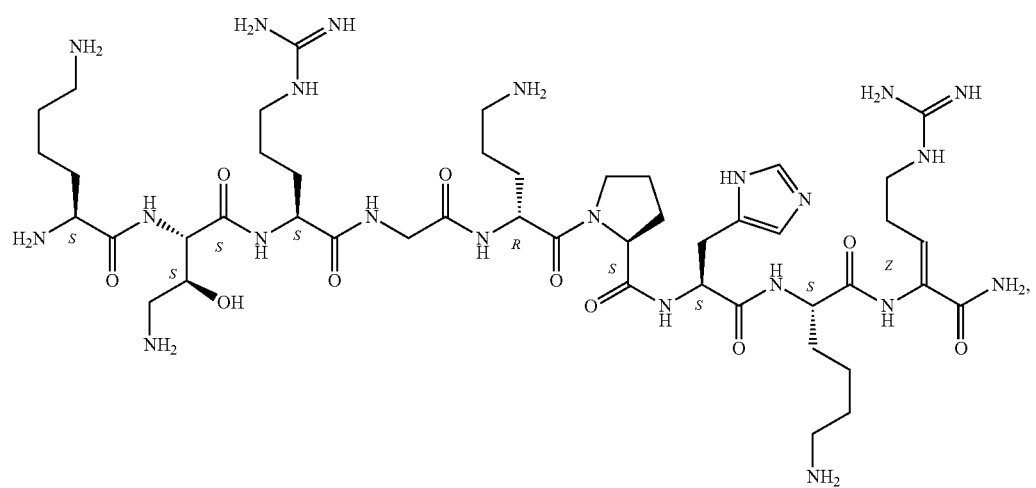
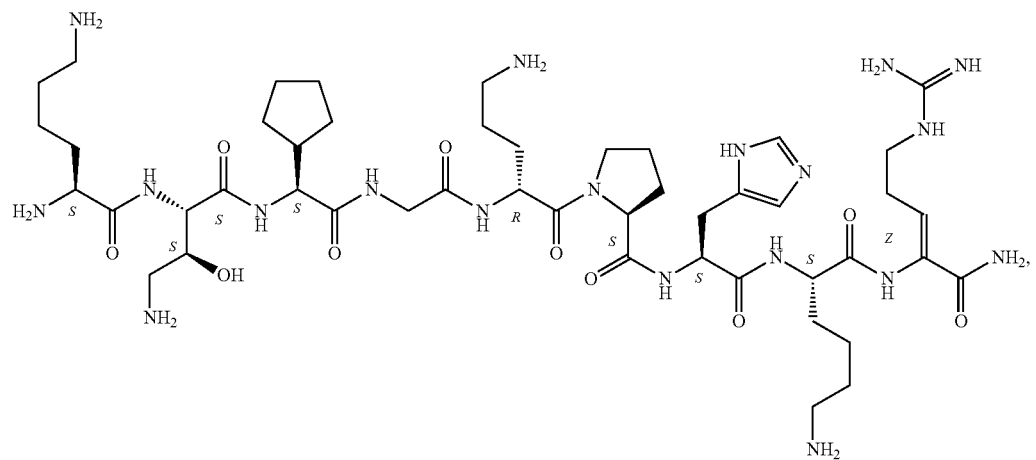

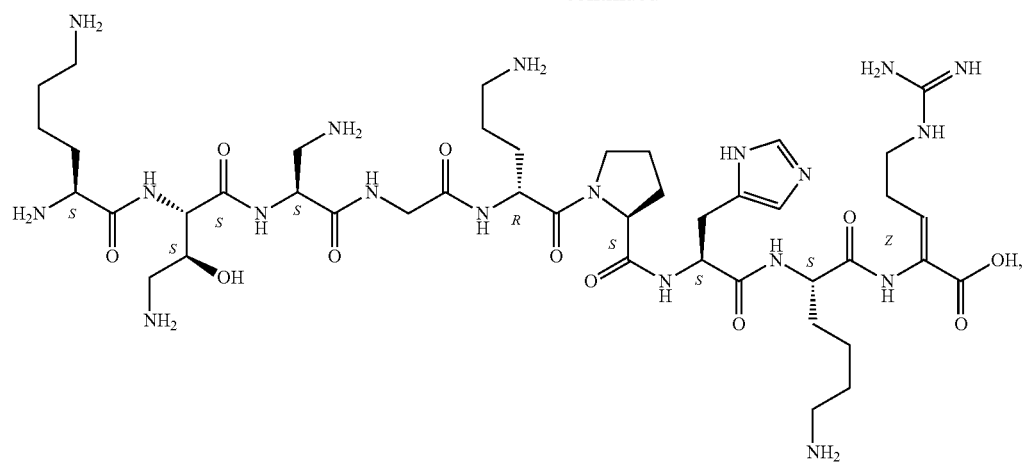
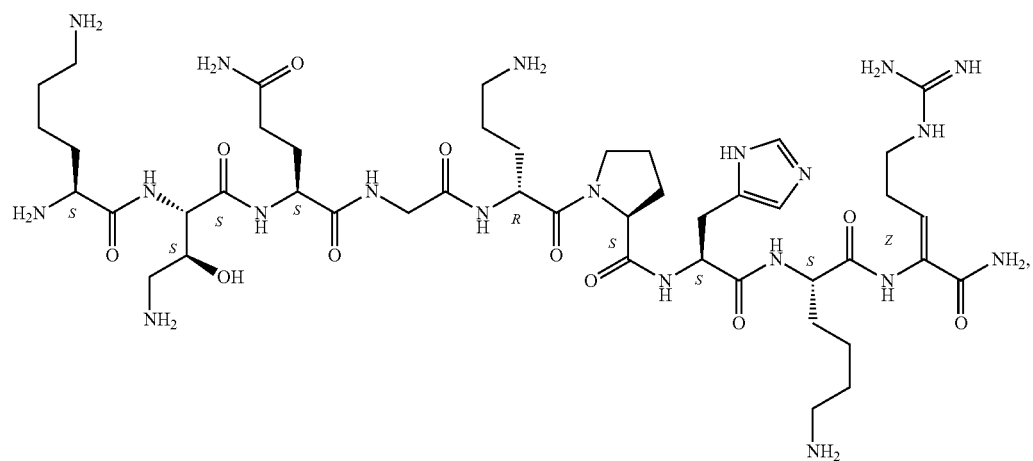
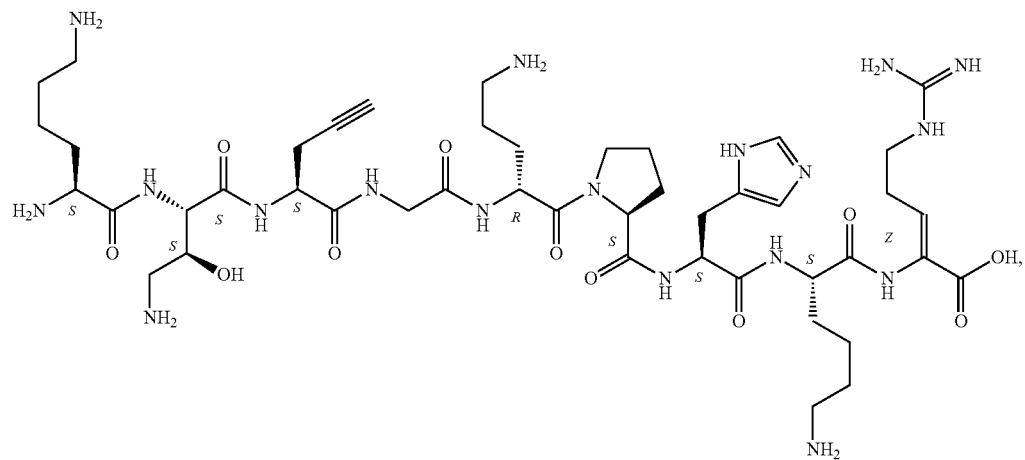

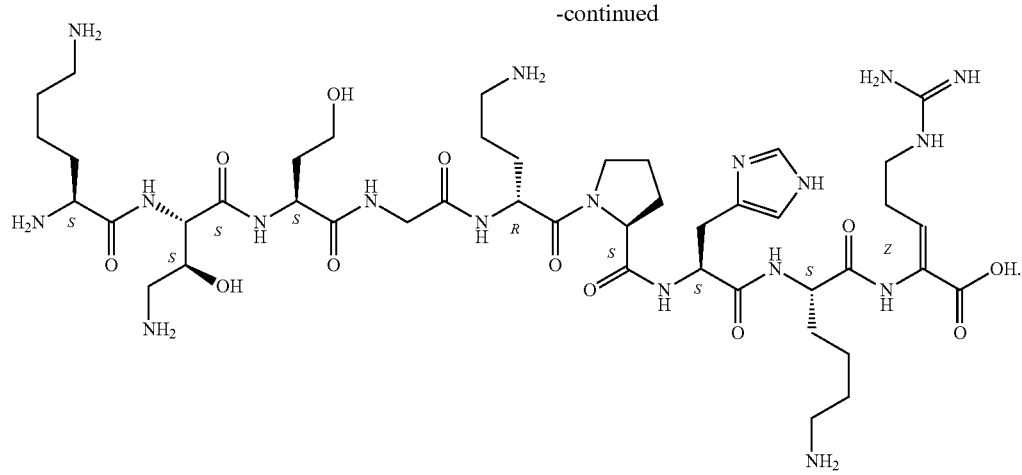

In some embodiments, the present invention provides a method for treating a subject suffering from a bacterial infection comprising administering to said subject a compound of formula (I) or a composition comprising a compound of formula (I).

In some embodiments, the present invention provides a method for suppressing a bacterial infection in a subject comprising administering to the subject a compound of formula (I) or a composition comprising a compound of formula (I).

In some embodiments, the present invention provides a method for preventing a bacterial infection in a subject comprising administering to the subject a compound of formula (I) or a composition comprising a compound of formula (I).

In some embodiments, the present invention provides a method for treating a subject suffering from multi-drug resistant bacterial infection comprising administering to said subject an effective amount of a compound of formula (I) or a composition comprising an effective amount of a compound of formula (I).

In some embodiments, the present invention provides a method for suppressing a multi-drug resistant bacterial infection comprising administering to a subject an effective amount of a compound of formula (I) or a composition comprising an effective amount of a compound of formula (I).

In some embodiments, the present invention provides a method for preventing a multi-drug resistant bacterial infection comprising administering to a subject an effective amount of a compound of formula (I) or a composition comprising an effective amount of a compound of formula (I).

In some embodiments, methods of the present invention provide for inhibition of bacteria, or infection related thereto, that are resistant to other drugs or antibiotics. In some embodiments, the methods provide for treatment, suppression, and/or prevention of infection from multi-drug resistant bacteria.

In some embodiments, the methods further comprise administration of a second antibiotic compound.

In some embodiments, the bacterial infection is multi-drug resistant. In some embodiments, the bacterial strain is hospital-acquired. In some embodiments, the bacterial strain is nosocomial.

In some embodiments, the bacterial infection comprises infection from Gram-negative bacteria. In some embodiments, the bacterial infection comprises infection from Gram-positive bacteria. In some embodiments, the bacterial infection comprises infection by more than one bacterial strain.

In another aspect, the invention is directed to pharmaceutical compositions comprising a compound of formula (I) and a pharmaceutically acceptable carrier. In some embodiments, the compositions further comprise a second antibiotic compound.

In some embodiments, a compound of formula (I) is administered. In some embodiments, a composition comprising a compound of formula (I) is administered.

In some embodiments, the compound of formula (I) or composition comprising a compound of formula (I) is effective against multi-drug resistant bacteria.

Compounds of formula (I) can be incorporated into pharmaceutical compositions suitable for administration. Such compositions can comprise a compound of formula (I) and a pharmaceutically acceptable carrier. Thus, in some embodiments, the compounds of the invention are present in a pharmaceutical composition.

In one aspect, the invention is also related compounds of formula (I) for their use in the manufacture of a medicament for treatment of microbial infection or microbial disease.

In another aspect, the invention is also related to compounds of formula (I) for their use in the manufacture of a medicament in particular as an antibiotic such as for the suppression of microbial infection or microbial disease.

In another aspect, the invention is also related to compounds of formula (I) for their use in the manufacture of a medicament in particular as an antibiotic such as for the suppression of microbial infection or microbial disease.

In the meaning of the present invention, an antibiotic is to be understood as an agent that either kills or inhibits the growth of a microorganism. A microorganism is an organism which is microscopic and which may be constituted by a single cell or multiple cells. The term antibiotic thus concerns agents which either kill or inhibit growth of eukaryote or prokaryote microorganisms. Such examples of antibiotics in the context of the present invention are antibacterial agents, antifungal agents, antialgae agents, and so-on. Preferably in the context of the present invention, the antibiotic is an antibacterial agent.

In another aspect, the invention is also related to compounds of formula (I) for their use in the manufacture of a medicament for treatment of multi-drug resistant microbial infection or microbial disease.

In another aspect, the invention is also related to compounds of formula (I) for their use in the manufacture of a medicament for suppression of multi-drug resistant microbial infection or microbial disease.

In another aspect, the invention is also related to compounds of formula (I) for their use in the manufacture of a medicament for prevention of multi-drug resistant microbial infection or microbial disease.

In another aspect, the invention is also related to compounds of formula (I) their use in for the manufacture of an antibiotic composition.

In one aspect, the invention is also related to compounds of formula (I) for their use in the manufacture of an antibiotic composition for treatment of microbial infection or microbial disease.

In one aspect, the invention is also related to compounds of formula (I) for their use in the manufacture of an antibiotic composition for suppression of microbial infection or microbial disease.

In one aspect, the invention is also related to compounds of formula (I) for their use in the manufacture of an antibiotic composition for prevention of microbial infection or microbial disease.

In another aspect, the invention is also related to compounds of formula (I) for their use in the manufacture of an antibiotic composition for treatment of multi-drug resistant microbial infection or microbial disease.

In another aspect, the invention is also related to compounds of formula (I) for their use in the manufacture of an antibiotic composition for suppression of multi-drug resistant microbial infection or microbial disease.

In another aspect, the invention is also related to compounds of formula (I) for their use in the manufacture of an antibiotic composition for prevention of multi-drug resistant microbial infection or microbial disease.

In one aspect, the invention is also related to compounds of formula (I) for their use in the manufacture of a medicament for prevention of microbial infection or microbial. According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

In another aspect, the invention is also related to the use of compounds of formula (I) for the manufacture of a medicament for one or more of the indications recited above.

Any of the therapeutic applications described herein can be applied to any subject in need of such therapy, including, for example, a mammal such as a mouse, a rat, a dog, a cat, a cow, a horse, a rabbit, a monkey, a pig, a sheep, a goat, or a human. In some embodiments, the subject is a mammal. In some embodiments, the subject is an avian, swine, bovine or human. In some embodiments, the subject is a mouse, rat or human. In some embodiments, the subject is a mouse. In some embodiments, the subject is a rat. In some embodiments, the subject is a human.

In some embodiments, the compound or composition is administered orally. In some embodiments, the compound or composition is administered parenterally. In some embodiments, the compound or composition is administered intravenously. In some embodiments, the compound or composition is administered topically.

In some embodiments, the compounds of formula (I) are used to treat or bacterial infections in a subject. Multiresistant bacterial pathogens that cause infection comprise methicillin-resistant *Staphylococcus aureus* (MRSA), vancomycin-resistant enterococci (VRE), extended spectrum ß-lactamase formers (ESBL), carbapenem-resistant Enterobacteriaceae, multiresistant *Pseudomonas* and *Acinetobacter* species. In some embodiments, the bacterial or microbial infection is an infection caused in whole or in part by bacteria of the *Achromobacter, Actinobacillus, Actinomyces, Acinetobacter, Aeromonas, Anaplasma, Bacillus, Bacteroides, Bartonella, Bdellovibrio, Bifidobacterium, Bordetella, Borrelia, Brucella, Burkholderia, Campylobacter, Capnocytophaga, Cardiobacterium, Chlamydia, Chlamydophila, Chromobacterium, Citrobacter, Clostridium, Corynebacterium, Coxiella, Ehrlichia, Enterobacter, Enterococcus, Erysipelothrix, Escherichia, Francisella, Fusobacterium, Haemophilus, Helicobacter, Hemobartonella, Klebsiella, Lactobacillus, Legionella, Leptospira, Listeria, Mannheimia, Moraxella, Morganella, Mycobacterium, Mycoplasma, Neisseria, Neorickettsia, Nocardia, Pasteurella, Peptostreptococcus, Photorhabdus, Porphyromonas, Prevotella, Propionibacterium, Proteus, Pseudomonas, Rickettsia, Salmonella, Serratia, Shigella,* Sphaerophorus, Spirillum, *Staphylococcus, Stenotrophomonas, Streptobacillus, Streptococcus, Treponema, Tropheryma, Ureaplasma, Vibrio,* or *Yersinia* families.

In some embodiments, the bacterial or microbial infection is an infection caused in whole or in part by bacteria of *Acinetobacter* sp., *Bacillus* sp., *Burkholderia* sp., *Enterobacter* sp., *Enterococcus* sp., *Escherichia* sp., *Klebsiella* sp., *Staphylococcus* sp., *Stenotrophomonas* sp., *Serratia* sp. and *Pseudomonas* sp. In some embodiments, the bacteria is selected from the group consisting of *Staphylococcus* sp., *Escherichia* sp., *Klebsiella* sp., *Pseudomonas* sp., or *Acinetobacter* sp.

In some embodiments, the bacterial or microbial infection is an infection caused in whole or in part by *Acinetobacter baumannii, Bacillus subtilis, Burkholderia cepacia, Enterobacter clocae, Enterococcus faecalis, Escherichia coli, Klebsiella pneumoniae, Staphylococcus aureus, Staphylococcus epidermidis, Stenotrophomonas maltophilia, Serratia marescens* or *Pseudomonas aeruginosa*. In some embodiments, bacterial or microbial infection is an infection caused in whole or in part by *Acinetobacter baumannii, Escherichia coli, Klebsiella pneumoniae, Staphylococcus aureus,* or *Pseudomonas aeruginosa*.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Compounds of formula (I) are synthesized by methods within the purview of the ordinarily skilled artisan. Exemplary methods by which such compounds can be synthesized include, but are not limited to, solution phase organic synthesis and solid-phase organic synthesis. In some embodiments, solid-phase organic synthesis comprises synthesis via peptide synthesizer machinery. Such embodiments and execution thereof are well within the scope of the ordinarily skilled artisan. Exemplary synthetic methods are described in Bodanzky, et al. "The Practice of Peptide Synthesis," Springer-Verlag (1994); herein incorporated by reference in its entirety. Additional exemplary methods are shown in the Examples.

It will recognized that one or more features of any embodiments disclosed herein may be combined and/or rearranged within the scope of the invention to produce further embodiments that are also within the scope of the invention. Those skilled in the art will recognize, or be able to ascertain using no more than routine experimentation, many equivalents to the specific embodiments of the invention described herein. Such equivalents are intended to be within the scope of the present invention.

The invention is further described by the following non-limiting Examples.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are illustrative only, since alternative methods can be utilized to obtain similar results.

Abbreviations:
Boc: tert-butoxycarbonyl
DCM: Dichloromethane
DIAD: Diisopropyl Azodicarboxylate
DIPEA: N,N',N"-diisopropylethylamine
DMF: N,N'-dimethylformamide
Fmoc: 9-fluorenylmethyloxy carbonyl
TBME: tert-butyl methyl ether
TFA: Trifluoro acetic acid
Trt: Trityl Chemical analogs were obtained by solid-phase peptide synthesis (SPPS; Merrifield R. B. *J. Am. Chem. Soc.* 1963, 85, 2149; herein incorporated by reference in its entirety) applying the orthogonal Fmoc/tBu strategy. Classic peptide couplings were carried out using the uronium reagents HATU or HBTU. For each coupling, 3.0 equivalents of amino-acid and 2.9 equivalents of HATU or HBTU were used. Each coupling was repeated once, twice or three times. At the end of the coupling steps, Fmoc deprotection was carried out using a solution of DMF/piperidine, and the next amino acid was added using the same strategy. When required, dehydroarginine was introduced as a dipeptide building block, dehydroarginine being at the C-terminal position (Scheme 1).

Scheme 1. Dehydroarginine dipeptide building block.

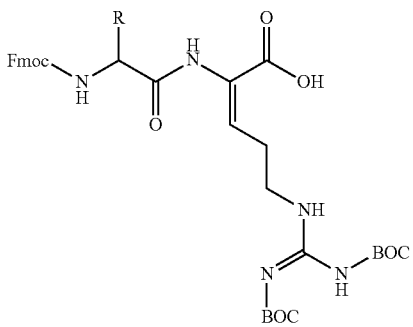

At the end of the synthesis, acid sensitive lateral chains' protections and cleavage of the peptide from the resin were made in one step using a solution of TFA, water and triisopropylsilane as scavenger. The final peptide product was eventually purified by preparative HPLC. The final compound purity was checked by LC-MS analysis.

HPLC-MS analytical method for final purity check:
Flow: 0.7 mL/min
Mobile phase A: $H_2O$ milliQ, TFA 0.1%
Mobile phase B: acetonitrile
Gradient: 0% to 30% of B in 15 minutes
Preparative HPLC purification method:
Flow: 2.5 mL/min
Mobile phase A: $H_2O$ milliQ, TFA 0.1%
Mobile phase B: acetonitrile
Gradient: 0% to 12% of B in 12 minutes
Run time: 19 minutes Example 1: Synthesis of Non-Commercial Amino-Acid Building Blocks: Aminothreonine Aminothreonine building block was prepared following the procedure described in patent application FR 1451623 (herein incorporated by reference in its entirety).

Step 1: Hydroxyectoin (50.0 g, 316.4 mmol) was dissolved in water (260 mL). NaOH (2.0 eq., 632.9 mmol, 25.3 g) was added portion wise and the mixture was stirred at room temperature until dissolution of all the NaOH. The solution obtained was heated at 50° C. for 6 hours then was cooled down to room temperature then to 5° C. with an ice bath. Aqueous HCl (6 N) was added carefully (~100 mL) until pH=4. The solution obtained was frozen to −80° C. then lyophilized. The white solid obtained was dissolved in aqueous HCl (6 N, 300 mL) and the mixture was heated at 110° C. for 3 hours. The solution obtained was diluted with water (300 mL), frozen to −80° C. then lyophilized to give (2S,3S)-2,4-diamino-3-hydroxy-butanoic acid (1-1) as pale yellow solid (107 g, contains 2.0 eq. of NaCl, purity>90%). LC-MS (0.7 mL/min; 100:0 to 90:10 of water (0.1% TFA)/AcCN in 10 min): Rt=2.30 min, $[M+H]^+$=135. $^1H$ NMR ($D_2O$, 600 MHz, mixture of 2 diastereoisomers 70:30): δ (ppm) 3.22 (dd, J=10.2 and 13.2 Hz, 0.3H), 3.34-3.47 (m, 1.7H), 4.08 (d, J=4.8 Hz, 0.3H), 4.24 (d, J=3.0 Hz, 0.7H), 4.46 (td, J=3.0 and 10.2 Hz, 0.7H), 4.48-4.52 (m, 0.3H). $^{13}C$ NMR ($D_2O$, 150 MHz, mixture of 2 diastereoisomers): δ (ppm) 42.65, 43.38, 57.70, 66.92, 67.45, 170.45. Marfey's analysis: 2S,3S/2R,3S=73:27 (2S,3S: Rt=96.01 min, 73%; 2R,3S: Rt=97.84 min, 27%).

Step 2: (2S,3S)-2,4-diamino-3-hydroxy-butanoic acid (1-1) (53 g, ~160 mmol) was put in a 2 L round bottom flask and dissolved in water (250 mL). NaOH (3.0 eq., 480 mmol, 19.0 g) was added portion wise (slightly exothermic). The mixture was stirred until dissolution of the solids then a solution of $CuSO_4 \cdot 5H_2O$ (0.5 eq., 80 mmol, 20.0 g) in water (125 mL) was added slowly. The dark blue solution obtained was put in an oil bath at room temperature. The system was heated at 110° C. for 30 minutes then was cooled down slowly to room temperature for 4 hours. A solution of $Boc_2O$ (2.0 eq., 320 mmol, 52.0 g) in dioxane (275 mL) was added and the reaction stirred at room temperature for 70 hours. A solution of $Boc_2O$ (0.5 eq., 80 mmol, 13.0 g) in dioxane (60 mL) was added slowly and the mixture was stirred at room temperature for 24 hours. The suspension obtained was filtered. The pale blue solid obtained was rinsed with water (~700 mL), $Et_2O$ (~300 mL) then dried to give ((2S,3S)-2-amino-4-(tert-butoxycarbonylamino)-3-hydroxy-butanoic acid)$_2$Cu (1-2) as pale blue solid (17.1 g, 40% yield over 2 steps). The product was used as a crude in the next step without further purification.

Step 3: ((2S,3S)-2-amino-4-(tert-butoxycarbonylamino)-3-hydroxy-butanoic acid)$_2$Cu (1-2) (17.1 g, 32.0 mmol) was suspended in water (300 mL). A solution of $Na_2EDTA$ (1.5 eq., 48.0 mmol, 15.9 g) and NaOH (3.0 eq., 96.0 mmol, 3.84 g) in water (300 mL) was added. The mixture was stirred at room temperature for 4 hours until full dissolution of the suspension. The solution obtained was cooled down in an ice bath then a solution of FmocOSu (2.5 eq., 80.0 mmol, 35.7 g) in dioxane (500 mL) was added slowly. At the end of the addition, $Na_2CO_3$ (2.5 eq., 80.0 mmol, 8.5 g) was added and the mixture was risen to room temperature then stirred at room temperature for 18 hours. The limpid blue solution obtained was washed with $Et_2O$ (4*200 mL) then cooled down in an ice bath. Aqueous 1 N HCl was added slowly until pH=3-4 (~250 mL). This aqueous phase was extracted with AcOEt (5*200 mL). Organic phases were combined, washed with brine (2*150 mL), dried over $MgSO_4$, filtered and concentrated down to give pale yellow oil. Acetonitrile (200 mL) was added and the mixture stirred at room temperature for 70 hours. The suspension was filtered, the solid rinsed with AcCN (100 mL) then dried to give (2S,3S)-4-(tert-butoxycarbonylamino)-2-(9H-fluoren-9-ylmethoxycarbonylamino)-3-hydroxy-butanoic acid (1-3) as white powder (29.1 g, quant. yield, 95% purity by LC-MS (5% of DBF, no diastereoisomer observed)). LC-MS (0.7 mL/min; 100:0 to 70:30 of water (0.1% TFA)/AcCN in 15 min): Rt=13.96 min, 95% (254 nm), $[M+H-Boc]^+$=357. $^1H$ NMR (DMSO-$d_6$, 600 MHz, 343 K): δ (ppm) 1.39 (s, 9H), 3.00-3.04 (m, 1H), 3.12-3.20 (m, 1H), 3.85-3.88 (m, 1H), 4.00-4.13 (m, 1H), 4.22-4.25 (m, 1H), 4.28-4.31 (m, 2H), 6.61 (br s, 0.8H), 7.33 (t, J=7.2 Hz, 2H), 7.42 (t, J=7.2 Hz, 2H), 7.71 (d, J=7.2 Hz, 2H), 7.87 (d, J=7.2 Hz, 2H). $^{13}C$ NMR (DMSO-$d_6$, 150 MHz, 343 K): δ (ppm) 27.93, 42.88, 46.48, 57.26, 65.69, 69.96, 77.56, 119.65, 124.87, 126.70, 127.24, 140.40, 143.50, 143.54, 151.30, 155.41, 155.65, 171.06. Marfey's analysis: Rt=95.60 min (2S, 3S), 100% (340 nm), $[M+H]^+$=695.

Step 4: (2S,3 S)-4-(tert-butoxycarbonylamino)-2-(9H-fluoren-9-ylmethoxycarbonylamino)-3-hydroxy-butanoic acid (1-3) (29.1 g, 63.6 mmol) was suspended in a mixture of acetone and 2,2-dimethoxypropane (1:1, 480 mL). The suspension was cooled down with an ice bath then $BF_3 \cdot OEt_2$ (catalytic, 900 μL) was added drop wise. The reaction was stirred in the melting ice bath until obtaining a limpid orange/brown solution (about 2.5 hours, completion of the reaction was checked by LC-MS). An aqueous saturated solution of $NaHCO_3$ (200 mL), AcOEt (400 mL) then water (300 mL) were added and the phases were separated. The aqueous phase was extracted with AcOEt (2*200 mL). The organic phases were combined, washed with aqueous 0.1 N HCl (200 mL), brine (200 mL), dried over MgSO₄, filtered and concentrated down. The pale yellow oil obtained was dissolved in Et₂O (100 mL), the solution was cooled down in an ice bath then hexane (400 mL) was added. Formation of a suspension was observed while adding hexane. At the end of the addition a sticky solid was observed at the bottom of the flask. Et₂O was added at room temperature and the mixture was triturated to obtain a white solid which was triturated for 18 hours. The suspension obtained was filtered off to give (2S)-2-[(5S)-3-tert-butoxycarbonyl-2,2-dimethyl-oxazolidin-5-yl]-2-(9H-fluoren-9-ylmethoxycarbonylamino)acetic acid (1-4) as white powder (22.9 g, 73% yield, 96% purity by LC-MS (2% of DBF and 1.5% of starting material were observed, no diastereoisomer was observed)). LC-MS (0.7 mL/min; 100:0 to 70:30 of water (0.1% TFA)/AcCN in 15 min): Rt=19.66 min, 96% (254 nm), [M+H-Boc-CH(CH₃)₂]⁺=357. ¹H NMR (DMSO-d₆, 600 MHz, 343 K): δ (ppm) 1.43 (s, 12H), 1.47 (s, 3H), 3.36-3.41 (m, 1H), 3.54-3.59 (m, 1H), 4.22-4.25 (m, 2H), 4.30-4.33 (m, 2H), 4.38 (br s, 1H), 7.30-7.34 (m, 2H), 7.39-7.44 (m, 2H), 7.58 (br s, 1H), 7.69-7.72 (m, 2H), 7.87 (d, J=7.8, 2H). ¹³C NMR (DMSO-d₆, 150 MHz, 343 K): δ (ppm) 27.78, 46.48, 46.84, 65.72, 72.81, 78.86, 92.94, 119.65, 124.83, 126.66, 127.25, 140.41, 143.48, 151.04, 155.51, 170.37. The regioselectivity of protections was determined using HMBC and HSQC analyses. A clear signal was observed in HMBC between the CHα (4.25 ppm) and the CO of the Fmoc protecting the amine in the alpha position (155.5 ppm) proving the regioselectivity of the protections. Marfey's analysis: Rt=96.19 min (2S, 3S), 100% (340 nm), [M+H]⁺=695.

Example 2: Synthesis of Non-Commercial Amino-Acid Building Blocks: Lysine-Dehydroarginine Dipeptide Lysine-dehydroarginine dipeptide building block was prepared in accordance with the procedures described in Schmidt, U. and Wild, J. *Ang. Chem. Int. Ed.* 1984, 23, 991 (herein incorporated by reference in its entirety) and applied in Berwe, M. et al., *Org. Process Res. Dev.* 2011, 15, 1348; and Freeman, N. S. et al., *J. Org. Chem.* 2011, 76, 3078 (each herein incorporated by reference in its entirety).

Scheme 2. Synthesis of lysine-dehydroarginine dipeptide building block

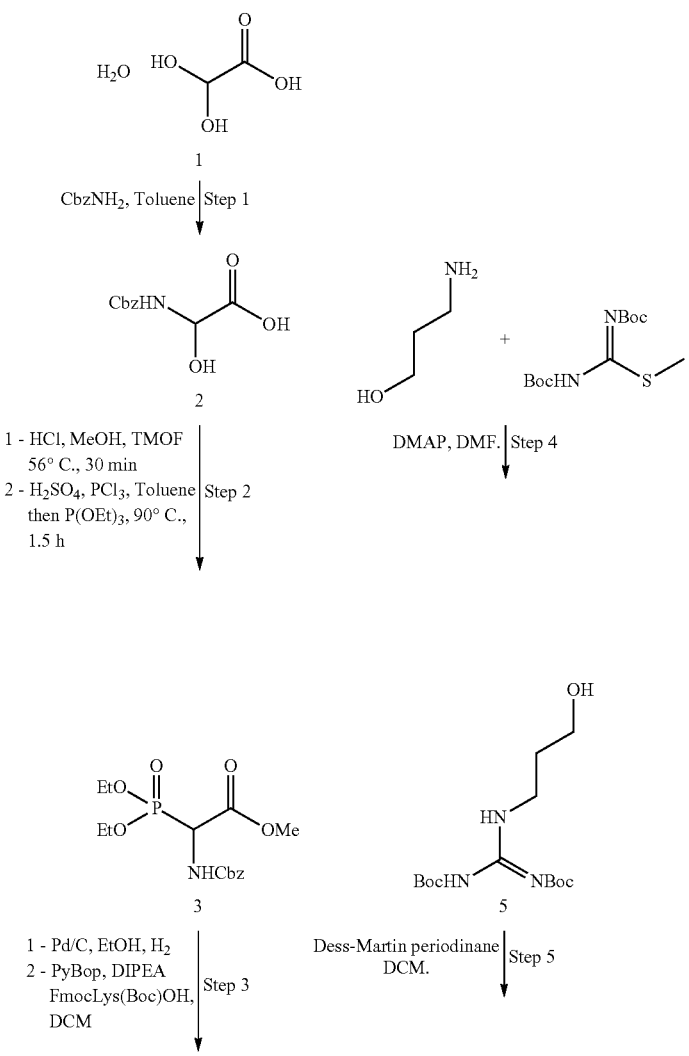

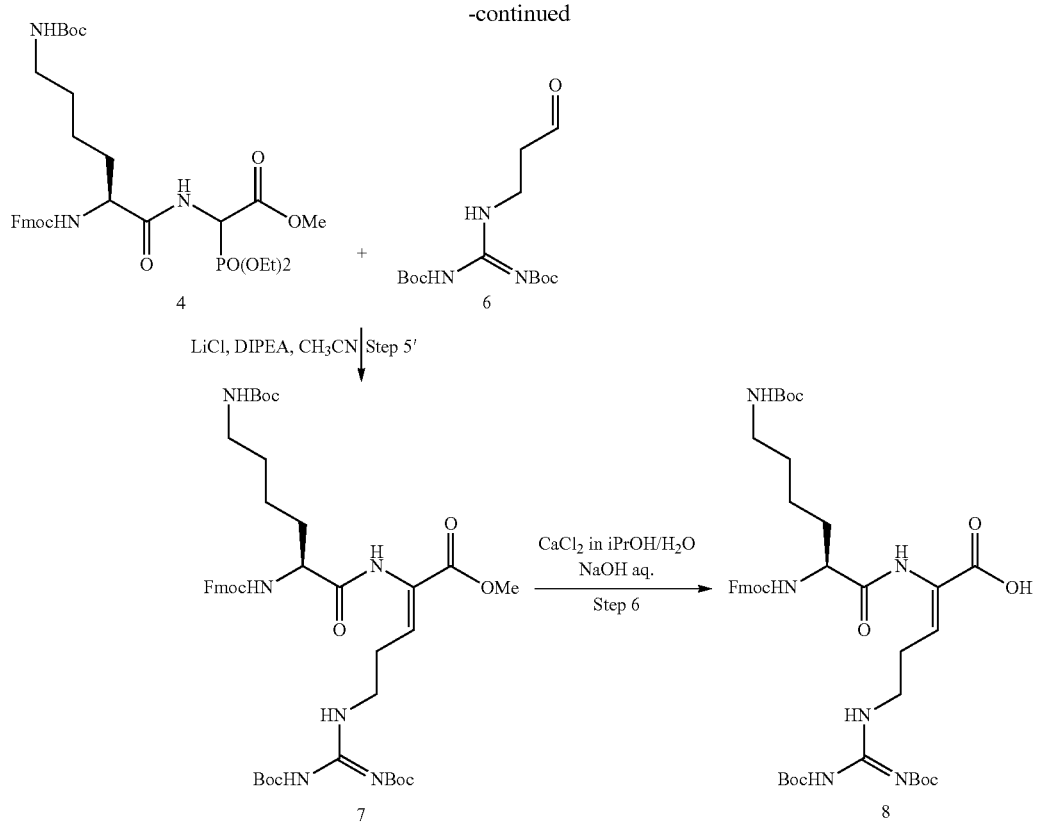

Step 1: A solution of benzyl carbamate (90.0 g, 0.59 mol, 1.0 eq.) and monohydrate dihydroxyacetic acid 1 (60.3 g, 1.1 mol, 1.1 eq.) in toluene (840 mL) was introduced in a 2 L flask and the solution was heated at 40° C. for 1.5 hours. Half of the solvent was concentrated down under reduce pressure. Toluene (540 mL) was added and half of the solvent was concentrated down under reduce pressure. Toluene (540 mL) was added and the reaction was stirred at 40° C. for 2 hours and then cooled down to 20° C. The white solid was filtered, rinsed with toluene and dried under vacuum. The expected compound 2 (133.0 g, quant. yield, 95% purity ($^1$H NMR)) was obtained as a white solid. $^1$H NMR (400 MHz, DMSO-$d_6$): δ (ppm): 5.05 (s, 2H), 5.21 (d, J=8.8 Hz, 1H), 6.62-6.80 (br s, 1H), 7.26-7.44 (m, 5H), 8.14 (d, J=8.8 Hz, 1H), 12.10-13.60 (br s, 1H).

Step 2:

Step i: 2-(((benzyloxy)carbonyl)amino)-2-hydroxyacetic acid 2 (133.0 g, 0.59 mol, 1.0 eq.) was diluted in methanol (480 mL). Trimethyl orthoformate (TMOF, 130.2 mL, 1.11 mol, 2.0 eq.) and hydrochloric acid in methanol (1.25 M, 24 mL, 0.03 mol, 0.05 eq.) were added successively. The mixture was stirred at 56° C. for 40 min. Solvent was concentrated down under reduce pressure and 600 mL of Et$_2$O were added. If necessary starting material was filtered off. The filtrate was concentrated down and dried under reduce pressure. The expected intermediate (149.6 g) was obtained as a white solid. Purity was assessed by NMR, and was >95%. $^1$HNMR (400 MHz, DMSO-$d_6$) δ (ppm): 3.26 (s, 3H), 3.66 (s, 3H), 5.08 (s, 2H), 5.16 (d, J=9.2 Hz, 1H), 7.28-7.44 (m, 5H), 8.49 (d, J=8.8 Hz, 1H).

Step ii: A 2 L three-necked round bottom flask equipped with a dropping funnel and a condenser was dried by three heating+vacuum/argon cycles. The previous intermediate (149.5 g, 0.59 mol, 1.0 eq.) was introduced under argon followed by anhydrous toluene (720 mL). Three drops of concentrated sulfuric acid were added. Phosphorus trichloride (80 mL, 0.69 mol, 1.2 eq.) was introduced in the dropping funnel. The mixture was heated at 75° C. and PCl3 was added over 1 h at this temperature. At the end of the addition, the mixture was stirred at 75° C. for 13 h. After cooling down to room temperature, the solid was filtered off and the filtrate was concentrated down under vacuum to remove excess of PCl3. The crude mixture was diluted in 720 mL of anhydrous toluene under argon. Triethyl phosphite (100 mL, 0.65 mol, 1.1 eq.) was then added and the mixture was stirred at 75° C. for 2 h and then at 90° C. for 30 min. The reaction mixture was cooled down to room temperature; solvent and excess of triethyl phosphite were removed under vacuum. The crude mixture was dissolved in EtOAc. Organic phase was washed twice with saturated Na$_2$CO$_3$, dried over MgSO$_4$, filtered and concentrated down under vacuum. The crude mixture was precipitated in Et$_2$O (1 h at 5° C.). The suspension was filtered off and the solid was dried under vacuum to give 3 as a white solid (165.1 g, 70% yield over 2 steps, 90% purity ($^1$H NMR)). $^1$H NMR (400 MHz, CDCl$_3$): δ (ppm) 3.74-3.87 (m, 9H), 4.93 (dd, J=22.4 and 9.6 Hz, 1H), 5.13-5.14 (m, 2H), 5.60 (d, J=8.4 Hz, 1H), 7.28-7.43 (m, 5H). $^{31}$P NMR (400 MHz, CDCl$_3$): δ (ppm) 18.45.

Step 3: Methyl 2-(((benzyloxy)carbonyl)amino)-2-(diethoxyphosphoryl)acetate 3 (20.1 g, 55.7 mmol, 1.0 eq.) was dissolved in 600 mL of EtOH. 10% palladium on charcoal (2.0 g, cat.) was added and the reaction mixture was stirred under H$_2$ atmosphere for 8 to 14 h. Deprotection was monitored by $^{31}$P NMR. After completion the mixture was filtered through celite. The filtrate was concentrated down under vacuum. The crude was dissolved in DCM and concentrated down under reduce pressure. The operation was repeated three times in order to remove traces of EtOH. The free amine was used directly in the next step.

The crude product was dissolved in 60 mL of DCM. Fmoc-Lys(Boc)-OH (26.0 g, 55.7 mmol, 1.0 eq.) was added followed by PyBOP (29.0 g, 55.7 mmol, 1.0 eq.). The reaction mixture was cooled down to 0° C. before adding diisopropylethylamine drop wise (28.0 mL, 160.7 mmol, 3.0 eq.). The reaction mixture was stirred at room temperature for 2 h. After completion, the reaction mixture was diluted with EtOAc. The organic phase was washed twice with a 5% $KHSO_4$ aqueous solution, twice with a saturated aqueous solution of $NaHCO_3$ and once with brine. Organic phases were dried over $MgSO_4$, filtered and concentrated down under vacuum. The crude product was purified by column chromatography over silica (40-63 µm, pore 60 Å, 1.4 kg, 100% EtOAc). In order to remove traces of EtOAc, the crude mixture was dissolved in $CHCl_3$ and concentrated under reduce pressure to give 4 as white foam (33.4 g, 83% yield, 95% purity ($^1H$ NMR)). $^1H$ NMR (400 MHz, DMSO-$d_6$): δ (ppm) 1.15-1.62 (m, 21H), 2.87-2.90 (m, 2H), 3.70 (d, J=4.8 Hz, 3H), 4.03-4.25 (m, 8H), 4.90-5.15 (m, 1H), 6.75 (br s, 1H), 7.32 (t, J=7.2 Hz, 2H), 7.42 (t, J=7.6 Hz, 2H), 7.50-7.58 (m, 1H), 7.72 (d, J=7.2 Hz, 2H), 7.89 (d, J=7.6 Hz, 2H), 8.77-8.85 (m, 1H). $^{13}C$ NMR (100 MHz, DMSO-$d_6$): δ (ppm) 16.08, 22.76, 28.24, 29.18, 31.54, 31.73, 46.60, 49.43, 50.88, 52.67, 52.71, 54.16, 63.06, 63.11, 63.28, 63.35, 65.63, 77.32, 120.07, 125.26, 127.03, 127.60, 140.66, 143.74, 143.83, 155.52, 155.89, 167.11, 172.71. $^{31}P$ NMR (400 MHz, $CDCl_3$): δ (ppm) 18.25.

Step 4: 1.3-bis(tert-butoxycarbonyl)-2-methyl-2-thiopseudourea (50.0 g, 172.1 mmol, 1.0 eq.) was dissolved in 400 mL of DMF. Aminopropan-3-ol (52.5 mL, 688.0 mmol, 4.0 eq.) was added drop wise followed by dimethylaminopyridine (2.1 g, 17.2 mmol, 0.1 eq.). The reaction mixture was stirred at room temperature for 4 h. The reaction mixture was dissolved in 4 L of $Et_2O$. The organic phase was washed with 800 mL of aqueous 0.1 M AcOH, 800 mL of saturated aqueous $NaHCO_3$, 800 mL of $H_2O$ and 800 mL of brine. The organic phase was dried over $MgSO_4$, filtered and concentrated down under vacuum. 5 was obtained as a white solid (51.1 g, quant. yield, 95% purity ($^1H$ NMR)). $^1H$ NMR (250 MHz, $CDCl_3$): δ (ppm) 1.47 (s, 9H), 1.50 (s, 9H), 1.64-1.76 (m, 2H), 3.52-3.63 (m, 4H), 8.42-8.61 (br s, 1H), 11.44 (s, 1H).

Step 5 and 5': 1.2 eq. of the aldehyde was prepared for the Homer-Wadsworth-Emmons (1.0 eq. of 4).

Step 5: In a 2 L flask, 5 (20.5 g, 64.6 mmol, 1.2 eq.) was dissolved in DCM (stabilized over amylene, 410 mL). Pyridine (30.9 mL, 465.1 mmol, 7.2 eq.) was added followed by Dess-Martin periodinane (29.7 g, 70 mmol, 1.3 eq.). The reaction was stirred at room temperature for 3 h. A saturated aqueous solution of $Na_2CO_3$ (600 ml) and 300 mL of $Et_2O$ were added. The mixture was stirred at room temperature for 10 min. The suspension obtained was filtered through celite. 1.1 L of $Et_2O$ was added and the organic phase was washed with water (3×1 L). The organic phase was dried over $MgSO_4$, filtered and concentrated down under vacuum. The aldehyde 6 was obtained as yellow oil (22.1 g, quant.) and used directly in the next step without purification. $^1H$ NMR (400 MHz, $CDCl_3$): δ (ppm) 1.48 (s, 9H), 1.50 (s, 9H), 2.79 (t, J=6.0 Hz, 2H), 3.74 (q, J=6.4 Hz, 2H), 8.56-8.64 (m, 1H), 9.83 (s, 1H), 11.44 (s, 1H).

Step 5': In a 500 mL flask under argon 4 (36.1 g, 53.4 mmol, 1.0 eq.) was dissolved with 300 mL of anhydrous $CH_3CN$. Dry lithium chloride (2.73 g, 64.1 mmol, 1.2 eq.) was added and the reaction mixture was stirred at room temperature for 30 min. The aldehyde 6 (22.1 g) was dissolved in 40 mL of anhydrous $CH_3CN$. The solution was added to the reaction mixture then diisopropylethyl-amine (10.83 ml, 64.1 mmol, 1.2 eq.) was added dropwise. The reaction mixture was stirred at room temperature for 3 to 4 days. The reaction was monitored by $^{31}P$ NMR. After completion, 1 L of EtOAc was added and the organic phase was washed with 100 mL of $H_2O$. The organic phase was dried over $MgSO_4$, filtered and concentrated down under vacuum. After HPLC analysis, the Z/E ratio was determined as 86/14. The crude product was purified by column chromatography on silica (40-63 µm, pore 60 Å, 1.5 kg, 3/2 petroleum ether/EtOAc≈2 L, then 1/1 petroleum ether/EtOAc≈3 L then ⅔ petroleum ether/EtOAc). 3 fractions were obtained, the first one containing the alkene E, the second a mixture of Z and E alkene and the third the alkene Z with a good purity (>95% by HPLC). The second fraction was purified again by column chromatography. After combining the various fractions, (Z)-7 was obtained as white foam (30.0 g, 71% yield, 90% purity ($^1H$ NMR)). (Z)-7: $^1H$ NMR (400 MHz, DMSO-$d_6$): δ (ppm) 1.23-1.46 (m, 31H), 1.53-1.68 (m, 2H), 2.31-2.36 (m, 2H), 2.90 (br s, 2H), 3.37 (br s, 2H), 3.64 (s, 3H), 4.08-4.26 (m, 4H), 6.41-6.43 (m, 1H), 6.77-6.79 (m, 1H), 7.31-7.34 (m, 2H), 7.39-7.42 (m, 2H), 7.52-7.54 (m, 1H), 7.70-7.73 (m, 2H), 7.87-7.90 (m, 2H), 8.37-8.41 (m, 1H), 9.32 (br s, 1H), 11.47 (br s, 1H). $^{13}C$ NMR (100 MHz, DMSO-$d_6$): δ (ppm) 22.74, 27.34, 27.55, 27.95, 28.25, 29.23, 31.51, 46.63, 51.87, 54.42, 65.61, 77.30, 78.12, 82.80, 120.06, 125.28, 127.01, 127.59, 128.04, 132.93, 140.67, 143.73, 143.84, 151.85, 155.27, 155.51, 155.93, 163.04, 164.39, 171.31. NOESY experiment (2D NMR) showed a clear interaction between the $CH_2$ vicinal to the vinylic CH and the NH of the amide bond proving the Z stereochemistry of the double bond. To confirm it, NOESY experiment was done on the other isomer and showed a clear interaction between the vinylic CH and the NH of the amide bond proving the E stereochemistry of the double bond.

Step 6: 1 L of 0.8 M $CaCl_2$ solution in a mixture of $iPrOH/H_2O$ (7/3) was prepared. (Z)-7 (30.0 g, 35.8 mmol, 1.0 eq.) was dissolved in 580 mL of the 0.8 M $CaCl_2$ solution. The mixture was stirred at room temperature for 20 min then was cooled down to 0° C. and aqueous NaOH (1 M, 71.6 mL, 71.6 mmol, 2.0 eq.) was added dropwise. The mixture was stirred at room temperature for 16 h then EtOAc and saturated $NH_4Cl$ aqueous solution were added. Aqueous phase was extracted twice with EtOAc. The combined organic phases were washed with brine. Organic phase was concentrated down under vacuum. The crude mixture was purified by column chromatography on silica (40-63 µm, pore 60 Å, 1 kg, crude absorbed on silica, 100% DCM, then MeOH/DCM 2/98, 4/96, 6/94, 8/92 10/90). (Z)-8 was obtained as a white foam (17.0 g, 55% yield, >95% purity (LC-MS)). $^1H$ NMR (400 MHz, DMSO-$d_6$): δ (ppm) 1.23-1.46 (m, 31H), 1.55-1.71 (m, 2H), 2.22-2.26 (m, 2H), 2.90 (br s, 2H), 3.37 (br s, 2H), 4.08-4.29 (m, 4H), 6.26-6.34 (m, 1H), 6.75-6.78 (m, 1H), 7.29-7.33 (m, 2H), 7.38-7.42 (m, 2H), 7.57-7.60 (m, 1H), 7.70-7.74 (m, 2H), 7.84-7.89 (m, 2H), 8.32-8.34 (m, 1H), 8.94 (br s, 1H), 11.49 (br s, 1H). $^{13}C$ NMR (100 MHz, DMSO-$d_6$): δ (ppm) 22.91, 27.54, 27.95, 28.23, 29.20, 31.60, 46.64, 54.92, 65.66, 77.26, 78.09, 82.77, 120.03, 121.34, 125.28, 127.01, 127.24, 127.56, 128.87, 140.66, 143.72, 143.84, 151.94, 155.22, 155.50, 155.99, 163.04, 170.19. LC-MS (0.7 mL/min; 60:40 to 10:90 of water (0.1% TFA)/AcCN in 25 min): Rt=17.30 min, 90% (254 nm), [M+H]$^+$=823. The same reaction was done starting from (E)-7 to give the corresponding (E)-8: $^1H$ NMR (400 MHz, DMSO-d$_6$): δ (ppm) 1.23-1.46 (m, 31H), 1.55-1.71 (m, 2H), 2.60-2.68 (m, 2H), 2.90 (br s, 2H), 3.37 (br s, 2H), 3.96-4.02 (br s, 1H), 4.08-4.29 (m, 3H), 6.12-6.18 (m, 1H), 6.75-6.78 (m, 1H), 7.29-7.33 (m, 2H), 7.38-7.42 (m, 2H), 7.60-7.68 (m, 1H), 7.70-7.74 (m, 2H), 7.84-7.89 (m, 2H), 8.32-8.34 (m, 1H), 9.20 (br s, 1H), 11.49 (br s, 1H). LC-MS (0.7 mL/min; 60:40 to 10:90 of water (0.1% TFA)/AcCN in 25 min): Rt=20.97 min, 96% (254 nm), [M+H]$^+$ =823.

Example 3: Synthesis of Non-Commercial Amino-Acid Building Blocks: Alanine-Dehydroarginine Dipeptide Alanine-dehydroarginine dipeptide building block was prepared in accordance with the procedures described in Schmidt, U. and Wild, J. *Ang. Chem. Int. Ed.* 1984, 23, 991 (herein incorporated by reference in its entirety) and applied in Berwe, M. et al., *Org. Process Res. Dev.* 2011, 15, 1348; and Freeman, N. S. et al., *J. Org. Chem.* 2011, 76, 3078 (each herein incorporated by reference in its entirety). The compound was obtained following the procedure described in Example 2, using Fmoc-Ala-OH instead of Fmoc-Lys (Boc)-OH in Step 3. $^1$H NMR (400 MHz, DMSO-d$_6$): δ (ppm) 1.23-1.46 (m, 21H), 2.90 (br s, 2H), 3.37 (br s, 2H), 4.08-4.29 (m, 4H), 6.26-6.34 (m, 1H), 6.75-6.78 (m, 1H), 7.29-7.33 (m, 2H), 7.38-7.42 (m, 2H), 7.70-7.74 (m, 2H), 7.84-7.89 (m, 2H), 8.32-8.34 (m, 1H), 8.94 (br s, 1H), 11.49 (br s, 1H).

Example 4: Synthesis of Peptides with CONH$_2$, CONH(CH$_2$)$_5$NH$_2$, CONH(CH$_2$)$_4$NH$_2$, CONH (CH$_2$)$_3$NH$_2$ and CONH(CH$_2$)$_2$NH$_2$ at the C-Terminal Position The same protocol was used to synthesize this type of peptides using:
  Rink amide resin for CONH$_2$ at the C-terminal position. After the first swelling, the resin was deprotected (a solution of DMF/piperidine (80:20, 4.0 mL) was added to the resin; the mixture was shaken for 20 minutes then filtered under vacuum to remove the solvent. This step was repeated once. DMF (2.5 mL) was added; the mixture was shaken for 20 seconds then filtered. The cap and the edge of the tube were washed with DMF (2.5 mL), shaken for 20 seconds and filtered under vacuum. This washing was repeated 4 times. The reaction vessel was filled with MeOH (2.5 mL), shaken for 20 seconds and filtered under vacuum. The reaction vessel was filled with DCM (2.5 mL), shaken for 20 seconds and filtered under vacuum).
  1,5-diamino pentane trityl resin for CONH(CH$_2$)$_5$NH$_2$ at the C-terminal position
  1,4-diamino butane trityl resin for CONH(CH$_2$)$_4$NH$_2$ at the C-terminal position
  1,3-diamino propane trityl resin for CONH(CH$_2$)$_3$NH$_2$ at the C-terminal position
  1,2-diamino ethane trityl resin for CONH(CH$_2$)$_2$NH$_2$ at the C-terminal position
  Step 1: Resin swelling. Resin (1.0 eq., 0.08 mmol) was put in the reaction vessel. DCM (3.0 mL) was added to immerse all the resin, the mixture was shaken for 30 min. The DCM was removed by filtration under vacuum.
  Step 2: Standard coupling with HBTU. DMF (2.5 mL) was added to the swollen resin, the mixture was shaken for 20 seconds and the solvent was removed under vacuum. A solution of the first amino-acid or dipeptide (3.0 eq., 0.24 mmol) in DMF (1.3 mL) with DIPEA (4.0 eq., 0.32 mmol, 55 µL) was added and shaken for 20 seconds. HBTU (2.9 eq., 0.23 mmol, 88 mg) was added, the reaction vessel was closed with a cap and the system shaken for 60 min. The mixture was filtered under vacuum and the coupling was repeated twice except when the dipeptide was reacted (one coupling). The mixture was filtered under vacuum then filled with DMF (2.5 mL), shaken for 20 seconds and filtered. This washing was repeated 4 times. The reaction vessel was filled with MeOH (2.5 mL), shaken for 20 seconds and filtered under vacuum. This washing was repeated 4 times. The reaction vessel was filled with DCM (2.5 mL), shaken for 20 seconds and filtered under vacuum. This washing was repeated 5 times.
  Step 3: Fmoc Removal. To the resin obtained at the end of the coupling (Step 2) was added DMF (2.5 mL). The mixture was shaken for 20 seconds, then the solvent was removed by filtration under vacuum. A solution of DMF/piperidine (80:20, 4.0 mL) was added to the resin; the mixture was shaken for 20 minutes, then filtered under vacuum. This step was repeated once. DMF (2.5 mL) was added; the mixture was shaken for 20 seconds then filtered. The cap and the edge of the tube were washed with DMF (2.5 mL), shaken for 20 seconds and filtered under vacuum. This washing was repeated 4 times. The reaction vessel was filled with MeOH (2.5 mL), shaken for 20 seconds and filtered under vacuum. This washing was repeated 4 times. The reaction vessel was filled with DCM (2.5 mL), shacked for 20 seconds and filtered under vacuum. This washing was repeated 5 times. The cycle from Step 2 to Step 3 was repeated for each amino acid or dipeptide of the sequence. Two couplings were made except for the last amino acid (three couplings) and when the protected aminothreonine (one coupling, time increased to 120 min) and the dipeptide containing dehydroarginine (one coupling followed by a capping) were introduced.
  The capping procedure was as follows: the resin was swollen in DCM (2.5 mL) and shaken for 20 seconds. The solvent was removed by filtration. 0.8 mL of a 0.5 M solution of Ac$_2$O/DIPEA in DMF was added to the reaction vessel, and the vessel was shaken for 3 min. The solution was removed by filtration, then 1.3 mL of the same solution was added, and the tube was shaken for 7 min. The solution was removed by filtration and the resin was washed three times with DCM (2.5 mL). The capping was monitored using the Kaiser test. If a blue color appeared, the capping step was repeated once.
  Step 4: Cleavage of the peptide from the resin and deprotection of the lateral chains. After the last Fmoc removal, the resin was rinsed carefully with DCM (5*2.5 mL). 5 mL of cleavage cocktail were freshly prepared (TFA/H2O/TIS, 85/7.5/7.5: 4.25 mL/0.4 mL/0.4 mL) and 2 mL were added to the resin. The mixture was shaken for 3 hours. The reaction vessel was put on top of a centrifuge tube containing 30 mL of cold (0° C.) stirred TBME. The solution on the reaction vessel was added drop wise to the cold TBME. 2 mL of cleavage cocktail were added again to the resin, the mixture shaken for 20 min and the solution added drop wise to the previous cold solution. The mixture was stirred at 0° C. for 30 min. The precipitate obtained was isolated by centrifugation (2,200 g, 5 min), washed with cold (0° C.) TBME (10 mL) and then centrifuged again (2,200 g, 5 min). The crude product obtained was air-dried (3 hours) at room temperature to give brown oil. The crude product was dissolved in water (4 mL), the solution was frozen and freeze-dried.

Step 5: Purification. The crude product was dissolved in milliQ water (~100 mg/mL) and was purified applying the HPLC purification method described in 2). Tubes containing pure product were combined and the solution was frozen to −80° C. and freeze-dried to give the final product. This final product was analyzed by HPLC-MS applying the HPLC-MS analytical method for final purity check described above.

Example 5: Synthesis of Peptides with Lysine and CO$_2$H at the C-Terminal Position Chloro-trityl resin (0.08 mmol) was put in the reaction vessel. DCM (3.0 mL) was added to immerse all the resin and the mixture was shacked for 30 min. The DCM was removed by filtration under vacuum. Fmoc-Lys-OAll.HCl (3.0 eq.) was dissolved with a minimum amount of DCM (1 mL) to effect total dissolution. DIPEA (5.0 eq.) was added and the solution was mixed thoroughly. The solution was immediately added to the resin. The reaction vessel was closed with a cap and the system shaken for 60 min. The mixture was filtered under vacuum and the procedure was repeated once. The resin was washed with DMF (2.5 mL), shaken for 20 seconds and filtered. This washing was repeated twice. A mixture of DCM/MeOH/DIPEA (80/15/5) (1 mL) was added to the resin. The reaction vessel was closed with a cap and the system was shaken for 10 min. The mixture was filtered under vacuum and the process was repeated once. The mixture was filtered under vacuum then filled with DMF (2.5 mL), shaken for 20 seconds and filtered. The cap and the edge of the tube were washed with DMF (2.5 mL), shaken for 20 seconds and filtered under vacuum. This washing was repeated twice. A solution of DMF/piperidine (80:20, 4.0 mL) was added to the resin, the mixture was shaken for 20 minutes then filtered under vacuum to remove the solvent. This step was repeated once. DMF (2.5 mL) was added, the mixture shaken for 20 seconds then filtered. The cap and the edge of the tube were washed with DMF (2.5 mL), shaken for 20 seconds and filtered under vacuum. This washing was repeated 4 times. The reaction vessel was filled with isopropanol (2.5 mL), shaken for 20 seconds and filtered under vacuum. This washing was repeated twice. The reaction vessel was filled with hexane (2.5 mL), shaken for 20 seconds, and filtered and dried under vacuum for 24 hours.

The cycle from Step 2 to Step 3 described in Example 4 was repeated for each amino-acid or dipeptide of the sequence.

After the coupling of the last amino-acid, the C-terminal position was deprotected using the following protocol:

Tetrakis(triphenylphosphine)palladium(0) (0.1 eq.) was dissolved in DCM (1.3 mL). Phenylsilane (10.0 eq.) was added to the solution and this solution was introduced in the reaction vessel. The mixture was shaken for 45 minutes, then was filtered under vacuum. A solution of sodium N,N-diethyldithiocarbamate (0.02 M in DMF, 4 mL) was added to the resin, the mixture was shaken for 15 minutes then filtered under vacuum to remove the solvent. This step was repeated twice. DMF (2.5 mL) was added to the resin and the mixture shaken for 20 seconds then filtered. The cap and the edge of the tube were washed with DMF (2.5 mL), shaken for 20 seconds and filtered under vacuum. This washing was repeated 4 times.

The N-terminal position was deprotected following Step 3 described in Example 4. Cleavage of the peptide from the resin and deprotection of the lateral chains were made following Step 4 described in Example 4. Final purification was made following Step 5 described in Example 4.

Example 6. Synthesis of Peptides with Dehydroarginine and CO$_2$H at the C-Terminal Position Chloro-trityl resin (0.08 mmol) was put in the reaction vessel. DCM (3.0 mL) was added to immerse all the resin and the mixture was shaken for 30 min. The DCM was removed by filtration under vacuum. The dipeptide Fmoc-Lys(Boc)-α,β-dehydroArg(Boc)$_2$-OH (3.0 eq.) was dissolved with a minimum amount of DCM (1 mL) to effect total dissolution. DIPEA (4.0 eq.) was added and the solution was mixed thoroughly. The solution was immediately added to the resin. The reaction vessel was closed with a cap and the system shaken for 60 min. The mixture was filtered under vacuum and the procedure was repeated once. The resin was washed with DMF (2.5 mL), shaken for 20 seconds and filtered. This washing was repeated twice. A mixture of DCM/MeOH/DIPEA (80/15/5) (1 mL for 0.08 mmol of resin) was added to the resin. The reaction vessel was closed with a cap and the system was shaken for 10 min. The mixture was filtered under vacuum and the procedure was repeated once. The mixture was filtered under vacuum then filled with DMF (2.5 mL), shaken for 20 seconds and filtered. The cap and the edge of the tube were washed with DMF (2.5 mL), shaken for 20 seconds and filtered under vacuum. This washing was repeated twice. A solution of DMF/piperidine (80:20, 4.0 mL) was added to the resin, the mixture was shaken for 20 minutes then filtered under vacuum to remove the solvent. This step was repeated once. DMF (2.5 mL) was added, the mixture shaken for 20 seconds then filtered. The cap and the edge of the tube were washed with DMF (2.5 mL), shaken for 20 seconds and filtered under vacuum. This washing was repeated 4 times. The reaction vessel was filled with isopropanol (2.5 mL), shaken for 20 seconds and filtered under vacuum. This washing was repeated twice. The reaction vessel was filled with hexane (2.5 mL), shaken for 20 seconds and filtered and dried under vacuum.

The cycle from Step 2 to Step 3 described in Example 4 was repeated for each amino-acid or dipeptide of the sequence. The N-terminal position was deprotected following Step 3 described in Example 4. Cleavage of the peptide from the resin and deprotection of the lateral chains were made following Step 4 described in Example 4. Final purification was made following Step 5 described in Example 4.

Example 7. Synthesis of Peptides with an Ester Function at the C-Terminal Position Chloro-trityl resin (0.08 mmol) was put in the reaction vessel. DCM (3.0 mL) was added to immerse all the resin and the mixture was shaken for 30 min. The DCM was removed by filtration under vacuum. Allyl ester of the corresponding Fmoc protected amino-acid (unprotected on the lateral chain) (3.0 eq.) was dissolved with a minimum amount of DCM (1 mL) to observe total dissolution. DIPEA (5.0 eq.) was added and the solution was mixed thoroughly. The solution was immediately added to the resin. The reaction vessel was closed with a cap and the system shaken for 60 min. The mixture was filtered under vacuum and the procedure was repeated once. The resin was washed with DMF (2.5 mL) shaken for 20 seconds and filtered. This washing was repeated twice. A mixture of DCM/MeOH/

DIPEA (80/15/5) (1 mL) was added to the resin. The reaction vessel was closed with a cap and the system was shaken for 10 min. The mixture was filtered under vacuum and the all process was repeated once. The mixture was filtered under vacuum then filled with DMF (2.5 mL), shaken for 20 seconds and filtered. The cap and the edge of the tube were washed with DMF (2.5 mL), shaken for 20 seconds and filtered under vacuum. This washing was repeated twice. To the resin was added DMF (2.5 mL). The mixture was shaken for 20 seconds then the solvent was removed by filtration under vacuum.

Tetrakis(triphenylphosphine)palladium(0) (0.1 eq.) was dissolved in DCM (1.3 mL). Phenylsilane (10.0 eq.) was added to the solution and this solution was introduced in the syringe. The mixture was shaken 45 minutes then was filtered under vacuum. A solution of sodium N,N-diethyldithiocarbamate (0.02 M in DMF, 4 mL) was added to the resin, the mixture was shaken for 15 minutes then filtered under vacuum to remove the solvent. This step was repeated twice. DMF (2.5 mL) was added to the resin and the mixture shaken for 20 seconds then filtered. The cap and the edge of the tube were washed with DMF (2.5 mL), shaken for 20 seconds and filtered under vacuum. This washing was repeated 4 times.

Mitsunobu process: The resin was rinsed with three small volumes of anhydrous THF to remove trace amounts water. Triphenylphosphine (5.0 eq.) was transferred to a small vial and dissolved in a minimal amount of anhydrous THF (about 1.3 mL). Anhydrous alcohol ROH was added (10.0 eq.) and the resulting solution was transferred to the reaction vessel containing the resin. DIAD (5.0 eq.) was added dropwise. After the DIAD addition was completed, the reaction vessel was capped and shaken for 15 minutes. The mixture was filtered under vacuum then filled with DMF (2.5 mL), shaken for 20 seconds and filtered. The cap and the edge of the tube were washed with DMF (2.5 mL), shaken for 20 seconds and filtered under vacuum. This washing was repeated three times and the Mitsunobu process was repeated once.

A solution of DMF/piperidine (80:20, 4.0 mL for 0.08 mmol of resin) was added to the resin, the mixture was shaken for 20 minutes then filtered under vacuum to remove the solvent. This step was repeated once. DMF (2.5 mL) was added, the mixture shaken for 20 seconds then filtered. The cap and the edge of the tube were washed with DMF (2.5 mL), shaken for 20 seconds and filtered under vacuum. This washing was repeated 4 times. The reaction vessel was filled with isopropanol (2.5 mL), shaken for 20 seconds and filtered under vacuum. This washing was repeated twice. The reaction vessel was filled with hexane (2.5 mL), shaken for 20 seconds and filtered and dried under vacuum for 24 hours.

The cycle from Step 2 to Step 3 described in Example 4 was repeated for each amino-acid or dipeptide of the sequence. The N-terminal position was deprotected following Step 3 described in Example 4. Cleavage of the peptide from the resin and deprotection of the lateral chains were made following Step 4 described in Example 4. Final purification was made following Step 5 described in Example 4.

Example 8. Synthesis of Peptides Containing N-Me Amino-Acids or α,β-Dehydroaminobutyric acid To introduce N-Me amino acids or α,β-dehydroaminobutyric acid in the sequence, a specific procedure was used for the coupling of these amino acids and for the coupling of the next amino acid. For the rest of the synthesis, previously described procedures were used.

DMF (2.5 mL) was added to the swollen resin, the mixture shaken for 20 seconds and the solvent removed under vacuum. The Fmoc-protected N-Me amino-acid or α,β-dehydroaminobutyric (3.0 eq.) and HATU (2.9 eq.) were dissolved in a minimum amount of DMF (1.3 mL). DIPEA (6.0 eq.) was added and the solution was mixed thoroughly. The solution was immediately added to the N-deprotected peptidyl resin. The reaction vessel was closed with a cap and the system shaken for 60 min. The mixture was filtered under vacuum and the coupling was repeated once. The mixture was filtered under vacuum then filled with DMF (2.5 mL), shaken for 20 seconds and filtered. The cap and the edge of the tube were washed with DMF (2.5 mL), shaken for 20 seconds and filtered under vacuum. This washing was repeated once. The reaction vessel was filled with MeOH (2.5 mL), shaken for 20 seconds and filtered under vacuum. The reaction vessel was filled with DCM (2.5 mL), shaken for 20 seconds and filtered under vacuum. This washing was repeated 4 times.

Example 9. Compounds Synthesized Via Examples 1-8 and Analytical Data (Table 1)

TABLE 1

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 11.1 | 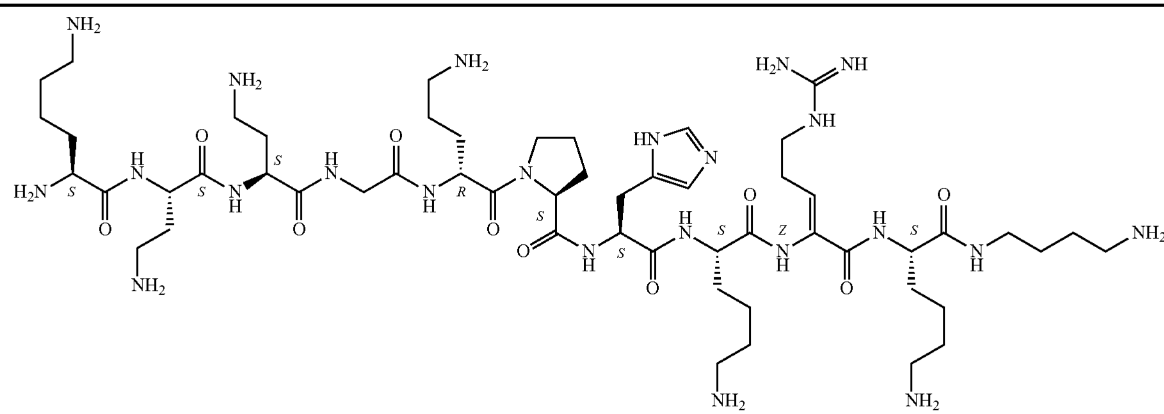 | $C_{54}H_{101}N_{23}O_{10}$ | 1232.54 | 1233.60 | 96% | 10.18 |
| 12.1 | 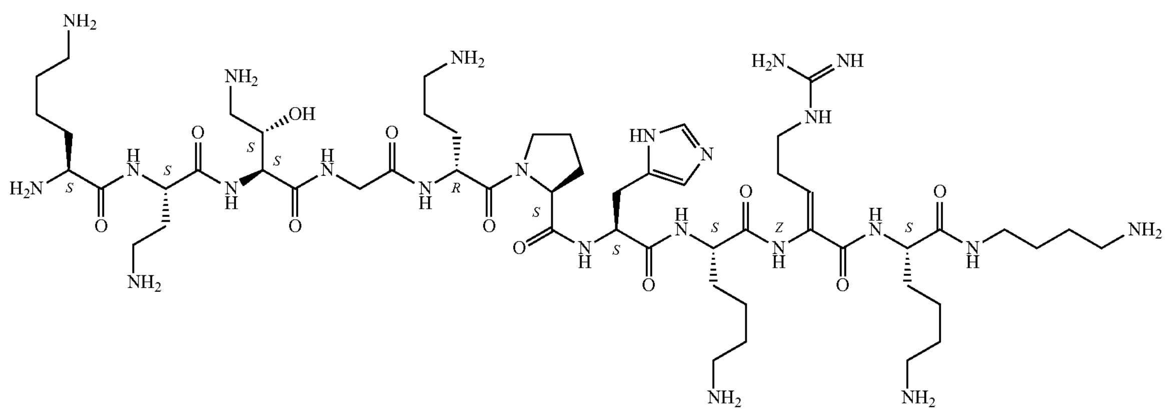 | $C_{54}H_{101}N_{23}O_{11}$ | 1248.54 | 1249.65 | 96% | 10.29 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 13.1 | 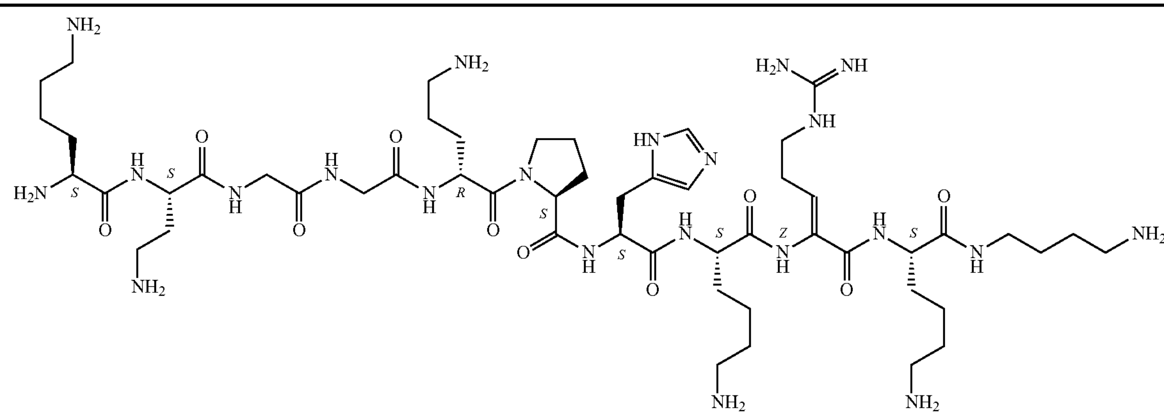 | $C_{52}H_{96}N_{22}O_{10}$ | 1189.47 | 1190.60 | 99% | 9.92 |
| 14.1 | 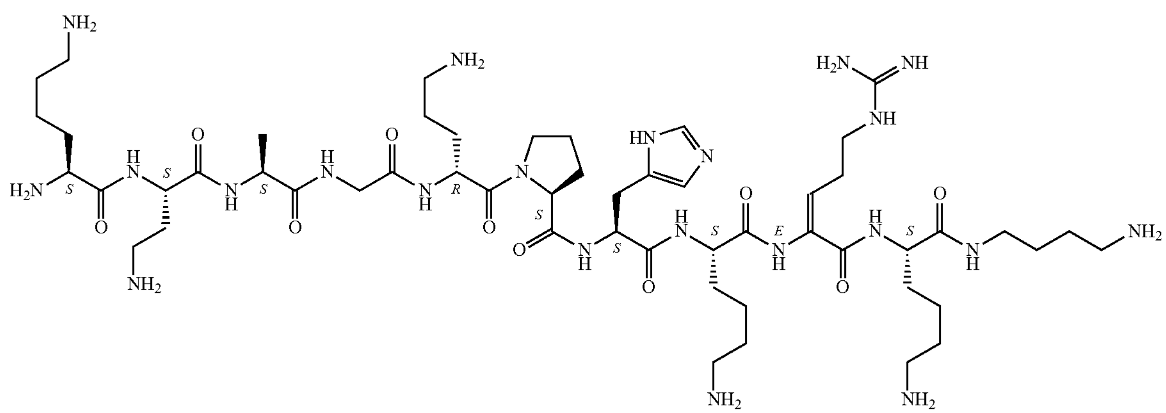 | $C_{53}H_{98}N_{22}O_{10}$ | 1203.50 | 1204.60 | 99% | 10.04 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 14.2 | 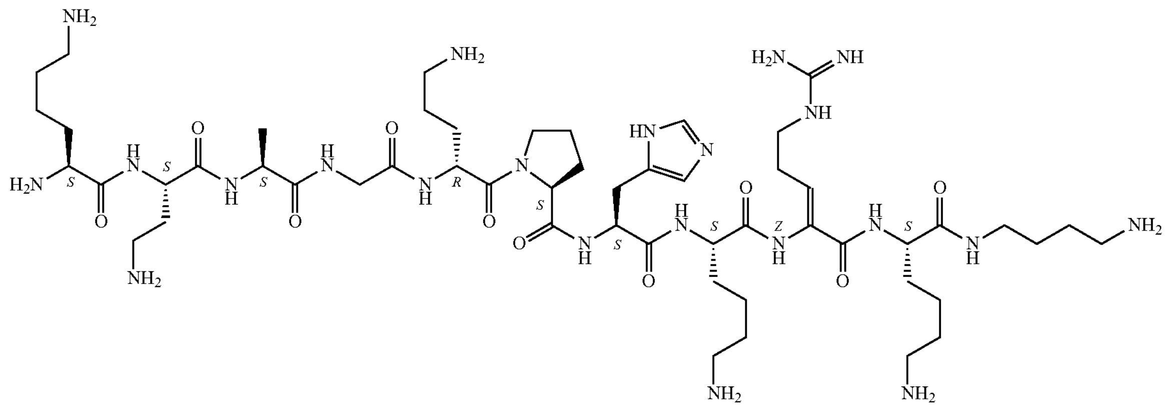 | $C_{53}H_{98}N_{22}O_{10}$ | 1203.50 | 1204.65 | 96% | 10.12 |
| 14.4 | 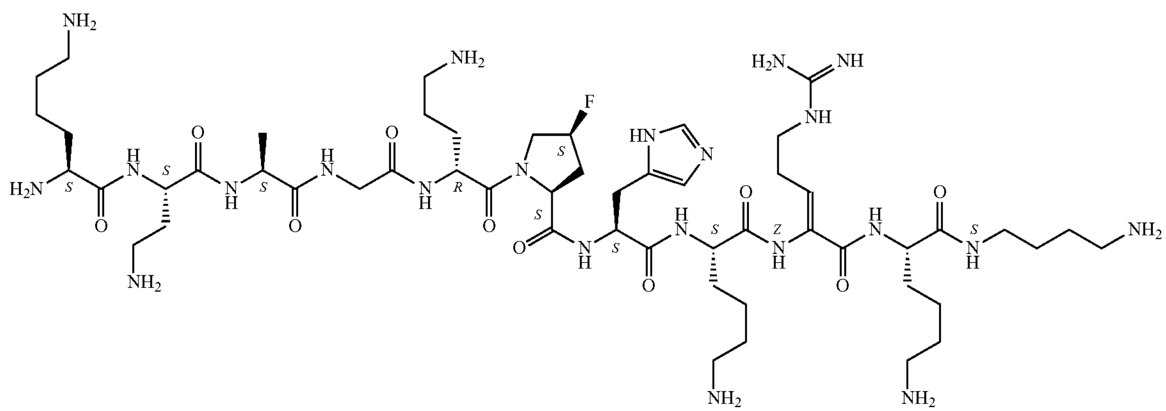 | $C_{53}H_{97}FN_{22}O_{10}$ | 1221.49 | 1222.60 | 97% | 9.99 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 14.5 | 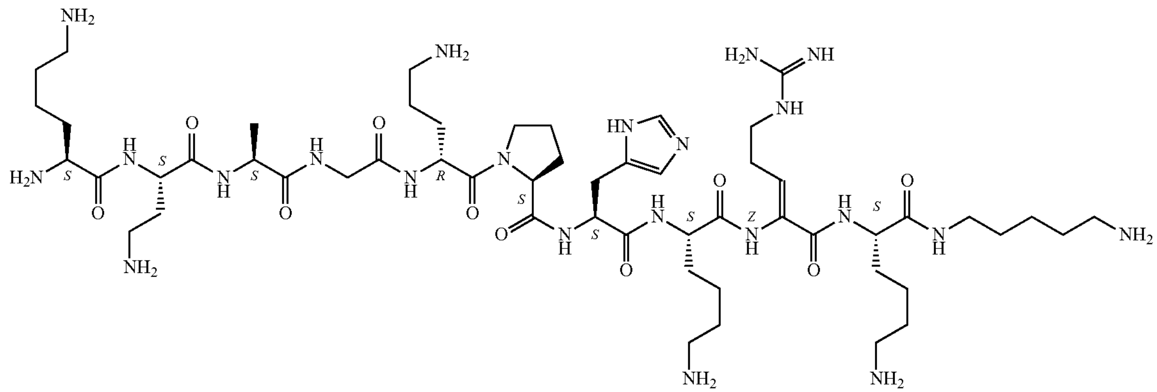 | $C_{54}H_{100}N_{22}O_{10}$ | 1217.53 | 1218.65 | 98% | 10.16 |
| 14.6 | 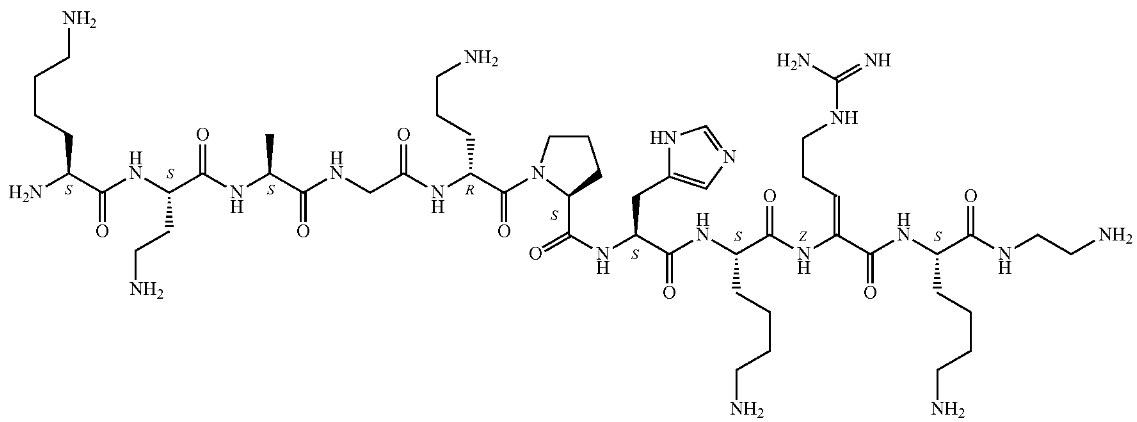 | $C_{51}H_{94}N_{22}O_{10}$ | 1175.45 | 1176.00 | 99% | 9.74 |

TABLE 1-continued

Compounds and analytical data

| Cmpd | Structure | Molecular formula | MW (g/mol) | [M + H]⁺ (g/mol) | UV purity (λ = 230 nm) | Rt (min) |
|---|---|---|---|---|---|---|
| 14.7 | 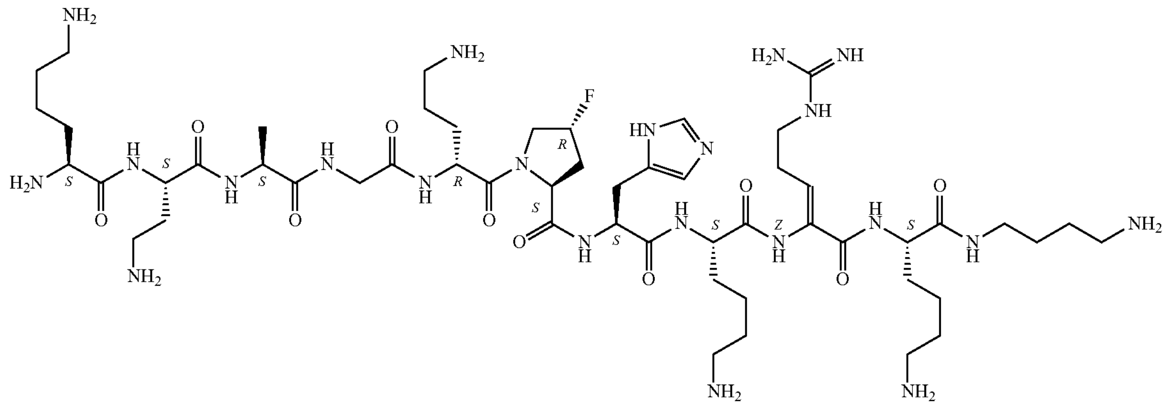 | $C_{53}H_{97}FN_{22}O_{10}$ | 1221.49 | 1222.65 | 99% | 10.03 |
| 14.9 | 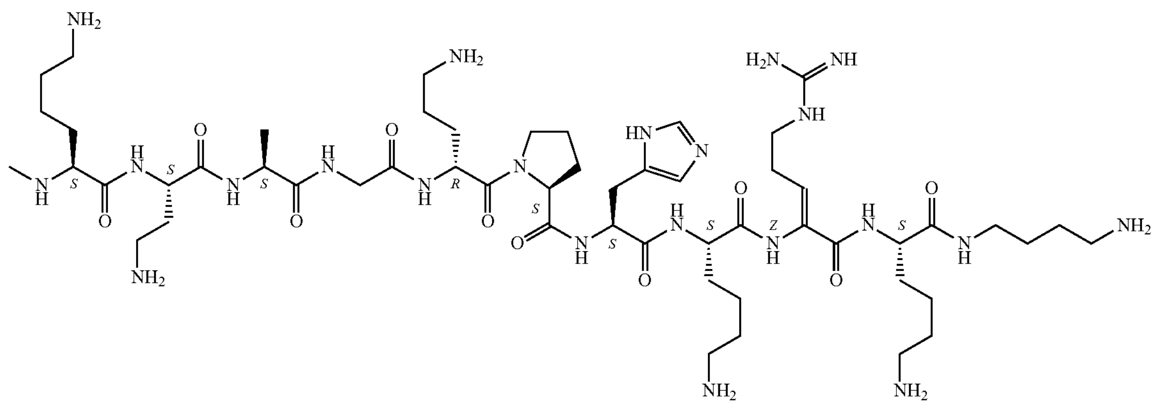 | $C_{54}H_{100}N_{22}O_{10}$ | 1217.53 | 1218.60 | 99% | 10.13 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 14.10 | 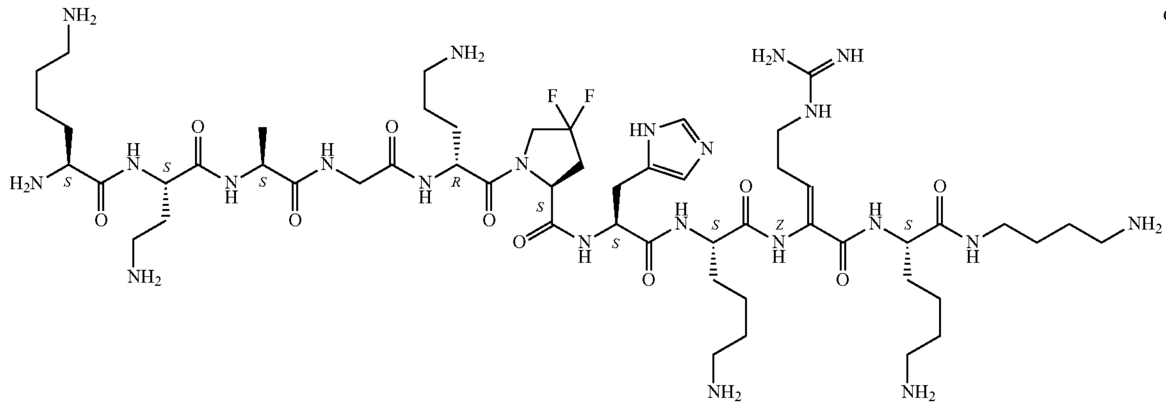 | C₅₃H₉₆F₂N₂₂O₁₀ | 1239.48 | 1240.60 | 99% | 10.32 |
| 14.11 | 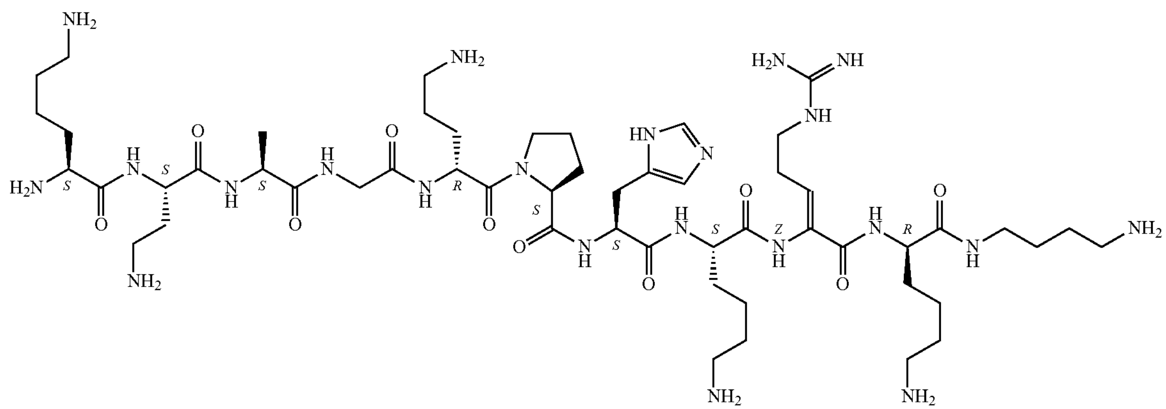 | C₅₃H₉₈N₂₂O₁₀ | 1203.50 | 1204.60 | 99% | 10.04 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 14.12 | 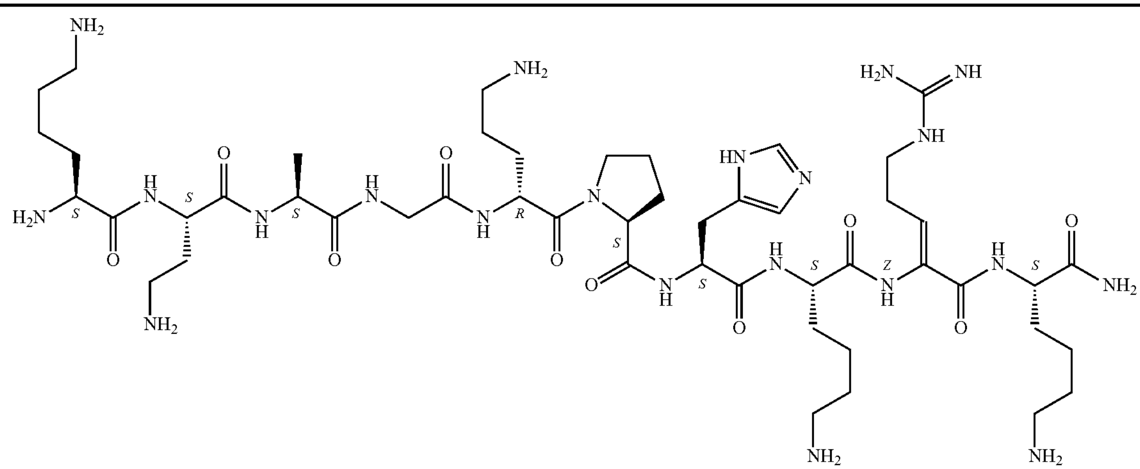 | C₄₉H₈₉N₂₁O₁₀ | 1132.38 | 1133.60 | 99% | 9.61 |
| 14.13 | 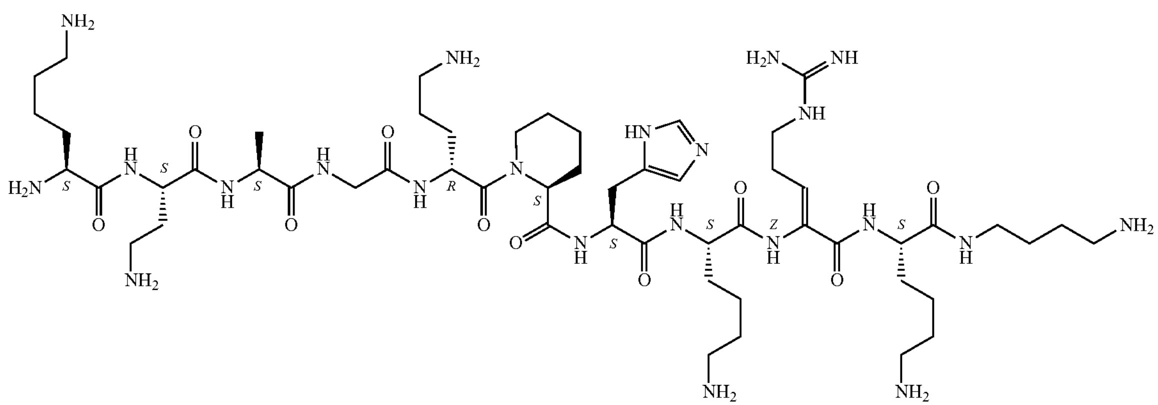 | C₅₄H₁₀₀N₂₂O₁₀ | 1217.53 | 1218.70 | 99% | 10.24 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 14.14 | 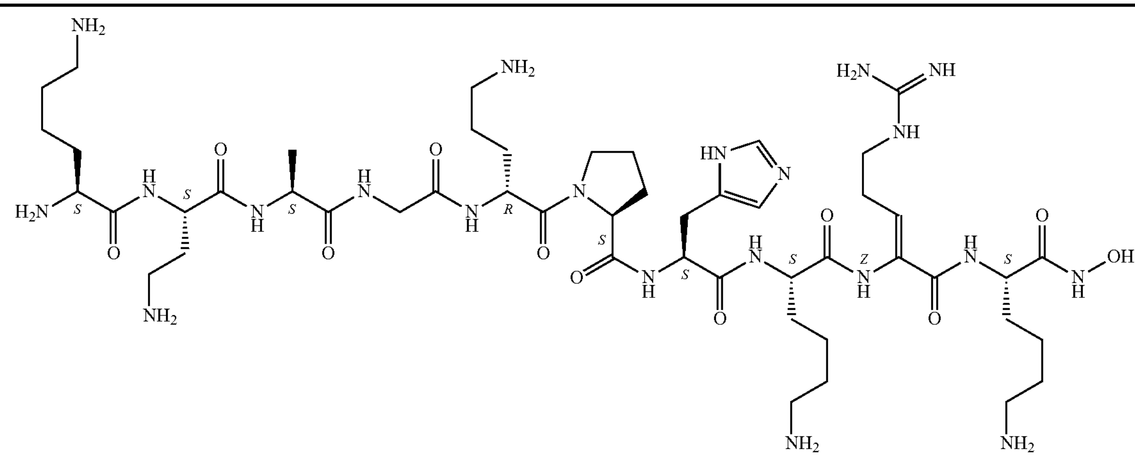 | C$_{49}$H$_{89}$N$_{21}$O$_{11}$ | 1148.38 | 1149.55 | 99% | 9.65 |
| 14.15 | 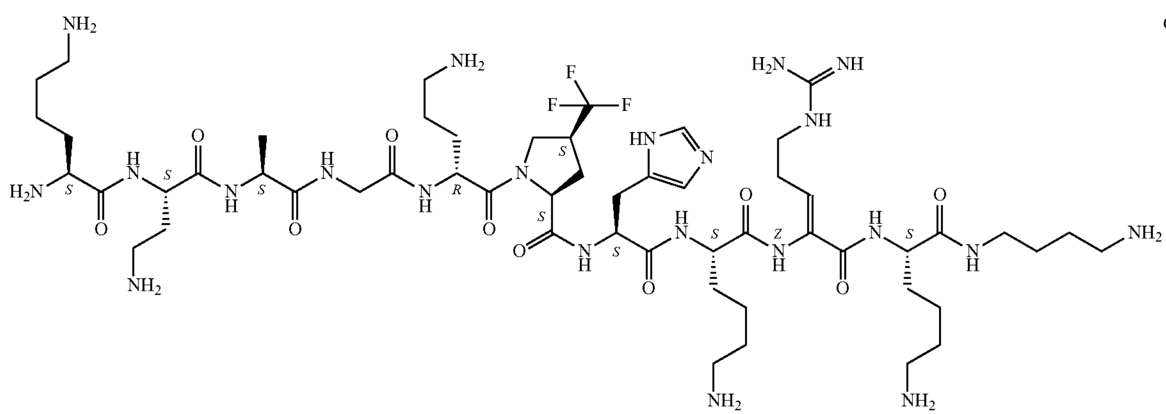 | C$_{54}$H$_{97}$F$_3$N$_{22}$O$_{10}$ | 1271.50 | 1272.65 | 99% | 10.85 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 14.16 | 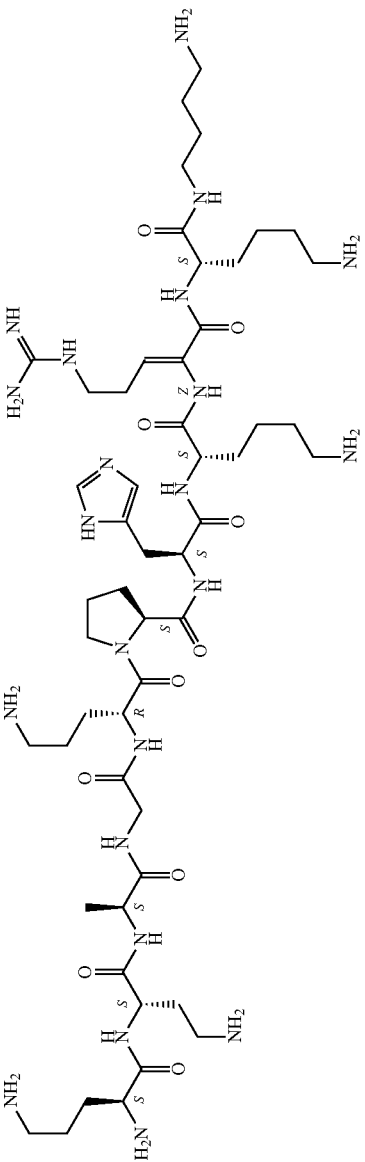 | $C_{52}H_{96}N_{22}O_{10}$ | 1189.47 | 1190.65 | 99% | 10.14 |
| 14.17 | 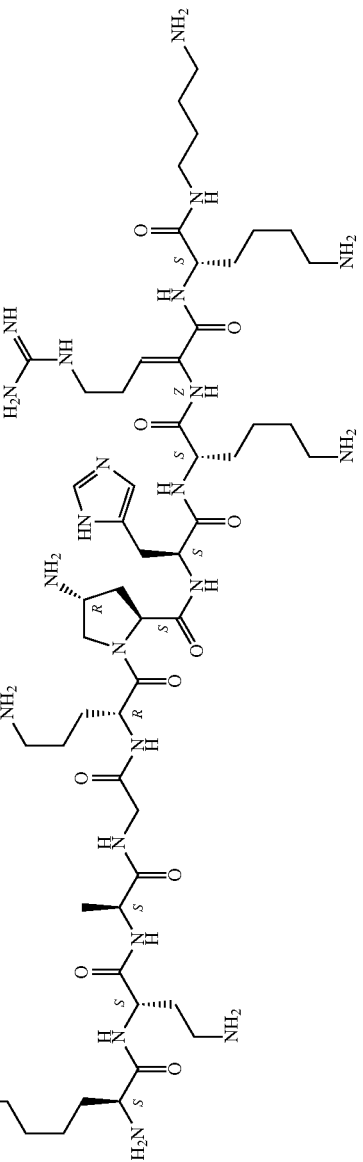 | $C_{53}H_{99}N_{23}O_{10}$ | 1218.52 | 1219.60 | 99% | 9.97 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 14.18 | 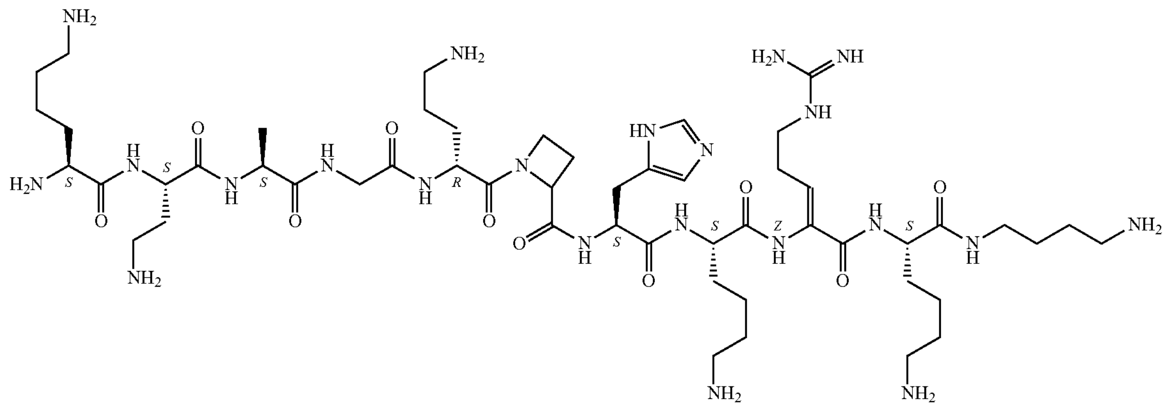 | $C_{52}H_{96}N_{22}O_{10}$ | 1189.47 | 1190.65 | 99% | 9.81 |
| 14.19 | 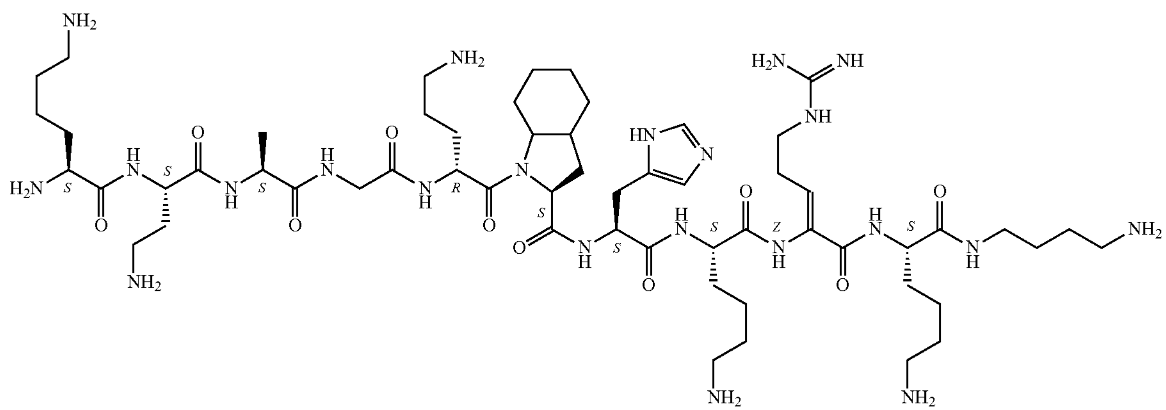 | $C_{57}H_{104}N_{22}O_{10}$ | 1257.59 | 1258.65 | 99% | 11.45 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 14.20 | 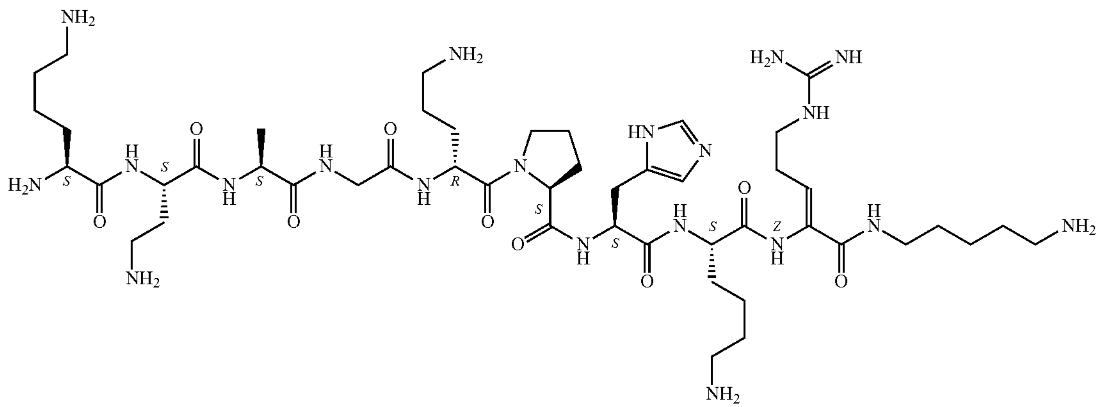 | C$_{48}$H$_{88}$N$_{20}$O$_{9}$ | 1089.35 | 1090.55 | 99% | 10.20 |
| 14.21 | 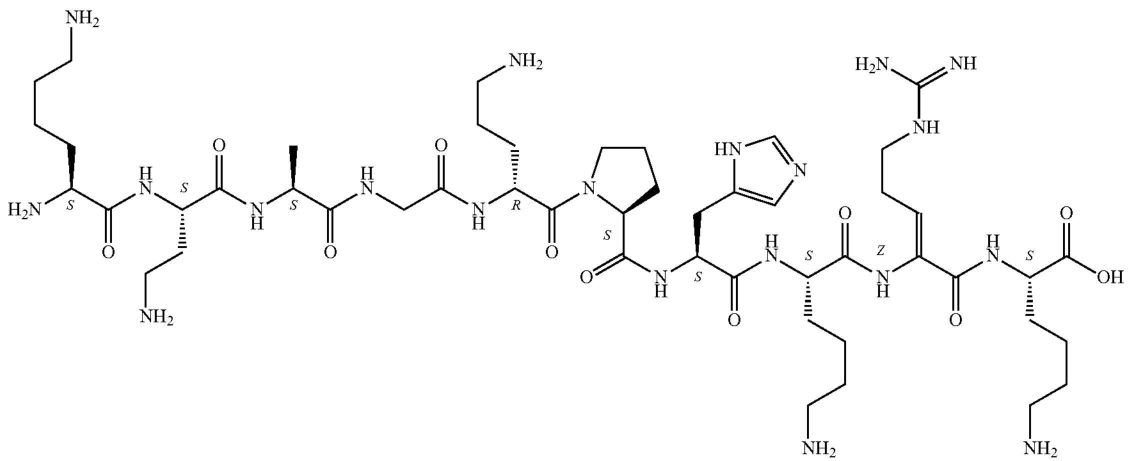 | C$_{49}$H$_{88}$N$_{20}$O$_{11}$ | 1133.36 | 1134.50 | 99% | 9.78 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 14.22 | 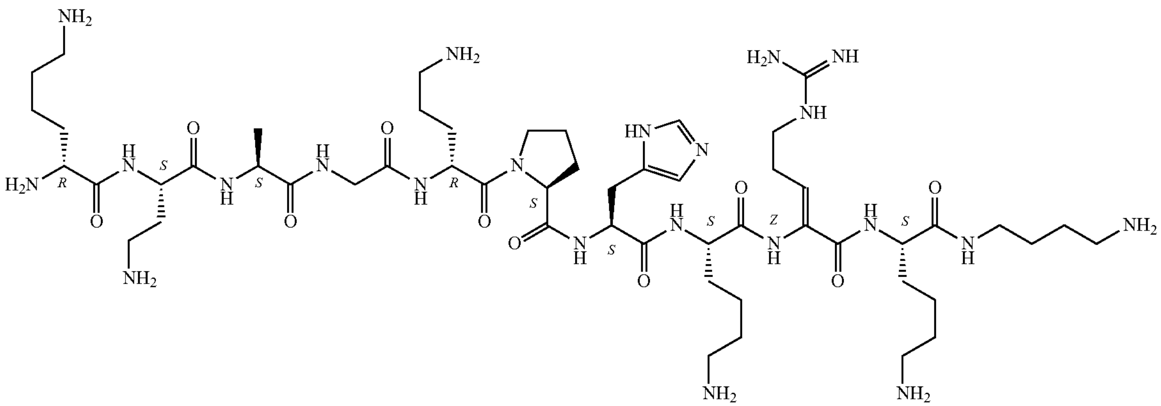 | C53H98N22O10 | 1203.50 | 1204.60 | 99% | 10.03 |
| 14.23 | 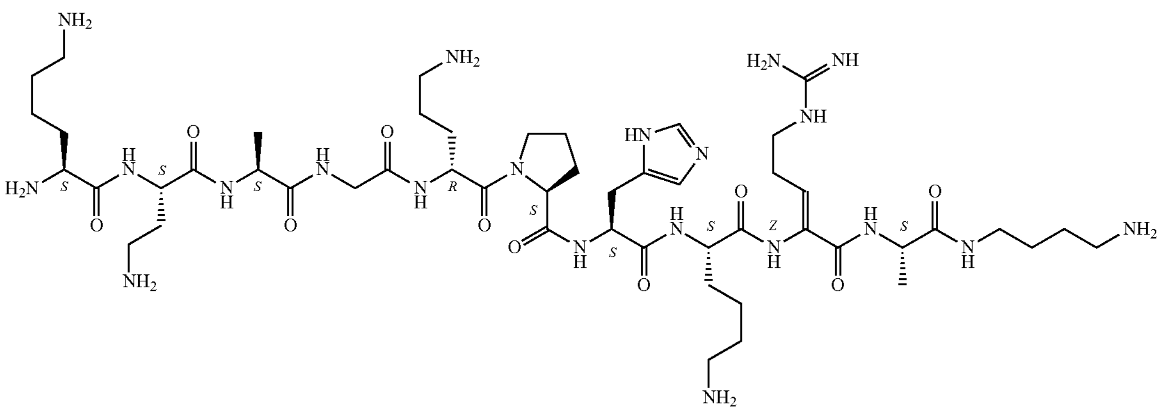 | C50H91N21O10 | 1146.41 | 1147.55 | 99% | 10.13 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 14.24 | 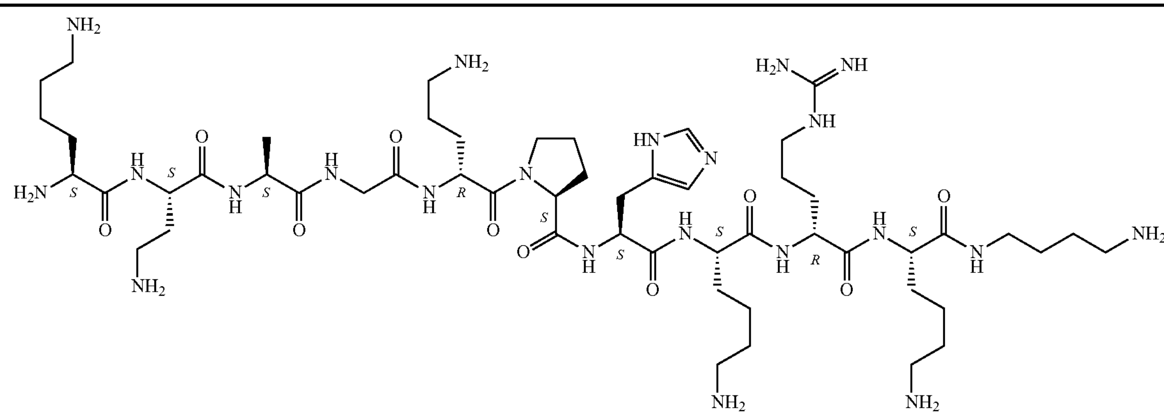 | C₅₃H₁₀₀N₂₂O₁₀ | 1205.52 | 1206.70 | 99% | 10.02 |
| 14.25 | 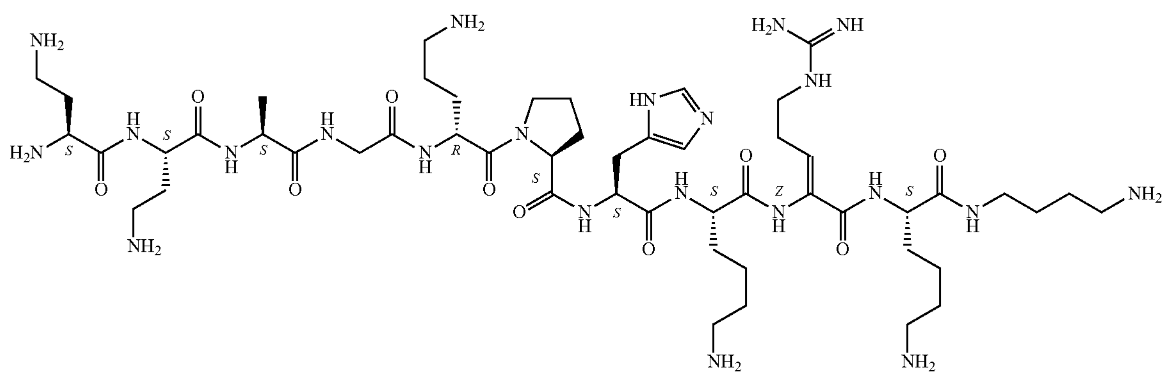 | C₅₁H₉₄N₂₂O₁₀ | 1175.45 | 1176.90 | 99% | 10.02 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 15.1 | 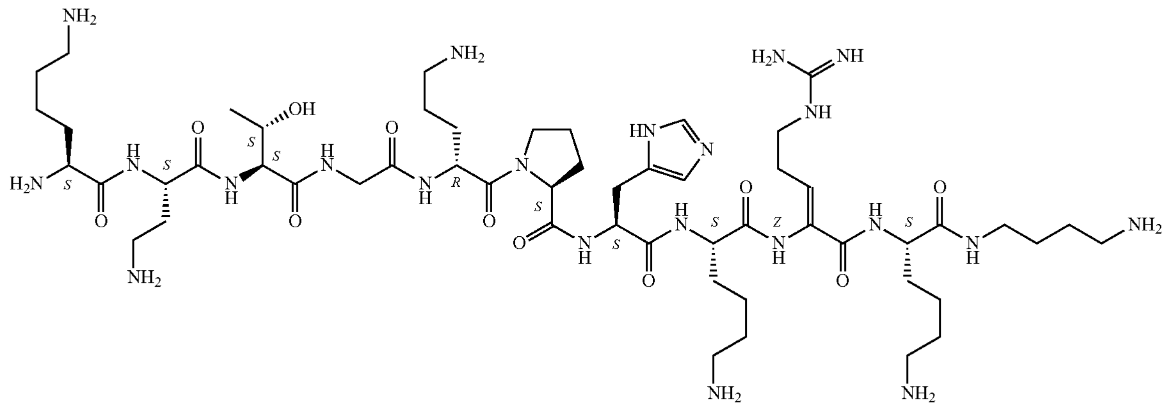 | C54H100N22O11 | 1233.53 | 1234.65 | 82% | 10.25 |
| 15.3 | 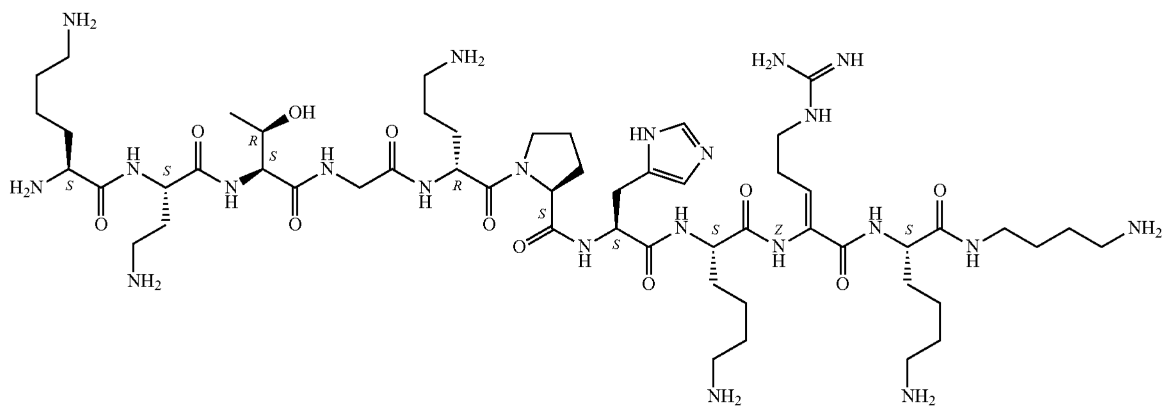 | C54H100N22O11 | 1233.53 | 1234.65 | 87% | 10.54 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 16.1 | 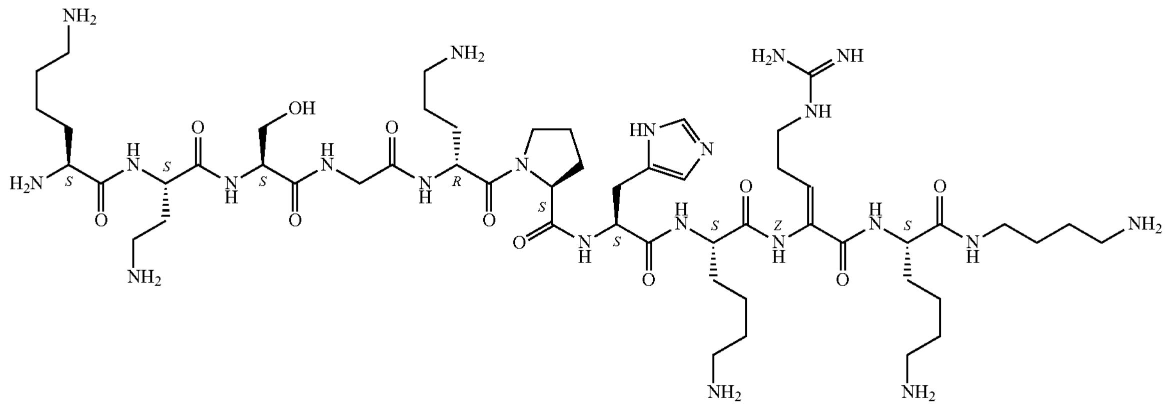 | $C_{53}H_{98}N_{22}O_{11}$ | 1219.50 | 1220.60 | 99% | 10.00 |
| 21.1 | 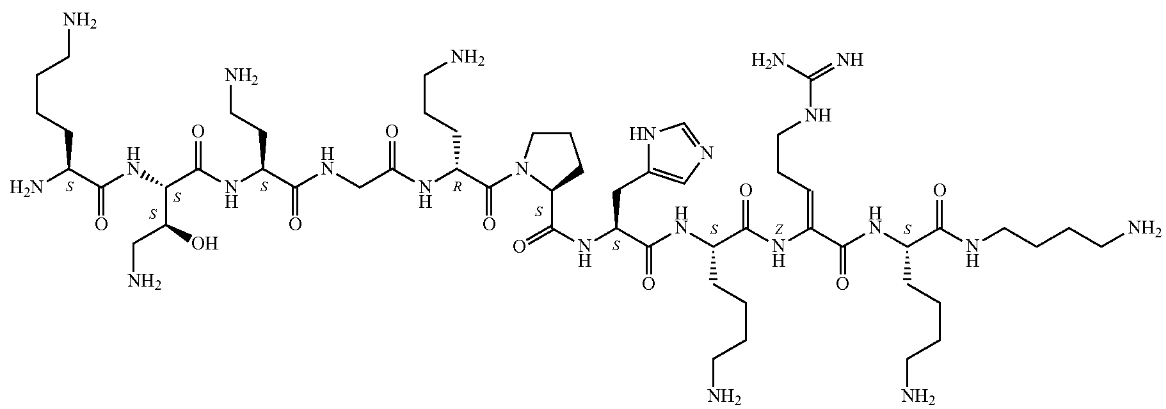 | $C_{54}H_{101}N_{23}O_{11}$ | 1248.54 | 1249.60 | 99% | 10.04 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 21.2 | 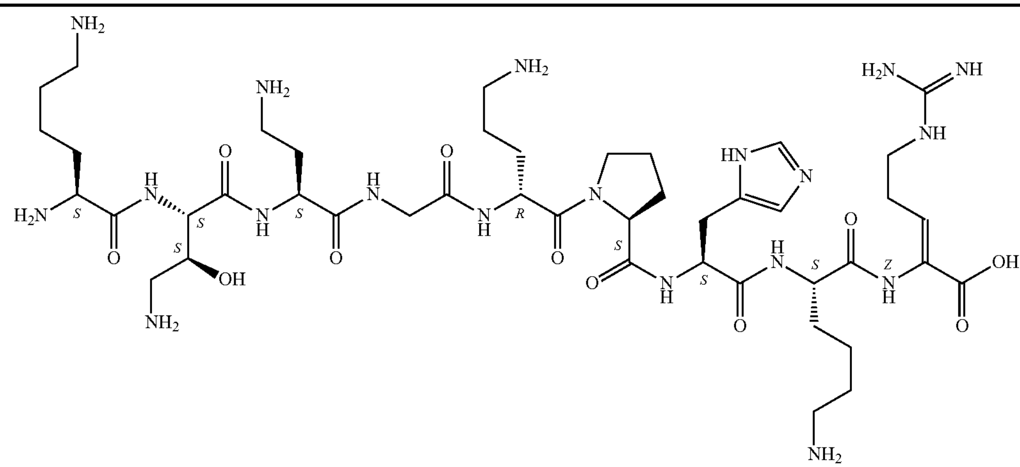 | $C_{44}H_{79}N_{19}O_{11}$ | 1050.22 | 1051.55 | 94% | 8.82 |
| 21.3 | 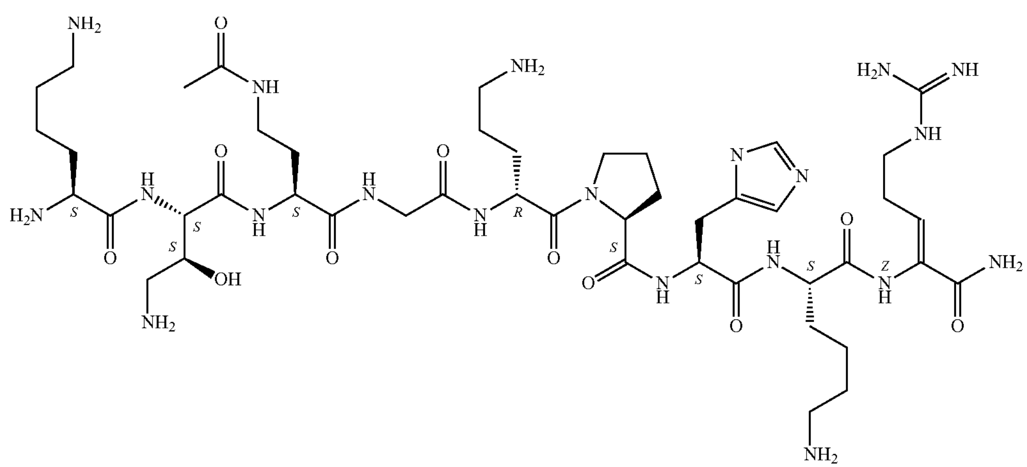 | $C_{46}H_{82}N_{20}O_{11}$ | 1091.27 | 1092.60 | 86% | 8.65 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 21.4 | 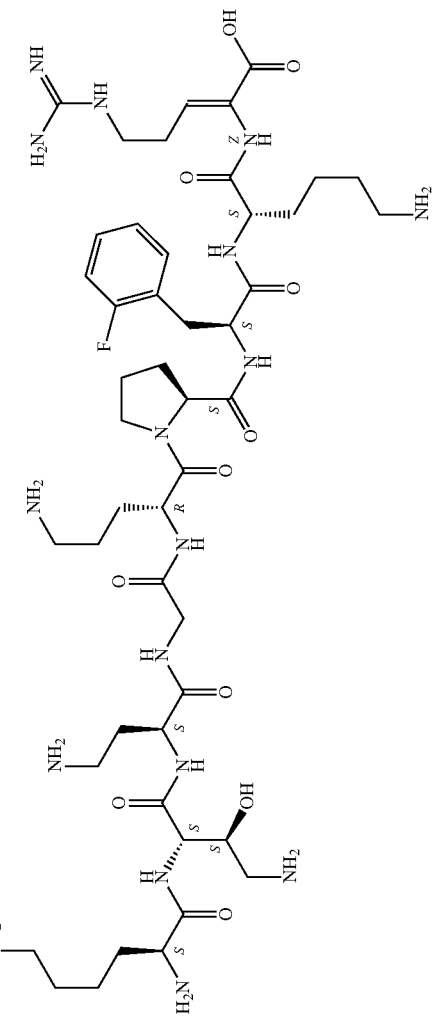 | $C_{47}H_{80}FN_{17}O_{11}$ | 1078.24 | 1079.55 | 99% | 12.76 |
| 21.5 | 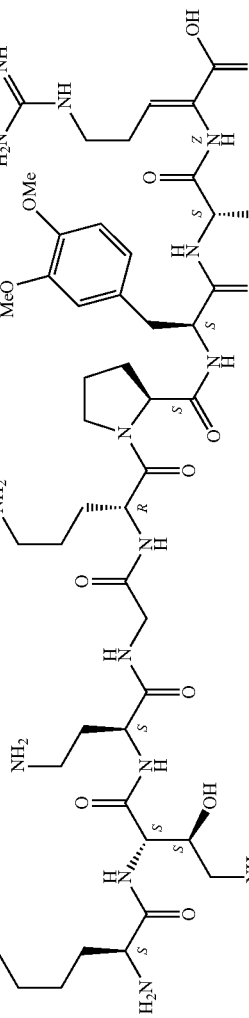 | $C_{49}H_{85}N_{17}O_{13}$ | 1120.30 | 1121.60 | 99% | 12.39 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 21.6 | 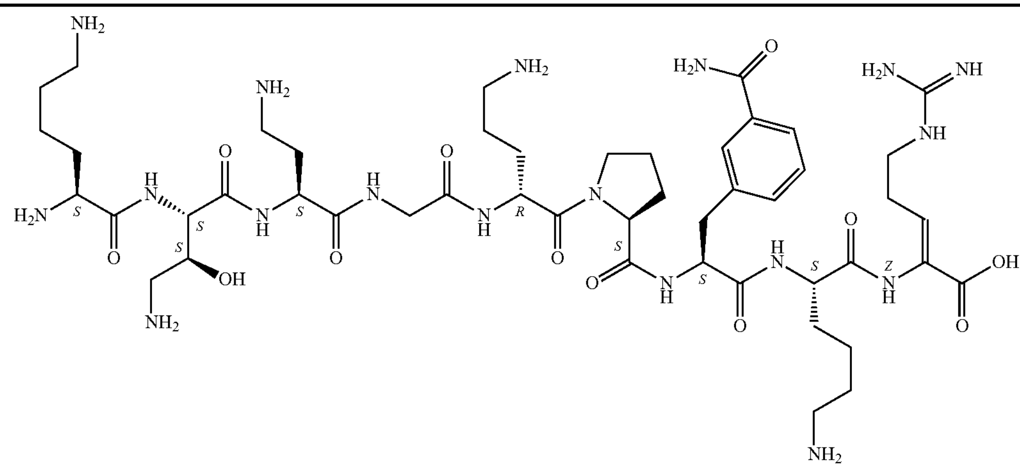 | $C_{48}H_{82}N_{18}O_{12}$ | 1103.28 | 1104.50 | 99% | 11.07 |
| 21.7 | 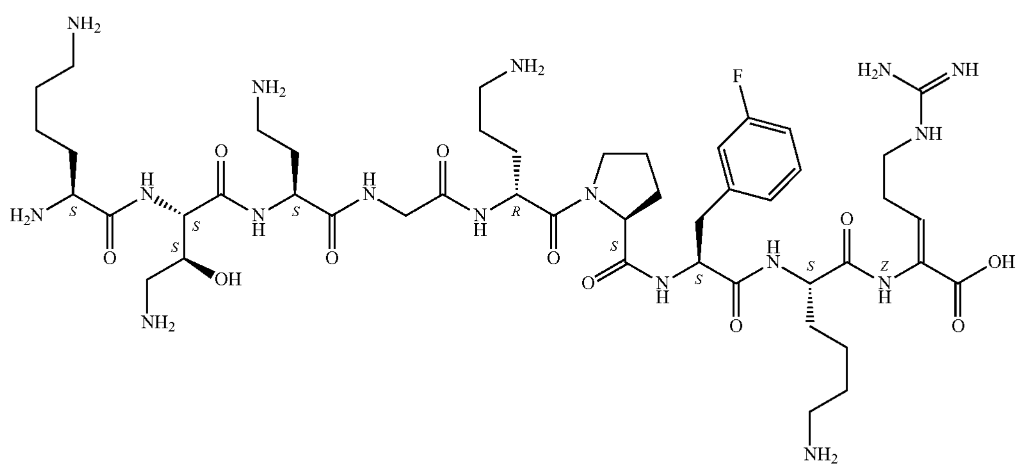 | $C_{47}H_{80}FN_{17}O_{11}$ | 1078.24 | 1079.55 | 99% | 12.88 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 21.8 | 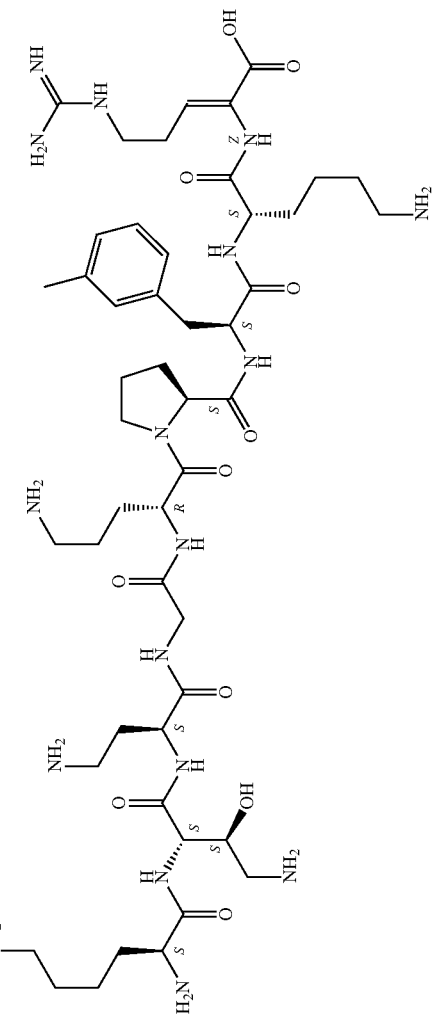 | C48H83N17O11 | 1074.28 | 1075.50 | 99% | 13.40 |
| 21.9 | 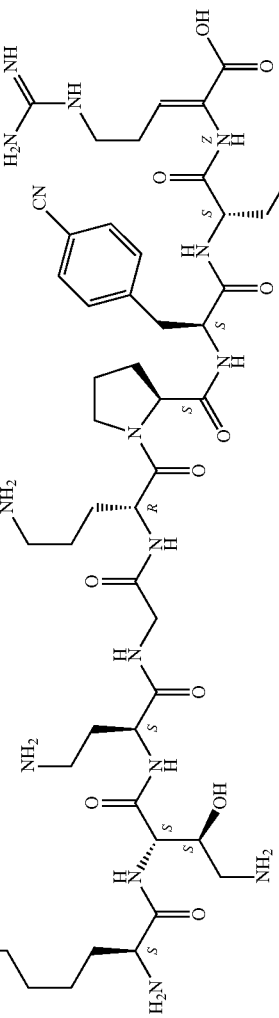 | C48H80N18O11 | 1085.26 | 1086.50 | 99% | 12.34 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 21.10 | 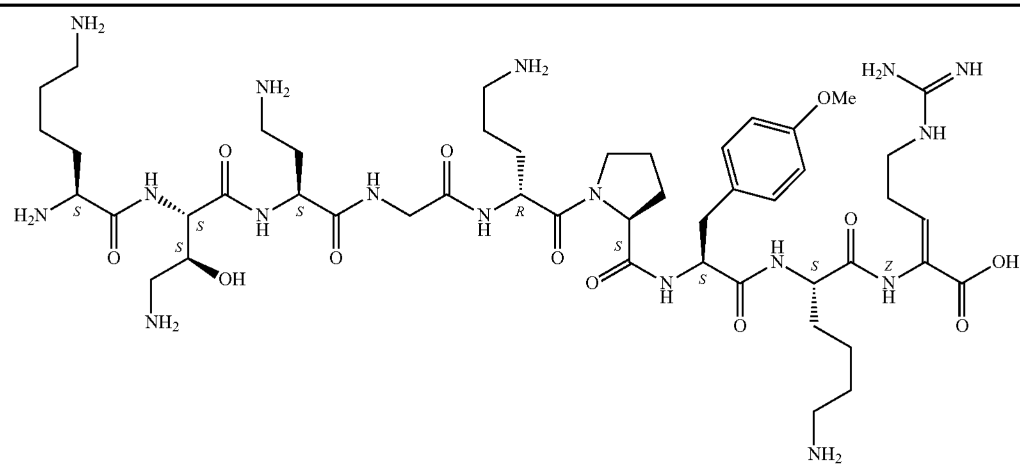 | $C_{48}H_{83}N_{17}O_{12}$ | 1090.28 | 1091.55 | 99% | 12.64 |
| 21.11 | 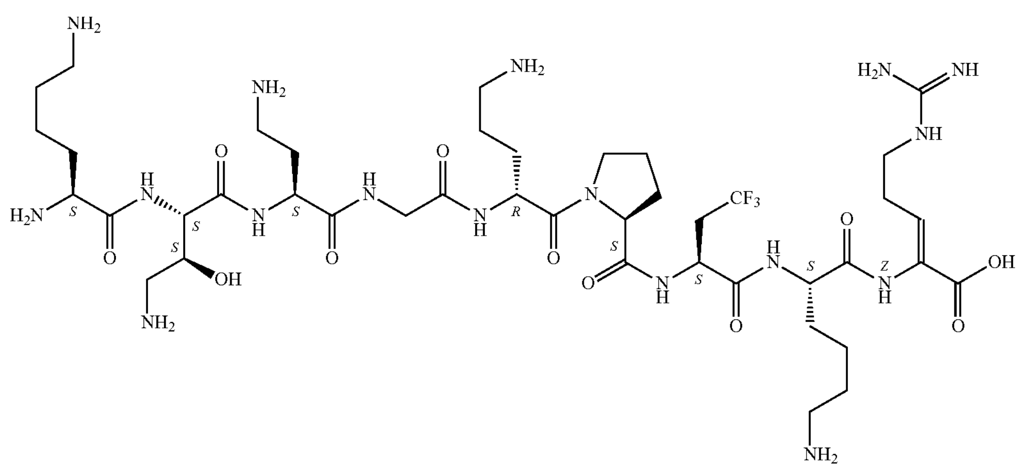 | $C_{42}H_{76}F_3N_{17}O_{11}$ | 1052.16 | 1053.50 | 99% | 11.56 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 21.12 | 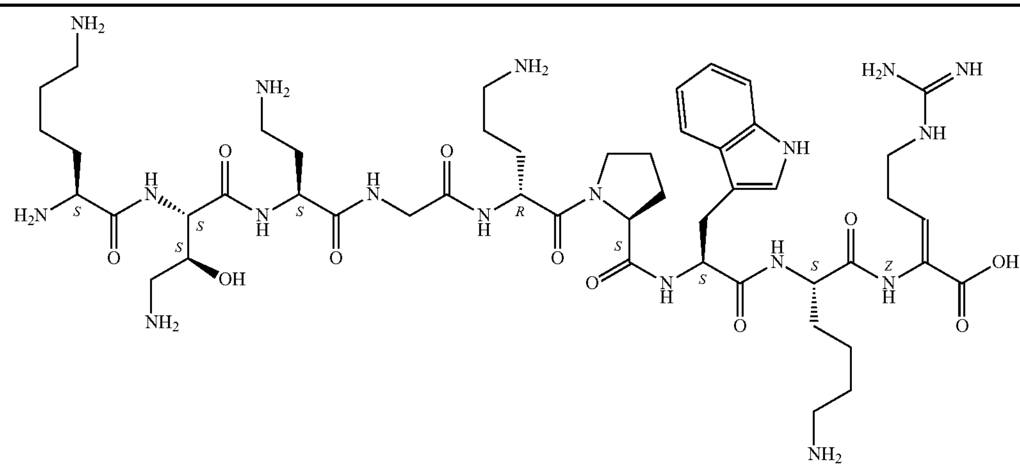 | $C_{49}H_{82}N_{18}O_{11}$ | 1099.29 | 1100.50 | 99% | 12.78 |
| 22.1 | 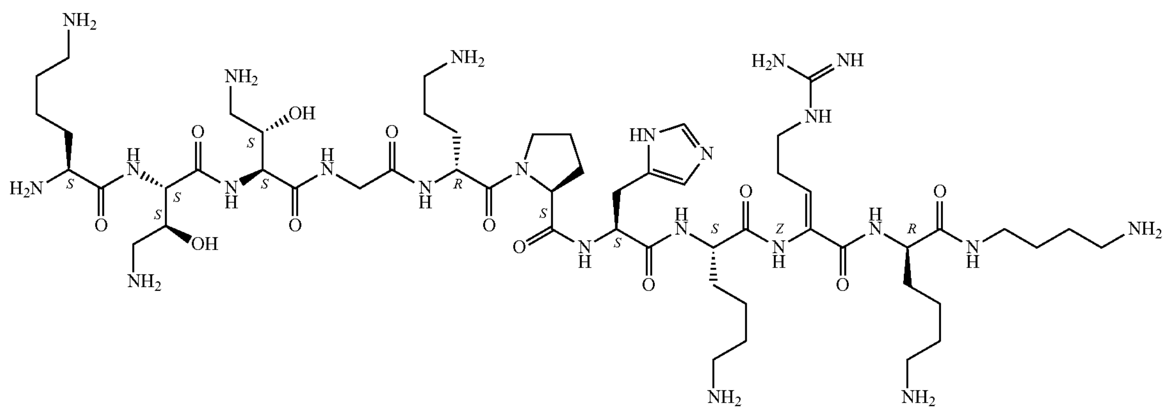 | $C_{54}H_{101}N_{23}O_{12}$ | 1264.54 | 1265.65 | 97% | 10.09 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 22.2 | 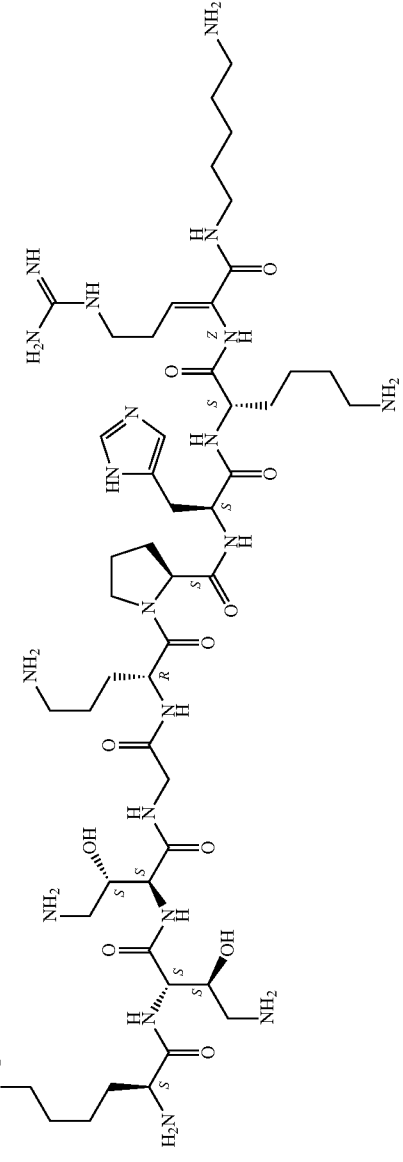 | C<sub>49</sub>H<sub>91</sub>N<sub>21</sub>O<sub>11</sub> | 1150.39 | 1151.55 | 95% | 10.35 |
| 22.3 | 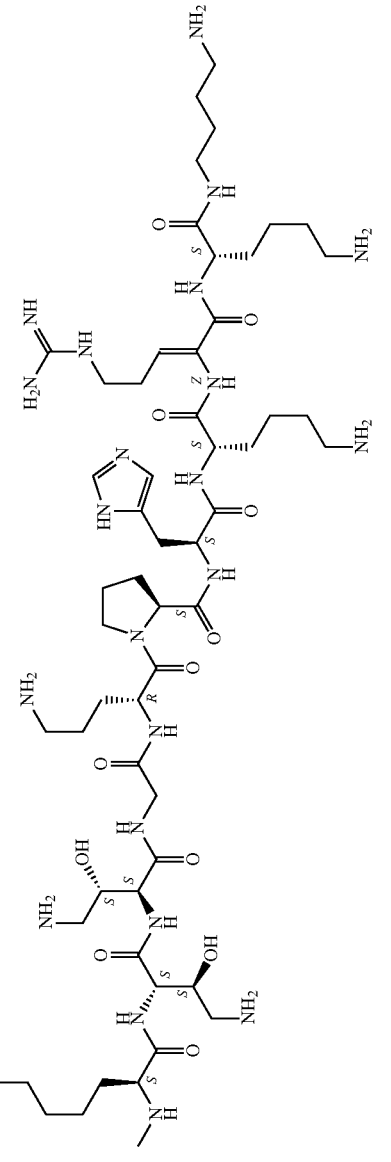 | C<sub>55</sub>H<sub>103</sub>N<sub>23</sub>O<sub>12</sub> | 1278.57 | 1279.55 | 96% | 10.26 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.4 | 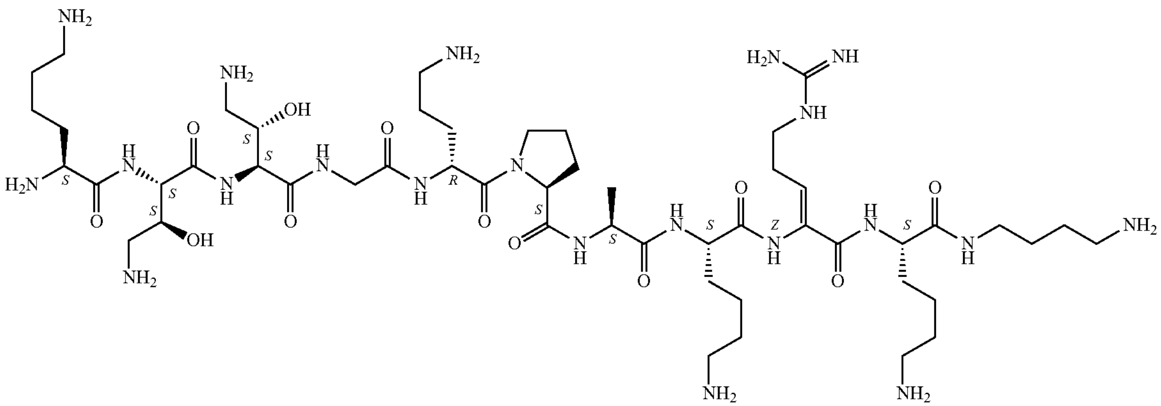 | C₅₁H₉₉N₂₁O₁₂ | 1198.48 | 1199.60 | 99% | 9.88 |
| 22.5 | 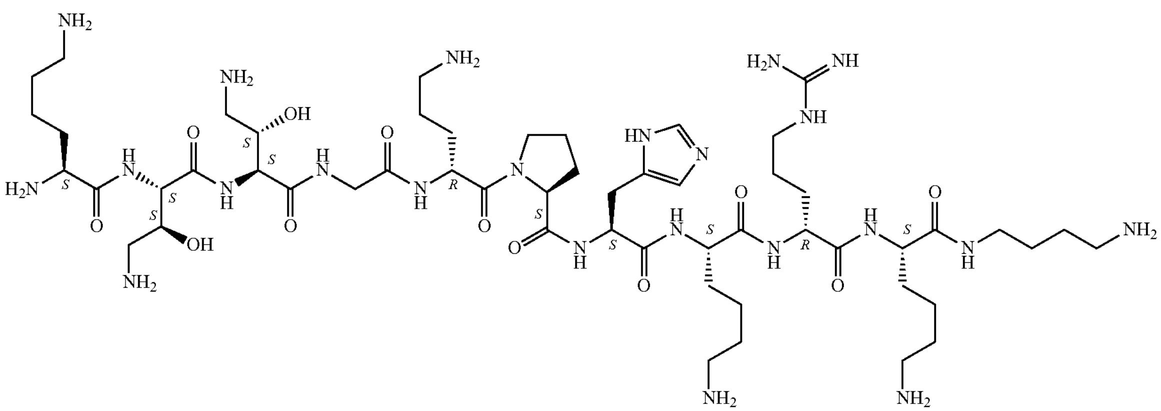 | C₅₄H₁₀₃N₂₃O₁₂ | 1266.56 | 1267.65 | 91% | 10.04 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.6 | 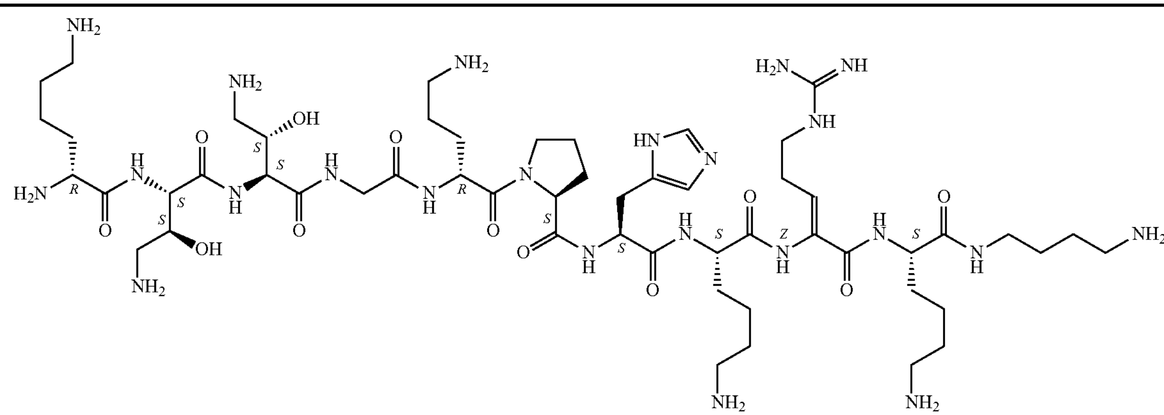 | C$_{54}$H$_{101}$N$_{23}$O$_{12}$ | 1264.54 | 1265.60 | 96% | 10.12 |
| 22.7 | 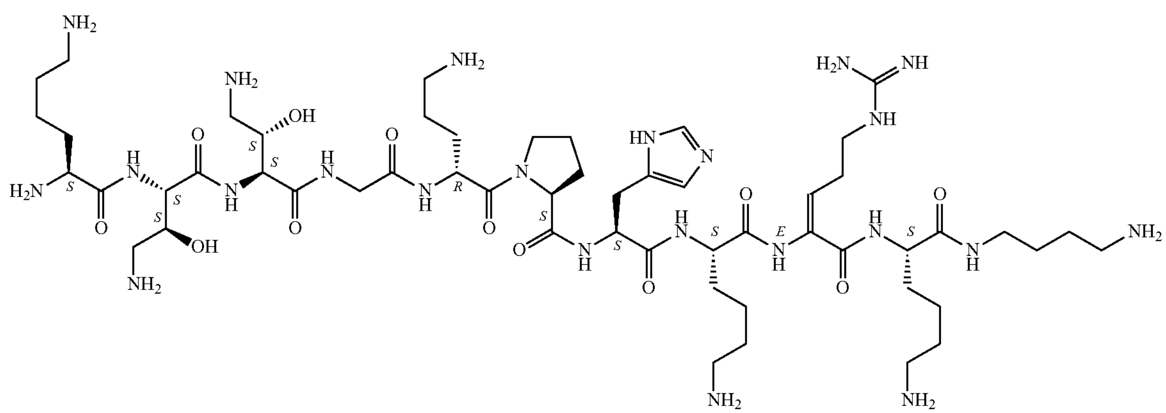 | C$_{54}$H$_{101}$N$_{23}$O$_{12}$ | 1264.54 | 1265.60 | 93% | 10.14 |

TABLE 1-continued

Compounds and analytical data

| Cmpd | Structure | Molecular formula | MW (g/mol) | [M + H]⁺ (g/mol) | UV purity (λ = 230 nm) | Rt (min) |
|---|---|---|---|---|---|---|
| 22.8 | 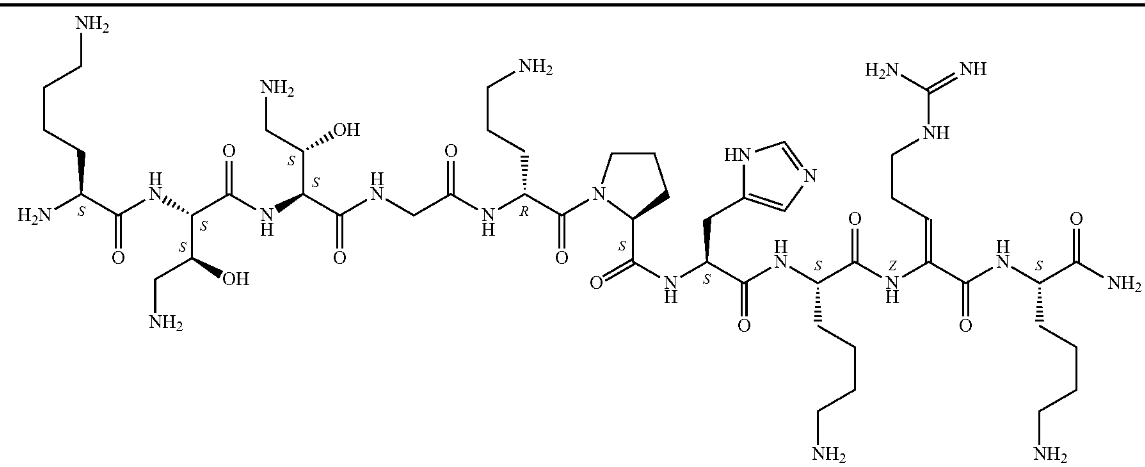 | $C_{50}H_{92}N_{22}O_{12}$ | 1193.42 | 1194.50 | 94% | 9.72 |
| 22.9 | 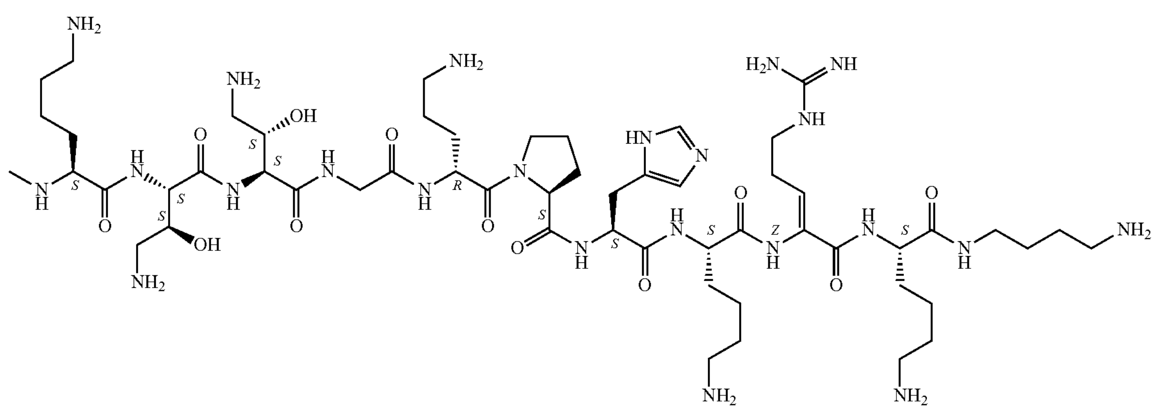 | $C_{51}H_{94}N_{22}O_{12}$ | 1207.45 | 1208.60 | 91% | 10.29 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.10 | 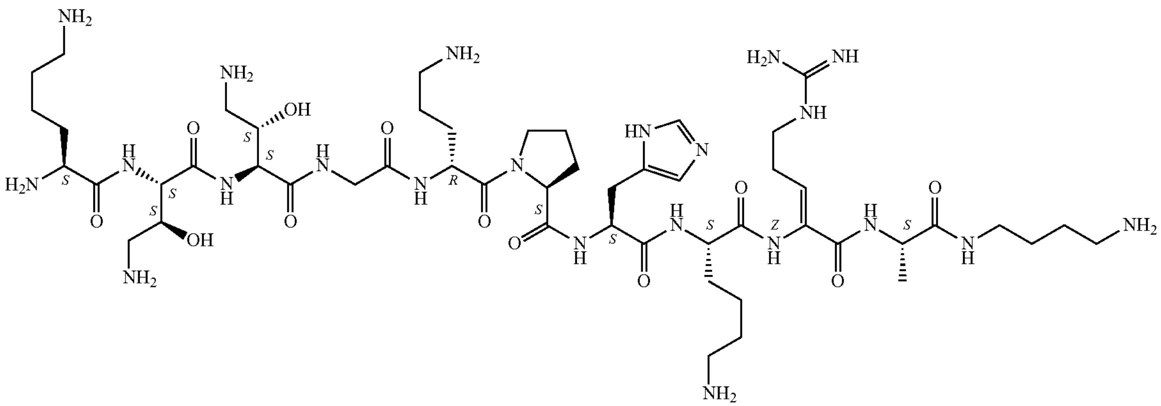 | C₅₁H₉₄N₂₂O₁₂ | 1207.45 | 1208.55 | 90% | 10.27 |
| 22.11 | 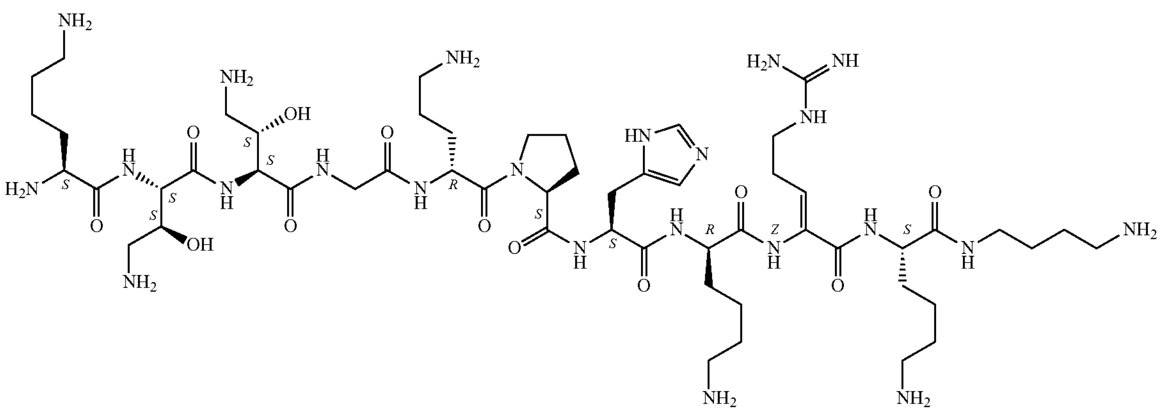 | C₅₄H₁₀₁N₂₃O₁₂ | 1264.54 | 1265.65 | 93% | 10.05 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.12 | 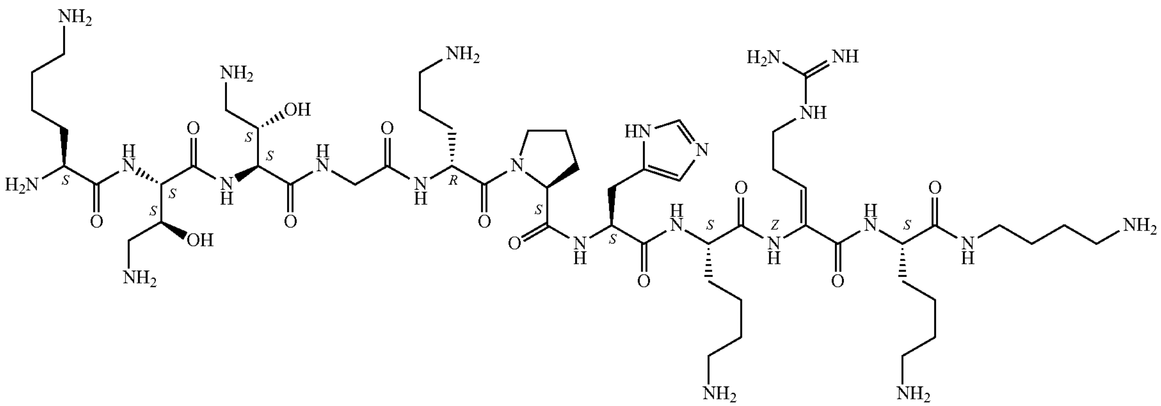 | C$_{55}$H$_{103}$N$_{23}$O$_{12}$ | 1278.57 | 1279.60 | 96% | 10.11 |
| 22.13 | 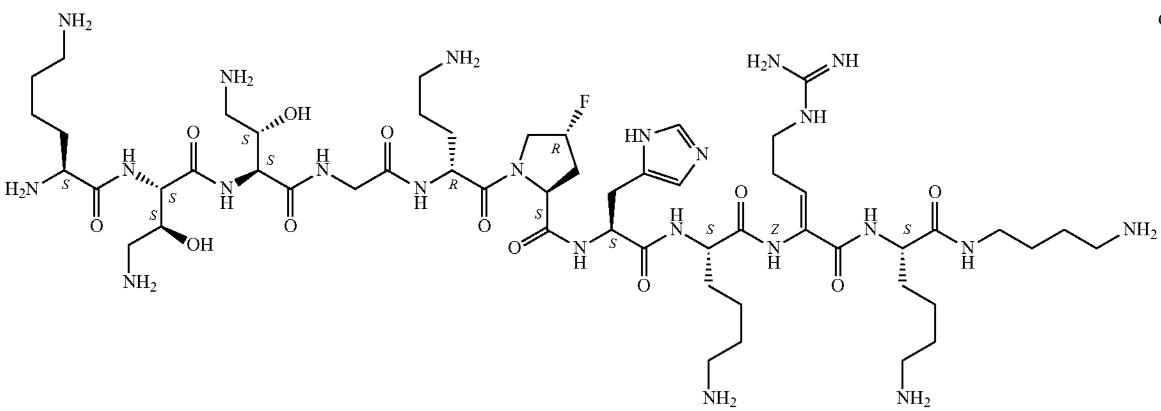 | C$_{54}$H$_{100}$FN$_{23}$O$_{12}$ | 1282.53 | 1283.60 | 99% | 10.10 |

TABLE 1-continued

Compounds and analytical data

| Cmpd | Structure | Molecular formula | MW (g/mol) | [M + H]⁺ (g/mol) | UV purity (λ = 230 nm) | Rt (min) |
|---|---|---|---|---|---|---|
| 22.14 | 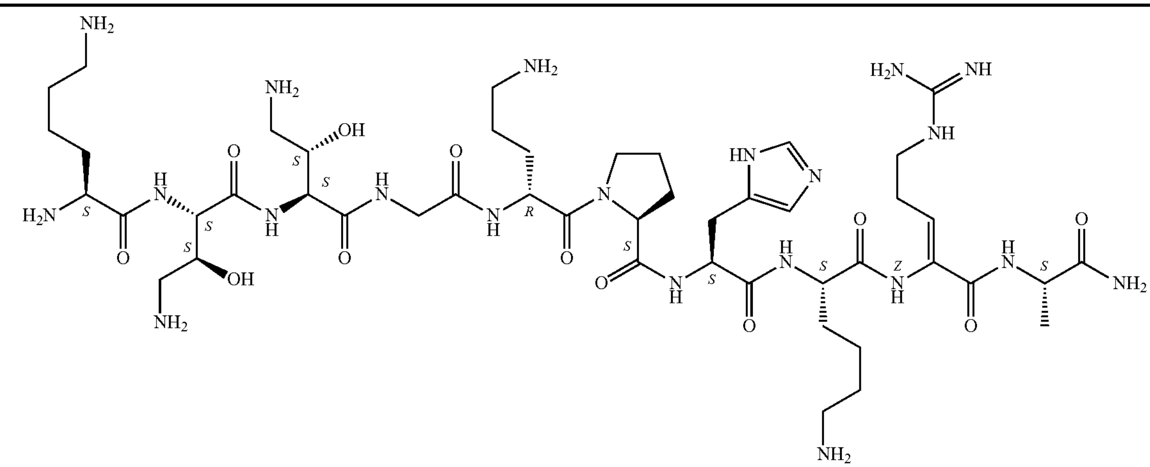 | $C_{47}H_{85}N_{21}O_{12}$ | 1136.32 | 1137.40 | 94% | 9.91 |
| 22.15 | 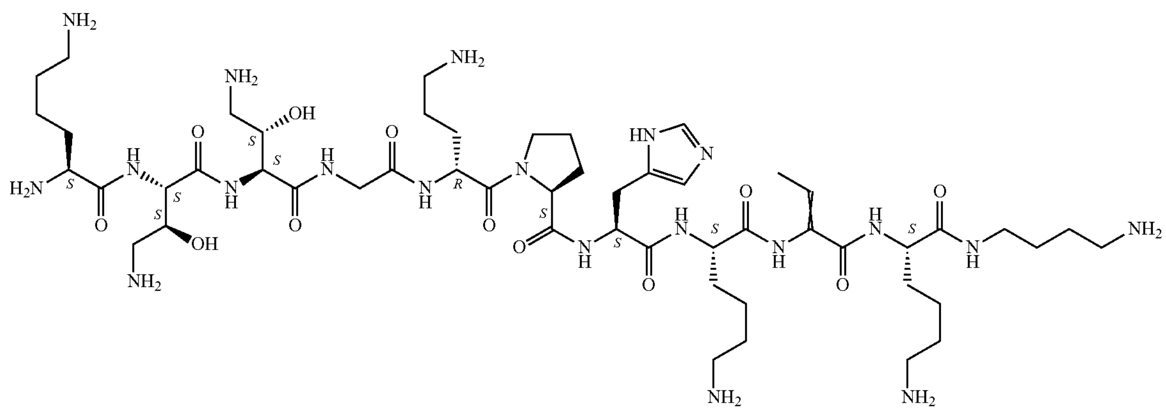 | $C_{52}H_{96}N_{20}O_{12}$ | 1193.46 | 1194.60 | 91% | 9.98 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.16 | 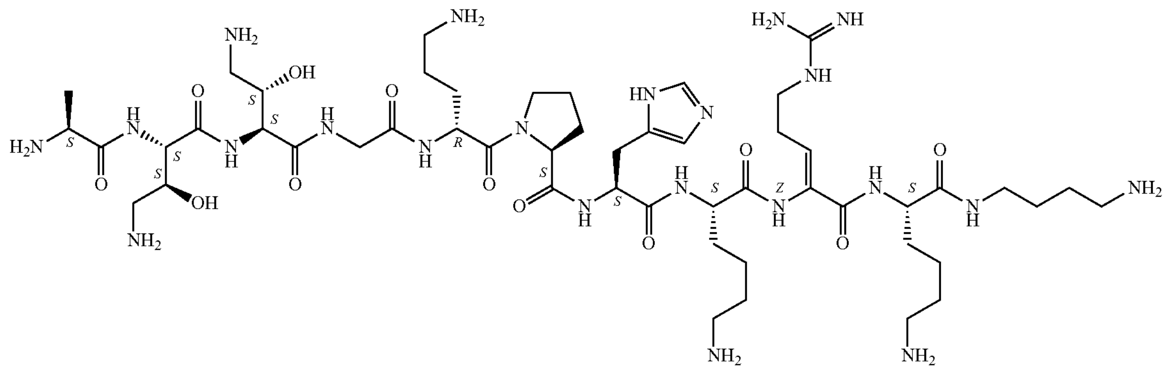 | $C_{51}H_{94}N_{22}O_{12}$ | 1207.45 | 1208.50 | 95% | 9.97 |
| 22.17 | 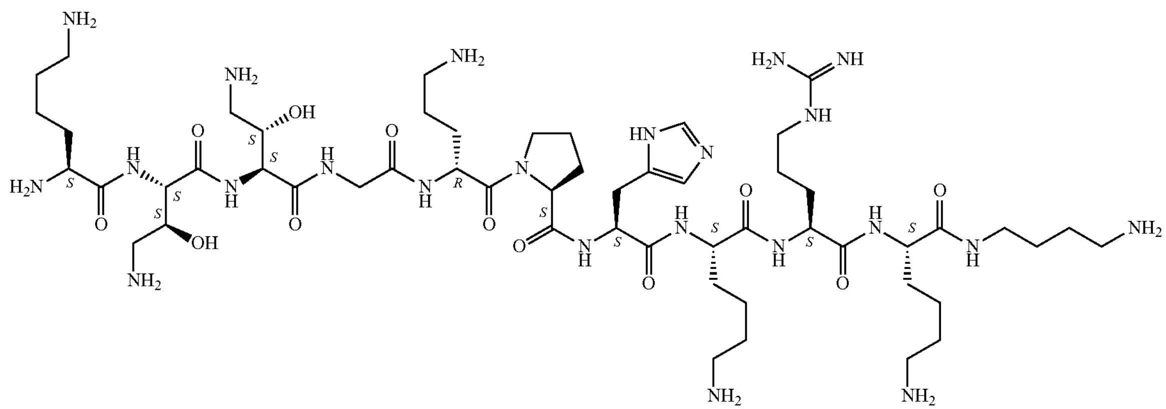 | $C_{54}H_{103}N_{23}O_{12}$ | 1266.56 | 1267.60 | 82% | 10.03 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.18 | 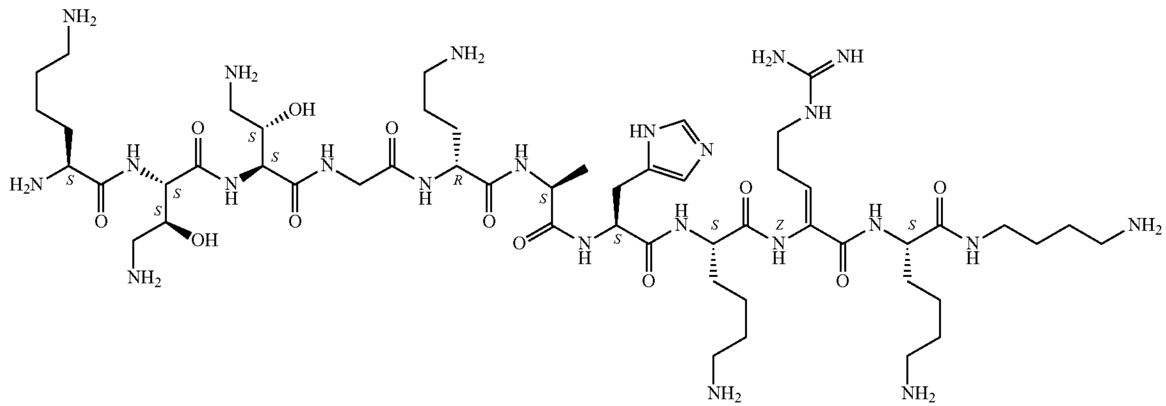 | C₅₂H₉₉N₂₃O₁₂ | 1238.50 | 1239.60 | 92% | 9.97 |
| 22.20 | 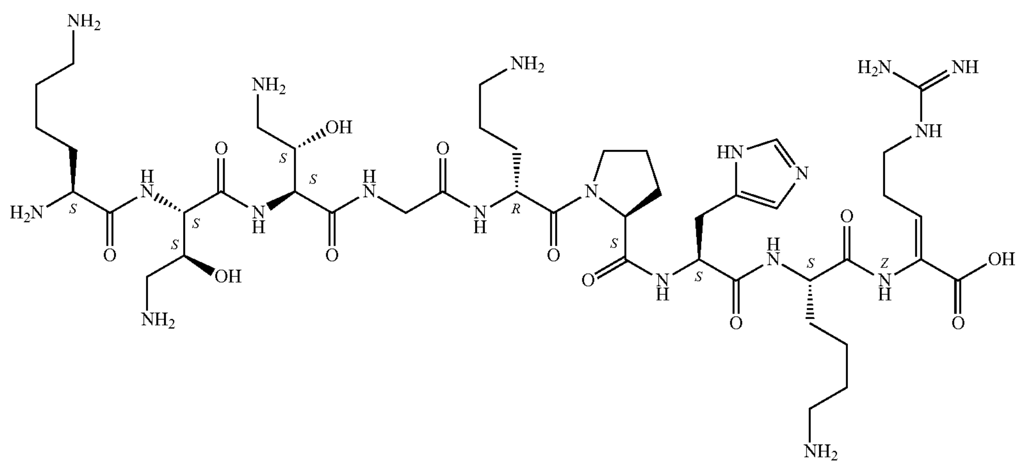 | C₄₄H₇₉N₁₉O₁₂ | 1066.23 | 1067.40 | 95% | 5.59 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.21 | 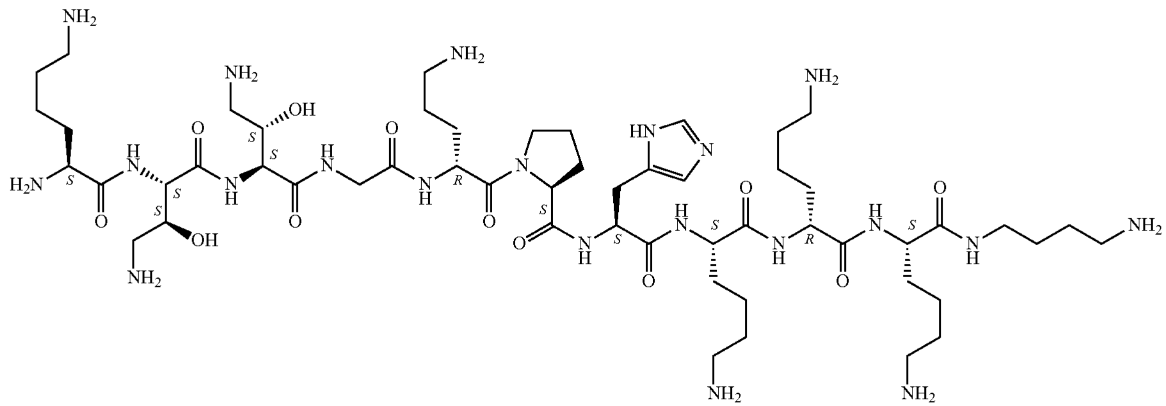 | C$_{54}$H$_{103}$N$_{21}$O$_{12}$ | 1238.54 | 1239.65 | 96% | 9.68 |
| 22.22 | 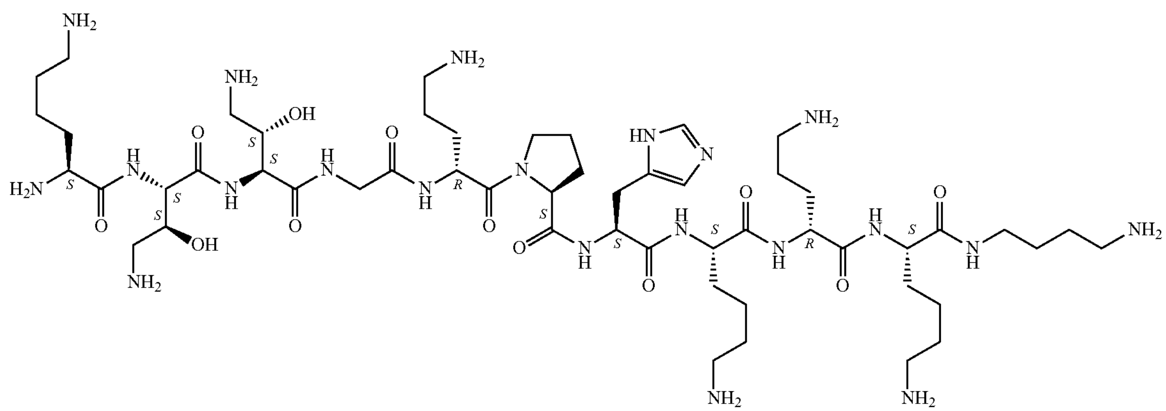 | C$_{53}$H$_{101}$N$_{21}$O$_{12}$ | 1224.52 | 1225.60 | 92% | 9.59 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.23 | 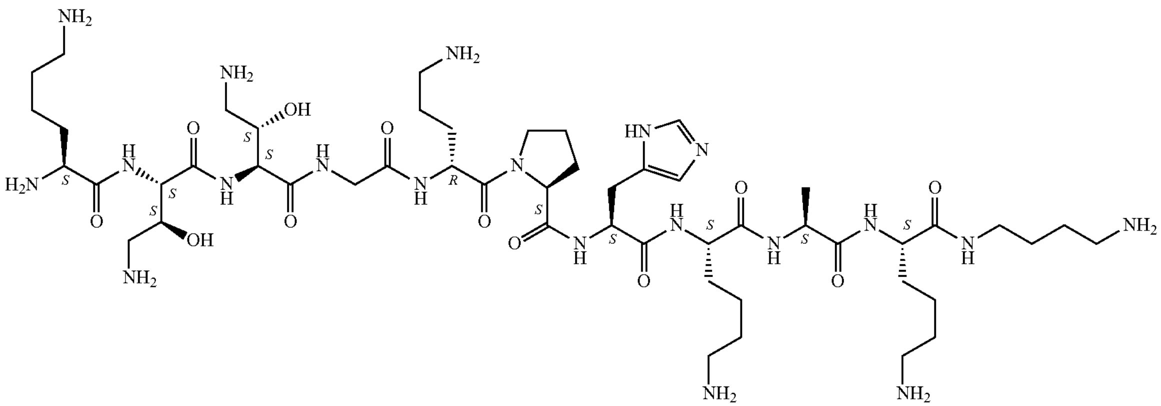 | $C_{51}H_{96}N_{20}O_{12}$ | 1181.45 | 1182.55 | 92% | 9.54 |
| 22.24 | 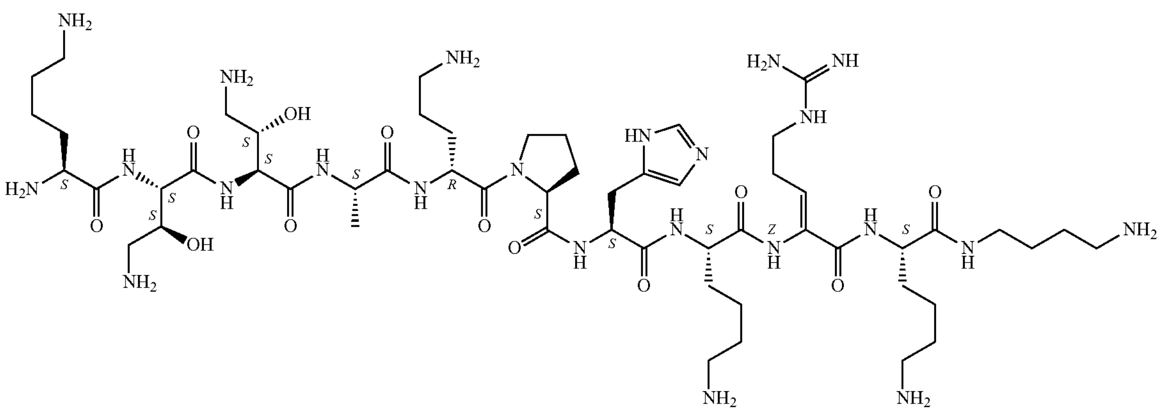 | $C_{55}H_{103}N_{23}O_{12}$ | 1278.57 | 1279.60 | 97% | 10.20 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.28 | 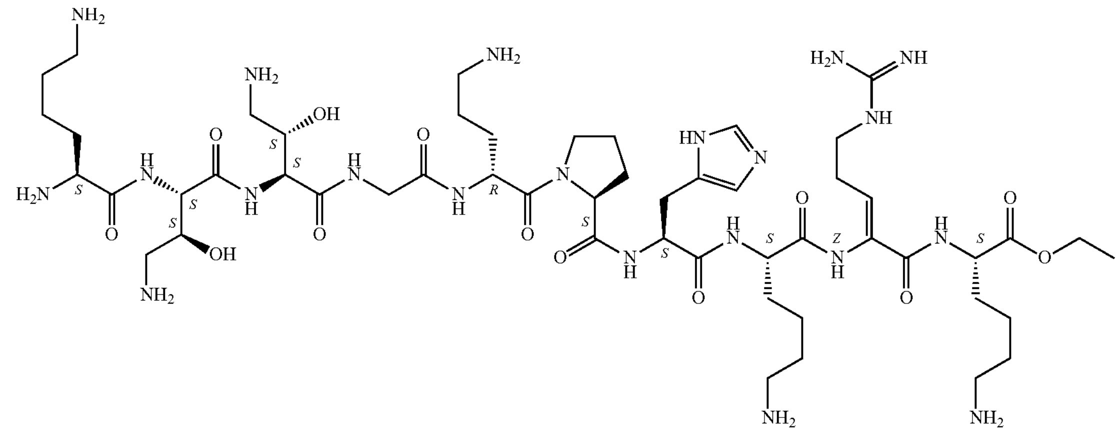 | $C_{52}H_{95}N_{21}O_{13}$ | 1222.46 | 1223.55 | 98% | 11.47 |
| 22.29 | 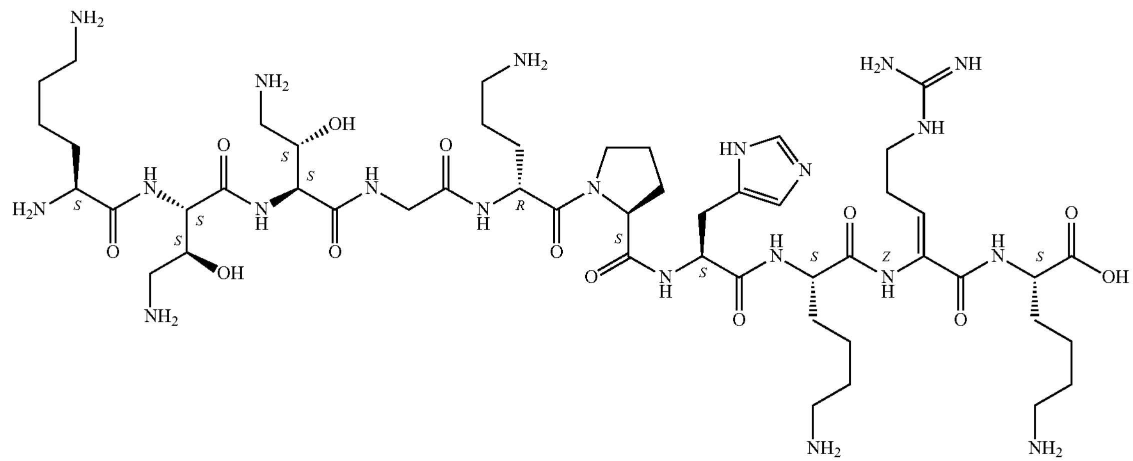 | $C_{50}H_{91}N_{21}O_{13}$ | 1194.40 | 1195.50 | 99% | 9.81 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.30 | 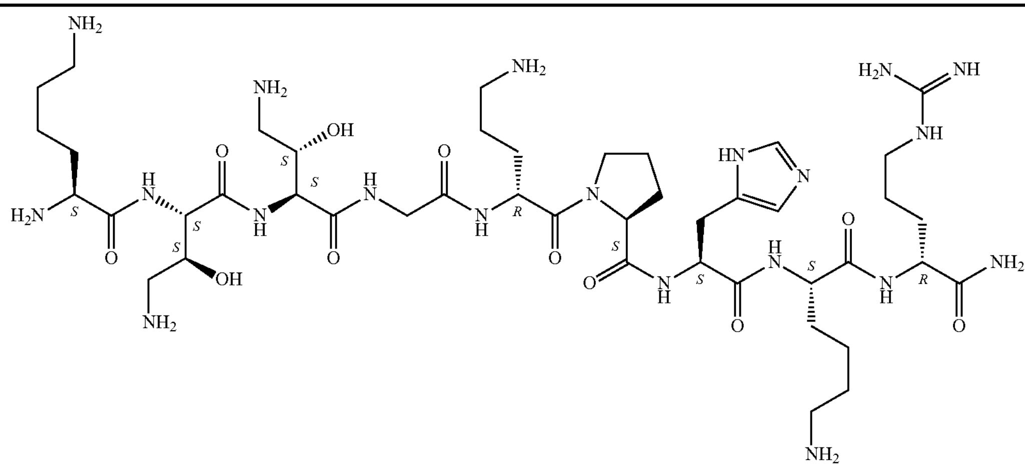 | C₄₄H₈₂N₂₀O₁₁ | 1067.25 | 1068.55 | 89% | 10.29 |
| 22.31 | 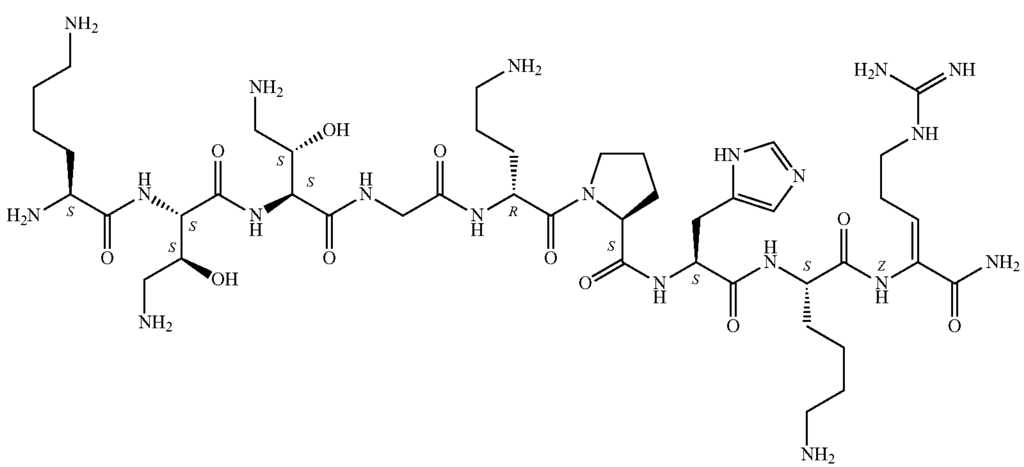 | C₄₄H₈₀N₂₀O₁₁ | 1065.23 | 1065.50 | 87% | 8.80 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.32 | 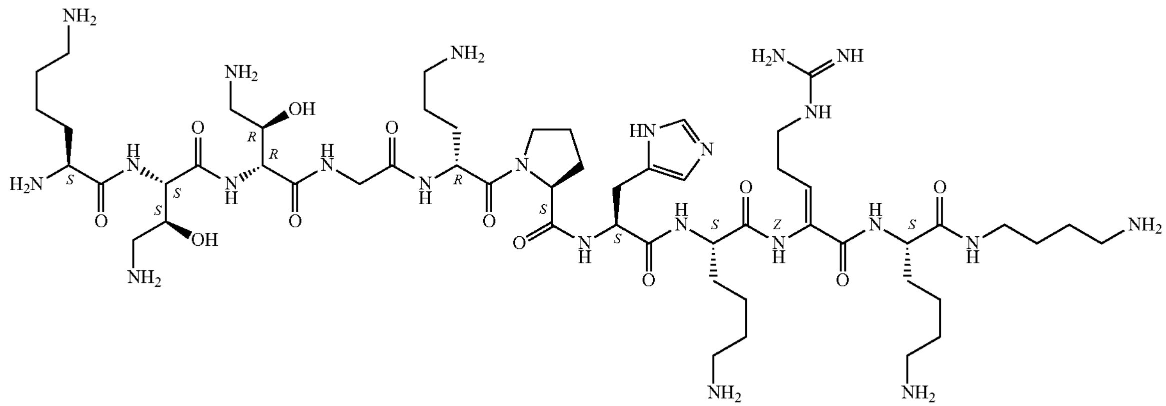 | $C_{54}H_{101}N_{23}O_{12}$ | 1264.53 | 1265.70 | 90% | 10.00 |
| 22.33 | 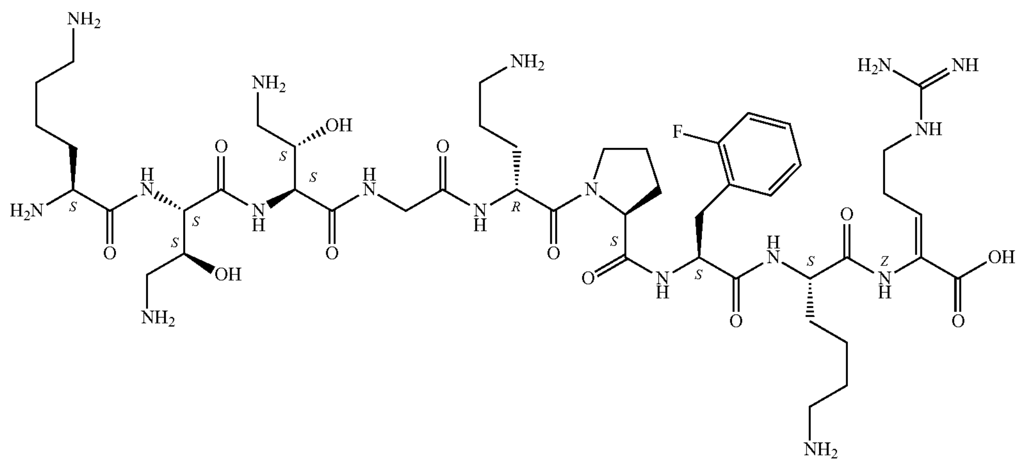 | $C_{47}H_{80}FN_{17}O_{12}$ | 1094.24 | 1095.50 | 99% | 12.54 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.34 | 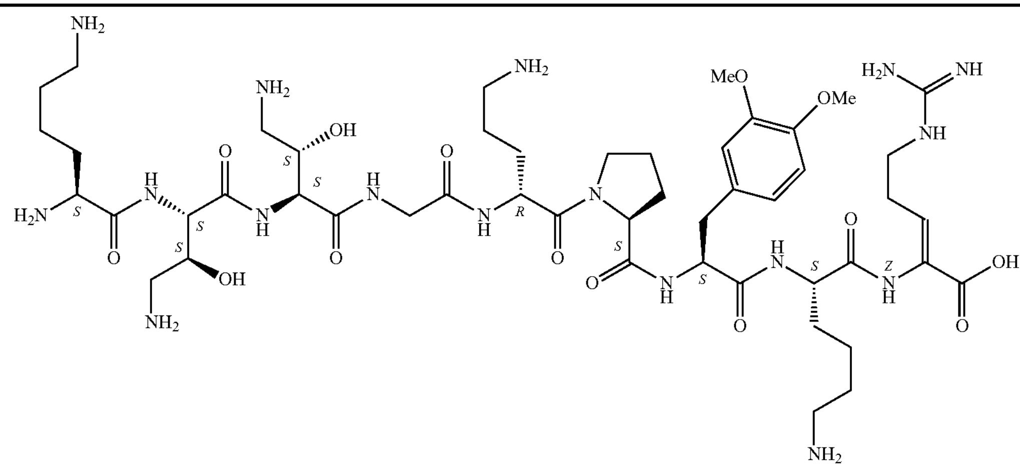 | C₄₉H₈₅N₁₇O₁₄ | 1136.30 | 1137.55 | 99% | 12.37 |
| 22.35 | 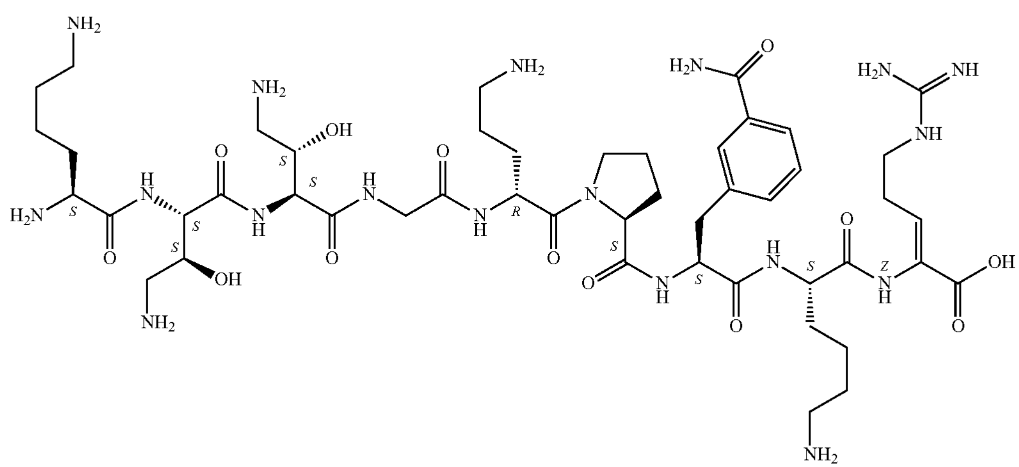 | C₄₈H₈₂N₁₈O₁₄₃ | 1119.28 | 1120.45 | 98% | 11.07 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.36 | 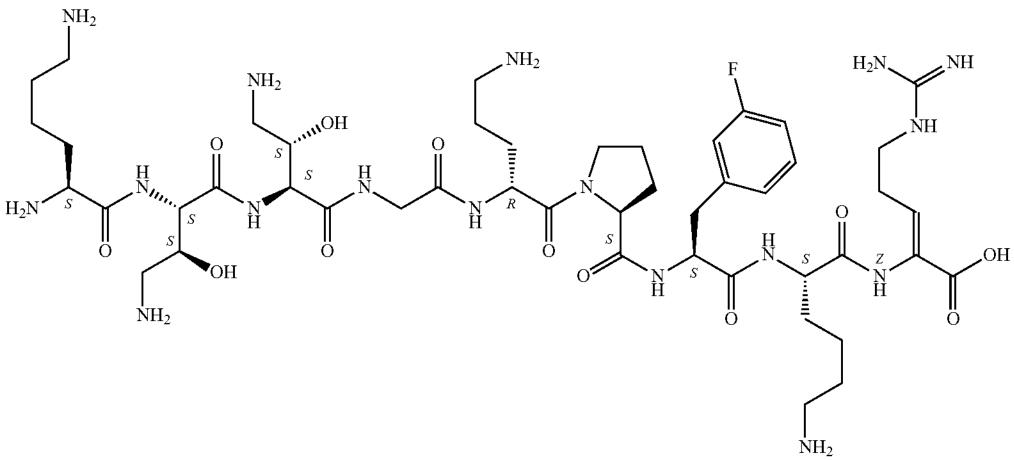 | $C_{47}H_{80}FN_{17}O_{12}$ | 1094.24 | 1095.45 | 99% | 12.91 |
| 22.37 | 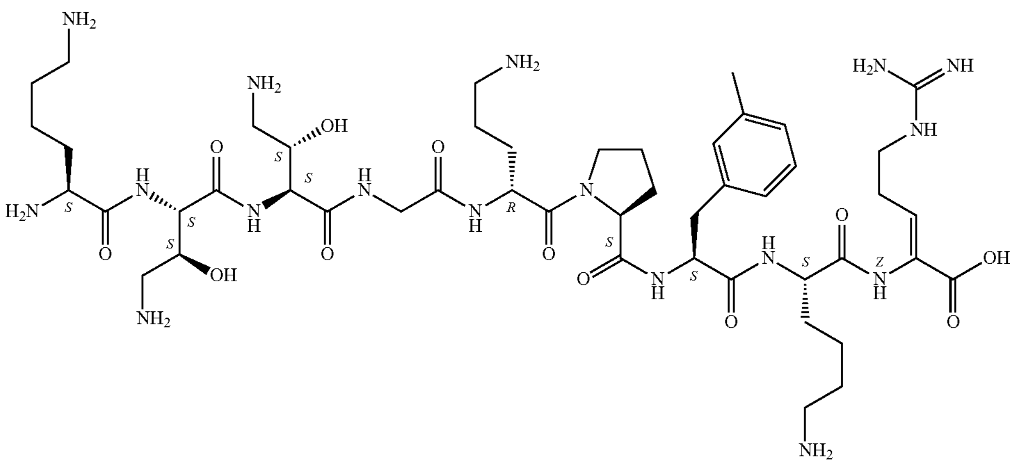 | $C_{48}H_{83}N_{17}O_{12}$ | 1090.28 | 1091.50 | 99% | 13.52 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 22.38 | 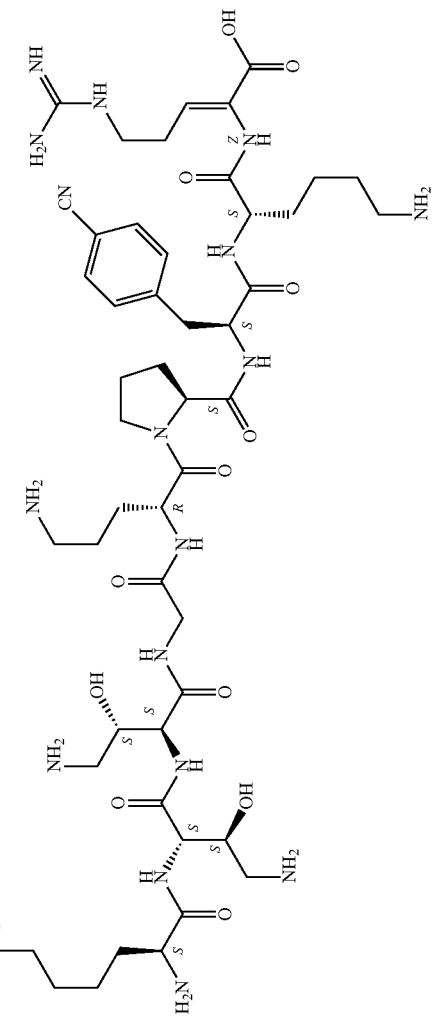 | $C_{48}H_{80}N_{18}O_{12}$ | 1101.26 | 1102.50 | 99% | 12.42 |
| 22.39 | 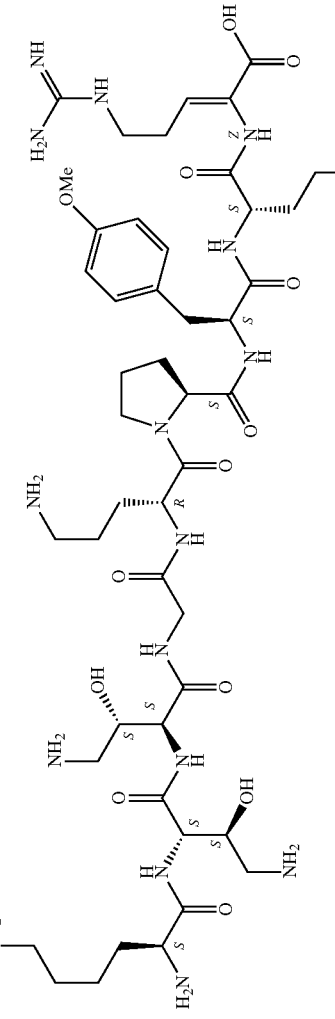 | $C_{48}H_{83}N_{17}O_{13}$ | 1106.28 | 1107.50 | 99% | 12.52 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 22.40 | 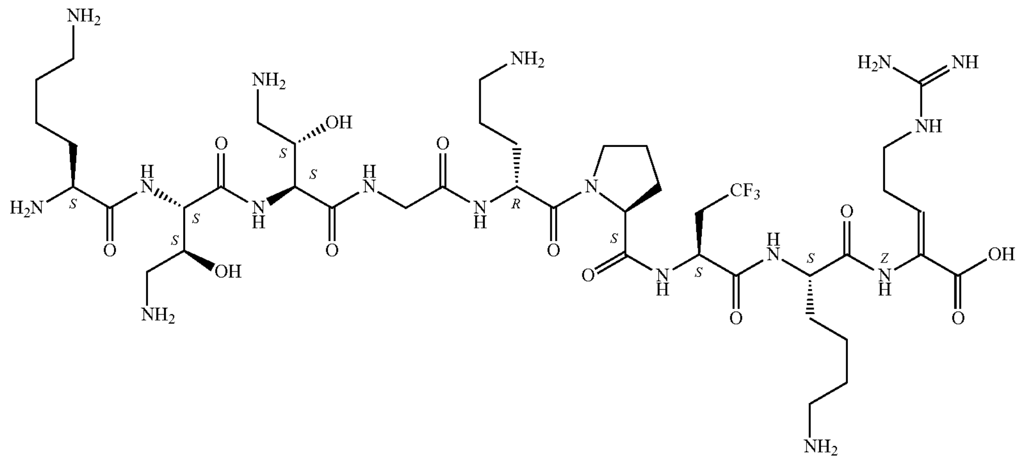 | $C_{42}H_{76}F_3N_{17}O_{12}$ | 1068.15 | 1069.50 | 99% | 11.50 |
| 22.41 | 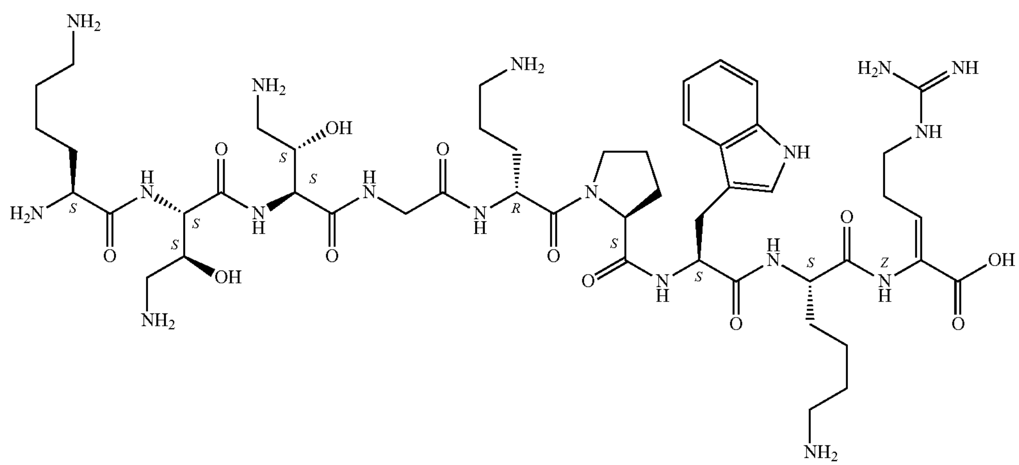 | $C_{49}H_{82}N_{18}O_{12}$ | 1115.29 | 1116.50 | 99% | 12.63 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 23.1 | 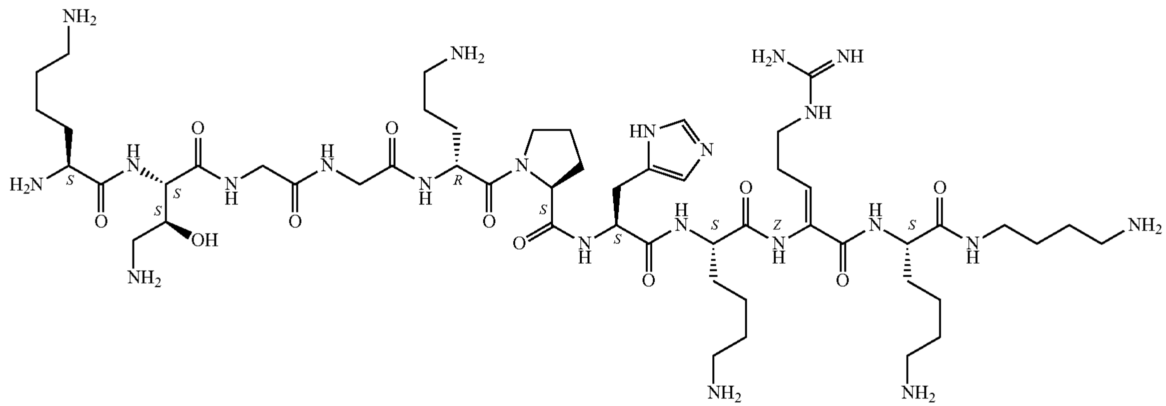 | $C_{52}H_{96}N_{22}O_{11}$ | 1205.47 | 1206.60 | 98% | 9.91 |
| 24.1 | 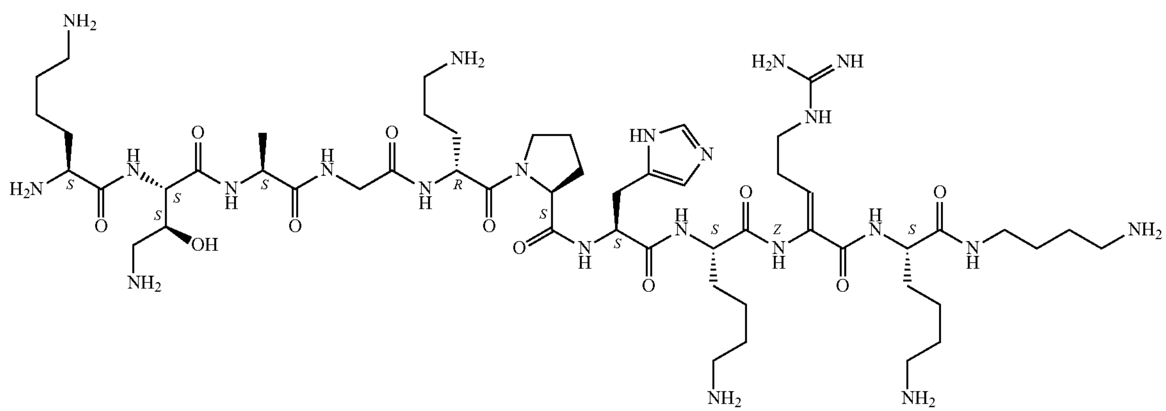 | $C_{53}H_{98}N_{22}O_{11}$ | 1219.50 | 1220.60 | 99% | 10.00 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.2 | 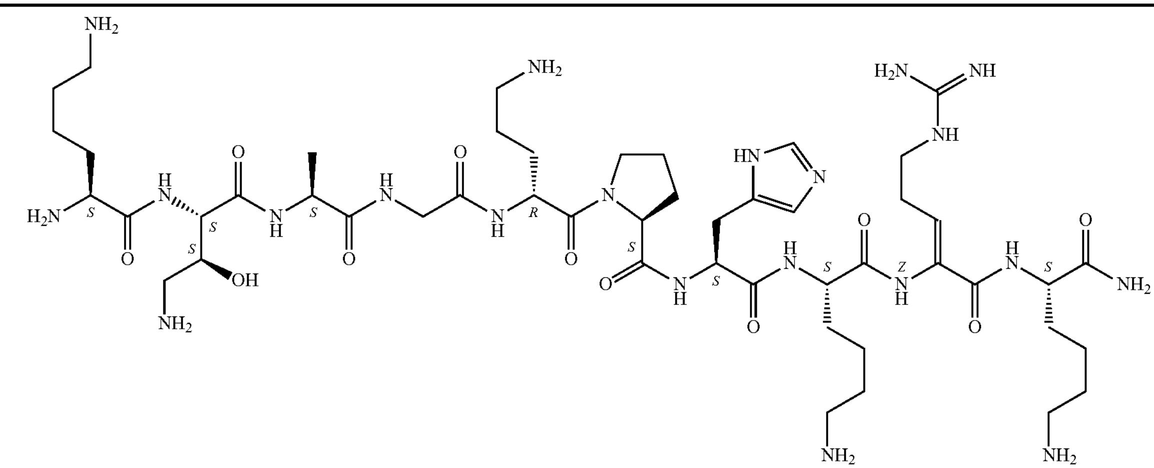 | $C_{49}H_{89}N_{21}O_{11}$ | 1148.38 | 1149.60 | 99% | 9.65 |
| 24.3 | 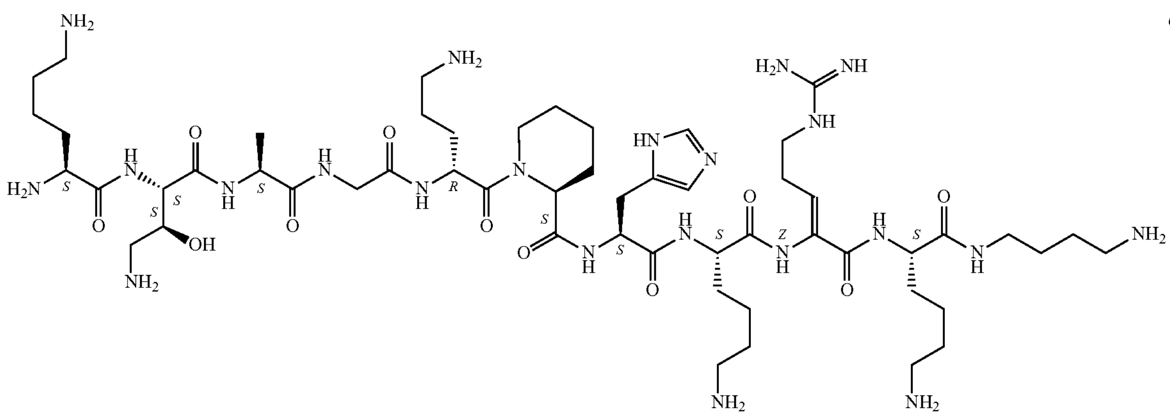 | $C_{54}H_{100}N_{22}O_{11}$ | 1233.53 | 1234.65 | 99% | 10.37 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.4 | 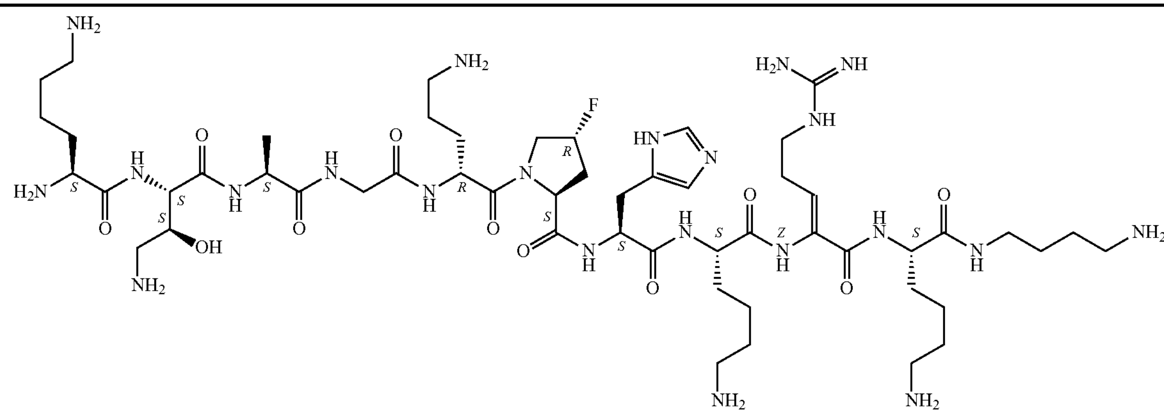 | C₅₃H₉₇FN₂₂O₁₁ | 1237.49 | 1238.55 | 99% | 10.00 |
| 24.5 | 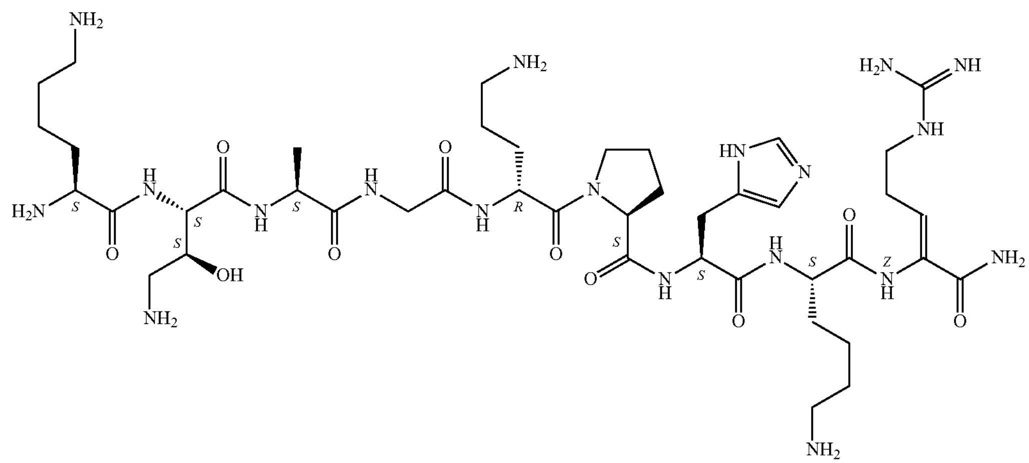 | C₄₃H₇₇N₁₉O₁₀ | 1020.20 | 1021.40 | 99% | 9.48 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.6 | 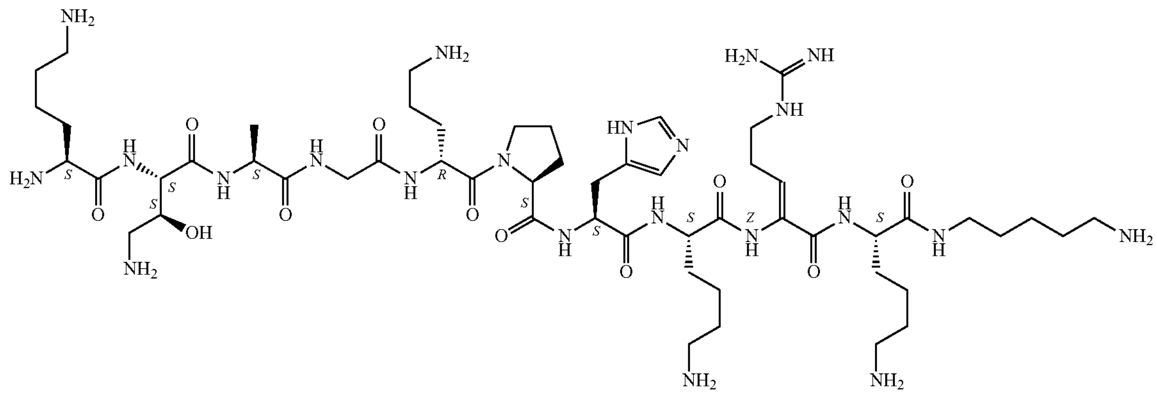 | $C_{54}H_{100}N_{22}O_{11}$ | 1233.53 | 1234.65 | 99% | 10.26 |
| 24.7 | 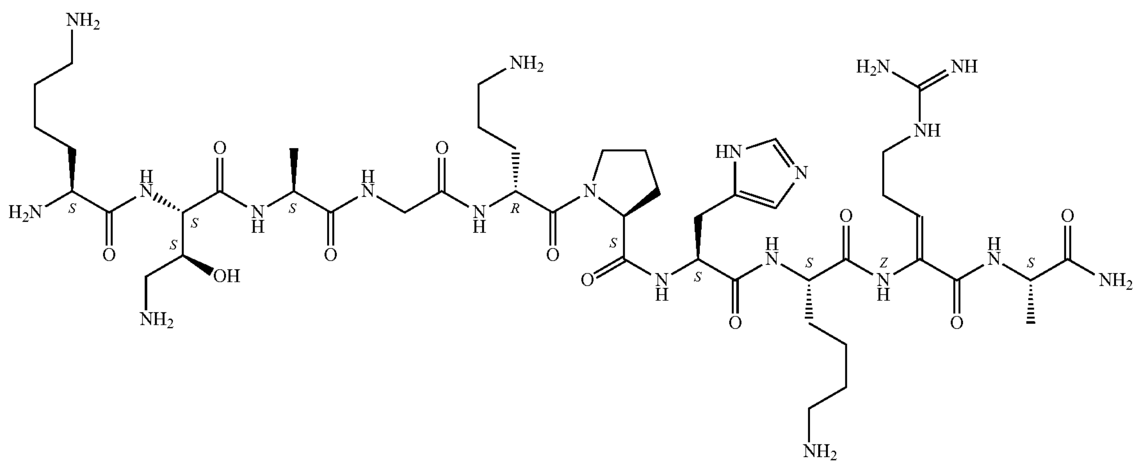 | $C_{46}H_{82}N_{20}O_{11}$ | 1091.28 | 1092.45 | 99% | 9.81 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.8 | 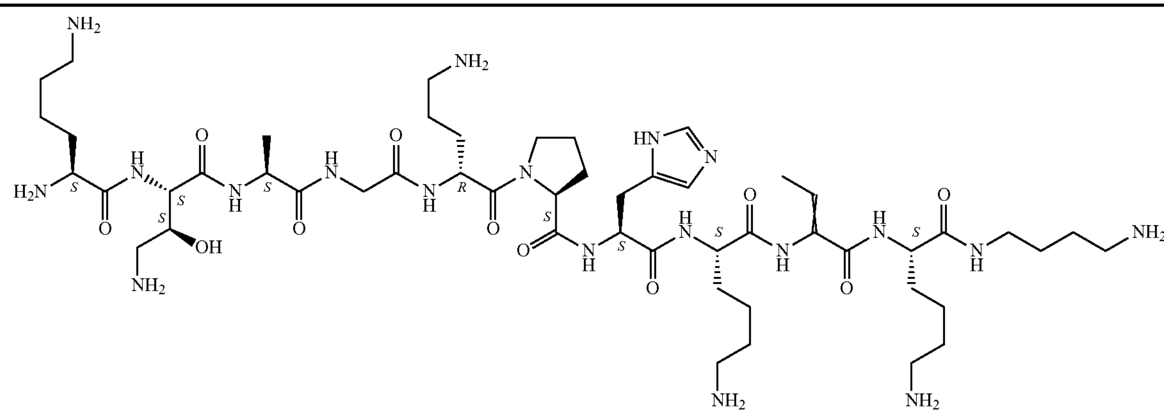 | $C_{51}H_{93}N_{19}O_{11}$ | 1148.42 | 1149.50 | 99% | 9.83 |
| 24.9 | 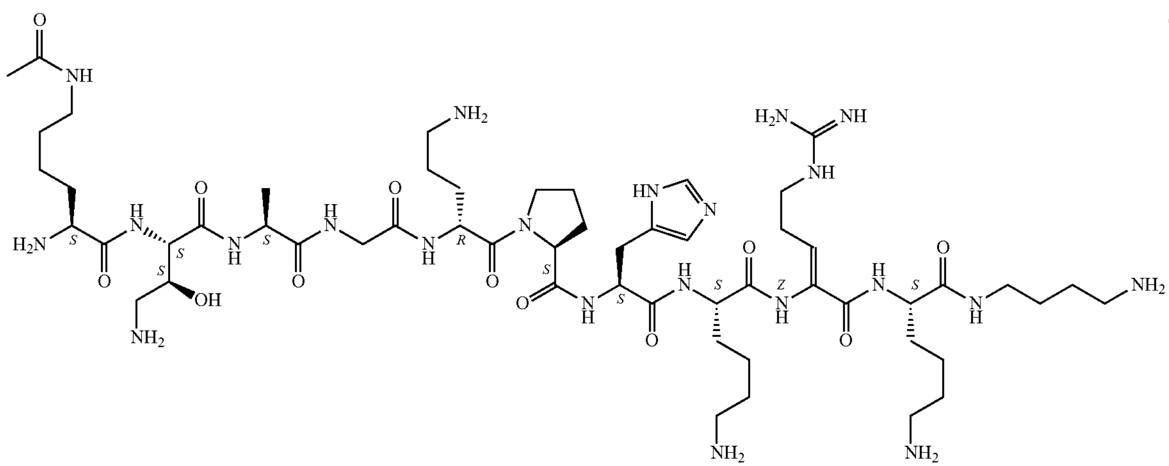 | $C_{55}H_{100}N_{22}O_{12}$ | 1261.52 | 1262.55 | 97% | 10.93 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.14 | 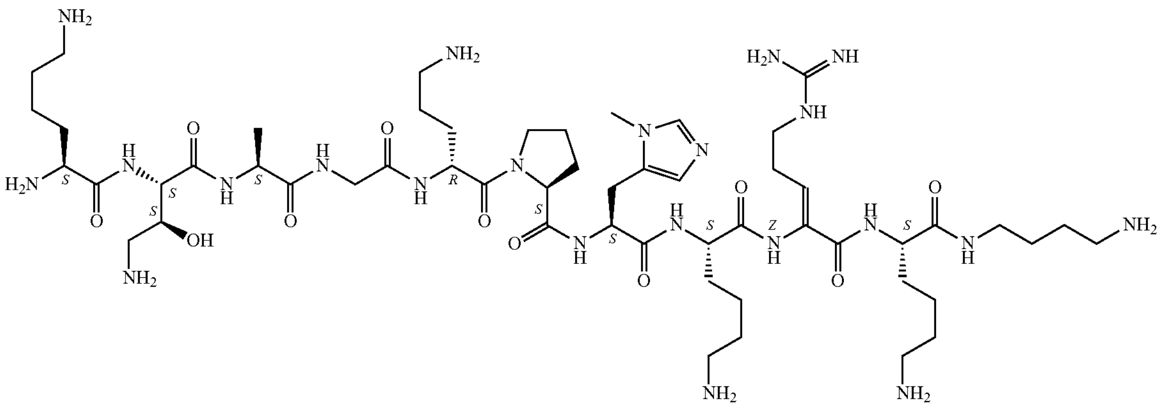 | C₅₄H₁₀₀N₂₂O₁₁ | 1233.53 | 1234.70 | 95% | 10.84 |
| 24.15 | 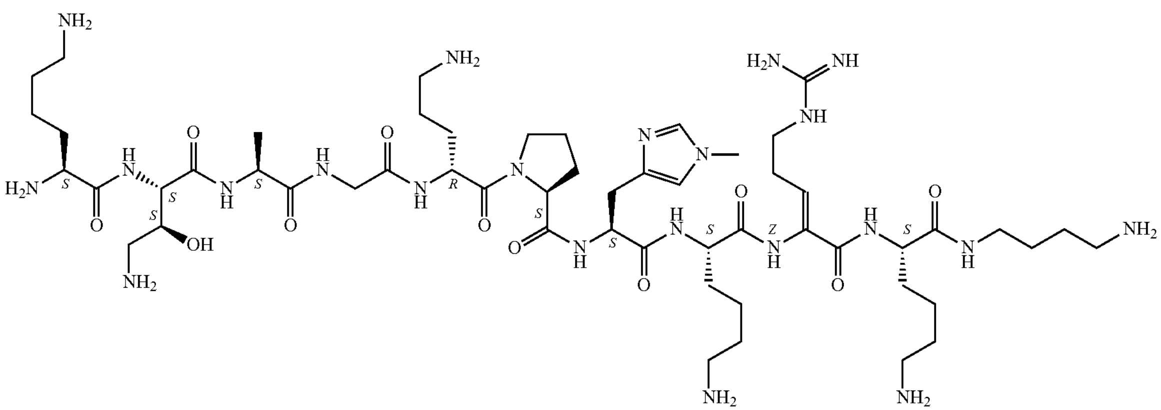 | C₅₄H₁₀₀N₂₂O₁₁ | 1233.53 | 1234.70 | 98% | 10.94 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.17 | 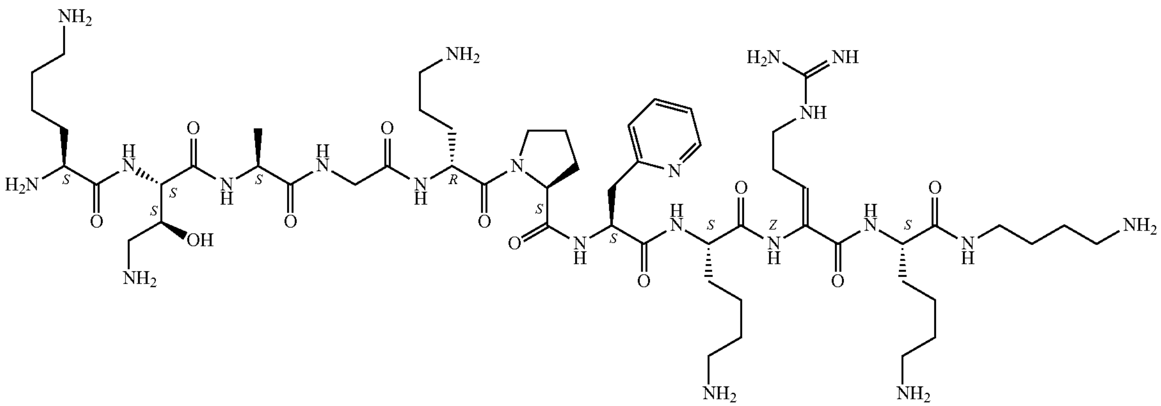 | C₅₅H₉₉N₂₁O₁₁ | 1230.52 | 1231.70 | 99% | 11.10 |
| 24.18 | 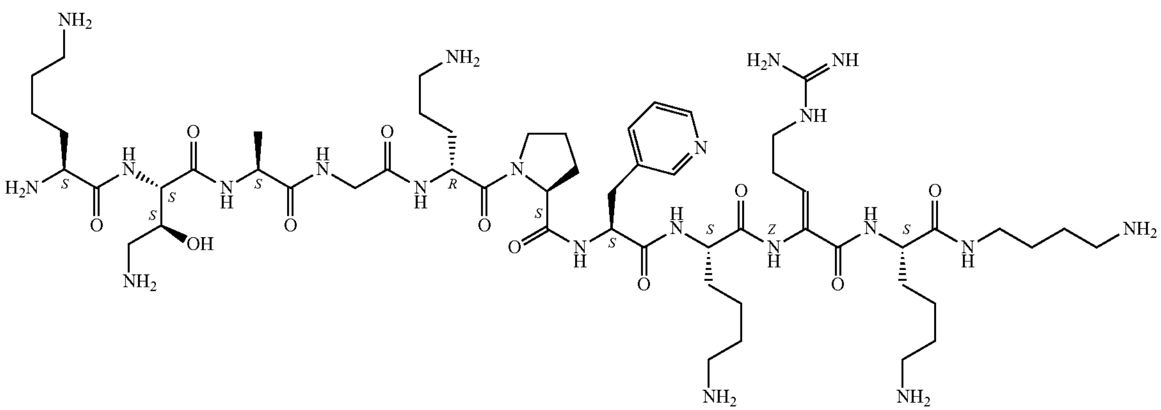 | C₅₅H₉₉N₂₁O₁₁ | 1230.52 | 1231.70 | 99% | 10.95 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.19 | 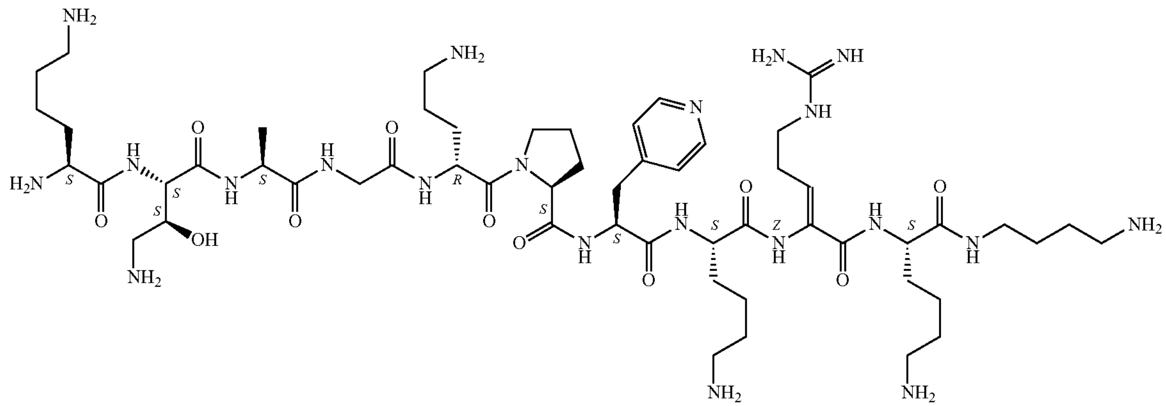 | C$_{55}$H$_{99}$N$_{21}$O$_{11}$ | 1230.52 | 1231.70 | 96% | 10.88 |
| 24.20 | 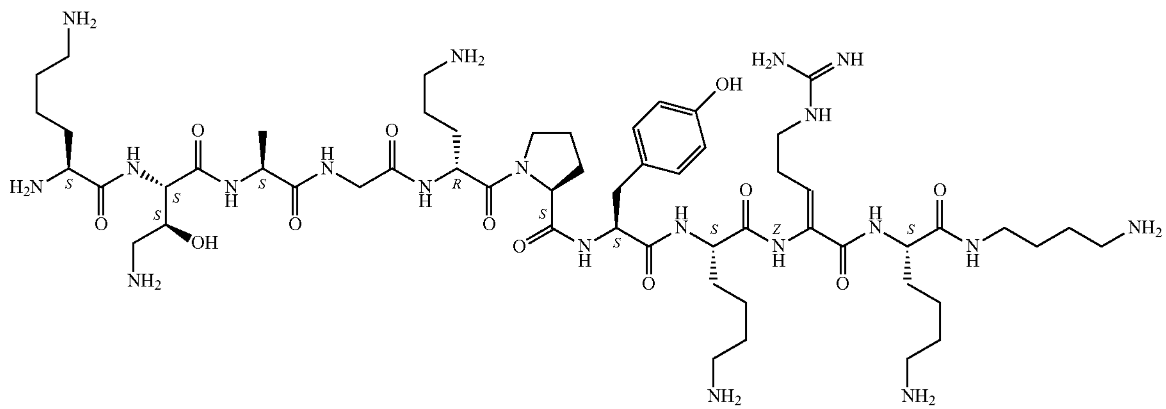 | C$_{56}$H$_{100}$N$_{20}$O$_{12}$ | 1245.53 | 1246.65 | 99% | 11.58 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.21 | 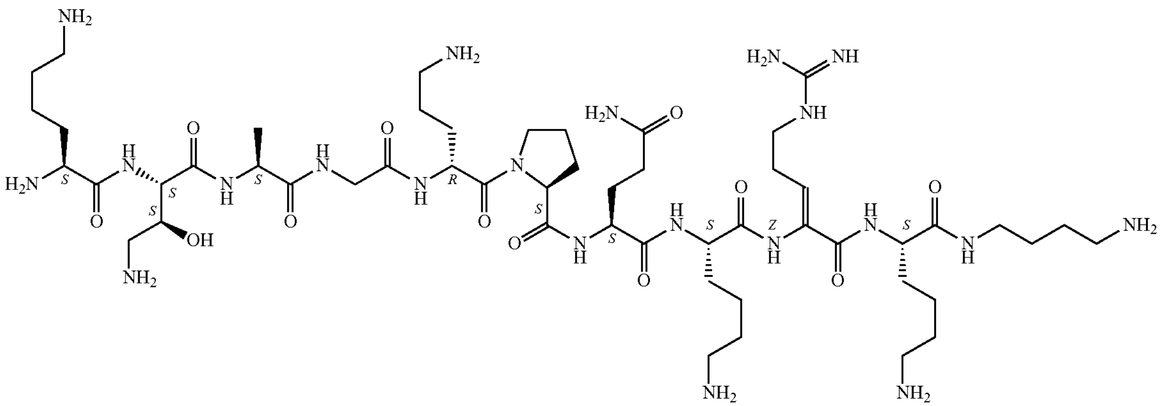 | C₅₂H₉₉N₂₁O₁₂ | 1210.49 | 1211.70 | 98% | 10.55 |
| 24.22 | 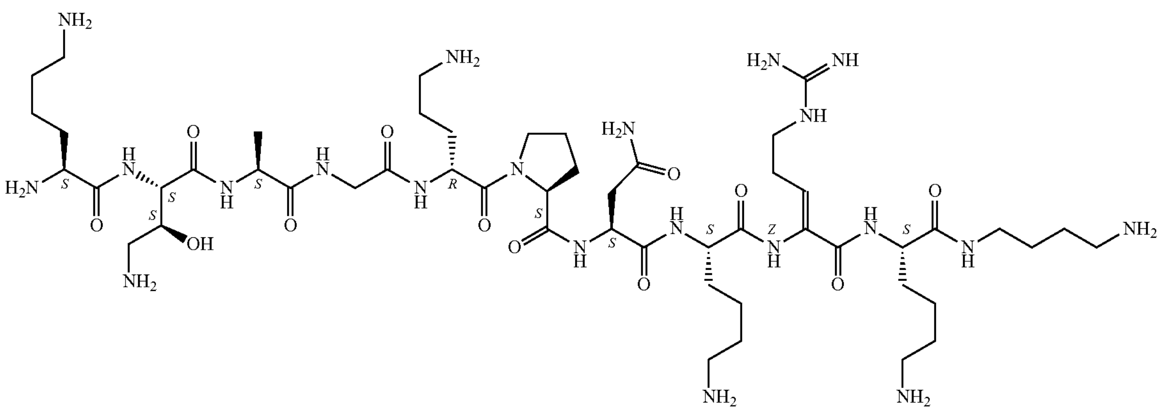 | C₅₁H₉₇N₂₁O₁₂ | 1196.46 | 1197.70 | 99% | 10.55 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.43 | 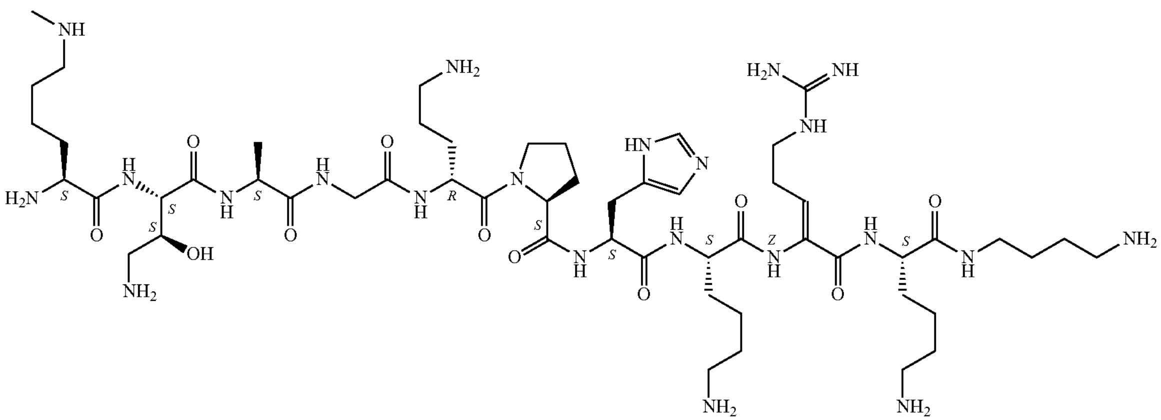 | C$_{54}$H$_{100}$N$_{22}$O$_{11}$ | 1233.51 | 1234.65 | 99% | 10.69 |
| 24.61 | 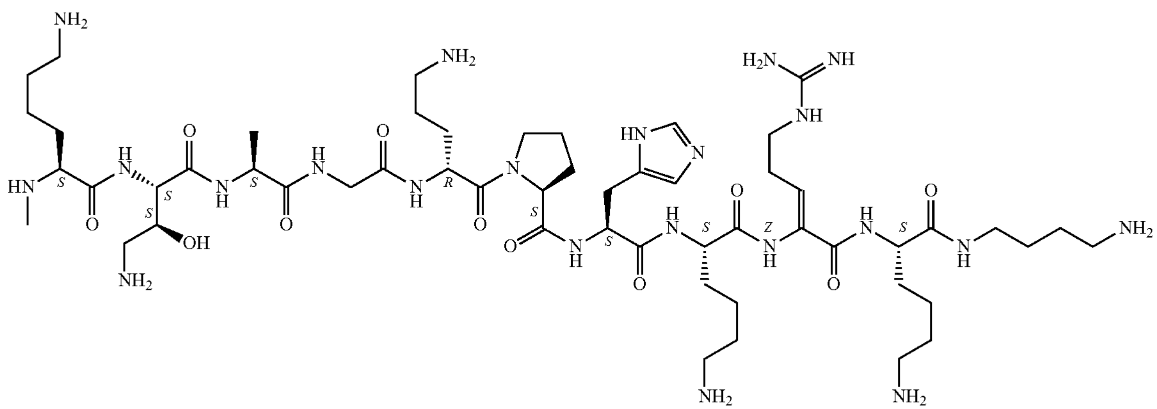 | C$_{54}$H$_{100}$N$_{22}$O$_{11}$ | 1233.51 | 1234.70 | 98% | 10.63 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.62 | 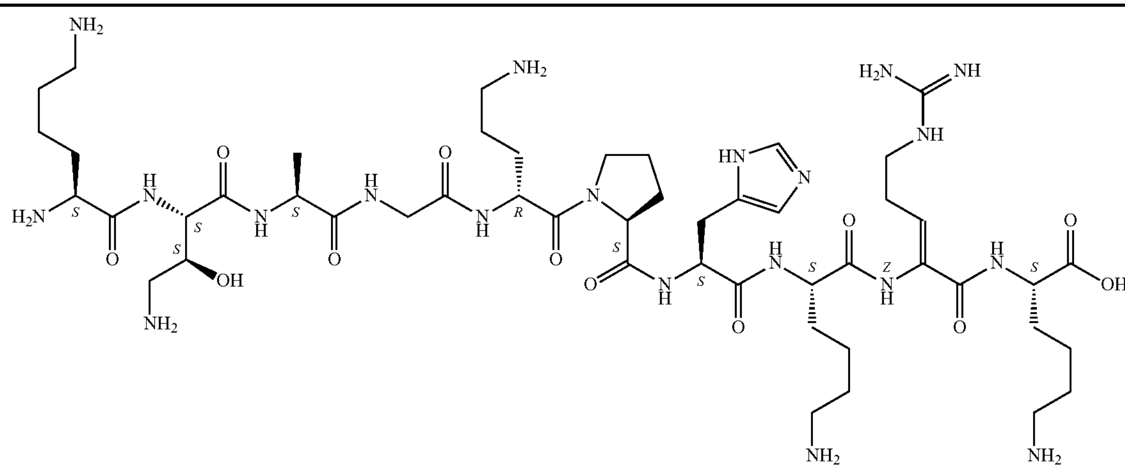 | $C_{49}H_{88}N_{20}O_{12}$ | 1149.35 | 1150.60 | 98% | 10.62 |
| 24.63 | 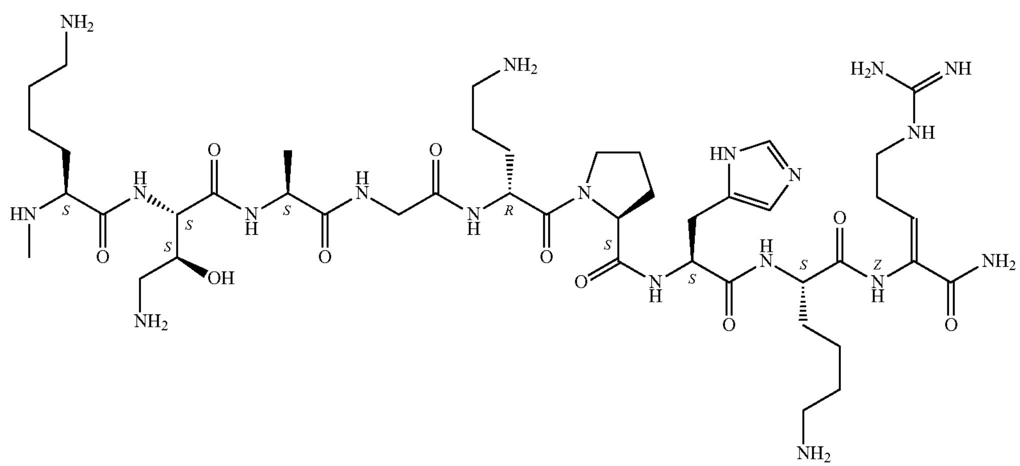 | $C_{44}H_{79}N_{19}O_{10}$ | 1034.22 | 1035.60 | 98% | 10.10 |

TABLE 1-continued

Compounds and analytical data

| Cmpd | Structure | Molecular formula | MW (g/mol) | [M + H]$^+$ (g/mol) | UV purity ($\lambda$ = 230 nm) | Rt (min) |
|---|---|---|---|---|---|---|
| 24.64 | 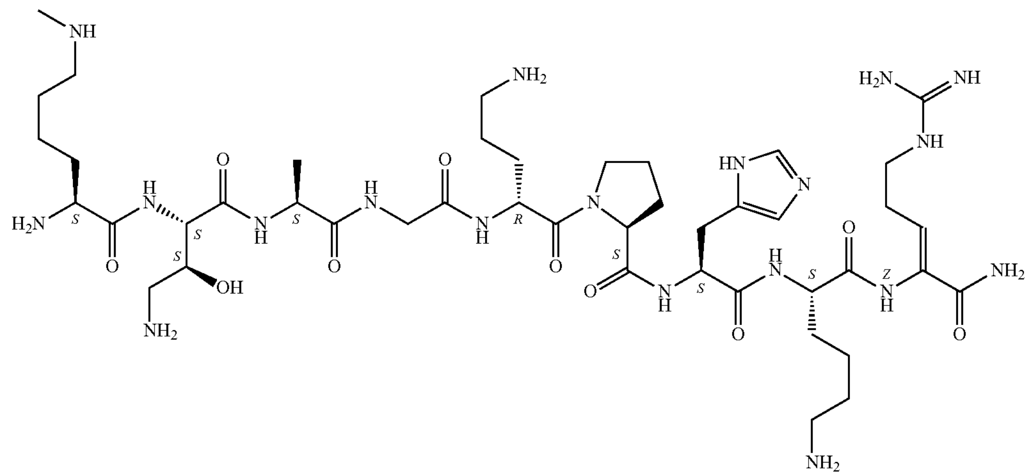 | $C_{44}H_{79}N_{19}O_{10}$ | 1034.22 | 1035.60 | 98% | 10.23 |
| 24.65 | 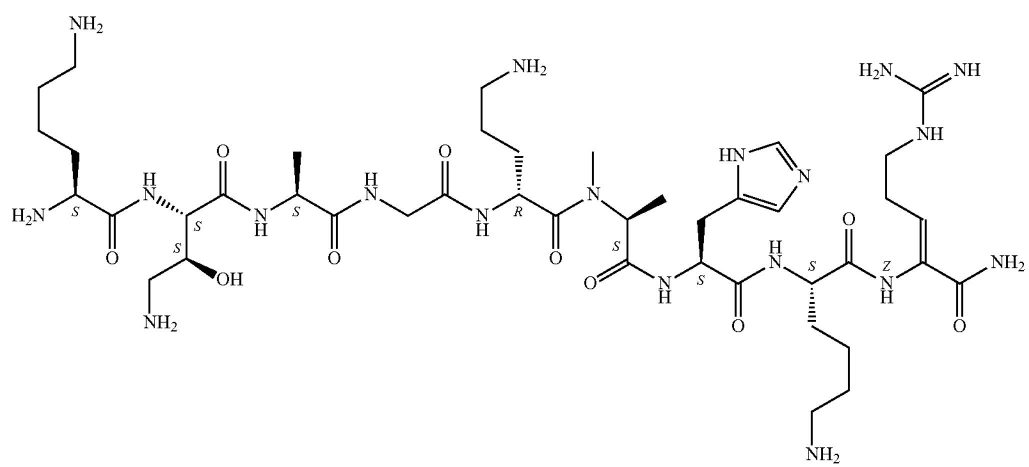 | $C_{42}H_{77}N_{19}O_{10}$ | 1008.18 | 1009.60 | 96% | 10.00 |

TABLE 1-continued

Compounds and analytical data

| Cmpd | Structure | Molecular formula | MW (g/mol) | [M + H]⁺ (g/mol) | UV purity (λ = 230 nm) | Rt (min) |
|---|---|---|---|---|---|---|
| 24.66 | 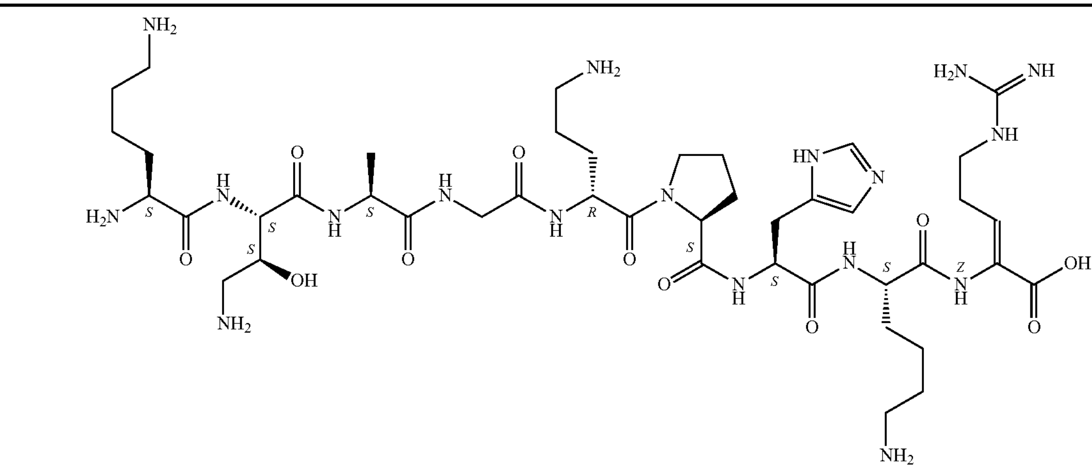 | $C_{43}H_{76}N_{18}O_{11}$ | 1021.18 | 1022.50 | 99% | 10.27 |
| 24.67 | 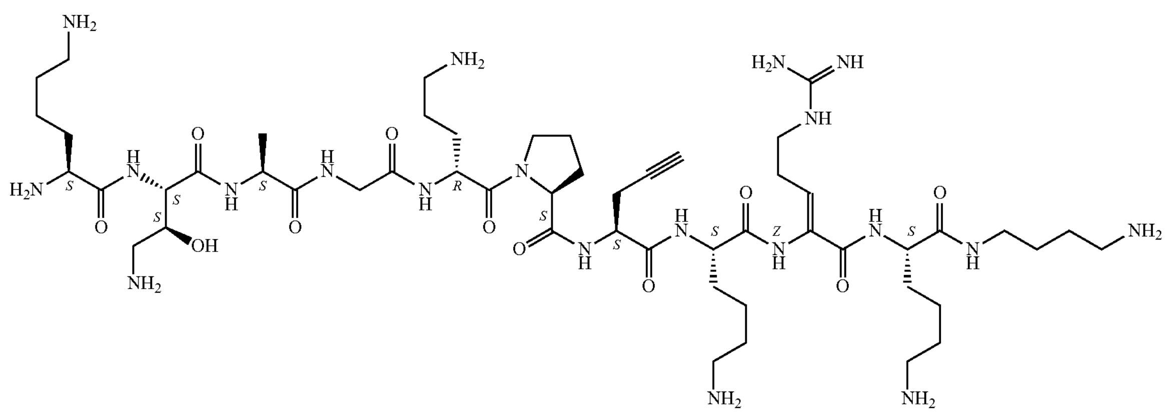 | $C_{52}H_{96}N_{20}O_{11}$ | 1177.45 | 1178.70 | 99% | 10.79 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.68 | 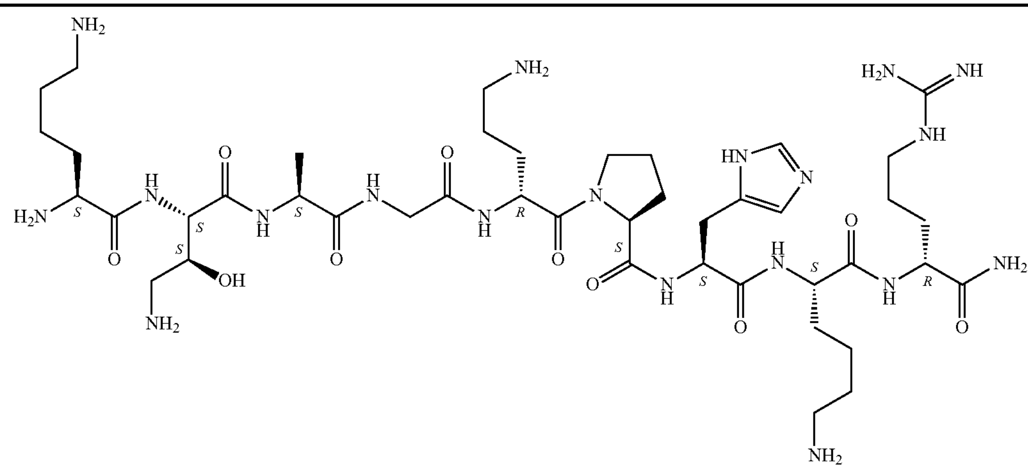 | $C_{43}H_{79}N_{19}O_{10}$ | 1022.21 | 1023.60 | 99% | 10.09 |
| 24.69 | 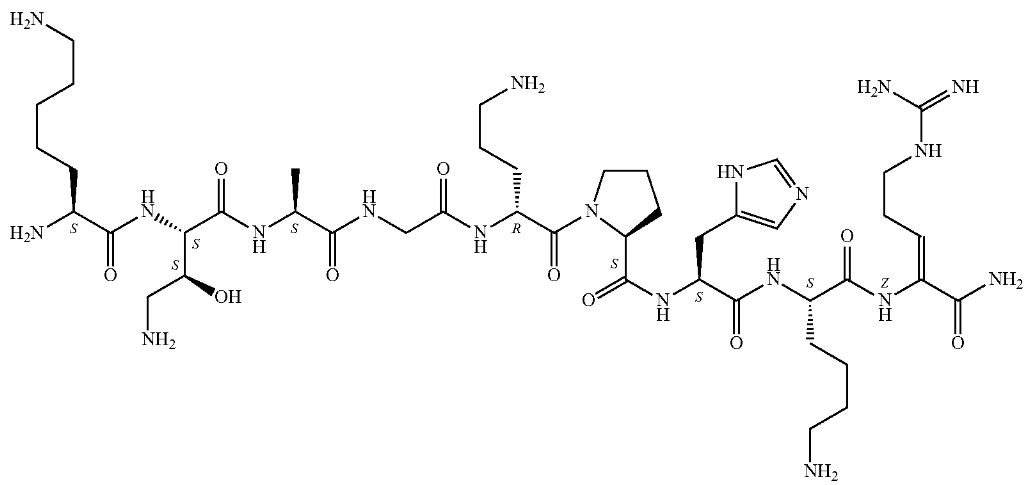 | $C_{44}H_{79}N_{19}O_{10}$ | 1034.22 | 1035.60 | 98% | 9.69 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.70 | 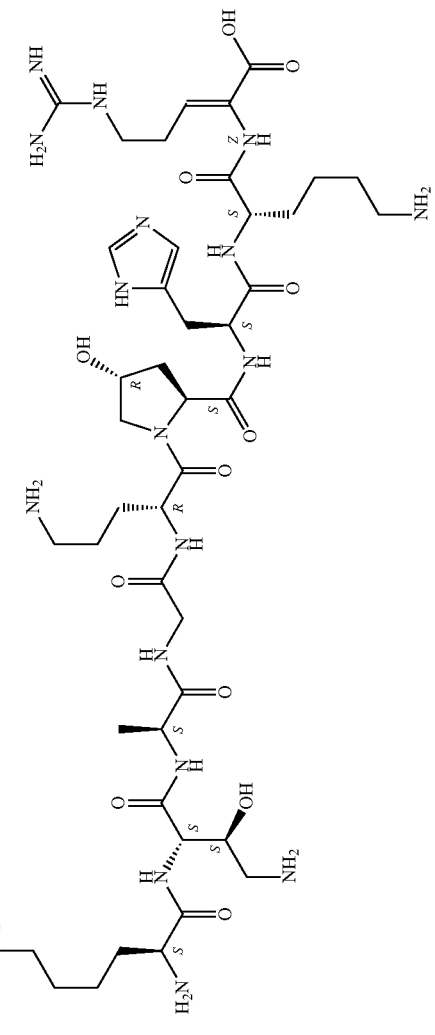 | C43H76N18O12 | 1037.18 | 1038.45 | 99% | 9.99 |
| 24.71 | 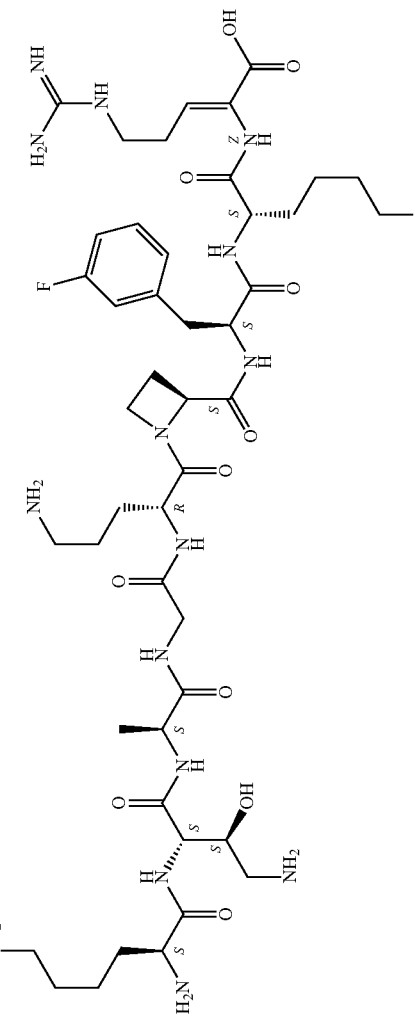 | C45H75FN16O11 | 1035.18 | 1036.50 | 97% | 12.34 |

TABLE 1-continued

Compounds and analytical data

| Cmpd | Structure | Molecular formula | MW (g/mol) | [M + H]$^+$ (g/mol) | UV purity ($\lambda$ = 230 nm) | Rt (min) |
|---|---|---|---|---|---|---|
| 24.72 | 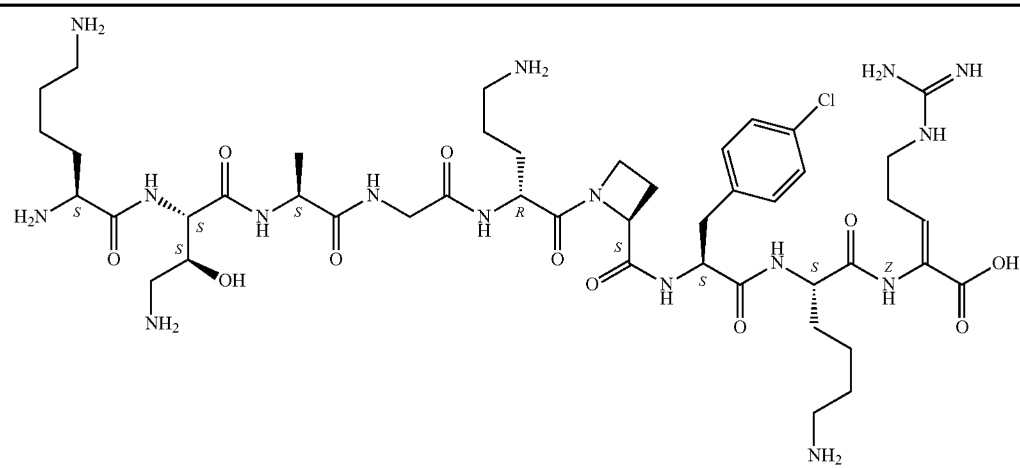 | $C_{45}H_{75}ClN_{16}O_{11}$ | 1051.63 | 1051.65 | 96% | 13.27 |
| 24.73 | 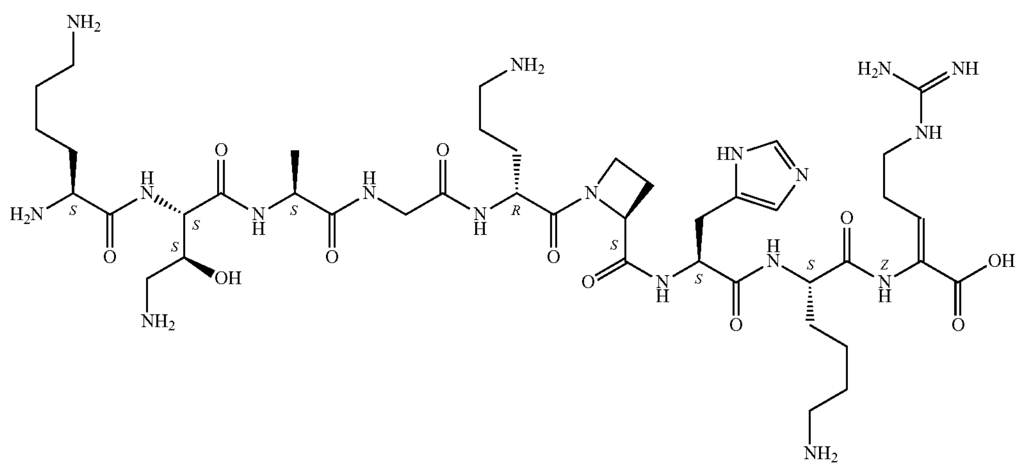 | $C_{42}H_{74}N_{18}O_{11}$ | 1007.15 | 1007.70 | 98% | 10.01 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.74 | 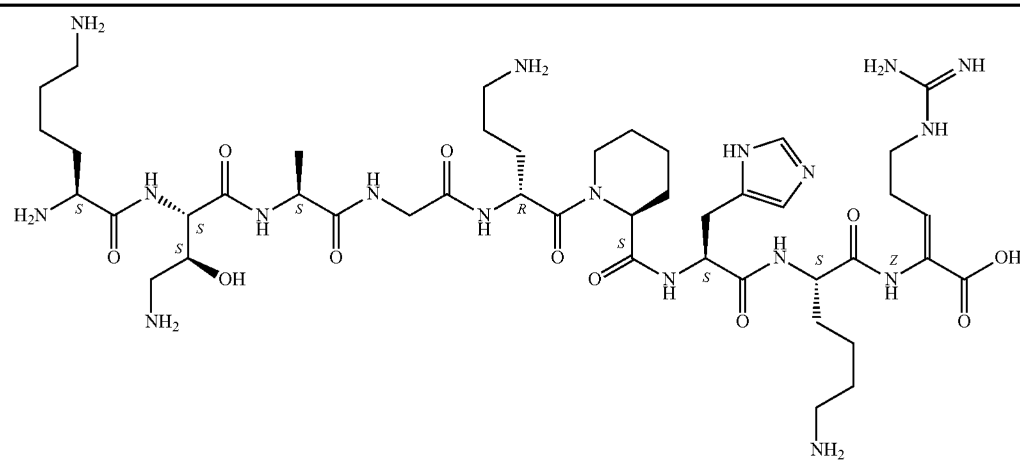 | $C_{44}H_{78}N_{18}O_{11}$ | 1035.20 | 1036.46 | 98% | 10.87 |
| 24.75 | 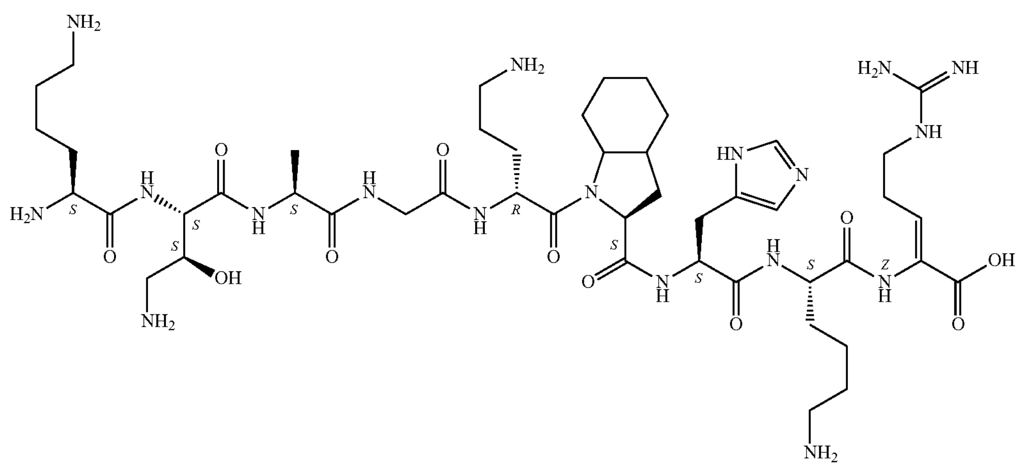 | $C_{47}H_{82}N_{18}O_{11}$ | 1075.27 | 1076.55 | 98% | 12.05 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.76 | 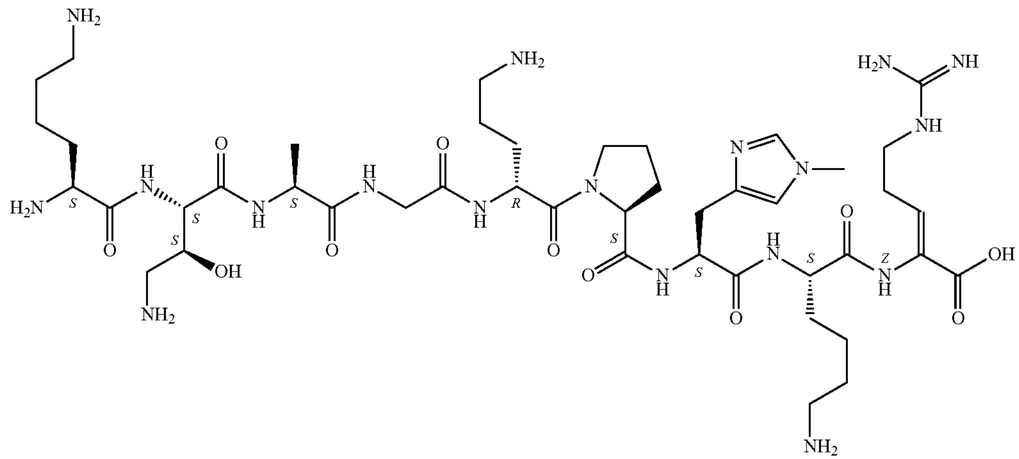 | $C_{44}H_{78}N_{18}O_{11}$ | 1035.20 | 1036.45 | 98% | 10.67 |
| 24.77 | 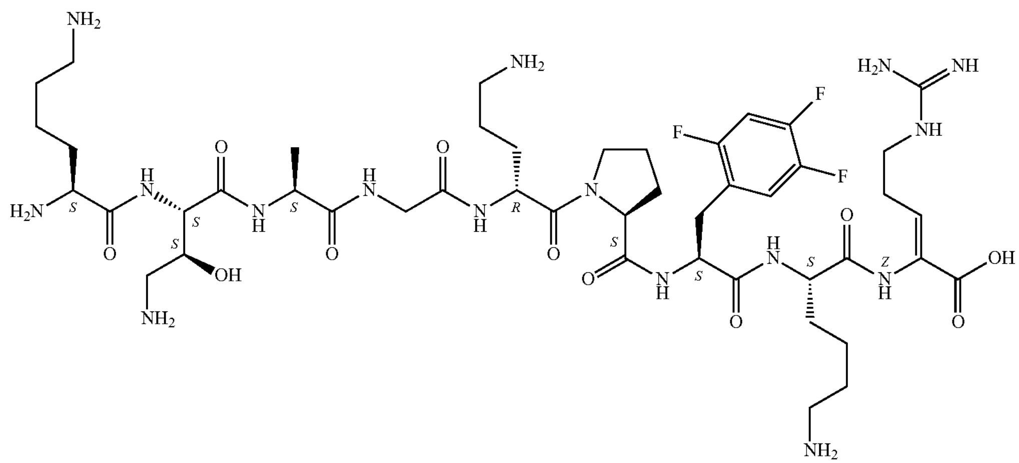 | $C_{46}H_{75}F_3N_{16}O_{11}$ | 1085.18 | 1086.45 | 99% | 13.92 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.78 | 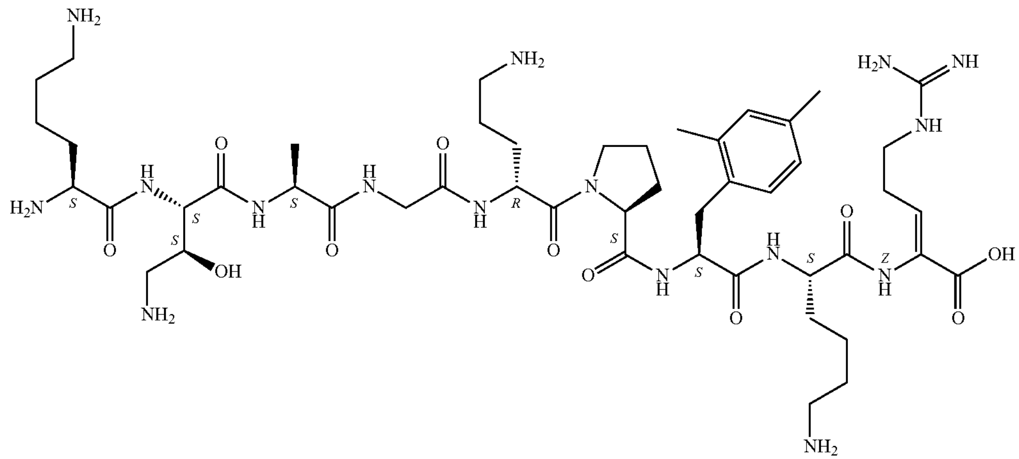 | C₄₈H₈₂N₁₆O₁₁ | 1059.26 | 1060.50 | 98% | 14.49 |
| 24.79 | 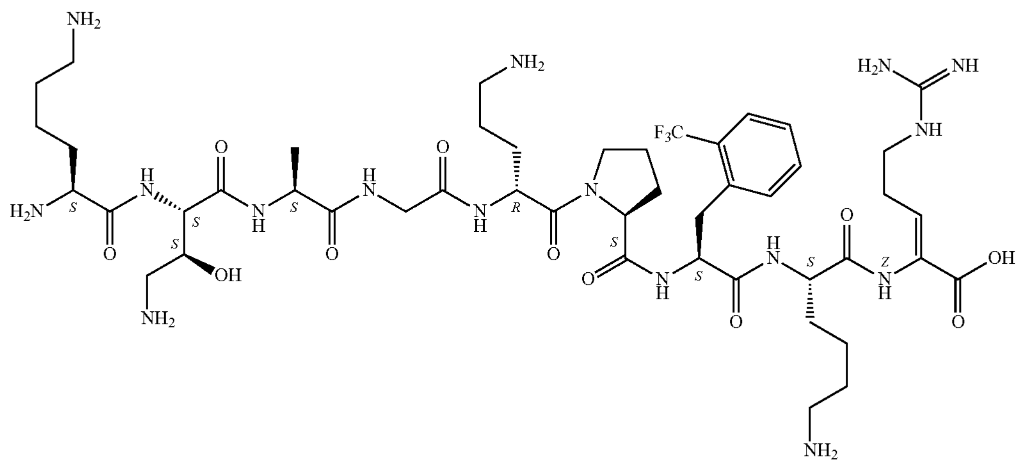 | C₄₇H₇₇F₃N₁₆O₁₁ | 1099.21 | 1100.50 | 99% | 14.55 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.80 | 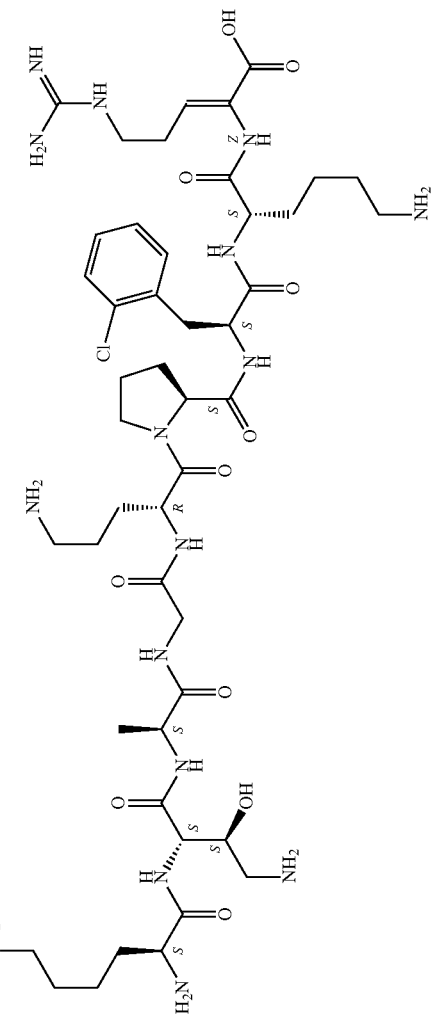 | C<sub>46</sub>H<sub>77</sub>ClN<sub>16</sub>O<sub>11</sub> | 1065.66 | 1066.40 | 99% | 13.98 |
| 24.81 | 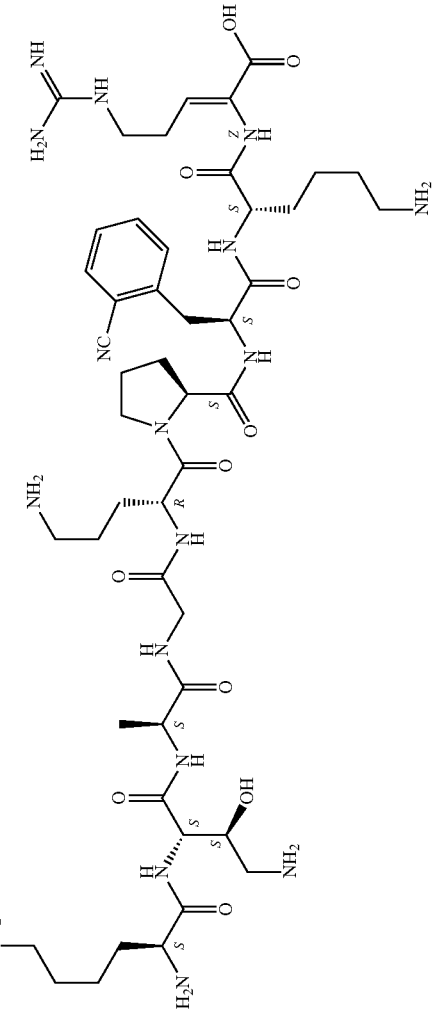 | C<sub>47</sub>H<sub>77</sub>N<sub>17</sub>O<sub>11</sub> | 1056.22 | 1057.45 | 99% | 13.18 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.82 | 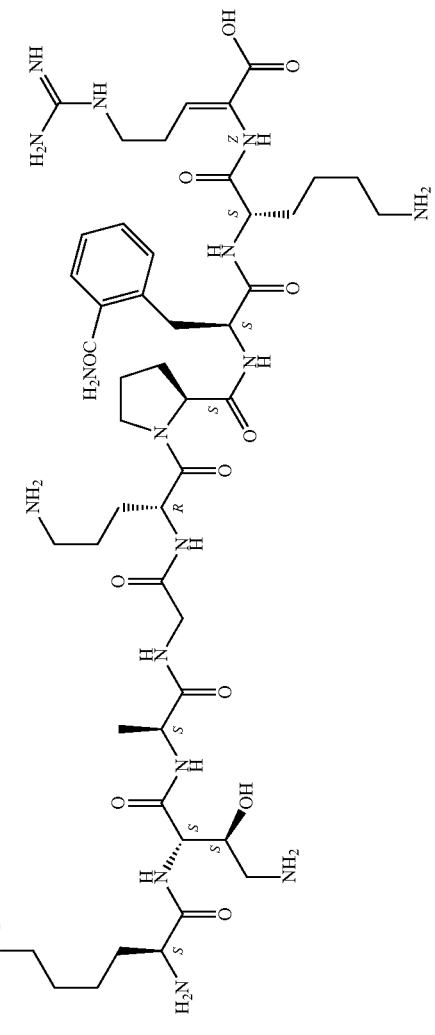 | $C_{47}H_{79}N_{17}O_{12}$ | 1074.24 | 1074.50 | 99% | 12.31 |
| 24.83 | 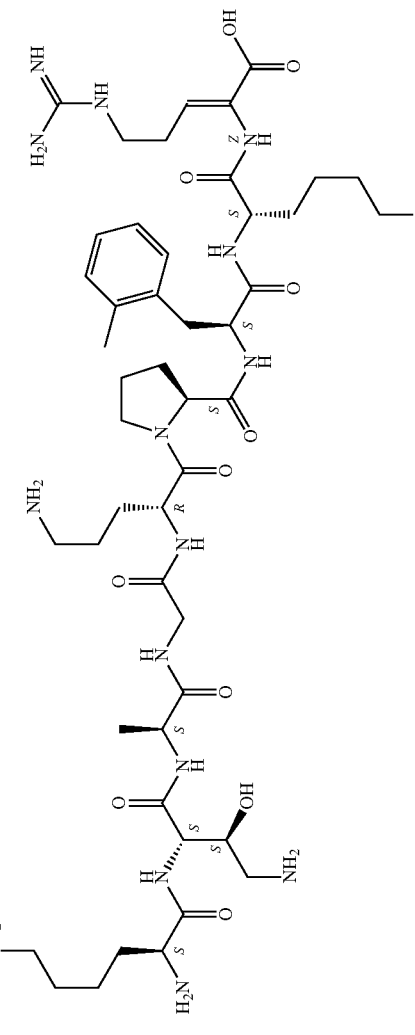 | $C_{47}H_{80}N_{16}O_{11}$ | 1045.24 | 1046.50 | 99% | 15.91 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.84 | 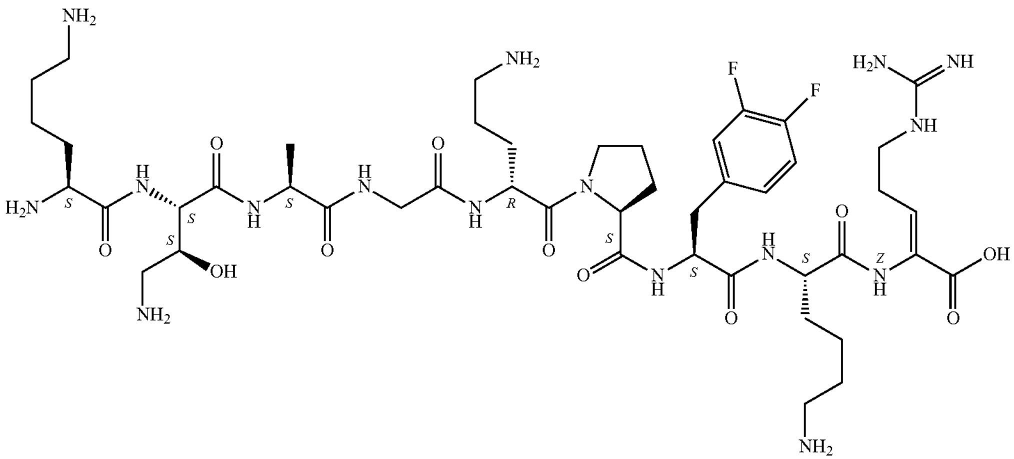 | $C_{46}H_{76}F_2N_{16}O_{11}$ | 1067.19 | 1068.45 | 98% | 13.95 |
| 24.85 | 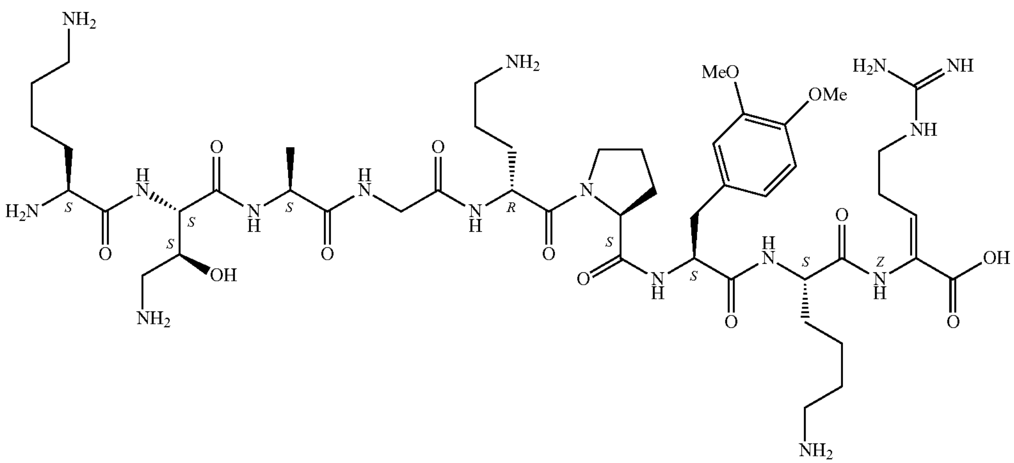 | $C_{48}H_{82}N_{16}O_{13}$ | 1091.26 | 1092.50 | 99% | 12.74 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.86 | 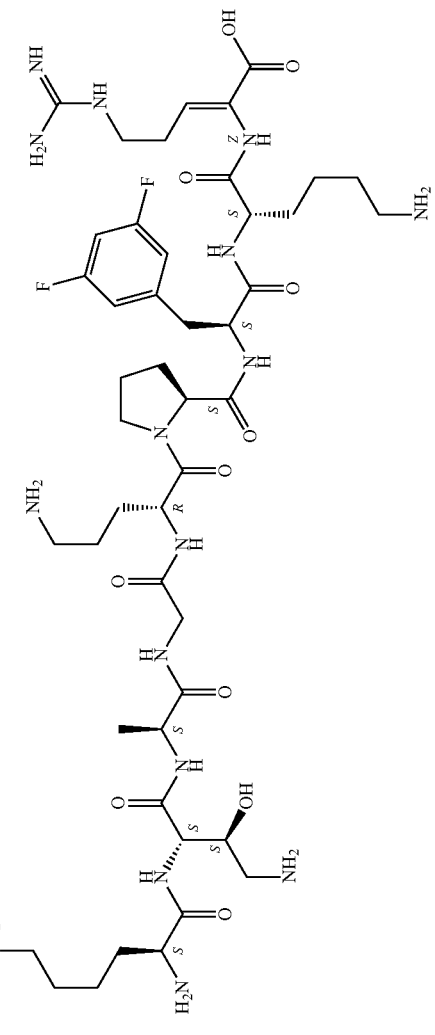 | $C_{46}H_{76}F_2N_{16}O_{11}$ | 1067.19 | 1068.50 | 99% | 13.98 |
| 24.87 | 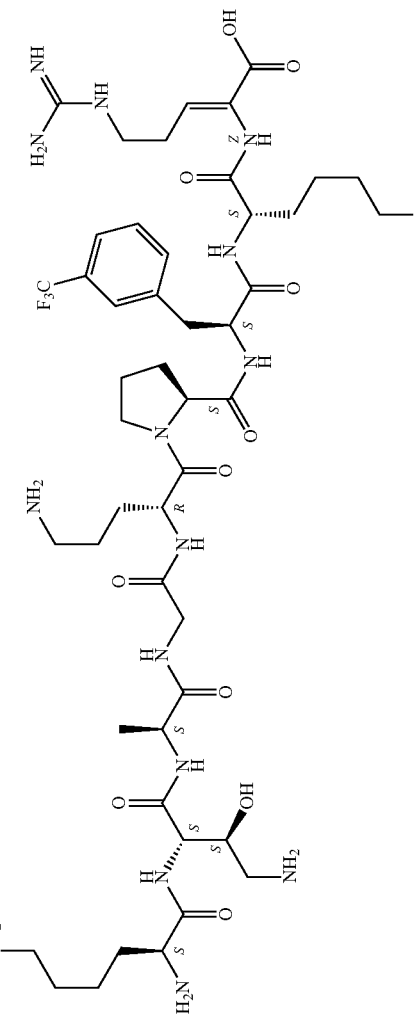 | $C_{47}H_{77}F_3N_{16}O_{11}$ | 1099.21 | 1100.45 | 99% | 15.32 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.88 | 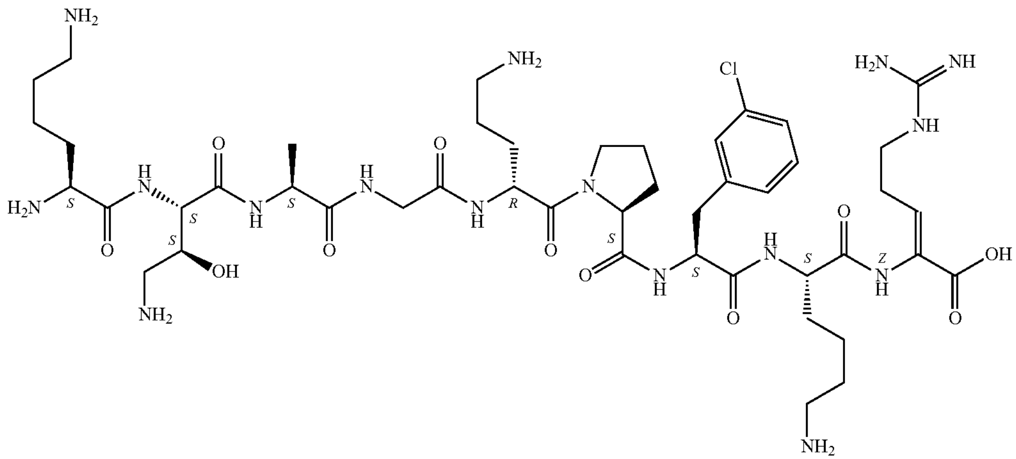 | C₄₆H₇₇ClN₁₆O₁₁ | 1065.66 | 1066.40 | 97% | 14.40 |
| 24.89 | 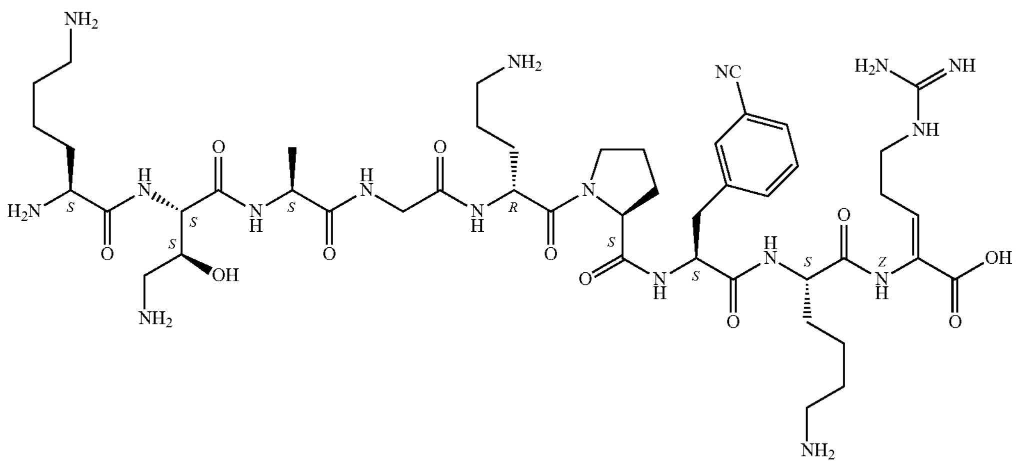 | C₄₇H₇₇N₁₇O₁₁ | 1056.22 | 1057.55 | 99% | 13.07 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.90 | 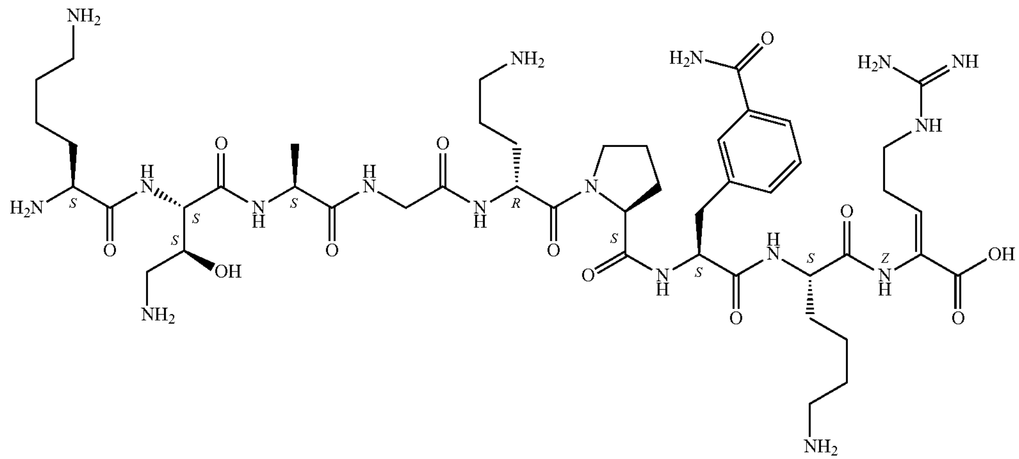 | C₄₇H₇₉N₁₇O₁₂ | 1074.24 | 1075.50 | 99% | 11.55 |
| 24.91 | 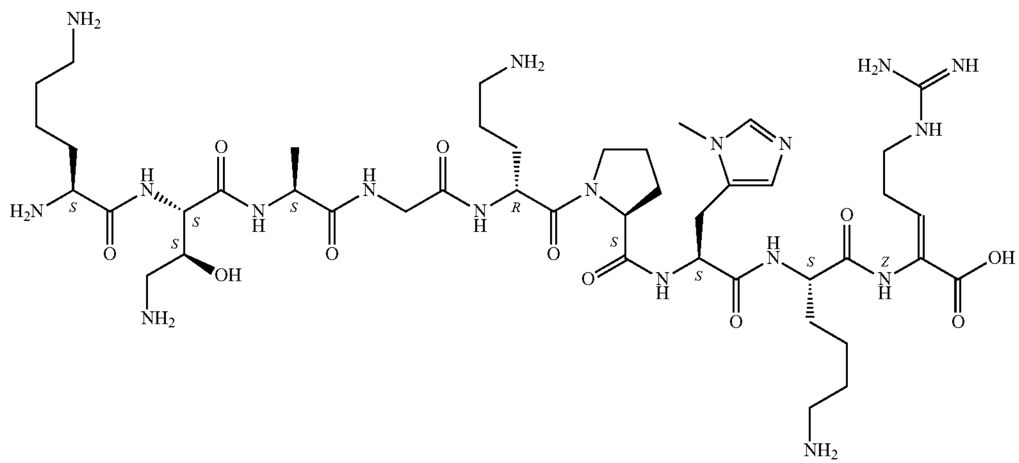 | C₄₄H₇₈N₁₈O₁₁ | 1035.20 | 1036.50 | 98% | 10.53 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.92 | 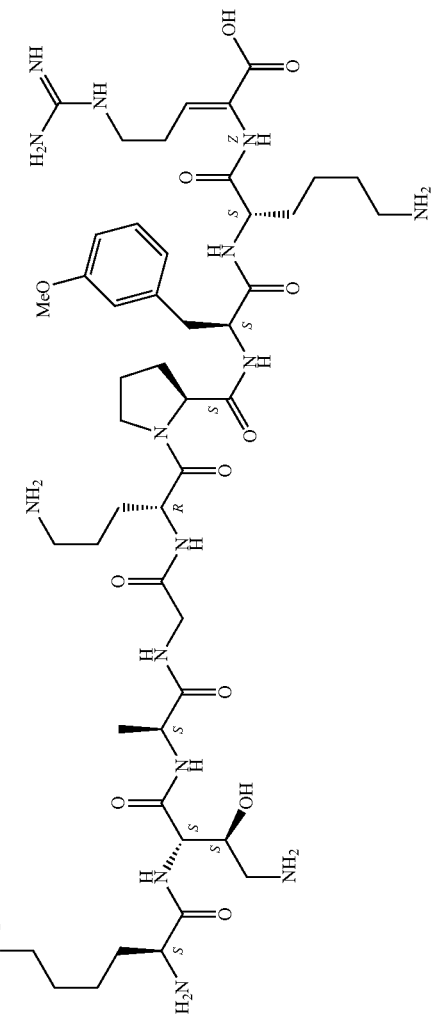 | C47H80N16O12 | 1061.24 | 1062.55 | 99% | 13.43 |
| 24.93 | 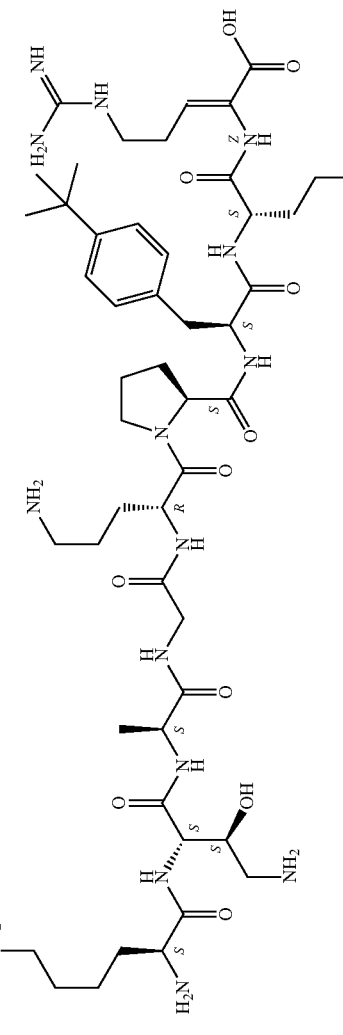 | C50H86N16O11 | 1087.32 | 1088.55 | 99% | 16.55 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.94 | 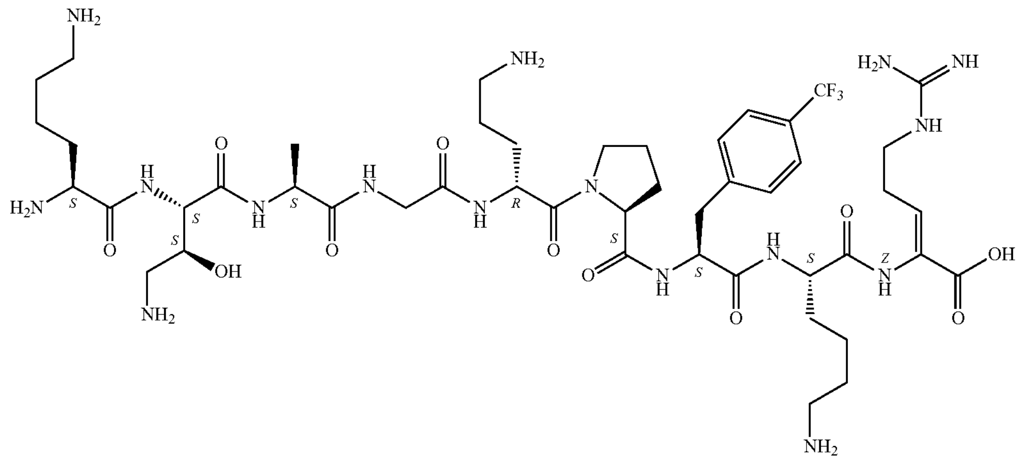 | C$_{47}$H$_{77}$F$_3$N$_{16}$O$_{11}$ | 1099.21 | 1100.45 | 99% | 15.33 |
| 24.97 | 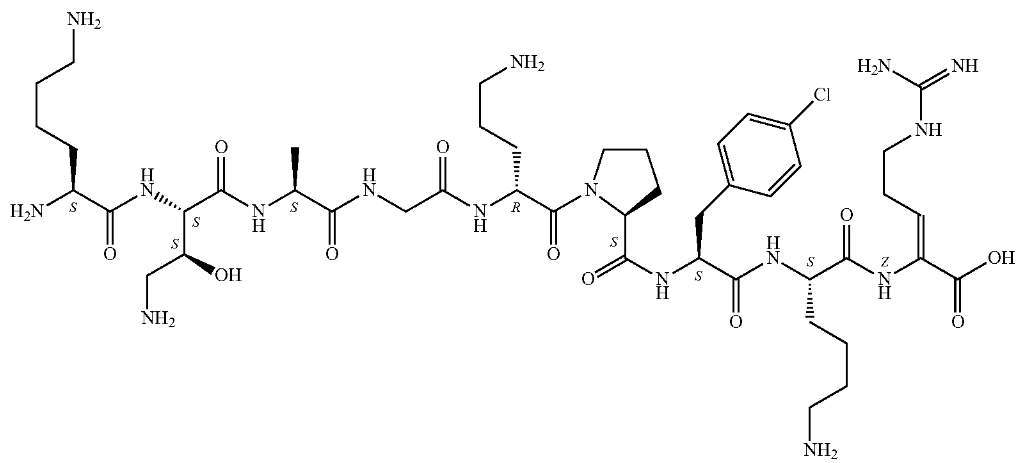 | C$_{46}$H$_{77}$ClN$_{16}$O$_{11}$ | 1065.66 | 1066.46 | 96% | 14.50 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.98 | 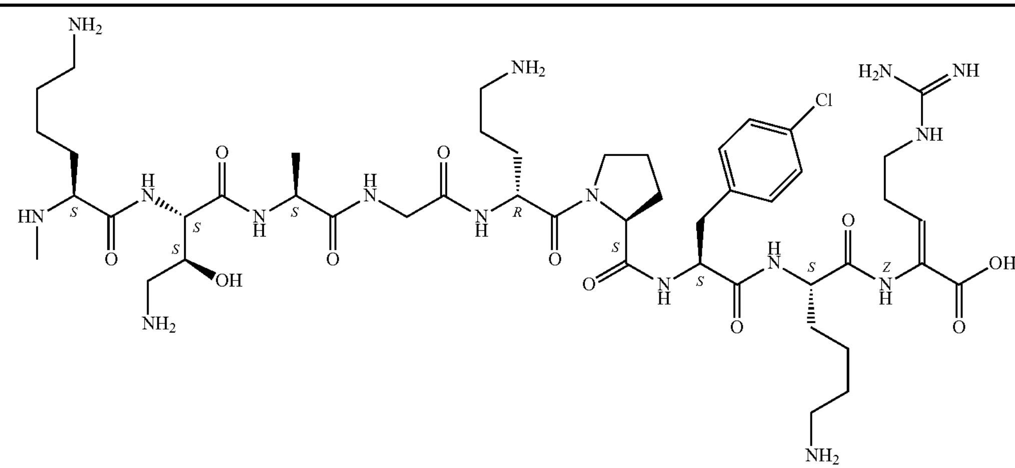 | $C_{47}H_{79}ClN_{16}O_{11}$ | 1079.68 | 1079.70 1081.60 | 97% | 14.19 |
| 24.100 | 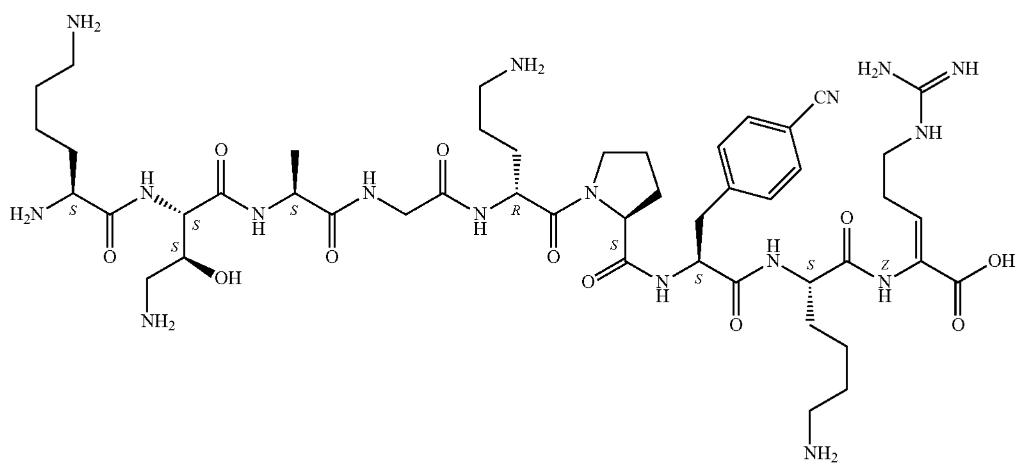 | $C_{47}H_{77}N_{17}O_{11}$ | 1056.22 | 1057.50 | 99% | 12.89 |

TABLE 1-continued

Compounds and analytical data

| Cmpd | Structure | Molecular formula | MW (g/mol) | [M + H]⁺ (g/mol) | UV purity (λ = 230 nm) | Rt (min) |
|---|---|---|---|---|---|---|
| 24.101 | 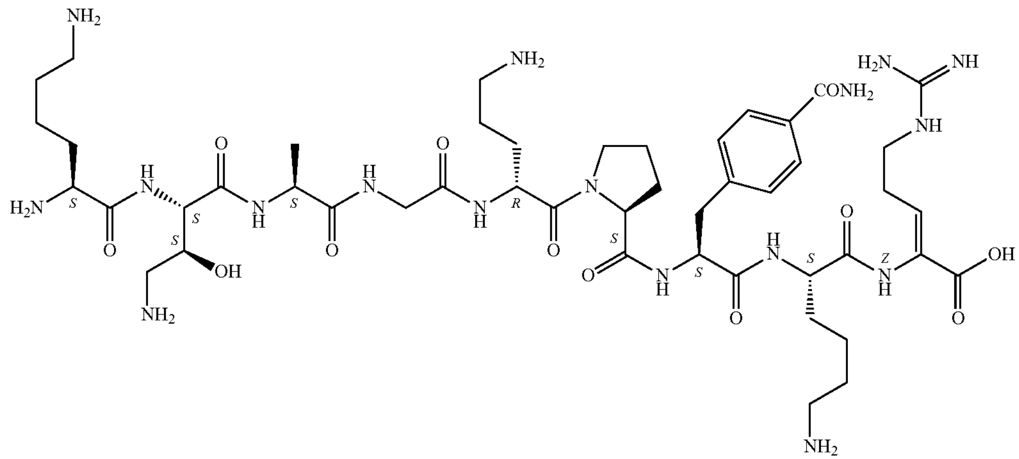 | $C_{47}H_{79}N_{17}O_{12}$ | 1074.24 | 1075.50 | 99% | 11.21 |
| 24.102 | 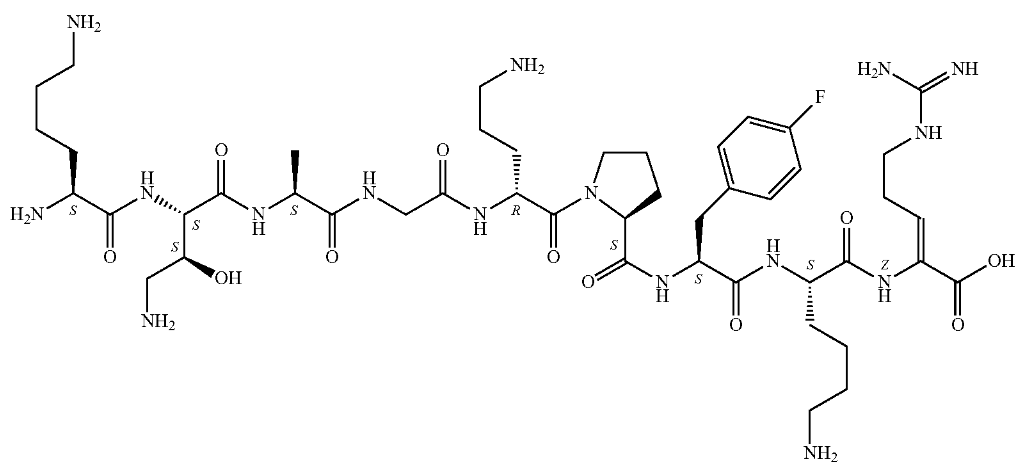 | $C_{46}H_{77}FN_{16}O_{11}$ | 1049.20 | 1050.45 | 99% | 13.67 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.103 | 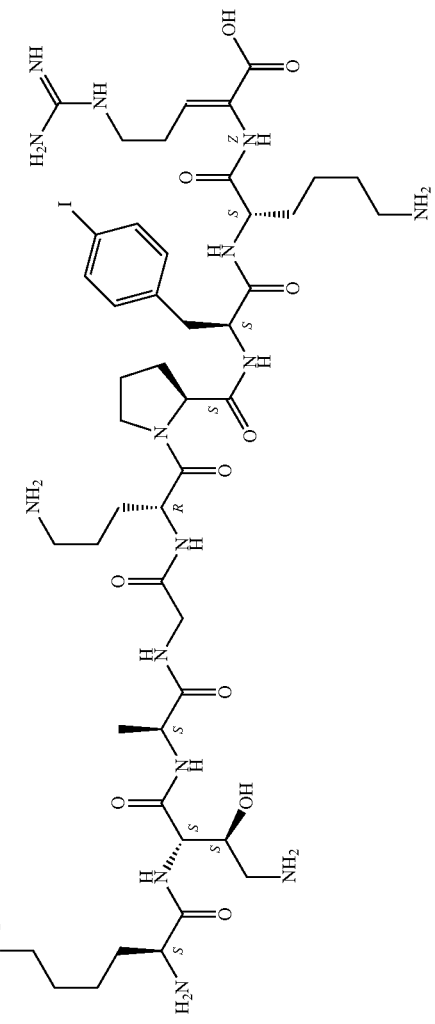 | C₄₆H₇₇IN₁₆O₁₁ | 1157.11 | 1158.35 | 99% | 15.13 |
| 24.104 | 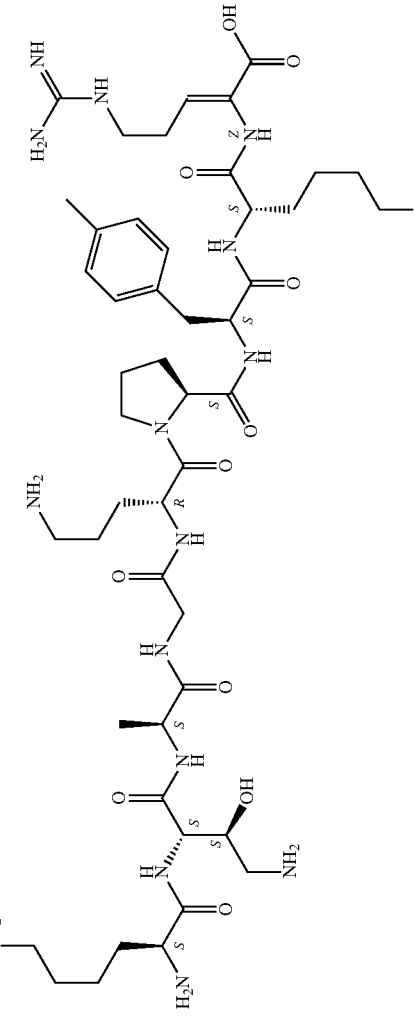 | C₄₇H₈₀N₁₆O₁₁ | 1045.24 | 1046.55 | 98% | 14.06 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.105 | 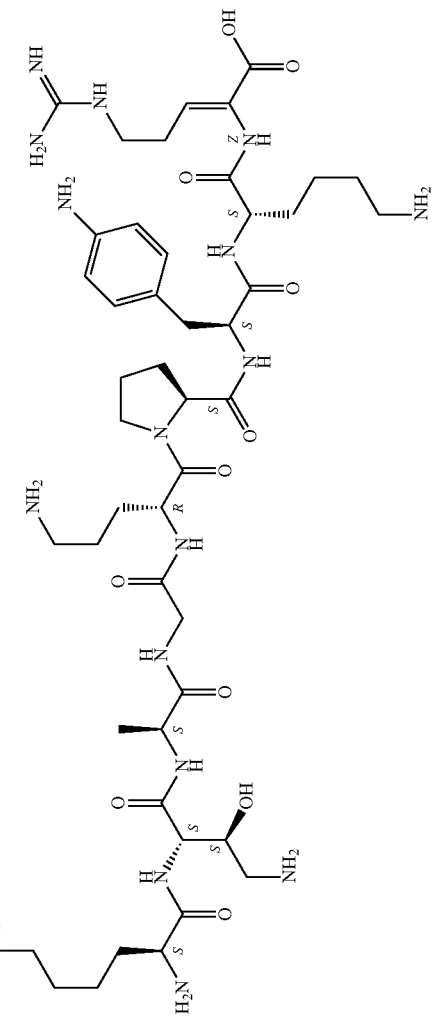 | $C_{46}H_{79}N_{17}O_{11}$ | 1046.23 | 1047.55 | 98% | 10.42 |
| 24.106 | 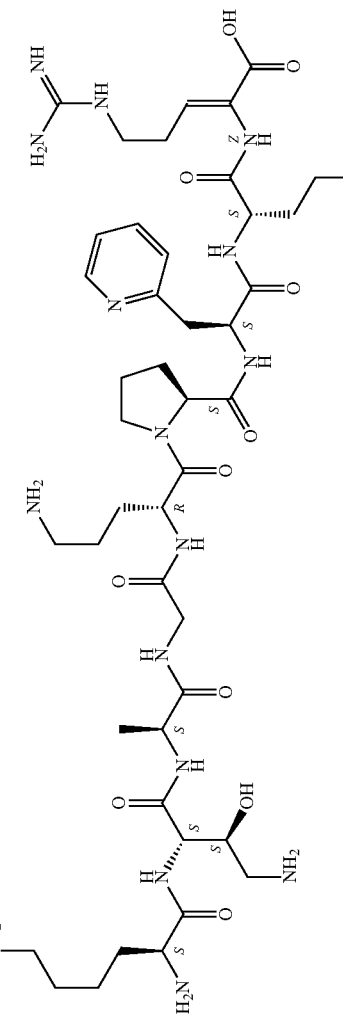 | $C_{45}H_{77}N_{17}O_{11}$ | 1032.20 | 1033.50 | 99% | 10.88 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.107 | 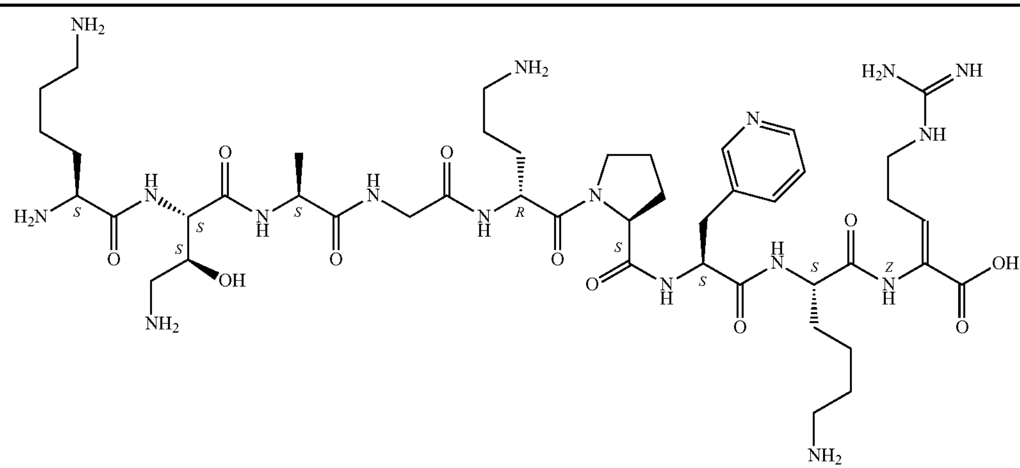 | $C_{45}H_{77}N_{17}O_{11}$ | 1032.20 | 1033.45 | 99% | 10.68 |
| 24.108 | 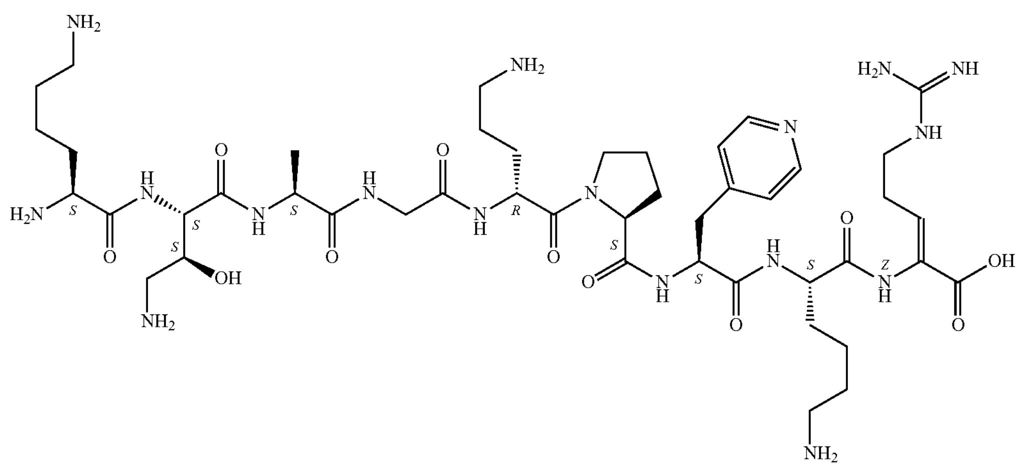 | $C_{45}H_{77}N_{17}O_{11}$ | 1032.20 | 1033.45 | 99% | 10.61 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.109 | 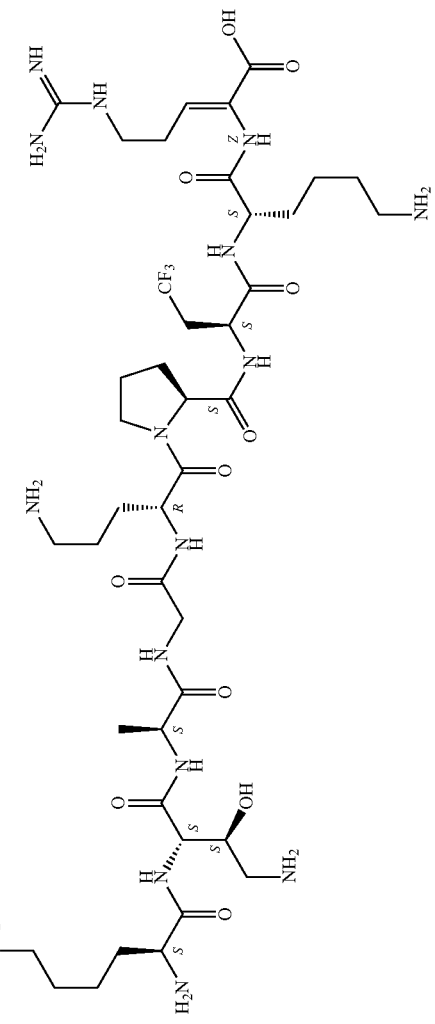 | C₄₁H₇₃F₃N₁₆O₁₁ | 1023.11 | 1024.45 | 99% | 12.14 |
| 24.110 | 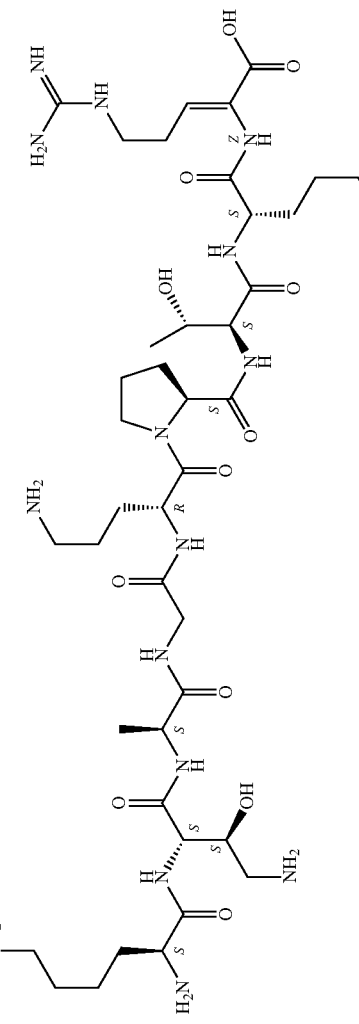 | C₄₁H₇₆N₁₆O₁₂ | 985.14 | 986.50 | 99% | 10.28 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.111 | 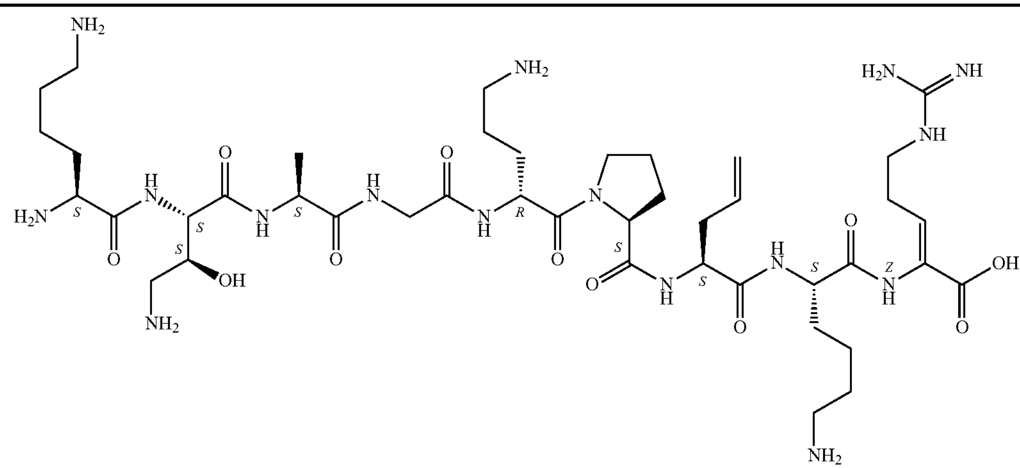 | $C_{42}H_{76}N_{16}O_{11}$ | 981.15 | 982.50 | 99% | 11.33 |
| 24.112 | 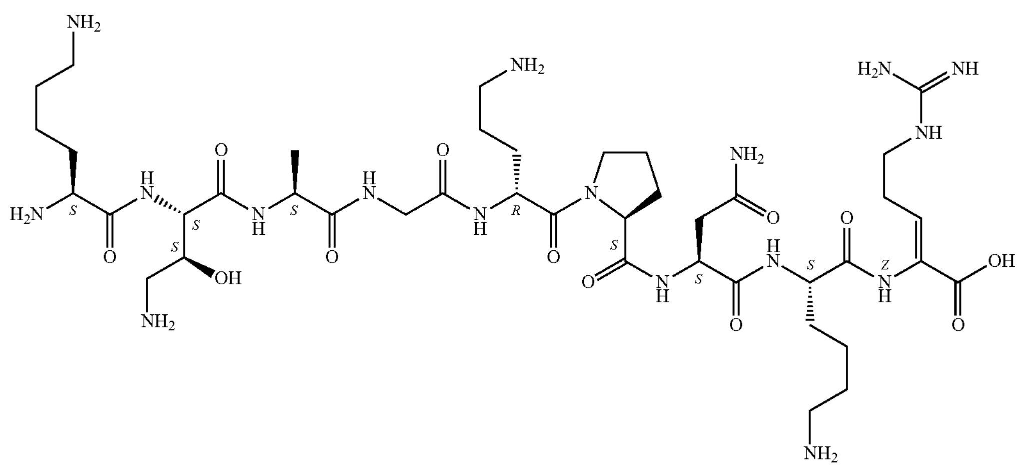 | $C_{41}H_{75}N_{17}O_{12}$ | 998.14 | 999.50 | 99% | 10.05 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.116 | 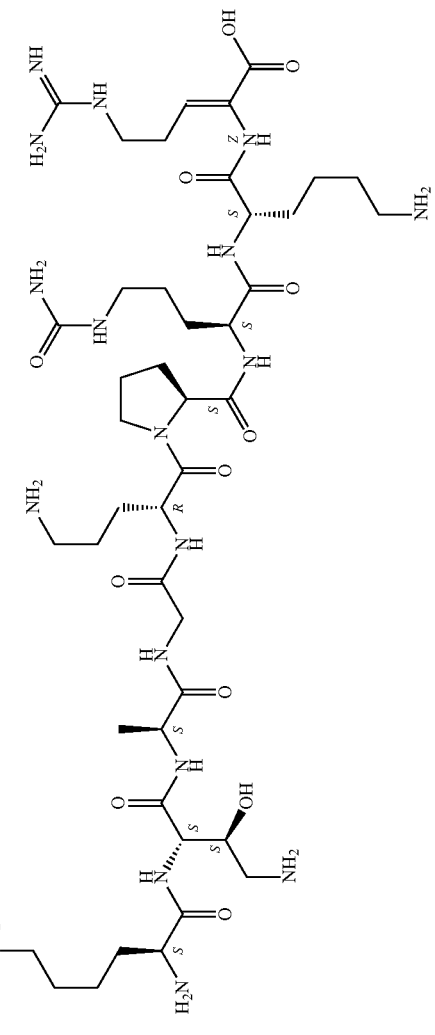 | C43H80N18O12 | 1041.21 | 1042.50 | 99% | 10.27 |
| 24.117 | 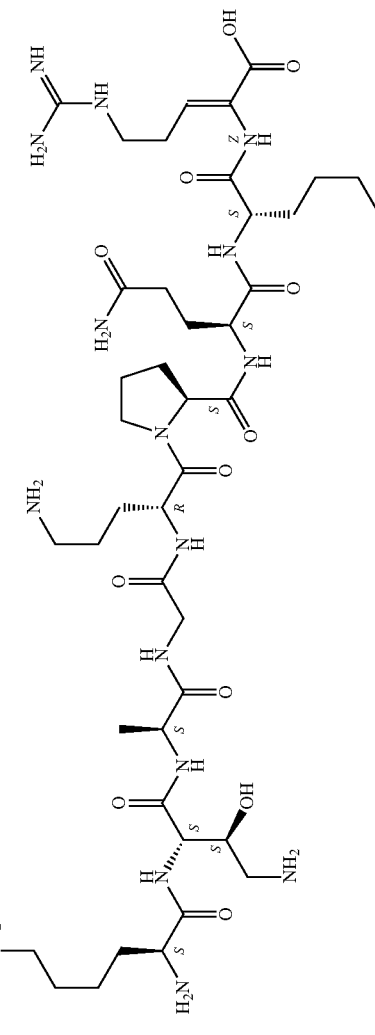 | C42H77N17O12 | 1012.17 | 1013.50 | 99% | 10.11 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.118 | 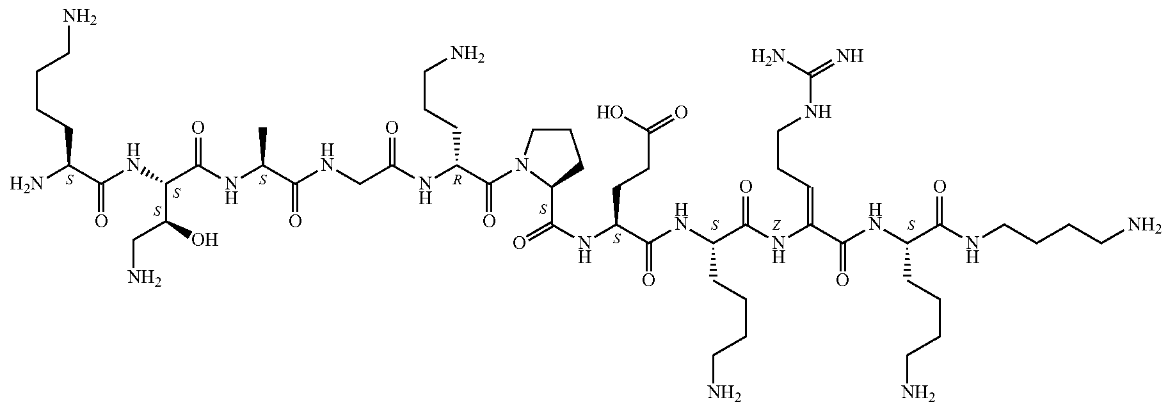 | C₅₂H₉₈N₂₀O₁₃ | 1211.46 | 1212.70 | 99% | 10.38 |
| 24.120 | 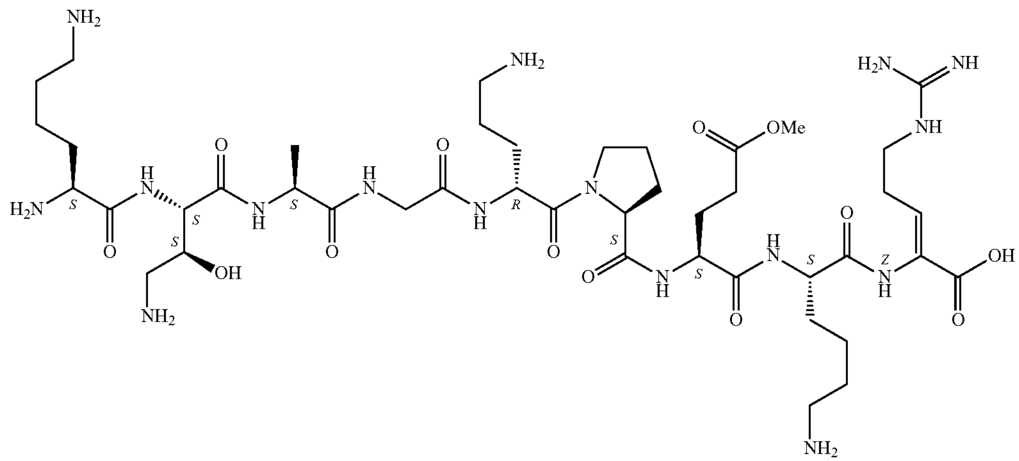 | C₄₃H₇₈N₁₆O₁₃ | 1027.18 | 1028.50 | 89% | 11.23 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.121 | 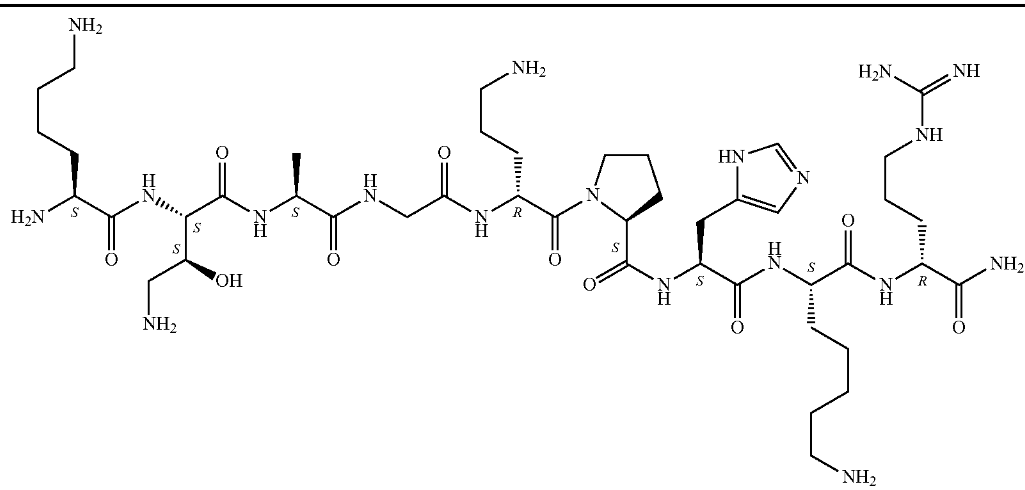 | $C_{44}H_{81}N_{19}O_{10}$ | 1036.24 | 1037.50 | 98% | 10.62 |
| 24.122 | 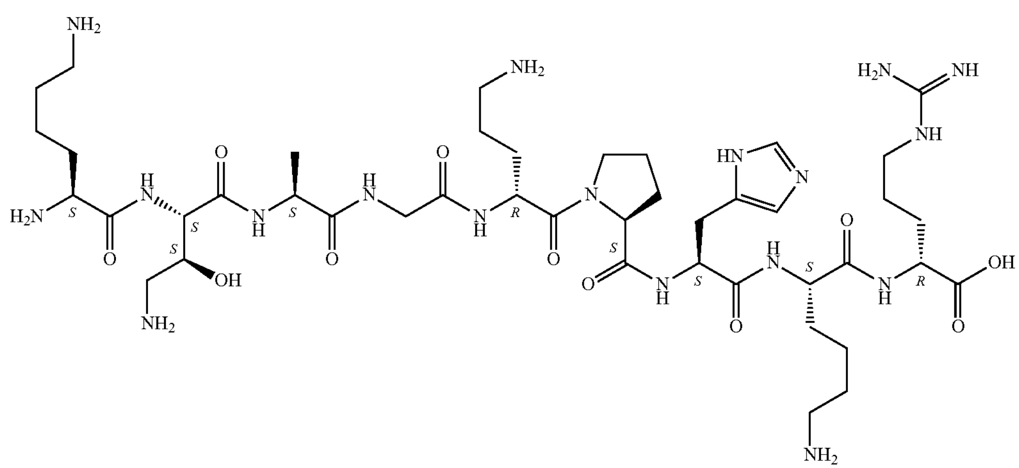 | $C_{43}H_{78}N_{18}O_{11}$ | 1023.19 | 1024.55 | 99% | 10.16 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.123 | 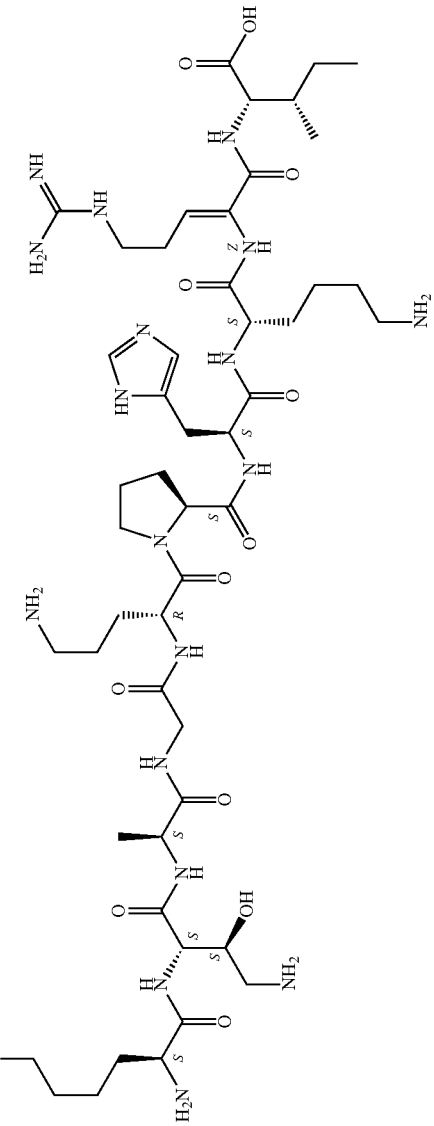 | C49H87N19O12 | 1134.34 | 1135.55 | 99% | 12.96 |
| 24.125 | 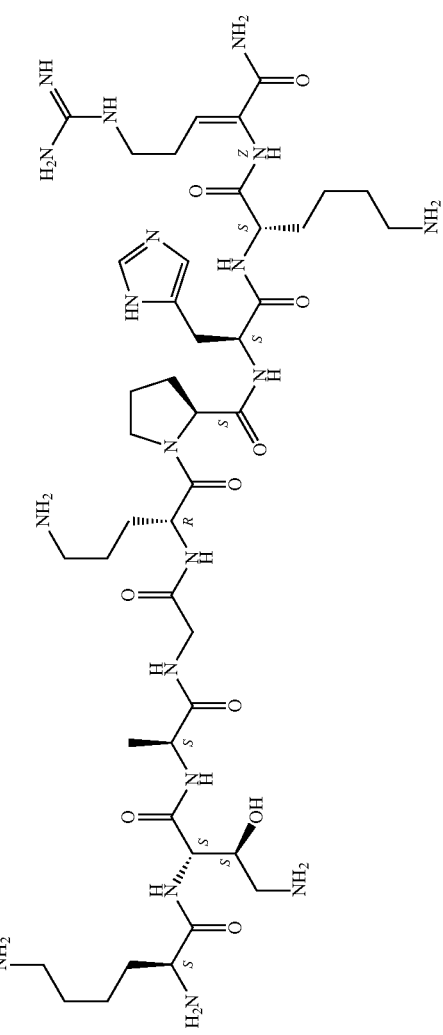 | C43H77N19O10 | 1020.19 | 1021.50 | 98% | 9.70 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.126 | 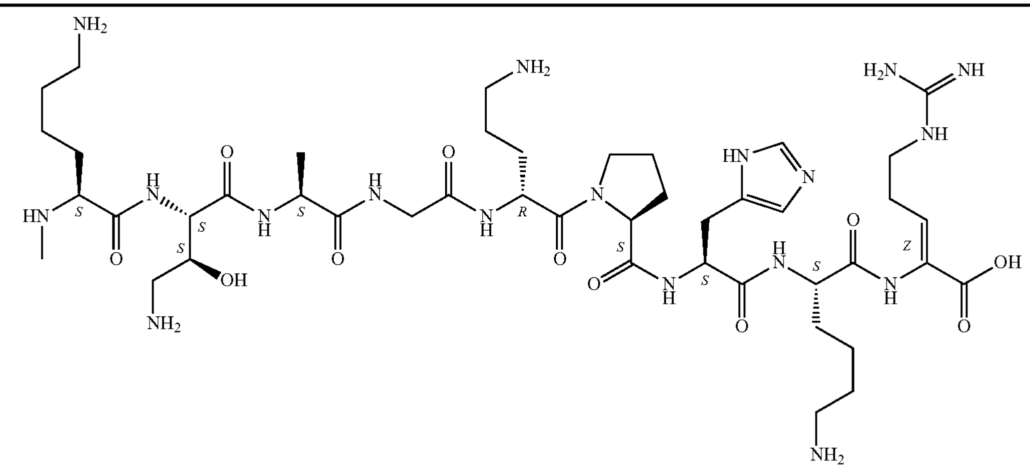 | $C_{44}H_{78}N_{18}O_{11}$ | 1035.20 | 1035.80 | 99% | 10.34 |
| 24.127 | 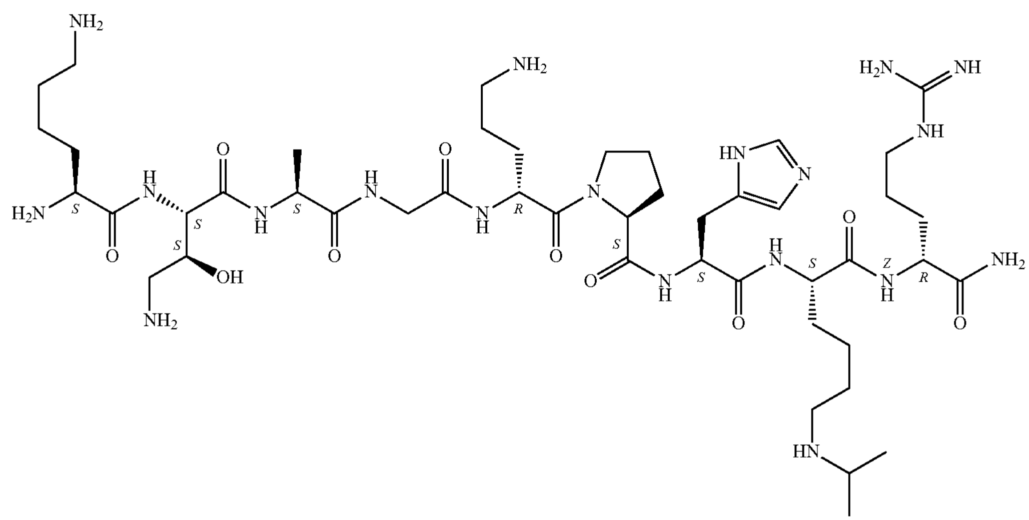 | $C_{46}H_{85}N_{19}O_{10}$ | 1064.29 | 1065.50 | 99% | 11.34 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.128 | 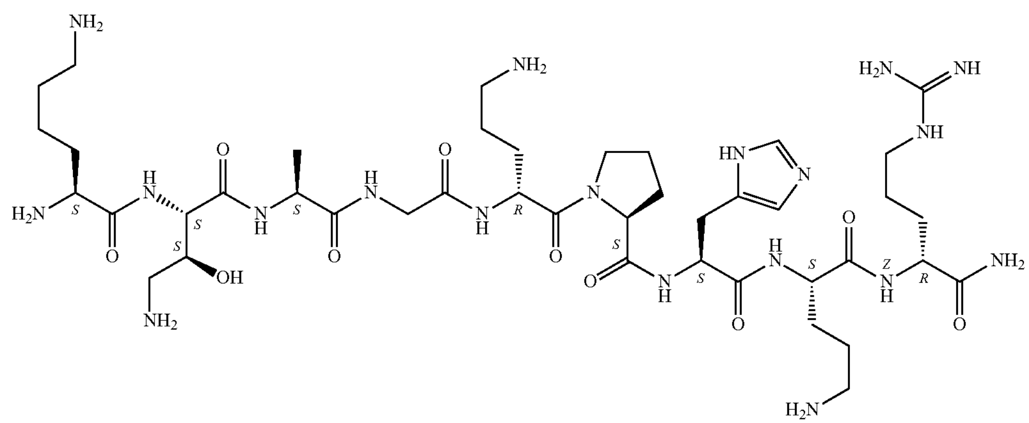 | C₄₂H₇₇N₁₉O₁₀ | 1008.18 | 1009.45 | 99% | 10.10 |
| 24.129 | 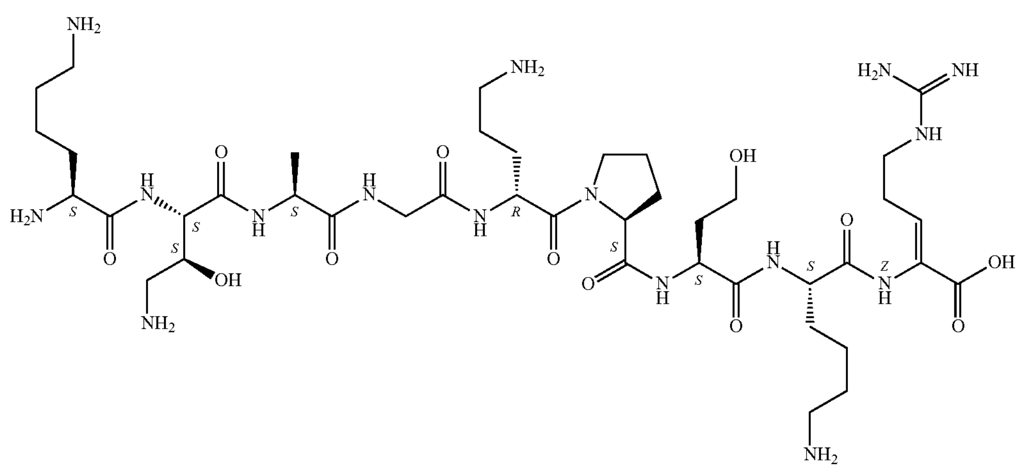 | C₄₁H₇₆N₁₆O₁₂ | 985.14 | 986.50 | 99% | 10.10 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.130 | 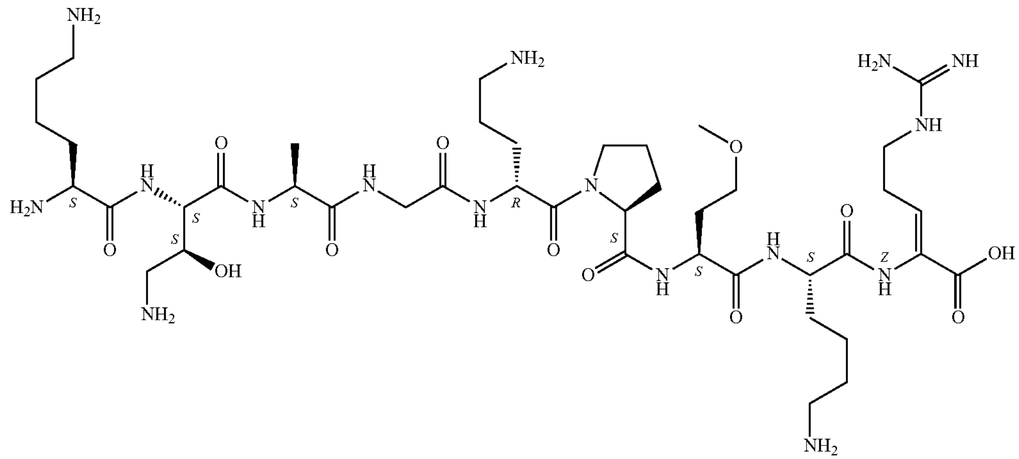 | C₄₂H₇₈N₁₆O₁₂ | 999.17 | 1000.50 | 99% | 10.94 |
| 24.131 | 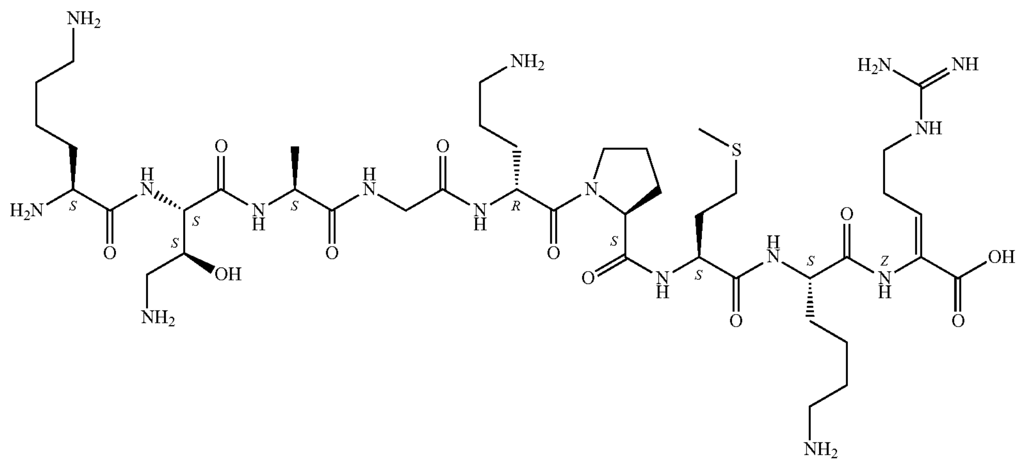 | C₄₂H₇₈N₁₆O₁₁S | 1015.23 | 1016.50 | 99% | 11.60 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.132 | 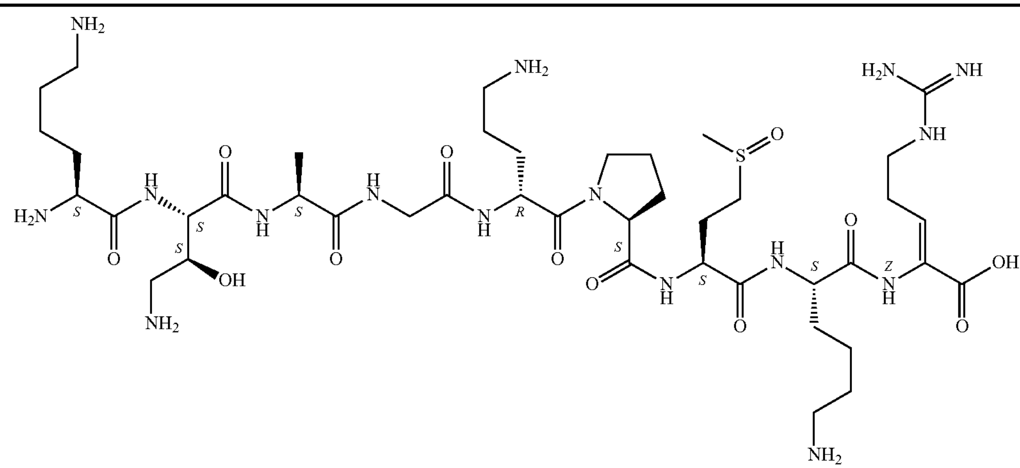 | C₄₂H₇₈N₁₆O₁₂S | 1031.23 | 1032.50 | 99% | 10.29 |
| 24.133 | 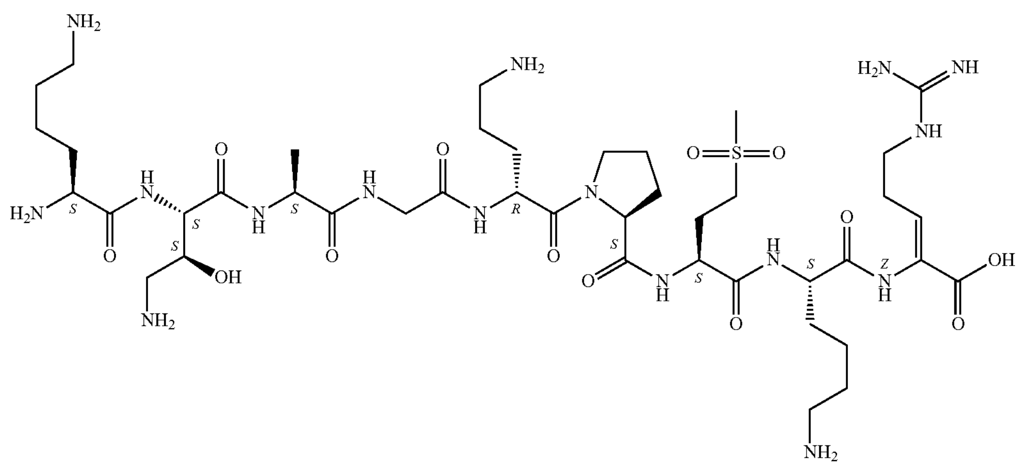 | C₄₂H₇₈N₁₆O₁₃S | 1047.23 | 1048.45 | 98% | 10.49 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.134 | 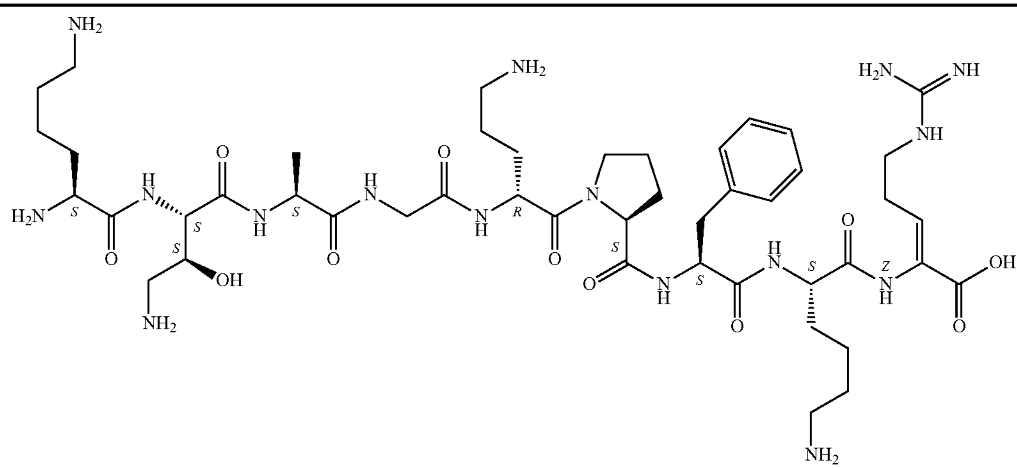 | C<sub>48</sub>H<sub>78</sub>N<sub>16</sub>O<sub>11</sub> | 1031.21 | 1032.45 | 99% | 13.14 |
| 24.135 | 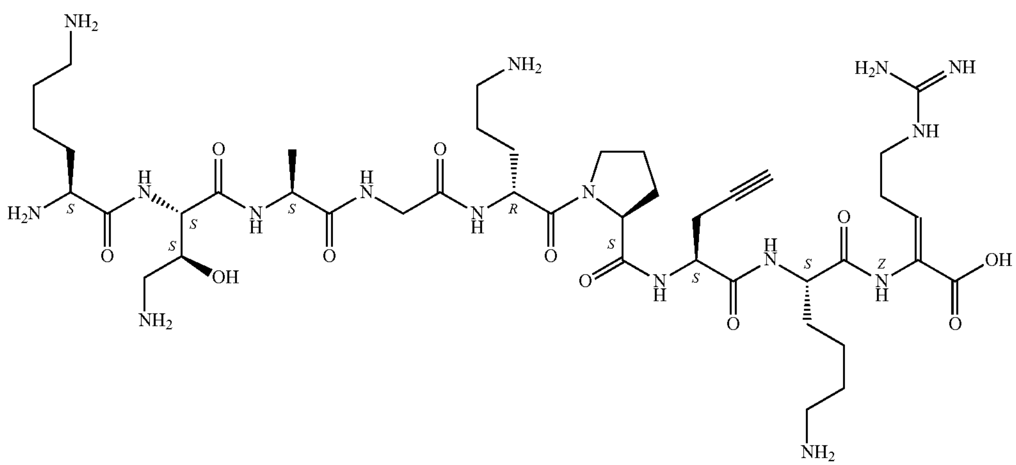 | C<sub>42</sub>H<sub>74</sub>N<sub>16</sub>O<sub>11</sub> | 979.14 | 980.40 | 99% | 11.04 |

TABLE 1-continued

Compounds and analytical data

| Cmpd | Structure | Molecular formula | MW (g/mol) | [M + H]⁺ (g/mol) | UV purity (λ = 230 nm) | Rt (min) |
|---|---|---|---|---|---|---|
| 24.136 | 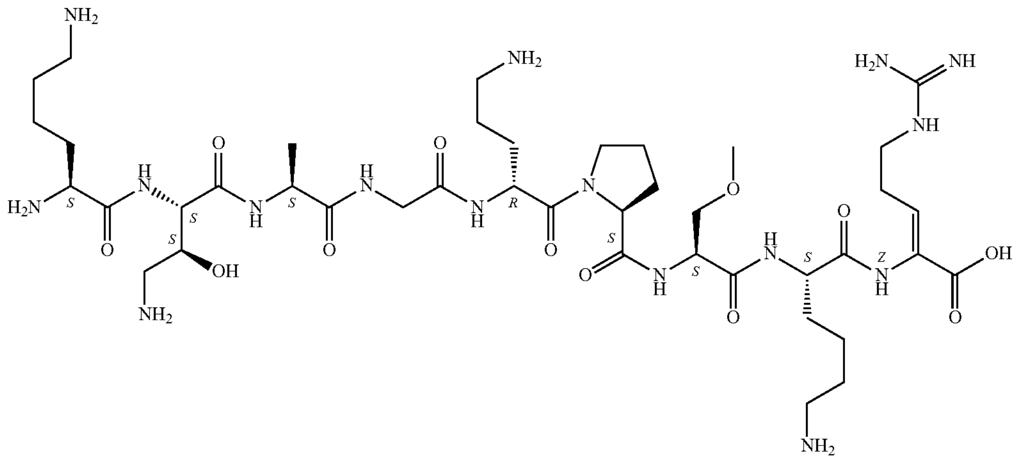 | $C_{41}H_{76}N_{16}O_{12}$ | 985.14 | 986.50 | 99% | 10.55 |
| 24.137 | 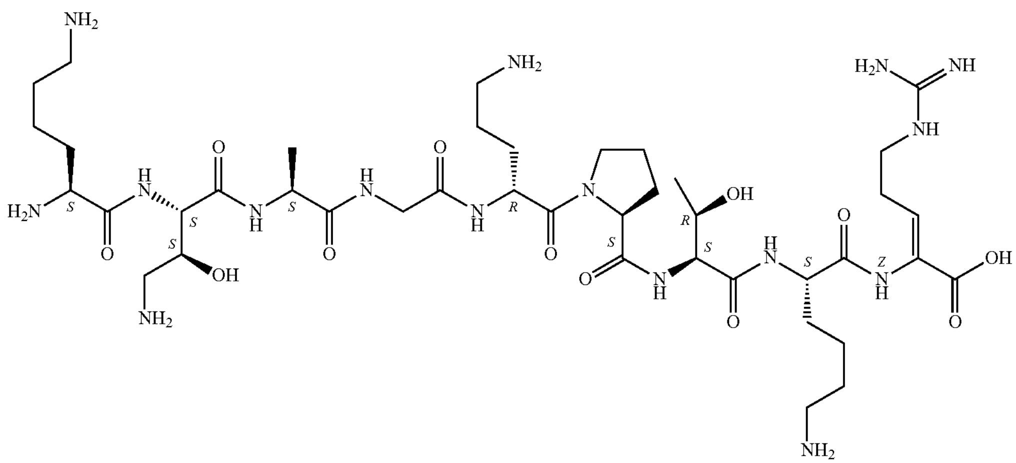 | $C_{41}H_{76}N_{16}O_{12}$ | 985.14 | 986.55 | 99% | 10.31 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.138 | 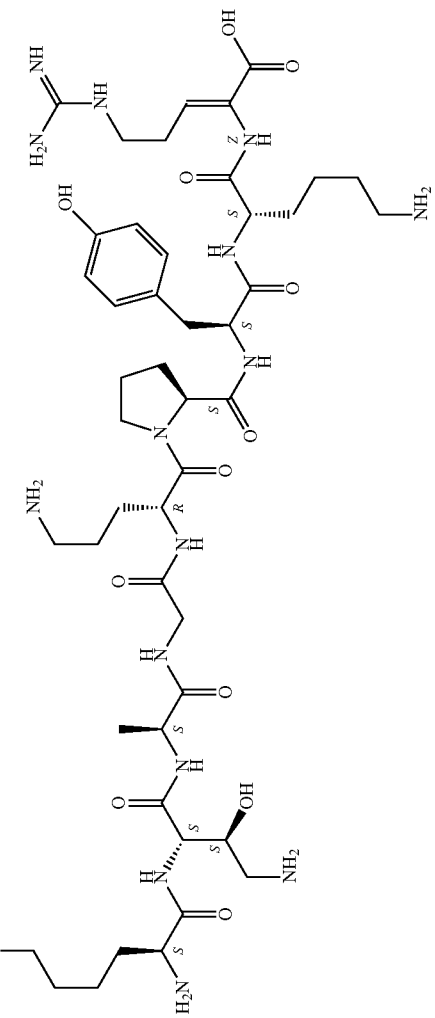 | $C_{46}H_{78}N_{16}O_{12}$ | 1047.21 | 1048.45 | 99% | 11.71 |
| 24.141 | 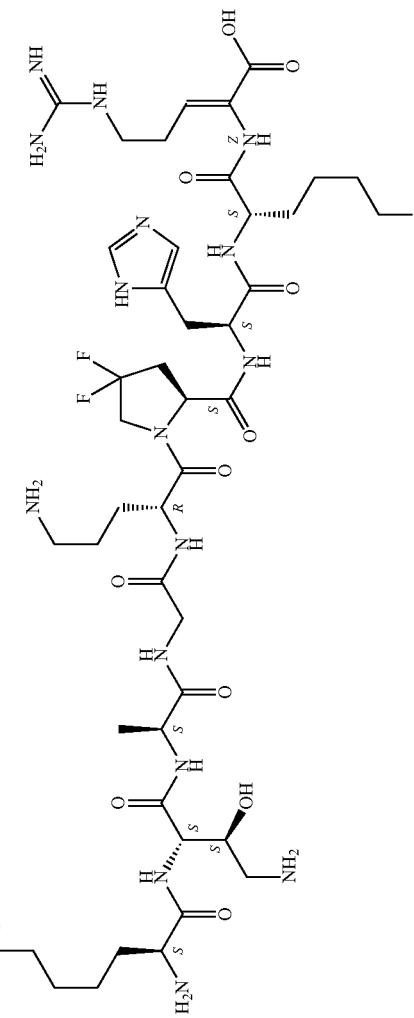 | $C_{43}H_{74}F_2N_{18}O_{11}$ | 1057.16 | 1058.50 | 99% | 10.79 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.142 | 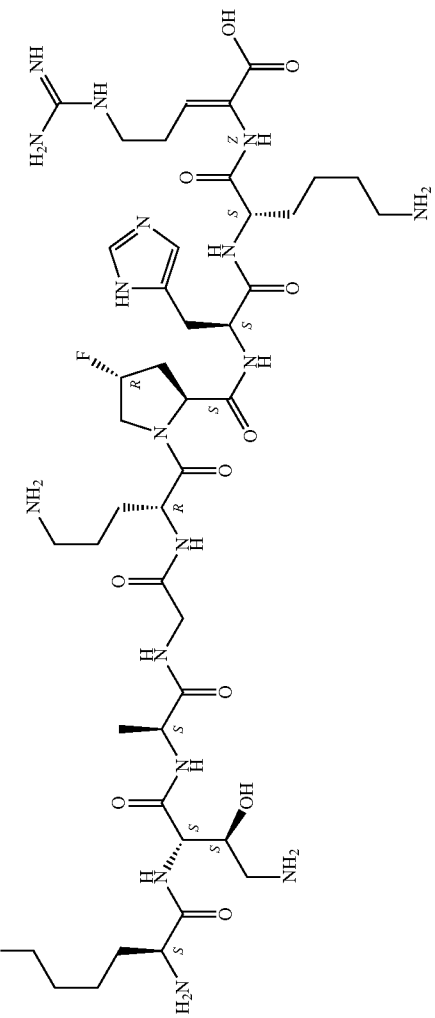 | $C_{43}H_{75}FN_{18}O_{11}$ | 1039.17 | 1040.45 | 98% | 10.44 |
| 24.143 | 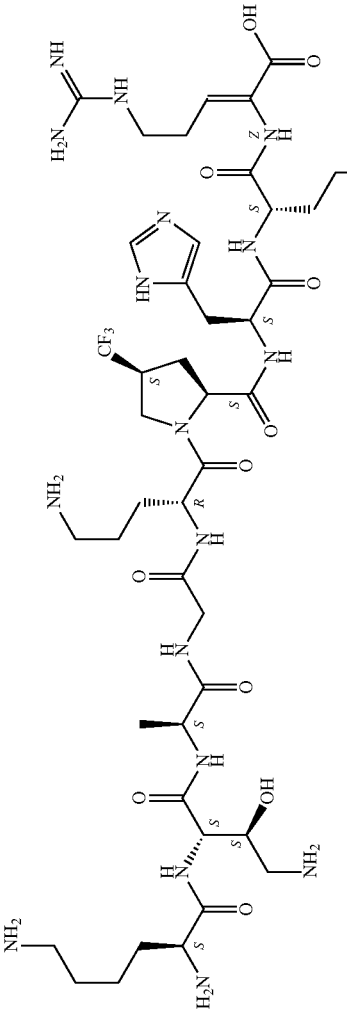 | $C_{44}H_{75}F_3N_{18}O_{11}$ | 1089.18 | 1090.50 | 99% | 11.45 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.144 | 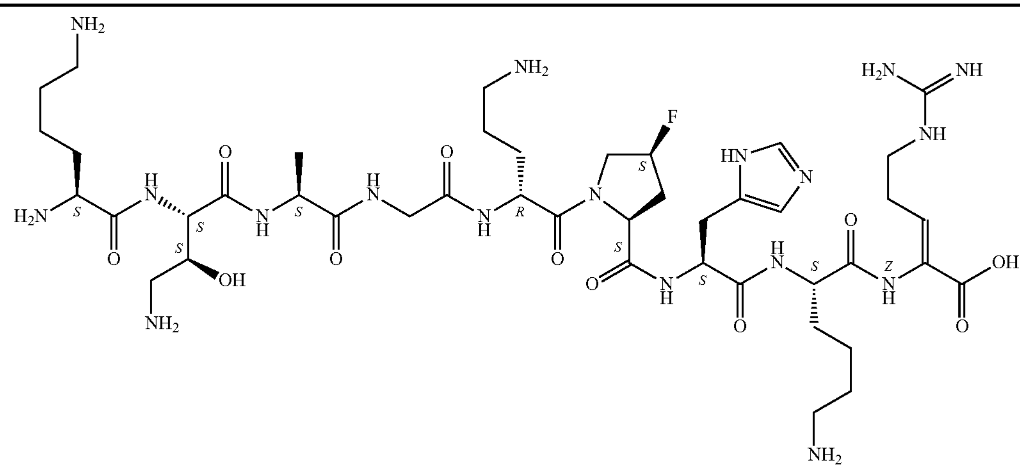 | C₄₃H₇₅FN₁₈O₁₁ | 1039.17 | 1040.45 | 97% | 10.35 |
| 24.145 | 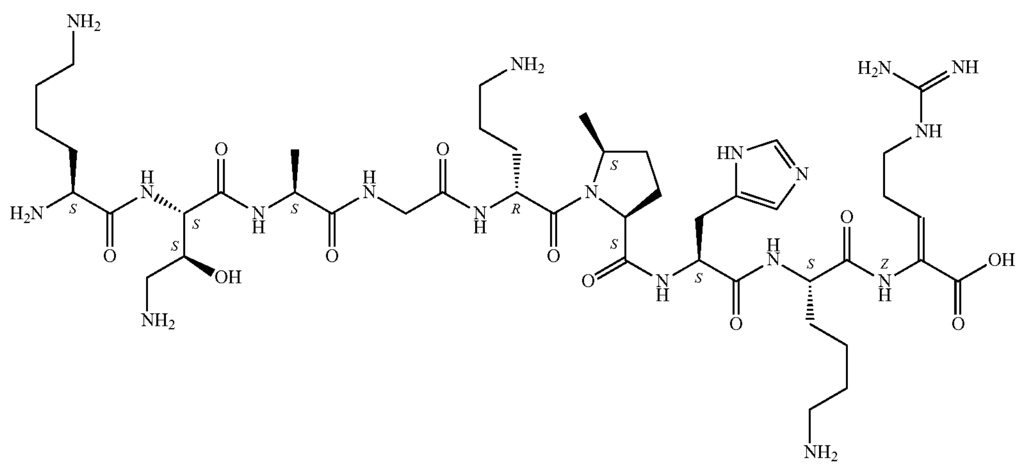 | C₄₄H₇₈N₁₈O₁₁ | 1035.20 | 1036.50 | 99% | 10.77 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.146 | 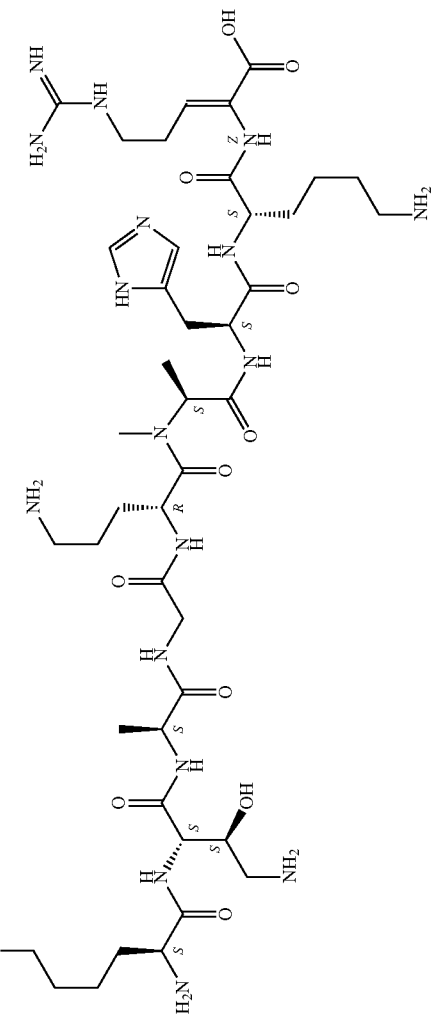 | C42H76N18O11 | 1009.17 | 1010.45 | 99% | 10.38 |
| 24.147 | 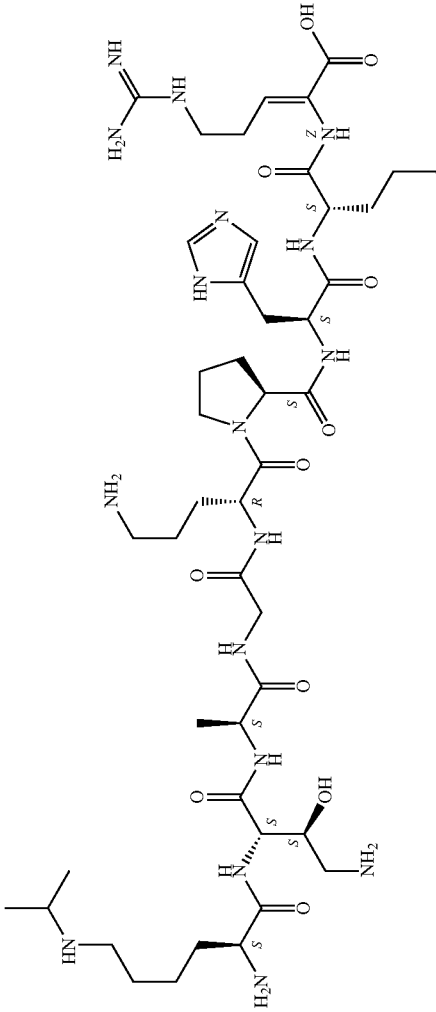 | C46H82N18O11 | 1063.26 | 1064.45 | 99% | 11.21 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.148 | 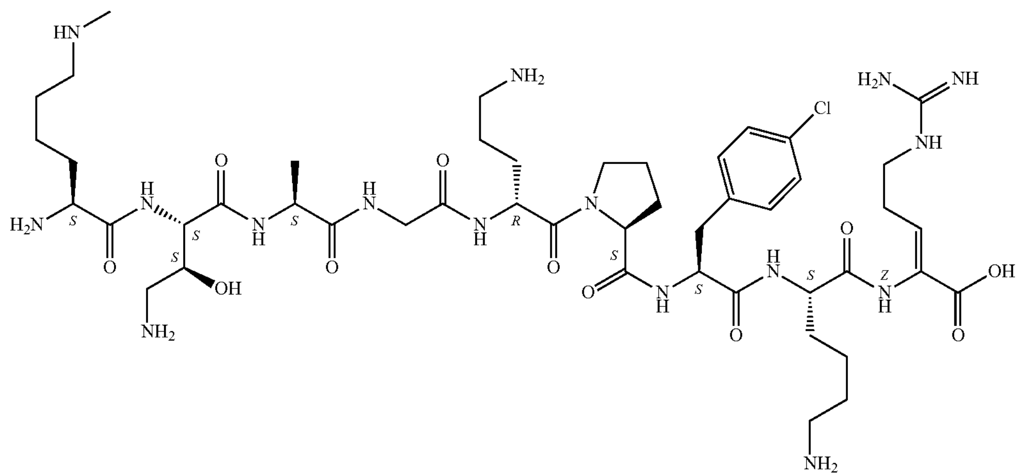 | C₄₇H₇₉ClN₁₆O₁₁ | 1079.68 | 1079.75 | 99% | 14.28 |
| 24.149 | 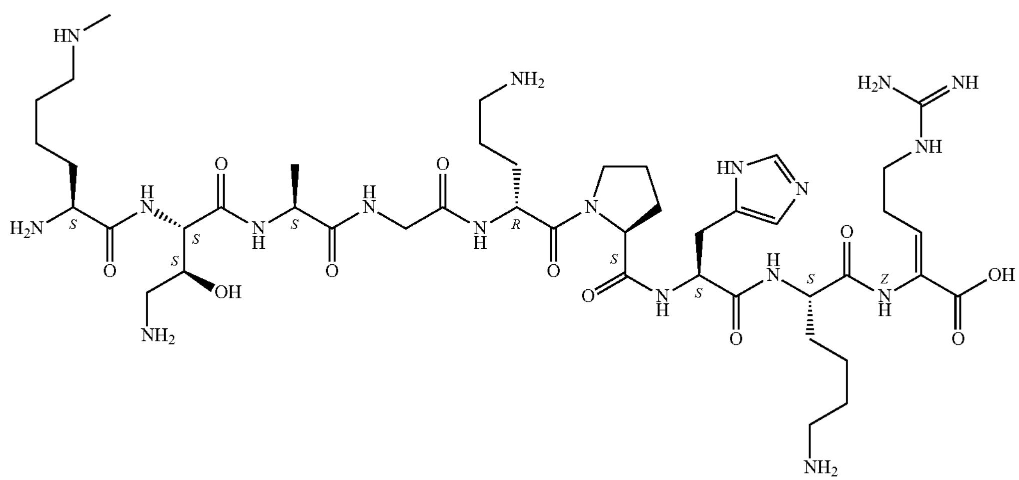 | C₄₄H₇₈N₁₈O₁₁ | 1035.20 | 1035.75 | 99% | 10.40 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.150 | 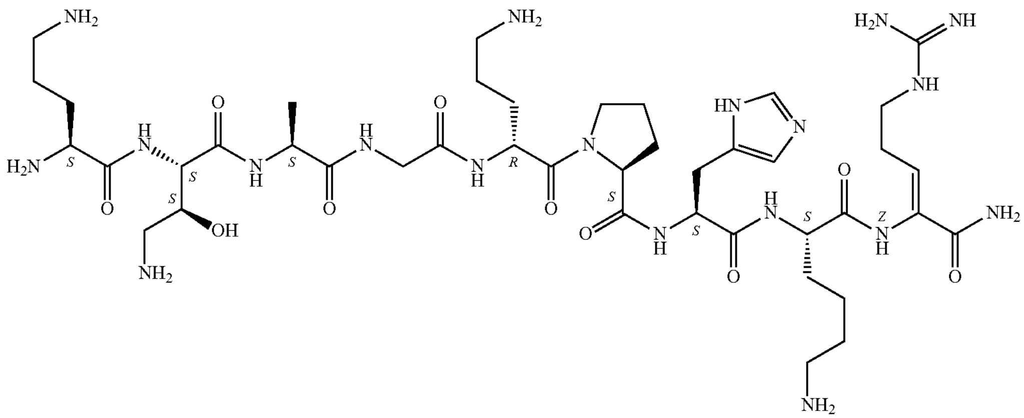 | $C_{42}H_{75}N_{19}O_{10}$ | 1006.17 | 1007.60 | 99% | 9.74 |
| 24.151 | 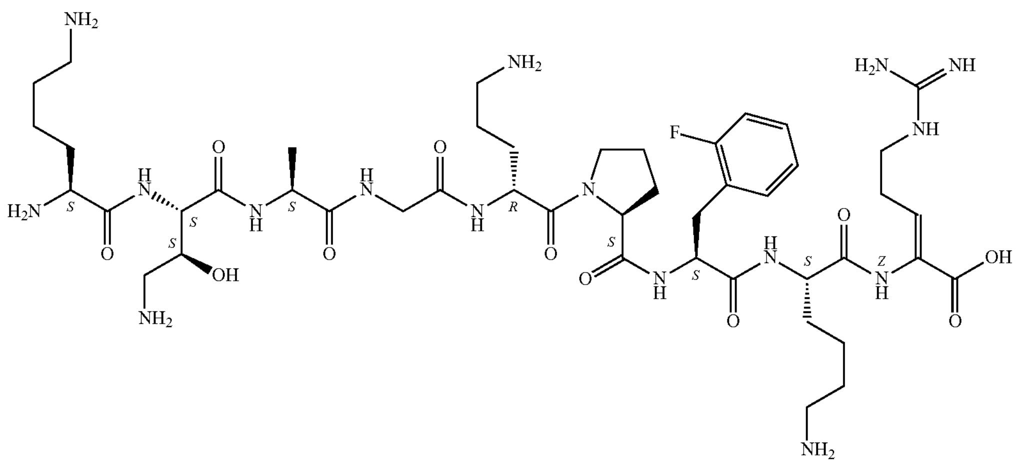 | $C_{46}H_{77}FN_{16}O_{11}$ | 1049.20 | 1049.45 | 99% | 13.34 |

TABLE 1-continued

Compounds and analytical data

| Cmpd | Structure | Molecular formula | MW (g/mol) | [M + H]⁺ (g/mol) | UV purity (λ = 230 nm) | Rt (min) |
|---|---|---|---|---|---|---|
| 24.152 | 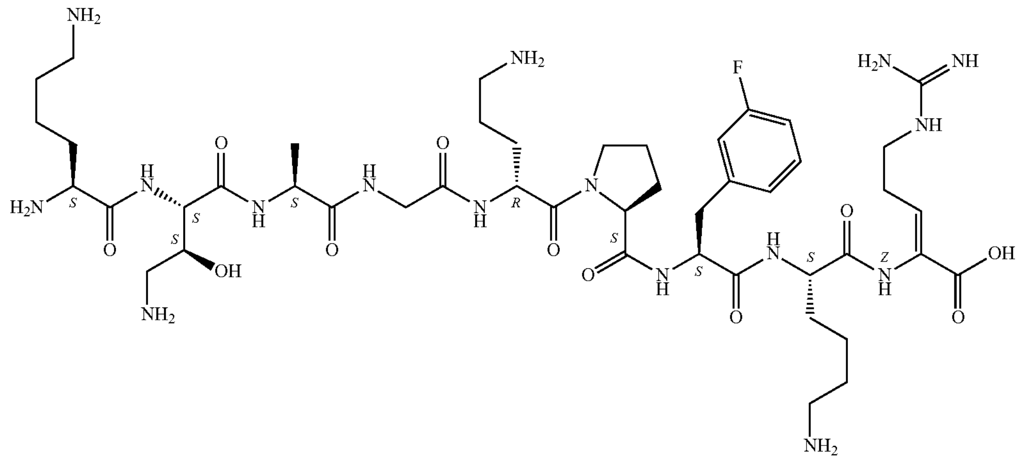 | $C_{46}H_{77}FN_{16}O_{11}$ | 1049.20 | 1050.45 | 99% | 13.54 |
| 24.153 | 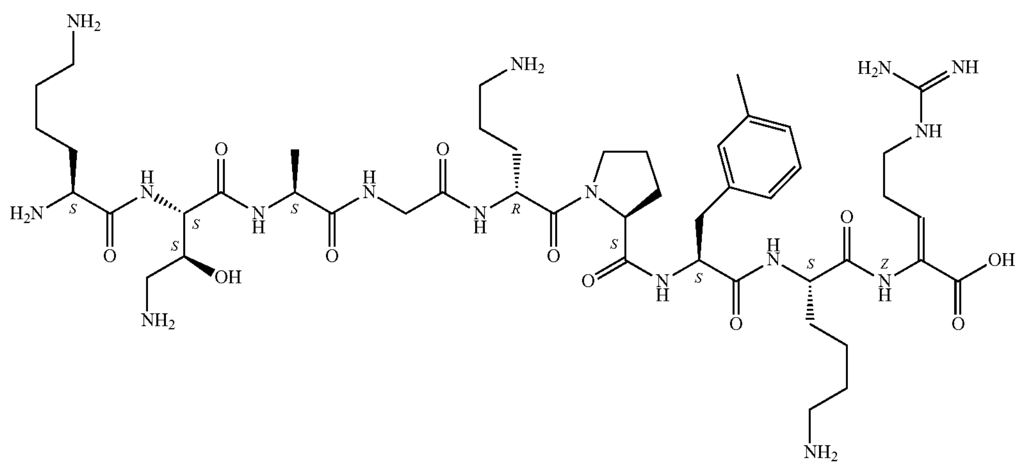 | $C_{47}H_{80}N_{16}O_{11}$ | 1045.24 | 1046.50 | 99% | 14.07 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.154 | 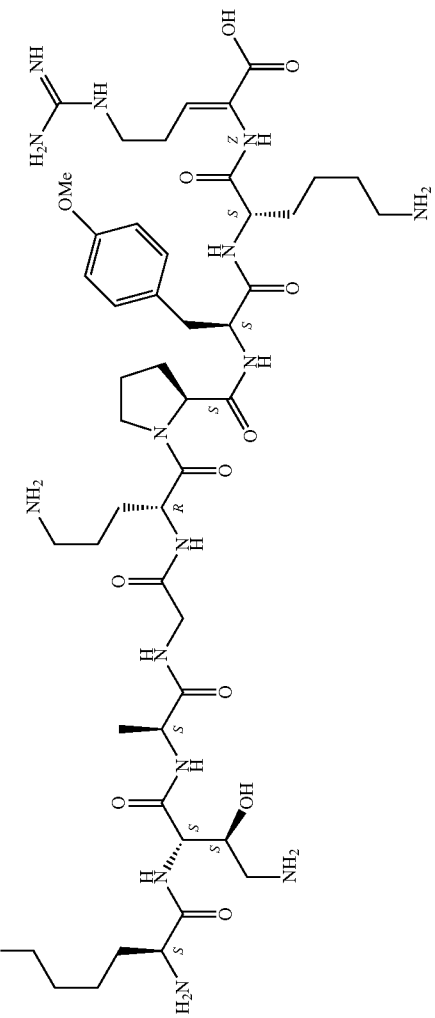 | $C_{47}H_{80}N_{16}O_{12}$ | 1061.24 | 1062.50 | 99% | 13.19 |
| 24.155 | 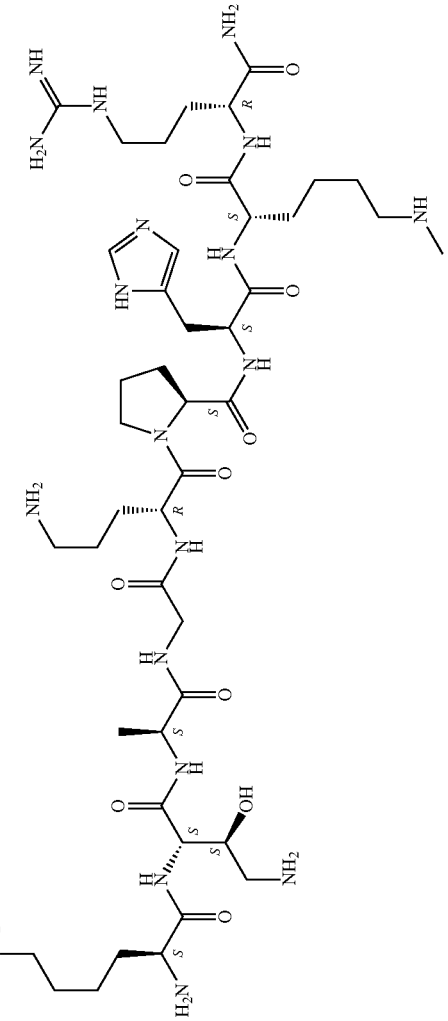 | $C_{44}H_{81}N_{19}O_{10}$ | 1036.24 | 1037.50 | 93% | 10.48 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 24.156 | 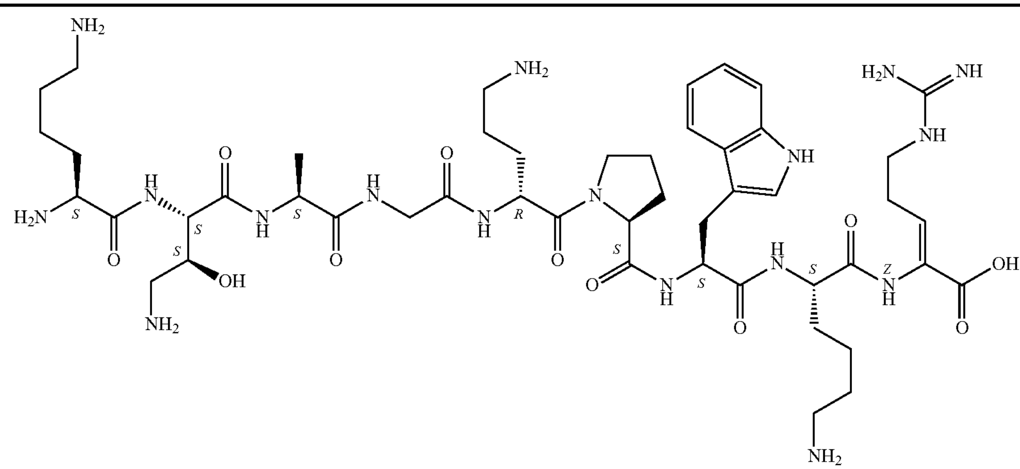 | C48H79N17O11 | 1070.25 | 1071.45 | 99% | 13.21 |
| 24.157 | 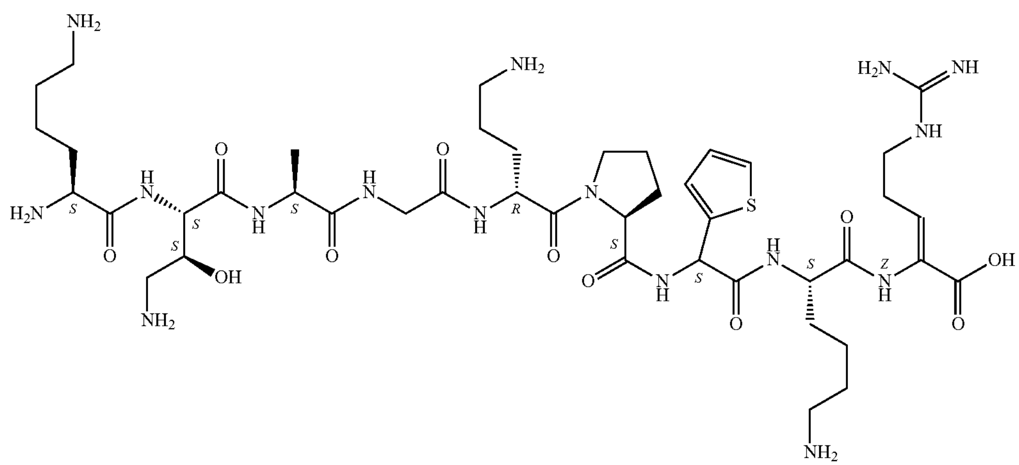 | C43H74N16O11S | 1023.21 | 1024.45 | 85% | 12.24 / 12.26 |

TABLE 1-continued

Compounds and analytical data

| Cmpd | Structure | Molecular formula | MW (g/mol) | [M + H]⁺ (g/mol) | UV purity (λ = 230 nm) | Rt (min) |
|---|---|---|---|---|---|---|
| 24.158 | 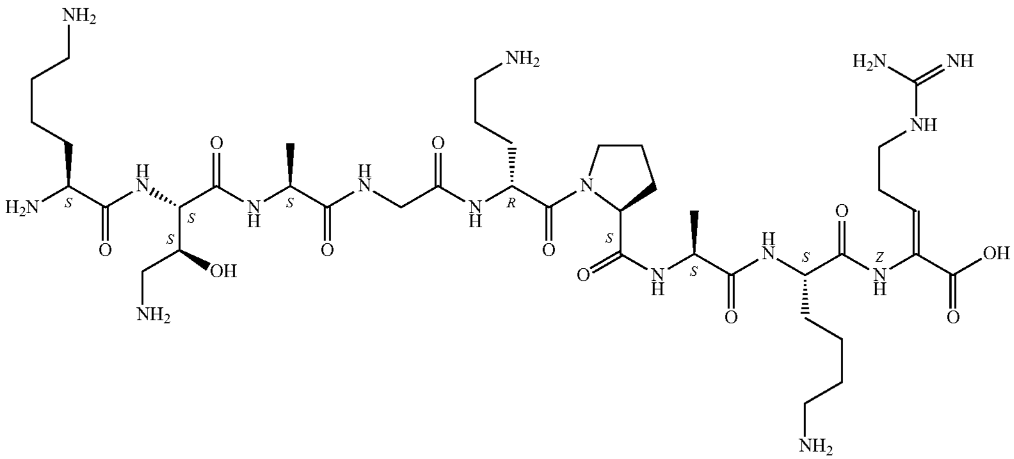 | $C_{40}H_{74}N_{16}O_{11}$ | 955.12 | 956.50 | 99% | 9.88 |
| 24.160 | 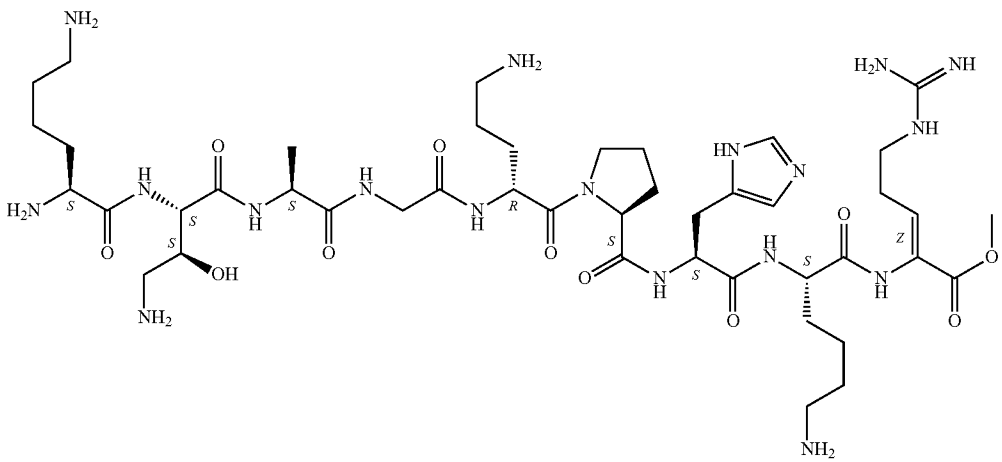 | $C_{44}H_{78}N_{18}O_{11}$ | 1035.20 | 1036.55 | 99% | 10.96 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 24.161 | 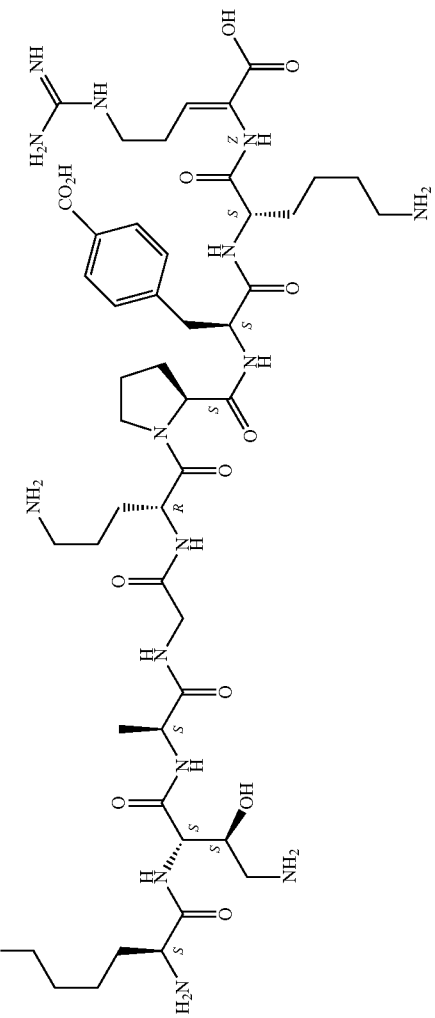 | $C_{47}H_{78}N_{16}O_{13}$ | 1075.22 | 1075.55 | 95% | 10.79 |
| 24.162 | 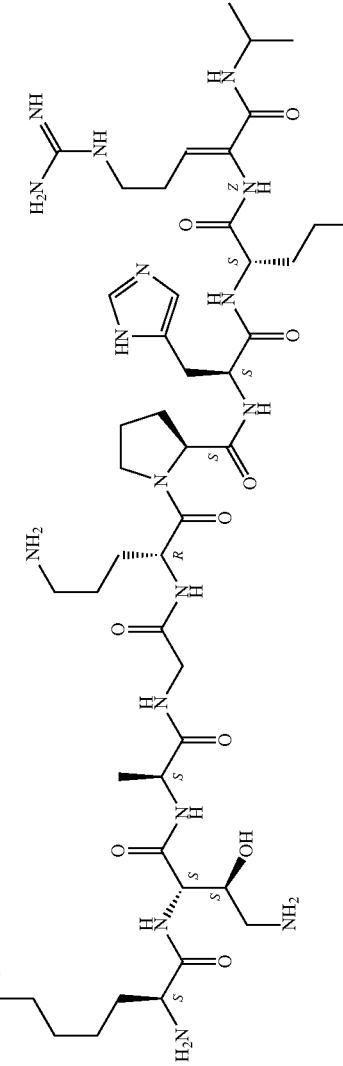 | $C_{46}H_{83}N_{19}O_{10}$ | 1062.27 | 1063.55 | 99% | 11.40 |

TABLE 1-continued

Compounds and analytical data

| Cmpd | Structure | Molecular formula | MW (g/mol) | [M + H]⁺ (g/mol) | UV purity (λ = 230 nm) | Rt (min) |
|---|---|---|---|---|---|---|
| 25.1 | 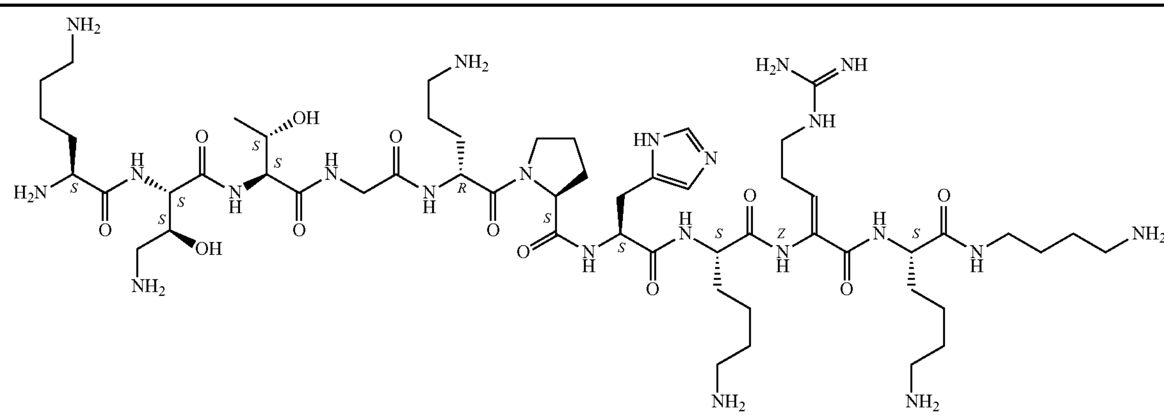 | $C_{54}H_{100}N_{22}O_{12}$ | 1249.53 | 1250.65 | 99% | 10.06 |
| 25.2 | 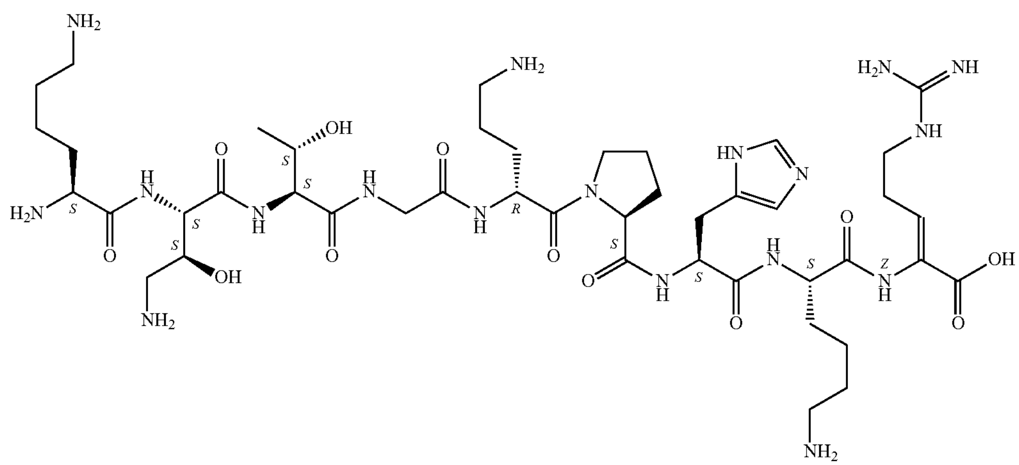 | $C_{44}H_{78}N_{18}O_{12}$ | 1051.20 | 1052.55 | 99% | 8.71 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 25.3 | 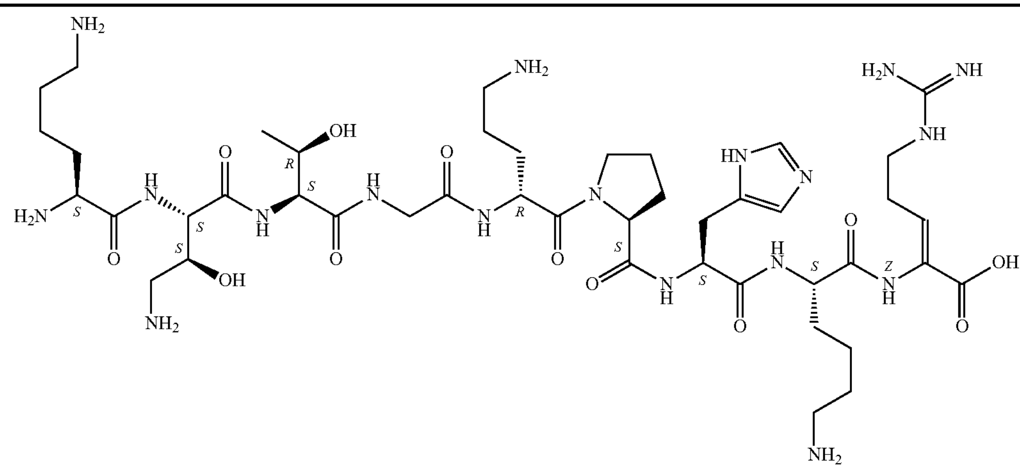 | $C_{44}H_{78}N_{18}O_{12}$ | 1051.20 | 1052.50 | 99% | 8.68 |
| 26.1 | 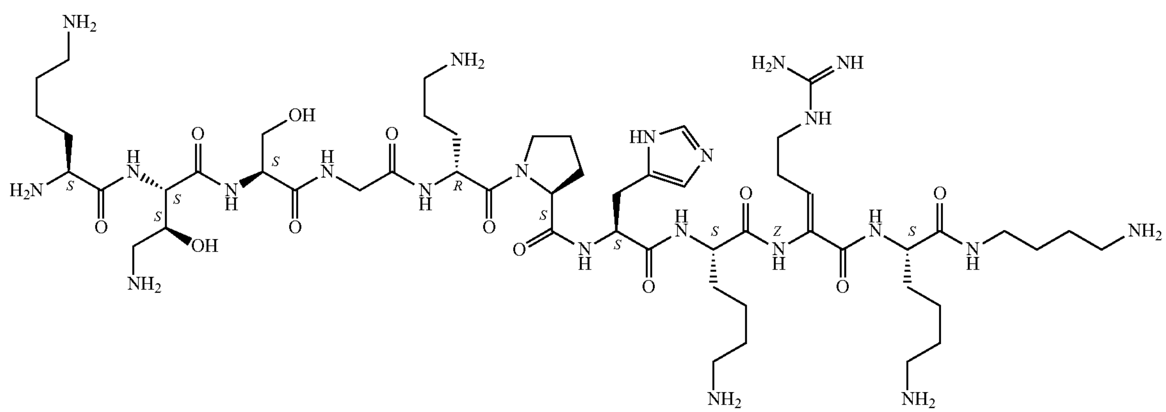 | $C_{53}H_{98}N_{22}O_{12}$ | 1235.50 | 1236.60 | 99% | 9.88 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 26.2 | 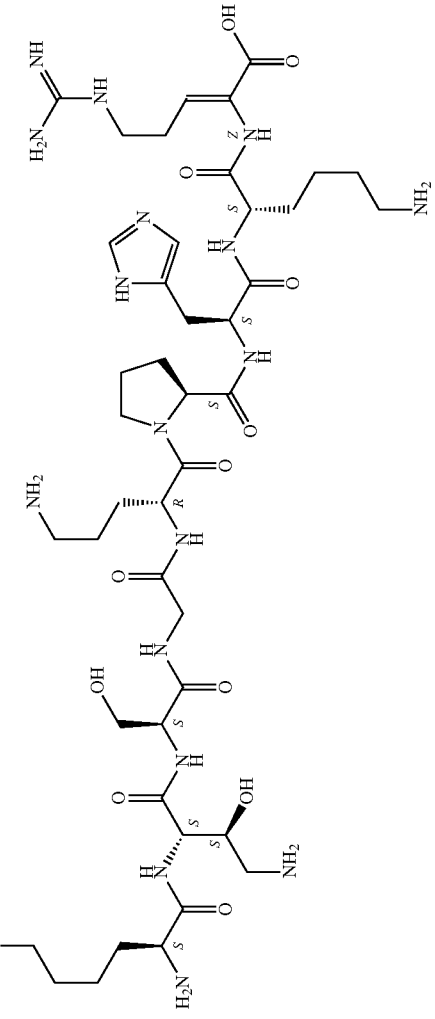 | C₄₃H₇₆N₁₈O₁₂ | 1037.18 | 1038.60 | 99% | 8.67 |
| 27.1 | 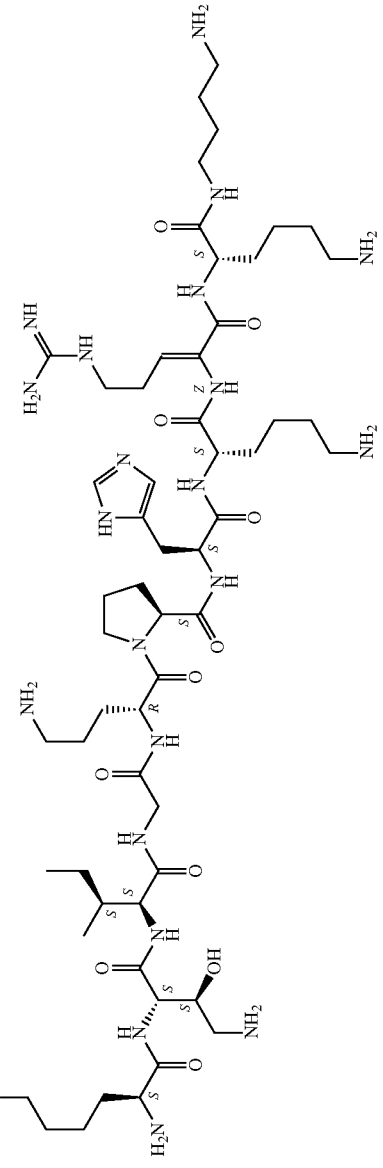 | C₅₆H₁₀₄N₂₂O₁₁ | 1261.58 | 1262.65 | 99% | 10.94 |

TABLE 1-continued

Compounds and analytical data

| Cmpd | Structure | Molecular formula | MW (g/mol) | [M + H]+ (g/mol) | UV purity (λ = 230 nm) | Rt (min) |
|------|-----------|-------------------|------------|------------------|------------------------|----------|
| 27.2 | 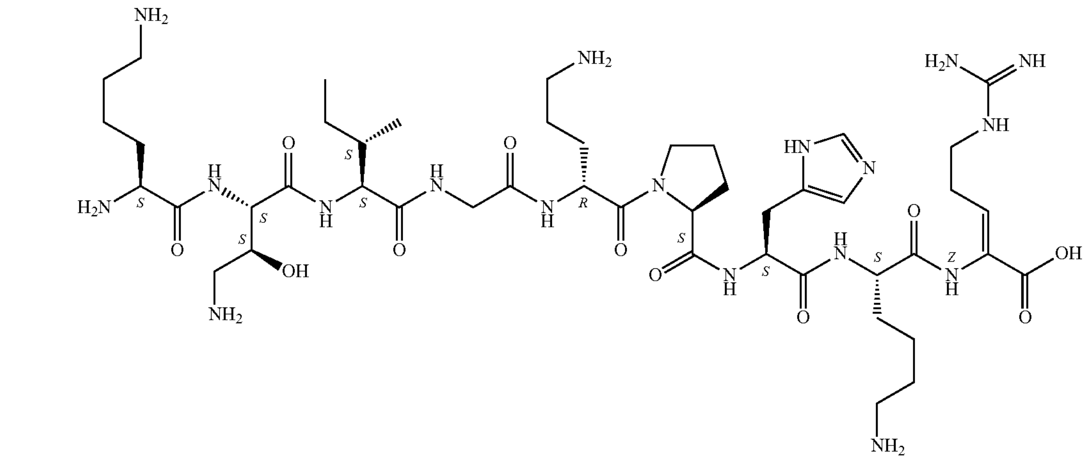 | $C_{46}H_{82}N_{18}O_{11}$ | 1063.26 | 1064.60 | 99% | 9.10 |
| 28.1 | 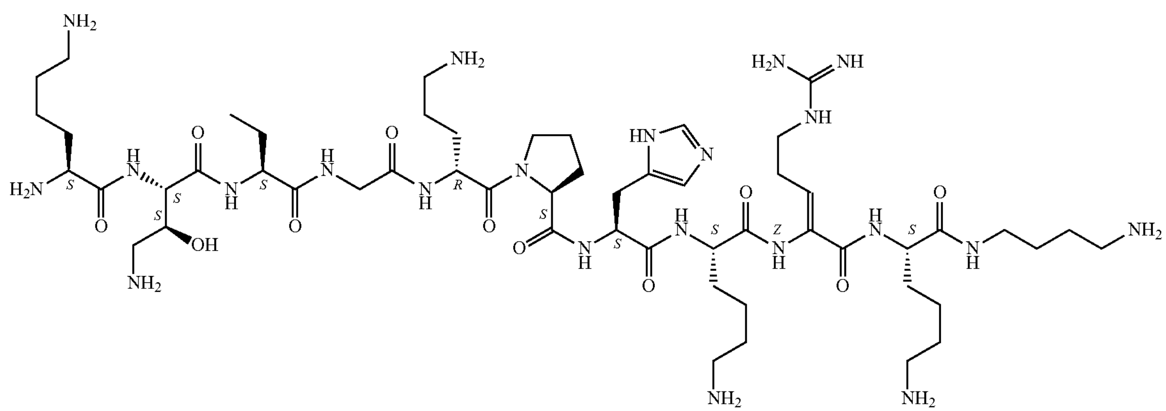 | $C_{54}H_{100}N_{22}O_{11}$ | 1233.53 | 1234.65 | 99% | 10.23 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 28.2 | 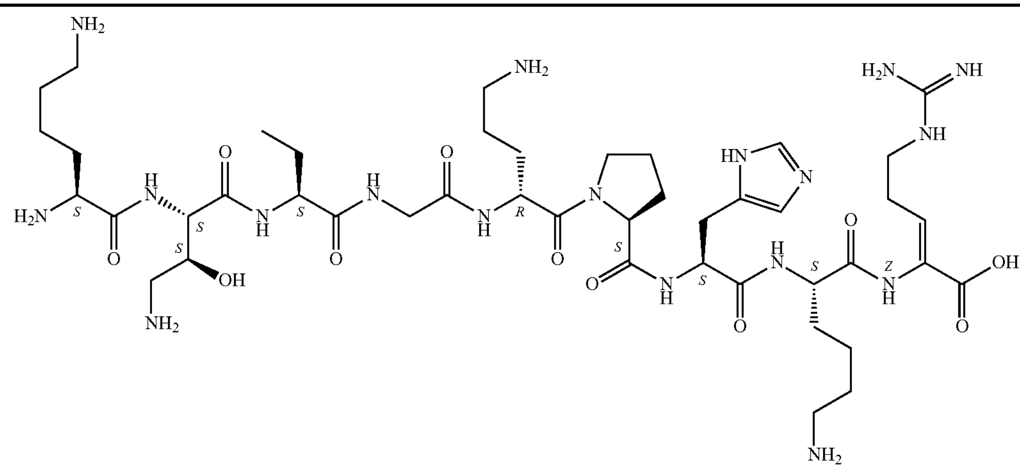 | C$_{44}$H$_{78}$N$_{18}$O$_{11}$ | 1035.20 | 1036.55 | 99% | 10.36 |
| 29.1 | 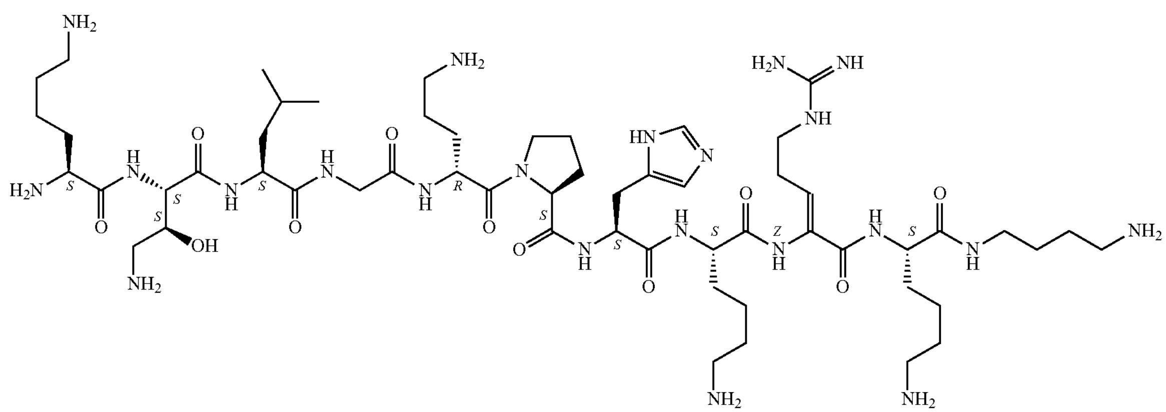 | C$_{56}$H$_{104}$N$_{22}$O$_{11}$ | 1261.58 | 1262.65 | 99% | 11.08 |

TABLE 1-continued

Compounds and analytical data

| Cmpd | Structure | Molecular formula | MW (g/mol) | [M + H]⁺ (g/mol) | UV purity (λ = 230 nm) | Rt (min) |
|---|---|---|---|---|---|---|
| 210.1 | 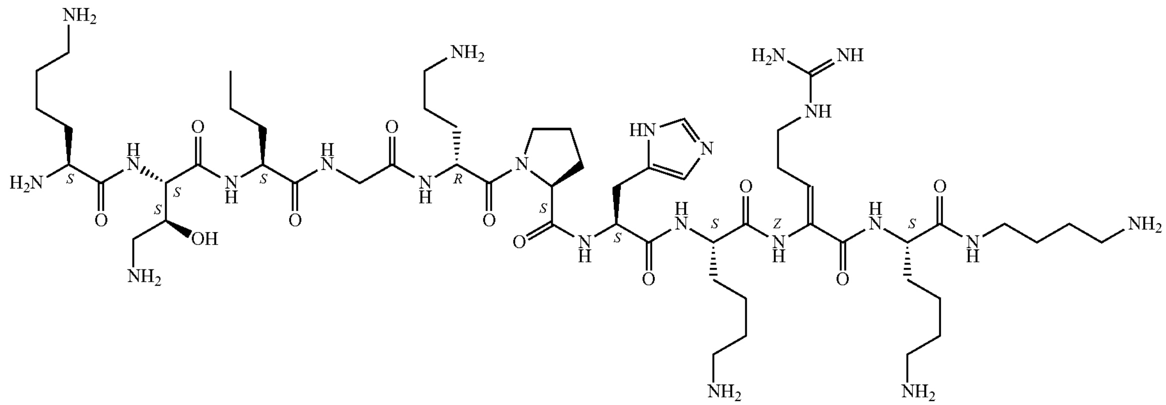 | $C_{55}H_{102}N_{22}O_{11}$ | 1247.55 | 1248.60 | 99% | 10.6 |
| 211.1 | 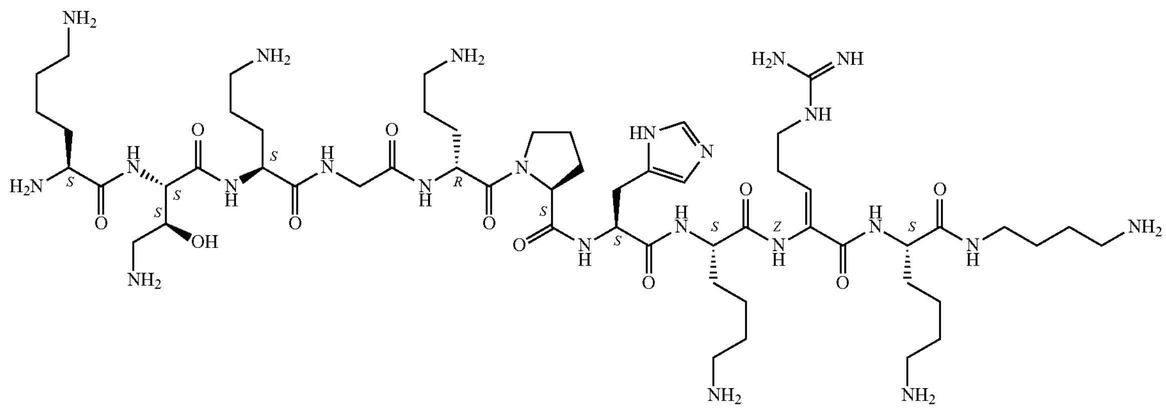 | $C_{55}H_{103}N_{23}O_{11}$ | 1262.57 | 1263.60 | 95% | 9.53 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 211.2 | 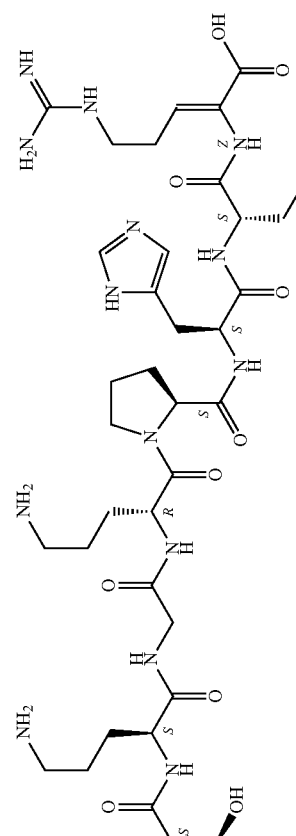 | C$_{45}$H$_{81}$N$_{19}$O$_{11}$ | 1064.24 | 1065.60 | 99% | 8.88 |
| 211.3 | 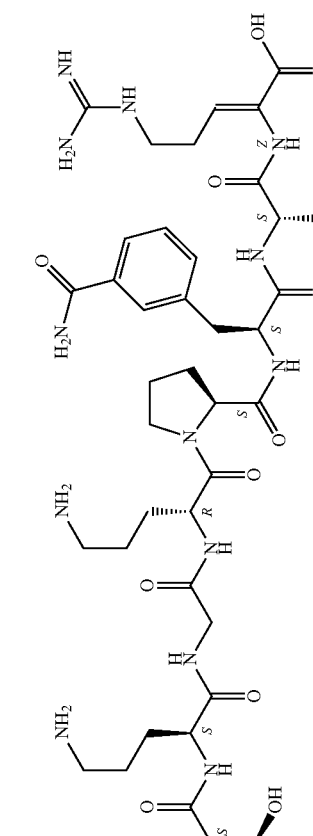 | C$_{49}$H$_{84}$N$_{18}$O$_{12}$ | 1117.30 | 1118.50 | 99% | 11.12 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 211.4 | 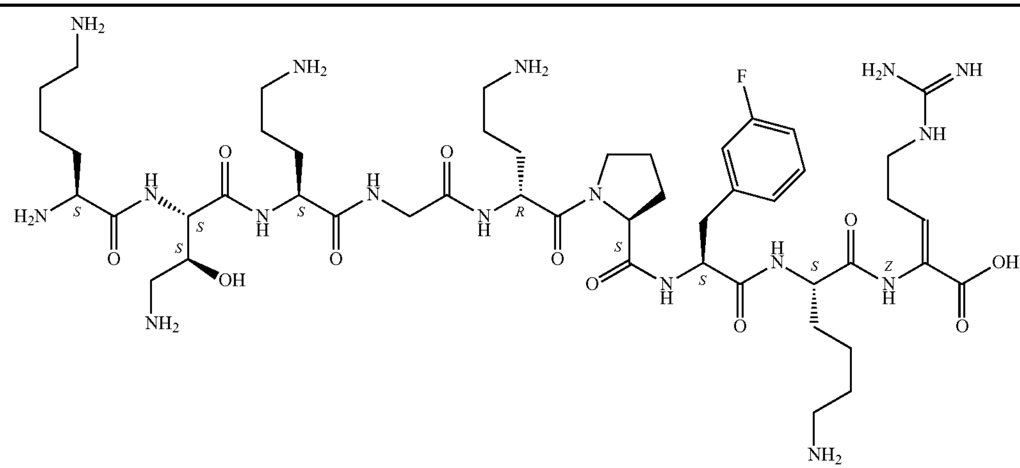 | C$_{48}$H$_{82}$FN$_{17}$O$_{11}$ | 1092.27 | 1093.55 | 99% | 12.85 |
| 211.5 | 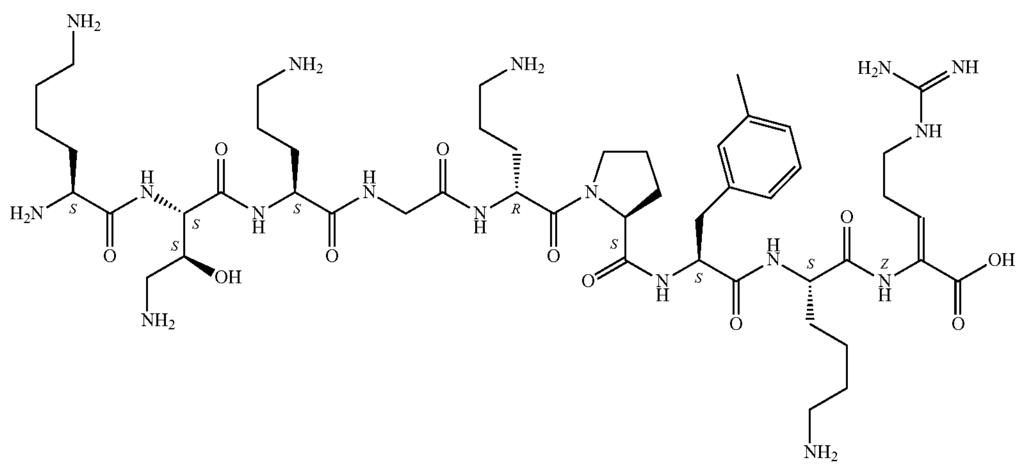 | C$_{49}$H$_{85}$N$_{17}$O$_{11}$ | 1088.31 | 1089.55 | 99% | 13.39 |

TABLE 1-continued

Compounds and analytical data

| Cmpd | Structure | Molecular formula | MW (g/mol) | [M + H]⁺ (g/mol) | UV purity (λ = 230 nm) | Rt (min) |
|---|---|---|---|---|---|---|
| 211.6 | 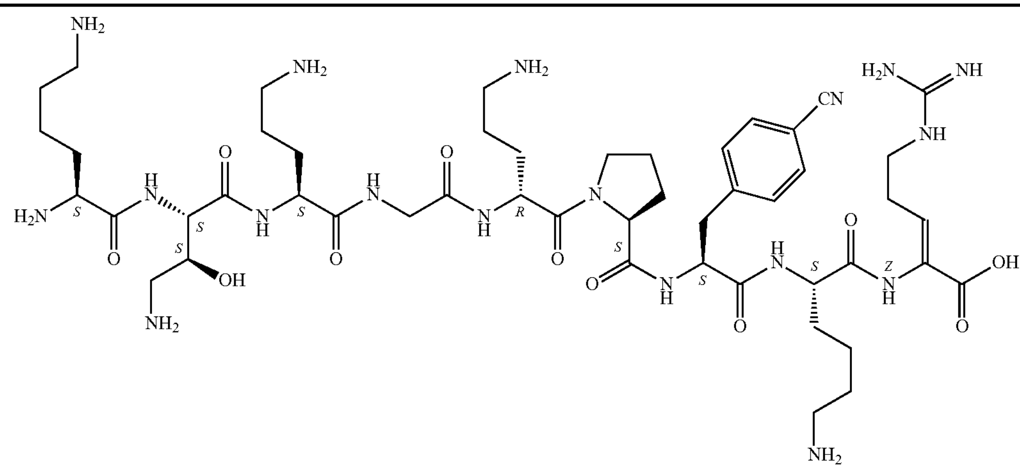 | $C_{49}H_{82}N_{18}O_{11}$ | 1099.29 | 1100.55 | 99% | 12.34 |
| 211.7 | 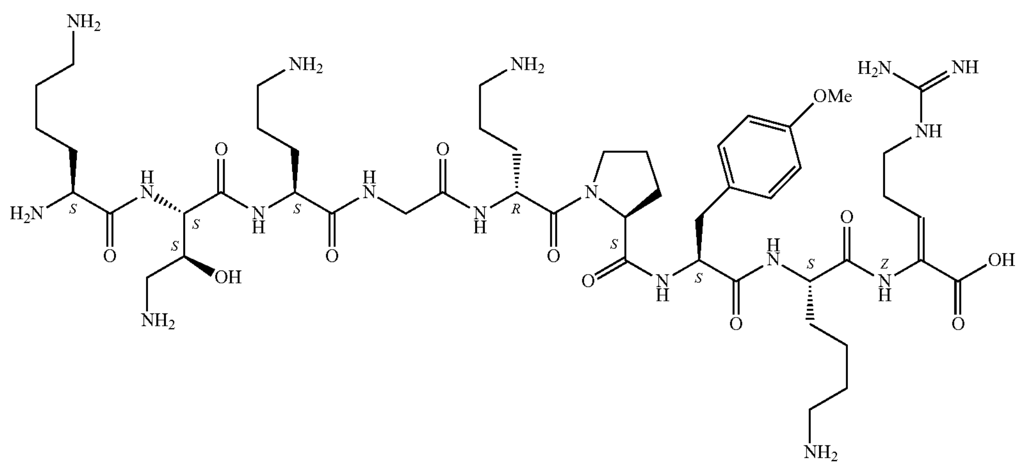 | $C_{49}H_{85}N_{17}O_{12}$ | 1104.30 | 1105.60 | 99% | 12.64 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 211.8 | 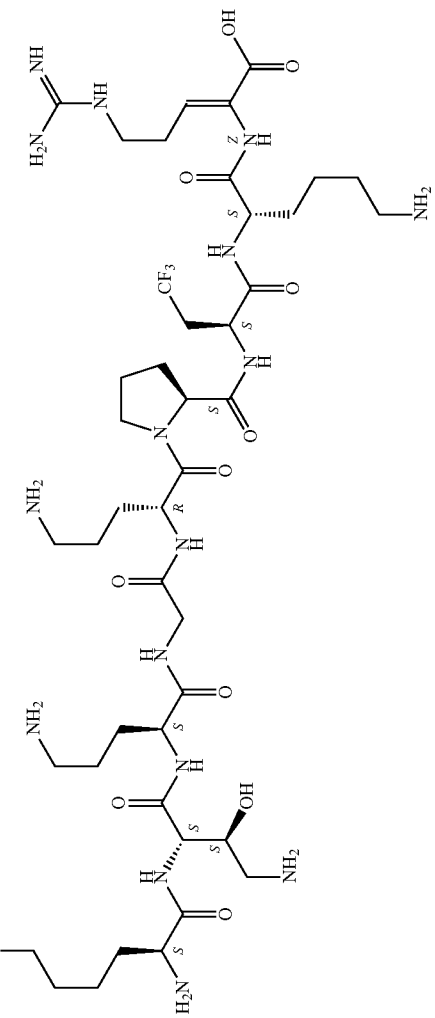 | C₄₃H₇₈F₃N₁₇O₁₁ | 1066.18 | 1067.55 | 99% | 11.54 |
| 211.9 | 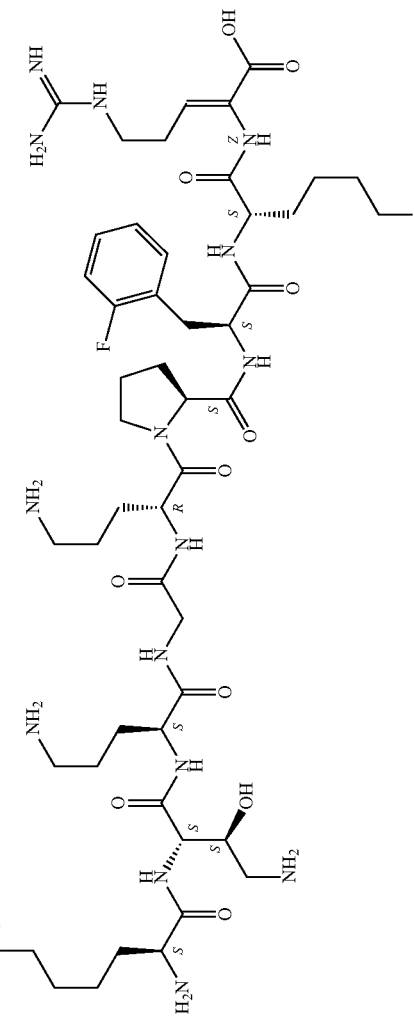 | C₄₈H₈₂FN₁₇O₁₁ | 1092.27 | 1093.50 | 99% | 12.55 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 211.10 | 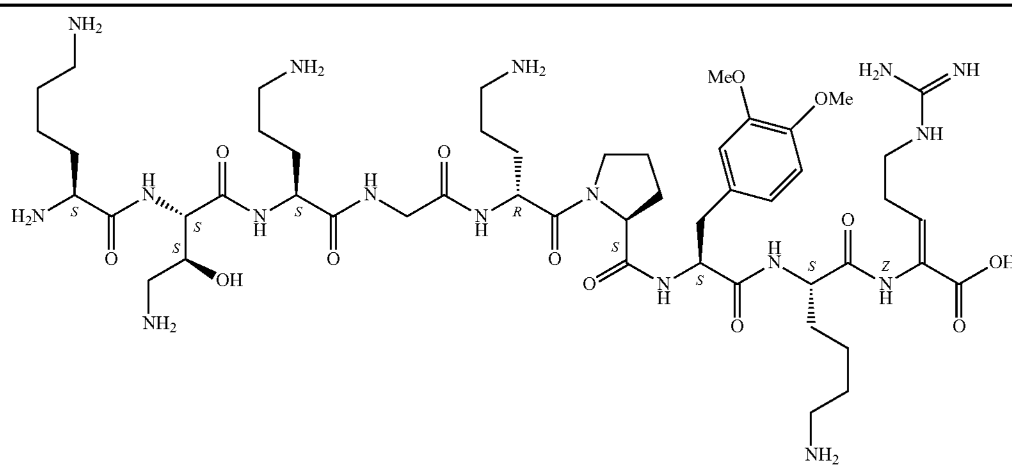 | C₅₀H₈₇N₁₇O₁₃ | 1134.33 | 1135.60 | 99% | 12.19 |
| 211.11 | 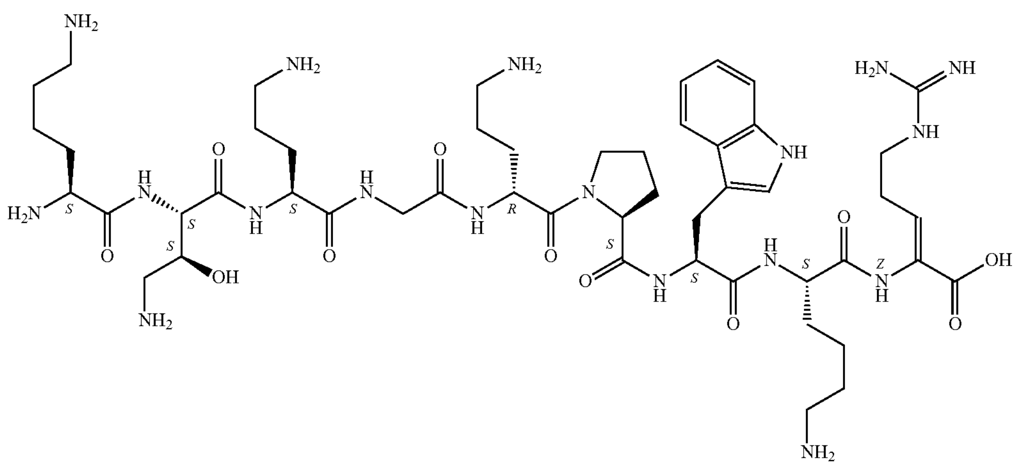 | C₅₀H₈₄N₁₈O₁₁ | 1113.32 | 1114.55 | 99% | 12.60 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 212.1 | 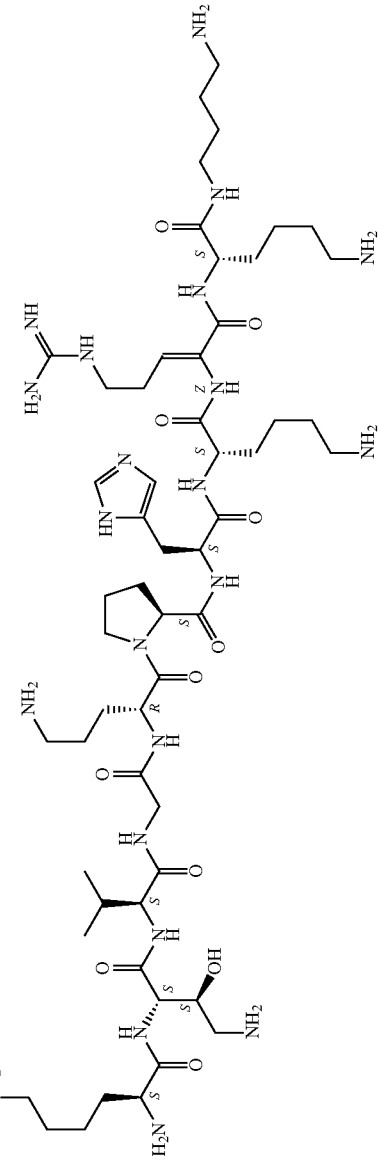 | $C_{55}H_{102}N_{22}O_{11}$ | 1247.55 | 1248.60 | 99% | 10.57 |
| 212.2 | 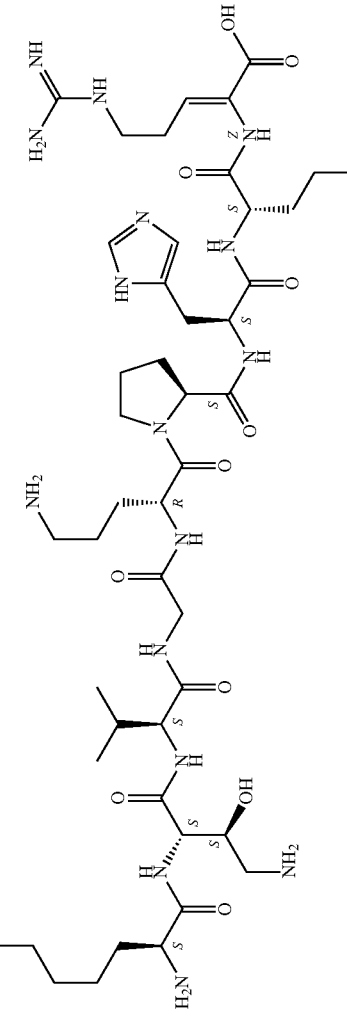 | $C_{45}H_{80}N_{18}O_{11}$ | 1049.23 | 1050.60 | 99% | 9.05 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 213.1 | 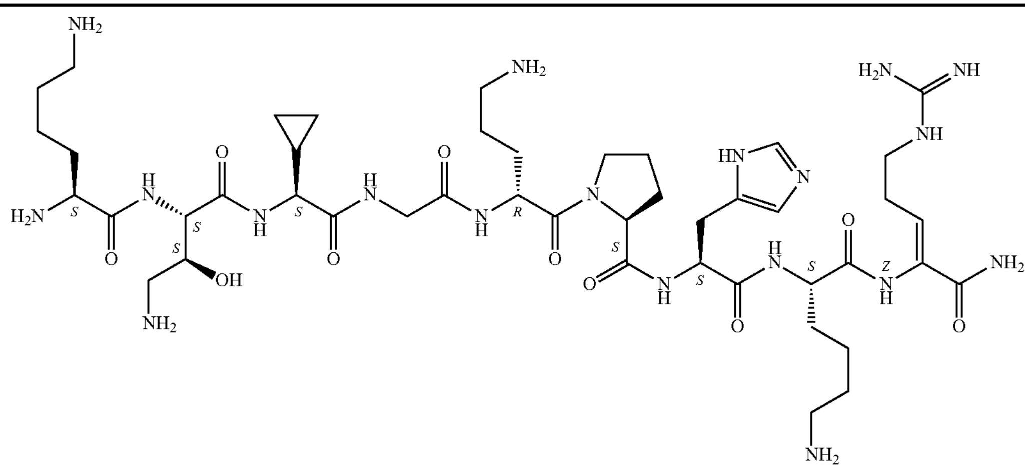 | C₄₅H₇₉N₁₉O₁₀ | 1046.23 | 1047.55 | 99% | 10.37 |
| 213.2 | 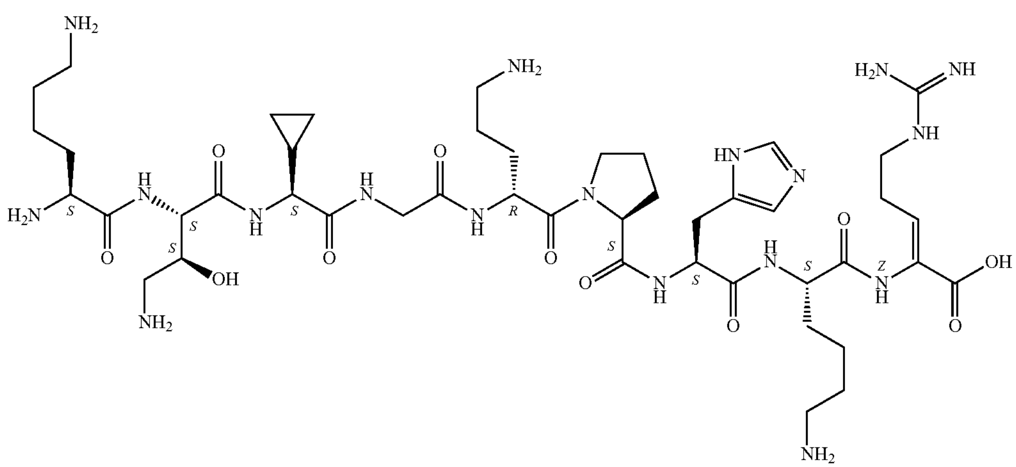 | C₄₅H₇₈N₁₈O₁₀ | 1047.21 | 1048.70 | 98% | 8.91 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 214.1 | 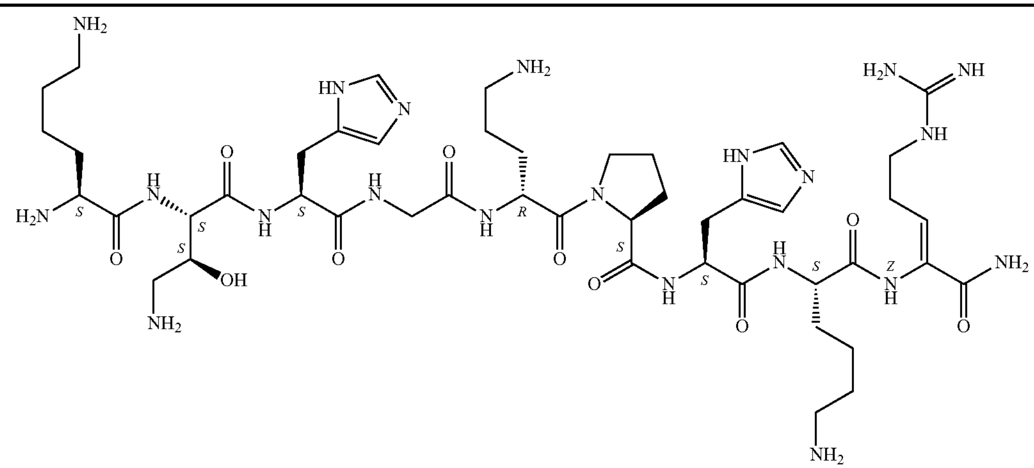 | $C_{46}H_{79}N_{21}O_{10}$ | 1086.25 | 1087.55 | 98% | 10.42 |
| 214.2 | 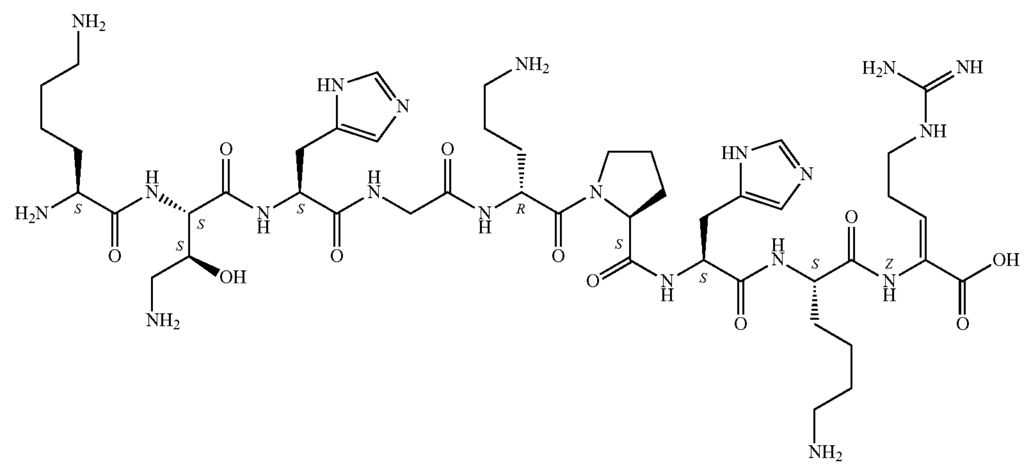 | $C_{46}H_{78}N_{20}O_{11}$ | 1087.24 | 1088.70 | 99% | 8.98 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 215.1 | 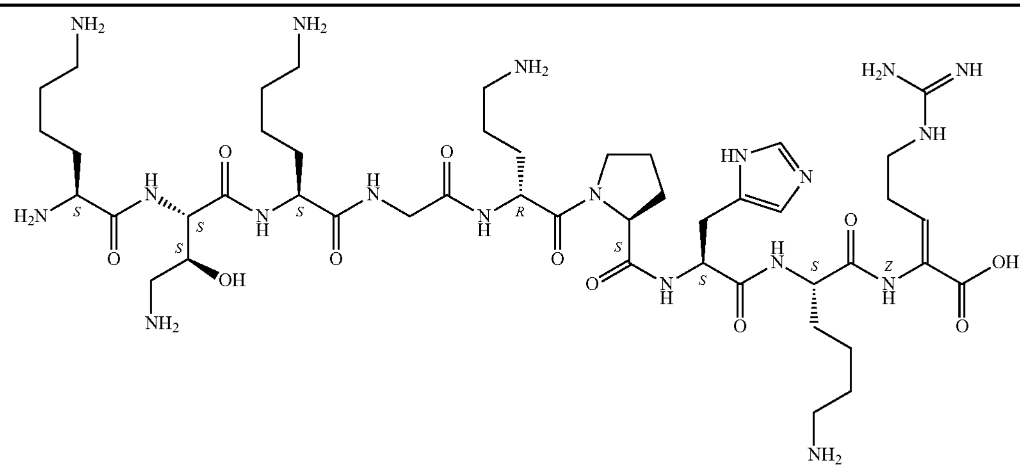 | $C_{46}H_{83}N_{19}O_{11}$ | 1078.27 | 1079.60 | 99% | 8.94 |
| 215.2 | 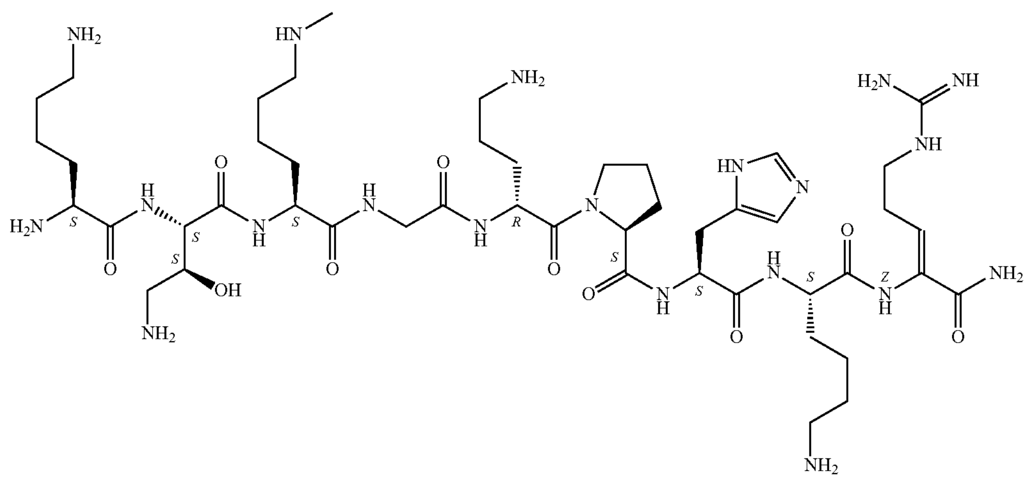 | $C_{47}H_{86}N_{20}O_{10}$ | 1091.31 | 1092.60 | 99% | 10.25 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 216.1 | 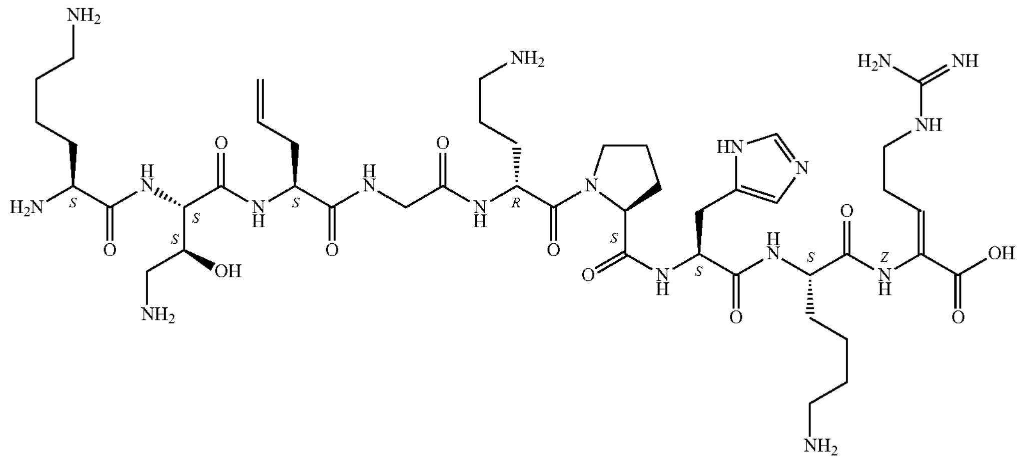 | $C_{45}H_{78}N_{18}O_{11}$ | 1047.21 | 1048.60 | 99% | 8.95 |
| 217.1 | 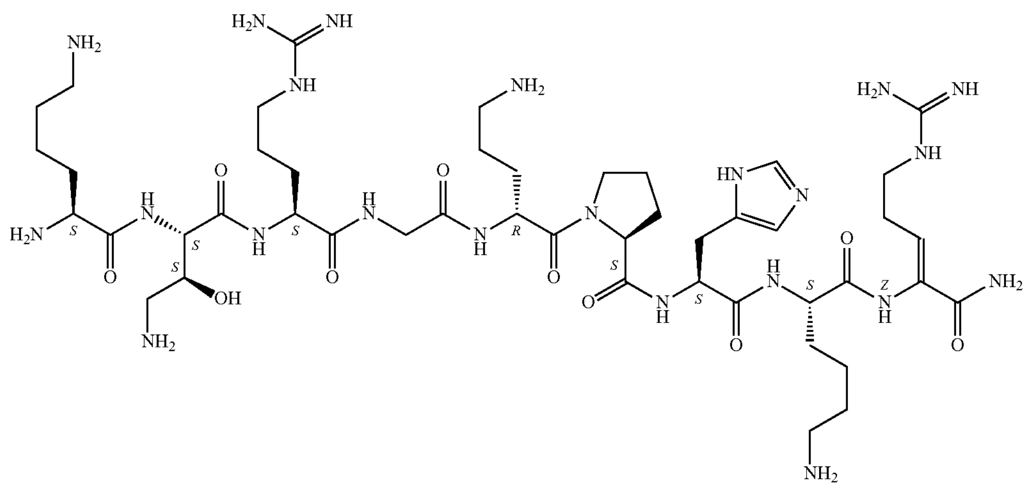 | $C_{46}H_{84}N_{22}O_{10}$ | 1105.30 | 1106.60 | 98% | 10.49 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 220.1 | 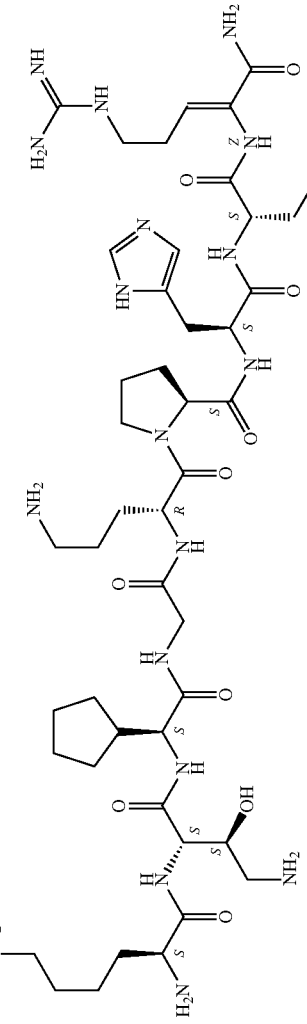 | C47H83N19O10 | 1074.28 | 1075.60 | 99% | 11.37 |
| 221.1 | 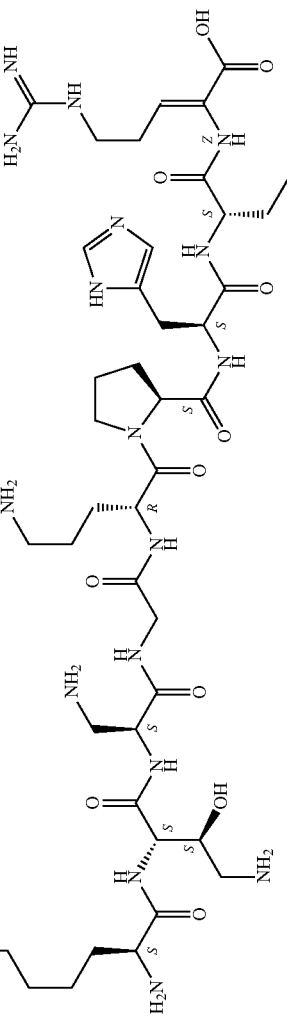 | C43H77N19O11 | 1036.19 | 1037.60 | 99% | 8.83 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 222.1 | 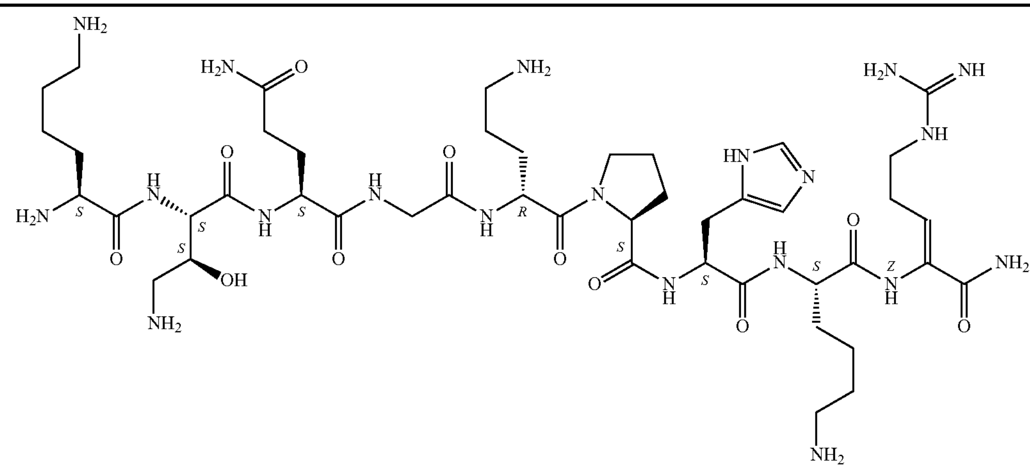 | C$_{45}$H$_{80}$N$_{20}$O$_{11}$ | 1077.24 | 1078.55 | 96% | 8.73 |
| 223.1 | 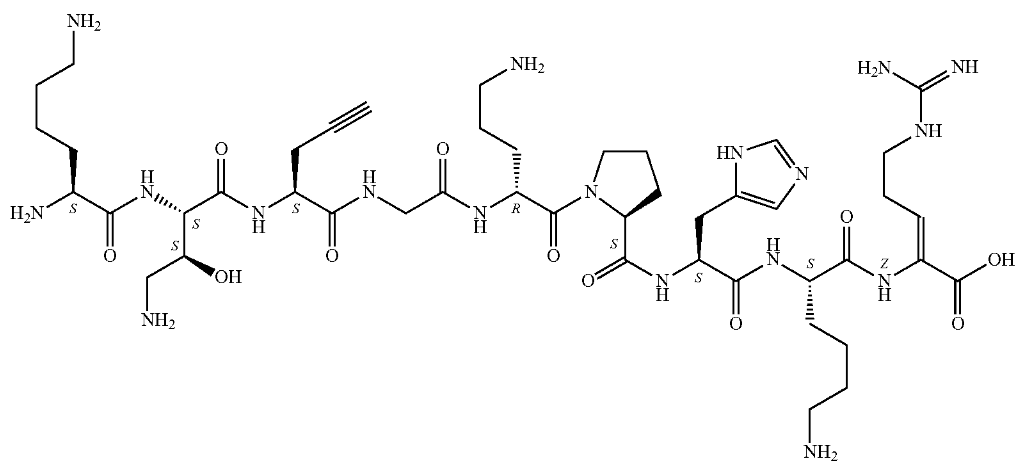 | C$_{45}$H$_{76}$N$_{18}$O$_{11}$ | 1045.20 | 1046.55 | 96% | 8.89 |

TABLE 1-continued

Compounds and analytical data

| Cmpd | Structure | Molecular formula | MW (g/mol) | [M + H]+ (g/mol) | UV purity (λ = 230 nm) | Rt (min) |
|---|---|---|---|---|---|---|
| 224.1 | 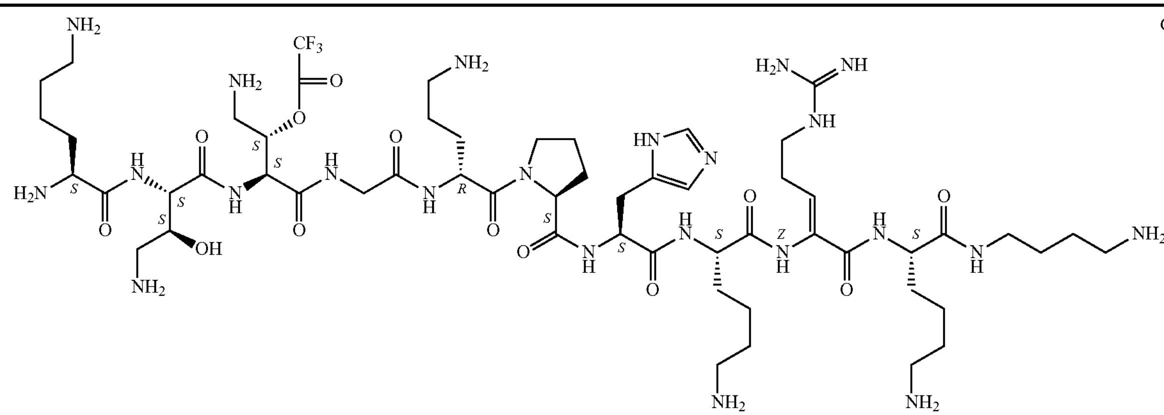 | $C_{56}H_{100}F_3N_{23}O_{13}$ | 1360.53 | 1361.65 | 85% | 11.62 |
| 225.1 | 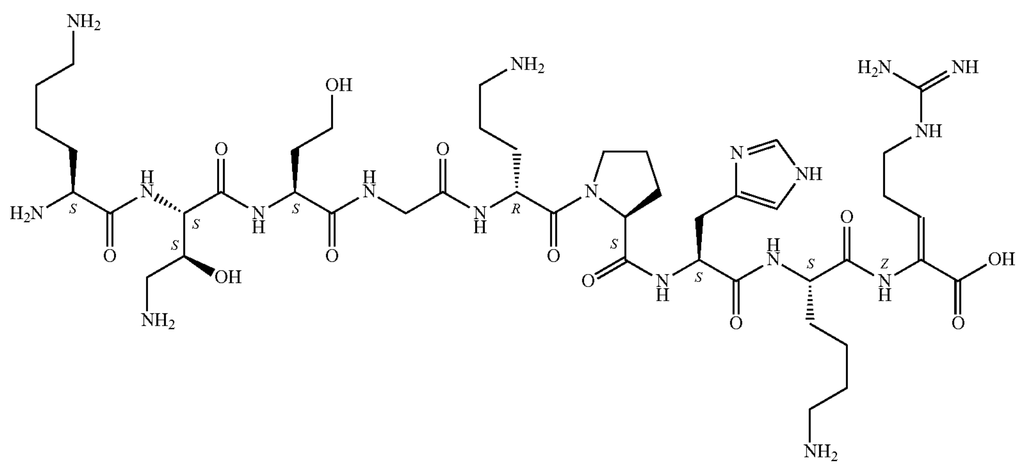 | $C_{44}H_{78}N_{18}O_{12}$ | 1051.20 | 1052.50 | 99% | 8.68 |

TABLE 1-continued
Compounds and analytical data
| Cmpd | Structure | Molecular formula | MW (g/mol) | [M + H]+ (g/mol) | UV purity (λ = 230 nm) | Rt (min) |
|---|---|---|---|---|---|---|
| 32.1 | 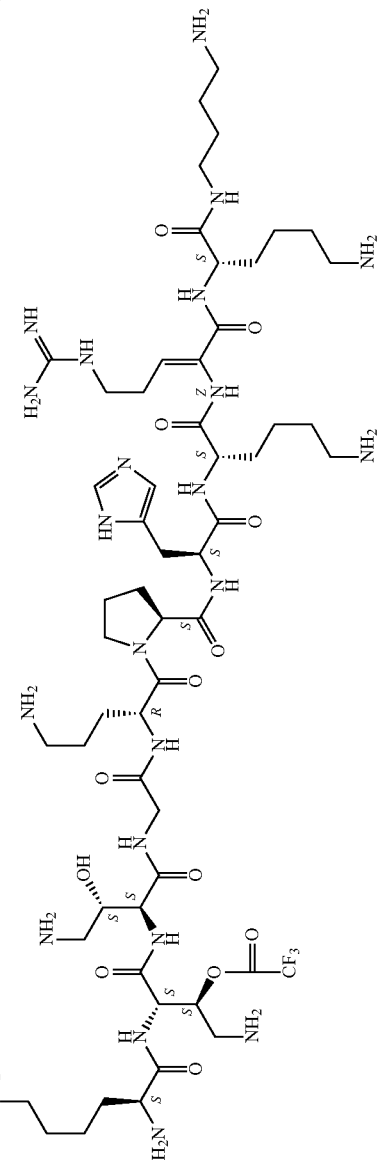 | $C_{56}H_{100}F_3N_{23}O_{13}$ | 1360.53 | 1362.65 | 81% | 11.86 |

Example 10. Antibacterial Activity

Minimal Inhibitory Concentration (MIC) determination procedure was determined as recommended by the CLSI (Clinical and Laboratory Standards Institute, Methods for Dilution Antimicrobial Susceptibility Tests for Bacteria that Grow Aerobically—Ninth Edition: Approved Standard M07-A9, 2012). The method used is called Broth Microdilution.

The following reference strains were used for evaluation of antimicrobial activity: *Pseudomonas aeruginosa* ATCC 27853, *Escherichia coli* ATCC 25922, *Staphylococcus aureus* ATCC 13709, *Klebsiella pneumoniae* ATCC 43816 and *Acinetobacter baumannii* ATCC 19606. The following multidrug-resistant *E. coli* and *K. pneumoniae* strains were used for evaluation of antimicrobial activity: Ec #1 (NCTC13476), Ec #2 (MIN), Ec #3 (EGB957), Ec #4 (GUE), Ec #5 (DSM22315), Kp #1 (NCTC13439), Kp #2 (DUB), Kp #3 (A33504), Kp #4 (ATCC BAA1904), Kp #5 (6560). The profiles of resistance of these strains are given in Table 2.

TABLE 2

Resistance profiles of multidrug resistant strains of *E. coli* and *K. pneumoniae*

| Antibiotic | Ec#1 | Ec#2 | Ec#3 | Ec#4 | Ec#5 | Kp#1 | Kp#2 | Kp#3 | Kp#4 | Kp#5 |
|---|---|---|---|---|---|---|---|---|---|---|
| Ceftriaxone | R | R | R | S | R | R | R | R | R | R |
| Ciprofloxacin | R | S | R | R | S | R | R | R | S | R |
| Gentamicin | R | S | R | S | R | S | R | R | R | R |
| Imipenem | I | I | R | S | S | R | R | R | R | R |
| Tigecycline | S | S | I | I | S | R | R | R | I | R |

Broth Microdilution Method:
The test medium was Cation-Adjusted Mueller-Hinton Broth (CAMHB)
Prepare the inoculum by making a direct 3 mL CAMHB suspension of isolated colonies selected from an 18- to 24-hours Mueller-Hinton agar plate to achieve an Absorbance at 600 nm (A600) of 0.11 to 0.15.
Dilute the suspension 1:20 in saline.
Dispense 100 µL of sterile water into all peripheral wells of a 96 wells microtitre plate
Dispense 190 µL of CAMHB into wells of column 2 and 100 µL of CAMHB into all wells of columns 3 to 11.
Pipette 10 µl of 1.28 mg/mL antibiotics solution into the wells of column 2.
Mix the antibiotics into the wells in column 2 by sucking up and down 6-8 times.
Withdraw 100 µL from column 2 and add this to column 3. This makes column 3 a twofold dilution of column 2.
Repeat the procedure down to column 10. Antibiotics were tested at final concentrations (prepared from serial twofold dilutions) ranging from 0.25 to 64 µg/mL.
Discard 100 µL from column 10.
Dispense 10 µL of bacteria suspension into wells of columns 2 to 10. Do not add bacteria to column 11 (sterility control). The appropriate inoculum size for standard MIC is $5 \times 10^5$ CFU/mL.
The inoculated microplates were incubated at 35° C. for 16- to 20-hours before reading.
The MIC was defined as the lowest antibiotic concentration that yielded no visible growth. Activity results are shown in Table 3 and Table 4.

TABLE 3

Antibacterial Activity Results.

| Cmpd | Sa | Ec | Kp | Pa | Ab |
|---|---|---|---|---|---|
| 11.1 | ++ | − | + | − | − |
| 12.1 | ++ | − | − | − | − |
| 13.1 | + | − | − | − | − |
| 14.1 | ++ | + | + | − | − |
| 14.2 | ++ | + | + | − | − |
| 14.4 | ++ | − | + | − | − |
| 14.5 | ++ | + | + | − | − |
| 14.6 | ++ | + | − | − | − |
| 14.7 | ++ | − | − | − | − |
| 14.9 | ++ | − | − | − | − |
| 14.10 | ++ | − | − | − | − |
| 14.11 | ++ | − | − | − | − |
| 14.12 | ++ | + | + | − | − |
| 14.13 | ++ | + | + | − | − |
| 14.14 | ++ | − | − | − | − |
| 14.15 | ++ | − | − | − | − |
| 14.16 | ++ | − | + | − | − |
| 14.17 | ++ | − | − | − | − |

TABLE 3-continued

Antibacterial Activity Results.

| Cmpd | Sa | Ec | Kp | Pa | Ab |
|---|---|---|---|---|---|
| 14.18 | ++ | − | − | − | − |
| 14.19 | ++ | − | − | − | − |
| 14.20 | + | − | − | − | − |
| 14.21 | + | − | − | − | − |
| 14.22 | + | − | − | − | − |
| 14.23 | + | − | − | − | − |
| 14.24 | + | − | − | − | − |
| 14.25 | + | − | − | − | − |
| 15.1 | + | − | − | − | − |
| 15.3 | ++ | − | − | − | − |
| 16.1 | ++ | − | − | − | − |
| 21.1 | ++ | ++ | ++ | ++ | ++ |
| 21.2 | ++ | ++ | ++ | − | − |
| 21.3 | ++ | − | + | − | − |
| 21.4 | ++ | ++ | ++ | − | − |
| 21.5 | ++ | ++ | ++ | − | − |
| 21.6 | ++ | ++ | ++ | − | − |
| 21.7 | ++ | ++ | ++ | − | − |
| 21.8 | ++ | ++ | ++ | − | − |
| 21.9 | ++ | ++ | ++ | − | − |
| 21.10 | ++ | ++ | ++ | − | − |
| 21.11 | ++ | ++ | ++ | − | − |
| 21.12 | ++ | ++ | ++ | − | − |
| 22.1 | ++ | ++ | ++ | ++ | + |
| 22.2 | ++ | ++ | ++ | + | − |
| 22.3 | ++ | ++ | ++ | + | + |
| 22.4 | ++ | ++ | ++ | + | − |
| 22.5 | ++ | + | ++ | + | − |
| 22.6 | ++ | + | + | − | − |
| 22.7 | ++ | ++ | ++ | ++ | + |
| 22.8 | ++ | ++ | ++ | ++ | + |
| 22.9 | ++ | + | ++ | − | − |
| 22.10 | ++ | ++ | ++ | + | − |
| 22.11 | ++ | ++ | ++ | + | − |
| 22.12 | ++ | ++ | ++ | − | − |

TABLE 3-continued

Antibacterial Activity Results.

| Cmpd | Sa | Ec | Kp | Pa | Ab |
|---|---|---|---|---|---|
| 22.13 | ++ | + | ++ | ++ | − |
| 22.14 | ++ | ++ | ++ | − | − |
| 22.15 | ++ | + | ++ | − | − |
| 22.16 | ++ | + | ++ | − | − |
| 22.17 | ++ | + | ++ | − | − |
| 22.18 | ++ | + | + | − | − |
| 22.20 | ++ | + | ++ | ++ | − |
| 22.21 | ++ | − | − | − | − |
| 22.22 | ++ | − | − | − | − |
| 22.23 | ++ | − | − | − | − |
| 22.24 | ++ | − | − | − | − |
| 22.28 | ++ | + | ++ | − | − |
| 22.29 | ++ | + | ++ | − | − |
| 22.30 | ++ | + | ++ | − | − |
| 22.31 | ++ | ++ | ++ | − | − |
| 22.32 | ++ | − | + | − | − |
| 22.33 | ++ | ++ | ++ | − | − |
| 22.34 | ++ | ++ | ++ | − | − |
| 22.35 | − | − | + | − | − |
| 22.36 | ++ | ++ | ++ | − | − |
| 22.37 | ++ | + | ++ | − | − |
| 22.38 | ++ | ++ | ++ | − | − |
| 22.39 | ++ | + | ++ | − | − |
| 22.40 | ++ | + | ++ | − | − |
| 22.41 | ++ | ++ | ++ | − | − |
| 23.1 | ++ | ++ | ++ | − | − |
| 24.1 | ++ | ++ | ++ | + | + |
| 24.2 | ++ | ++ | ++ | + | − |
| 24.3 | ++ | ++ | ++ | + | − |
| 24.4 | ++ | ++ | ++ | + | + |
| 24.5 | ++ | ++ | ++ | − | − |
| 24.6 | ++ | ++ | ++ | ++ | + |
| 24.7 | ++ | ++ | ++ | − | − |
| 24.8 | ++ | + | + | − | − |
| 24.9 | + | − | − | − | − |
| 24.14 | ++ | ++ | ++ | + | − |
| 24.15 | ++ | ++ | ++ | + | − |
| 24.17 | ++ | ++ | ++ | − | − |
| 24.18 | ++ | ++ | ++ | − | − |
| 24.19 | ++ | ++ | ++ | + | − |
| 24.20 | ++ | ++ | ++ | − | − |
| 24.21 | ++ | ++ | ++ | − | − |
| 24.22 | ++ | ++ | ++ | − | − |
| 24.43 | ++ | ++ | ++ | + | − |
| 24.61 | ++ | ++ | ++ | + | + |
| 24.62 | ++ | + | ++ | − | − |
| 24.63 | ++ | ++ | ++ | − | − |
| 24.64 | ++ | ++ | ++ | − | − |
| 24.65 | ++ | + | ++ | − | − |
| 24.66 | + | + | ++ | − | − |
| 24.67 | − | ++ | ++ | + | − |
| 24.68 | ++ | + | ++ | − | − |
| 24.69 | ++ | + | ++ | − | − |
| 24.70 | + | − | + | − | − |
| 24.71 | + | + | ++ | − | − |
| 24.72 | ++ | + | ++ | − | − |
| 24.73 | + | + | ++ | − | − |
| 24.74 | + | + | ++ | − | − |
| 24.75 | + | + | + | − | − |
| 24.76 | + | − | + | − | − |
| 24.77 | ++ | ++ | ++ | − | − |
| 24.78 | ++ | + | + | − | − |
| 24.79 | ++ | + | + | − | − |
| 24.80 | ++ | + | ++ | − | − |
| 24.81 | − | − | + | − | − |
| 24.82 | + | − | + | − | − |
| 24.83 | ++ | + | ++ | − | − |
| 24.84 | ++ | ++ | ++ | − | − |
| 24.85 | + | ++ | ++ | − | − |
| 24.86 | ++ | + | ++ | − | − |
| 24.87 | ++ | + | ++ | − | − |
| 24.88 | ++ | ++ | ++ | − | − |
| 24.89 | ++ | + | ++ | − | − |
| 24.90 | ++ | ++ | ++ | − | − |
| 24.91 | + | + | ++ | − | − |
| 24.92 | ++ | + | ++ | − | − |
| 24.93 | ++ | ++ | ++ | − | − |
| 24.94 | ++ | ++ | ++ | − | − |
| 24.97 | ++ | ++ | ++ | − | − |
| 24.98 | ++ | + | ++ | − | − |
| 24.100 | ++ | ++ | ++ | − | − |
| 24.101 | ++ | + | ++ | − | − |
| 24.102 | ++ | + | ++ | − | − |
| 24.103 | ++ | ++ | ++ | − | − |
| 24.104 | ++ | + | ++ | − | − |
| 24.105 | + | + | ++ | − | − |
| 24.106 | + | + | ++ | − | − |
| 24.107 | + | + | ++ | − | − |
| 24.108 | + | − | ++ | − | − |
| 24.109 | ++ | ++ | ++ | − | − |
| 24.110 | + | − | + | − | − |
| 24.111 | ++ | + | ++ | − | − |
| 24.112 | + | − | + | − | − |
| 24.116 | + | − | + | − | − |
| 24.117 | + | − | + | − | − |
| 24.118 | ++ | − | + | − | − |
| 24.120 | − | + | + | − | − |
| 24.121 | ++ | − | + | − | − |
| 24.122 | − | − | + | − | − |
| 24.123 | + | − | + | − | − |
| 24.125 | ++ | ++ | ++ | | |
| 24.126 | + | + | ++ | − | − |
| 24.127 | ++ | + | + | − | − |
| 24.128 | ++ | − | + | − | − |
| 24.129 | − | − | + | − | − |
| 24.130 | + | − | + | − | − |
| 24.131 | + | + | + | − | − |
| 24.132 | − | − | + | − | − |
| 24.133 | + | − | + | − | − |
| 24.134 | ++ | + | ++ | − | − |
| 24.135 | + | + | + | − | − |
| 24.136 | − | − | + | − | − |
| 24.137 | + | − | + | − | − |
| 24.138 | + | + | ++ | − | − |
| 24.141 | ++ | − | ++ | − | − |
| 24.142 | + | + | ++ | − | − |
| 24.143 | ++ | + | ++ | − | − |
| 24.144 | ++ | + | ++ | − | − |
| 24.145 | ++ | + | ++ | − | − |
| 24.146 | − | − | + | − | − |
| 24.147 | − | − | + | − | − |
| 24.148 | ++ | ++ | ++ | − | − |
| 24.149 | + | + | ++ | − | − |
| 24.150 | ++ | + | ++ | − | − |
| 24.151 | ++ | ++ | ++ | − | − |
| 24.152 | ++ | ++ | ++ | − | − |
| 24.153 | ++ | ++ | ++ | − | − |
| 24.154 | ++ | ++ | ++ | − | − |
| 24.155 | ++ | − | + | − | − |
| 24.156 | ++ | ++ | ++ | − | − |
| 24.157 | + | − | + | − | − |
| 24.158 | + | − | + | − | − |
| 24.160 | ++ | ++ | ++ | − | − |
| 24.161 | ++ | ++ | ++ | − | − |
| 24.162 | ++ | + | ++ | − | − |
| 25.1 | ++ | ++ | ++ | + | − |
| 25.2 | − | − | + | − | − |
| 25.3 | + | + | + | − | − |
| 26.1 | ++ | ++ | ++ | ++ | + |
| 26.2 | + | + | ++ | − | − |
| 27.1 | ++ | ++ | ++ | − | − |
| 27.2 | + | − | + | − | − |
| 28.1 | ++ | ++ | ++ | − | − |
| 28.2 | + | − | ++ | − | − |
| 29.1 | + | − | − | − | − |
| 210.1 | ++ | − | − | − | − |
| 211.1 | ++ | ++ | ++ | ++ | + |
| 211.2 | ++ | + | ++ | − | − |
| 211.3 | ++ | ++ | ++ | − | − |
| 211.4 | ++ | ++ | ++ | − | − |
| 211.5 | ++ | ++ | ++ | − | − |
| 211.6 | ++ | ++ | ++ | − | − |

TABLE 3-continued

Antibacterial Activity Results.

| Cmpd | Sa | Ec | Kp | Pa | Ab |
|---|---|---|---|---|---|
| 211.7 | ++ | ++ | ++ | − | − |
| 211.8 | ++ | ++ | ++ | − | − |
| 211.9 | ++ | ++ | ++ | − | − |
| 211.10 | ++ | ++ | ++ | − | − |
| 211.11 | ++ | ++ | ++ | − | − |
| 212.1 | ++ | ++ | ++ | − | − |
| 212.2 | + | − | + | − | − |
| 213.1 | ++ | + | + | − | − |
| 213.2 | + | + | + | − | − |
| 214.1 | ++ | + | + | − | − |
| 214.2 | + | − | + | − | − |
| 215.1 | ++ | + | ++ | − | − |
| 215.2 | ++ | ++ | ++ | − | − |
| 216.1 | + | − | + | − | − |
| 217.1 | ++ | ++ | ++ | − | − |
| 220.1 | ++ | + | + | − | − |
| 221.1 | + | − | + | − | − |
| 222.1 | + | − | + | − | − |
| 223.1 | + | + | + | − | − |
| 224.1 | ++ | ++ | ++ | + | − |
| 225.1 | + | − | + | − | − |
| 32.1 | ++ | + | + | − | − |

Sa: MIC *Staphylococcus aureus* ATCC 13709
Ec: MIC *Escherichia coli* ATCC 25922
Kp: MIC *Klebsiella pneumoniae* ATCC 43816
Pa: MIC *Pseudomonas aeruginosa* ATCC 27853
Ab: MIC *Acinetobacter baumannii* ATCC 19606
++: ≤8 µg/mL
+: ≤32 µg/mL
−: >32 µg/mL

TABLE 4

Antibacterial Activity Results against multidrug-resistant strains.

| Cmpd | Ec#1 | Ec#2 | Ec#3 | Ec#4 | Ec#5 | Kp#1 | Kp#2 | Kp#3 | Kp#4 | Kp #5 |
|---|---|---|---|---|---|---|---|---|---|---|
| 24.66 | + | N/A | + | + | + | ++ | ++ | ++ | ++ | ++ |
| 24.151 | + | + | + | + | ++ | ++ | ++ | ++ | ++ | ++ |
| 24.153 | ++ | ++ | ++ | + | ++ | ++ | ++ | ++ | ++ | ++ |
| 24.152 | + | + | + | + | ++ | ++ | ++ | ++ | ++ | ++ |
| 24.154 | ++ | ++ | ++ | ++ | ++ | ++ | ++ | ++ | ++ | ++ |
| 24.156 | + | ++ | ++ | ++ | ++ | ++ | ++ | ++ | ++ | ++ |
| 24.109 | + | + | + | + | + | ++ | ++ | ++ | ++ | ++ |
| 24.100 | ++ | ++ | ++ | ++ | + | ++ | ++ | ++ | ++ | ++ |
| 24.90 | ++ | ++ | ++ | ++ | ++ | ++ | ++ | ++ | ++ | ++ |
| 24.77 | + | + | ++ | + | + | ++ | ++ | ++ | ++ | ++ |
| 24.85 | ++ | + | + | ++ | + | ++ | ++ | ++ | ++ | + |

Example 11. Calcium Channels Interaction

Interaction with N-type calcium channels was assessed with radiolabelled a competitive binding assay, applying the procedure described by Wagner et al. (J. Neurosci. 8: 3354-3359). N-type calcium channels were prepared from rat cerebral cortex, and were incubated with [$^{125}$I]ω-conotoxin GVIA (0.001 nM). The investigated molecules were added, and the reactants were incubated over 30 minutes at room temperature. Binding shifts were monitored by scintillation counting.

TABLE 5

Calcium Channels

| Compound | IC$_{50}$ Ca$_v$2.2 |
|---|---|
| Odilomycin A | A (25 nM) |
| Odilomycin C | A (9 nM) |
| 21.1 | A |
| 22.3 | A |
| 22.4 | A |
| 22.5 | A |
| 22.12 | A |
| 22.15 | A (4 nM) |
| 22.16 | A |
| 22.23 | A |
| 22.24 | A |
| 24.1 | A |
| 24.14 | A |
| 24.15 | A |
| 24.17 | A |
| 24.20 | A |
| 24.22 | A |
| 24.66 | B |
| 24.67 | A |
| 24.76 | B |
| 24.85 | B (1200 nM) |
| 24.88 | B |
| 24.93 | B |
| 24.97 | B |
| 24.103 | B |
| 24.109 | B (1000 nM) |
| 24.112 | B (790 nM) |
| 24.135 | B |
| 24.138 | B |
| 24.151 | B |
| 24.152 | B |
| 24.153 | B |
| 24.154 | B |
| 25.1 | A (3 nM) |
| 25.2 | B |
| 27.1 | A |
| 27.2 | B |
| 28.1 | A |
| 28.2 | B |
| 212.1 | A |
| 212.2 | B |
| 224.1 | A |

A: ≤30 nM
B: >300 nM

Example 12. Challenge in Murine Peritonitis/Sepsis Model with Analog 24.66

Female CD-1 mice (weight, 25 g; Charles River) were used throughout the study. Six groups of 8 mice were inoculated by intraperitoneal (i.p.) injection of 0.5 ml *Klebsiella pneumoniae* ATCC BAA2470 suspension containing $10^{8.1}$ CFU/ml in 0.9% sterile saline and 5% (wt/vol) mucin. One hour after bacterial challenge on day 0, mice were treated by intravenous (i.v.) route with the antibiotic solutions formulated in 0.9% sterile saline.

Four groups were administered with single bolus dose of analog 24.66 at 6 mg/kg, 12.5 mg/kg, 25 mg/kg and 50 mg/kg, respectively. One group was administered with single bolus dose of tigecycline at 20 mg/kg. One group received no treatment. Mice were observed 24 hours following the injection of the inoculum (Table 1). $ED_{50}$ of analog 24.66 was assessed using GraphPad Prism 6.05, and was calculated as 20.4 mg/kg.

| Group | N | Treatment | Dose (mg/kg) | Alive animals at 24 hrs |
|---|---|---|---|---|
| 1 | 8 | None | N/A | 0 |
| 2 | 8 | Tigecycline | 20 | 8 |
| 3 | 8 | Analog 24.66 | 6 | 0 |
| 4 | 8 | Analog 24.66 | 12.5 | 2 |
| 5 | 8 | Analog 24.66 | 25 | 5 |
| 6 | 8 | Analog 24.66 | 50 | 7 |

Example 13. Challenge in Murine Peritonitis/Sepsis Model with Odilorhabdin A

Female CD-1 mice (weight, 20 g; Charles River) were used throughout the study. Six groups of 6-8 mice were inoculated by intraperitoneal (i.p.) injection of 0.5 ml *Klebsiella pneumoniae* ATCC BAA2470 suspension containing $10^{7.7}$ CFU/ml in 0.9% sterile saline and 5% (wt/vol) mucin. One hour after bacterial challenge on day 0, mice were treated by intravenous (i.v.) route with the antibiotic solutions formulated in 0.9% sterile saline.

Four groups were administered with single bolus dose of Odilorhabdin A at 5 mg/kg, 10 mg/kg, 15 mg/kg and 20 mg/kg, respectively. One group was administered with single bolus dose of tigecycline at 15 mg/kg. One group received no treatment. Mice were observed 24 hours following the injection of the inoculum (Table 2). $ED_{50}$ of Odilorhabdin A was assessed using GraphPad Prism 6.05, and was calculated as 13.9 mg/kg (FIG. 1). Odilorhabdin A and analog 24.66 have similar efficacy in this murine *K. pneumoniae* NDM-1 peritonitis/sepsis model.

| Group | n | Treatment | Dose (mg/kg) | Alive animals at 24 hrs |
|---|---|---|---|---|
| 1 | 6 | None | N/A | 0 |
| 2 | 8 | Tigecycline | 15 | 8 |
| 3 | 6 | Odilorhabdin A | 5 | 0 |
| 4 | 8 | Odilorhabdin A | 10 | 2 |
| 5 | 7 | Odilorhabdin A | 15 | 4 |
| 6 | 8 | Odilorhabdin A | 20 | 6 |

Example 14. Tolerability of Odilorhabdin A and Analog 24.66 in Mice

Female CD-1 mice (weight, 20 g; Charles River) were used throughout the study. Seven groups of 5 mice were inoculated by intravenous (i.v.) route with the antibiotic solutions formulated in 0.9% sterile saline. Five groups were administered with single bolus dose of Odilorhabdin A at 5 mg/kg, 10 mg/kg, 15 mg/kg, 20 mg/kg, and 30 mg/kg, respectively. Six groups were administered with single bolus dose of analog 24.66 at 100 mg/kg, 200 mg/kg, 300 mg/kg, 400 mg/kg, 500 mg/kg, and 600 mg/kg, respectively. Mice were observed over 5 days following the injection of the antibiotic. $LD_{50}$ of Odilorhabdin A and analog 24.66 were assessed using GraphPad Prism 6.05, and were calculated as 18.6 mg/kg and 494.3 mg/kg, respectively.

Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and/or rearranged in various ways within the scope and spirit of the invention to produce further embodiments that are also within the scope of the invention. Those skilled in the art will recognize, or be able to ascertain, using no more than routine experimentation, numerous equivalents to the specific embodiments described specifically in this disclosure. Such equivalents are intended to be encompassed in the scope of the following claims.

The invention claimed is:

1. A compound of formula (I):

$R_a$-Xaa$_1$-Xaa$_2$-Xaa$_3$-Xaa$_4$-Xaa$_5$-Xaa$_6$-Xaa$_7$-Xaa$_8$-Xaa$_9$-R$_b$ (I)

wherein $R_a$ is H, —($C_1$-$C_3$)-alkyl, —C(O)—($C_1$-$C_3$)-alkyl, or —C(O)—($C_1$-$C_3$)-haloalkyl;

$R_b$ is $R_c$;

$R_c$ is OH, —N($R_d$)($R'_d$), —($C_3$-$C_8$)-aminocycloalkyl, or —($C_1$-$C_6$)-alkoxy;

$R_d$, $R'_d$ is independently H, OH, —($C_1$-$C_6$)-alkyl, —($C_1$-$C_3$)-hydroxyalkyl, —($C_1$-$C_6$)-alkyl-N($R_e$)($R'_e$), —C(O)—($C_1$-$C_3$)-haloalkyl, aryl or heteroaryl;

$R_e$, $R'_e$ is independently H, —($C_1$-$C_6$)-alkyl, or —C(O)—($C_1$-$C_3$)-haloalkyl;

Xaa$_1$ is

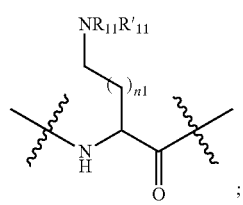

$R_{11}$, $R'_{11}$ is independently H or —($C_1$-$C_3$)-alkyl;

$n_1$ is an integer from 1-4;

Xaa$_2$ is

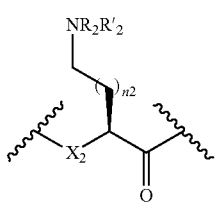 or 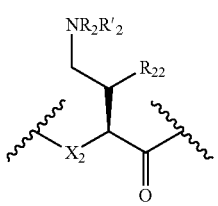 ;

$X_2$ is independently NH, N(Me), or O;

$R_2$, $R'_2$ is independently H, —($C_1$-$C_3$)-alkyl, —C(O)—($C_1$-$C_3$)-alkyl, or —C(O)—($C_1$-$C_3$)-haloalkyl;

$R_{22}$ is independently OH, halogen, —($C_1$-$C_3$)-alkyl, —($C_1$-$C_3$)-alkoxy, O—C(O)—($C_1$-$C_6$)-alkyl or —O—C(O) —($C_1$-$C_6$)-haloalkyl;

$n_2$ is an integer from 1-3;

Xaa$_3$ is

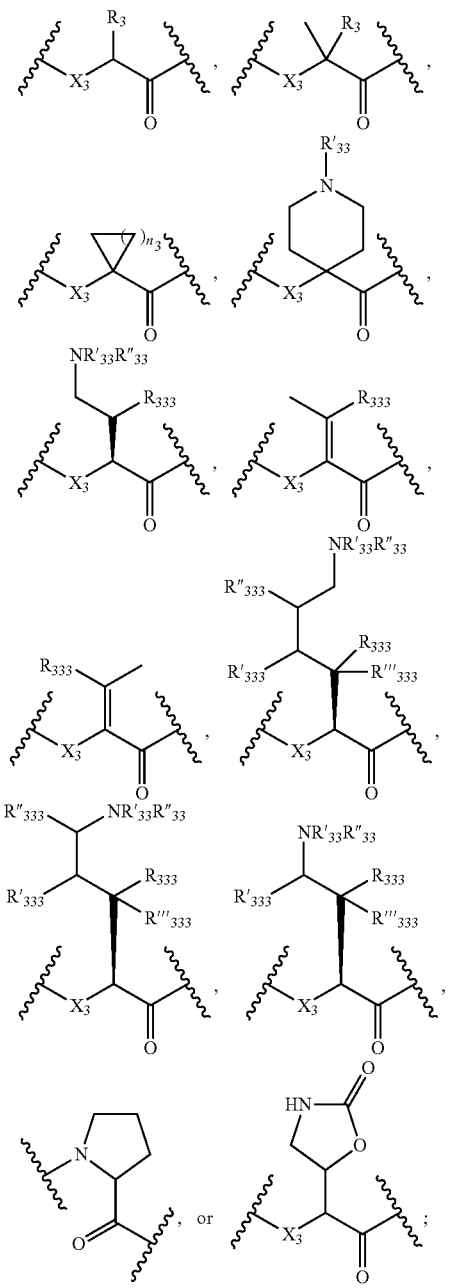

$X_3$ is independently N($R_{33}$), or O;

$R_3$ is independently H, halogen, NH$_2$, —($C_1$-$C_6$)-alkyl, —($C_1$-$C_6$)-haloalkyl, —($C_3$-$C_8$)-cycloalkyl, —($C_1$-$C_6$)-alkenyl, —($C_1$-$C_6$)-alkynyl, —($C_1$-$C_6$)-alkyl-OR$_{33}$, ($C_1$-$C_6$)-alkyl-SR$_{33}$, ($C_1$-$C_6$)-alkyl-N R$_{33}$R'$_{33}$, ($C_1$-$C_6$)-alkyl- C(O)N R$_{33}$R'$_{33}$, ($C_1$-$C_6$)-alkyl-C(O) OR$_{33}$, ($C_1$-$C_6$)-alkyl-heteroaryl wherein said alkyl is optionally substituted with —OH or —O—C(O)

—($C_1$-$C_6$)-alkyl or —O—C(O) —($C_1$-$C_6$)-haloalkyl, wherein said heteroaryl is optionally substituted with —($C_1$-$C_3$)-alkyl, or ($C_1$-$C_6$)-alkyl-aryl wherein said aryl is optionally substituted with —OH, —($C_1$-$C_3$)-alkyl, —($C_1$-$C_3$)-alkoxy or halogen;

$R_{33}$, $R'_{33}$, $R''_{33}$ is independently H, —C(NH)NH$_2$, —($C_1$-$C_3$)-alkyl, —C(O)—($C_1$-$C_3$)-alkyl, or —C(O)—($C_1$-$C_3$)-haloalkyl;

$R_{333}$, $R'_{333}$, $R''_{333}$, $R'''_{333}$ is independently H, OH, halogen, —($C_1$-$C_3$)-alkyl, —($C_1$-$C_3$)-alkoxy, —O—CO—($C_1$-$C_3$)-alkyl or —O—CO—($C_1$-$C_3$)-haloalkyl;

$n_3$ is an integer from 1-3;

Xaa$_4$ is

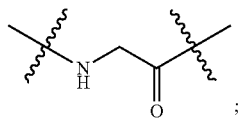 [SMILES: *NCC(*)=O]

Xaa$_5$ is

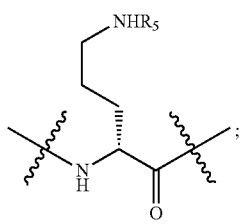

$R_5$ is H;

Xaa$_6$ is

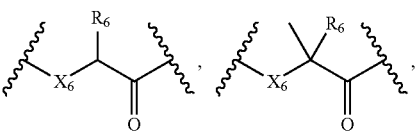

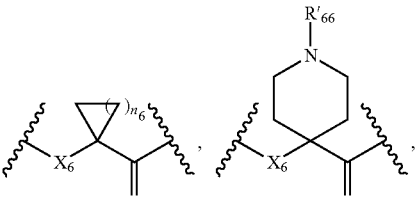

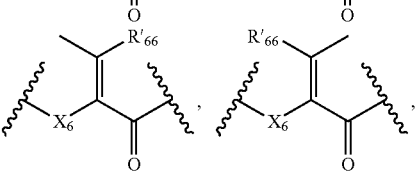

$R'_{66}$, $R_{66}$

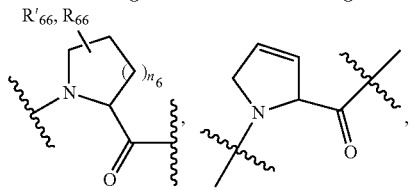

407

-continued

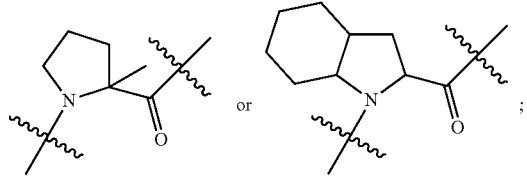

$X_6$ is independently $N(R_{66})$, or O;

$R_6$ is independently H, halogen, $NH_2$, —$(C_1-C_6)$-alkyl, —$(C_1-C_6)$-haloalkyl, —$(C_3-C_8)$-cycloalkyl, —$(C_1-C_6)$-alkenyl, —$(C_1-C_6)$-alkynyl, —$(C_1-C_6)$-alkyl-$OR_{66}$, $(C_1-C_6)$-alkyl-$SR_{66}$ $(C_1-C_6)$-alkyl-$NR_{66}R'_{66}$, $(C_1-C_6)$-alkyl- $C(O)NR_{66}R'_{66}$, $(C_1-C_6)$-alkyl-$C(O)OR_{66}$, $(C_1-C_6)$-alkyl-heteroaryl wherein said alkyl is optionally substituted with —OH or —O—C(O)—$(C_1-C_6)$-alkyl or —O—C(O)—$(C_1-C_6)$-haloalkyl, wherein said heteroaryl is optionally substituted with —$(C_1-C_3)$-alkyl, or $(C_1-C_6)$-alkyl-aryl wherein said aryl is optionally substituted with —OH, —$(C_1-C_3)$-alkyl, —$(C_1-C_3)$-alkoxy or halogen;

$R_{66}$, $R'_{66}$ is independently H, OH, halogen, —$C(NH)NH_2$, —$(C_1-C_3)$-alkyl, —$(C_1-C_3)$-haloalkyl, —$C(O)$—$(C_1-C_3)$-alkyl, —$C(O)$—$(C_1-C_3)$-haloalkyl, —$NH_2$, $NH(C_1-C_3)$-alkyl, or $N[(C_1-C_3)$-alkyl][$(C_1-C_3)$-alkyl];

$n_6$ is an integer from 0-3;

$Xaa_7$ is

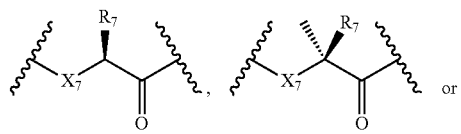

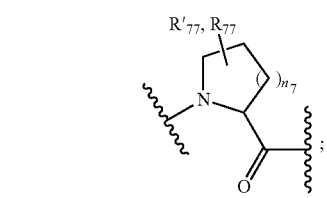

$X_7$ is independently $N(R_{77})$, or O;

$R_7$ is H, —$(C_1-C_6)$-alkyl, —$(C_1-C_6)$-haloalkyl, —$(C_1-C_6)$-alkenyl, —$(C_1-C_6)$-alkynyl, —$(C_1-C_6)$-alkyl-$OR_{77}$, $(C_1-C_6)$-alkyl-$SR_{77}$, $(C_1-C_6)$-alkyl-$S(O)_2$—$R_{77}$, $(C_1-C_6)$-alkyl-$S(O)_2$—$R_{77}$, —$(C_1-C_6)$-alkyl-$NR_{77}R'_{77}$, —$(C_1-C_6)$- alkyl-$C(O)OR_{77}$, —$(C_1-C_6)$-alkyl-$C(O)NR_{77}R'_{77}$, —$(C_1-C_6)$-alkyl-heteroaryl or —$(C_1-C_6)$-alkyl-aryl wherein aryl or heteroaryle is optionally mono- or poly-substituted with —OH, —$NH_2$, —COOH, —$CONH_2$, —CN, —$CF_3$, —$(C_1-C_6)$-alkyl, —$(C_1-C_3)$-alkoxy or halogen;

$R_{77}$ $R'_{77}$ is independently H, OH, halogen, —$(C_1-C_3)$-alkyl, —$(C_1-C_3)$-haloalkyl, —$C(O)$—$NH_2$, —$C(NH)$—$NH_2$, —$C(O)$—$(C_1-C_3)$-alkyl, —$C(O)$—$(C_1-C_3)$-haloalkyl, —$NH_2$, $NH(C_1-C_3)$-alkyl, or $N[(C_1-C_3)$-alkyl][$(C_1-C_3)$-alkyl];

$n_7$ is an integer from 0-3;

408

$Xaa_8$ is

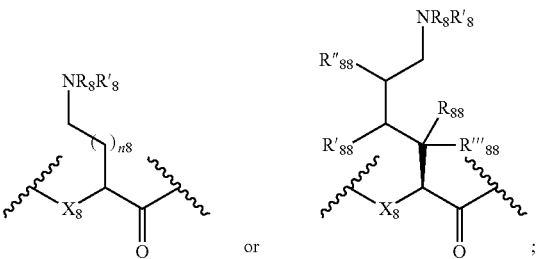

$X_8$ is independently NH, N(Me), or O;

$R_8$, $R'_8$ is independently H or —$(C_1-C_3)$-alkyl;

$R_{88}$, $R'_{88}$, $R''_{88}$, $R'''_{88}$ is independently H, OH, —$(C_1-C_3)$-alkyl, —$(C_1-C_3)$-alkoxy, or halogen;

$n_8$ is independently an integer from 1-4;

$Xaa_9$ is

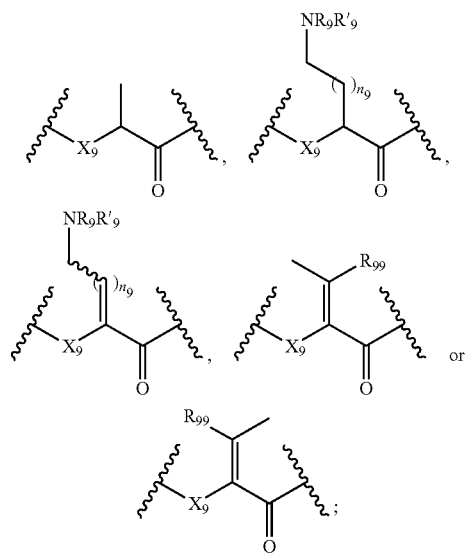

$X_9$ is NH;

$R_9$, $R'_9$ is independently H, —$C(NH)NH_2$, —$C(O)NH_2$, —$(C_1-C_6)$-alkyl, —$(C_1-C_6)$-haloalkyl, —$C(O)$—$(C_1-C_3)$-alkyl, or —$C(O)$—$(C_1-C_3)$-haloalkyl; $R_{99}$ is H, or —$(C_1-C_3)$-alkyl;

$R_{99}$ is H, or —$(C_1-C_3)$-alkyl;

$n_9$ is independently an integer from 1-3;

or a pharmaceutically acceptable salt thereof.

2. The compound of claim 1, wherein $X_2$ is independently NH, N(Me), $X_3$ is $N(R_{33})$, $X_6$ is $N(R_{66})$, $X_7$ is $N(R_{77})$, and $X_8$ is independently NH or N(Me).

3. The compound of claim 1, wherein $R_2$ is OH, —$N(R_d)_2$, —$(C_3-C_8)$-aminocycloalkyl, or —$(C_1-C_3)$-alkoxy;

$R_d$ is independently H, OH, —$(C_1-C_3)$-alkyl, —$(C_1-C_3)$-hydroxyalkyl, —$(C_1-C_6)$-alkyl-$N(R_e)(R'_e)$, —$C(O)$—$(C_1-C_3)$-haloalkyl or phenyl;

Xaa2 is

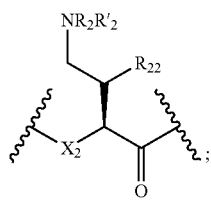

Xaa7 is

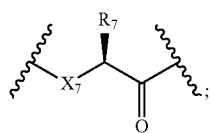

R$_{88}$, R'$_{88}$, R"$_{88}$ is independently H or OH; and

R$_9$, R'$_9$ is independently H, —C(NH)NH$_2$, —C(O)NH$_2$, —(C$_1$-C$_6$)-alkyl, —C(O)—(C$_1$-C$_3$)-alkyl, or —C(O)—(C$_1$-C$_3$)-haloalkyl.

4. The compound of claim 1, wherein R$_{333}$, R'$_{333}$, R"$_{333}$ is OH, halogen or —(C1-C3)-alkoxy.

5. The compound of claim 1, wherein

R$_a$ is H, methyl, —C(O)—(C$_1$-C$_2$)-alkyl, or trifluoroacetyl;

R$_b$ is R$_c$;

R$_c$ is OH, NH$_2$, NHOH, —(C$_2$-C$_6$)-alkyl-NH(R$_e$), —NH(C$_1$-C$_3$)-alkyl, —NH(C$_2$-C$_4$)-alkyl-OH, —NH— phenyl, N-piperidinyl, or —(C$_1$-C$_3$)-alkoxy;

R$_e$ is H or trifluroacetyl;

Xaa$_1$ is

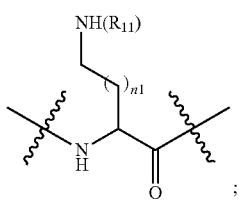

R$_1$ is H or —(C$_1$-C$_2$)-alkyl;

n$_1$ is an integer from 1-3;

Xaa$_2$ is

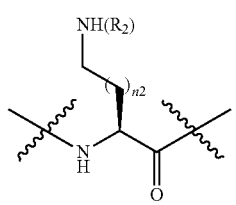 or 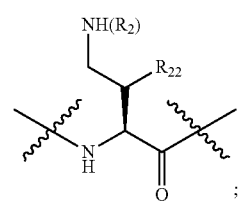 ;

R$_2$ is H, —(C$_1$-C$_2$)-alkyl, acetyl or trifluoroacetyl;

R$_{22}$ is OH, fluorine, methyl, or methoxy;

Xaa$_3$ is

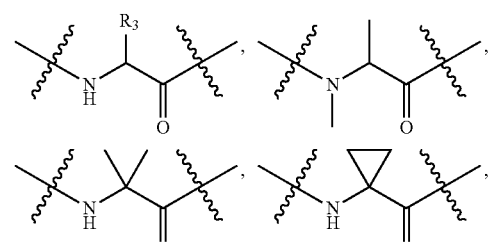

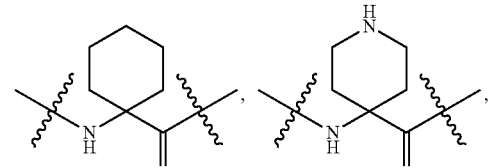

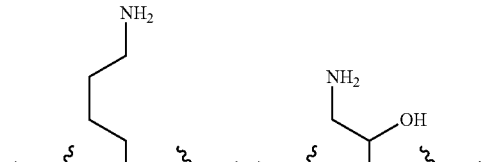

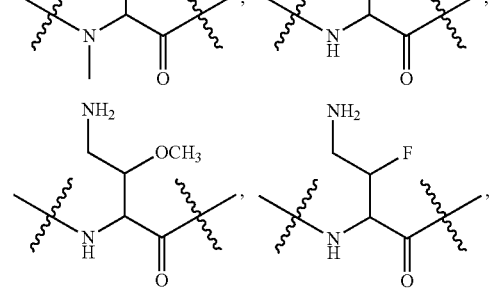

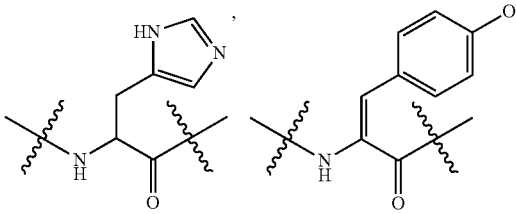

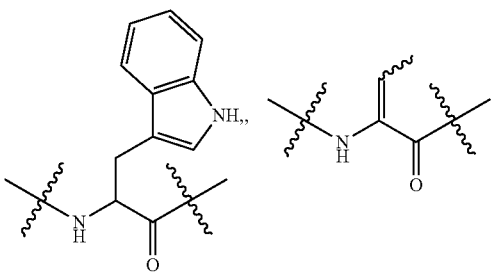

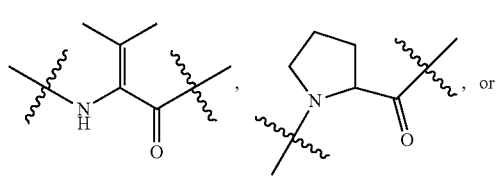

411
-continued
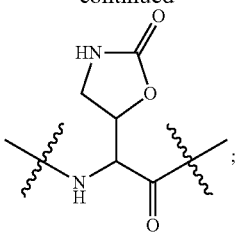
R₃ is H, fluoro, NH$_2$, —(C$_1$-C$_6$)-alkyl, —(C$_1$-C$_6$)-alkenyl, —(C$_1$-C$_6$)-alkynyl, —(C$_1$-C$_2$)-haloalkyl, —(C$_3$-C$_5$)-cycloalkyl, —(C$_1$-C$_2$)-hydroxyalkyl, —CH$_2$SH, —CH$_2$CH$_2$SCH$_3$, (C$_1$-C$_4$)-alkyl-NH(R$_{33}$), (C$_1$-C$_6$)-alkyl-C(O)NH$_2$, or (C$_1$-C$_6$)-alkyl-C(O)OH;
R$_{33}$ is H, —(C$_1$-C$_3$)-alkyl, acetyl, trifluoroacetyl, or —C(NH)NH$_2$;
Xaa$_6$ is
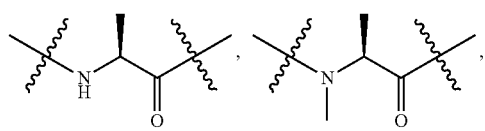
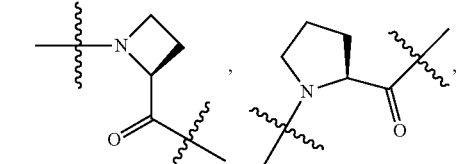
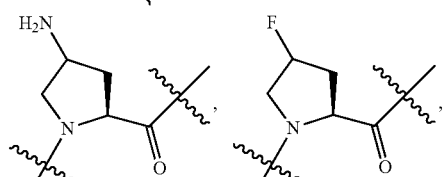
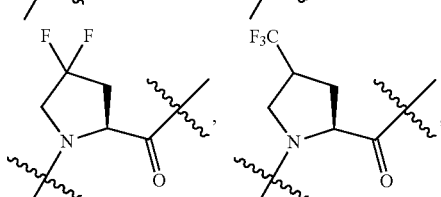
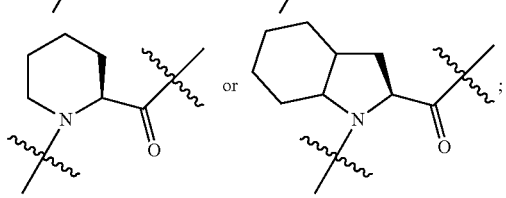
Xaa$_7$ is
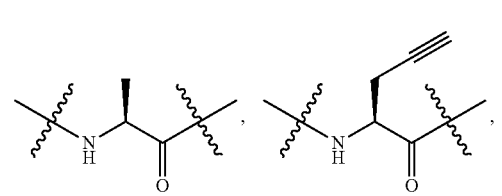
412
-continued
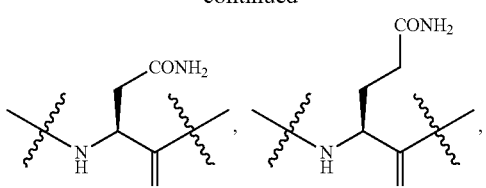
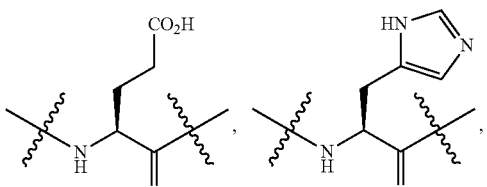
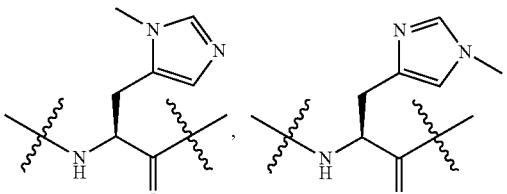
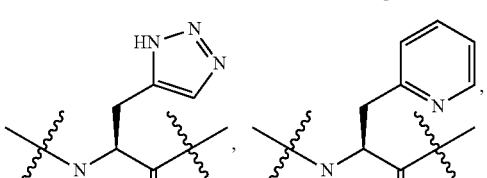
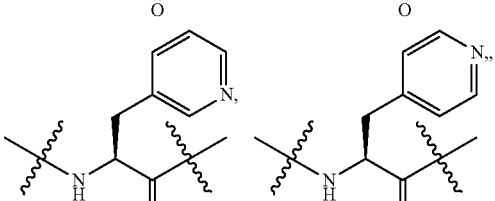
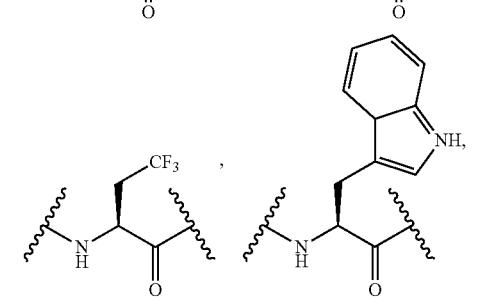
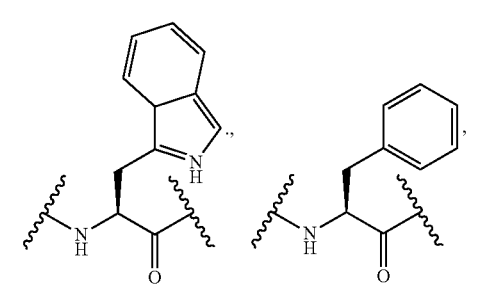

413
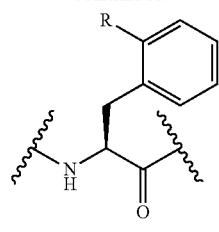
with R is —C(O)NH₂, F, Cl, I, CH₃, CF₃, CN, OH, OMe, tBu, NH₂, COOH,
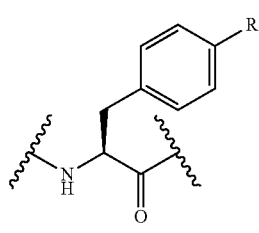
with R is —C(O)NH₂, F, Cl, I, CH₃, CF₃, CN, OH, OMe, tBu, NH₂, COOH,
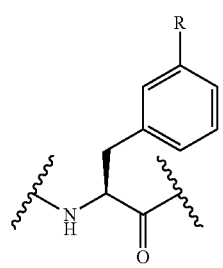
with R is —C(O)NH₂, F, Cl, I, CH₃, CF₃, CN, OH, OMe, tBu, NH₂, COOH,
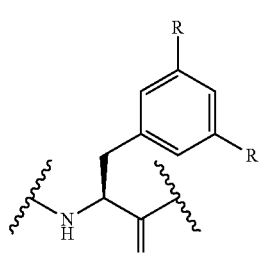
with R is —C(O)NH₂, F, Cl, I, CH₃, CF₃, CN, OH, OMe, tBu, NH₂, COOH,
414
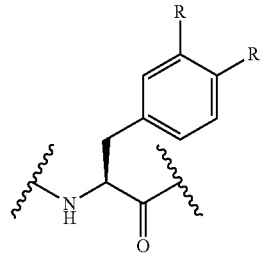
with R is —C(O)NH₂, F, Cl, I, CH₃, CF₃, CN, OH, OMe, tBu, NH₂, COOH,
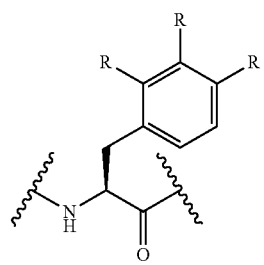
with R is —C(O)NH₂, F, Cl, I, CH₃, CF₃, CN, OH, OMe, tBu, NH₂, COOH,
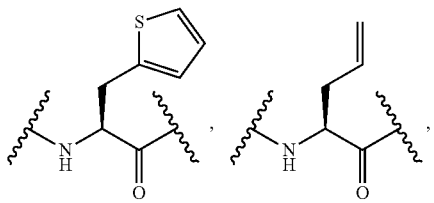
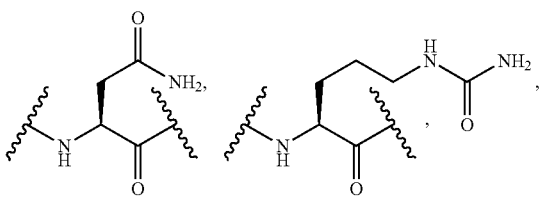
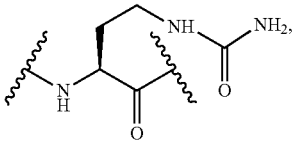

-continued
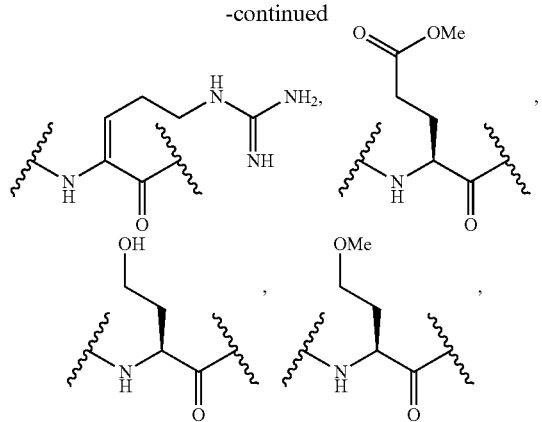, 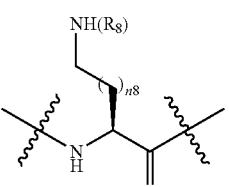,
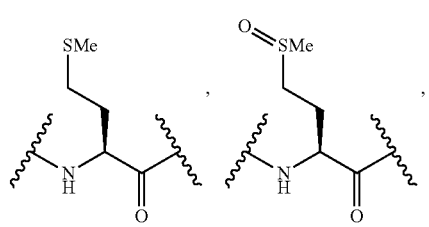,
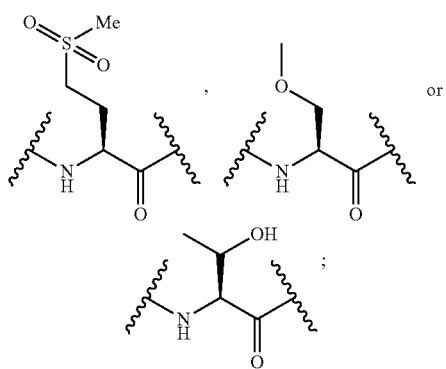;
Xaa$_8$ is
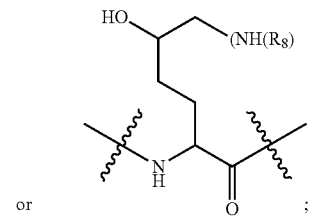 or 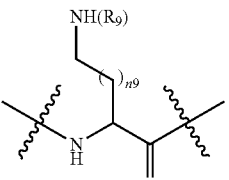;
R$_8$ is H;
n$_8$ is independently an integer from 2-4;
Xaa$_9$ is
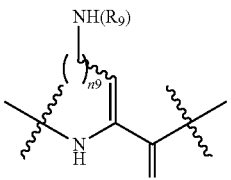,
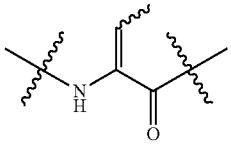 or 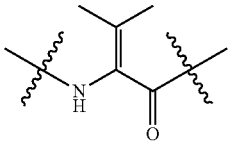;
R$_9$ is H or —C(NH)NH$_2$; and
n$_9$ is an integer from 2-4.
6. The compound of claim 1, wherein the compound is selected from the group consisting of
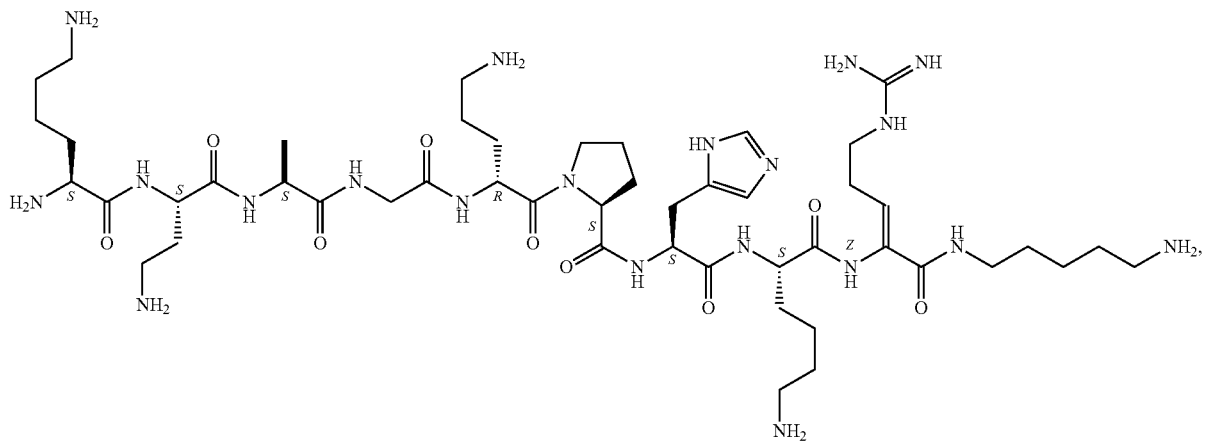

417
418
-continued
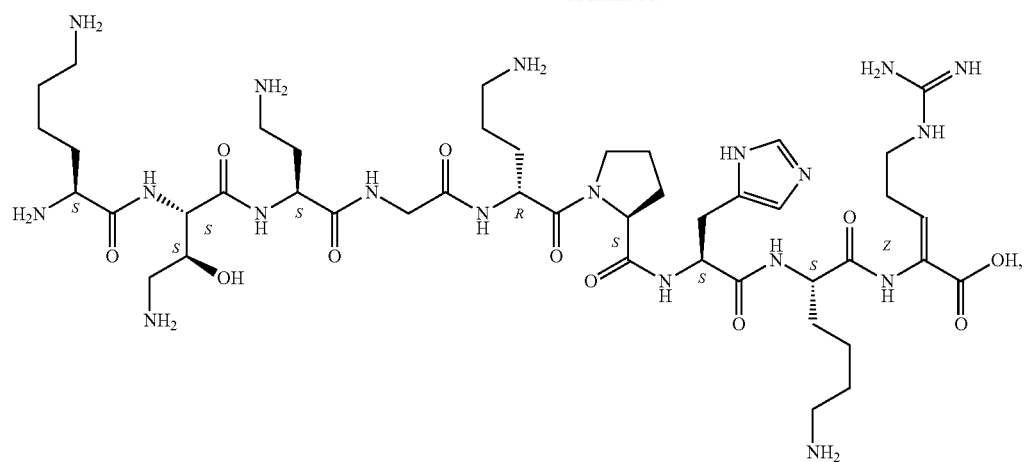
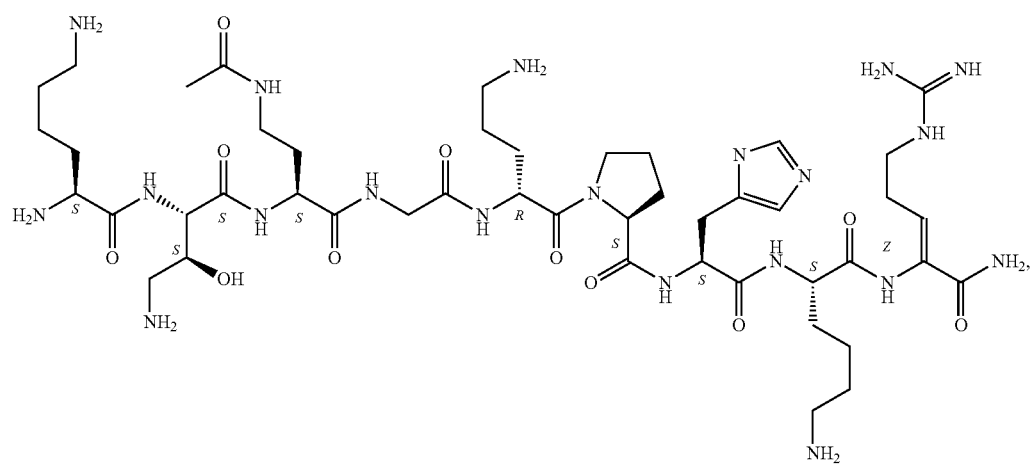
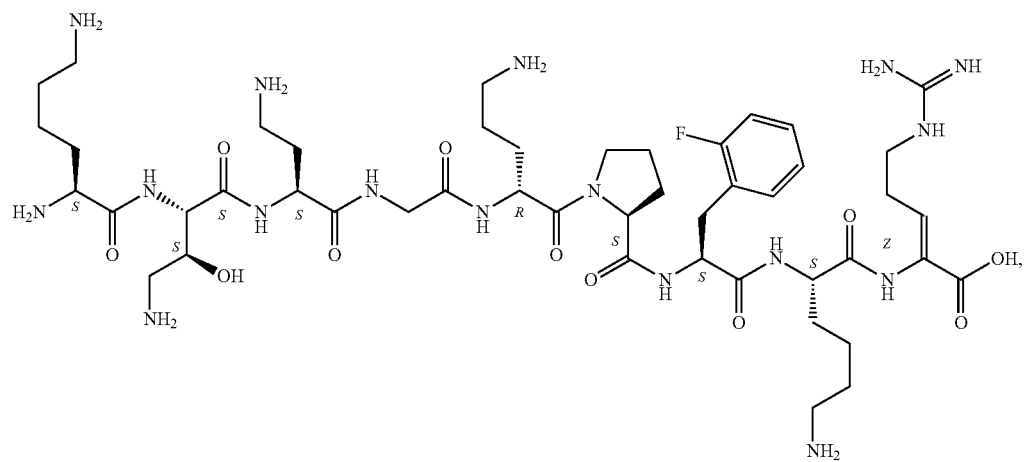

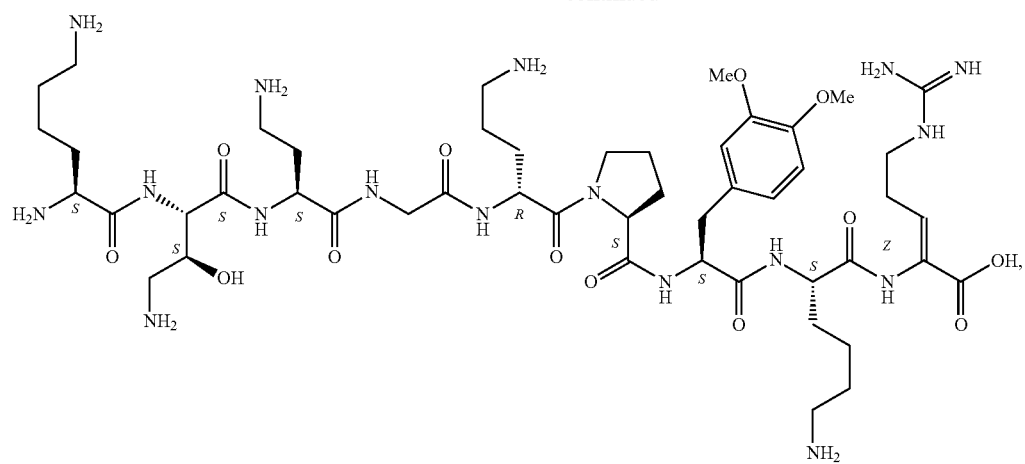
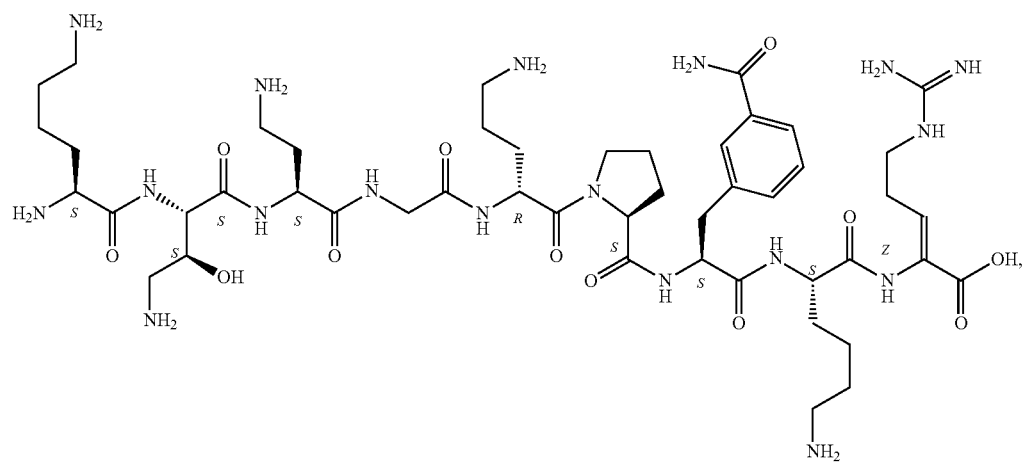
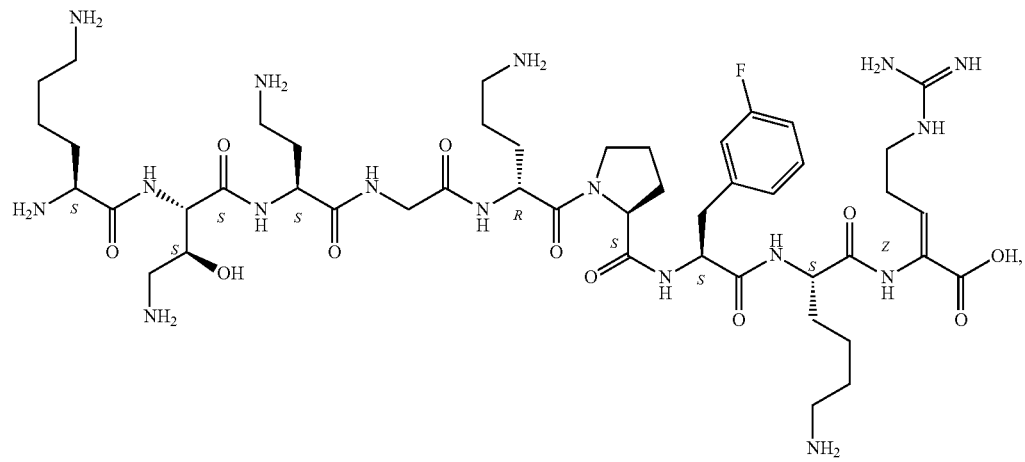

421
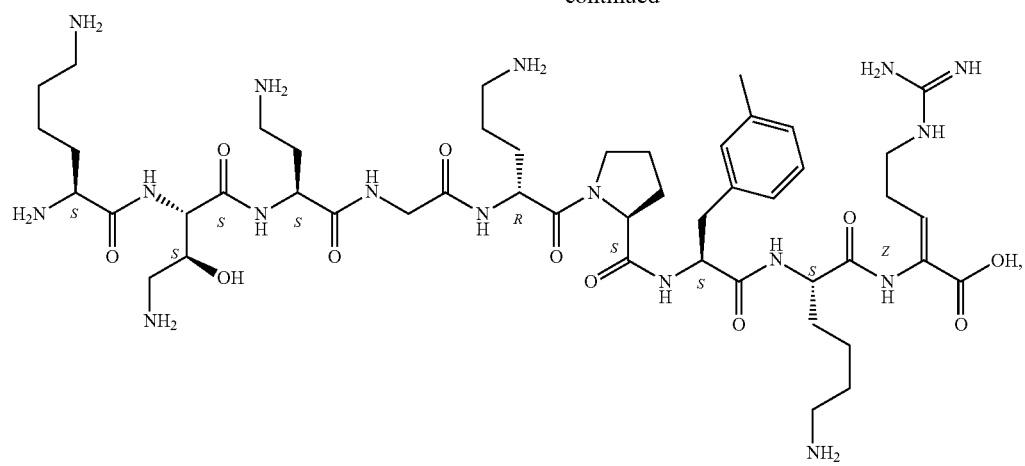
422
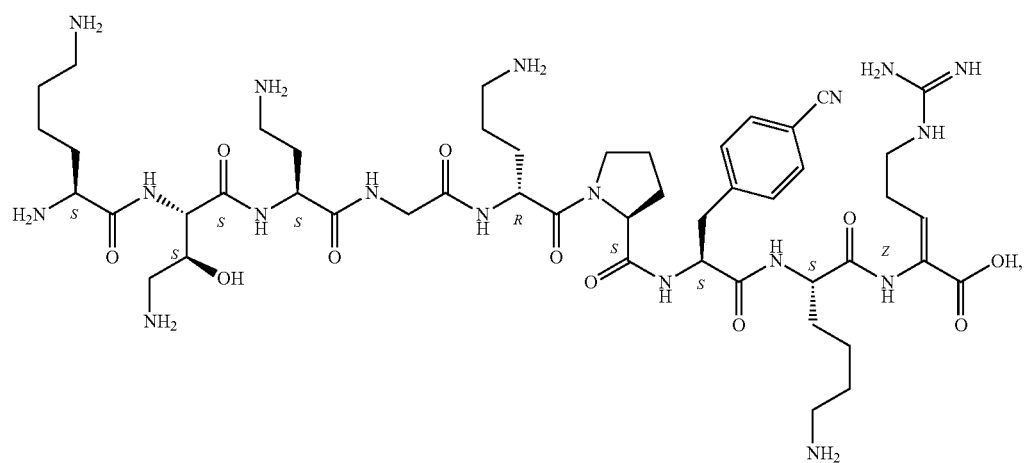
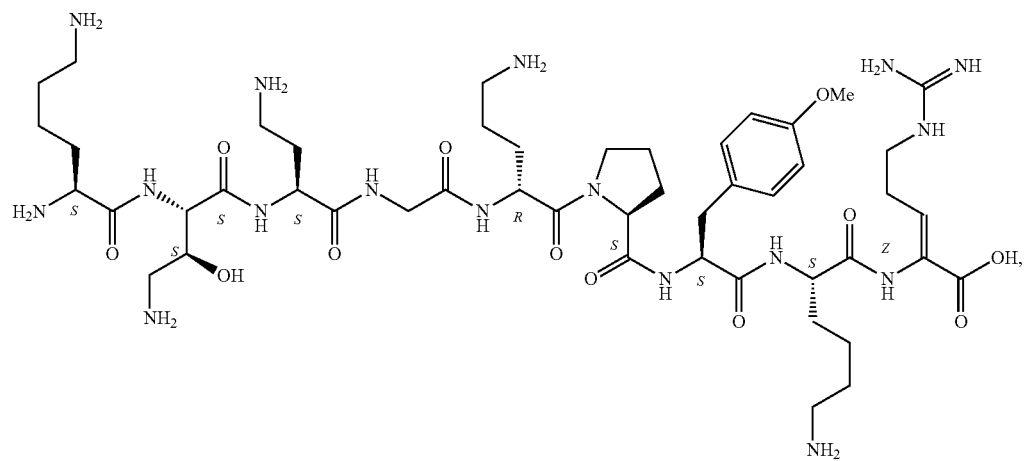

423
424
-continued
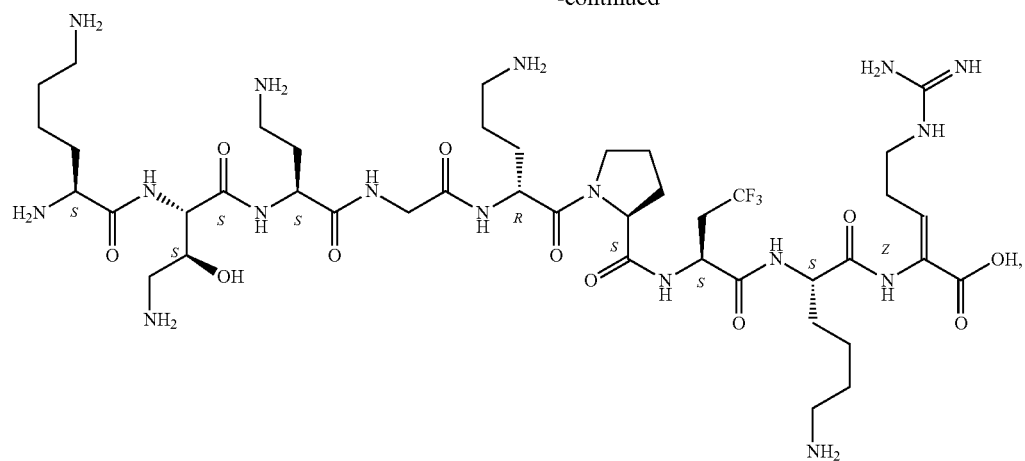
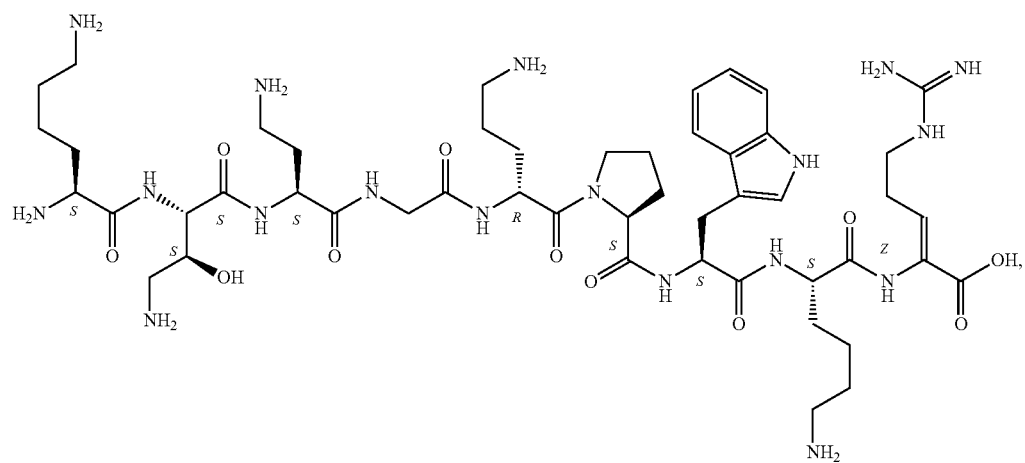
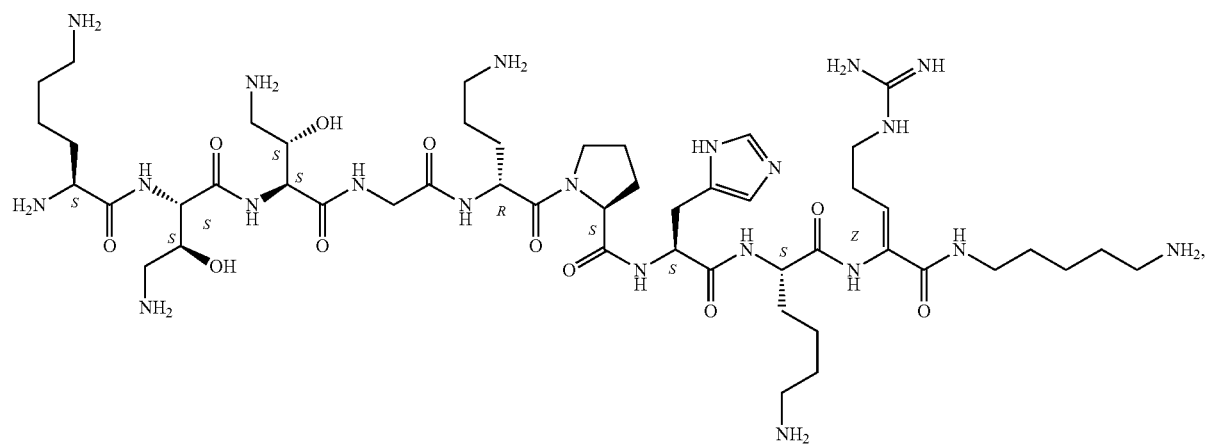

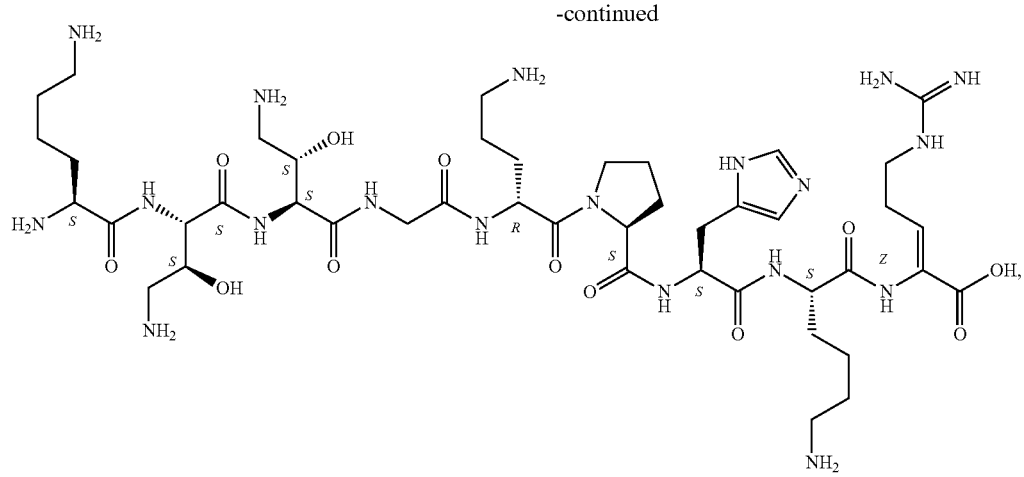
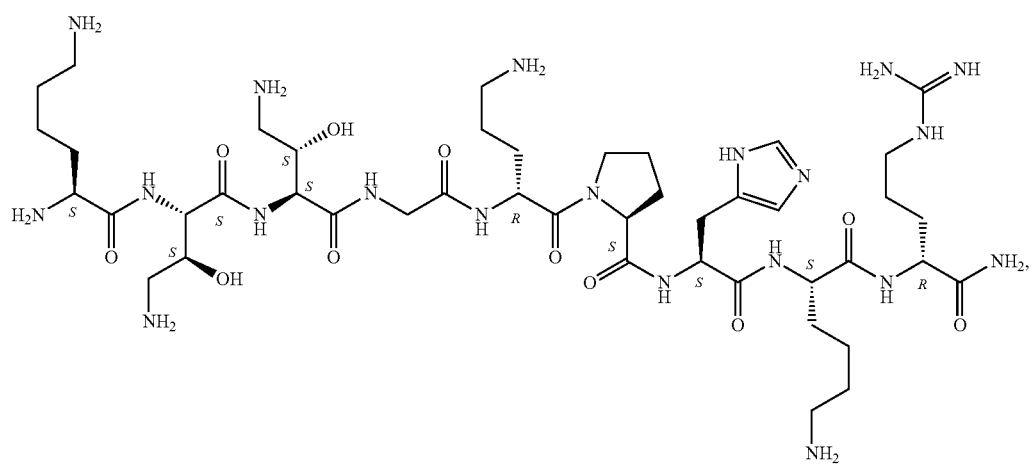
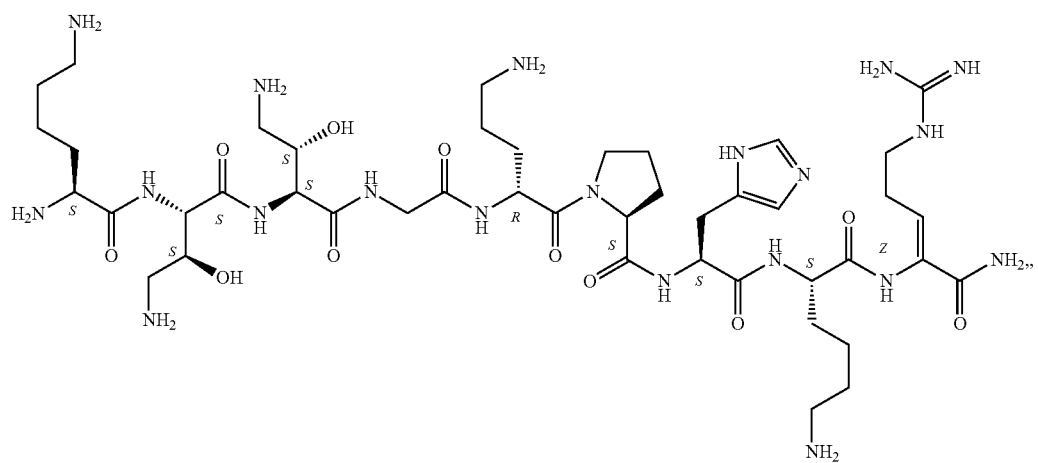

427
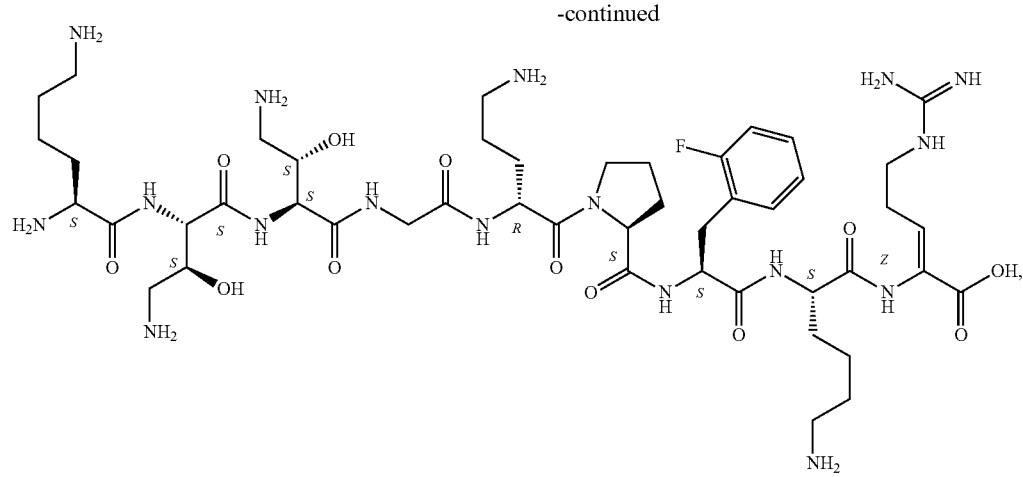
428
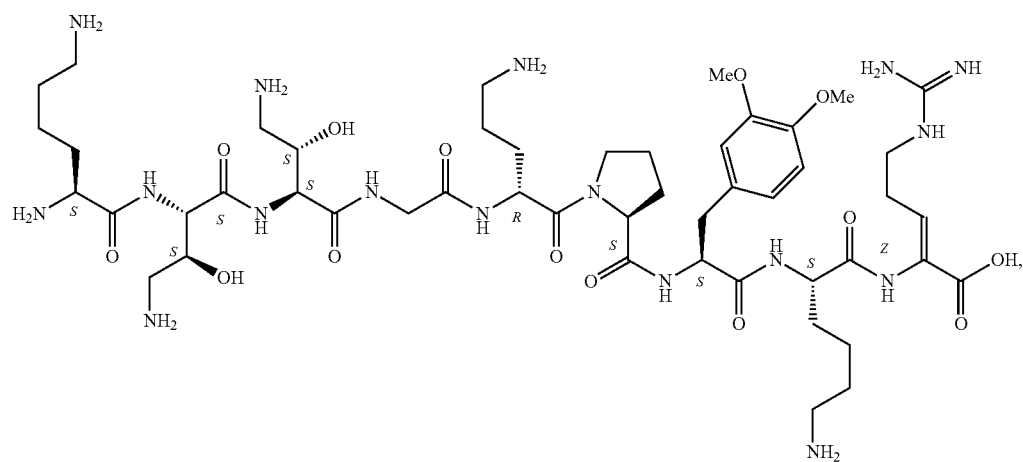
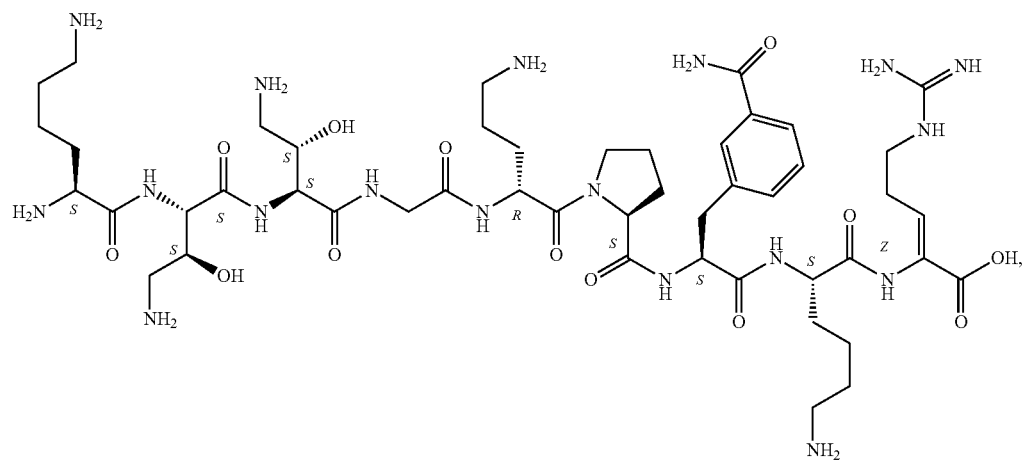

429
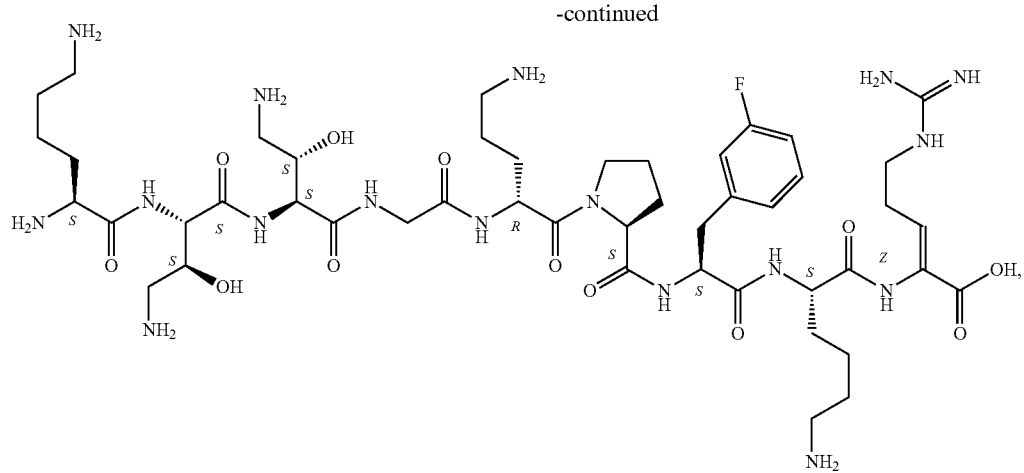
430
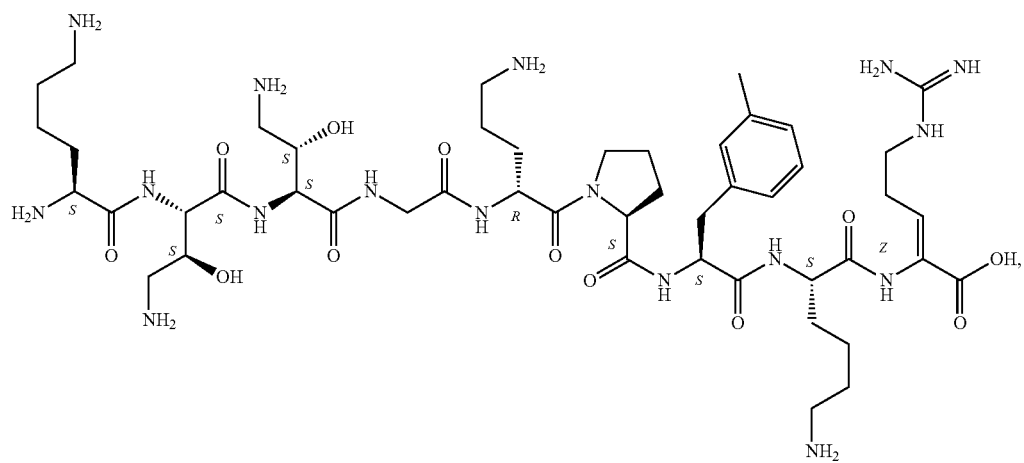
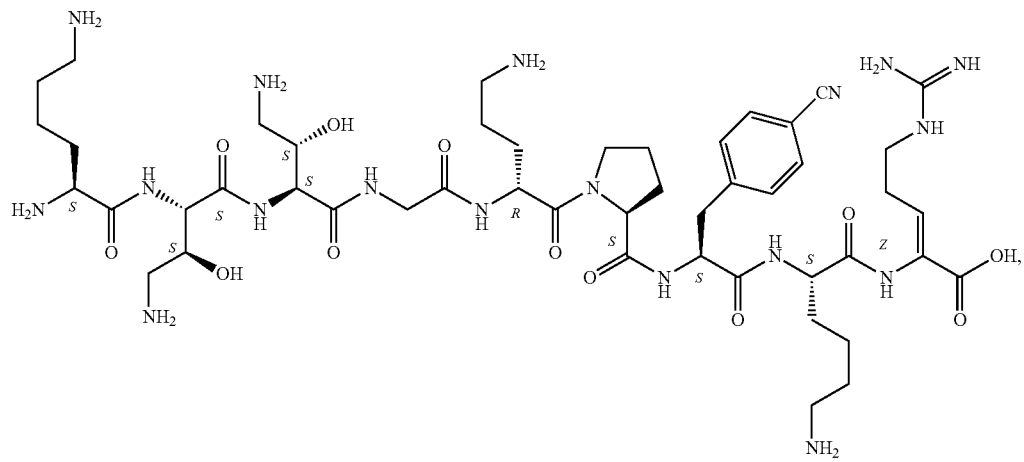

431
-continued
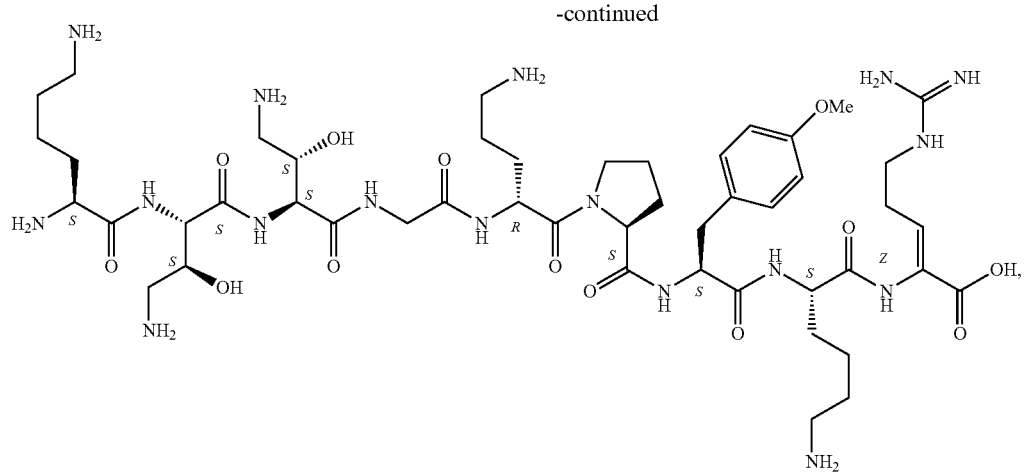
432
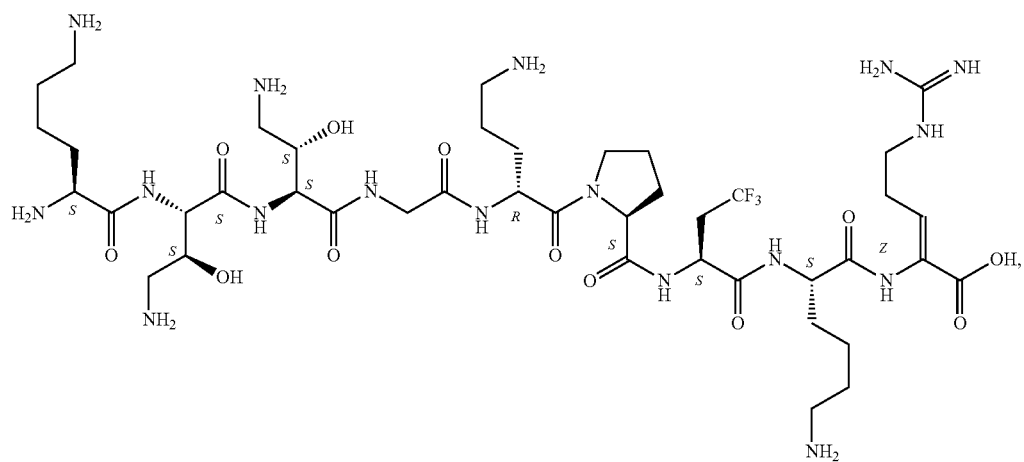
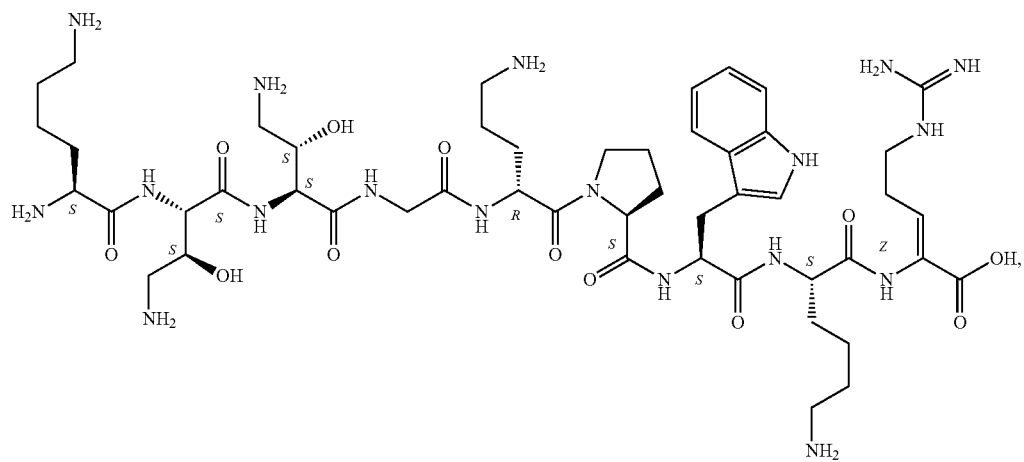

-continued
433
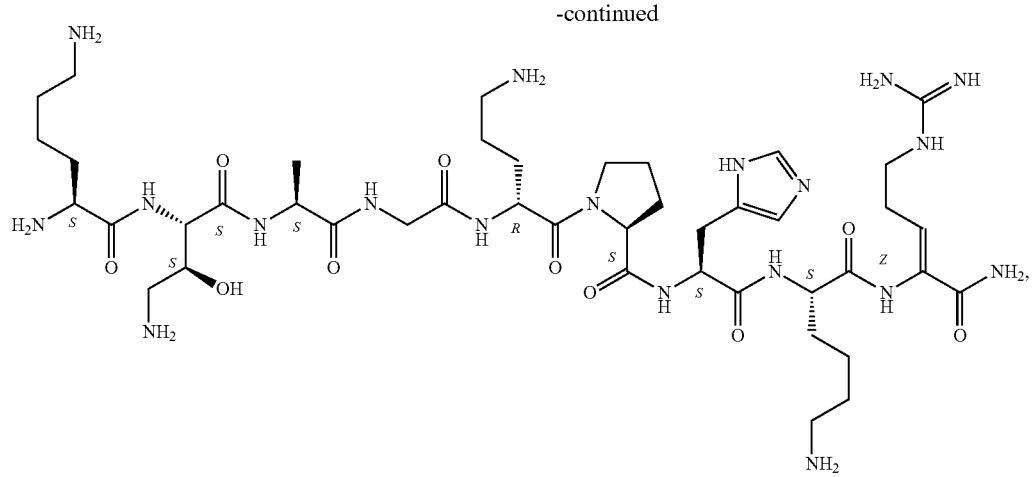
434
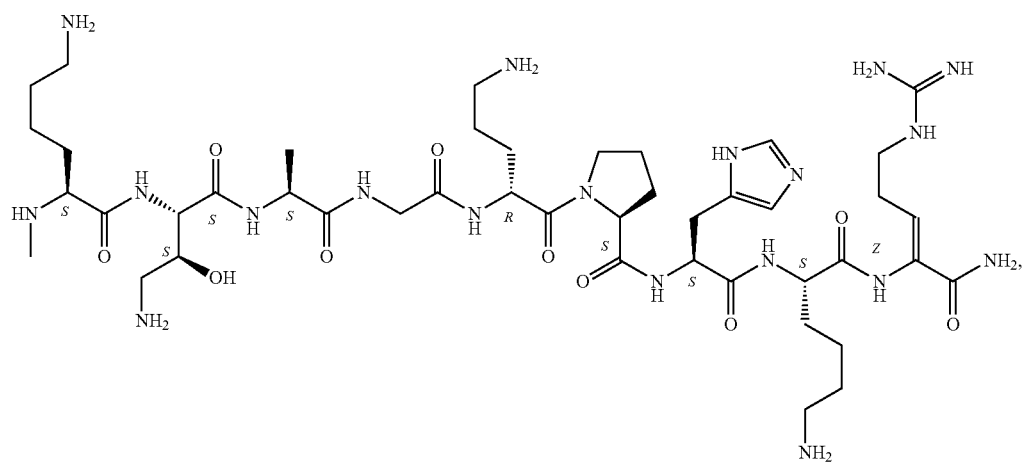
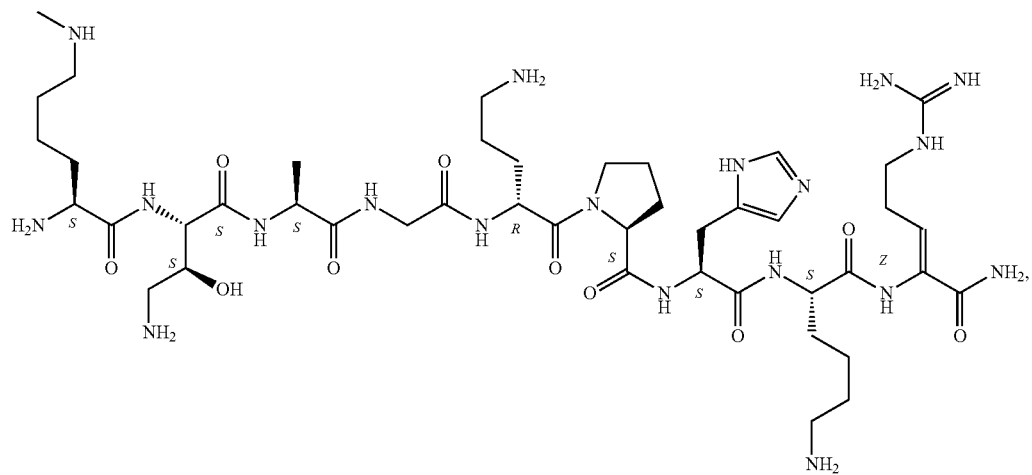

-continued
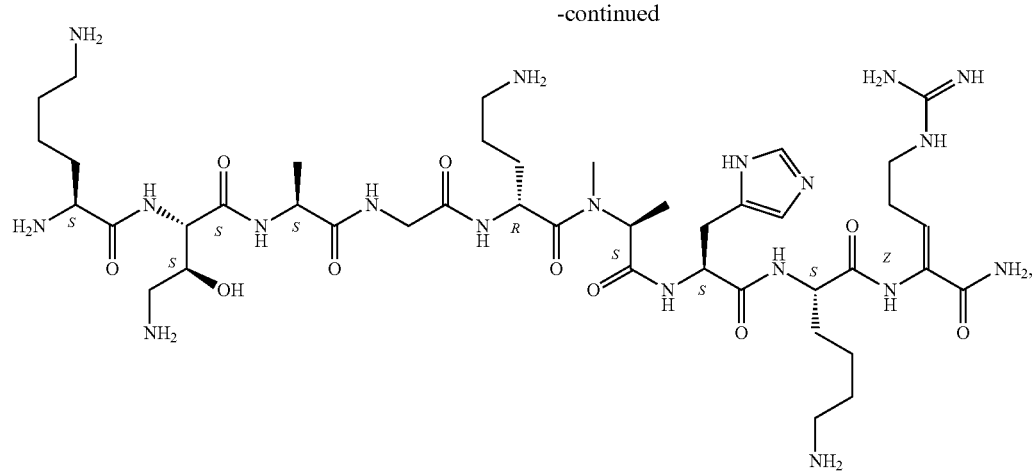
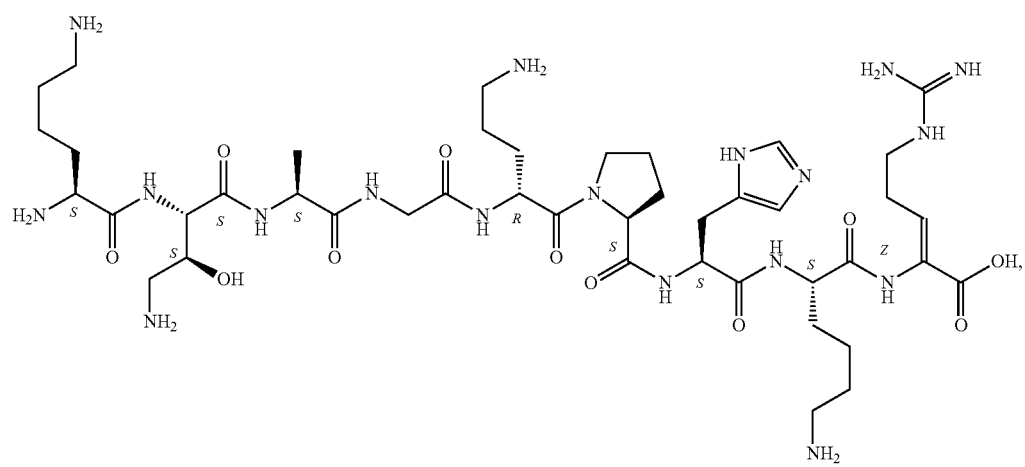
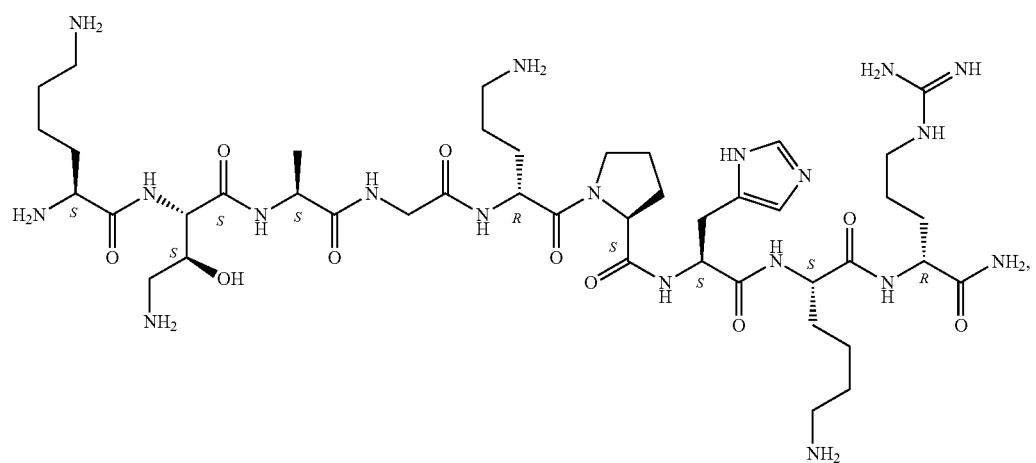

-continued
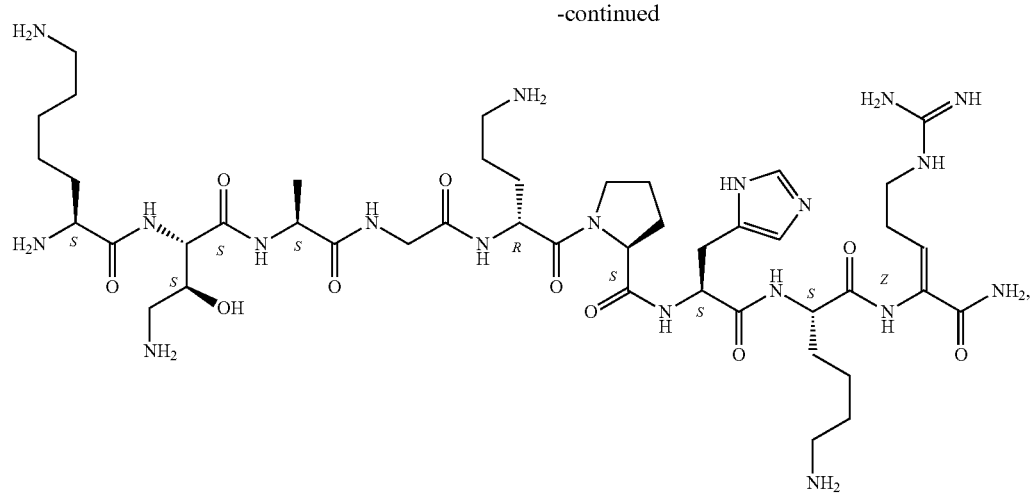
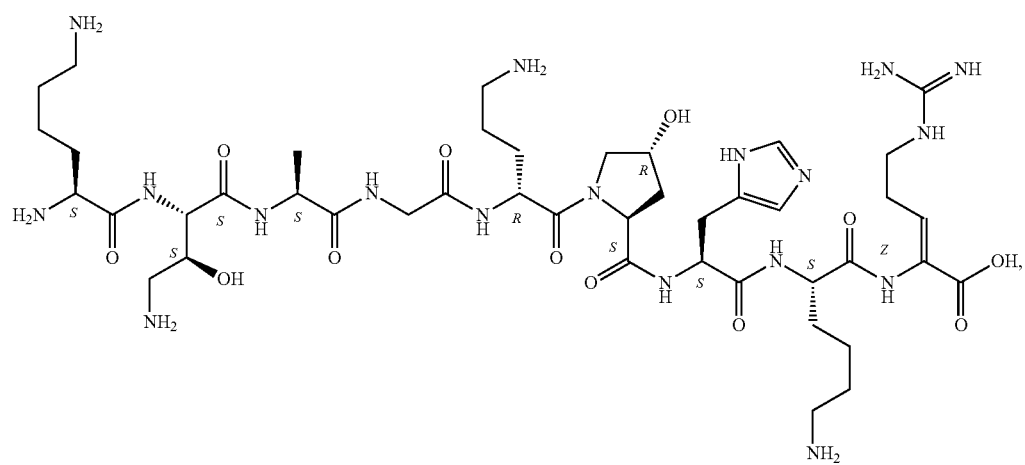
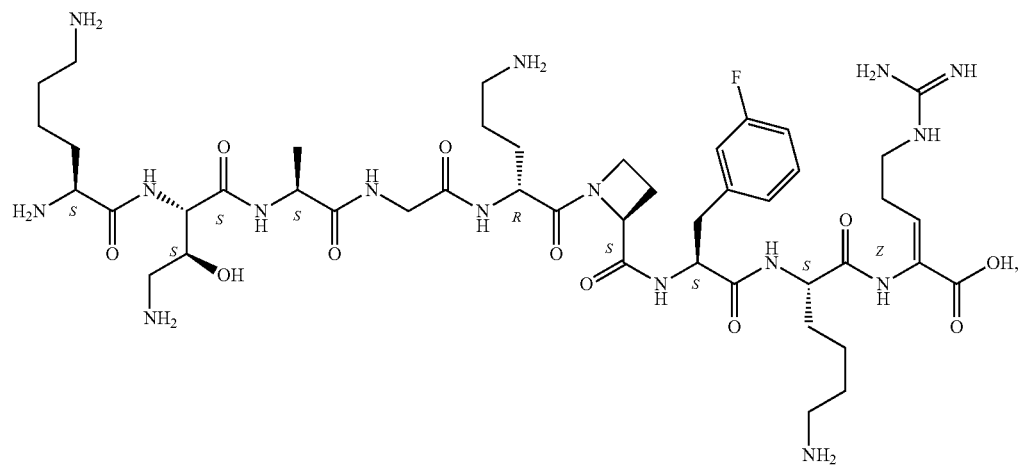

-continued
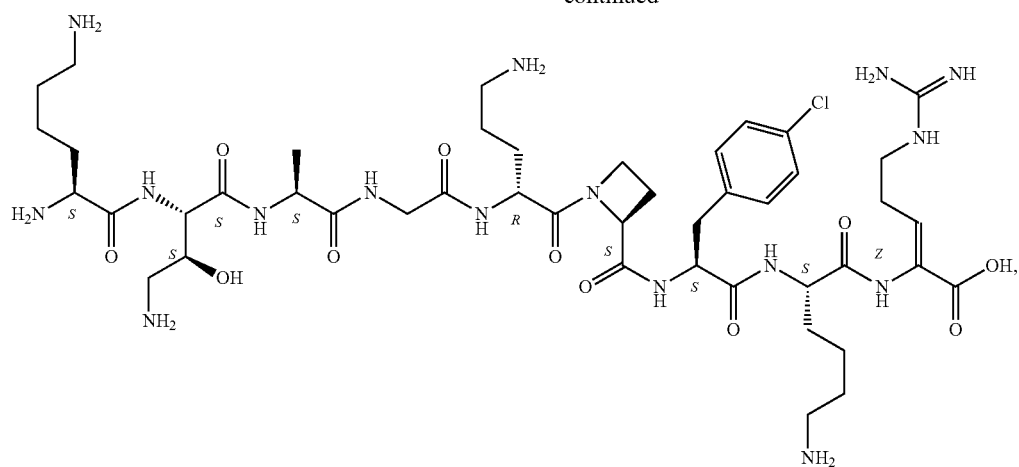
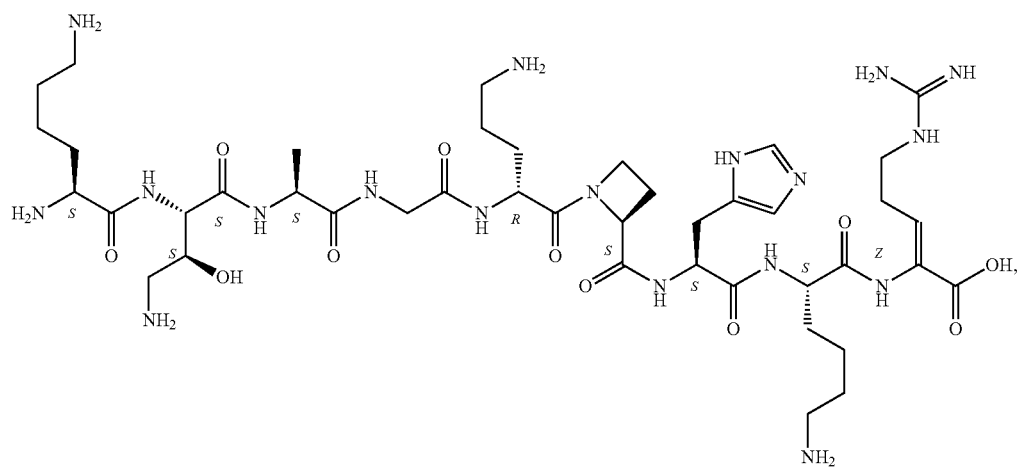
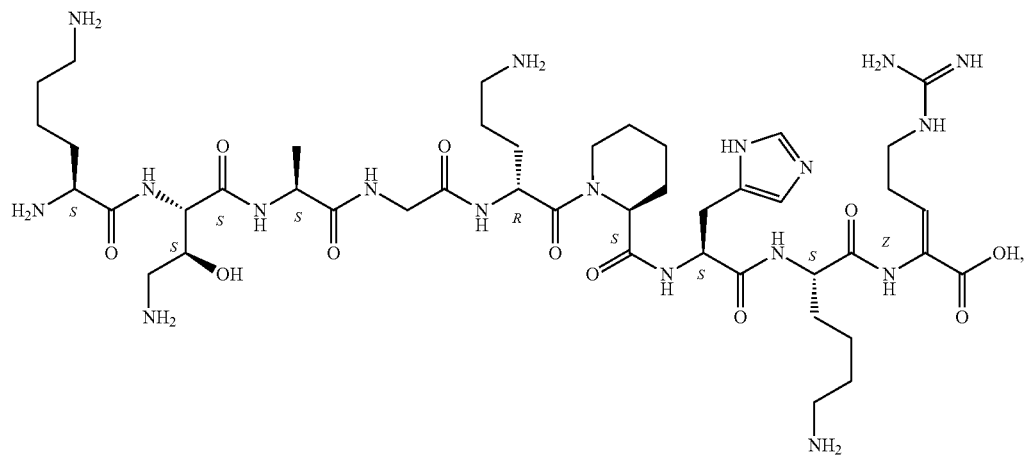

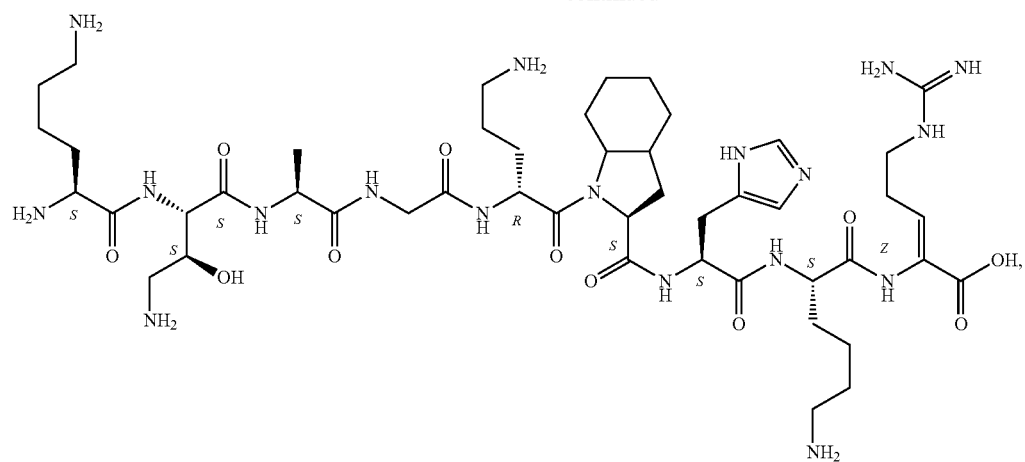
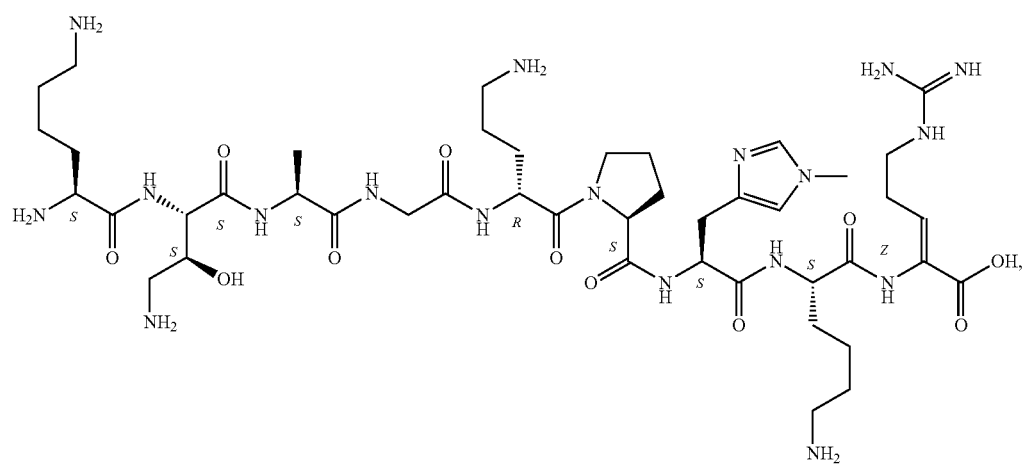
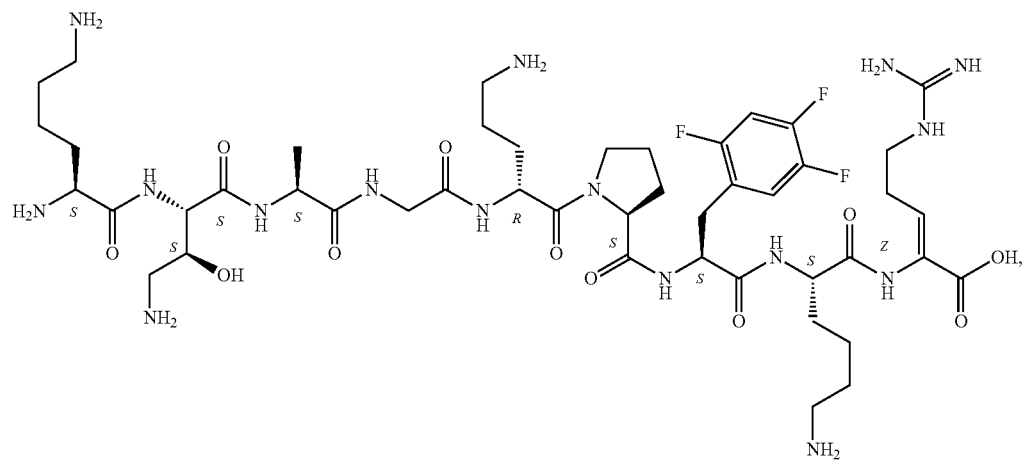

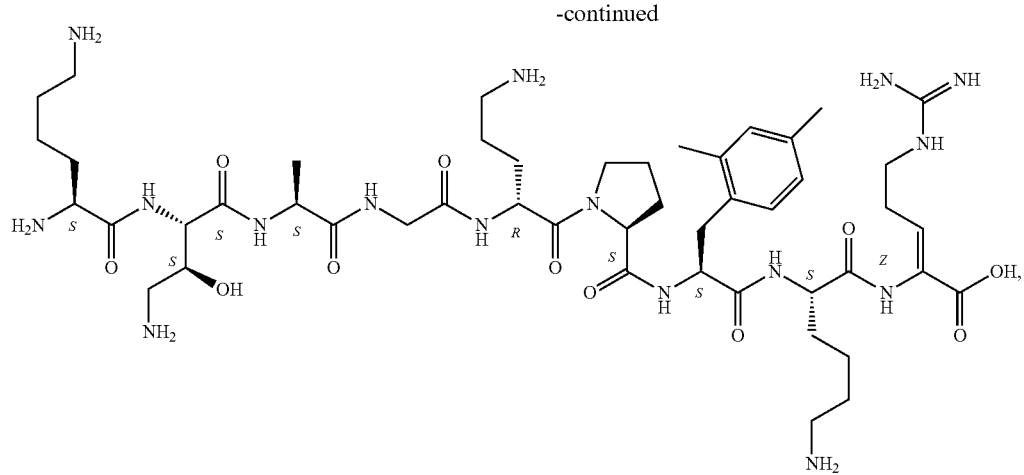
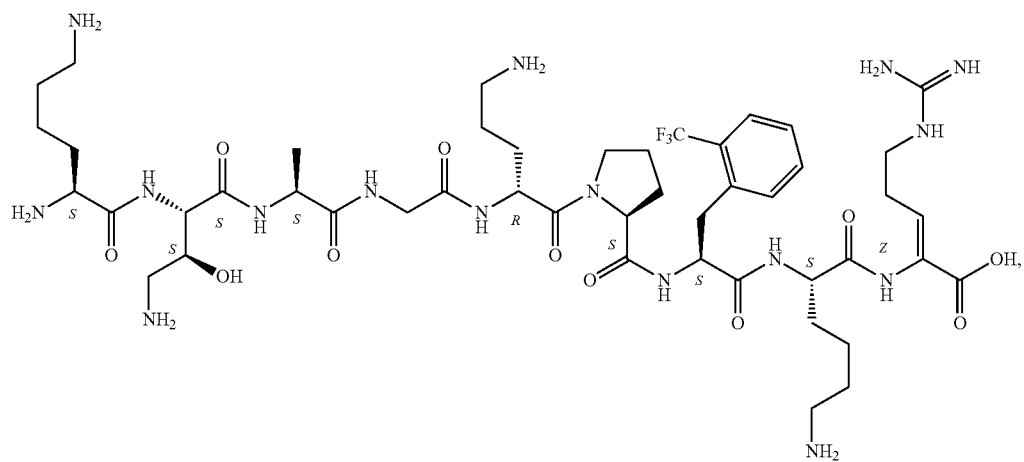
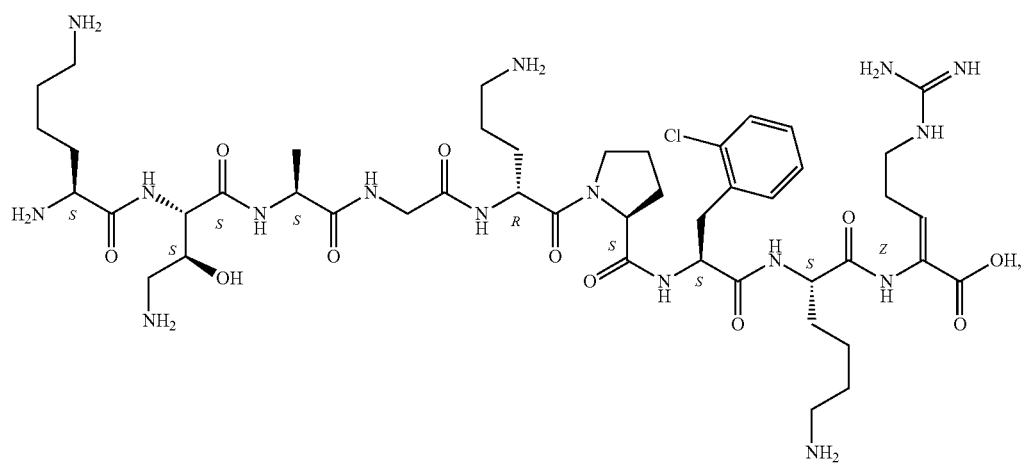

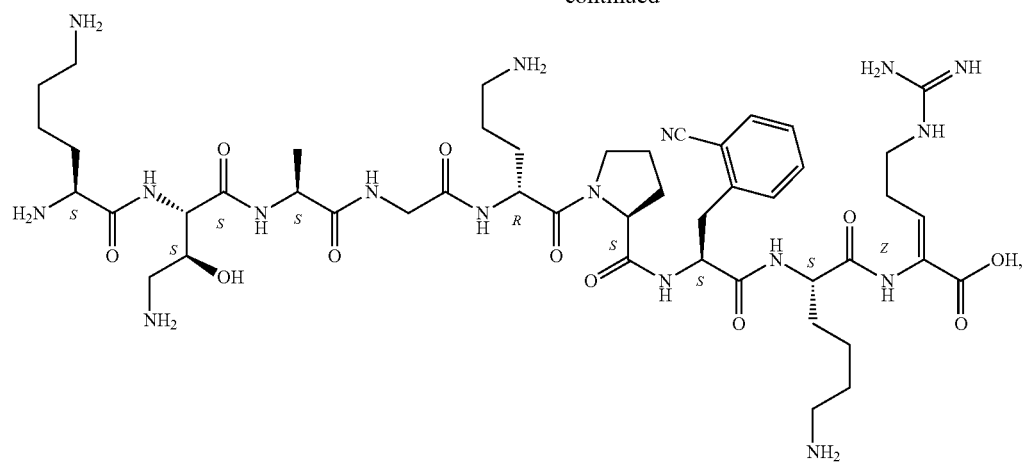
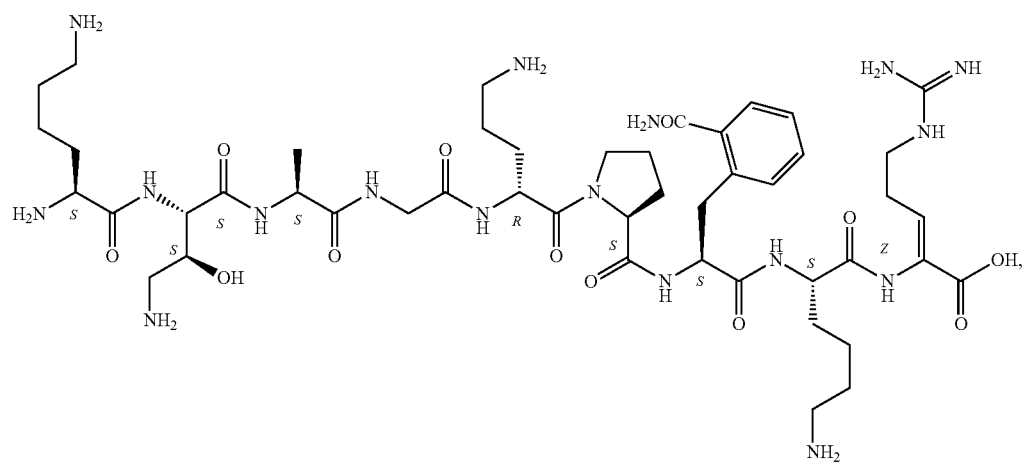
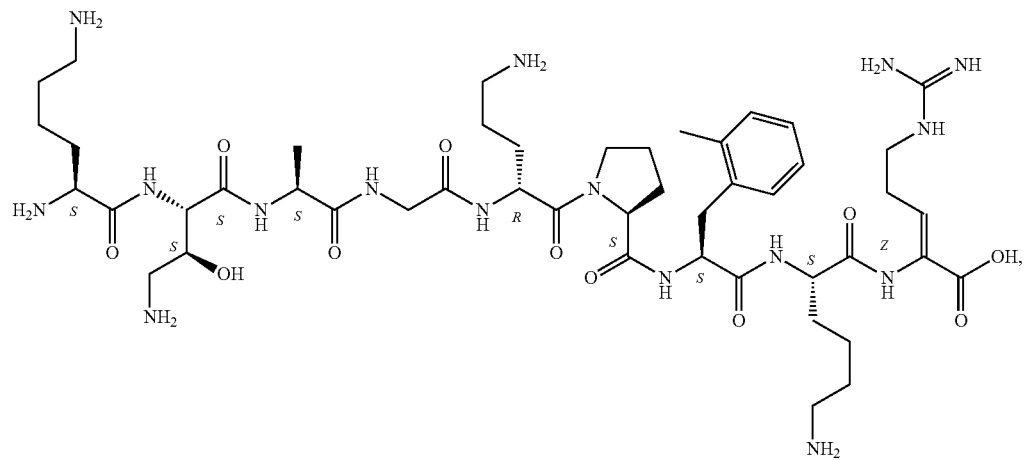

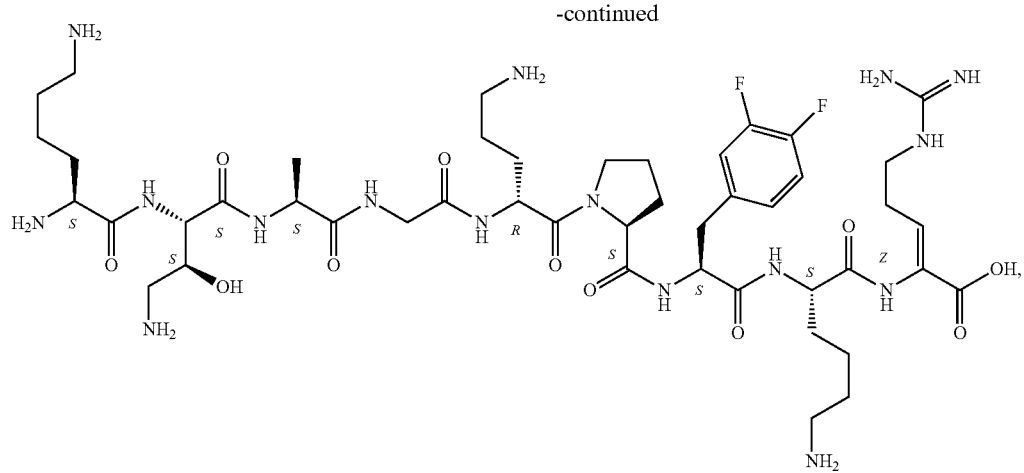
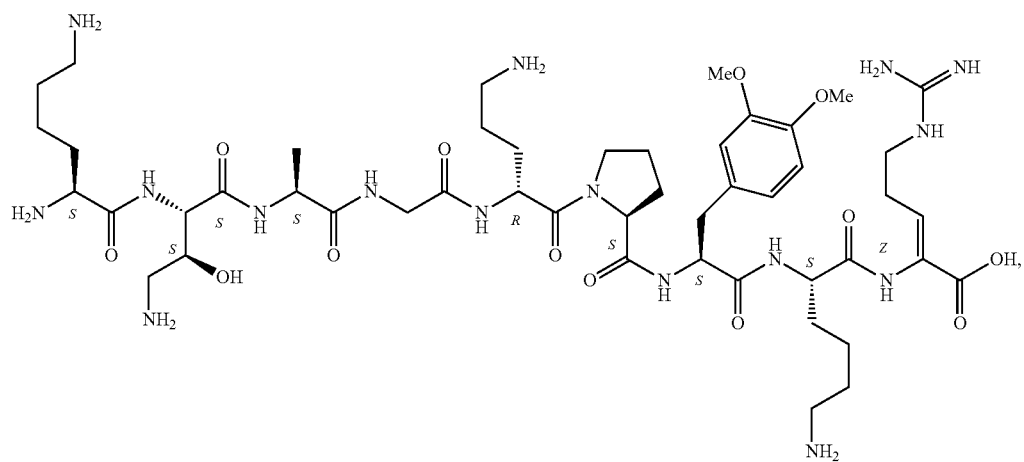
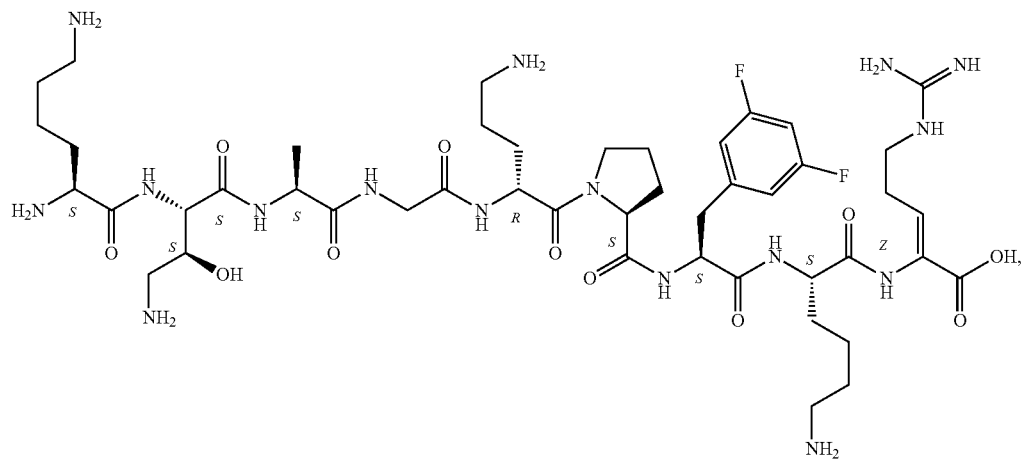

449
450
-continued
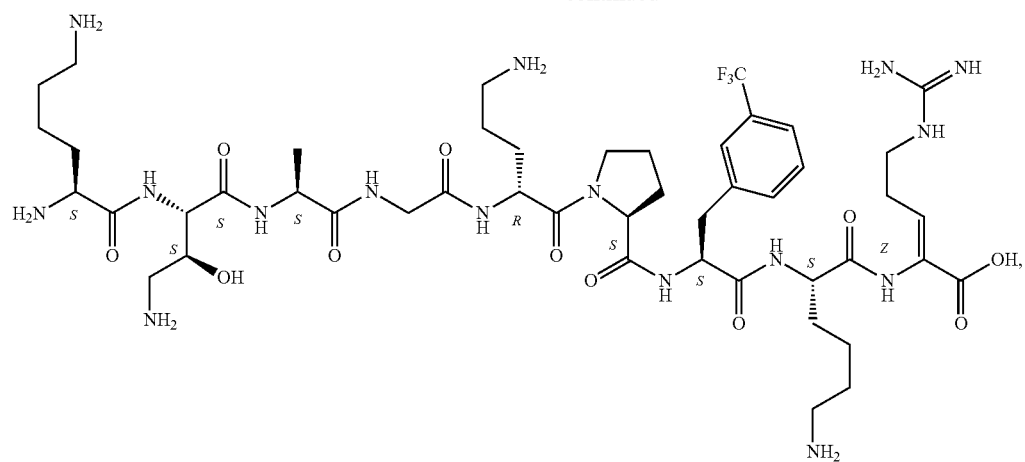
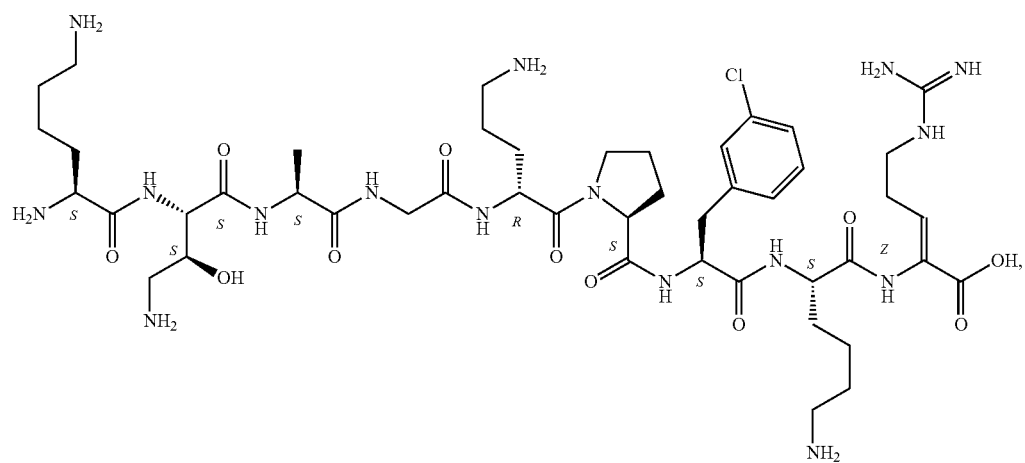
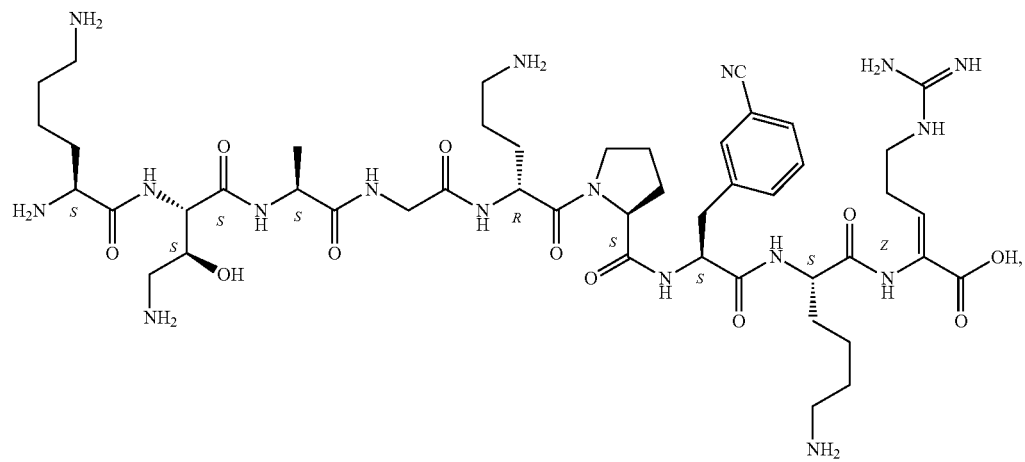

-continued
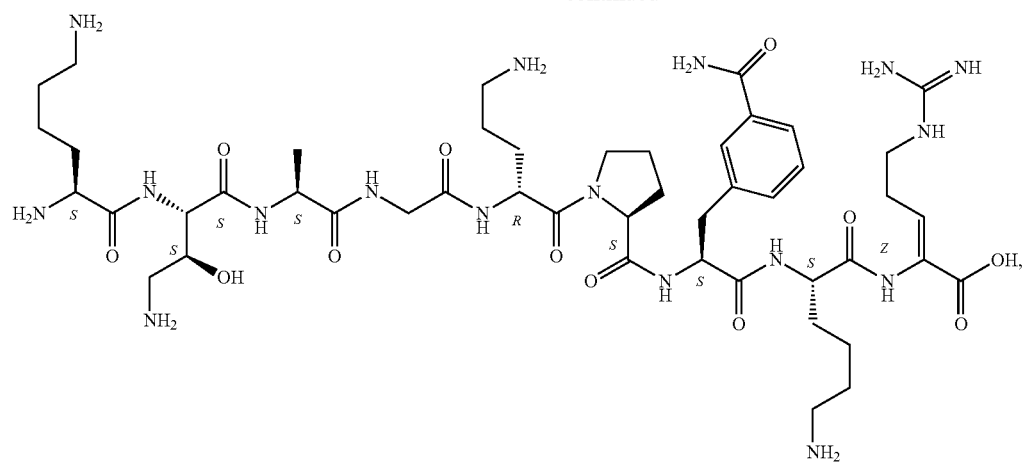
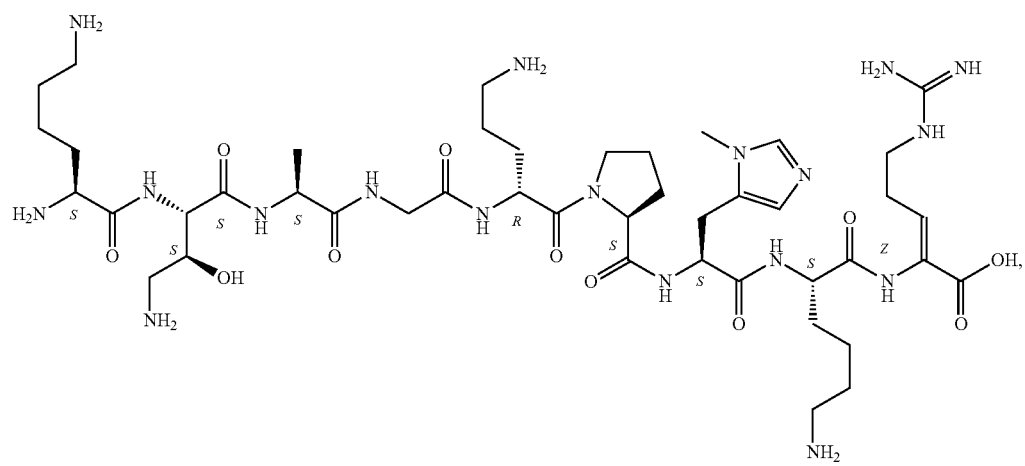
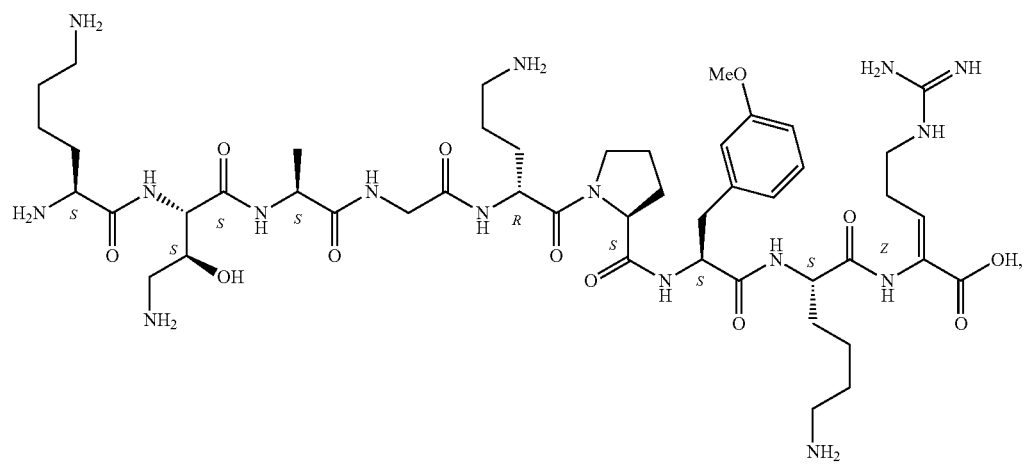

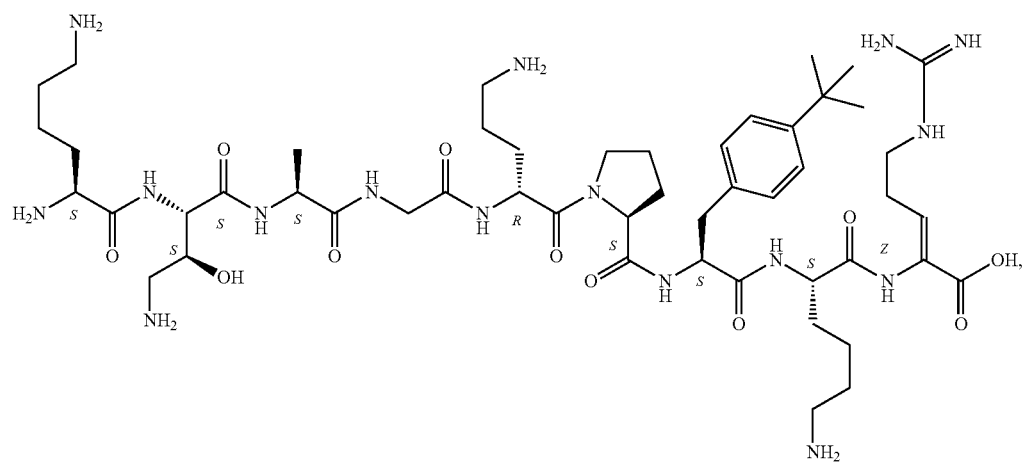
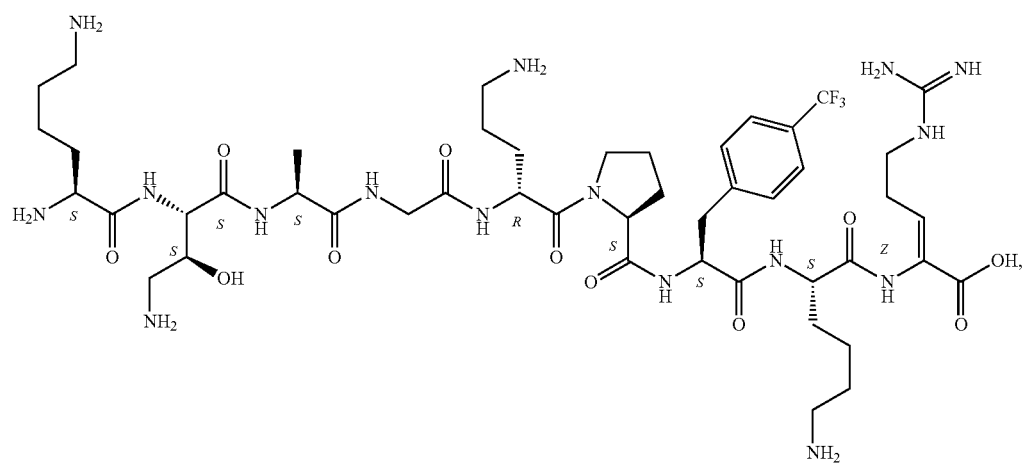
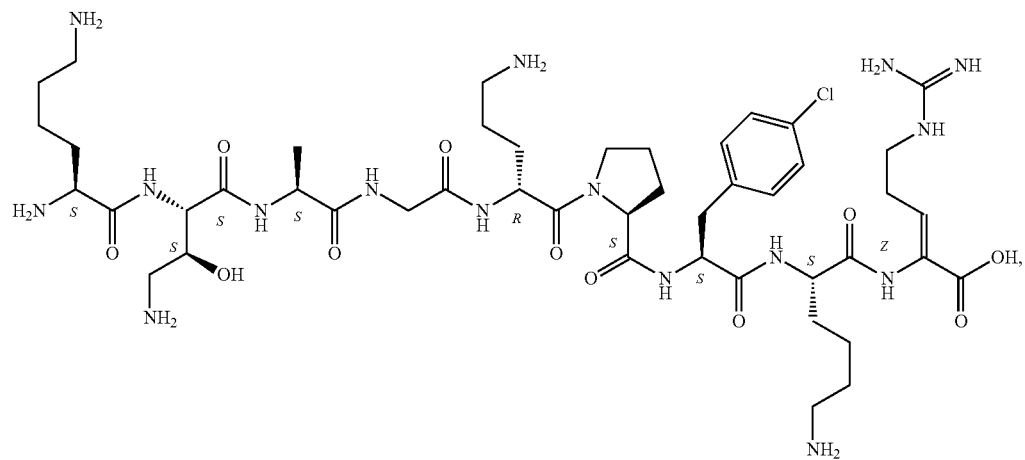

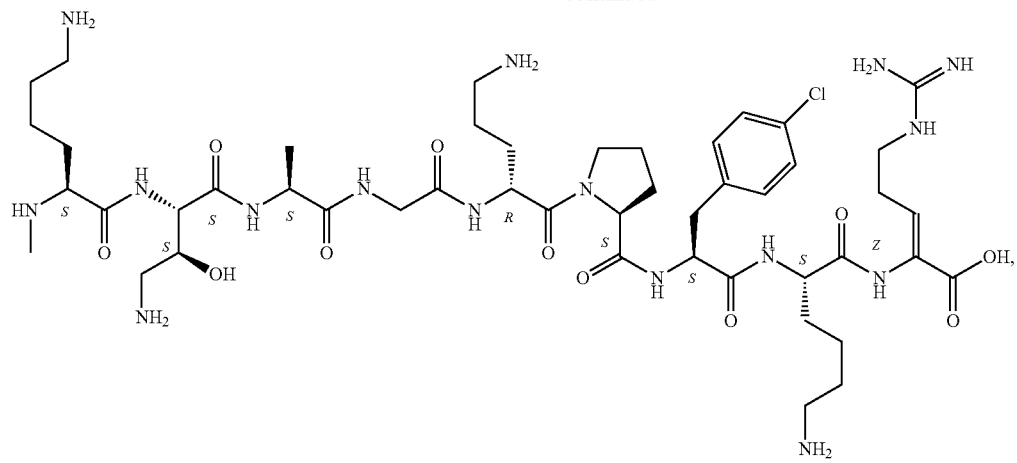
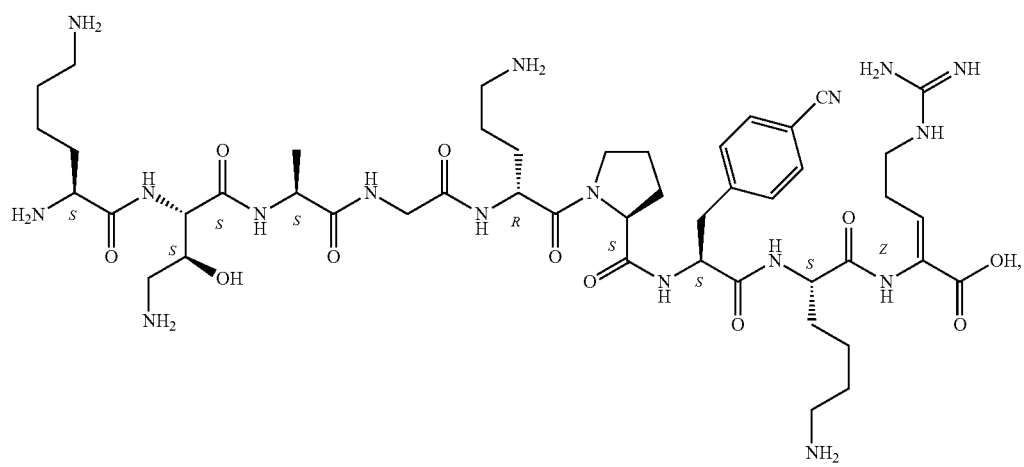
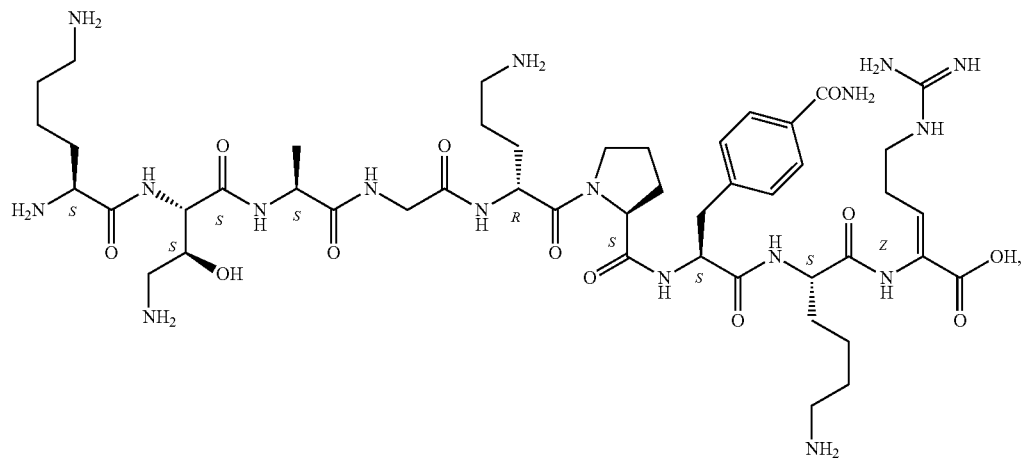

-continued
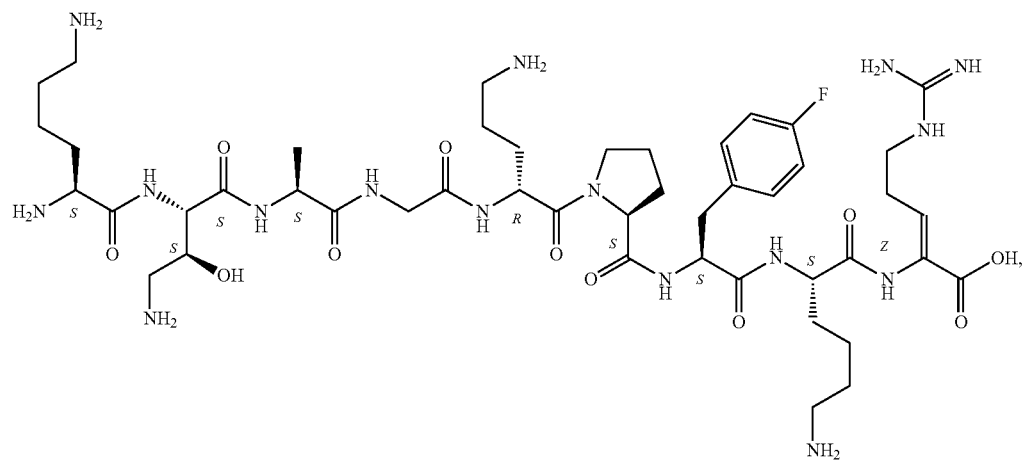
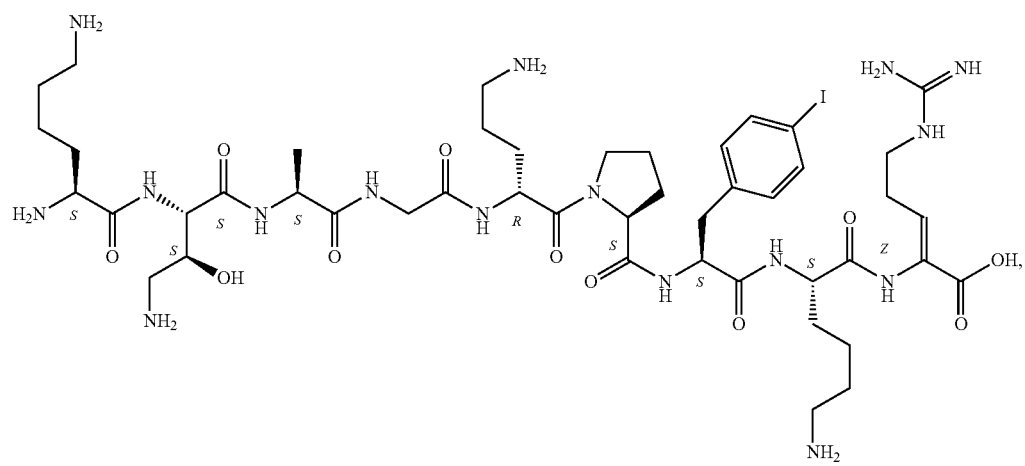
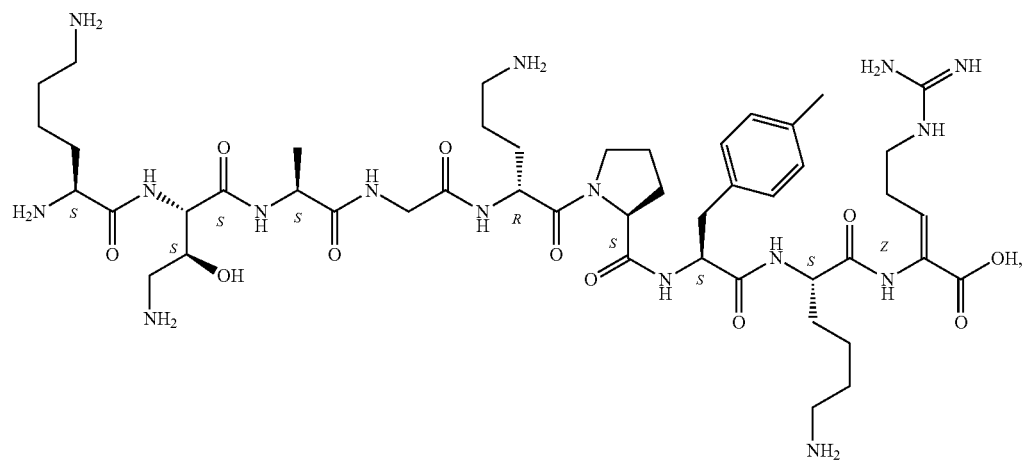

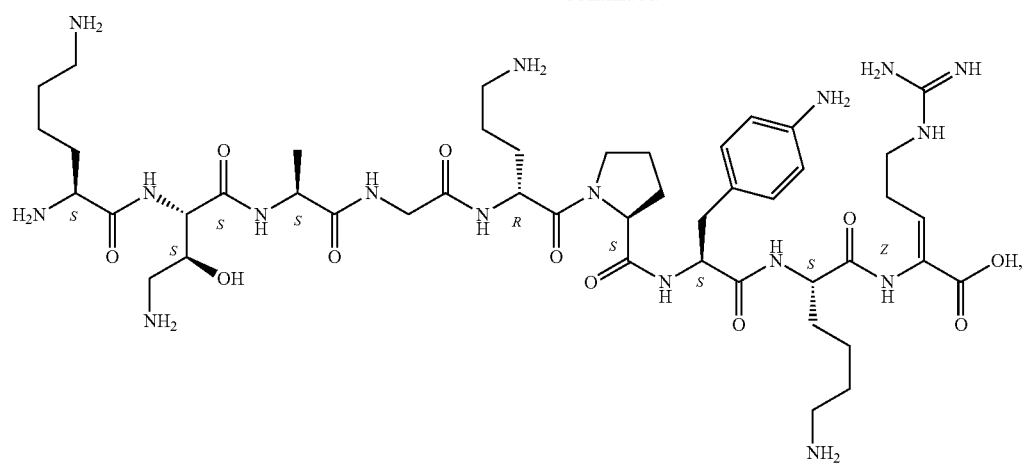
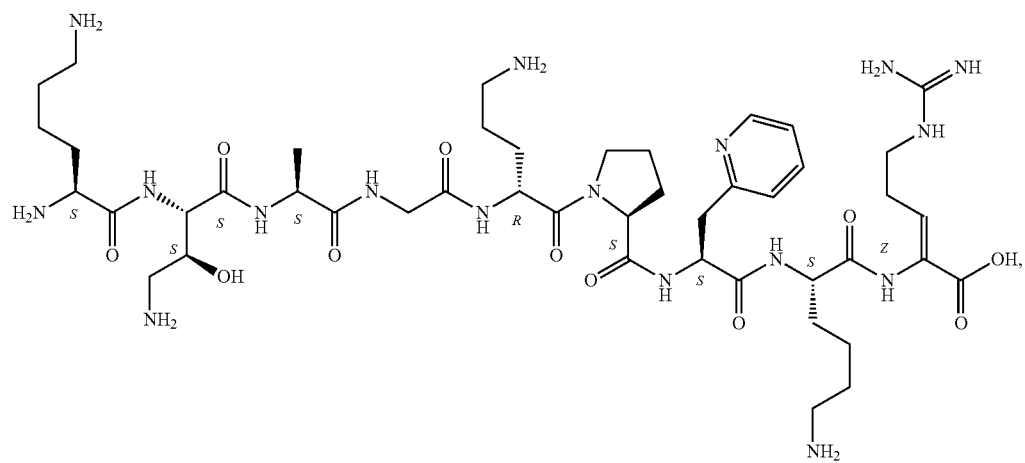
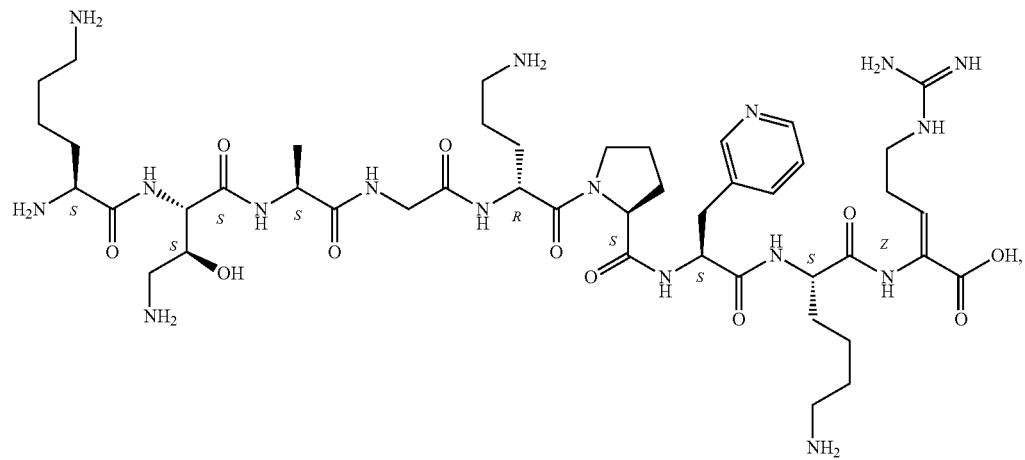

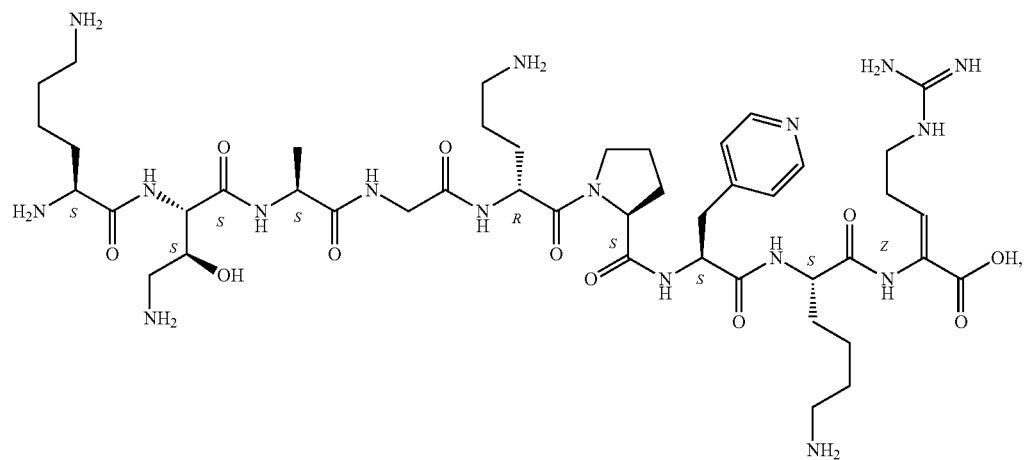
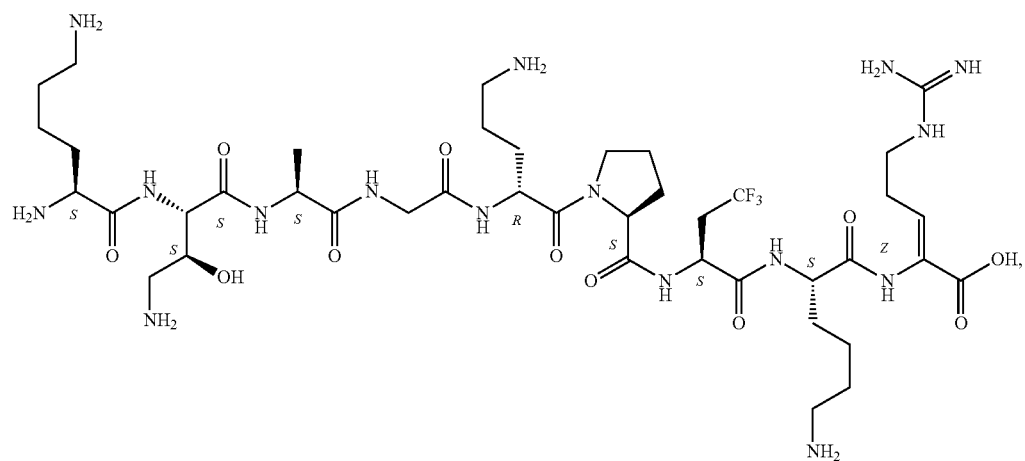
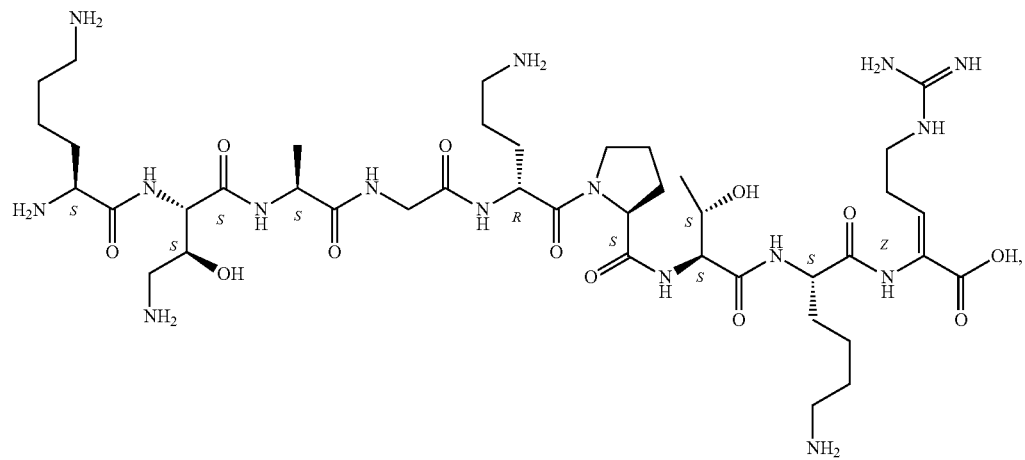

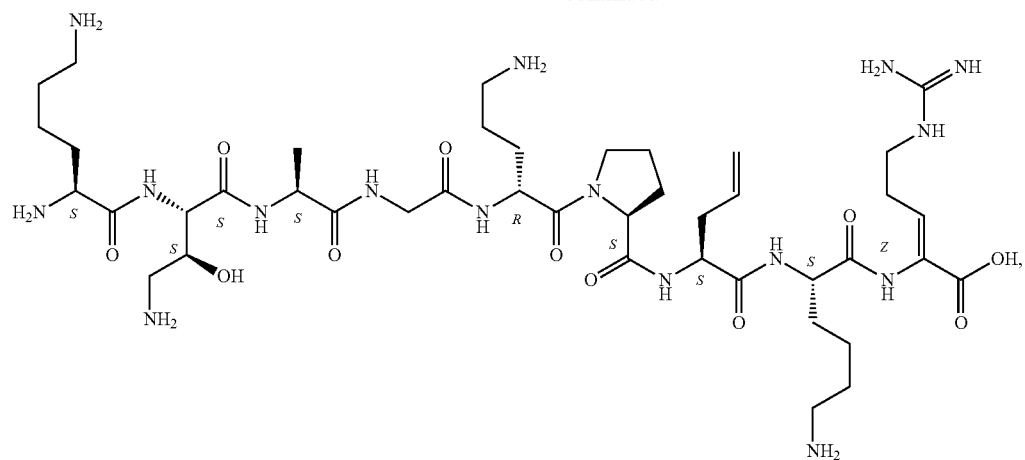
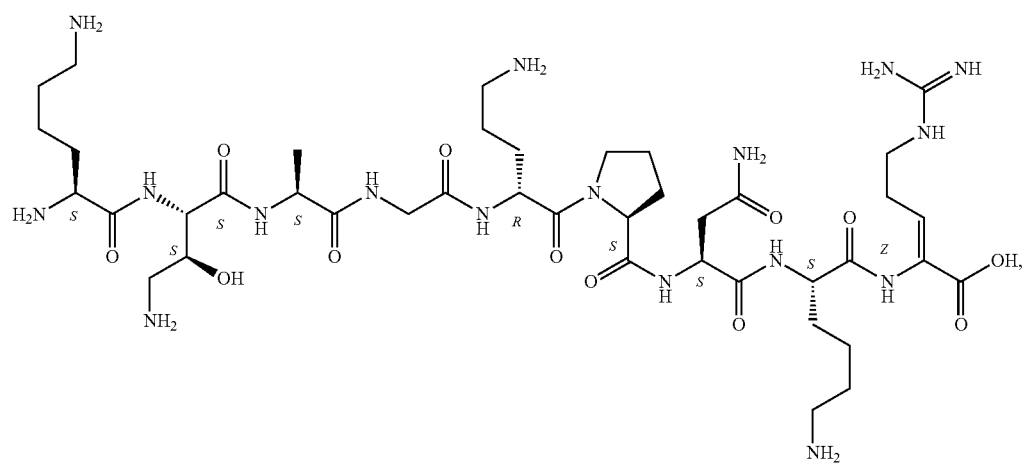
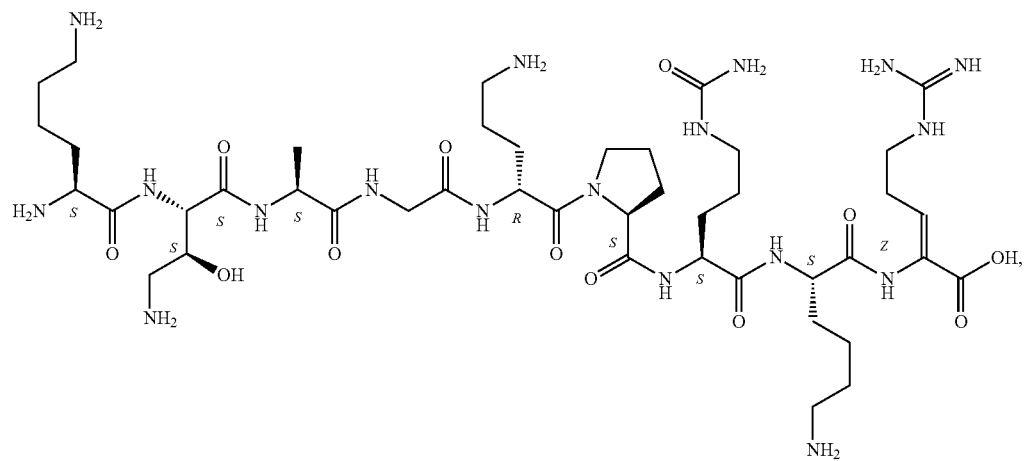

465
466
-continued
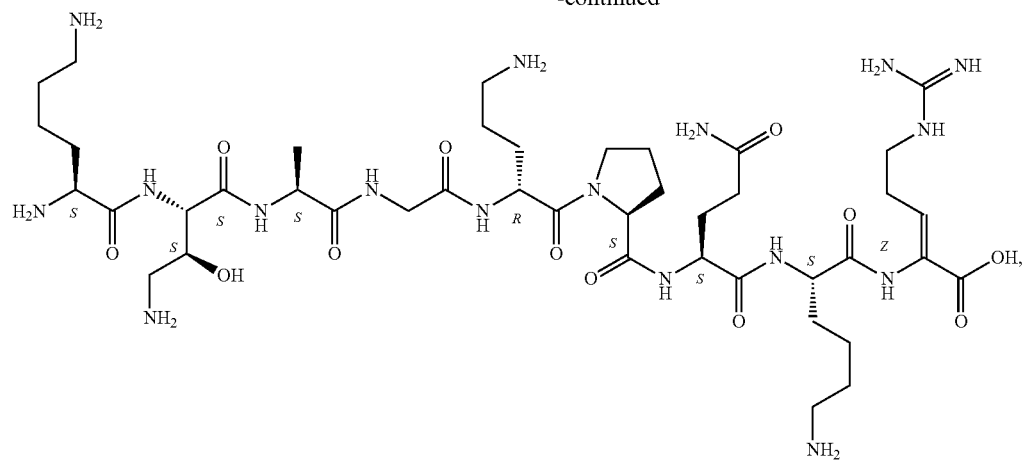
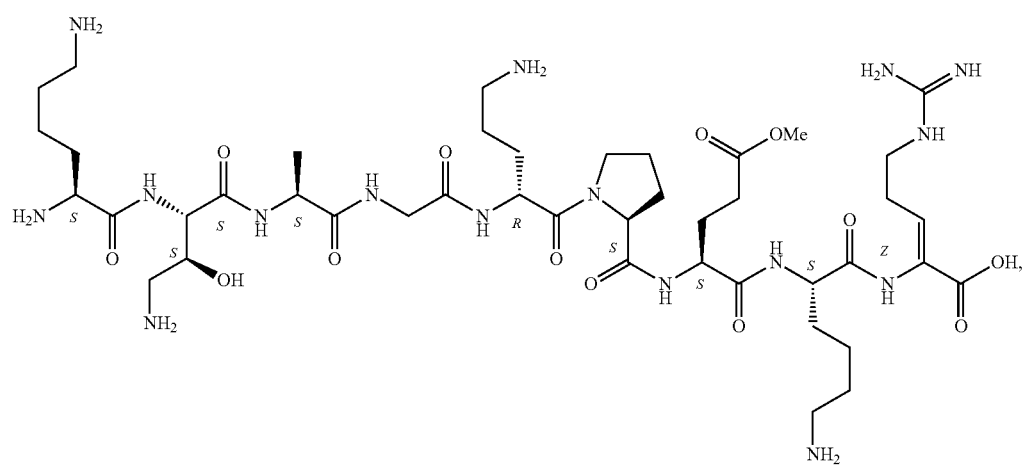
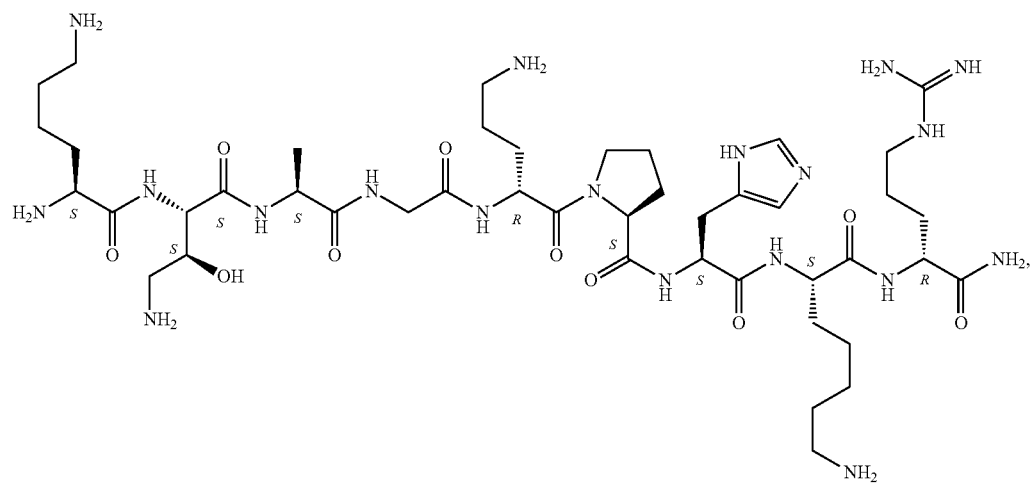

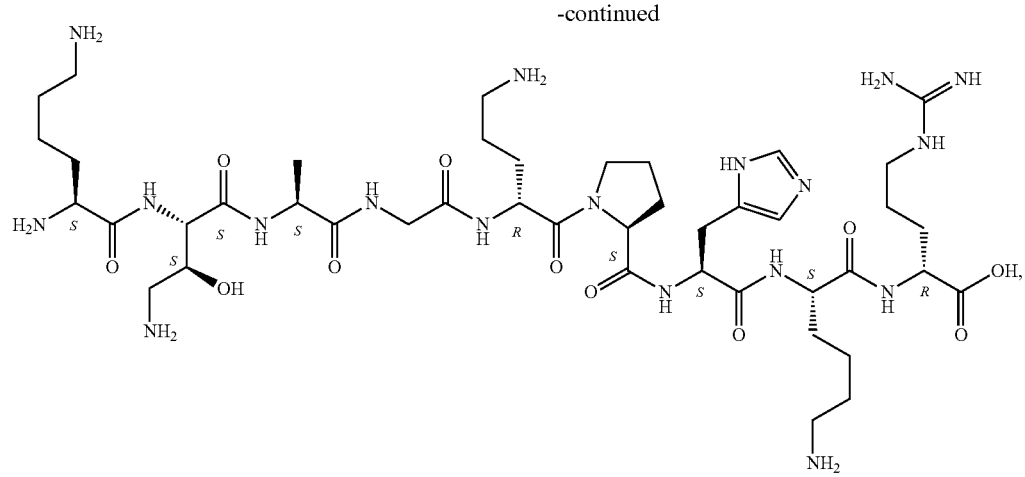
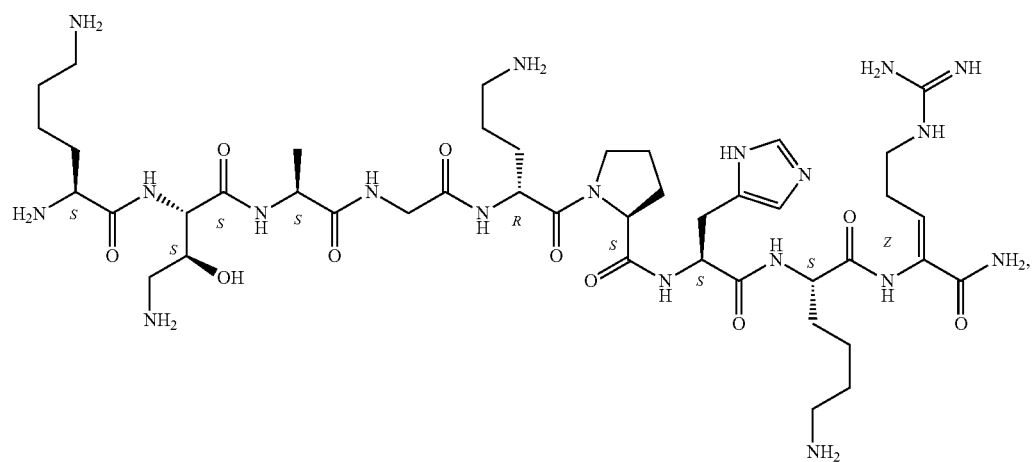
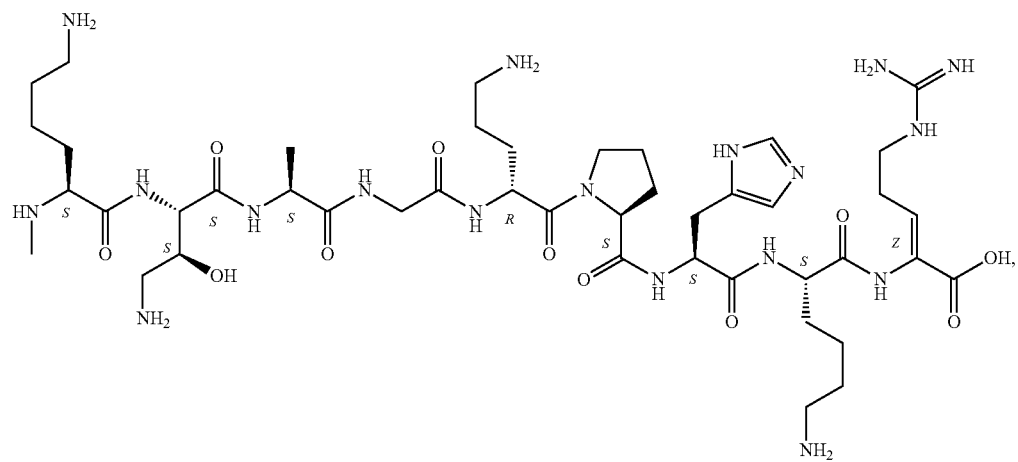

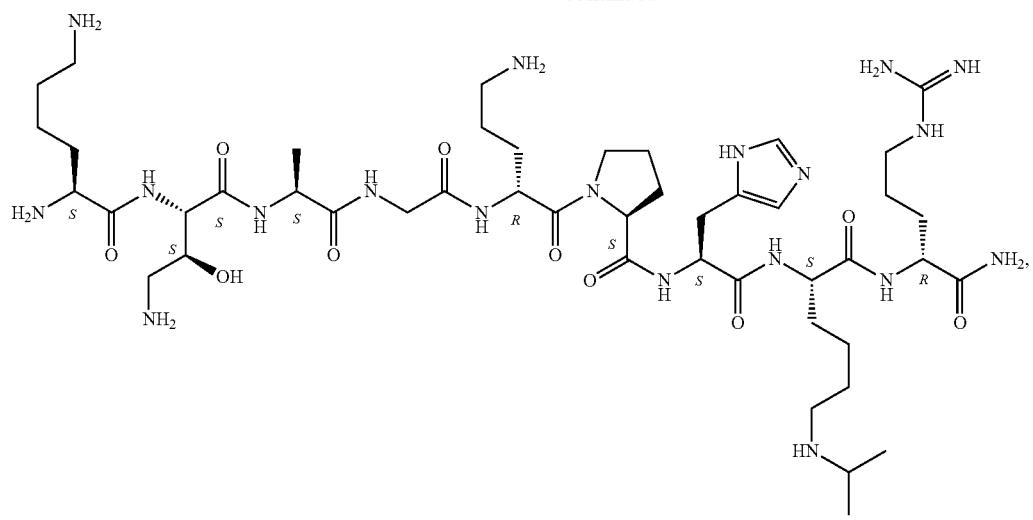
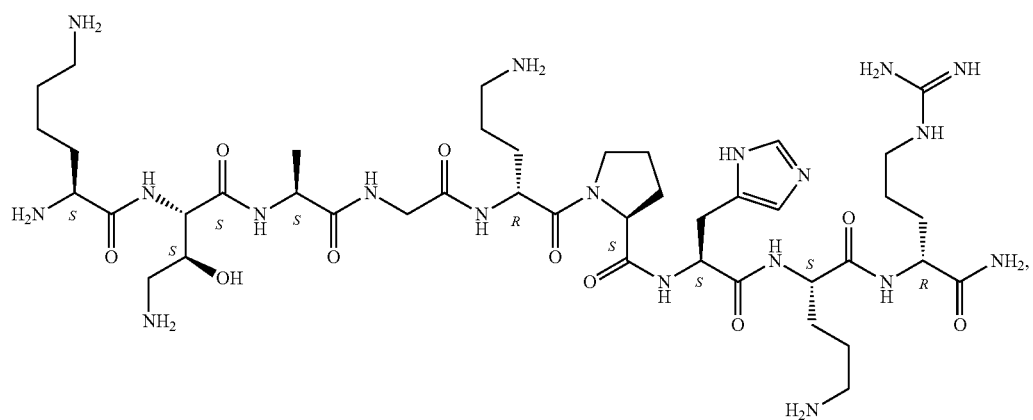
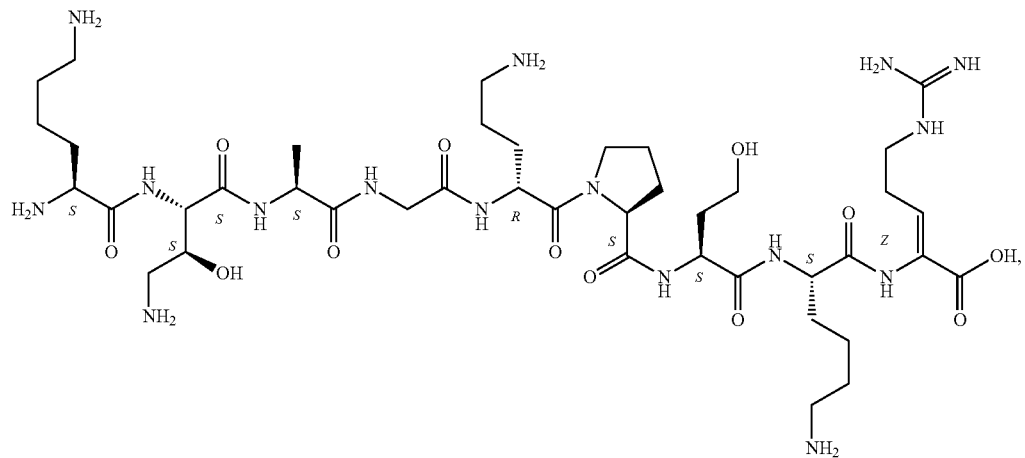

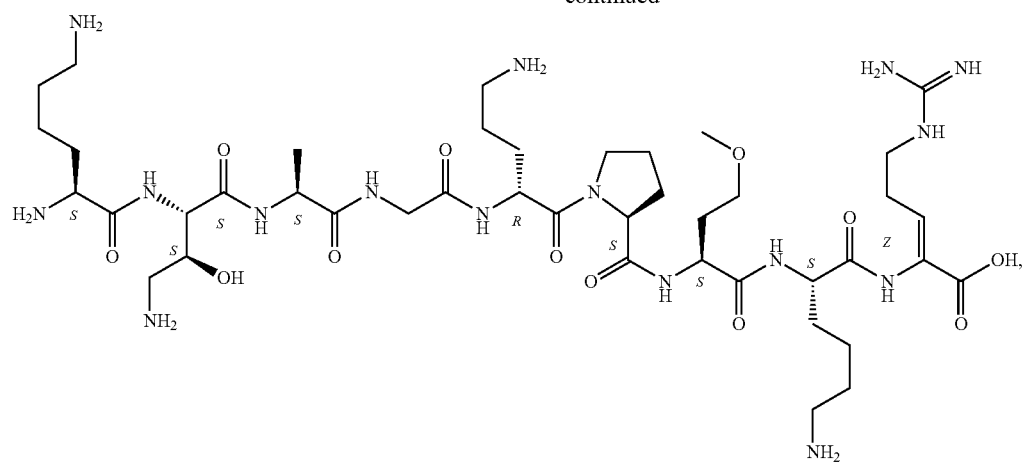
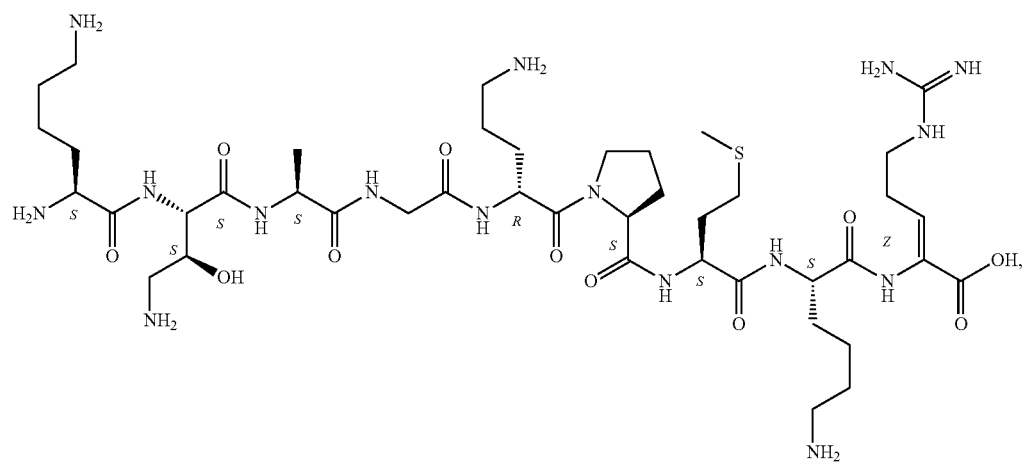
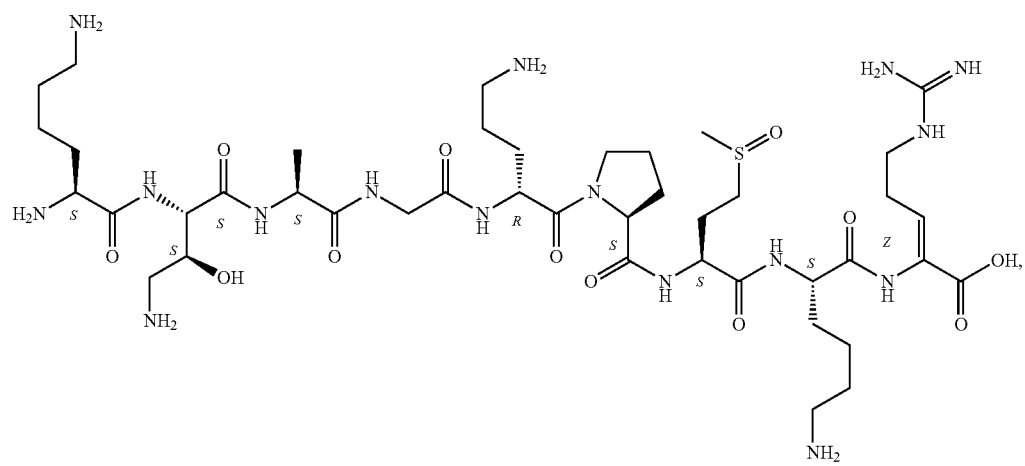

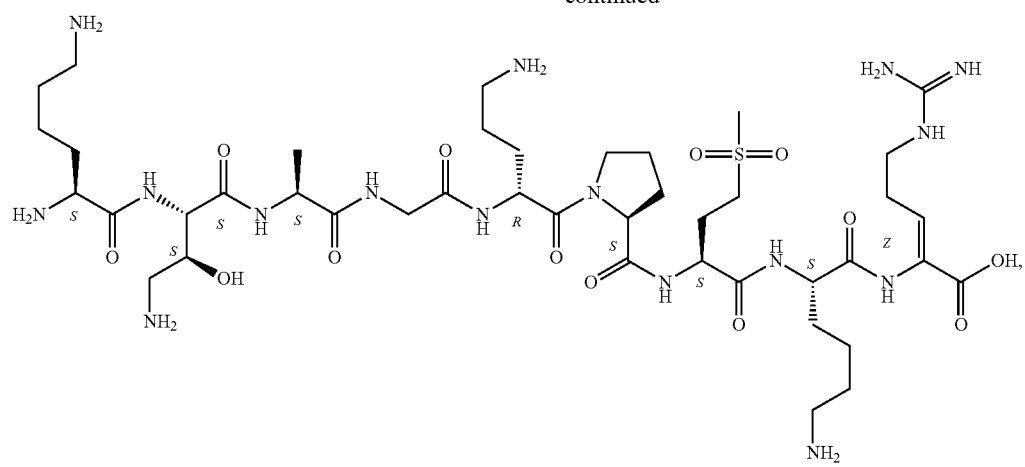
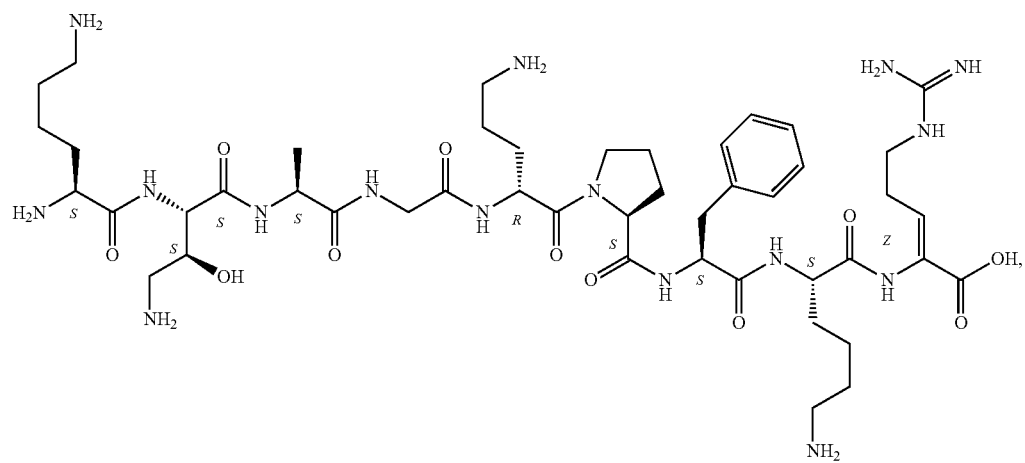
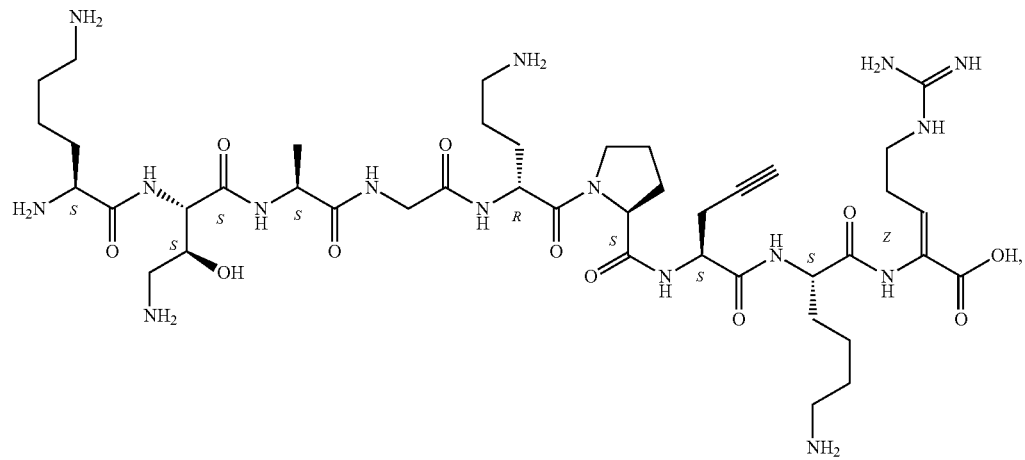

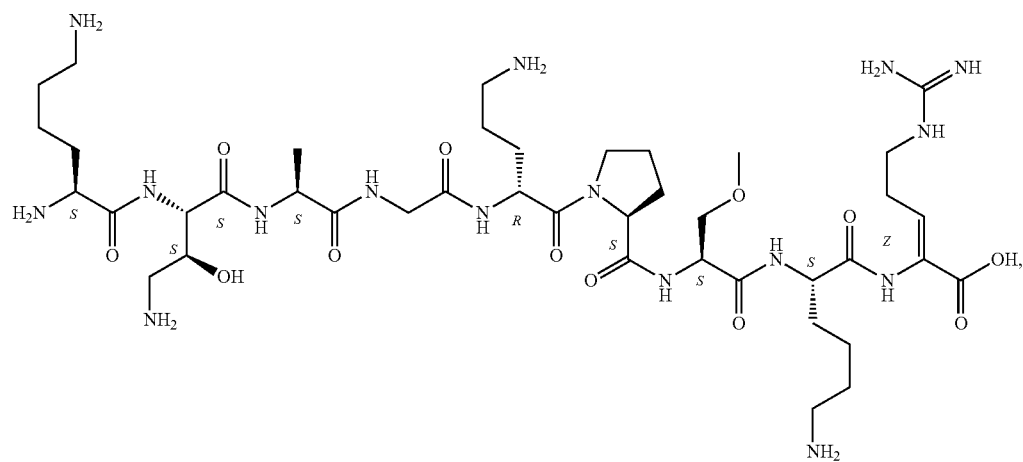
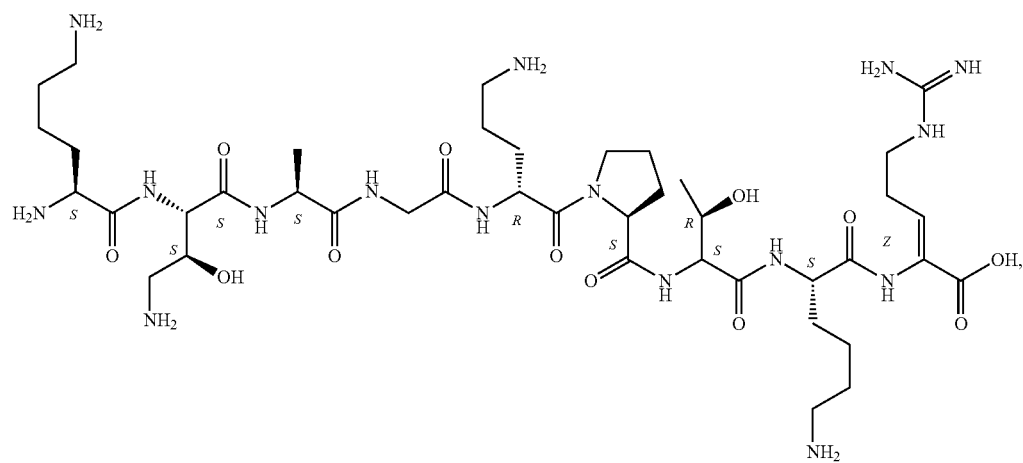
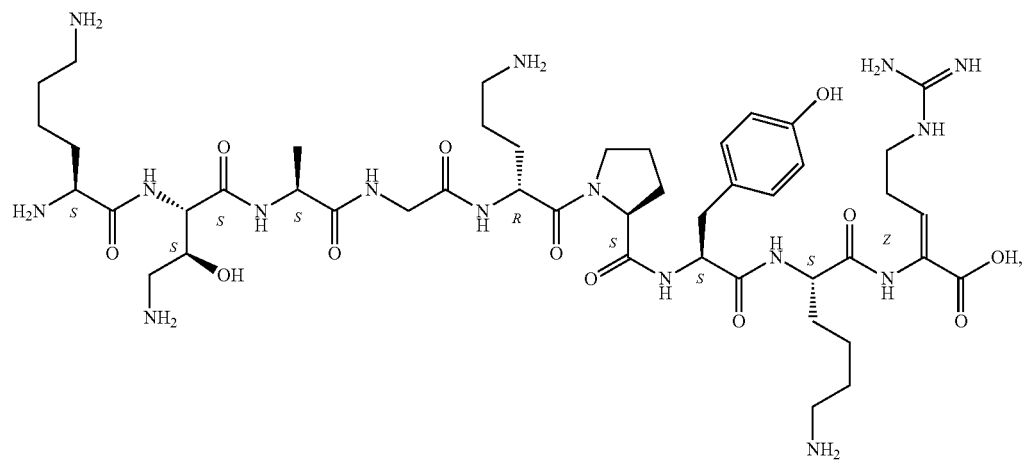

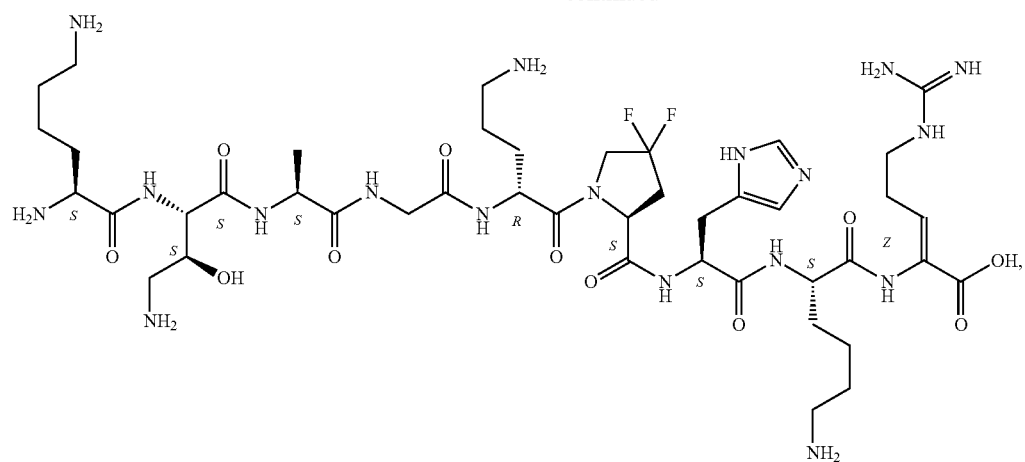
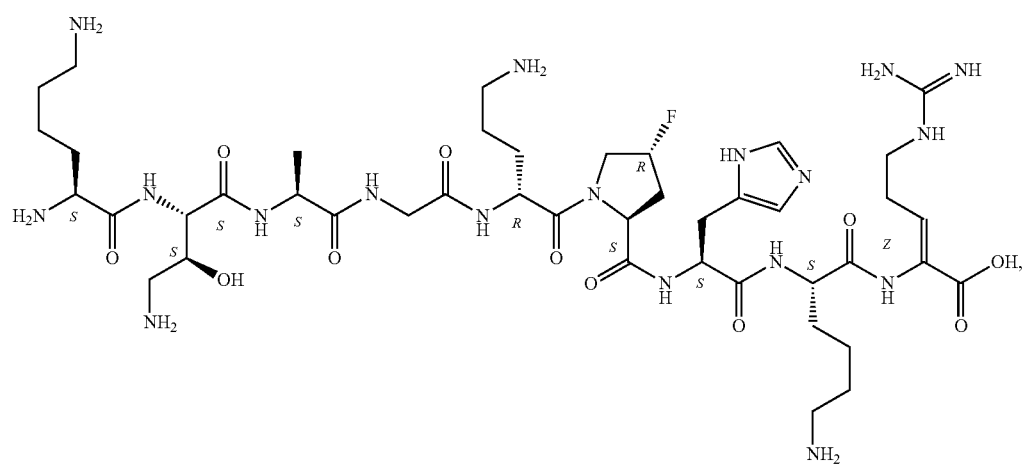
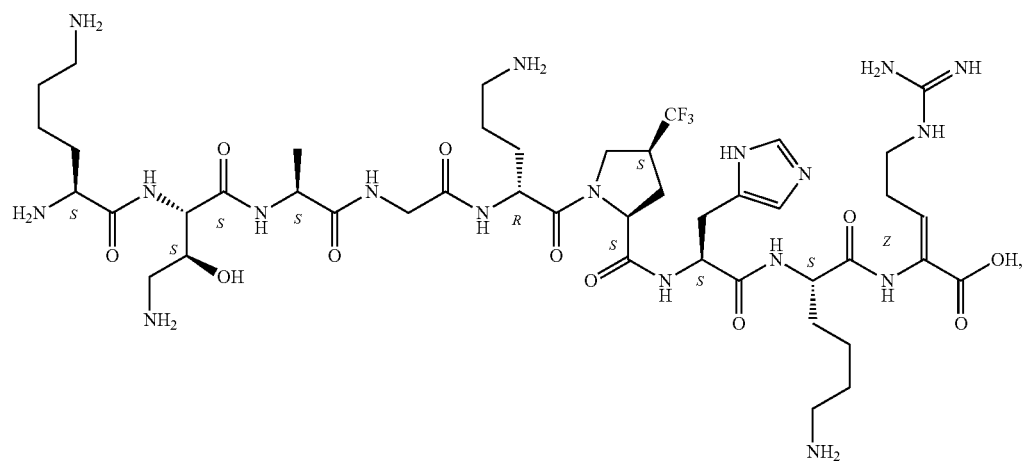

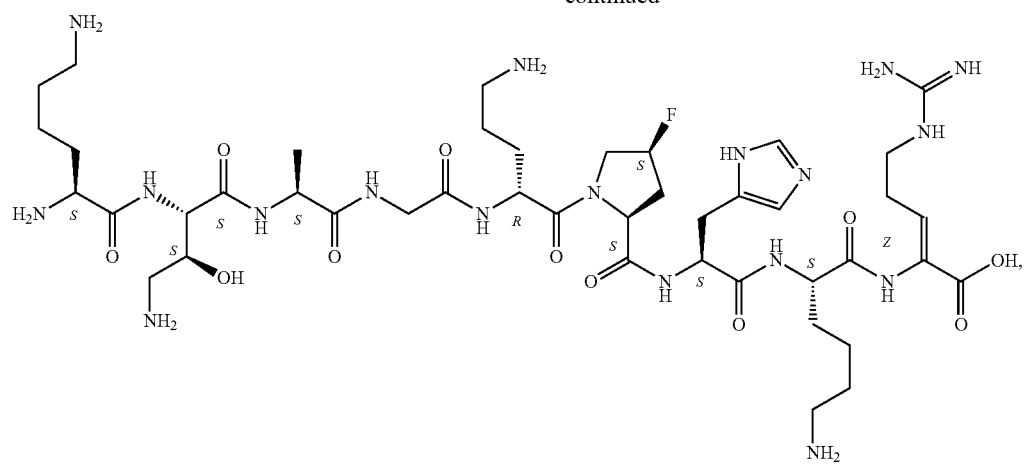
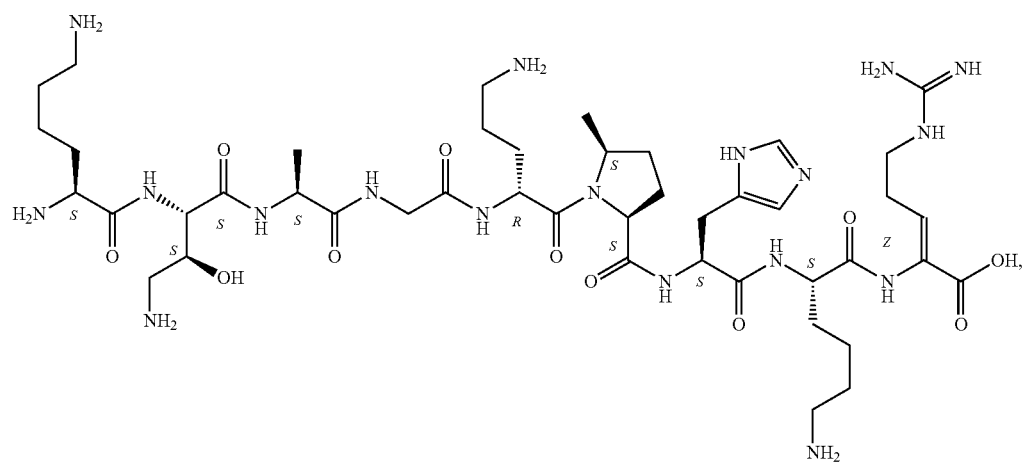
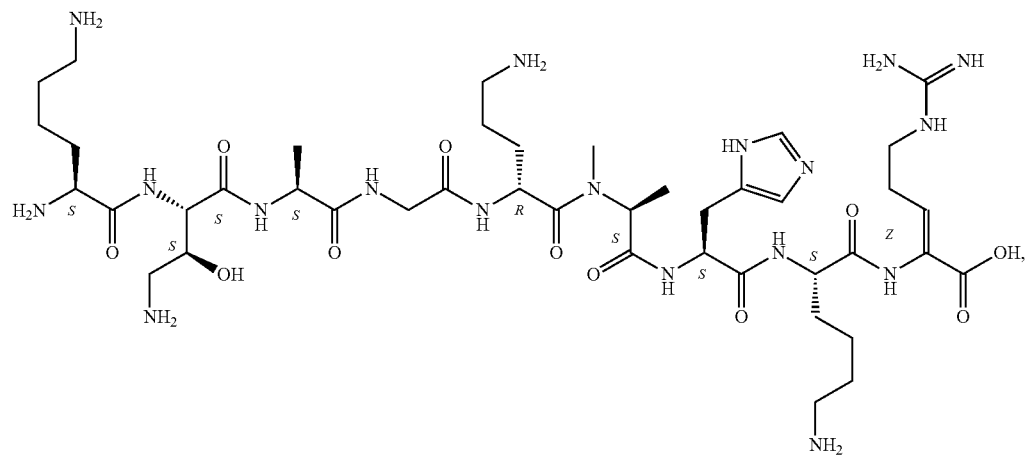

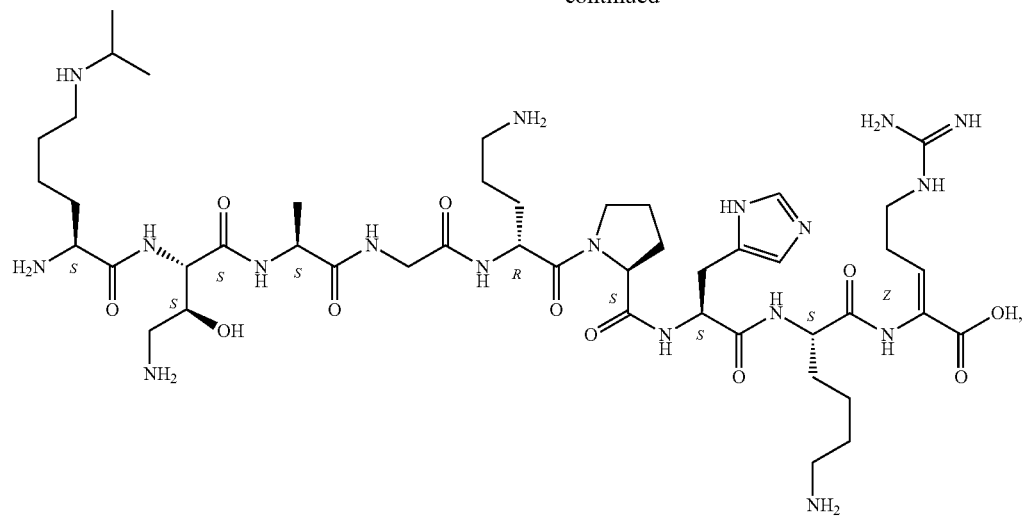
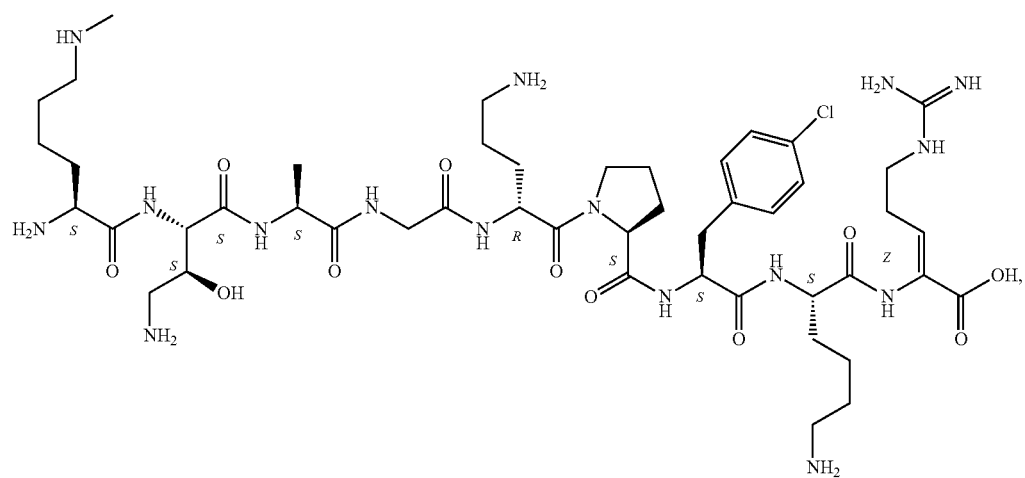
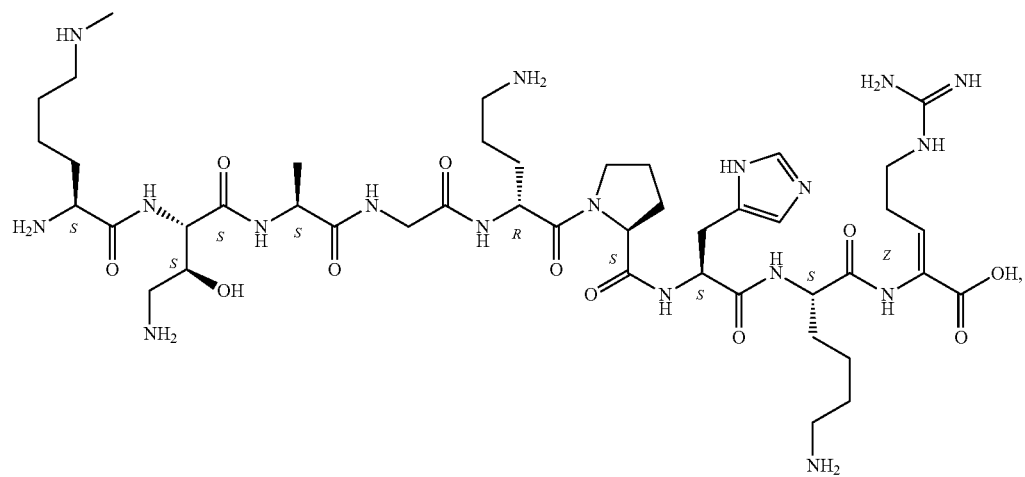

-continued
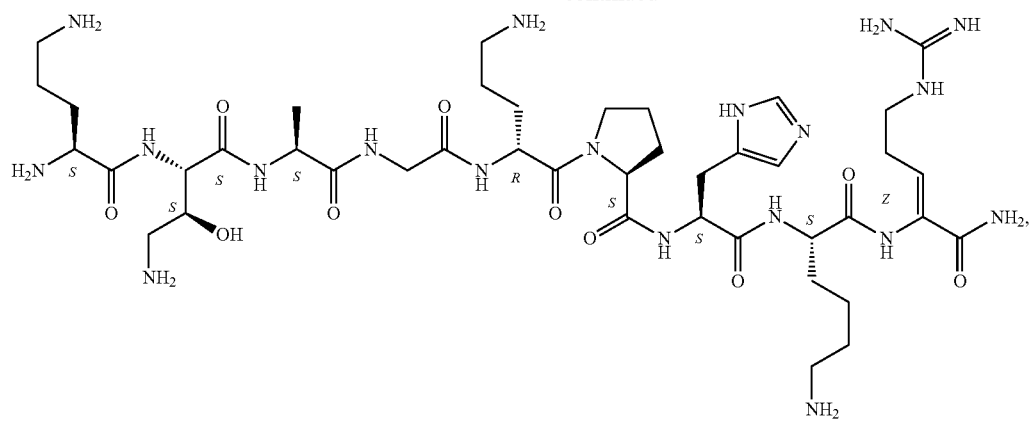
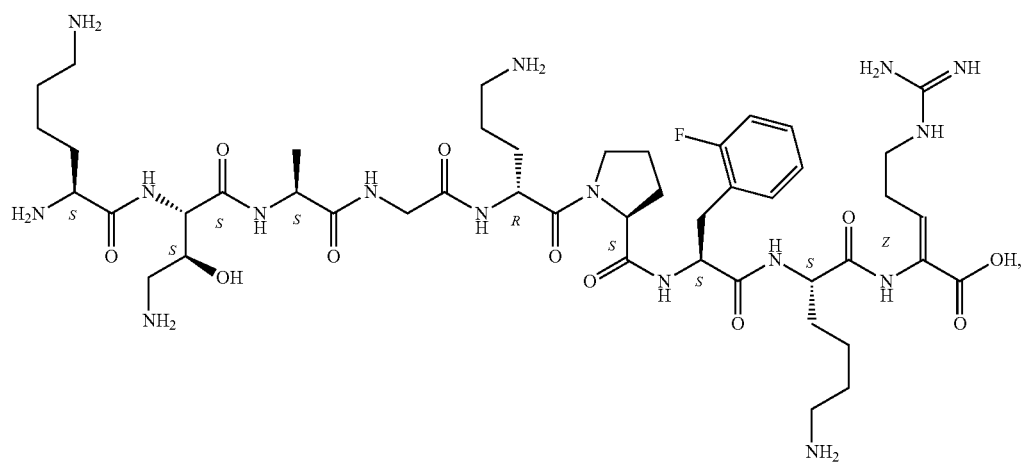
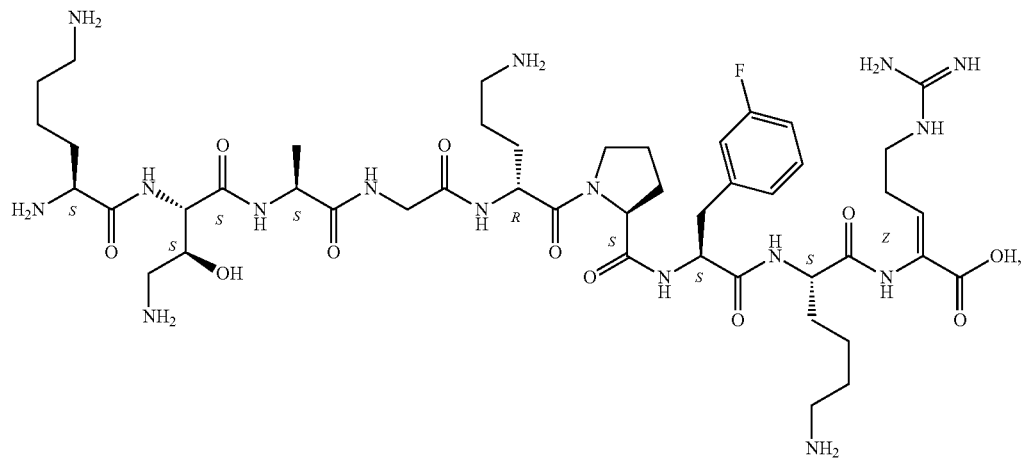

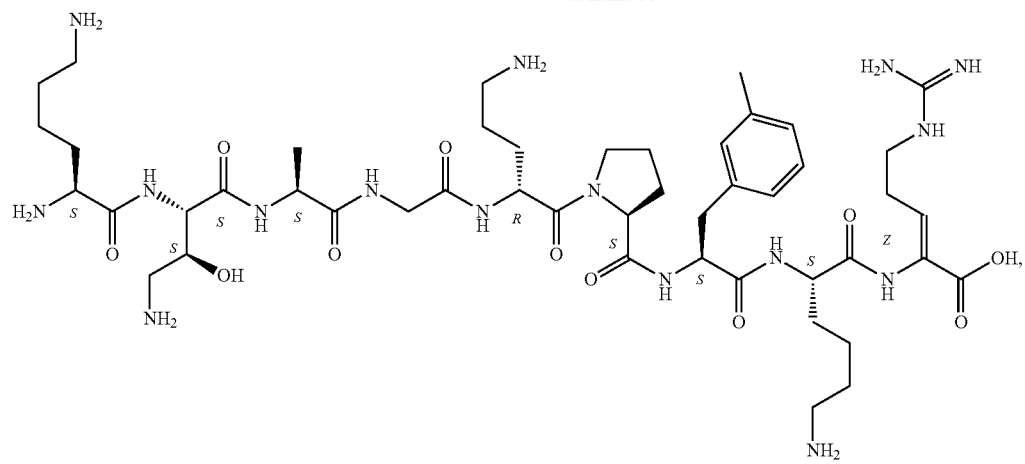
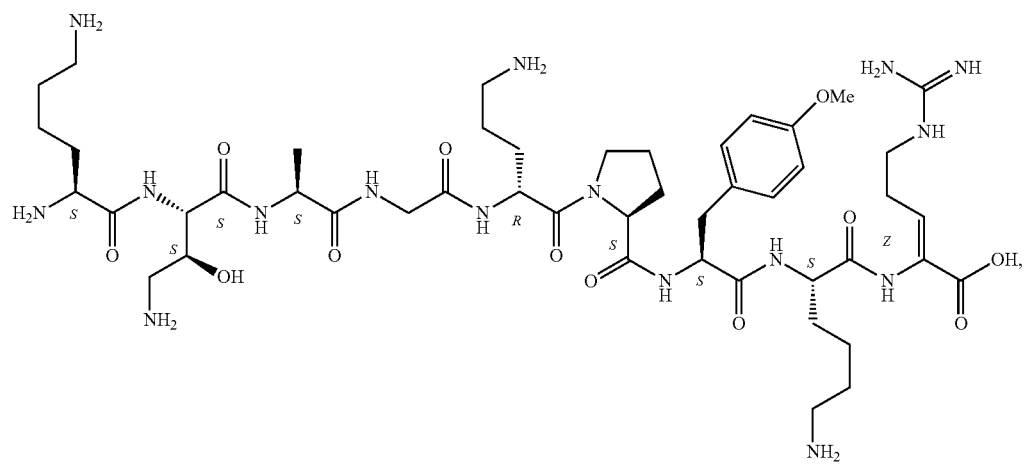
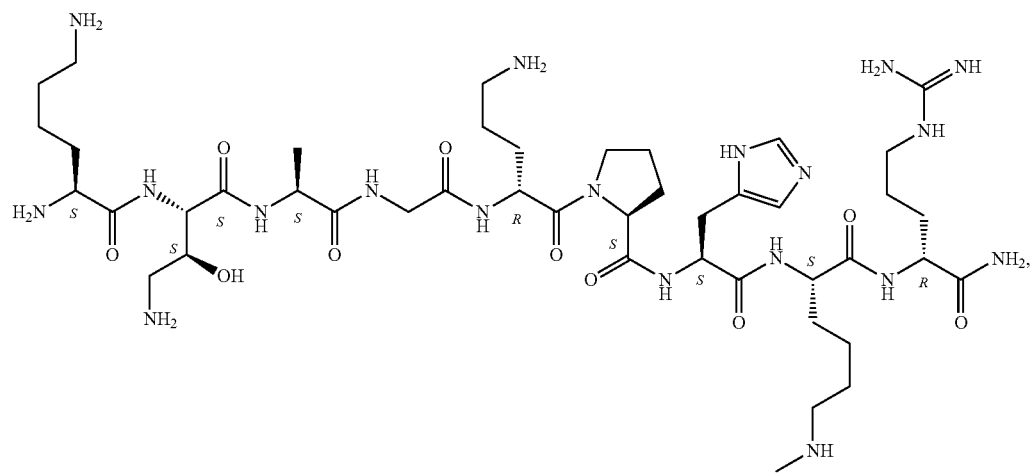

-continued
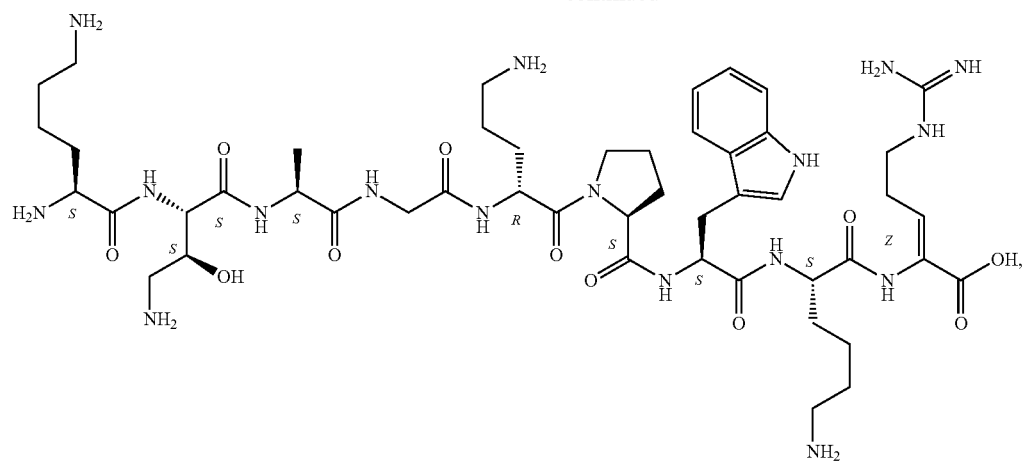
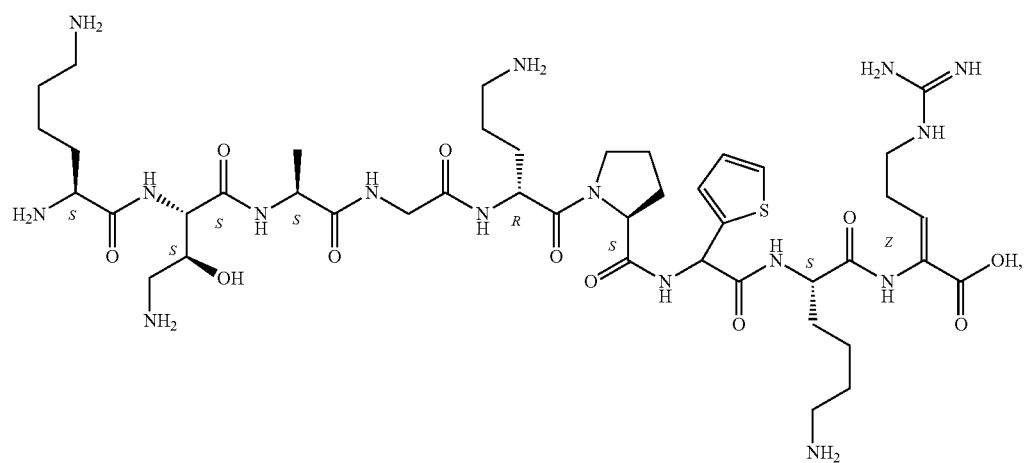
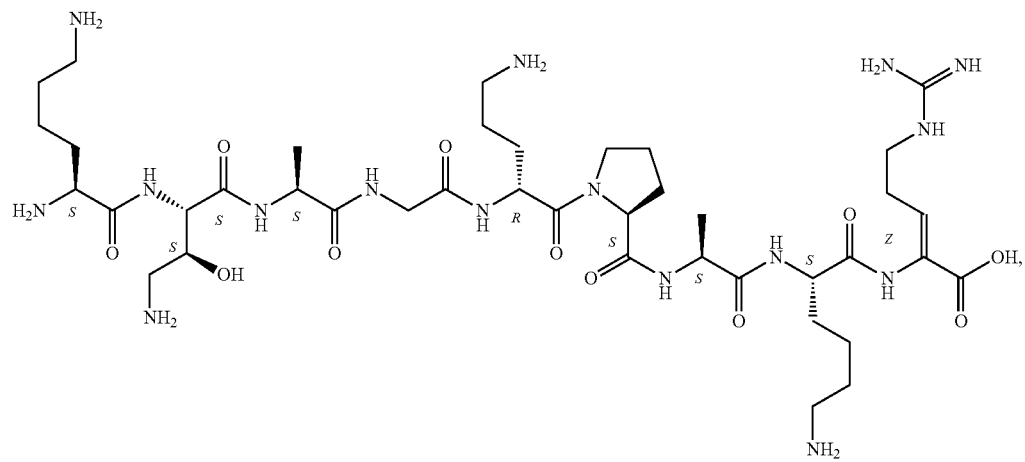

489
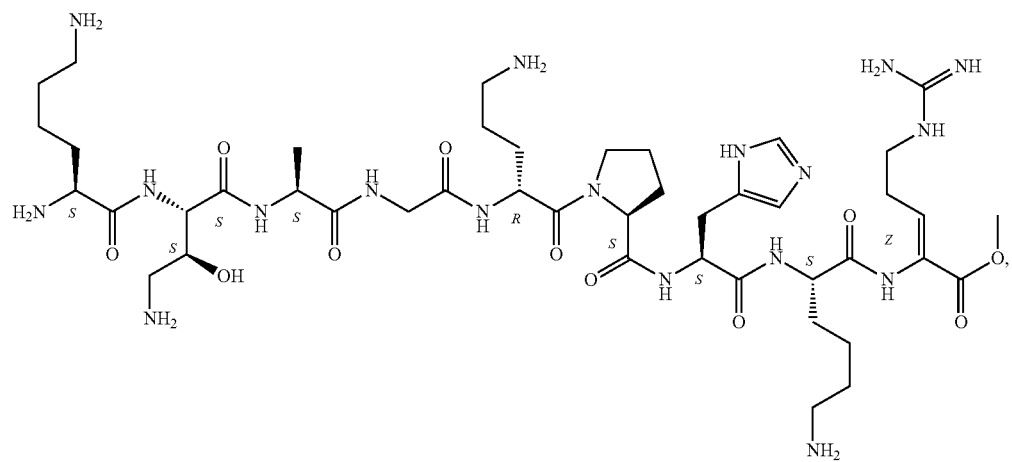
-continued
490
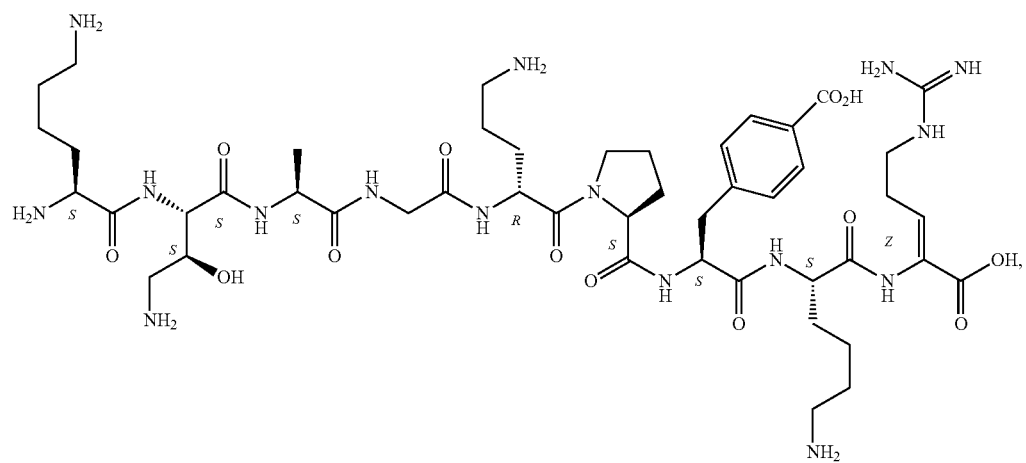
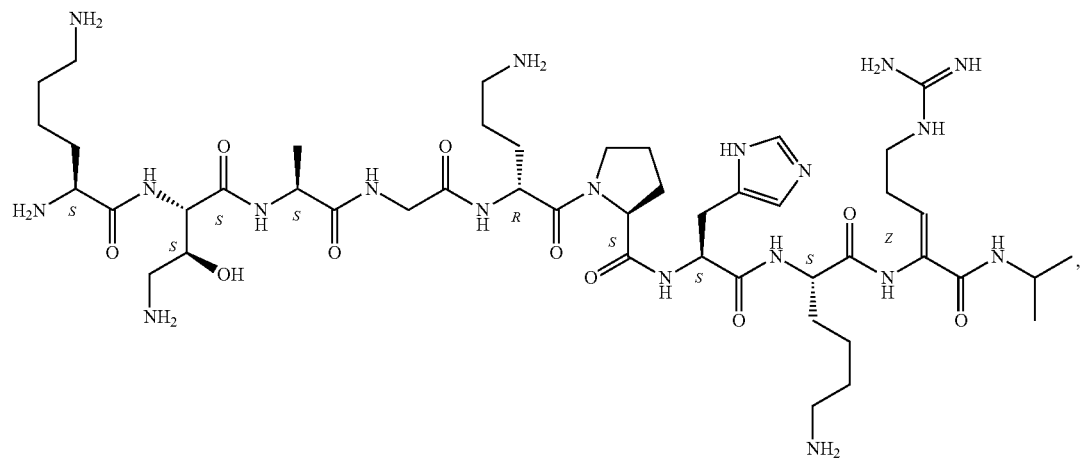

491
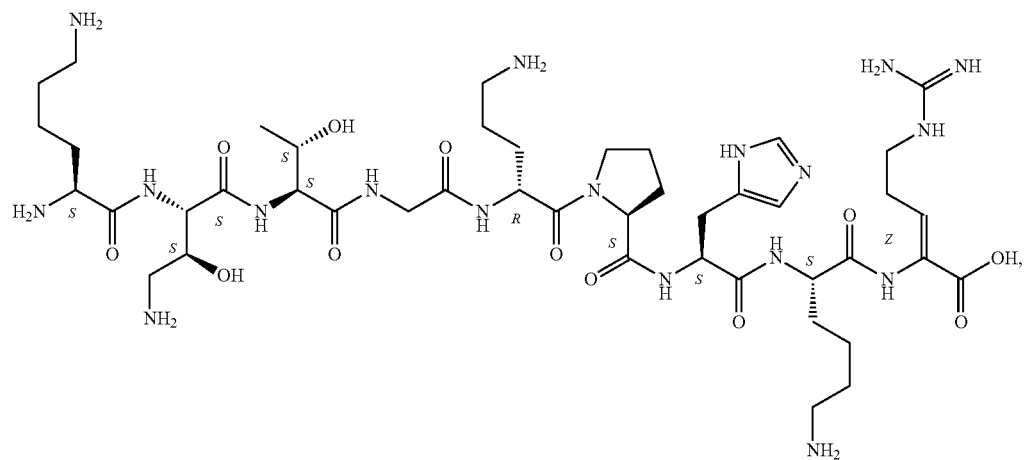
-continued
492
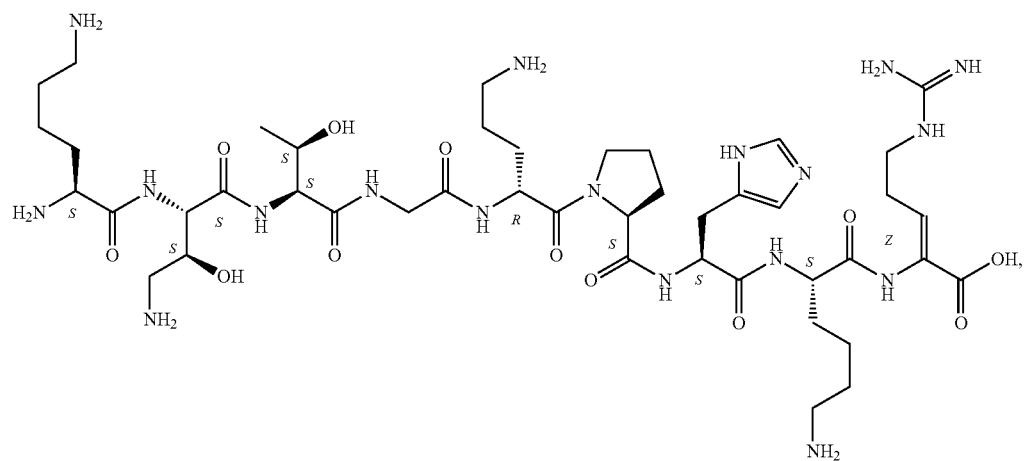
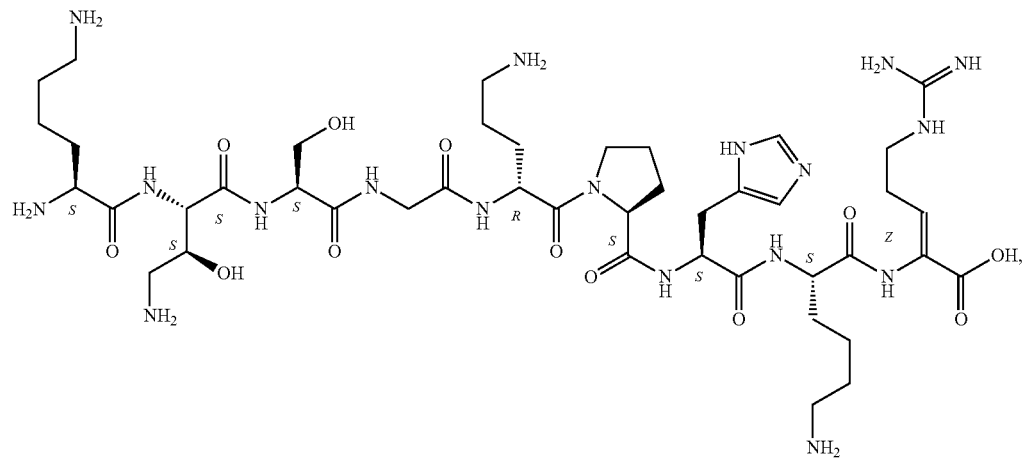

493
494
-continued
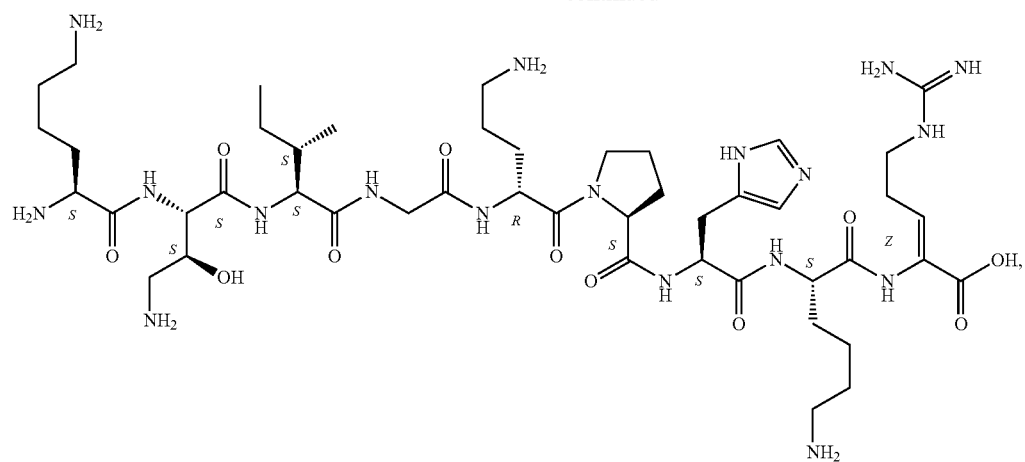
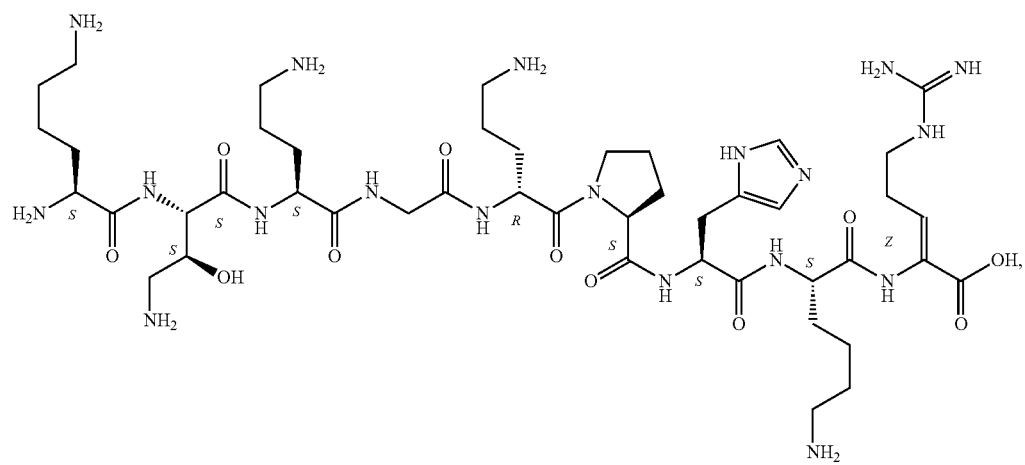
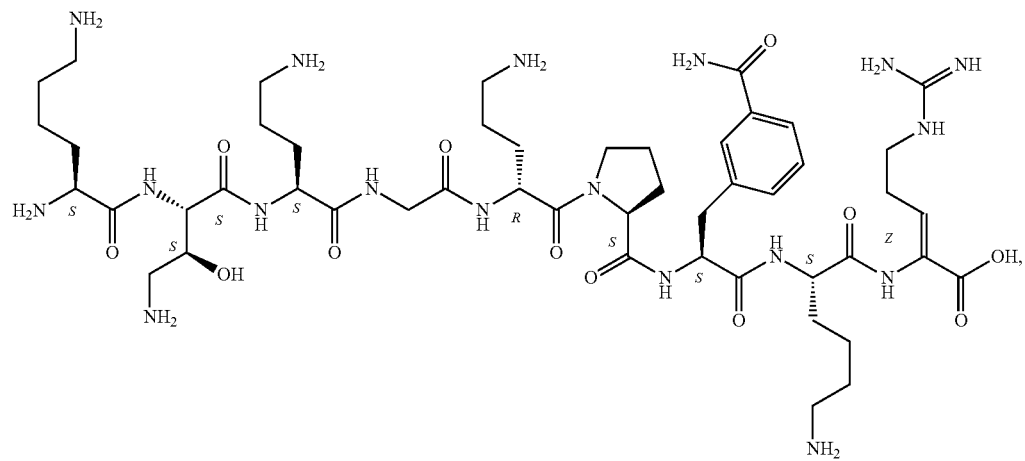

495
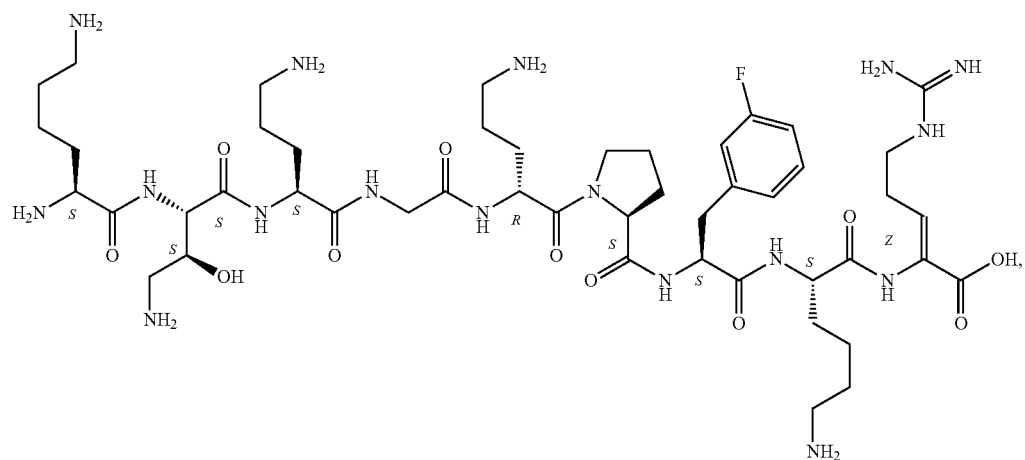
-continued
496
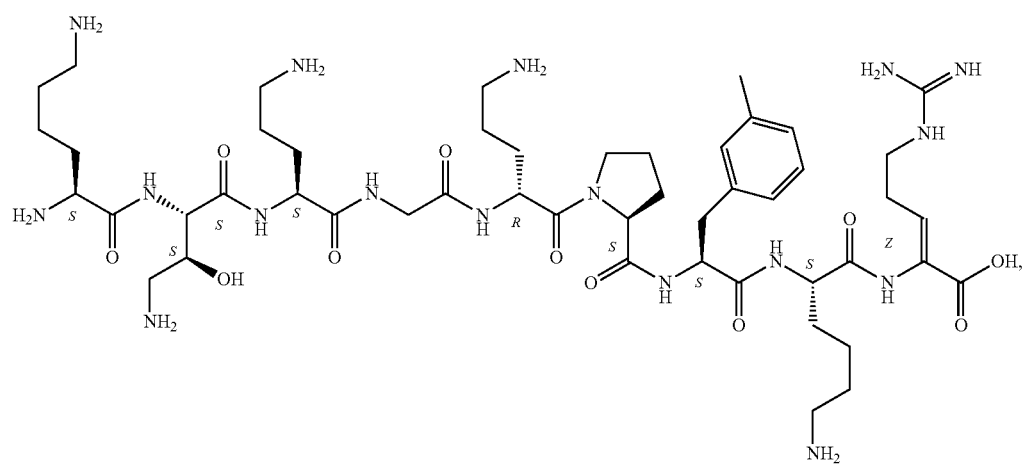
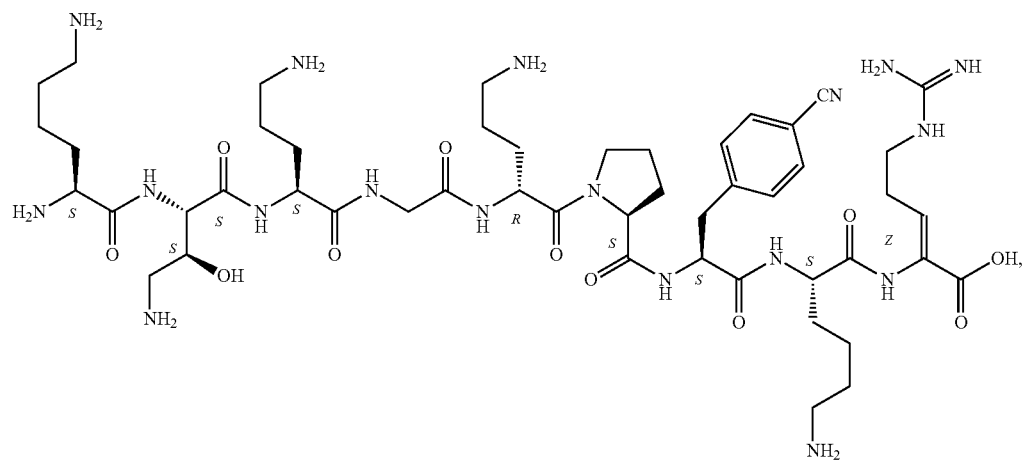

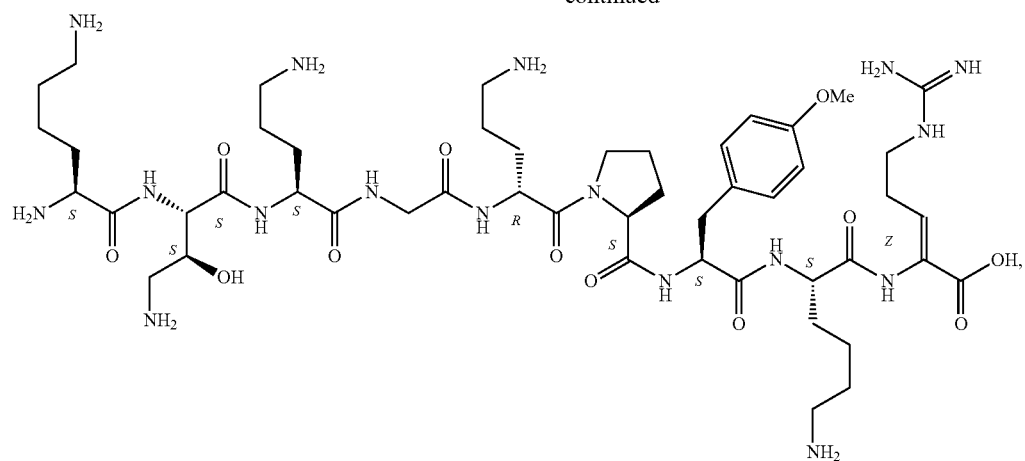
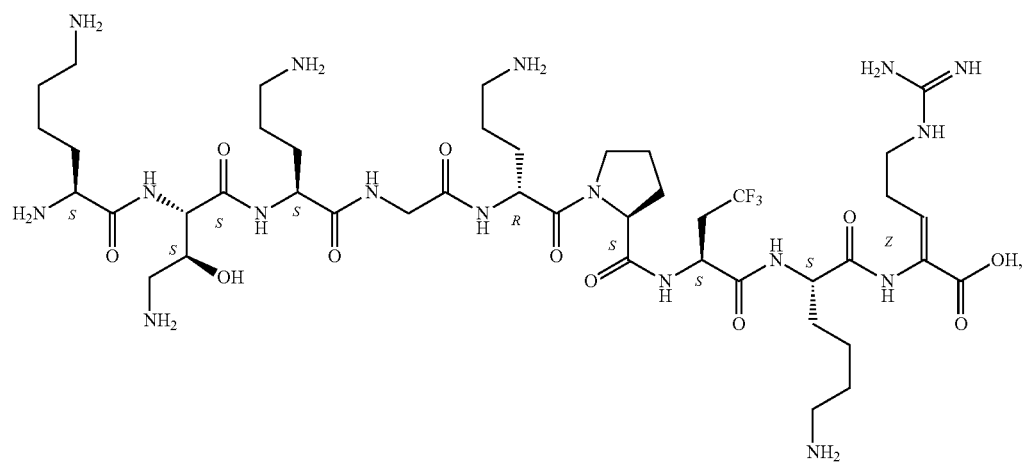
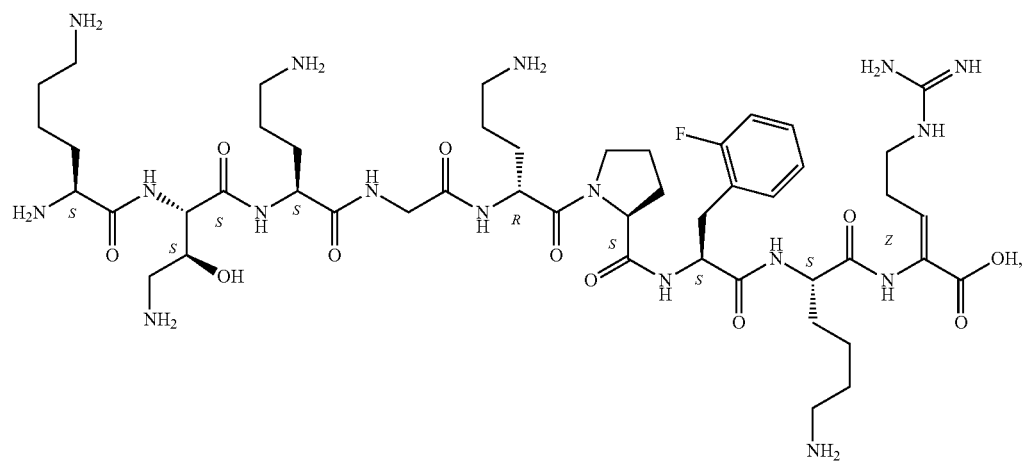

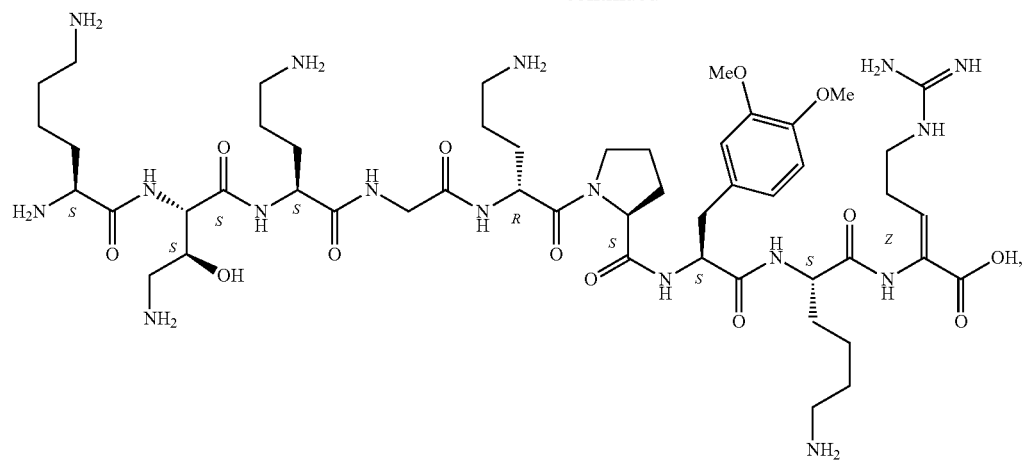
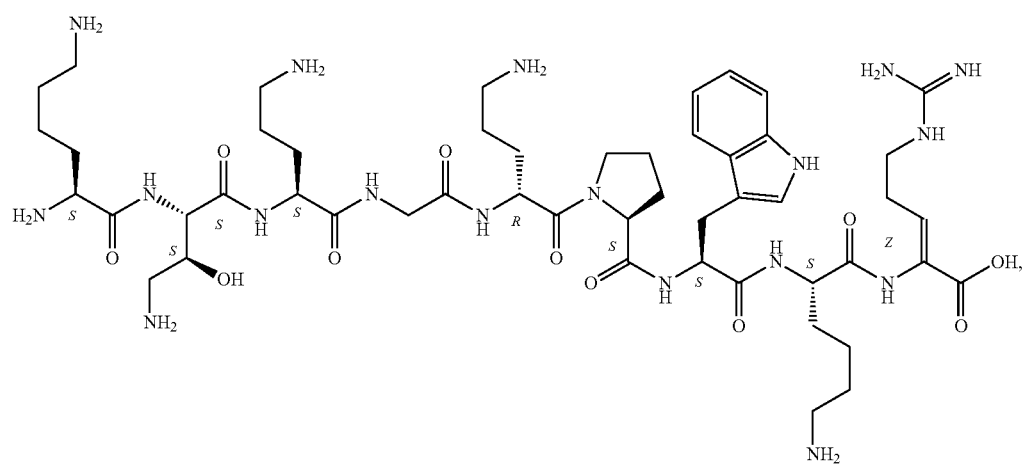
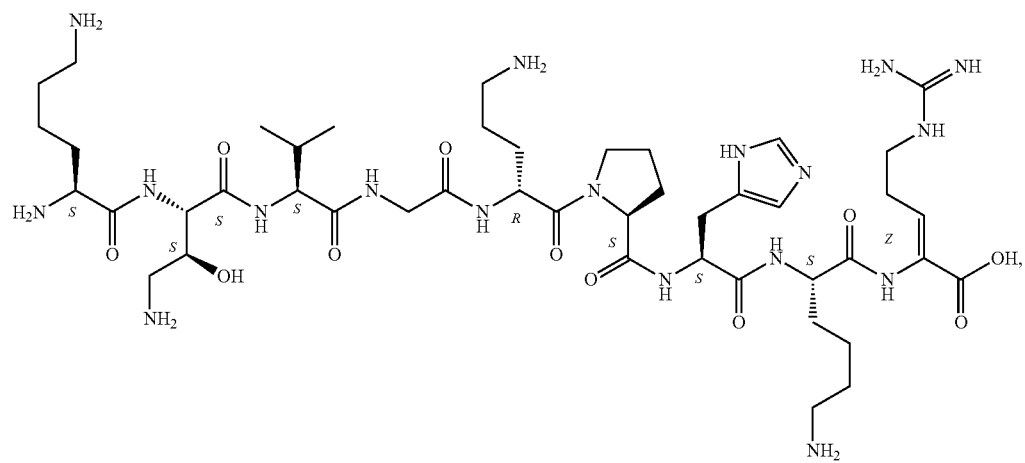

501
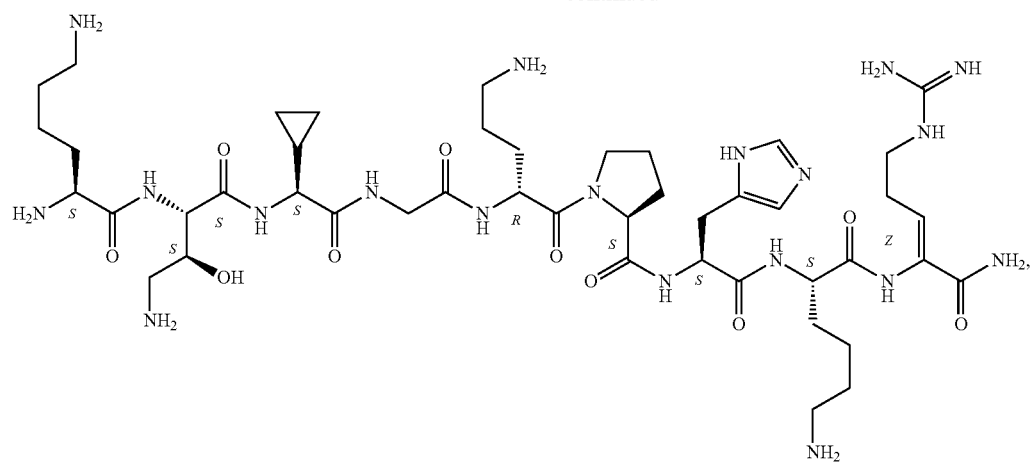
502
-continued
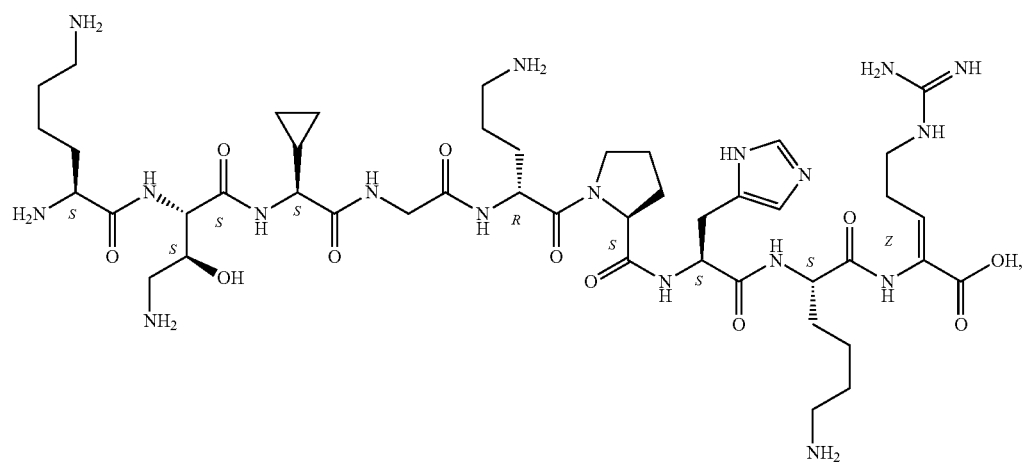
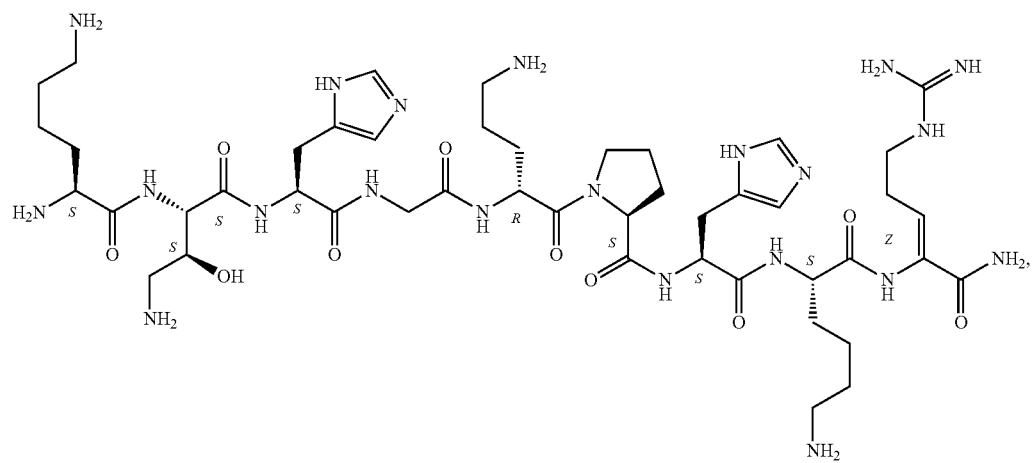

503
-continued
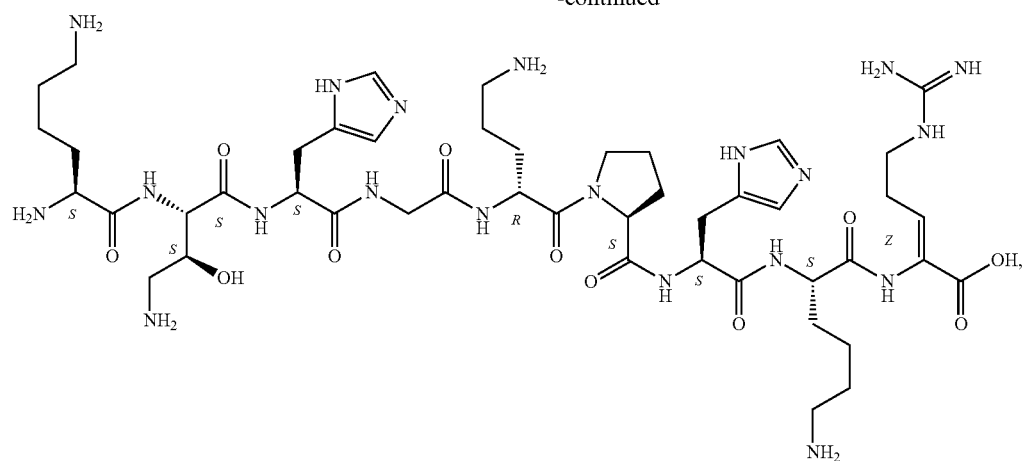
504
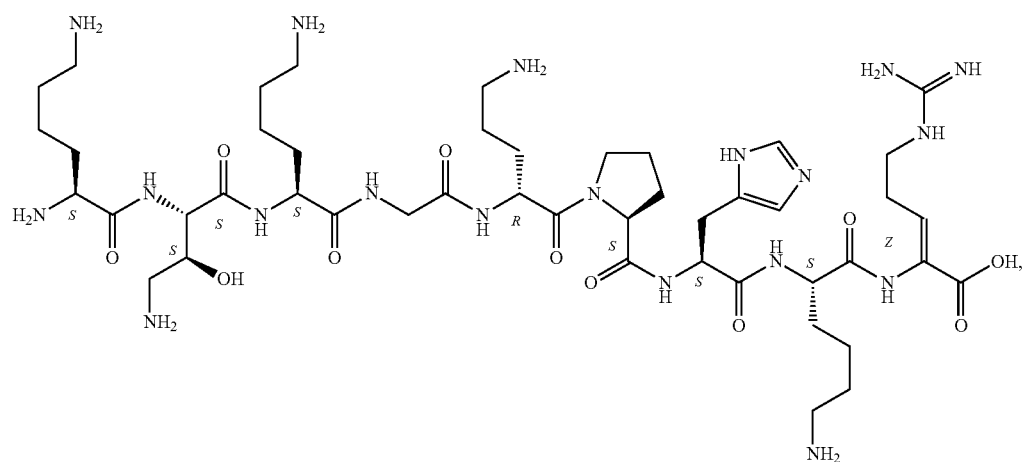
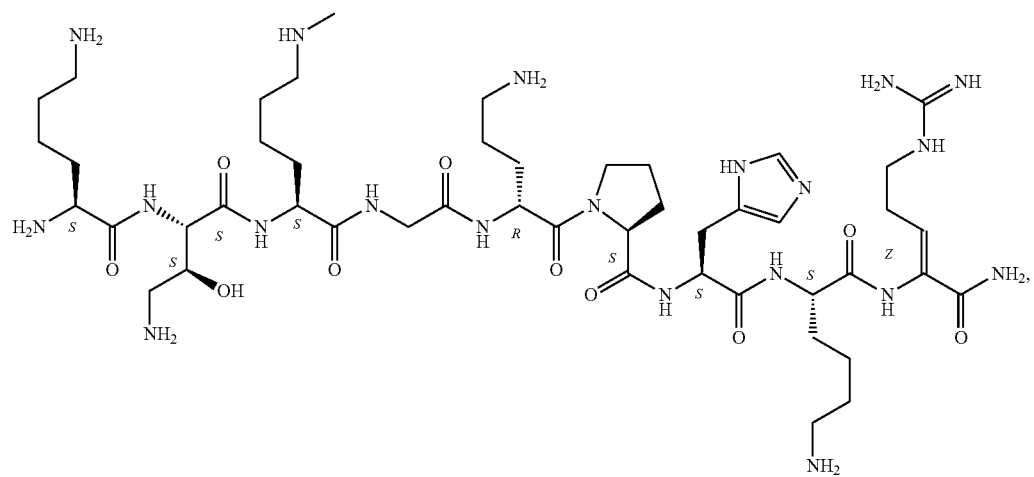

505
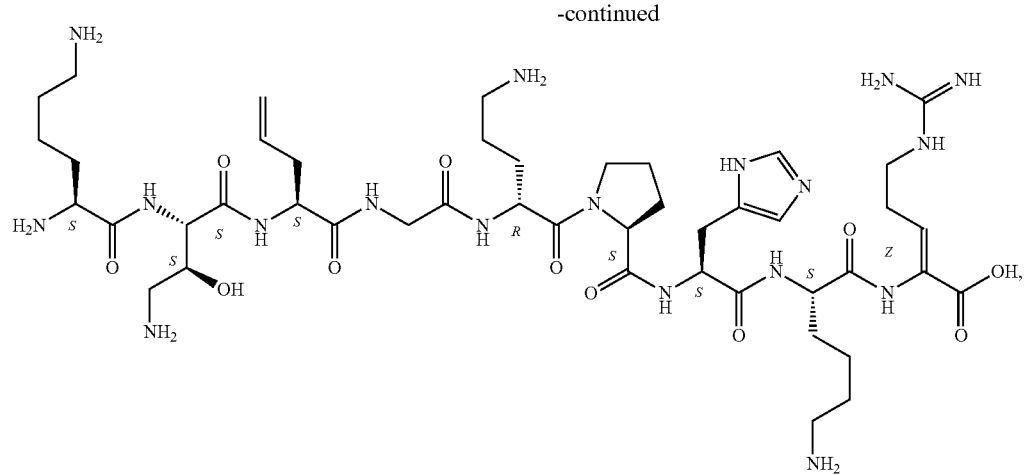
506
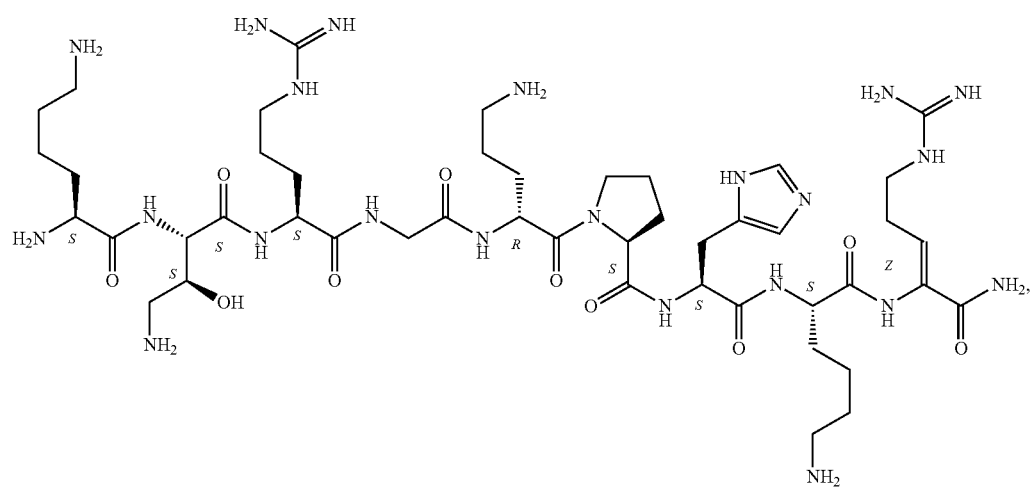
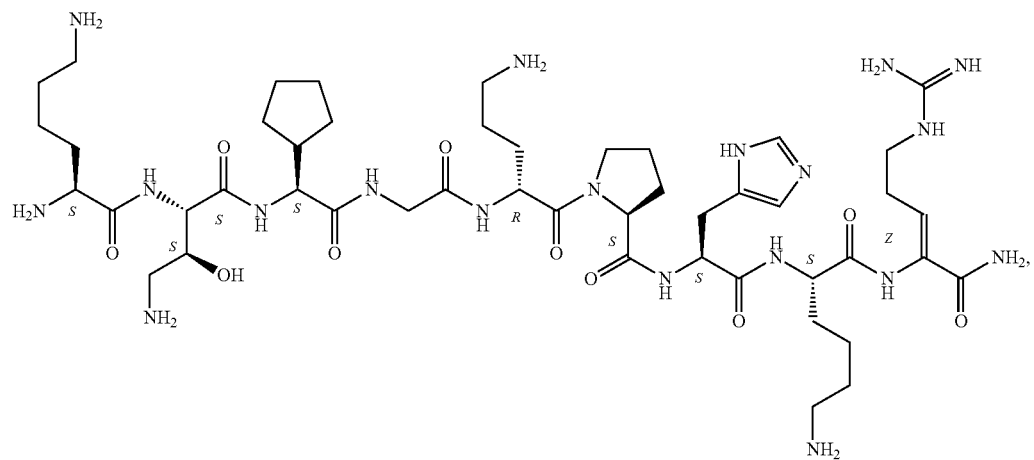

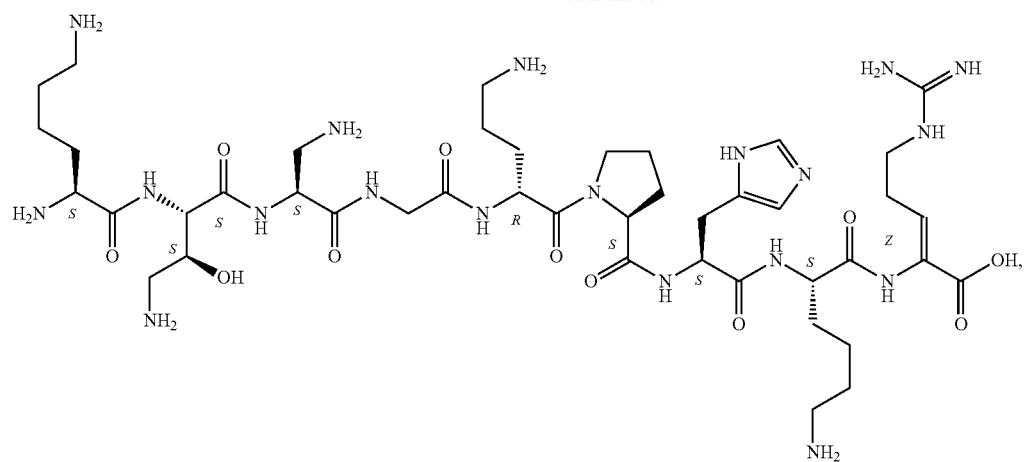
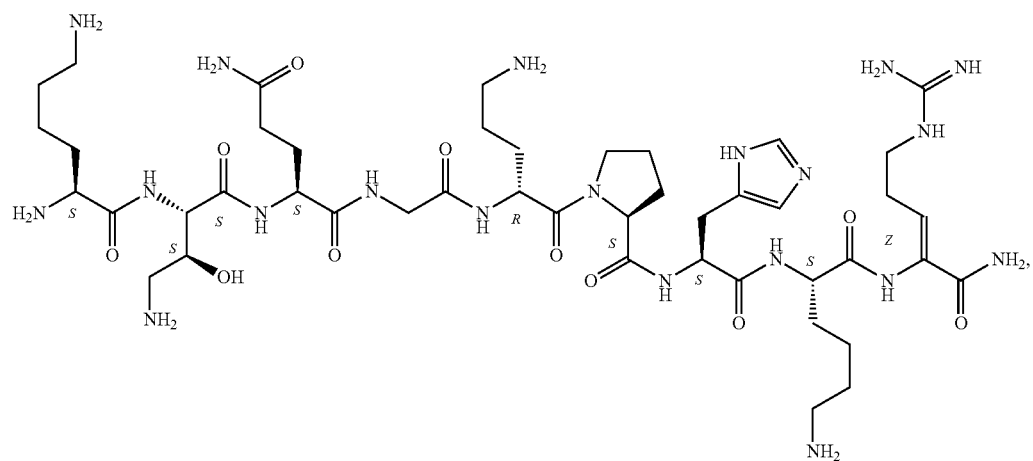
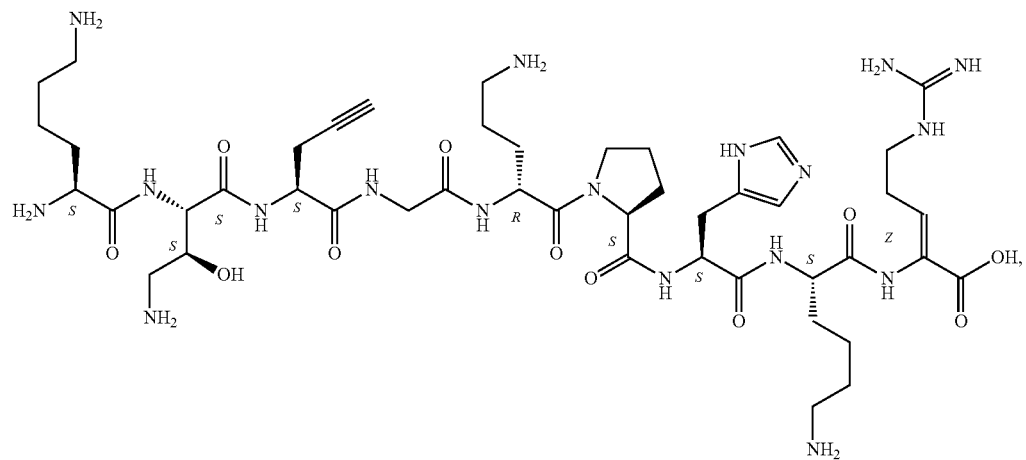

-continued

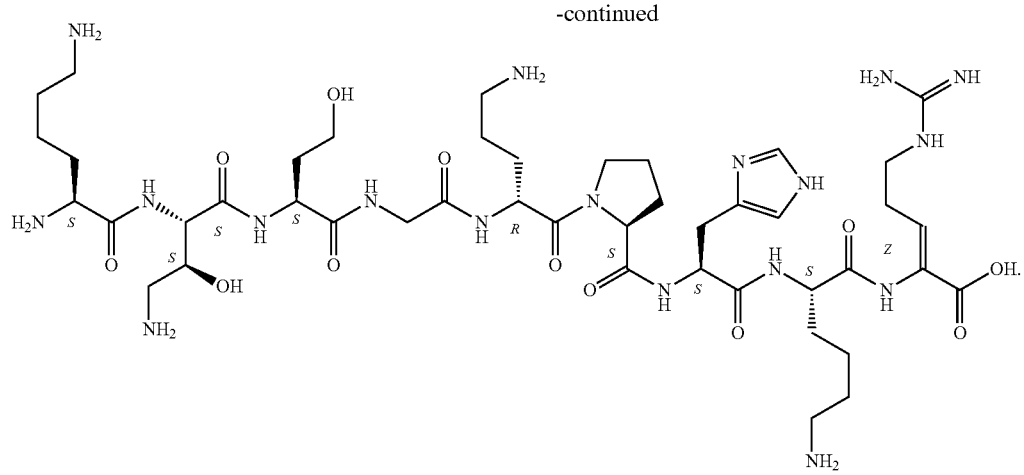

7. Combination of compounds comprising at least one compound of claim 1 with at least one antibiotic compound.

8. A pharmaceutical or veterinary composition comprising at least a compound of claim 1 and at least one pharmaceutically acceptable carrier.

9. A drug comprising at least a compound of claim 1.

10. The drug according to claim 9 further comprising an antibiotic compound.

11. The drug of claim 9 which is an antibiotic.

12. A method for treating a bacterial infection in a subject in need thereof comprising the administration of at least a compound of claim 1.

13. The method of claim 12, wherein the subject is a mammal.

14. The method of claim 12, wherein the bacterial infection is induced by a multiresistant bacteria.

15. The method of claim 12, wherein the compound is administered orally, parenterally or topically.

16. The method of claim 12, further comprising administering an antibiotic compound.

\* \* \* \* \*